United States Patent [19]

Harpold et al.

[11] Patent Number: 5,792,846

[45] Date of Patent: Aug. 11, 1998

[54] HUMAN CALCIUM CHANNEL COMPOSITIONS AND METHODS

[75] Inventors: Michael M. Harpold; Steven B. Ellis, both of San Diego; Mark E. Williams, Carlsbad; Daniel H. Feldman, San Diego; Ann F. McCue, La Mesa, all of Calif.; Robert Brenner, Austin, Tex.

[73] Assignee: Sibia Neurosciences, Inc., La Jolla, Calif.

[21] Appl. No.: 455,543

[22] Filed: May 31, 1995

Related U.S. Application Data

[63] Continuation of Ser. No. 223,305, Apr. 4, 1994, which is a continuation-in-part of Ser. No. 745,206, Aug. 15, 1991, Pat. No. 5,429,921, which is a continuation-in-part of Ser. No. 620,250, Nov. 30, 1990, abandoned, which is a continuation-in-part of Ser. No. 176,899, Apr. 4, 1988, abandoned, and a continuation-in-part of Ser. No. 482,384, Feb. 20, 1990, Pat. No. 5,386,025, and a continuation-in-part of Ser. No. 603,751, Apr. 4, 1989, abandoned.

[51] Int. Cl.[6] .............................. C12Q 1/68; C07H 21/04
[52] U.S. Cl. .................... 536/23.1; 435/6; 435/69.1; 435/240.2; 436/501; 536/23.1; 536/24.1; 536/24.3; 536/24.31; 536/24.32; 536/24.33; 935/77; 935/78
[58] Field of Search .................... 435/6, 69.1, 240.2, 435/810; 436/501; 536/22.1, 23.1, 24.1, 24.3–24.33; 935/77, 78

[56] References Cited

U.S. PATENT DOCUMENTS

| | | | |
|---|---|---|---|
| 4,788,135 | 11/1988 | Davis et al. | 435/6 |
| 4,912,202 | 3/1990 | Campbell et al. | 530/387 |
| 4,954,436 | 9/1990 | Froehner et al. | 435/7 |
| 5,024,939 | 6/1991 | Gorman | 435/69.1 |
| 5,051,403 | 9/1991 | Miljanich et al. | 514/12 |
| 5,189,020 | 2/1993 | Miljanich et al. | 514/12 |
| 5,264,371 | 11/1993 | Miljanich et al. | 436/503 |
| 5,386,025 | 1/1995 | Jay et al. | 536/23.5 |
| 5,407,820 | 4/1995 | Ellis et al. | 435/240.2 |
| 5,424,218 | 6/1995 | Miljanich et al. | 436/503 |
| 5,429,921 | 7/1995 | Harpold et al. | 435/4 |

FOREIGN PATENT DOCUMENTS

| | | |
|---|---|---|
| 2085502 | 2/1993 | Canada . |
| 0507170 | 3/1992 | European Pat. Off. . |
| 0556651 | 4/1993 | European Pat. Off. . |
| 8907608 | 8/1989 | WIPO . |
| 8909834 | 10/1989 | WIPO . |
| 9113077 | 6/1991 | WIPO . |
| 9308469 | 4/1993 | WIPO . |
| 9504144 | 2/1995 | WIPO . |

OTHER PUBLICATIONS

New England Biolabs Catalog [published by New England Biolabs, Beverly, MA, USA (1986/87)], pp. 60–62.

Brust et al., Human neuronal voltage–dependent calcium channels: studies on sununit structure and role in channel assembly, *Neuropharmacology* 32(11): 1089–1102 (1993).

Williams et al., "Structure and functional characterization of neuronal $\alpha_{1E}$ calcium channel subtypes," *J. Biol. Chem.* 269(35):22347–22357 (1994).

Powers, et al., "Assignment of the human gene for the $\alpha_1$ subunit of the cardiac DHP–sensitive $Ca^{2+}$ channel (CCHL1A1) to Chromosome 12p12–pter," *Genomics*, 10:835–839 (1991).

Kim, et al., "IgG from patients with Lambert–Eaton syndrome blocks voltage–dependent calcium channels," *Science*, 239:405–408 (1988).

(List continued on next page.)

*Primary Examiner*—Ardin H. Marschel
*Attorney, Agent, or Firm*—Stephanie L. Seidman; Brown Martin Haller & McClain LLP

[57] ABSTRACT

Isolated DNA encoding each of human calcium channel $\alpha_1$-, $\alpha_2$-, β- and γ-subunits, including subunits that arise as splice variants of primary transcripts, is provided. Cells and vectors containing the DNA and methods for identifying compounds that modulate the activity of human calcium channels are also provided.

21 Claims, 4 Drawing Sheets

OTHER PUBLICATIONS

Claudio, et al., "Genetic reconstitution of functional acetylcholine receptor channels in mouse fibroblasts," *Science*, 238:1688–1694 (1987).

Tanabe, et al., "Primary structure of the receptor for calcium channel blockers from skeletal muscle," *Nature*, 328:313–318 (1987).

Nakayama, et al., "Purification of a putative $Ca^{2+}$ channel protein from rabbit skeletal muscle," *J.Biol.Chem.*, 262:6572–6576 (1987).

Vaghy, et al., "Identification of a novel 1,4–dihydropyridine- and phenylalkylamine–binding polypeptide in calcium channel preparations," *J.Biol.Chem.*, 262(29):14337–14342 (1987).

Leung, et al., "Structural characterization of the 1,4–dihydropyridine receptor of the voltage–dependent $Ca^{2+}$ channel from rabbit skeletal muscle," *J.Biol.Chem.*, 262(17):7943–7946 (1987).

Sharp, et al., "Identification and characterization of the dihydropyridine–binding subunit of the skeletal muscle dihydropyridine receptor," *J.Biol.Chem.*, 62(25):12309–12315 (1987).

Takahashi, et al., "Subunit structure of dihydropyridine–sensitive calcium channels from skeletal muscle," *Proc.Natl.Acad.Sci. (USA)*, 84:5478–5482 (1987).

Morton and Froehner, "Monoclonal antibody identifies a 200–kDA subunit of the dihydropyridine–sensitive calcium channel," *J.Biol.Chem.*, 262(25):11904–11907 (1987).

Barhanin, et al., "The calcium channel antagonists receptor from rabbit skeletal muscle: reconstitution after purification and subunit characterization," *Eur.J.Biochem.*, 164:525–531 (1987).

Sieber, et al., "The 165–kDa peptide of the purified skeletal muscle dihydropyridine receptor contains the known regulatory sites of the calcium channel," *Eur.J.Biochem.*, 167:117–122 (1987).

Lang, et al., "The effect of myasthenic syndrome antibody on presynaptic calcium channels in the mouse," *J.Physiol.*, 390:257–270 (1987).

Curran and Morgan, "Barium modules c–fos expression and post–translational modification," *Proc.Natl.Acad.Sci.*, 83:3521–8524 (1986).

Fisch, et al., "c–fos sequences necessary for basal expression and induction by epidermal growth factor, 12–0–tetradecanoyl phorbol–13–acetate, and the calcium inophore," *Mol.Cell.Biol.*, 7(10):3490–3502 (1987).

Noda, et al., "Existence of distinct sodium channel messenger RNAs in rat brain," *Nature*, 320:188–192 (1986).

Noda, et al., "Expression of functional sodium channels from cloned cDNA," *Nature*, 322:826–828 (1986).

Mierendorf, et al., "Gene isolation by screening kgtll libraries with antibodies," *Methods in Enz.*, 152:458–469 (1986).

Gustin, et al., "Ion channels in yeast," *Science*, 233:1195–1197 (1986).

Striessnig, et al., "Photoaffinity labelling of the phenylalkylamine receptor of the skeletal muscle transverse–tubule calcium channel," *FEBS Letters*, 212(2):247–253 (1987).

Froehner, "New insights into the molecular structure of the dihydropyridine–sensitive calcium channel," *TINS*, 11(3):90–92 (1988).

Catterall, et al., "Molecular properties of dihydropyridine–sensitive calcium channels in skeletal muscle," *J.Biol.Chem.*, 263(8):3535–3538 (1988).

Curtis, et al., "Purification fo the calcium antagonist receptor of the voltage–sensitive calcium channel from skeletal muscle transverse tubules," *Biochemistry*, 23(10):2113–2118 (1984).

Borsotto, et al., "The 1,4–dihydropyridine receptor associated with the skeletal muscle voltage–dependent $Ca^{2+}$ channel," *J.Biol.Chem.*, 260(26):14255–14263 (1985).

Cooper, et al., "Purification and characterization of the dihydropyridine–sensitive voltage–dependent calcium channel from cardiac tissue," *J.Biol.Chem.*, 262(2):509–512 (1987).

Wood, "Gene cloning based on long oligonucleotide probes," *Methods in Enzymology*, 152:443–447 (1987).

Schmid, et al., "Immunochemical analysis of subunit structure of 1,4–dihydropyridine receptors associated with voltage–dependent $Ca^{2+}$ channels in skeletal, cardiac, and smooth muscles," *Biochemistry*, 25:3492–3495 (1986).

Mishina, et al., "Location of functional regions of acetylcholine receptor α–subunit by site–directed mutagenesis," *Nature*, 313:364–369 (1985).

Hamill, et al., "Improved patch–clamp techniques for high–resolution current recording from cells and cell–free membrane patches," *Pfluger Archiv.European Journal of Physiology*, 391:85–100 (1981).

Hess, et al., "Different modes of Ca channel gating behavior favored by dihydropyridine Ca agonist and antagonists," *Nature*, 311:538–544 (1984).

Leung, et al., "Biochemical and ultrastructural characterization of the 1,4–dihydropyridine receptor from rabbit skeletal muscle," *J. of Biol.Chem.*, 263(2):994–1001 (1988).

Imagawa, et al., "Phosphorylation of the 1,4–dihydropyridine receptor of the voltage–dependent $Ca^{2+}$ channel by an intrinsic protein kinase in isolated triads from rabbit skeletal muscle," *J. of Biol.Chem.*, 262(17):8333–8339 (1987).

Miller, "Multiple calcium channels and neuronal function," *Science*, 235:46–52 (1987).

Kozak, "An analysis of 5'–noncoding sequences from 699 vertebrate messenger RNAs," *Nucleic Acids Research*, 15(20):8125–8148 (1987).

von Heijne, "Signal sequences: the limits of variation," *Jour. of Mol.Biol.*, 184:99–105 (1985).

Hubbard, et al., "Synthesis and processing of aspargine–linked oligosaccharides[1,2]," *Ann.Rev.Biochem.*, 50:555–583 (1981).

Feramisco, et al., "Optimal spatial requirements for the location of basic residues in peptide substrates for th cyclic AMP–dependent protein kinase," *Journal of Biological Chemistry*, 255(9):4240–4245 (1980).

Takahashi, et al., "Identification of an α subunit of dihydropyridine–sensitive brain calcium channels," *Science*, 236:88–91 (1987).

Hofmann, et al., "Regulation of the L–type calcium channel," *TINS*, 8:393–398 (1987).

Curtis, et al., "Reconstitution of the voltage–sensitive calcium channel purified from skeletal muscle transverse tubules," *Biochemistry*, 25:3077–3083 (1986).

Smith, et al., "Calcium channel activity in a purified dihydropyridine–receptor preparation of skeletal muscle," *Biochemistry*, 26:7182–7188 (1987).

Meshi, et al., "Nucleotide sequence of the 30K protein cistron of cowpea strain of tobacco mosaic virus," *Nucleic Acids Research*, 10(19):6111–6117 (1982).

Nikaido, et al., "Molecular cloning of cDNA encoding human interleukin–2 receptor," *Nature*, 311:631–636 (1984).

Roberts, et al., "Paraneoplastic myasthenic syndrome IgG inhibits $^{45}Ca^{2+}$ flux in a human small cell carcinoma line," *Nature*, 317:737–739 (1985).

Starr, et al., "Primary structure of a calcium channel that is highly expressed in rat cerebellum." *Proc.Natl.Acad.Sci. USA*, 88:5621–5625 (1991).

Snutch, et al., "Distinct calcium channels are generated by alternative splicing and are differentially expressed in the mammalian CNS," *Neuron*, 7:45–57 (1991).

Hui, et al., "Molecular cloning of multiple sybtypes of a novel rat brain isoform of the $a_1$ subunit of the voltage–dependent calcium channel," *Neuron*, 7:35–44 (1991).

Bean et al., "Classes of calcium channels in vertebrate cells," *Annu.Rev. Physiol.*, 51:367–384 (1989).

Swandulla, et al., "Do calcium channel classifications account for neuronal calcium channel diversity?" *TINS*, 14(2):46–51 (1991).

Ruth, et al., "Primary structure of the α subunit of the DHP–sensitive calcium channel from skeletal muscle," *Science*, 245:1115–1118 (1989).

Mikami, et al., "Primary structure and functional expression of the cardiac dihydropyridine–sensitive calcium channel," *Nature*, 340:230–233 (1989).

Biel, et al., "Primary structure and functional expression of a high voltage activated calcium channel from rabbit lung" *FEBS Letters*, 269(2):409–412 (1990).

Mori, et al., "Primary structure and functional expression from complementary DNA of a brain calcium channel," *Nature*, 350:398–402 (1991).

Snutch, et al., "Rat brain expresses a heterogeneous family of calcium channels," *Proc.Natl.Acad.Sci. USA*, 87:3391–3395 (1990).

Perez–Reyes, et al., "Molecular diversity of L–type calcium channels," *J. of Biol.Chem.*, 265(33):20430–20436 (1990).

Perez–Reyes, et al., "Induction of calcium currents by the expression of the $α_1$–subunit of the dihydropyridine receptor from skeletal muscle," *Nature*, 340:233–236 (1989).

Koch, et al., "Characterization of cDNA clones encoding two putative isoforms of the $α_1$–subunit of the dihydropyridine–sensitive voltage–dependent calcium channel isolated from rat brain and rat aorta," *FEBS Letters*, 250(2):386–388 (1989).

Slish, et al., "Evidence for the existence of a cardiac specific isoform of the $α_1$–subunit of the voltage dependent calcium channel," *FEBS Letters*, 250(2):509–514 (1989).

Varadi, et al., "Development regulation of expression of the $α_1$ and $α_2$ subunits mRNAs of the voltage–dependent calcium chanel in a differentiating myogenic cell line," *FEBS Letters*, 250(2)CE:515–518 (1989).

Jongh, et al., "Subunits of purified calcium channels: a 212–kDa form of $α_1$ and partial amino acid sequence of a phosphorylation site of an independent β–subunit," *Proc.Natl.Acad.Sci. USA*, 86:8585–8589 (1989).

Hamilton, et al., "Subunit composition of the purified dihydropyridine binding protein from skeletal muscle," *Biochemistry*, 28:7820–7828 (1989).

Nunoki, et al., "Activation of purified calcium channels by stoichiometric protein phosphorylaton," *Proc.Natl.Acad.Sci. USA*, 86:6816–6820 (1989).

Ichida, et al., "Photoaffinity labeling with dihydropridine derivatives of crude membranes from rat skeletal, cardiac, ileal, and uterine muscles and whole brain," *J.Biochem.*, 105:767–774 (1989).

Sharp and Campbell, "Characterization of the 1,4–dihydropyridine receptor using subunit–specific polyclonal antibodies," *J.Biol.Chem.*, 264(5):2816–2825 (1989).

Campbell, et al., "The biochemistry and molecular biology of the dihydropyridine–sensitive calcium channel," *TINS*, 11(10):425–430 (1988).

Pelzer, et al., "Properties and regulation of calcium channels in muscle cells," *Rev.Physiol.Biochem.Pharmacol.*, 114:107–207 (1990).

Kim, et al., "Studies on the structural requirements for the activity of the skeletal muscle dihydropyridine receptor/slowCa$^{2+}$ channel," *J.Biol.Chem.*, 11858–11863 (1990).

Lotan, et al., "Specific block of calcium channel expression by a fragment of dihydropyridine receptor cDNA," *Science*, 243:666–669 (1989).

Rampe, et al., "[$^{3}$H]Pn200–110 bibnding in a fibroblast cell line transformed with the $α_1$ subunit of the skeletal muscle L–type Ca$^{2+}$ channel," *Biochem. and Biophys.Research Communications*, 169(3):825–831 (1990).

Adams, et al., "Intramembrane charge movement restored in dysgenic skeletal muscle by injection of dihydropyridine receptor cDNAs," *Nature*, 346:569–572 (1990).

Tanabe, et al., "Cardiac–type excitation–contraction coupling in dysgenic skeletal muscle injected with cardiac dihydropyridine receptor cDNA," *Nature*, 344:451–453 (1990).

Tanabe, et al., "Regions of the skeletal muscle dihydropyridine receptor critical for excitation–contraction coupling," *Nature*, 346:567–569 (1991).

Regulla, et al., "Identification of the site of interaction of the dihydropyridine channel blockers nitrendipine and azidopine with the calcium–channel $α_1$ subunit," *EMBO Journal*, 10(1):45–49 (1991).

Williams, et al., "Structure and functional expression of $α_1$, $α_2$ and β subunits of a novel human neuronal calcium channel subtype," *Neuron*, 8:71–84 (1992).

Olivera, et al., "Conotoxins," *J. of Biol.Chem.*, 266(33):22067–22070 (1991).

Seino, et al., "Cloning of $α_1$ subunit of a voltage–dependent calcium channel expressed in pancreatic β cells," *Proc.natl.Acad.Sci. USA*, 89:584–588 (1992).

Perez–Reyes, et al., "Cloning and expression of a cardiac/brain β subunit of the L–type calcium channel," *J. of Biol.Chem.*, 267(3):1792–1797 (1992).

Miller, R., "Voltage–sensitive Ca$^{2+}$ channels," *J. of Biol.Chem.*, 267(3):1403–1406 (1992).

Artalejo, et al., "w–Conotoxin GVIA blocks a Ca$^{2+}$ current in bovine chromaffin cells that is not of the 'classic' N type," *Neuron*, 8:85–95 (1992).

Kasai, H., "Tonic inhibition and rebound facilitation of a neuronal calcium channel by a GTP–binding protein," *Proc.Natl.Acad.Sci. USA*, 88:8855–8859 (1991).

Sher, et al., "Voltage–operated calcium channels in small cell lung carcinoma cell lines: pharmacological, functional, and immunological properties," *Cancer Research*, 5:3892–3896 (1990).

Sher, et al., "w–Conotoxin binding and effects on calcium channel function in human neuroblastoma and rat pheochromocytoma cell lines," *FEBS Letters*, 235:(1,2):178–182 (1988).

Koh, et al., "cDNA cloning of a dihydropyridine–sensitive calcium channel from rat aorta," *J. of Biol.Chem.*, 265(29):17786–17791 (1990).

Cohen, et al., "Distribution of $Ca^{2+}$ channels on frog motor nerve terminals revealed by fluorescent w–conotoxin," *J. of Neuroscience*, 11(4):1032–1039 (1991).

Bosse, et al., "The cDNA and deduced amino acid sequence of the γ subunit of the L–type calcium channel from rabbit skeletal muscle," *FEBS*, 267(1):153–156 (1990).

Burns, et al., "Calcium channel activity of purified human synexin and structure of the human synexin gene," *P.N.A.S.*, 86:3798–3802 (1989).

Campbell, et al., "32,000–Dalton subunit of the 1,4–dihydropyridine receptor," *Ann.N.Y.Acad.Sci.*, 560:251–257 (1989).

Dascal, N., "The use of Xenopus oocytes for the study of ion channels," *CRC Critical Rev.Biochem.*, 22(4):317–387 (1987).

DeJongh, et al., "Subunits of purified calcium channels," *J.Biol.Chem.*, 265(25):14738–14741 (1990).

Jay, et al., "Primary Structure of the γ subunit of the DHP–sensitive calcium channel from skeletal muscle," *Science.*, 248:490–492 (1990).

Jay, et al., "Structural characterization of the dihydropyridine–sensitive calcium channel $\alpha_2$–subunit and the associated$_{13}$ peptides." *J.Biol.Chem.*, 266(5):3287–3293 (1991).

Leung, et al., "Monoclonal antibody characterization of the 1,4–dihydropyridine receptor of rabbit skeletal muscle," *Ann.N.Y.Acad.Sci.*, 522:43–46 (1988).

Vaghy, et al., "Mechanism of action of calcium channel modulator drugs," *Ann.N.Y.Acad.Sci.*, 522:176–186 (1988).

Ahlijanian, et al., "Subunit structure and localization of dihydropyridine–sensitive calcium channels in mammalian brain, spinal cord, and retina," *Neuron*, 4:819–832 (1990).

Blount, et al., "Assembly intermediates of the mouse muscle nicotinic Acetylcholine receptor in stably transfected fibroblasts," *J.Cell.Biol.*, 111:2601 (1990).

Carbone, et al., "Ca currents in human neuroblastoma IMR32 cells: kinetics permeability and pharmacology," *Pfluegers Arch.* 416:170–179 (1990).

Dascal, et al., "Expression of modulation of voltage–gated calcium channels after RNA injection in Xenopus oocytes," *Science*, 231:1147–1150 (1986).

Hess, et al., "Calcium channels in vertebrate cells," *Ann.Rev.Neurosci.*, 13:337–356 (1990).

Stanley, et al., "Characterization of a calcium current in a vertebrate cholinergic presynaptic nerve terminal," *J. Neurosci.*, 11:985 (1991).

Wei, et al., "Heterologous regulation of the cardiac $Ca^{2+}$ channel $\alpha_1$ subunit by skeletal muscle β and γ subunits," *J.Biol.Chem.*, 266:21943–21947 (1991).

Ahlijanian, et al., "Phosphorylation of an α1–like subunit of an w–conotoxin–sensitive brain calcium channel by cAMP–dependent protein kinase and protein kinase C," *J.Biol.Chem.*, 266:20192 (1991).

Claudio, T., "Stable expression of transfected Torpedo acetylcholine receptor α subunits in mouse fibroblast L cells," *P.N.A.S.*, 84:5967–5971 (1987).

Hullin, et al., "Calcium channel β subunit heterogeneity: functional expression of cloned cDNA from heart, aorta and brain," *EMBO J.*, 11:885 (1992).

Kim, et al., "Rat brain expresses an alternatively spliced form of the dihydropyridine–sensitive L–type calcium channel α2 subunit," *P.N.A.S.*, 89:3251 (1992).

Pragnell, et al., "Cloning and tissue–specific expression of the brain calcium channel β–subunit," *FEBS Letters*, 291:253 (1991).

Sakamoto, et al., "A monoclonal antibody to the β subunit of the skeletal muscle dihydropyridine receptor immunoprecipitates the brain w–conotoxin GVIA receptor," *J.Biol.Chem.*, 266:18914 (1991).

Seager, et al., "Molecular properties of dehydropyrine–sensitive calcium channels," *Ann.N.Y.Acad.Sci.*, 552:162–175 (1988).

Tsien, et al., "Molecular diversity of voltage–dependent $Ca^{2+}$ channels," *Trends in Pharmacol.Sci.*, 12:349 (1991).

Takahashi and Catterall, "Dihydropyridine–sensitive calcium channels in cardiac and skeletal muscle membranes: studies with antibodies against the α–subunits," *Biochemistry*, 26(17): 1518–1526 (1987).

HUMAN CALCIUM CHANNEL COMPOSITIONS AND METHODS

This application is a continuation of U.S. application Ser. No. 08/223,305, filed Apr. 4, 1994, which is a continuation-in-part of U.S. Ser. No. 745,206, filed Aug. 15, 1991, now U.S. Pat. No. 5,429,921; which is a continuation-in-part of U.S. Ser. No. 620,250, filed Nov. 30, 1990, now abandoned which is a continuation-in-part of U.S. Ser. No. 176,899, filed Apr. 4, 1988, now abandoned, and is also a continuation-in-part of U.S. Ser. No. 482,384, filed Feb. 20, 1990; now U.S. Pat. No. 5,386,025 and is also a continuation-in-part of U.S. Ser. No. 603,751, filed Apr. 4, 1989, now abandoned, and is also a continuation-in-part of PCT/US89/01408; filed Apr. 4,1989.

TECHNICAL FIELD

The present invention relates to molecular biology and pharmacology. More particularly, the invention relates to calcium channel compositions and methods of making and using same.

BACKGROUND OF THE INVENTION

Calcium channels are membrane-spanning, multi-subunit proteins that allow controlled entry of $Ca^{2+}$ ions into cells from the extracellular fluid. Cells throughout the animal kingdom, and at least some bacterial, fungal and plant cells, possess one or more types of calcium channels.

The most common type of calcium channel is voltage dependent. All "excitable" cells in animals, such as neurons of the central nervous system, peripheral nerve cells, and muscle cells, including those of skeletal muscles, cardiac muscles, and venous and arterial smooth muscles, have voltage-dependent calcium channels.

In a voltage-dependent channel, the "opening" to allow an influx of $Ca^{2+}$ ions into the cells requires a depolarization to a certain level of the potential difference between the inside of the cell bearing the channel and the extracellular medium bathing the cell. The rate of influx of $Ca^{2+}$ into the cell depends on this potential difference.

Multiple types of calcium channels have been identified in mammalian cells from various tissues, including skeletal muscle, cardiac muscle, lung, smooth muscle and brain, [see, e.g., Bean, B. P.(1989) *Ann. Rev. Physiol.* 51:367–384 and Hess, P. (1990) *Ann. Rev. Neurosci.* 56:337]. The different types of calcium channels have been broadly categorized into four classes, L-, T-, N-, and P-type, distinguished by current kinetics, holding potential sensitivity and sensitivity to calcium channel agonists and antagonists. Four subtypes of neuronal voltage-dependent calcium channels have been proposed [Swandulla, D. et al. (1991) *Trends Neurosci.* 14:46].

At the present time, the rabbit skeletal muscle calcium channel is the most well-characterized of the calcium channels. It contains two large subunits, designated $\alpha_1$, and $\alpha_2$, which have molecular weights between about 130 and about 200 kilodaltons ("kD"), and a number, one to three, of different smaller subunits, of less than about 60 kD in molecular weight. At least one of the larger subunits and possibly some of the smaller subunits are glycosylated. Some of the subunits are capable of being phosphorylated.

The $\alpha_1$ subunit has a molecular weight of about 150 to about 170 kD when analyzed by sodium dodecylsulfate ("SDS")-polyacrylamide gel electrophoresis ("PAGE") after isolation from mammalian muscle tissue and has specific binding sites for various 1,4-dihydropyridines ("DHPs") and phenylalkylamines. Under non-reducing conditions (in the presence of N-ethylmaleimide), the $\alpha_2$ subunit migrates in SDS-PAGE as a band corresponding to a molecular weight of about 160–190 kD. Upon reduction, a large fragment, molecular weight about 130–150 kD, and smaller fragments are released. There is evidence that the $\alpha_2$ subunit and the large fragment produced under reducing conditions are glycosylated with at least N-linked sugars and do not specifically bind the 1,4-dihydropyridines and phenylalkylamines that specifically bind to the $\alpha_1$ subunit.

The $\beta$ subunit of the rabbit skeletal muscle calcium channel has an apparent molecular mass of 52–65 kD (as determined by SDS-PAGE analysis). It contains consensus phosphorylation sites and has been shown by biochemical methods to be phosphorylated. This subunit is insensitive to reducing conditions. The $\gamma$ subunit of the calcium channel is not observed in all purified preparations. It appears to be a glycoprotein with an apparent molecular mass of 30–33 kD, as determined by SDS-PAGE analysis.

Characterization of a particular type of calcium channel by analysis of whole cells is severely restricted by the presence of mixed populations of different types of calcium channels in the majority of cells. Although single-channel recording methods can be used to examine individual calcium channels, such analysis reveals nothing about the molecular structure or biochemical composition of the channel. Furthermore, in this type of analysis, the channel is isolated from other cellular constituents that might be important for natural functions and pharmacological interactions.

In order to study calcium channel structure and function, large amounts of pure channel protein are needed. Because of the complex nature of these multisubunit proteins, the varying concentrations of calcium channels in tissue sources of the protein, the presence of mixed populations of calcium channels in tissues, and the modifications of the native protein that can occur during the isolation procedure, it is extremely difficult to obtain large amounts of highly purified, completely intact calcium channel protein.

Characterization of the gene or genes encoding calcium channels provides another means of characterization of different types of calcium channels. The amino acid sequence determined based on the complete nucleotide sequence of the coding region of a gene encoding a calcium channel protein represents the actual primary structure of the protein. Furthermore, secondary structure of the calcium channel protein and the relationship of the protein to the membrane may be predicted based on analysis of the primary structure. For instance, hydropathy plots of the $\alpha_1$ subunit protein of the rabbit skeletal muscle calcium channel indicate that it contains four internal repeats, each containing six putative transmembrane regions [Tanabe, T. et al. (1987) *Nature* 328:313].

The cDNA and corresponding amino acid sequences of the $\alpha_1$, $\alpha_2$, $\beta$ and $\gamma$ subunits of the rabbit skeletal muscle calcium channel have been determined [see, Tanabe et al. (1987) *Nature* 328:313–318; International Application No. WO 89/09834, which is U.S. application Ser. No. 07/603, 751, which is a continution-in-part of U.S. application Ser. No. 07/176,899; Ruth et al. (1989) *Science* 245:1115–1118; and U.S. patent application Ser. No. 482,384, filed Feb. 20, 1990]. In addition, the cDNA and corresponding amino acid sequences of $\alpha_1$ subunits of rabbit cardiac muscle [Mikami, A. et al. (1989) *Nature* 340:230–233] and lung [Biel, M. (1990) *FEBS Letters* 269:409–412] calcium channels have been determined. In addition, cDNA clones encoding a rabbit brain calcium channel (designated the BI channel) have been isolated [Mori, Y. et al. (1991) *Nature* 350:398–402].

Partial cDNA clones encoding portions of several different subtypes, referred to as rat brain class A, B, C and D, of the calcium channel $\alpha_1$ subunit have been isolated from rat brain cDNA libraries [Snutch, T. et al. (1990) *Proc. Natl. Acad. Sci. USA* 87:3391–3395]. More recently full-length rat brain class A [Starr, T. et al. (1991) *Proc. Natl. Acad. Sci. USA* 88:5621–5625] and class C [Snutch, T. et al. (1991) *Neuron* 7:45–57] cDNA clones have been isolated. Although the amino acid sequence encoded by the rat brain class C DNA is approximately 95% identical to that encoded by the rabbit cardiac muscle calcium channel $\alpha_1$ subunit-encoding DNA, the amino acid sequence encoded by the rat brain class A DNA shares only 33% sequence identity with the amino acid sequence encoded by the rabbit skeletal or cardiac muscle $\alpha_1$ subunit-encoding DNA. A cDNA clone encoding another rat brain calcium channel $\alpha_1$ subunit has also been obtained [Hui, A. et al. (1991) *Neuron* 7:35–44]. The amino acid sequence encoded by this clone is ~70% homologous to the proteins encoded by the rabbit skeletal and cardiac muscle calcium channel DNA. A cDNA clone closely related to the rat brain class C $\alpha_1$ subunit-encoding cDNA and sequences of partial cDNA clones closely related to other partial cDNA clones encoding apparently different calcium channel $\alpha_1$ subunits have also been isolated [see Snutch, T. et al. (1991) *Neuron* 7:45–57; Perez-Reyes, E. et al. (1990) *J. Biol. Chem.* 265:20430; and Hui, A. et al. (1991) *Neuron* 7:35–44].

Successful expression of cDNA encoding calcium channel subunits has only been achieved with three of the six or seven different rabbit or rat $\alpha_1$ subunit cDNA clones discussed above. Voltage-dependent calcium currents have been detected in murine L cells transfected with DNA encoding the rabbit skeletal muscle calcium channel $\alpha_1$ subunit [Perez-Reyes et al. (1989) *Nature* 340:233–236 (1989)]. These currents were enhanced in the presence of the calcium channel agonist Bay K 8644. Bay K 8644–sensitive $Ba^{2+}$ currents have been detected in oocytes injected with in vitro transcripts of the rabbit cardiac muscle calcium channel $\alpha_1$ subunit cDNA [Mikami, A. et al. (1989) *Nature* 340:230–233]. These currents were substantially reduced in the presence of the calcium channel antagonist nifedipine. Barium currents of an oocyte co-injected with RNA encoding the rabbit cardiac muscle calcium channel $\alpha_1$ subunit and the RNA encoding the rabbit skeletal muscle calcium channel $\alpha_2$ subunit were more than 2-fold larger than those of oocytes injected with transcripts of the rabbit cardiac calcium channel $\alpha_1$ subunit-encoding cDNA. Similar results were obtained when oocytes were co-injected with RNA encoding the rabbit lung calcium channel $\alpha_1$ subunit and the rabbit skeletal muscle calcium channel $\alpha_2$ subunit. The barium current was greater than that detected in oocytes injected only with RNA encoding the rabbit lung calcium channel $\alpha_1$ subunit [Biel, M. et al. (1990) *FEBS Letters* 269:409–412]. Inward barium currents have been detected in oocytes injected with in vitro RNA transcripts encoding the rabbit brain BI channel [Mori et al. (1991) *Nature* 350:398–402]. These currents were increased by two orders of magnitude when in vitro transcripts of the rabbit skeletal muscle calcium channel $\alpha_2$, $\beta$, or $\alpha_2$, $\beta$ and $\gamma$ subunits were co-injected with transcripts of the BI-encoding cDNA. Barium currents in oocytes co-injected with transcripts encoding the BI channel and the rabbit skeletal muscle calcium channel $\alpha_2$ and $\beta$ were unaffected by the calcium channel antagonists nifedipine or $\omega$-CgTx and inhibited by Bay K 8644 and crude venom from *Agelenopsis aperta*.

The results of studies of recombinant expression of rabbit calcium channel $\alpha_1$ subunit-encoding cDNA clones and transcripts of the cDNA clones indicate that the $\alpha_1$ subunit forms the pore through which calcium enters cells. The relevance of the barium currents generated in these recombinant cells to the actual current generated by calcium channels containing as one component the respective $\alpha_1$ subunits in vivo is unclear. Because addition of in vitro transcripts of rabbit skeletal muscle calcium channel $\alpha_2$ and/or $\beta$ and $\gamma$-encoding cDNA significantly enhances the barium currents in the recombinant cells, it appears that in order to completely and accurately characterize and evaluate different calcium channel types, it is essential to examine the functional properties of recombinant channels containing all of the subunits as found in vivo.

Because calcium channels are present in various tissues and have a central role in regulating intracellular calcium ion concentrations, they are implicated in a number of vital processes in animals, including neurotransmitter release, muscle contraction, pacemaker activity, and secretion of hormones and other substances. These processes appear to be involved in numerous human disorders, such as central nervous system and cardiovascular diseases. Calcium channels, thus, are also implicated in numerous disorders.

Although there has been limited success in expressing DNA encoding rabbit and rat calcium channel subunits, far less has been achieved with respect to human calcium channels. Little is known about human calcium channel structure, function and gene expression. An understanding of the structure and function of calcium channels would permit identification of substances that, in some manner, modulate the activity of calcium channels and that have potential for use in treating such disorders.

A number of compounds useful for treating various cardiovascular diseases in animals, including humans, are thought to exert their beneficial effects by modulating functions of voltage-dependent calcium channels present in cardiac and/or vascular smooth muscle. Many of these compounds bind to calcium channels and block, or reduce the rate of, influx of $Ca^{2+}$ into the cells in response to depolarization of the cell membrane.

An understanding of the pharmacology of compounds that interact with calcium channels in other organ systems, such as the central nervous system ("CNS"), will aid in the rational design of compounds that specifically interact with the specific subtypes of human calcium channels to have desired therapeutic effects, such as in the treatment of neurodegenerative and cardiovascular disorders. Such understanding and the ability to rationally design therapeutically effective compounds have been hampered by an inability to independently determine the types of human calcium channels and the molecular nature of individual subtypes, particularly in the CNS, and by the unavailability of pure preparations of specific channel subtypes to use for evaluation of the specificity of calcium channel-effecting compounds. Thus, identification of DNA encoding human calcium channel subunits and the use of such DNA for expression of calcium channel subunits and functional calcium channels would aid in screening and designing therapeutically effective compounds.

Therefore, it is an object herein, to provide DNA encoding tissue specific calcium channel subunits and to provide eukaryotic cells bearing recombinant human calcium channels. It is also an object to provide assays for identification of potentially therapeutic compounds that act as calcium channel antagonists and agonists.

SUMMARY OF THE INVENTION

Eukaryotic cells containing DNA encoding one or more human calcium channel subunits or containing RNA transcripts of cDNA clones encoding one or more of the subunits are provided. In preferred embodiments, the cells contain DNA or RNA encoding an $\alpha_1$ subunit, preferably at least an $\alpha_{1D}$ or $\alpha_{1B}$ subunit. In more preferred embodiments, the cells containing DNA or RNA encoding additional heterologous subunits, including at least one human $\beta$, $\alpha_2$ or $\gamma$ subunits. In such embodiments, eukaryotic cells stably or transiently transfected with any combination of one, two, three or four of the subunit-encoding cDNA clones, such as $\alpha_1$, $\alpha_1+\beta$, $\alpha_1+\beta+\alpha$, etc., are provided.

In preferred embodiments, the cells express such heterologous calcium channel subunits and include one or more of the subunits in membrane spanning heterologous calcium channels. In more preferred embodiments, the eukaryotic cells express functional, heterologous calcium channels which are capable of gating the passage of calcium channel selective ions and/or binding a compound, which at a physiological concentration modulates the activity of the heterologous calcium channel. The heterologous calcium channels of such cells are distinguishable from endogenous calcium channels of the host cell. In certain embodiments, the eukaryotic cells express heterologous calcium channels that include at least one heterologous calcium channel subunit. In most preferred embodiments, the calcium channels that are expressed on the surface of the eukaryotic cells are composed substantially or entirely of subunits encoded by the heterologous DNA or RNA.

In certain embodiments the recombinant eukaryotic cells are produced by transfection with DNA encoding one or more of the subunits or are injected with RNA transcripts of cDNA encoding a human calcium channel subunits. The DNA may be introduced as a linear DNA fragment or may be included in an expression vector for stable or transient expression of the subunit-encoding DNA. Vectors containing DNA encoding human calcium channel subunits are also provided.

The eukaryotic cells that express heterologous receptors may be used in assays for calcium channel function or, in the case of cells transformed with fewer subunit-encoding nucleic acids than necessary to constitute a functional recombinant human calcium channel, such cells may be employed used to assess the effects of additional subunits on calcium channel activity. The additional subunits can be provided by subsequently transfecting such a cell with one or more DNA clones or RNA transcripts encoding human calcium channel subunits.

In preferred embodiments, the recombinant eukaryotic cells may be used in methods for identifying compounds that modulate calcium channel activity. In particular, the cells are used in assays that identify agonists and antagonists of calcium channel activity in humans and/or assessing the contribution of the various calcium channel subunits to the transport and regulation of transport of calcium ions.

Assays using the eukaryotic cells for identifying compounds that modulate calcium channel activity are provided.

Isolated and purified DNA fragments that encode human calcium channel subunits are provided. DNA encoding $\alpha_1$ subunits of a human calcium channel, and RNA, encoding such subunits, made upon transcription of such DNA are provided. In particular, DNA fragments encoding $\alpha_1$ subunits of voltage-dependent human calcium channels type B (also referred to as voltage-dependent calcium channel (hereinafter VDCC) IV), type C (also referred to as VDCC II) and type D (also referred to as VDCC III) are provided.

In particular, DNA encoding an $\alpha_{1D}$ subunit that includes the amino acids substantially as set forth as residues 10–2161 of sequence ID No. 1 is provided. DNA encoding an $\alpha_{1D}$ subunit that includes substantially the amino acids set forth as sequence ID No. 23 is also provided. DNA encoding an $\alpha_{1C}$ subunit that includes the amino acids substantially as set forth in sequence ID No. 3 or sequence ID No. 6 and DNA encoding an $\alpha_{1B}$ subunit that includes an amino acid sequence substantially as set forth in sequence ID No. 8 or in sequence ID No. 9 is also provided.

DNA encoding $\alpha_2$ subunits of a human calcium channel, and RNA, encoding such subunits, made upon transcription of such a DNA are provided. DNA encoding splice variants of the $\alpha_2$ subunit, including tissue specific splice variants are also provided. In particular, DNA encoding the $\alpha_{2a}$–$\alpha_{2c}$ subunit subtypes is provided. In particularly preferred embodiments, the DNA encoding the $\alpha_2$ subunit is produced by alternative processing of a primary transcript that includes DNA encoding the amino acids set forth in sequence ID Sequence ID No. 20.

Isolated and purified DNA fragments encoding human calcium channel $\beta$ subunits, including DNA encoding $\beta$ subunit splice variants are provided. In particular, DNA encoding the subunit splice variants $\beta_1$–$\beta_5$ is provided. RNA, encoding $\beta$ subunits, made upon transcription of the DNA is also provided.

In particular, DNA encoding a $\beta$ subunit that is produced by alternative processing of a primary transcript that includes DNA encoding the amino acids set forth in sequence ID No. 19, is provided. DNA encoding a $\beta$ subunit that is encoded by a transcript that lacks one or more of the following sequences of nucleotides: nucleotides 14–34 of Sequence ID No. 12, nucleotides 13–34 of Sequence ID No. 12, nucleotides 35–55 of Sequence ID No. 12, nucleotides 56–190 of Sequence ID No. 12 or nucleotides 191–271 of Sequence ID No. 12 is also provided.

DNA encoding $\gamma$ subunits of human calcium channels is also provided. RNA, encoding $\gamma$ subunits, made upon transcription of the DNA are also provided. In particular, DNA containing the sequence of nucleotides set forth in Sequence ID No. 14 is provided.

Full-length DNA clones and corresponding RNA transcripts, encoding the $\alpha_{1D}$, $\alpha_{1B}$, $\alpha_2$ and $\beta$ subunits of human calcium channels are provided. Also provided are DNA clones encoding substantial and significant portions of $\alpha_{1C}$ and $\gamma$ subunits of voltage-dependent human calcium channels for the preparation of full-length DNA clones encoding $\alpha_{1C}$ and $\gamma$ subunits.

Nucleic acid probes containing at least about 14 contiguous nucleotides of an $\alpha_{1D}$, $\alpha_{1C}$, $\alpha_{1B}$, $\alpha_2$, $\beta$ or $\gamma$ subunit DNA are provided. Methods using the probes for the isolation and cloning of calcium channel subunit-encoding cDNA, including splice variants within tissues and inter-tissue variants are also provided.

In other embodiments, purified human calcium channel subunits and purified human calcium channels are provided. The subunits and receptors can be isolated from a eukaryotic cell transfected with DNA that encodes the subunit.

In another embodiment, immunoglobulins or antibodies obtained from the serum of an animal immunized with a substantially pure preparation of a human calcium channel, human calcium channel subunit or epitope-containing fragment of a human calcium subunit are provided. Monoclonal antibodies produced using a human calcium channel, human calcium channel subunit or epitope-containing fragment thereof as an immunogen are also provided. *Escherichia coli* fusion proteins including a fragment of a human calcium channel subunit may also be used as immunogen. Such fusion proteins may contain a bacterial protein or portion thereof, such as the *E. coli* TrpE protein, fused to a calcium channel subunit peptide. The immunoglobulins that are produced using the calcium channel subunits or purified calcium channels as immunogens have, among other properties, the ability to specifically and preferentially bind to and/or cause the immunoprecipitation of a human calcium channel or a subunit thereof which may be present in a biological sample or a solution derived from such a biological sample.

A diagnostic method for determining the presence of Lambert Eaton Syndrome (LES) in a human, based on immunological reactivity of LES immunoglobulin G (IgG) with a human calcium channel subunit or a eukaryotic cell which expresses a recombinant human calcium channel subunit is also provided. In particular, an immunoassay method for diagnosing Lambert-Eaton Syndrome in a person by combining serum from the person (test serum) with $\alpha_1$ subunit of a human calcium channel and $\alpha_2$ subunit of a human calcium channel and ascertaining whether antibodies in the test serum react with one or both of the subunits, or a recombinant cell which expresses one or both of the subunits to a greater extent than antibodies in control serum (e.g., from a person or group of persons known to be free of the Syndrome) is provided. Any immunoassay procedure known in the art for detecting antibodies against a given antigen in serum can be employed in the method.

DETAILED DESCRIPTION OF THE INVENTION

Figure 1:
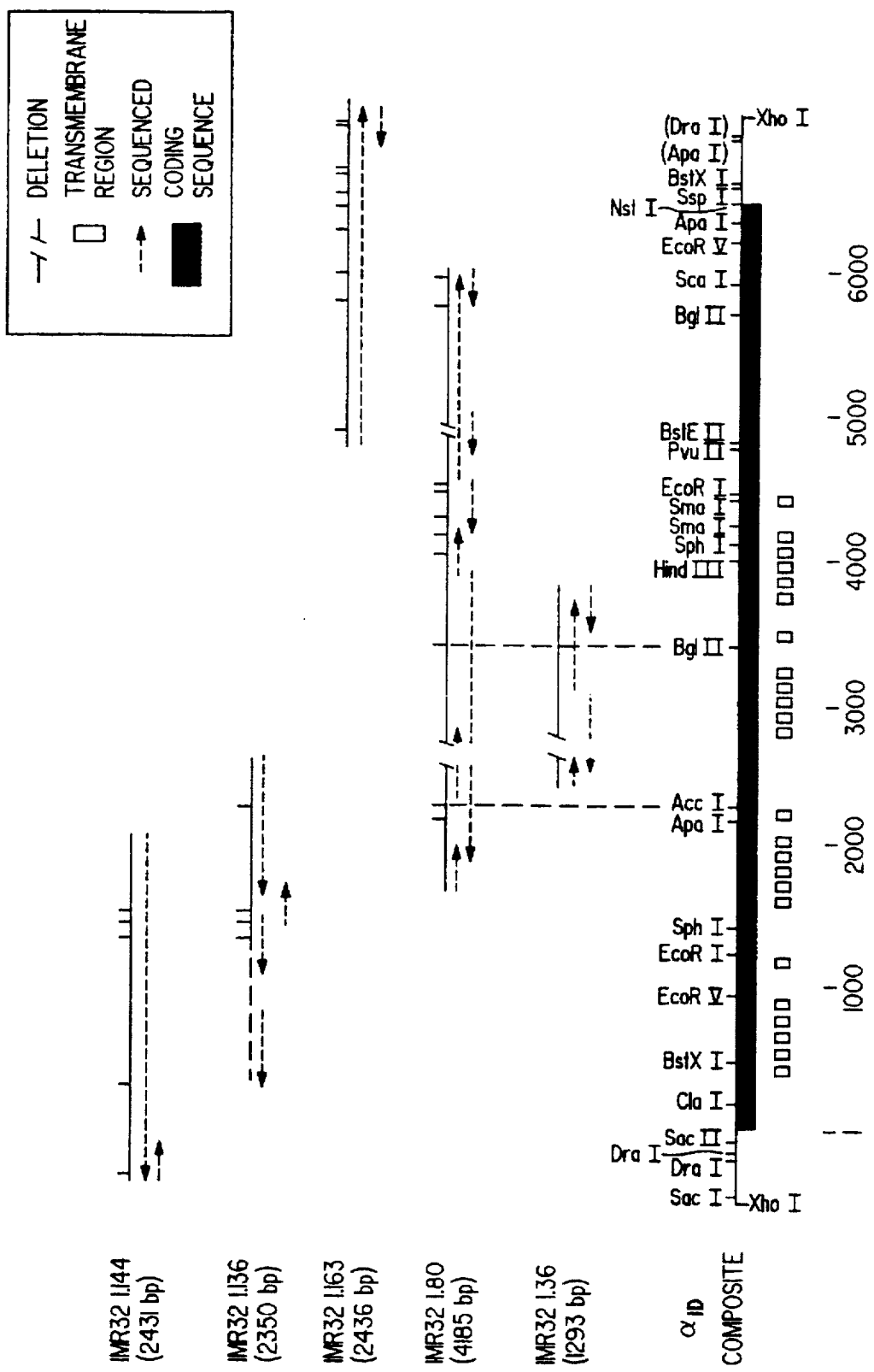
FIG. 1 represents a restriction map of a nucleic acid sequence encoding a human neuronal calcium channel $\alpha_{1D}$ subunit and the sequencing strategy used to derive the complete coding sequence from various partial cDNA clones.

Definitions:

Unless defined otherwise, all technical and scientific terms used herein have the same meaning as is commonly understood by one of skill in the art to which this invention belongs. All patents and publications referred to herein are incorporated by reference herein.

As used herein, the $\alpha_1$ subunit types are designated as type $\alpha_{1B}$, $\alpha_{1C}$, and $\alpha_{1D}$. These subtypes may also be also referred to as VDCC IV, VDCC II and VDCC III, respectively.

Subunit subtypes, which are splice variants, are referred to, for example as $\alpha_{1B-1}$, $\alpha_{1B-2}$. Subtypes of the β subunit that arise as splice variants are designated with a numerical subscript, such as $\beta_1$. Subtypes of the $\alpha_2$ subunit that arise as splice variants are designated by lower case letter, such as $\alpha_a$, . . . $\alpha_{2c}$.

As used herein, a splice variant refers to a variant produced by differential processing of a primary transcript of genomic DNA that results in more than one type of mRNA. Splice variants may occur within a single tissue type or among tissues (tissue-specific variants). Thus, cDNA clones that encode calcium channel subunit subtypes that have different amino acid sequences are referred to herein as "splice variants".

As used herein, a "calcium channel selective ion" is an ion that is capable of flowing through, or being blocked from flowing through, a calcium channel which spans a cellular membrane under conditions which would substantially similarly permit or block the flow of $Ca^{2+}$.

$Ba^{2+}$ is an example of an ion which is a calcium channel selective ion.

As used herein, a compound that modulates calcium channel activity is one that affects the ability of the calcium channel to pass calcium channel selective ions. Such compounds include calcium channel antagonists and agonists and compounds that exert their effect on the activity of the calcium channel directly or indirectly.

As used herein, a "substantially pure" subunit or protein is a subunit or protein that is sufficiently free of other polypeptide contaminants to appear homogeneous by SDS-PAGE or to be unambiguously sequenced.

As used herein, heterologous or foreign DNA and RNA are used interchangeably and refer to DNA or RNA that does not occur naturally as part of the genome in which it is present or which is found in a location or locations in the genome that differ from that in which it occurs in nature. It is DNA or RNA that is not endogenous to the cell and has been artificially introduced into the cell. Examples of heterologous DNA include, but are not limited to, DNA that encodes a calcium channel subunit and DNA that encodes RNA or proteins that mediate or alter expression of endogenous DNA by affecting transcription, translation, or other regulatable biochemical processes. The cell that expresses the heterologous DNA, such as DNA encoding the calcium channel subunit, may contain DNA encoding the same or different calcium channel subunits. The heterologous DNA need not be expressed and may be introduced in a manner such that it is integrated into the host cell genome or is maintained episomally.

As used herein, operative linkage of heterologous DNA to regulatory and effector sequences of nucleotides, such as promoters, enhancers, transcriptional and translational stop sites, and other signal sequences, refers to the functional relationship between such DNA and such sequences of nucleotides. For example, operative linkage of heterologous DNA to a promoter refers to the physical and functional relationship between the DNA and the promoter such that the transcription of such DNA is initiated from the promoter by an RNA polymerase that specifically recognizes, binds to and transcribes the DNA in reading frame.

As used herein, isolated, substantially pure DNA refers to DNA fragments purified according to standard techniques employed by those skilled in the art [see, e.g., Maniatis et al. (1982) *Molecular Cloning: A Laboratory Manual*, Cold Spring Harbor Laboratory Press, Cold Spring Harbor, N.Y.].

As used herein, expression refers to the process by which nucleic acid is transcribed into mRNA and translated into peptides, polypeptides, or proteins. If the nucleic acid is derived from genomic DNA, expression may, if an appropriate eukaryotic host cell or organism is selected, include splicing of the mRNA.

As used herein, vector or plasmid refers to discrete elements that are used to introduce heterologous DNA into cells for either expression of the heterologous DNA or for replication of the cloned heterologous DNA. Selection and use of such vectors and plasmids are well within the level of skill of the art.

As used herein, expression vector includes vectors capable of expressing DNA fragments that are in operative linkage with regulatory sequences, such as promoter regions, that are capable of effecting expression of such DNA fragments. Thus, an expression vector refers to a recombinant DNA or RNA construct, such as a plasmid, a phage, recombinant virus or other vector that, upon introduction into an appropriate host cell, results in expression of the cloned DNA. Appropriate expression vectors are well known to those of skill in the art and include those that are replicable in eukaryotic cells and/or prokaryotic cells and those that remain episomal or may integrate into the host cell genome.

As used herein, a promoter region refers to the portion of DNA of a gene that controls transcription of DNA to which it is operatively linked. The promoter region includes specific sequences of DNA that are sufficient for RNA polymerase recognition, binding and transcription initiation. This portion of the promoter region is referred to as the promoter. In addition, the promoter region includes sequences that modulate this recognition, binding and transcription initiation activity of the RNA polymerase. These sequences may be cis acting or may be responsive to trans acting factors. Promoters, depending upon the nature of the regulation, may be constitutive or regulated.

As used herein, a recombinant eukaryotic cell is a eukaryotic cell that contains heterologous DNA or RNA.

As used herein, a recombinant or heterologous calcium channel refers to a calcium channel that contains one or more subunits that are encoded by heterologous DNA that has been introduced into and expressed in a eukaryotic cells that expresses the recombinant calcium channel. A recombinant calcium channel may also include subunits that are produced by DNA endogenous to the cell. In certain embodiments, the recombinant or heterologous calcium channel may contain only subunits that are encoded by heterologous DNA.

As used herein, "functional" with respect to a recombinant or heterologous calcium channel means that the channel is able to provide for and regulate entry of calcium channel selective ions (e.g., $Ca^{2+}$ or $Ba^{2+}$) in response to a stimulus and/or bind ligands with affinity for the channel, and that such calcium channel activity is distinguishable (e.g., electrophysiologically, pharmacologically, etc.) from any identified endogenous calcium channel activity that might be present in the host cell.

As used herein, a peptide having an amino acid sequence substantially as set forth in a particular Sequence ID No. includes peptides that have the same function but may include minor variations in sequence, such as conservative amino acid changes or minor deletions or insertions that do not alter the activity of the peptide. The activity of a calcium channel receptor subunit peptide refers to its ability to form functional calcium channels with other such subunits.

As used herein, a physiological concentration of a compound is that which is necessary and sufficient for a biological process to occur. For example, a physiological concentration of a calcium channel selective ion is a concentration of the calcium channel selective ion necessary and sufficient to provide an inward current when the channels open.

As used herein, activity of a calcium channel refers to the movement of a calcium selective ion through a calcium channel. Such activity may be measured as the amount of current which flows through the recombinant channel in response to a stimulus.

As used herein, a "functional assay" refers to an assay that identifies functional calcium channels. A functional assay, thus, is an assay to assess function.

As understood by those skilled in the art, assay methods for identifying compounds, such as antagonists and agonists, that modulate calcium channel activity, generally requires comparison to a control. One type of a "control" cell or "control" culture is a cell or culture that is treated substantially the same as the cell or culture exposed to the test compound except that the control culture is not exposed to the test compound. Another type of a "control" cell or "control" culture may be a cell or a culture of cells which are identical to the transfected cells except the cells employed for the control culture do not express functional calcium channels. In this situation, the response of the test cell to the test compound compared to the response (or lack of response) of the receptor-negative cell to the test compound, when cells or cultures of each type of cell are exposed to substantially the same reaction conditions in the presence of the compound being assayed. For example, in methods that use patch clamp electrophysiological procedures, the same cell can be tested in the presence and absence of the test compound, by changing the external solution bathing the cell as known in the art.

Assays for identifying compounds that modulate calcium channel activity and assays for diagnosing Lambert-Eaton Syndrome.

Assays for identifying compounds that modulate calcium channel activity

In vitro methods for identifying compounds, such as calcium channel agonist and antagonists, that modulate the activity of calcium channels using eukaryotic cells that express heterologous human calcium channels are provided.

In particular, the assays use eukaryotic cells that express heterologous human calcium channel subunits encoded by heterologous DNA provided herein, for screening potential calcium channel agonists and antagonists which are specific for human calcium channels and particularly for screening for compounds that are specific for particular human calcium channel subtypes. Such assays may be used in conjunction with methods of rational drug design to select among agonists and antagonists, which differ slightly in structure, those particularly useful for modulating the activity of human calcium channels, and to design or select compounds that exhibit tissue specific calcium channel antagonist and agonist activities.

These assays should accurately predict the relative therapeutic efficacy of a compound for the treatment of certain disorders in humans. In addition, since tissue specific calcium channel subunits are provided, cells with tissue specific recombinant calcium channels may be prepared and used in assays for identification of human calcium channel subtype-specific drugs.

The assays involve contacting the cell membrane of a recombinant eukaryotic cell which expresses at least one subunit of a human calcium channel, preferably at least an $\alpha_1$ subunit of a human calcium channel, with a test compound and measuring the ability of the test compound to specifically bind to the membrane or alter or modulate the activity of a heterologous calcium channel on the membrane.

In preferred embodiments, the assay uses a recombinant cell which has a calcium channel containing an $\alpha_1$ subunit of a human calcium channel in combination with a $\beta$-subunit of a human calcium channel and/or an $\alpha_2$ subunit of a human calcium channel. Recombinant cell expressing heterologous calcium channels containing each of the $\alpha_1$, $\beta$ and $\alpha_2$ human subunits. and. optionally. a γ subunit of a human calcium channel are especially preferred for use in such assays.

In certain embodiments. the assays for identifying compounds that modulate calcium channel activity are practiced by measuring the calcium channel activity of a eukaryotic cell having a heterologous. functional calcium channel when such cell is exposed to a solution containing the compound being and a calcium channel selective ion and comparing the measured calcium channel activity to the calcium channel activity of the same cell or a substantially identical control cell in a solution not containing the test compound. The cell is maintained in a solution having a concentration of calcium channel selective ions sufficient to provide an inward current when the channels open. Especially preferred for use. is a recombinant cell expressing calcium channels that include each of the $\alpha_1$. β and $\alpha_2$ human subunits. and. optionally. a γ subunit of a human calcium channel. Methods for practicing such assays are known to those of skill in the art. For example. for similar methods applied with *Xenopus laevis* oocytes and acetylcholine receptors. see e.g.. Mishina et al. [(1985) *Nature* 313:364) and. with such oocytes and sodium channels see. e.g.. Noda et al. |(1986) *Nature* 322:826–828]. For similar studies which have been carried out with the acetylcholine receptor. see. e.g.. Claudio et al. [(1987) *Science* 238:1688–1694].

The assays provided herein. thus use cells. provided herein. that express heterologous functional calcium channels and measure functionally. such as electrophysiologically. the ability of a test compound to potentiate. antagonize or otherwise modulate the magnitude and duration of the flow of calcium channel selective ions. such as $Ca^{++}$ or $Ba^{++}$. through the heterologous functional channel. The amount of current which flows through the recombinant calcium channels of a cell may be determined directly. such as electrophysiologically. or by monitoring an independent reaction which occurs intracellularly and which is directly influenced in a calcium (or other) ion dependent manner.

Any method for assessing the activity of a calcium channel may be used in conjunction with the cells and assays provided herein. For example. in one embodiment of the method for testing a compound for its ability to modulate calcium channel activity. the amount of current is measured by its modulation of a reaction which is sensitive to calcium channel selective ions and uses a eukaryotic cell which expresses a heterologous calcium channel and also contains a transcriptional control element operatively linked for expression to a structural gene that encodes an indicator protein. The transcriptional control element used for transcription of the indicator gene is responsive in the cell to a calcium channel selective ion. such as $Ca^{2+}$ and $Ba^+$. The details of such transcriptional based assays are described in commonly owned PCT International patent application Ser. No. PCT/US91/5625. filed Aug. 7. 1991. which claims priority to copending commonly owned U.S. application Ser. No. 07/563,751. filed Aug. 7. 1990. the contents of which applications are herein incorporated by reference thereto.

Assays for diagnosis of LES

LES is an autoimmune disease characterized by an insufficient release of acetylcholine from motor nerve terminals which normally are responsive to nerve impulses. Immunoglobulins (IgG) from LES patients block individual voltage-dependent calcium channels and thus inhibit calcium channel activity [Kim and Neher. *Science* 239:405–408 (1988)]. A diagnostic assay for Lambert Eaton Syndrome (LES) is provided herein. The diagnostic assay for LES relies on the immunological reactivity of LES IgG with the human calcium channel $\alpha_1$ subunit alone or in combination with human calcium β subunit. For example. such an assay may be based on immunoprecipitation of LES IgG by the human calcium channel subunits provided herein.

Identification and isolation of DNA encoding human calcium channel subunits

Methods for identifying and isolating DNA encoding $\alpha_1$. $\alpha_2$. β and γ subunits of human calcium channels are provided.

Identification and isolation of such DNA may be accomplished by hybridizing. under appropriate conditions. generally high stringency. restriction enzyme-digested human DNA with a labeled probe having at least 14 nucleotides and derived from any contiguous portion of DNA having a sequence of nucleotides set forth herein by sequence identification number. Once a hybridizing fragment is identified in the hybridization reaction. it can be cloned employing standard cloning techniques known to those of skill in the art. This method can be used to identify genomic DNA encoding the subunit or cDNA encoding splice variants of human calcium channel subunits generated by alternative splicing of the primary transcript of genomic subunit DNA. For instance. DNA. cDNA or genomic DNA. encoding a calcium channel subunit may be identified by hybridization to a DNA probe and characterized by methods known to those of skill in the art. such as restriction mapping and DNA sequencing. and compared to the DNA provided herein in order to identify heterogeneity or divergence in the sequences the DNA. Such sequence differences may indicate that the transcripts from which the cDNA was produced result from alternative splicing of a primary transcript.

Oligonucleotides corresponding to regions of sequence differences have been used to isolate. by hybridization. DNA encoding the full-length splice variant and can be used to isolate genomic clones. A probe. based on a nucleotide sequence disclosed herein. which encodes at least a portion of a subunit of a human calcium channel. such as a tissue-specific exon. may be used as a probe to clone related DNA. to clone a full-length cDNA clone or genomic clone encoding the human calcium channel subunit.

Labeled (e.g.. radioactively or enzymatically labeled) RNA or single-stranded DNA of at least 14 substantially contiguous bases. preferably at least 30 contiguous bases of a nucleic acid which encodes at least a portion of a human calcium channel subunit. the sequence of which nucleic acid corresponds to a segment of a nucleic acid sequence disclosed herein by reference to a Sequence ID No. are provided. Such nucleic acid segments may be used as probes in the methods provided herein for cloning DNA encoding calcium channel subunits. See. generally. Sambrook et al. (1989) *Molecular Cloning: A Laboratory Manual*. 2nd Edition. Cold Spring Harbor Laboratory Press.

In addition. nucleic acid amplification techniques. which are well known in the art. can be used to locate splice variants of calcium channel subunits by employing oligonucleotides based on DNA sequences surrounding the divergent sequence primers for amplifying human RNA or genomic DNA. Size and sequence determinations of the amplification products can reveal splice variants. Furthermore. isolation of human genomic DNA sequences by hybridization can yield DNA containing multiple exons. separated by introns. that correspond to different splice variants of transcripts encoding human calcium channel subunits.

DNA encoding types and subtypes of each of the $\alpha_1$. $\alpha_2$. β and γ subunit of voltage-dependent human calcium channels has been cloned herein by screening human cDNA libraries prepared from isolated poly A$^+$ mRNA from cell lines or tissue of human origin having such calcium channels. Among the sources of such cells or tissue for obtaining mRNA are human brain tissue or a human cell line of neural origin, such as a neuroblastoma cell line, human skeletal muscle or smooth muscle cells, and the like. Methods of preparing cDNA libraries are well known in the art [see generally Ausubel et al. (1987) *Current Protocols in Molecular Biology*, Wiley-Interscience, New York; and Davis et al. (1986) *Basic Methods in Molecular Biology*, Elsevier Science Publishing Co., New York].

With respect to each of the respective subunits of a human calcium channel ($\alpha_1$, $\alpha_2$, $\beta$ or $\gamma$), once the DNA encoding the channel subunit was identified by a nucleic acid screening method, the isolated clone was used for further screening to identify overlapping clones. Some of the cloned DNA fragments can and have been subcloned into an appropriate vector such as pIBI24/25 (IBI, New Haven, Conn.), M13mp18/19, pGEM4, pGEM3, pGEM7Z, pSP72 and other such vectors known to those of skill in this art, and characterized by DNA sequencing and restriction enzyme mapping. A sequential series of overlapping clones may thus be generated for each of the subunits until a full-length clone can be prepared by methods, known to those of skill in the art, that include identification of translation initiation (start) and translation termination (stop) codons. For expression of the cloned DNA, the 5' noncoding region and other transcriptional and translational control regions of such a clone may be replaced with an efficient ribosome binding site and other regulatory regions as known in the art. Examples II–VI, below, describe in detail the cloning of each of the various subunits of a human calcium channel as well as subtypes and splice variants, including tissue-specific variants thereof. In the instances in which partial sequences of a subunit are disclosed, it is well within the skill of the art, in view of the teaching herein, to obtain the corresponding full-length nucleotide sequence encoding the subunit, subtype or splice variant thereof.

Identification and isolation of DNA encoding $\alpha_1$ subunits

At least three voltage-dependent calcium channel $\alpha_1$ subunit genes, which are expressed in the human central nervous system, have been identified and have been designated as $\alpha_{1B}$ (or VDCC IV), $\alpha_{1C}$ (or VDCC II) and $\alpha_{1D}$ (or VDCC III). DNA, isolated from a human neuronal cDNA library, that encodes each of the three VDCC subunit types has been isolated. DNA encoding subtypes of each of the types, which arise as splice variants are also provided. Subtypes are herein designated, for example, as $\alpha_{1B-1}$, $\alpha_{1B-2}$.

The $\alpha_1$ subunits types B, C, and D of voltage-dependent calcium channels, and subtypes thereof, differ with respect to sensitivity to known classes of calcium channel agonists and antagonists, such as dihydropyridines (DHPs), phenylalkylamines, omega conotoxin ($\omega$-CgTx) and pyrazonoylguanidines.

DNA that encodes an $\alpha_1$-subunit that binds to at least one compound selected from among dihydropyridines, phenylalkylamines, $\omega$-CgTx and pyrazonoylguanidines is provided. For example, the $\alpha_{1B}$ subunit provided herein appears to specifically interact with $\omega$-CgTx in N-type channels, and the $\alpha_{1D}$ subunit provided herein specifically interacts with DHPs in L-type channels.

Identification and isolation of DNA encoding the $\alpha_{1D}$ human calcium channel subunit The $\alpha_{1D}$ subunit cDNA has been isolated using fragments of the rabbit skeletal muscle calcium channel $\alpha_1$ subunit cDNA as a probe to screen a cDNA library of a human neuroblastoma cell line, IMR32, to obtain clone $\alpha$1.36. This clone was used as a probe to screen additional IMR32 cell cDNA libraries to obtain overlapping clones, which were then employed for screening until a sufficient series of clones to span the length of the nucleotide sequence encoding the human $\alpha_{D1}$ subunit were obtained. Full-length clones encoding $\alpha_{1D}$ were constructed by ligating portions of partial $\alpha_{1D}$ clones as described in Example II. The various cDNA clones from which the coding sequence for the $\alpha_{1D}$ subunit was derived are set forth in FIG. 1. In the Figure, the heavy line represents the $\alpha_{1D}$ coding sequence. Overlapping clones from which the complete sequence was derived are shown above the composite restriction map. Sequence ID No. 1 shows the 7,635 nucleotide sequence of the cDNA encoding the $\alpha_{1D}$ subunit. There is a 6,483 nucleotide sequence reading frame which encodes a sequence of 2,161 amino acids (as set forth in Sequence ID No. 1).

Sequence ID No. 2 provides the sequence of an alternative exon encoding the IS6 transmembrane domain [see Tanabe, T., et al. (1987) *Nature* 328:313–318 for a description of transmembrane domain terminology] of the $\alpha_{1D}$ subunit.

Sequence ID No. 1 also shows the 2,161 amino acid sequence deduced from the human neuronal calcium channel $\alpha_{1D}$ subunit DNA. Based on the amino acid sequence, the $\alpha_{1D}$ protein has a calculated Mr of 245,163. The amino acid sequence determined and reported here is about 70% identical to that described by Tanabe et al. (1987) *Nature* 328:313–318). The $\alpha_{1D}$ subunit of the calcium channel contains four putative internal repeated sequence regions. Four internally repeated regions represent 24 putative transmembrane segments, and the amino- and carboxyl-termini extend intracellularly.The sequence of another $\alpha_{1D}$ splice variant is set forth in Sequence ID No. 23 (see, e.g.; Example II A.2. d).

The $\alpha_{1D}$ subunit has been shown to mediate DHP-sensitive, high-voltage-activated, long-lasting calcium channel activity. This calcium channel activity was detected when oocytes were co-injected with RNA transcripts encoding an $\alpha_{1D}$ and $\beta$ or $\alpha_{1D}$, $\alpha_2$ and $\beta$ subunits. This activity was distinguished from Ba$^{2+}$ currents detected when oocytes were injected with RNA transcripts encoding the $\beta \pm \alpha_2$ subunits. These currents pharmacologically and biophysically resembled Ca$^{2+}$ currents reported for uninjected oocytes.

Identification and isolation of DNA encoding the $\alpha_{1B}$ human calcium channel subunit DNA encoding the $\alpha_{1B}$ subunit was isolated by screening a human basal ganglia cDNA library with fragments of the rabbit skeletal muscle calcium channel $\alpha_1$ subunit-encoding cDNA. A portion of one of the positive clones was used to screen an IMR32 cell cDNA library. Clones that hybridized to the basal ganglia DNA probe were used to further screen an IMR32 cell cDNA library to identify overlapping clones that in turn were used to screen a human hippocampus cDNA library. In this way, a sufficient series of clones to span nearly the entire length of the nucleotide sequence encoding the human $\alpha_{1B}$ subunit was obtained. PCR amplification of specific regions of the IMR32 cell $\alpha_{1B}$ mRNA yielded additional segments of the $\alpha_{1B}$ coding sequence.

A full-length $\alpha_{1B}$ DNA clone was constructed by ligating portions of the partial cDNA clones as described in Example II.C. Sequence ID Nos. 7 and 8 show the nucleotide sequences of DNA clones encoding the $\alpha_{1B}$ subunit as well as the deduced amino acid sequences. The $\alpha_{1B}$ subunit encoded by Sequence ID No. 7 is referred to as the $\alpha_{1B-1}$ subunit to distinguish it from another $\alpha_{1B}$ subunit, $\alpha_{1B-2}$, encoded by the nucleotide sequence shown as Sequence ID No. 8, which is derived from alternative splicing of the $\alpha_{1B}$ subunit transcript.

Additional splice variants of the $\alpha_{1B}$ transcript have been identified by PCR amplification of IMR32 cell mRNA using oligonucleotide primers designed according to nucleotide sequences within the $\alpha_{1B-1}$-encoding DNA. These divergent coding sequences correspond to $\alpha_{1B}$ subunits with variable amino acid sequences in the IS6 transmembrane domain.

Identification and isolation of DNA encoding the $\alpha_{1C}$ human calcium channel subunit Numerous $\alpha_{1C}$-specific DNA clones were isolated. Characterization of the sequence revealed the $\alpha_{1C}$ coding sequence, the $\alpha_{1C}$ initiation of translation sequence, and an alternatively spliced region of $\alpha_{1C}$. Alternatively spliced variants of the $\alpha_{1C}$ subunit have been identified. Sequence ID No. 3 sets forth DNA encoding an $\alpha_{1C}$ subunit. The DNA sequences set forth in Sequence ID No. 4 and No. 5 encode two possible amino terminal ends of the $\alpha_{1C}$ protein. Sequence ID No. 6 encodes an alternative exon for the IV S3 transmembrane domain.

The isolation and identification of DNA clones encoding portions of the $\alpha_{1C}$ subunit is described in detail in Example II.

Identification and isolation DNA encoding the β human calcium channel subunit

To isolate DNA encoding the β subunit, a human hippocampus cDNA library was screened by hybridization to a DNA fragment encoding a rabbit skeletal muscle calcium channel β subunit. A hybridizing clone was selected and was in turn used to isolate overlapping clones until the overlapping clones encompassing DNA encoding the entire the human calcium channel β subunit were isolated and sequenced.

Five alternatively spliced forms of the human calcium channel β subunit have been identified. These forms are designated $\beta_1$, expressed in skeletal muscle, $\beta_2$, expressed in the CNS, $\beta_3$, also expressed in the in the CNS, $\beta_4$, expressed in aorta tissue and HEK 293 cells, and $\beta_5$, expressed in HEK 293 cells. A full-length DNA clone encoding the $\beta_2$ subunit has been constructed. The subunits $\beta_1$, $\beta_2$, $\beta_4$ and $\beta_5$ have been identified by PCR analysis as alternatively spliced forms of the β subunit.

The alternatively spliced variants were identified by comparison of amino acid sequences encoded by the human neuronal and rabbit skeletal muscle calcium channel β subunit-encoding DNA. This comparison revealed a 45-amino acid deletion in the human β subunit compared to the rabbit β subunit. Using DNA from the region as a probe for DNA cloning, as well as PCR analysis and DNA sequencing of this area of sequence divergence, alternatively spliced forms of the human calcium channel β subunit transcript were identified. For example, the sequence of DNA encoding one splice variant $\beta_2$ is set forth in Sequence ID No. 9. Sequence ID No. 10 sets forth the sequence of the $\beta_3$ subunit (nt 1–1851, including 3' untranslated sequence nt 1795–1851), which is another splice variant of the β subunit primary transcript. $\beta_2$ and $\beta_3$ are human neuronal β subunits. DNA distinctive for a portion of a β subunit ($\beta_4$) of a human aortic calcium channel and also human embryonic kidney (HEK) cells is set forth in Sequence ID No. 12 (nt 1–13 and 191–271). The sequence of DNA encoding a portion of a human calcium channel β subunit expressed in skeletal muscle ($\beta_1$) is shown in Sequence ID No. 12, except that nt 14-34 are absent.

Identification and isolation of DNA encoding the β human calcium channel subunit DNA encoding a human neuronal calcium channel $\alpha_2$ subunit was isolated in a manner substantially similar to that used for isolating DNA encoding the $\alpha_1$ subunit, except that a human genomic DNA library was probed under low and high stringency conditions with a fragment of DNA encoding the rabbit skeletal muscle calcium channel $\alpha_2$ subunit. The fragment included nucleotides having a sequence corresponding to the nucleotide sequence between nucleotides 43 and 272 inclusive of rabbit back skeletal muscle calcium channel $\alpha_2$ subunit cDNA as disclosed in PCT International Patent Application Publication No. WO 89/09834, which corresponds to U.S. application Ser. No. 07/620,520, which is a continuation-in-part of U.S. Ser. No. 176,899, filed Apr. 4, 1988, which applications have been incorporated herein by reference.

Example IV describes the isolation of DNA clones encoding $\alpha_2$ subunits of a human calcium channel from a human DNA library using genomic DNA and cDNA clones, identified by hybridization to the genomic DNA, as probes.

Sequence ID No. 11 shows the sequence of DNA encoding an $\alpha_2$ subunit. As described in Example V, PCR analysis of RNA from human skeletal muscle, brain tissue and aorta using oligonucleotide primers specific for a region of the human neuronal $\alpha_2$ subunit cDNA that diverges from the rabbit skeletal muscle calcium channel $\alpha_2$ subunit cDNA identified splice variants of the human calcium channel $\alpha_2$ subunit transcript.

Identification and isolation of DNA encoding the γ human calcium channel subunit DNA encoding a human neuronal calcium channel γ subunit has been isolated as described in detail in Example VI. Sequence ID No. 14 shows the nucleotide sequence at the 3'-end of this DNA which includes a reading frame encoding a sequence of 43 amino acid residues.

Preparation of recombinant eukaryotic cells containing DNA encoding heterologous calcium channel subunits DNA encoding one or more of the calcium channel subunits or a portion of a calcium channel subunit may be introduced into a host cell for expression or replication of the DNA. Such DNA may be introduced using methods described in the hollowing examples or using other procedures well known to those skilled in the art. Incorporation of cloned DNA into a suitable expression vector, transfection of eukaryotic cells with a plasmid vector or a combination of plasmid vectors, each encoding one or more distinct genes or with linear DNA, and selection of transfected cells are also well known in the art [see, e.g., Sambrook et al. (1989) *Molecular Cloning: A Laboratory Manual*, Second Edition, Cold Spring Harbor Laboratory Press].

Cloned full-length DNA encoding any of the subunits of a human calcium channel may be introduced into a plasmid vector for expression in a eukaryotic cell. Such DNA may be genomic DNA or cDNA. Host cells may be transfected with one or a combination of said plasmids, each of which encodes at least one calcium channel subunit. Alternatively, host cells may be transfected with linear DNA using methods well known to those of skill in the art.

While the DNA provided herein may be expressed in any eukaryotic cell, including yeast cells such as *P. pastoris* (see, e.g., Cregg et al. (1987) *Bio/Technology* 5:479], mammalian expression systems for expression of the DNA encoding the human calcium channel subunits provided herein are preferred.

The heterologous DNA may be introduced by any method known to those of skill in the art, such as transfection with a vector encoding the heterologous DNA. Particularly preferred vectors for transfection of mammalian cells are the pSV2dhfr expression vectors, which contain the SV40 early promoter, mouse dhfr gene, SV40 polyadenylation and splice sites and sequences necessary for maintaining the vector in bacteria, cytomegalovirus (CMV) promoter-based vectors such as pCMV or pCDNA1, and MMTV promoter-based vectors. DNA encoding the human calcium channel subunits has been inserted in the vector pCDNA1 at a position immediately following the CMV promoter.

Stably or transiently transfected mammalian cells may be prepared by methods known in the art by transfecting cells with an expression vector having a selectable marker gene such as the gene for thymidine kinase, dihydrofolate reductase, neomycin resistance or the like, and growing the transfected cells under conditions selective for cells expressing the marker gene. Functional voltage-dependent calcium channels have been produced in HEK 293 cells transfected a derivative of the vector pCDNA1 that contains DNA encoding a human calcium channel subunit.

The heterologous DNA may be maintained in the cell as an episomal element or may be integrated into chromosomal DNA of the cell. The resulting recombinant cells may then be cultured or subcultured (or passaged, in the case of mammalian cells) from such a culture or a subculture thereof. Methods for tranfection, injection and culturing recombinant cells are known to the skilled artisan. Eukaryotic cells in which DNA or RNA may be introduced, include any cells that are transfectable by such DNA or RNA or into which such DNA may be injected. Virtually any eukaryotic cell can serve as a vehicle for heterologous DNA. Preferred cells are those that can also express the DNA and RNA and most preferred cells are those that can form recombinant or heterologous calcium channels that include one or more subunits encoded by the heterologous DNA. Such cells may be identified empirically or selected from among those known to be readily transfected or injected. Preferred cells for introducing DNA include those that can be transiently or stably transfected and include, but are not limited to cells of mammalian origin, such as COS cells, mouse L cells, CHO cells, human embryonic kidney cells, African green monkey cells and other such cells known to those of skill in the art, amphibian cells, such as *Xenopus laevis* oocytes, or those of yeast such as *Saccharomyces cerevisiae* or *Pichia pastoris*. Preferred cells for expressing injected RNA transcripts include *Xenopus laevis* oocytes. Cells that are preferred for transfection of DNA are those that readily and efficiently transfected. Such cells are known to those of skill in the art or may be empirically identified. Preferred cells include DG44 cells and HEK 293 cells, particularly HEX 293 cells that have been adapted for growth in suspension and that can be frozen in liquid nitrogen and then thawed and regrown. Such HEK 293 cells are described, for example in U.S. Pat. No. 5,024,939 to Gorman [see, also Stillman et al. (1985) *Mol. Cell.Biol.* 5:2051–2060].

The cells may be used as vehicles for replicating heterologous DNA introduced therein or for expressing the heterologous DNA introduced therein. In certain embodiments, the cells are used as vehicles for expressing the heterologous DNA as a means to produce substantially pure human calcium channel subunits or heterologous calcium channels. Host cells containing the heterologous DNA may be cultured under conditions whereby the calcium channels are expressed. The calcium channel subunits may be purified using protein purification methods known to those of skill in the art. For example, antibodies, such as those provided herein, that specifically bind to one or more of the subunits may be used for affinity purification of the subunit or receptors containing the subunits.

Substantially pure subunits of a human calcium channel $\alpha_1$ subunit of a human calcium channel, an $\alpha_2$ subunit of a human calcium channel, a $\beta$ subunit of a human calcium channel and a $\gamma$ subunit of a human calcium channel are provided. Substantially pure isolated calcium channels that contain at least one of the human calcium channel subunits are also provided.

In other embodiments, a eukaryotic cell that contains heterologous DNA encoding at least one of an $\alpha_1$ subunit of a human calcium channel, an $\alpha_2$ subunit of a human calcium channel, a $\beta$ subunit of a human calcium channel and a $\gamma$ subunit of a human calcium channel are provided. In accordance with one preferred embodiment, the heterologous DNA is expressed in the eukaryotic cell and preferably encodes a human calcium channel $\alpha_1$ subunit.

In particularly preferred aspects, the eukaryotic cell which contains the heterologous DNA expresses it and forms a recombinant functional calcium channel activity. In more preferred aspects, the recombinant calcium channel activity is readily detectable because it is a type that is absent from the untransfected host cell or is of a magnitude not exhibited in the untransfected cell.

Preferred among such cells is a recombinant eukaryotic cell with a functional heterologous calcium channel. The recombinant cell can be produced by introduction of and expression of heterologous DNA or RNA transcripts encoding an $\alpha_1$ subunit of a human calcium channel, more preferably also expressing, a heterologous DNA encoding a $\beta$ subunit of a human calcium channel and/or heterologous DNA encoding an $\alpha_2$ subunit of a human calcium channel. Especially preferred is the expression in such a recombinant cell of each of the $\alpha_1$, $\beta$ and $\alpha_2$ subunits encoded by such heterologous DNA or RNA transcripts, and optionally expression of heterologous DNA or an RNA transcript encoding a $\gamma$ subunit of a human calcium channel.

In certain embodiments, the eukaryotic cell with a heterologous calcium channel is produced by introducing into the cell a first composition, which contains at least one RNA transcript that is translated in the cell into a subunit of a human calcium channel. In preferred embodiments, the subunits that are translated include an $\alpha_1$ subunit of a human calcium channel. More preferably, the composition that is introduced contains an RNA transcript which encodes an $\alpha_1$ subunit of a human calcium channel and also contains (1) an RNA transcript which encodes a $\beta$ subunit of a human calcium channel and/or (2) an RNA transcript which encodes an $\alpha_2$ subunit of a human calcium channel. Especially preferred is the introduction of RNA encoding an $\alpha_1$, a $\beta$ and an $\alpha_2$ human calcium channel subunit, and, optionally, a $\gamma$ subunit of a human calcium channel.

Methods for in vitro transcription of a cloned DNA and injection of the resulting RNA into eukaryotic cells are well known in the art. Transcripts of any of the full-length DNA encoding any of the subunits of a human calcium channel may be injected alone or in combination with other transcripts into eukaryotic cells for expression in the cells. Amphibian oocytes are particularly preferred for expression of in vitro transcripts of the human calcium channel subunit cDNA clones provided herein.

The functional calcium channels may preferably include at least an $\alpha_1$ subunit and a $\beta$ subunit of a human calcium channel. Eukaryotic cells expressing these two subunits and also cells expressing additional subunits, have been prepared by transfection of DNA and by injection RNA transcripts. Such cells have exhibited voltage-dependent calcium channel activity attributable to calcium channels that contain one or more of the heterologous human calcium channel subunits. For example, eukaryotic cells expressing heterologous calcium channels containing an $\alpha_2$ subunit in addition to the $\alpha_1$ subunit and a $\beta$ subunit have been shown to exhibit increased calcium selective ion flow across the cellular membrane in response to depolarization, indicating that the, the $\alpha_2$ subunit may potentiate calcium channel function.

Eukaryotic cells which express heterologous calcium channels containing at least a human $\alpha_1$ subunit, a human $\beta$ subunit and a human $\alpha_2$ subunit are preferred. Eukaryotic cells transformed with a composition containing cDNA or an RNA of transcript that encodes an $\alpha_1$ subunit alone or in combination with a $\beta$ and/or an $\alpha_2$ subunit may be used to produce cells that express functional calcium channels. Since recombinant cells expressing human calcium channels containing all of the of the human subunits encoded by the injected heterologous cDNA or RNA are especially preferred, it is desirable to inject or transfect such host cells with a sufficient concentration of the subunit-encoding nucleic acids to form calcium channels that contain the human subunits encoded by heterologous DNA or RNA. The precise amounts and ratios of DNA or RNA encoding the subunits may be empirically determined and optimized for a particular combination of subunits, cells and assay conditions.

With respect to measurement of the activity of functional heterologous calcium channels, preferably, endogenous ion channel activity and, if desired, heterologous channel activity of channels that do not contain the desired subunits, of a host cell can be inhibited to a significant extent by chemical, such as pharmacological and electrophysiological, means, such as use of differential holding potential, to increase the S/N ratio of the measured heterologous calcium channel activity.

Among the uses for eukaryotic cells which recombinantly express one or more subunits are assays for determining whether a test compound has calcium channel agonist or antagonist activity. Desirably, a host cell for the expression of calcium channel subunits does not produce endogenous calcium channel subunits of the type or in an amount that substantially interferes with the detection of heterologous calcium channel subunits in ligand binding assays or detection of heterologous calcium channel function, such as generation of calcium current, in functional assays.

With respect to ligand binding assays, the host cells preferably should not produce endogenous calcium channels which interact with compounds having, at physiological concentrations (e.g., nanomolar or picomolar amounts), affinity for one or a combination of the heterologous or recombinant calcium channel subunits that contain one or all of the human calcium channel subunits provided herein.

With respect to ligand binding assays for identifying a compound which has affinity for calcium channels, cells are employed which express, preferably, at least a heterologous $\alpha_1$ subunit. Transfected eukaryotic cells which express at least an $\alpha_1$ subunit may be used to determine the ability of a test compound to specifically alter the activity of a calcium channel. Such ligand binding assays may be performed on intact transfected cells or membranes prepared therefrom.

The capacity of a test compound to bind to or otherwise interact with membranes that contain heterologous calcium channels or subunits thereof may be determined by using any appropriate method, such as competitive binding analysis, such as Scatchard plots, in which the binding capacity of such membranes is determined in the presence and absence of one or more concentrations of a compound having known affinity for the calcium channel. Where necessary, the results may be compared to a control experiment designed in accordance with methods known to those of skill in the art. For example, as a negative control, the results may be compared to those of assays of an identically treated membrane preparation from host cells which have not been transfected with one or more subunit-encoding nucleic acids.

Stably or transiently transfected cells or injected cells which express voltage-dependent human calcium channels containing one or more of the subunits of a human calcium channel desirably may be used in assays to identify agents, such as calcium, channel agonists and antagonists, that modulate calcium channel activity. Functionally testing the activity of test compounds, including compounds having unknown activity, for calcium channel agonist or antagonist activity to determine if the test compound potentiates, inhibits or otherwise alters the flow of calcium through a human calcium channel can be accomplished by (a) maintaining a eukaryotic cell which is transfected or injected to express a heterologous functional calcium channel capable of regulating the flow of calcium channel selective ions into the cell in a medium containing calcium channel selective ions (i) in the presence of and (ii) in the absence of a test compound; (b) maintaining the cell under conditions such that the heterologous calcium channels are substantially closed and endogenous calcium channels of the cell are substantially inhibited; (c) depolarizing the membrane of the cell maintained in step (b) to an extent and for an amount of time sufficient to cause (preferably, substantially only) the heterologous calcium channels to become permeable to the calcium channel selective ions; and (d) comparing the amount and duration of current flow into the cell in the presence of the test compound to that of the current flow into the cell, or a substantially similar cell, in the absence of the test compound.

Functional recombinant or heterologous calcium channels may be identified by any method known to those of skill in the art. For example, electrophysiological procedures for measuring the current across an ion-selective membrane of a cell, which are well known, may be used. The amount and duration of the flow of calcium selective ions through heterologous calcium channels of a recombinant cell containing DNA encoding one or more of the subunits provided herein has been measured using electrophysiological recordings using a voltage clamp, such as the whole-cell patch clamp technique. In order to improve the sensitivity of the assays, known methods can be used to eliminate or reduce non-calcium currents and calcium currents resulting from endogenous calcium channels, when measuring calcium currents through recombinant channels. For example, the dihydropyridine Bay K 8644 specifically enhances L-type calcium channel function by increasing the duration of the open state of the channels (see, e.g., Hess, J. B., et al. (1984) *Nature* 311:538–544). Prolonged opening of the channels results in calcium currents of increased magnitude and duration. Tail currents can be observed upon repolarization of the cell membrane after activation of ion channels by a depolarizing voltage command. The opened channels require a finite time to close or "deactivate" upon repolarization, and the current that flows through the channels during this period is referred to as a tail current. Because Bay K 8644 prolongs opening events in calcium channels, it tends to prolong these tail currents and make them more pronounced.

EXAMPLES

The following examples are included for illustrative purposes only and are not intended to limit the scope of the invention.

EXAMPLE I: PREPARATION OF LIBRARIES USED FOR ISOLATION OF DNA ENCODING HUMAN NEU-

RONAL VOLTAGE-DEPENDENT CALCIUM CHANNEL SUBUNITS

A. RNA Isolation

1. IMR32 cells

IMR32 cells were obtained from the American Type Culture Collection (ATCC Accession No. CCL127, Rockville, Md.) and grown in DMEM, 10% fetal bovine serum, 1% penicillin/streptomycin (GIBCO, Grand Island, N.Y.) plus 1.0 mM dibutyryl cAMP (dbcAMP) for ten days. Total RNA was isolated from the cells according to the procedure described by H.C. Birnboim |(1988) *Nucleic Acids Research* 16:1487–1497|. Poly(A⁺) RNA was selected according to standard procedures (see, e.g., Sambrook et al. (1989) *Molecular Cloning, A Laboratory Manual*, Cold Spring Harbor Laboratory Press; pg. 7.26–7.29).

2. Human thalamus tissue

Human thalamus tissue (2.34 g), obtained from the National Neurological Research Bank, Los Angeles, Calif., that had been stored frozen at −70° C. was pulverized using a mortar and pestle in the presence of liquid nitrogen and the cells were lysed in 12 ml of lysis buffer (5M guanidinium isothiocyanate, 50 mM TRIS, pH 7.4, 10 mM EDTA, 5% β-mercaptoethanol). Lysis buffer was added to the lysate to yield a final volume of 17 ml. N-laurylsarcosine and CsCl were added to the mixture to yield final concentrations of 4% and 0.01 g/ml, respectively, in a final volume of 18 ml.

The sample was centrifuged at 9,000 rpm in a Sorvall SS34 rotor for 10 min at room temperature to remove the insoluble material as a pellet. The supernatant was divided into two equal portions and each was layered onto a 2-ml cushion of a solution of 5.7M CsCl, 0.1M EDTA contained in separate centrifuge tubes to yield approximately 9 ml per tube. The samples were centrifuged in an SW41 rotor at 37,000 rpm for 24 h at 20° C.

After centrifugation, each RNA pellet was resuspended in 3 ml ETS (10 mM TRIS, pH 7.4, 10 mM EDTA, 0.2% SDS) and combined into a single tube. The RNA was precipitated with 0.25M NaCl and two volumes of 95% ethanol.

The precipitate was collected by centrifugation and resuspended in 4 ml PK buffer (0.05M TRIS, pH 8.4, 0.14M NaCl, 0.01M EDTA, 1% SDS). Proteinase K was added to the sample to a final concentration of 200 µg/ml. The sample was incubated at 22° C. for 1 h, followed by extraction with an equal volume of phenol:chloroform:isoamylalcohol (50:48:2) two times, followed by one extraction with an equal volume of chloroform: isoamylalcohol (24:1). The RNA was precipitated with ethanol and NaCl. The precipitate was resuspended in 400 µl of ETS buffer. The yield of total RNA was approximately 1.0 mg. Poly A⁺ RNA (30 µg) was isolated from the total RNA according to standard methods as stated in Example I.A.1.

B. Library Construction

Double-stranded cDNA was synthesized according to standard methods (see, e.g., Sambrook et al. (1989) IN: *Molecular Cloning, A Laboratory Manual*, Cold Spring Harbor Laboratory Press, Chapter 8). Each library was prepared in substantially the same manner except for differences in: 1) the oligonucleotide used to prime the first strand cDNA synthesis, 2) the adapters that were attached to the double-stranded cDNA, 3) the method used to remove the free or unused adapters, and 4) the size of the fractionated cDNA ligated into the λ phage vector.

1. IMR32 cDNA library #1

Single-stranded cDNA was synthesized using IMR32 poly(A⁺) RNA (Example I.A.1.) as a template and was primed using oligo (dT)$_{12-18}$ (Collaborative Research Inc., Bedford, Mass.). The single-stranded cDNA was converted to double-stranded cDNA and the yield was approximately 2 µg. EcoI adapters:

5'-AATTCGGTACGTACACTCGAGC-3'=22-mer (SEQ ID No.15)

3'-GCCATGCATGTGAGCTCG-5'=18-mer. (SEQ ID No.16)

also containing SnaBI and XhoI restriction sites were then added to the double-stranded cDNA according to the following procedure.

a. Phosphorylation of 18-mer

The 18-mer was phosphorylated using standard methods (see, e.g., Sambrook et al. (1989) IN: *Molecular Cloning, A Laboratory Manual*, Cold Spring Harbor Laboratory Press, Chapter 8) by combining in a 10 µl total volume the 18 mer (225 pmoles) with [$^{32}$P]γ-ATP (7000 Ci/mmole; 1.0 µl) kinase (2 U) and incubating at 37° C. for 15 minutes. After incubation 1 µL 10 mM ATP and an additional 2 U of kinase were added and incubated at 37° C. for 15 minutes. Kinase was then inactivated by boiling for 10 minutes.

b. Hybridization of 22-mer

The 22-mer was hybridized to the phosphorylated 18-mer by addition of 225 pmoles of the 22-mer (plus water to bring the volume to 15 µl), and incubation at 65° C. for 5 minutes. The reaction was then allowed to slow cool to room temperature.

The adapters were thus present at a concentration of 15 pmoles/µl, and were ready for cDNA-adapter ligation.

C. Ligation of adapters to cDNA

After the EcoRI, SnaBI, XhoI adapters were ligated to the double-stranded cDNA using a standard protocol (see, e.g., Sambrook et al. (1989) IN: *Molecular Cloning, A Laboratory Manual*, Cold Spring Harbor Laboratory Press, Chapter 8), the ligase was inactivated by heating the mixture to 72° C. for 15 minutes. The following reagents were added to the cDNA ligation reaction and heated at 37° C. for 30 minutes:

| cDNA ligation reaction | 20 µl |
| water | 24 µl |
| 10× kinase buffer | 3 µl |
| 10 mH ATP | 1 µl |
| kinase (2 U/µl) | 2 µl |
| | 50 µl |

The reaction was stopped by the addition of 2 µl 0.5M EDTA, followed by one phenol/chloroform extraction and one chloroform extraction.

d. Size Selection and Packaging of cDNA

The double-stranded cDNA with the EcoRI, SnaBI, XhoI adapters ligated was purified away from the free or unligated adapters using a 5 ml Sepharose CL-4B column (Sigma, St. Louis, Mo.). 100 µl fractions were collected and those containing the cDNA, determined by monitoring the radioactivity, were pooled, ethanol precipitated, resuspended in TE buffer and loaded onto a 1% agarose gel. After the electrophoresis, the gel was stained with ethidium bromide and the 1 to 3 kb fraction was cut from the gel. The cDNA embedded in the agarose was eluted using the "Geneluter Electroelution System" (Invitrogen, San Diego, Calif.). The eluted cDNA was collected by ethanol precipitation and resuspended in TE buffer at 0.10 pmol/µl. The cDNA was ligated to 1 µg of EcoRI digested, dephosphorylated λgt11 in a 5 µl reaction volume at a 2- to 4- fold molar excess ratio of cDNA over the λgt11 vector. The ligated λgt11 containing the cDNA insert was packaged into λ phage virions in vitro using the Gigapack (Stratagene, La Jolla, Calif.) kit. The packaged phage were plated on an *E. coli* Y1088 bacterial lawn in preparation for screening.

2. IMR32 cDNA library #2

This library was prepared as described (Example I.B.1.) with the exception that 3 to 9 kb cDNA fragments were ligated into the λgt11 phage vector rather than the 1 to 3 kb fragments.

3. IMR32 cDNA library #3

IMR32 cell poly($A^+$) RNA (Example I.A.1.) was used as a template to synthesize single-stranded cDNA. The primers for the first strand cDNA synthesis were random primers (hexadeoxy-nucleotides |pd(N)$_6$| Cat #5020-1, Clontech, Palo Alto, Calif.). The double-stranded cDNA was synthesized (Example I.B.1.). EcoRI, SnaBI, XhoI adapters were added to the cDNA (Example I.B.1.), the unligated adapters were removed (Example I.B.1.), and the double-stranded cDNA with the ligated adapters was fractionated on an agarose gel (Example I.B.1.). The cDNA fraction greater than 1.8 kb was eluted from the agarose (Example I.B.1.), ligated into λgt11, packaged, and plated into a bacterial lawn of Y1088 (Example I.B.1.).

4. IMR32 cDNA library #4

IMR32 cell poly($A^+$) RNA (Example I.A.1.) was used as a template to synthesize single-stranded cDNA. The primers for the first strand cDNA synthesis were oligonucleotides 89–365a specific for the $\alpha_{1D}$ (VDCC III) type $\alpha_1$-subunit (see Example II.A.) coding sequence (the complementary sequence of nt 2417 to 2446, Sequence ID No. 1), 89–495 specific for the $\alpha_{1C}$ (VDCC II) type $\alpha_1$-subunit (see Example II.B.) coding sequence (the complementary sequence of nt 852 to 873, Sequence ID No. 6), and 90–12 specific for the VDCC II type $\alpha_1$-subunit coding sequence (the complementary sequence of nt 2496 to 2520, Sequence ID No. 6). The cDNA library was then constructed as described (Example I.B.3), except that the cDNA size-fraction greater than 1.5 kb was eluted from the agarose rather than the greater than 1.8 kb fraction.

5. IMR32 cDNA library #5

The cDNA library was constructed as described (Example I.B.3.) with the exception that the size-fraction greater than 1.2 kb was eluted from the agarose rather than the greater than 1.8 kb fraction.

6. Human thalamus cDNA library #6

Human thalamus poly ($A^+$) RNA (Example I.A.2.) was used as a template to synthesize single-stranded cDNA. Oligo (dT) was used to prime the first strand synthesis (Example I.B.1.). The double-stranded cDNA was synthesized (Example I.B.1.) and EcoRI, KpnI, NcoI adapters of the following sequence:

5' CCATGGTACCTTCGTTGACG 3'=20 mer (SEQ. ID NO. 17)

3' GGTACCATGGAAGCAACTGCTTAA 5'=24 mer (SEQ. ID NO. 18)

were ligated to the double-stranded cDNA as described (Example I.B.1.) with the 20-mer replacing the 18-mer and the 24-mer replacing the 22-mer. The unligated adapters were removed by passing the cDNA-adapter mixture through a 1 ml Bio Gel A-50 (Bio-Rad Laboratories, Richmond, Calif.) column. Fractions (30 µl) were collected and 1 µl of each fraction in the first peak of radioactivity was electrophoresed on a 1% agarose gel. After electrophoresis, the gel was dried on a vacuum gel drier and exposed to x-ray film. The fractions containing cDNA fragments greater than 600 bp were pooled, ethanol precipitated, and ligated into λgt11 (Example I.B.1.). The construction of the cDNA library was completed as described (Example I.B.1.).

C. Hybridization and Washing Conditions

Hybridization of radiolabelled nucleic acids to immobilized DNA for the purpose of screening cDNA libraries, DNA Southern transfers, or northern transfers was routinely performed in standard hybridization conditions |5×SSPE, 5× Denhardt's, 50% deionized formamide, 200 µg/ml sonicated herring sperm DNA (Cat #223646, Boehringer Mannheim Biochemicals, Indianapolis, Ind.)|. The recipes for SSPE and Denhardt's and the preparation of deionized formamide are described, for example, in Sambrook et al. (1989) *Molecular Cloning, A Laboratory Manual*, Cold Spring Harbor Laboratory Press, Chapter 8). In some hybridizations, lower stringency conditions were used in that 10% deionized formamide replaced 50% deionized formamide described for the standard hybridization conditions.

The washing conditions for removing the non-specific probe from the filters was either high, medium, or low stringency as described below:

1) high stringency: 0.1×SSPE, 0.1% SDS, 65° C.
2) medium stringency: 0.2×SSPE, 0.1% SDS, 50° C.
3) low stringency: 1.0×SSPE, 0.1% SDS, 50° C.

EXAMPLE II: ISOLATION OF DNA ENCODING THE HUMAN NEURONAL CALCIUM CHANNEL $\alpha_1$ SUBUNIT The isolation and characterization of DNA encoding the three human neuronal VDCC $\alpha_1$ subunit genes are described in detail in this example.

A. Isolation of DNA encoding the $\alpha_{1D}$ subunit

1. Reference list of partial $\alpha_{1D}$ cDNA clones

Numerous $\alpha_{1D}$-specific cDNA clones were isolated in order to characterize the complete $\alpha_1$ D coding sequence plus portions of the 5' and 3' untranslated sequences. Sequence ID No. 1 shows the complete $\alpha_{1D}$ DNA coding sequence, plus 510 nucleotides of $\alpha_{1D}$5' untranslated sequence ending in the guanidine nucleotide adjacent to the adenine nucleotide of the proposed initiation of translation as well as 642 nucleotides of 3' untranslated sequence. Also shown in Sequence ID No. 1 is the deduced amino acid sequence. Shown below is a list of partial cDNA clones used to characterize the $\alpha_{1D}$ sequence and the nucleotide position of each clone relative to the full-length $\alpha_{1D}$ cDNA sequence (i.e., Sequence ID No. 1). Restriction maps of the partial $\alpha_{1D}$ cDNA clones are shown in FIG. 1. The isolation and characterization of these clones are described below (Example II.A.2.).

| IMR32 | 1.144 | nt. 1 to 510 of 5' untranslated sequence, nt. 511 to 2431, | Sequence ID No. 1 Sequence ID No. 1 |
|---|---|---|---|
| IMR32* | 1.136 | nt. 1627 to 2988, nt. 1 to 104 of additional exon, | Sequence ID No. 1 Sequence ID No. 2 |
| IMR32@ | 1.80 | nt. 2083 to 6468, | Sequence ID No. 1 |
| IMR32# | 1.36 | nt. 2857 to 4281, | Sequence ID No. 1 |
| IMR32 | 1.163 | nt. 5470 to 7635, | Sequence ID No. 1 |

*5' of nt 1627, IMR32 1.136 encodes an intron and an additional exon described in Example II.A.2.d.
@IMR32 1.80 contains two deletions, nt 2984 to 3131 and nt 5303 to 5349 (Sequence ID No. 1). The 148 nt deletion (nt. 2984 to 3131) was corrected by performing a polymerase chain reaction described in Example II.A.3.b.
IMR32 1.36 contains a 132 nt deletion (nt. 3081 to 3212)

2. Isolation and characterization of individual clones listed in Example II.A.1.

a. IMR32 1.36

Two million recombinants of the IMR32 cDNA library #1 (Example I.B.1.) were screened in duplicate at a density of approximately 200,000 plaques per 150 mm plate using a mixture of radiolabelled fragments of the coding region of the rabbit skeletal muscle calcium channel $\alpha_1$ cDNA |for the sequence of the rabbit skeletal muscle calcium channel $\alpha_1$ subunit cDNA, see, Tanabe et al. (1987). *Nature* 328:313–318]:

| Fragment | Nucleotides |
| --- | --- |
| KpnI-EcoRI | −78 to 1006 |
| EcoRI-XhoI | 1006 to 2653 |
| ApaI-ApaI | 3093 to 4182 |
| BglII-SacI | 4487 to 5310 |

The hybridization was performed using low stringency hybridization conditions (Example I.C.) and the filters were washed under low stringency (Example I.C.). Only one $\alpha_{1D}$-specific recombinant (IMR32 1.36) of the $2 \times 10^6$ screened was identified. IMR32 1.36 was plaque purified by standard methods (J. Sambrook et al. (1989) *Molecular Cloning, A Laboratory Manual*, Cold Spring Harbor Laboratory Press. Chapter 8) subcloned into pGEM3 (Promega, Madison, Wis.) and characterized by DNA sequencing.

b. IMR32 1.80

Approximately $1 \times 10^6$ recombinants of the IMR32 cDNA library #2 (Example I.B.2.) were screened in duplicate at a density of approximately 100,000 plaques per 150 mm plate using the IMR32 1.36 cDNA fragment (Example II.A.1) as a probe. Standard hybridization conditions were used (Example I.C), and the filters were washed under high stringency (Example I.C.). Three positive plaques were identified one of which was IMR32 1.80. IMR32 1.80 was plaque purified by standard methods, restriction mapped, subcloned, and characterized by DNA sequencing.

c. IMR32 1.144

Approximately $1 \times 10^6$ recombinants of the IMR32 cDNA library #3 (Example I.B.3) were screened with the EcoRI-PvuII fragment (nt 2083 to 2518, Sequence ID No. 1) of IMR32 1.80. The hybridization was performed using standard hybridization conditions (Example I.C.) and the filters were washed under high stringency (Example I.C.). Three positive plaques were identified one of which was IMR32 1.144. IMR32 1.144 was plaque purified, restriction mapped, and the cDNA insert was subcloned into pGEM7Z (Promega, Madison, Wis.) and characterized by DNA sequencing. This characterization revealed that IMR32 1.144 has a series of ATG codons encoding seven possible initiating methionines (nt 511 to 531, Sequence ID No. 1). PCR analysis, and DNA sequencing of cloned PCR products encoding these seven ATG codons confirmed that this sequence is present in the $\alpha_{1D}$ transcript expressed in dbcAMP-induced IMR32 cells.

d. IMR32 1.136

Approximately $1 \times 10^6$ recombinants of the IMR32 cDNA library #4 (Example I.B.4) were screened with the EcoRI-PvuII fragment (nt 2083 to 2518, Sequence ID No. 1) of IMR32 1.80 (Example II.A.1.). The hybridization was performed using standard hybridization conditions (Example I.C.) and the filters were washed under high stringency (Example I.C.). Six positive plaques were identified one of which was IMR32 1.136. IMR32 1.136 was plaque purified, restriction mapped, and the cDNA insert was subcloned into a standard plasmid vector, e.g., pSP72 (Promega, Madison, Wis.), and characterized by DNA sequencing. This characterization revealed that IMR32 1.136 encodes an incompletely spliced $\alpha_{1D}$ transcript. The clone contains nucleotides 1627 to 2988 of Sequence ID No. 1 preceded by an approximate 640 bp intron. This intron is then preceded by a 104 nt exon (Sequence ID No. 2) which is an alternative exon encoding the IS6 transmembrane domain [see, e.g., Tanabe et al. (1987) *Nature* 328:313–318 for a description of the IS1 to IVS6 transmembrane terminology] of the $\alpha_{1D}$ subunit and can replace nt 1627 to 1730, Sequence ID No. 1, to produce a completely spliced $\alpha_{1D}$ transcript Sequence ID No. 23.

e. IMR32 1.163

Approximately $1 \times 10^6$ recombinants of the 1MR32 cDNA library #3 (I.B.3.) were screened with the NcoI-XhoI fragment of IMR32 1.80 (Example II.A.1.) containing nt 5811 to 6468 (Sequence ID No. 1). The hybridization was performed using standard hybridization conditions (Example I.C.) and the filters were washed under high stringency (Example I.C.). Three positive plaques were identified one of which was IMR32 1.163. IMR32 1.163 was plaque purified, restriction mapped, and the cDNA insert was subcloned into a standard plasmid vector, e.g., pSP72 (Promega, Madison, Wis.), and characterized by DNA sequencing. This characterization revealed that IMR32 1.163 contains the $\alpha_{1D}$ termination codon, nt 6994 to 6996 (Sequence ID No. 1).

3. Construction of a full-length $\alpha_{1D}$ cDNA [pVDCCIII(A)]

$\alpha_{1D}$ cDNA clones IMR32 1.144, IMR32 1.136, IMR32 1.80, and IMR32 1.163 (Example II.A.2.) overlap and include the entire $\alpha_{1D}$ coding sequence, nt 511 to 6993 (Sequence ID No. 1), with the exception of a 148 bp deletion, nt 2984 to 3131 (Sequence ID No. 1). Portions of these partial cDNA clones were ligated to generate a full-length $\alpha_{1D}$ cDNA in a eukaryotic expression vector. The resulting vector was called PVDCCIII(A). The construction of pVDCCIII(A) was performed in four steps described in detail below: (1) the construction of pVDCCIII/5' using portions of IMR32 1.144, IMR32 1.136, and IMR32 1.80, (2) the construction of pVDCCIII/5'.3 that corrects the 148 nt deletion in the IMR32 1.80 portion of pVDccIII/5', (3) the construction of pVDCCIII/3'.1 using portions of IMR32 1.80 and IMR32 1.163, and (4) the ligation of a portion of the pVDCCIII/5'.3 insert, the insert of pVDCCIII/3'.1, and pcDNA1 (Invitrogen, San Diego, Calif.) to form pVDCCIII (A). The vector pcDNA1 is a eukaryotic expression vector containing a cytomegalovirus (CMV) promoter which is a constitutive promoter recognized by mammalian host cell RNA polymerase II.

Each of the DNA fragments used in preparing the full-length construct was purified by electrophoresis through an agarose gel onto DE81 filter paper (Whatman, Clifton, N.J.) and elution from the filter paper using 1.0M NaCl, 10 mM TRIS, pH 8.0, 1 mM EDTA. The ligations typically were performed in a 10 μl reaction volume with an equal molar ratio of insert fragment and a two-fold molar excess of the total insert relative to the vector. The amount of DNA used was normally about 50 ng to 100 ng.

a. pVDCCIII/5'

To construct pVDCCIII/5', IMR32 1.144 (Example II.A.2. c.) was digested with XhoI and EcoRI and the fragment containing the vector (pGEM7Z), $\alpha_{1D}$ nt 1 to 510 (Sequence ID No. 1), and $\alpha_{1D}$ nt 511 to 1732 (Sequence ID No. 1) was isolated by gel electrophoresis. The EcoRI-ApaI fragment of IMR32 1.136 (Example II.A.2.d.) nucleotides 1732 to 2667 (Sequence ID No. 1) was isolated, and the ApaI-HindIII fragment of IMR32 1.80 (Example II.A.2.b.), nucleotides 2667 to 4492 (Sequence ID No. 1) was isolated. The three DNA clones were ligated to form pVDCCIII/5' containing nt 1 to 510 (5' untranslated sequence; Sequence ID No. 1) and nt 511 to 4492 (Sequence ID No. 1).

b. pVDCCIII/5'.3

Comparison of the IMR32 1.36 and IMR32 1.80 DNA sequences revealed that these two cDNA clones differ through the $\alpha_{1D}$ coding sequence, nucleotides 2984 to 3212. PCR analysis of IMR32 1.80 and dbcAMP-induced (1.0 mM, 10 days) IMR32 cytoplasmic RNA (isolated according to Ausubel, F.M. et al. (Eds) (1988) *Current Protocols in Molecular Biology*, John Wiley and Sons, New York) revealed that IMR32 1.80 had a 148 nt deletion, nt 2984 to 3131 (Sequence ID No. 1), and that IMR32 1.36 had a 132 nt deletion, nt 3081 to 3212. To perform the PCR analysis, amplification was primed with $\alpha_{1D}$-specific oligonucleotides 112 (nt 2548 to 2572, Sequence ID No. 1) and 311 (the complementary sequence of nt 3928 to 3957, Sequence ID No. 1). These products were then reamplified using $\alpha_{1D}$-specific oligonucleotides 310 (nt 2583 to 2608 Sequence ID No. 1) and 312 (the complementary sequence of nt 3883 to 3909). This reamplified product contains AccI and BglII restriction sites (FIG. 1). The reamplified PCR product was digested with AccI and BglII and the AccI-BglII fragment, nt 2764 to 3890 (Sequence ID No. 1) was cloned into AccI-BglII digested pVDCCIII/5' to replace the AccI-BglII pVDCCIII/5' fragment that had the deletion. This new construct was named pVDCCIII/5'.3. DNA sequence determination of pVDCCIII/5'.3 through the amplified region confirmed the 148 nt deletion in IMR32 1.80.

c. pVDCCIII/3'.1

To construct pVDCCIII/3'.1, the cDNA insert of IMR32 1.163 (Example II.A.2.e.) was subcloned into pBluescript II (Stratagene, La Jolla, Calif.) as an XhoI fragment. The XhoI sites on the cDNA fragment were furnished by the adapters used to construct the cDNA library (I.B.3.). The insert was oriented such that the translational orientation of the insert of IMR32 1.163 was opposite to that of the lacZ gene present in the plasmid, as confirmed by analysis of restriction enzyme digests of the resulting plasmid. This was done to preclude the possibility of expression of $\alpha_{1D}$ sequences in DH5α cells transformed with this plasmid due to fusion with the lacZ gene. This plasmid was then digested with HindIII and BglII and the HindIII-BglII fragment (the HindIII site comes from the vector and the BglII site is at nt 6220, Sequence ID No. 1) was eliminated, thus deleting nt 5200 to 6220 (Sequence ID No. 1) of the IMR32 1.163 clone and removing this sequence from the remainder of the plasmid which contained the 3' BglII-XhoI fragment, nt 6220 to 7635 (Sequence ID No. 1). pVDCCIII/3'.1 was then made by splicing together the HindIII-PvuII fragment from IMR32 1.80 (nucleotides 4492–5294, Sequence ID No. 1), the PvuII-BglII fragment of IMR32 1.163 (nucleotides 5294 to 6220, Sequence ID No. 1) and the HindIII-BglII-digested pBluescript plasmid containing the 3' BglII/XhoI IMR32 1.163 fragment (nt 6220 to 7635, Sequence ID No. 1).

d. pVDCCIII(A): the full-length $\alpha_{1D}$ construct

To construct pVDCCIII(A), the DraI-HindIII fragment (5' untranslated sequence nt 327 to 510, Sequence ID No. 1 and coding sequence nt 511 to 4492, Sequence ID No. 1) of pVDCCIII/5'.3 (Example II.A.3.b.) was isolated; the HindIII-XhoI fragment of pVDCCIII/3'.1 (containing nt 4492 to 7635, Sequence ID No. 1, plus the XhoI site of the adapter) (Example II.A.3.c.) was isolated; and the plasmid vector, pcDNA1, was digested with EcoRV and XhoI and isolated on an agarose gel. These three DNA clones were ligated and MC1061-P3 (Invitrogen, San Diego, Calif.) was transformed. Isolated clones were analyzed by restriction mapping and DNA sequencing and pVDCCIII(A) was identified which had the fragments correctly ligated together: DraI-HindIII, HindIII-XhoI, XhoI-EcoRV with the blunt-end DraI and EcoRV site ligating together to form the circular plasmid.

The amino-terminus of the $\alpha_{1D}$ subunit is encoded by the seven consecutive 5' methionine codons (nt 511 to 531, Sequence ID No. 1). This 5' portion plus nt 532 to 537, encoding two lysine residues, were deleted from pVDCCIII (A) and replaced with an efficient ribosomal binding site (5'-ACCACC-3') to form pVDCCI II. RBS (A). Expression experiments in which transcripts of this construct were injected into *Xenopus laevis* oocytes did not result in an enhancement in the recombinant voltage-dependent calcium channel expression level relative to the level of expression in oocytes injected with transcripts of pVDCCIII(A).

B. Isolation of DNA encoding the $\alpha_{1C}$ subunit

1. Reference List of Partial $\alpha_{1C}$ cDNA clones

Figure 2:
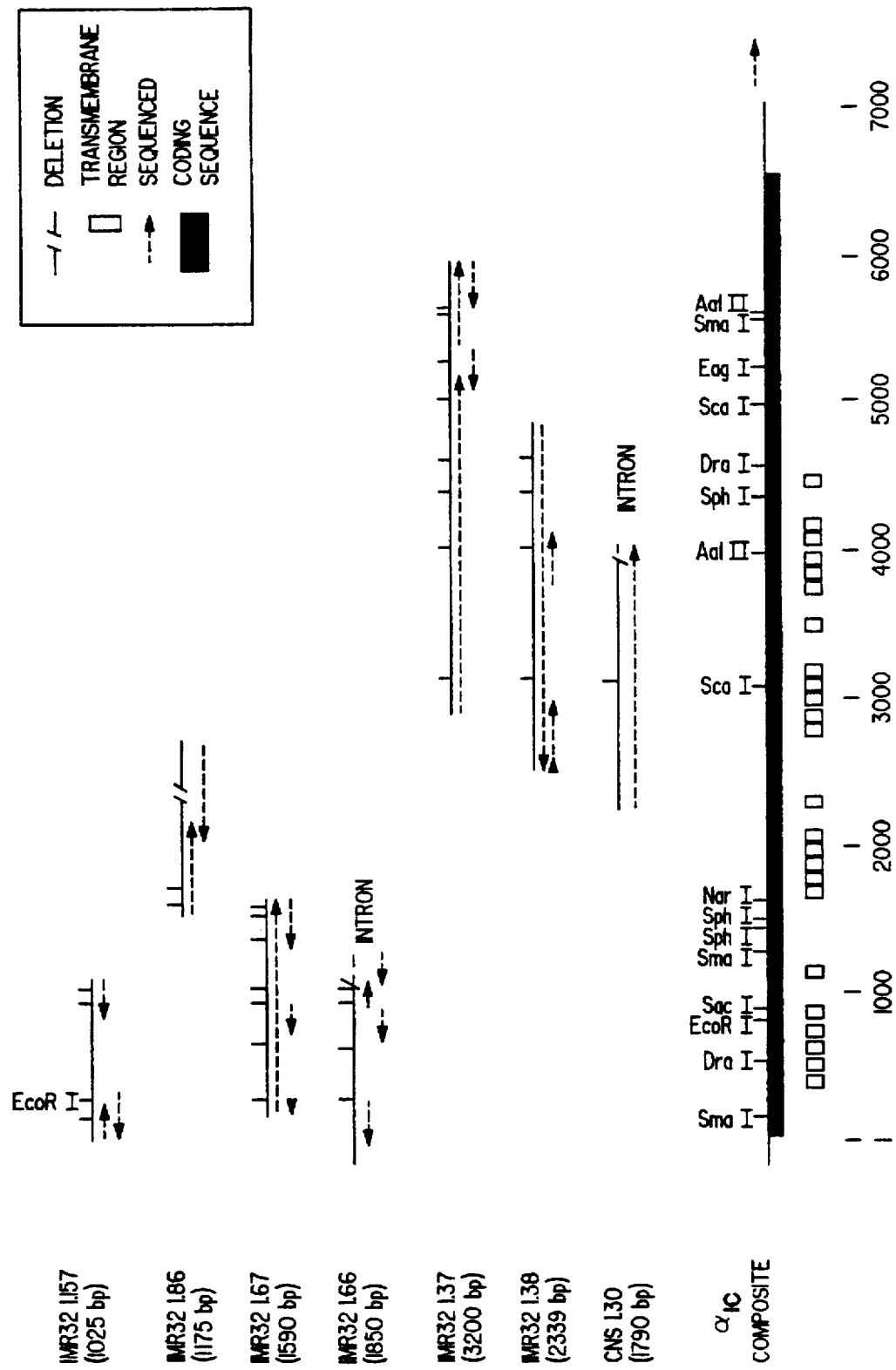
FIG. 2 represents a restriction map of a nucleic acid sequence encoding most of a human neuronal calcium channel $\alpha_{1C}$ subunit and the sequencing strategy used to derive the coding sequence from various cDNA clones.

Numerous $\alpha_{1C}$-specific cDNA clones were isolated in order to characterize the $\alpha_{1C}$ coding sequence, the $\alpha_{1C}$ initiation of translation, and an alternatively spliced region of $\alpha_{1C}$. Sequence ID No. 3 sets forth the characterized $\alpha_{1C}$ coding sequence (nt 1 to 5904) and deduced amino acid sequence. Sequence ID No. 4 and No. 5 encode two possible amino terminal ends of the $\alpha_{1C}$ protein. Sequence ID No. 6 encodes an alternative exon for the IV s3 transmembrane domain. Shown below is a list of clones used to characterize the $\alpha_{1C}$ sequence and the nucleotide position of each clone relative to the characterized $\alpha_{1C}$ sequence (Sequence ID No. 3). Restriction maps of the partial $\alpha_{1C}$ cDNA clones are shown in FIG. 2. The isolation and characterization of these cDNA clones are described below (Example II.B.2).

| IMR32 | 1.66 (sequence ID No. 30) | nt 1 to 916, Sequence ID No. 3 |
|---|---|---|
|  |  | nt 1 to 132, Sequence ID No. 4 |
| IMR32 | 1.157 (sequence ID No. 24) | nt 1 to 873, Sequence ID No. 3 |
|  |  | nt 1 to 89, Sequence ID No. 5 |
| IMR32 | 1.67 |  nt 50 to 1717, Sequence ID No. 3 |
| *IMR32 | 1.86 | nt 1366 to 2583, Sequence ID No. 3 |
| ⊛1.16 G |  | nt 758 to 867, Sequence ID No. 3 |
| IMR32 | 1.37 | nt 2804 to 5904, Sequence ID No. 3 |
| CNS | 1.30 (sequence ID No. 29, nt. 87-1875) | nt 2199 to 3903, Sequence ID No. 3 |
|  |  | nt 1 to 84 of alternative exon, Sequence ID No. 6 |
| IMR32 | 1.38 | nt 2448 to 4702, Sequence ID No. 3 |
|  |  | nt 1 to 84 of alternative exon, Sequence ID No. 6 |

*IMR32 1.86 has a 73 nt deletion compared to the rabbit cardiac muscle calcium channel $\alpha_1$ subunit cDNA sequence.
⊛1.16 G is an $\alpha_{1C}$ genomic clone.

2. Isolation and characterization of clones described Example II.B.1.

a. CNS 1.30

Approximately 1×10⁶ recombinants of the human thalamus cDNA library No. 6 (Example I.B.6.) were screened with fragments of the rabbit skeletal muscle calcium channel $\alpha_1$ cDNA described in Example II.A.2.a. The hybridization was performed using standard hybridization conditions (Example I.C.) and the filters were washed under low stringency (Example I.C.). Six positive plaques were identified, one of which was CNS 1.30. CNS 1.30 was plaque purified, restriction mapped, subcloned, and characterized by DNA sequencing. CNS 1.30 encodes a1c-specific sequence nt 2199 to 3903 (Sequence ID No. 3) followed by nt 1 to 84 of one of two identified alternative $\alpha_{1C}$ exons (Sequence ID No. 6). 3' of Sequence ID No. 6, CNS 1.30 contains an intron and, thus, CNS 1.30 (set forth in Sequence ID No. 29, nt. 87–1875) encodes a partially spliced $\alpha_{1C}$ transcript.

b. 1.16G

Approximately $1\times10^6$ recombinants of a λEMBL3-based human genomic DNA library (Cat # HL1006d Clontech Corp., Palo Alto, Calif.) were screened using a rabbit skeletal muscle cDNA fragment (nt–78 to 1006, Example II.A.2.a.). The hybridization was performed using standard hybridization conditions (Example I.C.) and the filters were washed under low stringency (Example I.C.). Fourteen positive plaques were identified, one of which was 1.16G. Clone 1.16G was plaque purified, restriction mapped, subcloned, and portions were characterized by DNA sequencing. DNA sequencing revealed that 1.16G encodes $\alpha_{1C}$-specific sequence as described in Example II.A.1.

c. IMR32 1.66 and IMR32 1.67

Approximately $1\times10^6$ recombinants of IMR32 cDNA library #5 (Example I.B.5.) were screened with a 151 bp KpnI-SacI fragment of 1.16G (Example II.B.2.b.) encoding $\alpha_{1C}$ sequence (nt 758 to 867, Sequence ID No. 3). The hybridization was performed using standard hybridization conditions (Example I.C.). The filters were then washed in 0.5×SSPE at 65° C. Of the positive plaques, IMR32 1.66 and IMR32 1.67 were identified. The hybridizing plaques were purified, restriction mapped, subcloned, and characterized by DNA sequencing. Two of these cDNA clones, IMR32 1.66 and 1.67, encode $\alpha_{1C}$ subunits as described (Example II.B.1.). In addition, IMR32 1.66 encodes a partially spliced $\alpha_{1C}$ transcript marked by a GT splice donor dinucleotide beginning at the nucleotide 3' of nt 916 (Sequence ID No. 3). The intron sequence within 1.66 is 101 nt long. IMR32 1.66 encodes the $\alpha_{1C}$ initiation of translation, nt 1 to 3 (Sequence ID No. 3) and 132 nt of 5' untranslated sequence (Sequence ID No. 4) precede the start codon in IMR32 1.66 (set forth in Sequence ID No. 30).

d. IMR32 1.37 and IMR32 1.38

Approximately $2\times10^6$ recombinants of IMR32 cDNA library #1 (Example I.B.1.) were screened with the CNS 1.30 cDNA fragment (Example II.B.2.a.). The hybridization was performed using low stringency hybridization conditions (Example I.C.) and the filters were washed under low stringency (Example I.C.). Four positive plaques were identified, plaque purified, restriction mapped, subcloned, and characterized by DNA sequencing. Two of the clones, IMR32 1.37 and IMR32 1.38 encode $\alpha_{1C}$-specific sequences as described in Example II.B.1.

Figure 3:
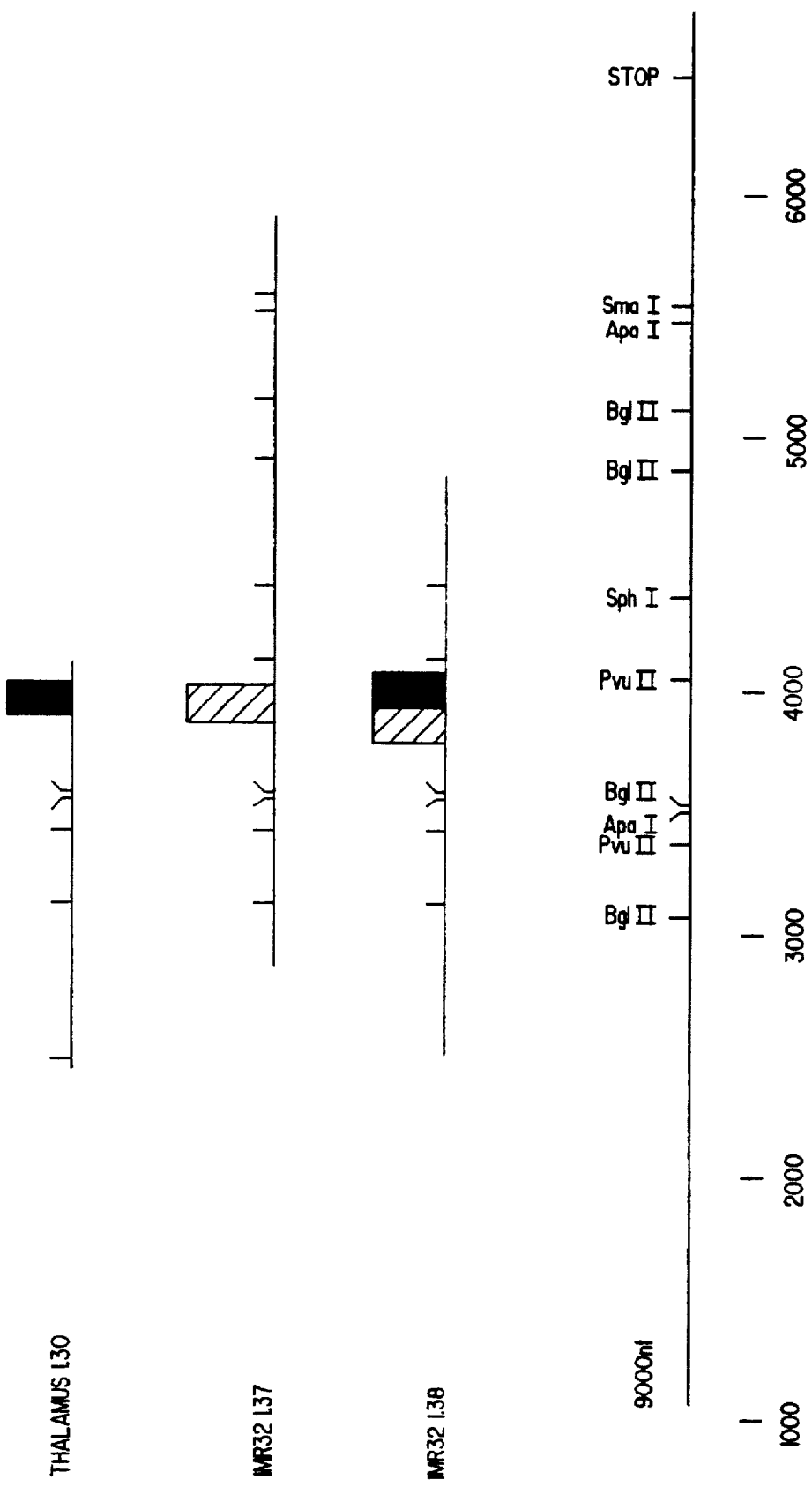
FIG. 3 depicts an alternative splicing pattern of a nucleic acid sequence encoding a human neuronal calcium channel $\alpha_{1C}$ subunit.

DNA sequence comparison of IMR32 1.37 and IMR32 1.38 revealed that the $\alpha_{1C}$ transcript includes two exons that encode the IVS3 transmembrane domain. IMR32 1.37 has a single exon, nt 3904 to 3987 (Sequence ID No. 3) and IMR32 1.38 (set forth in Sequence ID No. 31) appears to be anomalously spliced to contain both exons juxtaposed, nt 3904 to 3987 (Sequence ID No. 3) followed by nt 1 to 84 (Sequence ID No. 6). The alternative splice of the $\alpha_{1C}$ transcript to contain either of the two exons encoding the IVS3 region was confirmed by comparing the CNS 1.30 sequence to the IMR32 1.37 sequence. CNS 1.30 (set forth in Sequence ID No. 29, nt. 87–1875) contains nt 1 to 84 (Sequence ID No. 6) preceded by the identical sequence contained in IMR32 1.37 for nt 2199 to 3903 (Sequence ID No. 3). As described in Example II.B.2.a., an intron follows nt 1 to 84 (Sequence ID No. 6). Two alternative exons have been spliced adjacent to nt 3903 (Sequence ID No. 3) represented by CNS 1.30 and IMR32 1.37. The alternative splicing of this region is schematically depicted in FIG. 3 (see, also , Sequence ID Nos. 24, 29, 30 and 31). The solid box represents nt 1 to 84 (Sequence ID No. 6) and the striped box represents nt 3904 to 3987 (Sequence ID No. 3).

e. IMR32 1.86

IMR32 cDNA library #1 (Example I.B.1.) was screened in duplicate using oligonucleotide probes 90–9 (nt 1462 to 1491, Sequence ID No. 3) and 90–12 (nt 2496 to 2520, Sequence ID No. 3). These oligonucleotide probes were chosen in order to isolate a clone that encodes the $\alpha_{1C}$ subunit between the 3' end of IMR32 1.67 (nt 1717, Sequence ID No. 3) and the 5' end of CNS 1.30 (nt 2199, Sequence ID No. 3). The hybridization conditions were standard hybridization conditions (Example I.C.) with the exception that the 50% deionized formamide was reduced to 20%. The filters were washed under low stringency (Example I.C.). Three positive plaques were identified one of which was IMR32 1.86. IMR32 1.86 was plaque purified, subcloned, and characterized by restriction mapping and DNA sequencing. IMR32 1.86 encodes $\alpha_{1C}$ sequences as described in Example II.B.1. Characterization by DNA sequencing revealed that IMR32 1.86 contains a 73 nt deletion compared to the DNA encoding rabbit cardiac muscle calcium channel $\alpha_1$ subunit [Mikami et al. (1989) *Nature* 340:230], nt 2191 to 2263. These missing nucleotides correspond to nt 2176–2248 of Sequence ID No. 3. Because the 5'-end of CNS 1.30 overlaps the 3'-end of IMR32 1.86, some of these missing nucleotides, i.e., nt 2205–2248 of Sequence ID No. 3, are accounted for by CNS 1.30. The remaining missing nucleotides of the 73 nucleotide deletion in IMR32 1.86 (i.e., nt 2176–2204 Sequence ID No. 3) were determined by PCR analysis of dbcAMP-induced IMR32 cell RNA. The 73 nt deletion is a frame-shift mutation and, thus, needs to be corrected. The exact human sequence through this region, (which has been determined by the DNA sequence of CNS 1.30 and PCR analysis of IMR32 cell RNA) can be inserted into IMR32 1.86 by standard methods, e.g., replacement of a restriction fragment or site-directed mutagenesis.

f. IMR32 1.157

One million recombinants of IMR32 cDNA library #4 (Example I.B.4.) were screened with an XhoI-EcoRI fragment of IMR32 1.67 encoding $\alpha_{1C}$ nt 50 to 774 (Sequence ID No. 3). The hybridization was performed using standard hybridization conditions (Example I.C.). The filters were washed under high stringency (Example I.C.). One of the positive plaques identified was IMR32 1.157 (set forth in Sequence ID No. 24) . This plaque was purified, the insert was restriction mapped and subcloned to a standard plasmid vector (e.g., pGEM7Z, Madison, Wis.). The cDNA was characterized by DNA sequencing. IMR32 1.157 possibly encodes an alternative 5' portion of the $\alpha_{1C}$ sequence beginning with nt 1 to 89 (Sequence ID No. 5) which is then followed by nt 1 to 873 (Sequence ID No. 3). Analysis of the 1.66 and 1.157 5' sequence is described below (Example II.B.3.).

3. Characterization of the $\alpha_{1C}$ initiation of translation site

The human sequences represent possible alternative 5' ends of the $\alpha_{1C}$ transcript encoding the region of initiation of translation. IMR32 1.66 closely matches the CaCB receptor cDNA sequence and diverges from the CaCB receptor cDNA sequence in the 5' direction beginning at nt 122 (Sequence ID No. 4). The start codon identified in the CaCB receptor cDNA sequence is enclosed in a box and is the same start codon used to describe the $\alpha_{1C}$ coding sequence, nt 1 to 3 (Sequence ID No. 3). The functional significance of the IMR32 1.157 sequence, nt 1 to 89 (Sequence ID No. 5), is unknown, however, chimeric sequence between 1.157 and the $\alpha_{1C}$ coding sequence can be constructed and functional differences can be tested. IMR32 1.157 does not contain an initiation codon, however, one can be cloned by screening IMR32 cell cDNA libraries using probes corresponding to Sequence ID No. 5.

C. Isolation of partial cDNA clones encoding the $\alpha_{1B}$ subunit and construction of a full-length clone A human basal ganglia cDNA library was screened with the rabbit skeletal muscle $\alpha_1$ subunit cDNA fragments (see Example II.A.2.a for description of fragments) under low stringency conditions. One of the hybridizing clones was used to screen an IMR32 cell cDNA library to obtain additional partial $\alpha_{1B}$ cDNA clones, which were in turn used to further screen an IMR32 cell cDNA library for additional partial cDNA clones. One of the partial IMR32 $\alpha_{1B}$ clones was used to screen a human hippocampus library to obtain a partial $\alpha_{1B}$ clone encoding the 3' end of the $\alpha_{1B}$ coding sequence. The sequence of some of the regions of the partial cDNA clones was compared to the sequence of products of PCR analysis of IMR32 cell RNA to determine the accuracy of the cDNA sequences.

PCR analysis of IMR32 cell RNA and genomic DNA using oligonucleotide primers corresponding to sequences located 5' and 3' of the STOP codon of the DNA encoding the $\alpha_{1B}$ subunit revealed an alternatively spliced $\alpha_{1B}$-encoding MRNA in IMR32 cells. This second mRNA product is the result of differential splicing of the $\alpha_{1B}$ subunit transcript to include another exon that is not present in the mRNA corresponding to the other 3' $\alpha_{1B}$ cDNA sequence that was initially isolated. To distinguish these splice variants of the $\alpha_{1B}$ subunit, the subunit encoded by a DNA sequence corresponding to the form containing the additional exon is referred to as $\alpha_{1B-1}$ (Sequence ID No. 7), whereas the subunit encoded by a DNA sequence corresponding to the form lacking the additional exon is referred to as $\alpha_{1B-2}$ (Sequence ID No. 8). The sequence of $\alpha_{1B-1}$ diverges from that of $\alpha_{1B-2}$ beginning at nt 6633 (Sequence ID No. 7). Following the sequence of the additional exon in $\alpha_{1B-1}$ (nt 6633–6819; Sequence ID No. 7), the $\alpha_{1B-1}$ and $\alpha_{1B-2}$ sequences are identical (i.e., nt 6820–7362 in Sequence ID No. 7 and nt 6633–7175 in Sequence ID No. 8). Sequence ID No. 7 and No. 8 set forth 143 nt of 5' untranslated sequence (nt 1–143) as well as 202 nt of 3' untranslated sequence (nt 7161–7362, Sequence ID No. 7) of the DNA encoding $\alpha_{1B-1}$ and 321 nt of 3' untranslated sequence (nt 6855–7175, Sequence ID No. 8) of the DNA encoding $\alpha_{1B-2}$.

PCR analysis of the IS6 region of the $\alpha_{1B}$ transcript revealed additional splice variants based on multiple fragment sizes seen on an ethidium bromide-stained agarose gel containing the products of the PCR reaction.

A full-length $\alpha_{1B-1}$ cDNA clone designated pcDNA-$\alpha_{1B-1}$ was prepared in an eight-step process as follows.

STEP 1: The SacI restriction site of pGEM3 (Promega, Madison, Wis.) was destroyed by digestion at the SacI site, producing blunt ends by treatment with T4 DNA polymerase, and religation. The new vector was designated pGEMΔSac.

STEP 2: Fragment 1 (HindIII/KpnI; nt 2337 to 4303 of Sequence ID No. 7) was ligated into HindIII/KpnI digested pGEM3ΔSac to produce pαI.177HK.

STEP 3: Fragment 1 has a 2 nucleotide deletion (nt 3852 and 3853 of Sequence ID No. 7). The deletion was repaired by inserting a PCR fragment (fragment 2) of IMR32 RNA into pαI.177HK. Thus, fragment 2 (NarI/KpnI; nt 3828 to 4303 of Sequence ID No. 7) was inserted into NarI/KpnI digested pα1.177HK replacing the NarI/KpnI portion of fragment 1 and producing pα1.177HK/PCR.

STEP 4: Fragment 3 (KpnI/KpnI; nt 4303 to 5663 of Sequence ID No. 7) was ligated into KpnI digested pα1.177HK/PCR to produce pα1B5'K.

STEP 5: Fragment 4 (EcoRI/HindIII; EcoRI adaptor plus nt 1 to 2337 of Sequence ID No. 7) and fragment 5 (HindIII/XhoI fragment of pα1B5'K; nt 2337 to 5446 of Sequence ID No. 7) were ligated together into EcoRI/XhoI digested pcDNA1 (Invitrogen, San Diego, Calif.) to produce pα1B5'.

STEP 6: Fragment 6 (EcoRI/EcoRI; EcoRI adapters on both ends plus nt 5749 to 7362 of Sequence ID No. 7) was ligated into EcoRI digested pBluescript II KS (Stratagene, La Jolla, Calif.) with the 5'end of the fragment proximal to the KpnI site in the polylinker to produce pα1.230.

STEP 7: Fragment 7 (KpnI/XhoI; nt 4303 to 5446 of Sequence ID No. 7), and fragment 8 (xhoI/CspI; nt 5446 to 6259 of Sequence ID No. 7) were ligated into KpnI/CspI digested pα1.230 (removes nt 5749 to 6259 of Sequence ID No. γ that was encoded in pα1.230 and maintains nt 6259 to 7362 of Sequence ID No. 7) to produce pα1B3'.

STEP 8: Fragment 9 (SphI/XhoI; nt 4993 to 5446 of Sequence ID No. 7) and fragment 10 (XhoI/XbaI; nt 5446 to 7319 of Sequence ID No. 7) were ligated into SphI/XbaI digested pcDNA1 (removes nt 4993 to 5446 of Sequence ID No. 7 that were encoded in pα1B5' and maintains nt 1 to 4850 of Sequence ID No. 7) to produce pcDNAα$_{1B-1}$.

The resulting construct, pcDNAα$_{1B-1}$, contains, in pCDNA1, a full-length coding region encoding α$_{1B-1}$ (nt 144–7362, Sequence ID No. 7), plus 5' untranslated sequence (nt 1–143, Sequence ID No. 7) and 3' untranslated sequence (nt 7161–7362, Sequence ID No. 7) under the transcriptional control of the CMV promoter.

EXAMPLE III: ISOLATION OF CDNA CLONES ENCODING THE HUMAN

NEURONAL CALCIUM CHANNEL β subunit

A. Isolation of partial cDNA clones encoding the β subunit and construction of a full-length clone encoding the β subunit A human hippocampus cDNA library was screened with the rabbit skeletal muscle calcium channel β subunit cDNA fragment (nt 441 to 1379) [for isolation and sequence of the rabbit skeletal muscle calcium channel β subunit cDNA, see U.S. patent application Ser. No. 482,384 or Ruth et al. (1989) *Science* 245:1115] using standard hybridization conditions (Example I.C.). A portion of one of the hybridizing clones was used to rescreen the hippocampus library to obtain additional cDNA clones. The cDNA inserts of hybridizing clones were characterized by restriction mapping and DNA sequencing and compared to the rabbit skeletal muscle calcium channel β subunit cDNA sequence.

Portions of the partial β subunit cDNA clones were ligated to generate a full-length clone encoding the entire β subunit. Sequence ID No. 9 shows the β subunit coding sequence (nt 1–1434) as well as a portion of the 3' untranslated sequence (nt 1435–1546). The deduced amino acid sequence is also provided in Sequence ID No. 9. In order to perform expression experiments, full-length β subunit cDNA clones were constructed as follows.

Step 1: DNA fragment 1 (~800 bp of 5' untranslated sequence plus nt 1–277 of Sequence ID No. 9) was ligated to DNA fragment 2 (nt 277–1546 of Sequence ID No. 9 plus 448 bp of intron sequence) and cloned into pGEM7Z. The resulting plasmid, pβ1-1.18, contained a full-length β subunit clone that included a 448-bp intron.

Step 2: To replace the 5' untranslated sequence of pα1-1.18 with a ribosome binding site, a double-stranded adapter was synthesized that contains an EcoRI site, sequence encoding a ribosome binding site (5'-ACCACC-3') and nt 1-25 of Sequence ID No. 9. The adapter was ligated to SmaI-digested pβ1-1.18, and the products of the ligation reaction were digested with EcoRI.

Step 3: The EcoRI fragment from step α₂ containing the EcoRI adapter, efficient ribosome binding site and nt 1-1546 of Sequence ID No. 9 plus intron sequence was cloned into a plasmid vector and designated pβ1-1.18RBS.

Step 4: To generate a full-length clone encoding the β subunit lacking intron sequence, DNA fragment 3 (nt 69-1146 of Sequence ID No. 9 plus 448 bp of intron sequence followed by nt 1147–1546 of Sequence ID No. 9), was subjected to site-directed mutagenesis to delete the intron sequence, thereby yielding pβ1 (-). The EcoRI-XhoI fragment of pβ1-1.18RBS (containing the ribosome binding site and nt 1-277 of Sequence ID No. 9) was ligated to the XhoI-EcoRI fragment of pβ1 (-) (containing of nt 277–1546 of Sequence ID No. 9) and cloned into pcDNA1 with the initiation of translation proximal to the CMV promoter. The resulting expression plasmid was designated pHBCaCHβ1bA.

B. Splice Variant β₃

DNA sequence analysis of the DNA clones encoding the β subunit indicated that in the CNS at least two alternatively spliced forms of the same human β subunit primary transcript are expressed. One form is represented by the sequence shown in Sequence ID No. 9 and is referred to as β₂. The sequences of β₂ and the alternative form, β₃, diverge at nt 1334 (Sequence ID No. 9). The complete β₃ sequence (nt 1–1851), including 3' untranslated sequence (nt 1795–1851), is set forth in Sequence ID No. 10.

Figure 4:
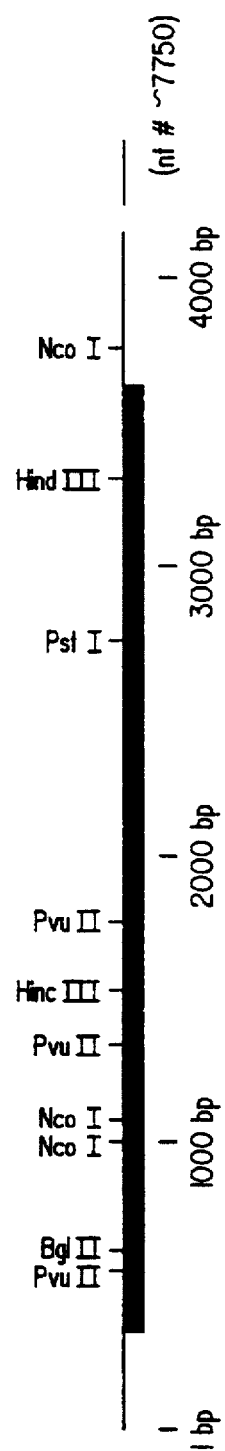
FIG. 4 is a restriction map of a nucleic acid sequence encoding a human neuronal calcium channel $\alpha_2$ subunit, and the various cDNA clones from which the complete coding sequence was derived.

EXAMPLE IV: ISOLATION OF CDNA CLONES ENCODING THE HUMAN NEURONAL CALCIUM CHANNEL α₂-subunit A. Isolation of cDNA clones A schematic of human neuronal calcium channel α₂ subunit cDNA clones that overlap to encode the complete coding sequence is shown in FIG. 4. The complete human neuronal α₂ coding sequence (nt 35–3307) plus a portion of the 5' untranslated sequence (nt 1 to 34) as well as a portion of the 3' untranslated sequence (nt 3308–3600) is set forth in Sequence ID No. 11.

To isolate DNA encoding the human neuronal α₂ subunit, human α₂ genomic clones first were isolated by probing human genomic Southern blots using a rabbit skeletal muscle calcium channel α₂ subunit cDNA fragment [nt 43 to 272, Ellis et al. (1988) *Science* 240:1661]. Human genomic DNA was digested with EcoRI, electrophoresed, blotted, and probed with the rabbit skeletal muscle probe using standard hybridization conditions (Example I.C.) and low stringency washing conditions (Example I.C.). Two restriction fragments were identified, 3.5 kb and 3.0 kb. These EcoRI restriction fragments were cloned by preparing a λgt11 library containing human genomic EcoRI fragments ranging from 2.2 kb to 4.3 kb. The library was screened as described above using the rabbit α₂ probe, hybridizing clones were isolated and characterized by DNA sequencing. HGCaCHα2.20 contained the 3.5 kb fragment and HGCaCHα2.9 contained the 3.0 kb fragment.

Restriction mapping and DNA sequencing revealed that HGCaCHα2.20 contains an 82 bp exon (nt 130 to 211 of the human α₂ coding sequence, Sequence ID No. 11) on a 650 bp PstI-XbaI restriction fragment and that HGCaCHα2.9 contains 105 bp of an exon (nt 212 to 316 of the coding sequence, Sequence ID No. 11) on a 750 bp XbaI-BglII restriction fragment. These restriction fragments were used to screen the human basal ganglia cDNA library (Example II.C.2.a.). HBCaCHα2.1 was isolated (nt 29 to 1163, Sequence ID No. 11) and used to screen a human brain stem cDNA library (ATCC Accession No. 37432) obtained from the American Type Culture Collection, Parklawn Drive, Rockville, Md. 20852. Two clones were isolated, HBCaCHα2.5 (nt 1 to 1162, Sequence ID No. 11) and HBCaCHα2.8 (nt 714 to 1562, Sequence ID No. 11, followed by 1600 nt of intervening sequence). A 2400 bp fragment of HBCaCHα2.8 (beginning at nt 759 of Sequence ID No. 11 and ending at a SmaI site in the intron) was used to rescreen the brain stem library and to isolate HBCaCHα2.11 (nt 879 to 3600, Sequence ID No. 11). Clones HBCaCHα2.5 and HBCaCHα2.11 overlap to encode an entire human brain α₂ protein.

B. Construction of pHBCaCHα₂A

To construct pHBCaCHα₂A containing DNA encoding a full-length human calcium channel α₂ subunit, an (EcoRI)-PvuII fragment of HBCaCHα2.5 (nt 1 to 1061, Sequence ID No. 11, EcoRI adapter, PvuII partial digest) and a PvuII-PstI fragment of HBCaCHα2.11 (nt 1061 to 2424 Sequence ID No. 11; PvuII partial digest) were ligated into EcoRI-PstI-digested pIBI24 (Stratagene, La Jolla, Calif.). Subsequently, an (EcoRI)-PstI fragment (nt 1 to 2424 Sequence ID No. 11) was isolated and ligated to a PstI-(EcoRI) fragment (nt 2424 to 3600 Sequence ID No. 11) of HBCaCHα2.11 in EcoRI-digested pIBI24 to produce DNA, HBCaCHα2, encoding a full-length human brain α₂ subunit. The 3600 bp EcoRI insert of HBCaCHα₂ (nt 1 to 3600, Sequence ID No. 11) was subcloned into pcDNA1 (pHBCaCHα2A) with the methionine initiating codon proximal to the CMV promoter. The 3600 bp EcoRI insert of HBCaCHα₂ was also subcloned into pSV2dHFR [Subramani et al. (1981). *Mol. Cell. Biol.* 1:854–864] which contains the SV40 early promoter, mouse dihydrofolate reductase (dhfr) gene, SV40 polyadenylation and splice sites and sequences required for maintenance of the vector in bacteria.

EXAMPLE V. DIFFERENTIAL PROCESSING OF THE HUMAN β TRANSCRIPT AND THE HUMAN α₂ TRANSCRIPT

A. Differential processing of the β transcript

PCR analysis of the human β transcript present in skeletal muscle, aorta, hippocampus and basal ganglia, and HEK 293 cells revealed differential processing of the region corresponding to nt 615–781 of Sequence ID No. 9 in each of the tissues. Four different sequences that result in five different processed β transcripts through this region were identified. The β transcripts from the different tissues contained different combinations of the four sequences, except for one of the β transcripts, expressed in HEK 293 cells ($β_5$), which lacked all four.

None of the β transcripts contained each of the four sequences; however, for ease of reference, all four sequences are set forth end-to-end as a single long sequence in Sequence ID No. 12 (nt. 1 to 323) and Sequence ID No. 19 (nt. 615 to 937). The four sequences that are differentially processed are sequence 1 (nt 14–34 in Sequence ID No. 12 nt. 628 to 648 in Sequence ID No. 19), sequence 2 (nt 35–55 in Sequence ID No. 12 nt. 649 to 669 in Sequence ID No. 19), sequence 3 (nt 56–190 in Sequence ID No. 12) and sequence 4 (nt 191–271 in Sequence ID No. 12 nt. 805 to 885 in Sequence ID No. 19). The forms of the β transcript that have been identified include: (1) a form that lacks sequence 1 called $β_1$ (expressed in skeletal muscle Sequence ID No. 19 in which nt. 628 to 648 are not present), (2) a form that lacks sequences 2 and 3 called $α_2$ (expressed in CNS Sequence ID No. 19 in which nt. 649 to 804 are not present), (3) a form that lacks sequences 1, 2 and 3 called $β_4$ (expressed in aorta and HEK cells Sequence ID No. 19 in which nt. 627 to 804 are not present) and (4) a form that lacks sequences 1–4 called $β_5$ (expressed in HEK cells). Additionally, the $β_4$ and $β_5$ forms contain the guanine nucleotide (nt 13 in Sequence ID No. 12 nt. 627 in Sequence ID No. 19) which is absent in the $β_1$ and $β_2$ forms.

B. Differential processing of transcripts encoding the $α_2$ subunit.

The complete human neuronal $α_2$ coding sequence (nt 35–3307) plus a portion of the 5' untranslated sequence (nt 1 to 34) as well as a portion of the 3' untranslated sequence (nt 3308–3600) is set forth as Sequence ID No. 11.

PCR analysis of the human $α_2$ transcript present in skeletal muscle, aorta, and CNS revealed differential processing of the region corresponding to nt 1595–1942 of Sequence ID #11 in each of the tissues.

The analysis indicated that the primary transcript of the genomic DNA that includes the nucleotides corresponding to nt. 1595–1942 also includes an additional sequence, Sequence ID No. 13: 5'CCTATTGGTGTAGGTATACCAA-CAATTAATTTAA GAAAAAGGAGACCCAATATCCAG 3' inserted between nt. 1624 and 1625 of Sequence ID No. 11. Five alternatively spliced variant transcripts that differ in the presence or absence of one to three different portions of the region of the primary transcript that includes the region of nt. 1595–1942 of Sequence ID No. 11 plus Sequence ID No. 13 inserted between nt. 1624 and 1625 have been identified. The five $α_2$-encoding transcripts from the different tissues include different combinations of the three sequences, except for one of the $α_2$ transcripts expressed in aorta which lacks all three sequences. None of the $α_1$ transcripts contained each of the three sequences. The sequences of the three regions that are differentially processed are sequence 1 (Sequence ID #13), sequence 2 (Sequence ID No. 21), and sequence 3, which is nt 1908–1928 of Sequence ID #11). The five $α_2$ forms identified are (1) a form that lacks sequence 3 called $α_{2a}$ (expressed in skeletal muscle), (2) a form that lacks sequence 1 called $α_{2b}$ (expressed in CNS), (3) a form that lacks sequences 1 and 2 called $α_{2c}$ expressed in aorta), (4) a form that lacks sequences 1, 2 and 3 called $α_{2d}$ (expressed in aorta) and (5) a form that lacks sequences 1 and 3 called $α_{2e}$ (expressed in aorta Sequence ID No. 11 in which nt. 1625 to 1639 and nucleotides 1908 to 1928 are not present).

EXAMPLE VI: ISOLATION OF DNA ENCODING A CALCIUM CHANNEL γ SUBUNIT FROM A HUMAN BRAIN CDNA LIBRARY

DNA encoding a human calcium channel γ subunit was isolated from a human hippocampus cDNA library.

A. Isolation of cDNA clones

Approximately $1 \times 10^6$ recombinants from a λgt11-based human hippocampus cDNA library (Clontech catalog #HL1088b, Palo Alto, Calif.) were screened by hybridization to a 484 bp sequence of the rabbit skeletal muscle calcium channel γ subunit cDNA (nucleotides 621–626 of the coding sequence plus 438 nucleotides of 3'-untranslated sequence) contained in vector γJ10 [Jay, S. et al. (1990). *Science* 248:490–492]. Hybridization was performed using moderate stringency conditions (20% deionized formamide, 5× Denhardt's, 6×SSPE, 0.2% SDS, 20 µg/ml herring sperm DNA, 42° C.) and the filters were washed under low stringency (see Example I.C.). A plaque that hybridized to this probe was purified and insert DNA was subcloned into pGEM7Z. This cDNA insert was designated γ1.4.

B. Characterization of γ1.4

γ1.4 was confirmed by DNA hybridization and characterized by DNA sequencing. The 1500 bp SstI fragment of γ1.4 hybridized to the rabbit skeletal muscle calcium channel γ subunit cDNA γJ10 on a Southern blot. Sequence analysis of this fragment revealed that it contains of approximately 500 nt of human DNA sequence and –1000 nt of λgt11 sequence (included due to apparent destruction of one of the EcoRI cloning sites in λgt11). The human DNA sequence contains of 129 nt of coding sequence followed immediately by a translational STOP codon and 3' untranslated sequence (Sequence ID No. 14).

To isolate the remaining 5' sequence of the human γ subunit cDNA, human CNS cDNA libraries and/or preparations of mRNA from human CNS tissues can first be assayed by PCR methods using oligonucleotide primers based on the γ cDNA-specific sequence of γ1.4. Additional human neuronal γ subunit-encoding DNA can isolated from cDNA libraries that, based on the results of the PCR assay, contain γ-specific amplifiable cDNA. Alternatively, cDNA libraries can be constructed from mRNA preparations that, based on the results of PCR assays, contain γ-specific amplifiable transcripts. Such libraries are constructed by standard methods using oligo dT to prime first-strand cDNA synthesis from poly $A^+$ RNA (see Example I.B.). Alternatively, first-strand cDNA can be specified by priming first-strand cDNA synthesis with a γ cDNA-specific oligonucleotide based on the human DNA sequence in γ1.4. A cDNA library can then be constructed based on this first-strand synthesis and screened with the γ-specific portion of γ1.4.

EXAMPLE VII: RECOMBINANT EXPRESSION OF HUMAN NEURONAL CALCIUM CHANNEL SUBUNIT-ENCODING cDNA AND RNA TRANSCRIPTS IN MAMMALIAN CELLS

A. Recombinant Expression of the Human Neuronal Calcium Channel $α_2$ subunit cDNA in DG44 Cells 1. Stable transfection of DG44 cells DG44 cells [dhfr Chinese hamster ovary cells; see, e.g., Urlaub, G. et al. (1986) *Som. Cell Molec. Genet.* 12:555–566] obtained from Lawrence Chasin at Columbia University were stably transfected by $CaPO_4$ precipitation methods [Wigler et al. (1979) *Proc. Natl. Acad. Sci. USA* 76:1373–1376] with pSV2dhfr vector containing the human neuronal calcium channel $α_2$-subunit cDNA (see Example IV) for polycistronic expression/selection in transfected cells. Transfectants were grown on 10% DMEM medium without hypoxanthine or thymidine in order to select cells that had incorporated the expression vector. Twelve transfectant cell lines were established as indicated by their ability to survive on this medium.

2. Analysis of $\alpha_2$ subunit cDNA expression in transfected DG44 cells

Total RNA was extracted according to the method of Birnboim [(1988) *Nuc. Acids Res.* 16:1487-1497] from four of the DG44 cell lines that had been stably transfected with pSV2dhfr containing the human neuronal calcium channel $\alpha_2$ subunit cDNA. RNA ($^{31}$ 15 µg per lane) was separated on a 1% agarose formaldehyde gel, transferred to nitrocellulose and hybridized to the random-primed human neuronal calcium channel $\alpha_2$ cDNA (hybridization: 50% formamide, 5×SSPE, 5× Denhardt's, 42° C.; wash :0.2×SSPE, 0.1% SDS, 65° C.). Northern blot analysis of total RNA from four of the DG44 cell lines that had been stably transfected with pSV2dhfr containing the human neuronal calcium channel $\alpha_2$ subunit cDNA revealed that one of the four cell lines contained hybridizing mRNA the size expected for the transcript of the $\alpha_2$ subunit cDNA (5000 nt based on the size of the cDNA) when grown in the presence of 10 mM sodium butyrate for two days. Butyrate nonspecifically induces transcription and is often used for inducing the SV40 early promoter [Gorman, C. and Howard, B. (1983) *Nucleic Acids Res.* 11:1631]. This cell line, 44$\alpha\alpha_1$, also produced mRNA species smaller (several species) and larger (6800 nt) than the size expected for the transcript of the $\alpha_2$ cDNA (5000 nt) that hybridized to the $\alpha_2$ cDNA-based probe. The 5000- and 6800-nt transcripts produced by this transfectant should contain the entire $\alpha_2$ subunit coding sequence and therefore should yield a full-length $\alpha_2$ subunit protein. A weakly hybridizing 8000-nucleotide transcript was present in untransfected and transfected DG44 cells. Apparently, DG44 cells transcribe a calcium channel $\alpha_2$ subunit or similar gene at low levels. The level of expression of this endogenous $\alpha_2$ subunit transcript did not appear to be affected by exposing the cells to butyrate before isolation of RNA for northern analysis.

Total protein was extracted from three of the DG44 cell lines that had been stably transfected with pSV2dhfr containing the human neuronal calcium channel $\alpha_2$ subunit cDNA. Approximately $10^7$ cells were sonicated in 300 µl of a solution containing 50 mM HEPES, 1 mM EDTA, and 1 mM PMSF. An equal volume of 2× loading dye [Laemmli, U.K. (1970). *Nature* 227:680] was added to the samples and the protein was subjected to electrophoresis on an 8% polyacrylamide gel and then electrotransferred to nitrocellulose. The nitrocellulose was incubated with polyclonal guinea pig antisera (1:200 dilution) directed against the rabbit skeletal muscle calcium channel $\alpha_2$ subunit (obtained from K. Campbell, University of Iowa) followed by incubation with [$^{125}$I]-protein A. The blot was exposed to X-ray film at −70° C. Reduced samples of protein from the transfected cells as well as from untransfected DG44 cells contained immunoreactive protein of the size expected for the $\alpha_2$ subunit of the human neuronal calcium channel (130–150 kDa). The level of this immunoreactive protein was higher in 44$\alpha_2$-9 cells that had been grown in the presence of 10 mM sodium butyrate than in 44$\alpha_2$-9 cells that were grown in the absence of sodium butyrate. These data correlate well with those obtained in northern analyses of total RNA from 44$\alpha_2$-9 and untransfected DG44 cells. Cell line 44$\alpha_2$-9 also produced a 110-kDa immunoreactive protein which may be either a product of proteolytic degradation of the full-length $\alpha_2$ subunit or a product of translation of one of the shorter (<5000 nt) mRNAs produced in this cell line that hybridized to the $\alpha_2$ subunit cDNA probe.

B. Expression of DNA encoding human neuronal calcium channel $\alpha_1$, $\alpha_2$ and $\beta$ subunits in HEK cells Human embryonic kidney cells (HEK 293 cells) were transiently and stably transfected with human neuronal DNA encoding calcium channel subunits. Individual transfectants were analyzed electrophysiologically for the presence of voltage-activated barium currents and functional recombinant voltage-dependent calcium channels.

1. Transfection of HEK 293 cells

Separate expression vectors containing DNA encoding human neuronal calcium channel $\alpha_{1D}$, $\alpha_2$ and $\beta$ subunits, plasmids pVDCCIII(A), pHBCaCH$\alpha_2$A, and pB1-1.18, respectively, were constructed as described in Examples II.A.3, IV.B. and III.B.3. , respectively. These three vectors were used to transiently co-transfect HEK 293 cells. For stable transfection of HEK 293 cells, vector pHBCaCH$\alpha_1$bA (Example III.B.3.) was used in place of pB1-1.18 to introduce the DNA encoding the $\beta$ subunit into the cells along with pVDCCIII(A) and pHBCaCH$\alpha_2$A.

a. Transient transfection Expression vectors pVDCCIII (A), pHBCaCH$\alpha_2$A and pB1-1.18 were used in two sets of transient transfections of HEK 293 cells (ATCC Accession No. CRL1573). In one transfection procedure, HEK 293 cells were transiently cotransfected with the $\alpha_1$ subunit cDNA expression plasmid, the $\alpha_2$ subunit cDNA expression plasmid, the $\beta$ subunit cDNA expression plasmid and plasmid pCMV$\beta$gal (Clontech Laboratories, Palo Alto, Calif.). Plasmid pCMV$\beta$gal contains the lacZ gene (encoding *E. coli* $\beta$-galactosidase) fused to the cytomegalovirus (CMV) promoter and was included in this transfection as a marker gene for monitoring the efficiency of transfection. In the other transfection procedure, HEK 293 cells were transiently co-transfected with the $\alpha_1$ subunit cDNA expression plasmid pVDCCIII(A) and pCMV$\beta$gal. In both transfections, 2–4×10$^6$ HEK 293 cells contained in a 10-cm tissue culture plate were transiently co-transfected with 5 µg of each of the plasmids included in the experiment according to standard CaPO$_4$ precipitation transfection procedures (Wigler et al. (1979) *Proc. Natl. Acad. Sci. USA* 76:1373–1376). The transfectants were analyzed for $\beta$-galactosidase expression by direct staining of the product of a reaction involving $\beta$-galactosidase and the X-gal substrate [Jones, J. R. (1986) *EMBO* 5:3133–3142] and by measurement of $\beta$-galactosidase activity [Miller, J. H. (1972) Experiments in Molecular Genetics, pp. 352–355, Cold Spring Harbor Press]. To evaluate subunit cDNA expression in these transfectants, the cells were analyzed for subunit transcript production (northern analysis), subunit protein production (immunoblot analysis of cell lysates) and functional calcium channel expression (electrophysiological analysis).

b. Stable transfection

HEK 293 cells were transfected using the calcium phosphate transfection procedure [*Current Protocols in Molecular Biology*, Vol. 1, Wiley Inter-Science, Supplement 14, Unit 9.1.1–9.1.9 (1990)]. Ten-cm plates, each containing one-to-two million HEX 293 cells, were transfected with 1 ml of DNA/calcium phosphate precipitate containing 5 µg pVDCCIII(A), 5 µg pHBCaCH$\alpha_2$A, 5 µg pHBCaCH$\beta_1$bA, 5 µg pCMVBgal and 1 µg pSV2neo (as a selectable marker). After 10–20 days of growth in media containing 500 µg G418, colonies had formed and were isolated using cloning cylinders.

2. Analysis of HEX 293 cells transiently transfected with DNA encoding human neuronal calcium channel subunits a. Analysis of $\beta$-galactosidase expression Transient transfectants were assayed for $\beta$-galactosidase expression by $\beta$-galactosidase activity assays (Miller, J. H., (1972) Experiments in Molecular Genetics, pp. 352–355, Cold Spring Harbor Press) of cell lysates (prepared as described in Example VII.A.2) and staining of fixed cells (Jones, J. R. (1986) *EMBO* 5:3133–3142). The results of these assays indicated that approximately 30% of the HEK 293 cells had been transfected.

b. Northern analysis

PolyA+ RNA was isolated using the Invitrogen Fast Trak Kit (InVitrogen, San Diego, Calif.) from HEK 293 cells transiently transfected with DNA encoding each of the $\alpha_1$, $\alpha_2$ and $\beta$ subunits and the lacZ gene or the $\alpha_1$ subunit and the lacZ gene. The RNA was subjected to electrophoresis on an agarose gel and transferred to nitrocellulose. The nitrocellulose was then hybridized with one or more of the following radiolabeled probes: the lacz gene, human neuronal calcium channel $\alpha_{1D}$ subunit-encoding cDNA, human neuronal calcium channel $\alpha_2$ subunit-encoding cDNA or human neuronal calcium channel $\beta$ subunit-encoding cDNA. Two transcripts that hybridized with the $\alpha_1$ subunit-encoding cDNA were detected in HEK 293 cells transfected with the DNA encoding the $\alpha_1$, $\alpha_2$, and $\beta$ subunits and the lacz gene as well as in HEK 293 cells transfected with the $\alpha_1$ subunit cDNA and the lacZ gene. One mRNA species was the size expected for the transcript of the $\alpha_1$ subunit cDNA (8000 nucleotides). The second RNA species was smaller (4000 nucleotides) than the size expected for this transcript. RNA of the size expected for the transcript of the lacz gene was detected in cells transfected with the $\alpha_1$, $\alpha_2$ and $\beta$ subunit-encoding cDNA and the lacZ gene and in cells transfected with the $\alpha_1$ subunit cDNA and the lacz gene by hybridization to the lacZ gene sequence.

RNA from cells transfected with the $\alpha_1$, $\alpha_2$ and $\beta$ subunit-encoding cDNA and the lacz gene was also hybridized with the $\alpha_2$ and $\beta$ subunit cDNA probes. Two MRNA species hybridized to the $\alpha_2$ subunit cDNA probe. One species was the size expected for the transcript of the $\alpha_2$ subunit cDNA (4000 nucleotides). The other species was larger (6000 nucleotides) than the expected size of this transcript. Multiple RNA species in the cells co-transfected with $\alpha_1$, $\alpha_2$ and $\beta$ subunit-encoding cDNA and the lacZ gene hybridized to the $\beta$ subunit cDNA probe. Multiple $\beta$-subunit transcripts of varying sizes were not unexpected since the $\beta$ subunit cDNA expression vector contains two potential polyA$^+$ addition sites.

c. Electrophysiological analysis

Individual transiently transfected HEK 293 cells were assayed for the presence of voltage-dependent barium currents using the whole-cell variant of the patch clamp technique [Hamill et al. (1981) Pflugers Arch. 391:85–100]. HEK 293 cells transiently transfected with pCMV$\beta$gal only were assayed for barium currents as a negative control in these experiments. The cells were placed in a bathing solution that contained barium ions to serve as the current carrier. Choline chloride, instead of NaCl or KCl, was used as the major salt component of the bath solution to eliminate currents through sodium and potassium channels. The bathing solution contained 1 mM $MgCl_2$ and was buffered at pH 7.3 with 10 mM HEPES (pH adjusted with sodium or tetraethylammonium hydroxide). Patch pipettes were filled with a solution containing 135 mM CsCl, 1 mM $MgCl_2$, 10 mM glucose, 10 mM EGTA, 4 mM ATP and 10 mM HEPES (pH adjusted to 7.3 with tetraethylammonium hydroxide). Cesium and tetraethylammonium ions block most types of potassium channels. Pipettes were coated with Sylgard (Dow-Corning, Midland, Mich.) and had resistances of 1–4 megohm. Currents were measured through a 500 megohm headstage resistor with the Axopatch IC (Axon Instruments, Foster City, Calif.) amplifier, interfaced with a Labmaster (Scientific Solutions, Solon, OH) data acquisition board in an IBM-compatible PC. PClamp (Axon Instruments) was used to generate voltage commands and acquire data. Data were analyzed with pClamp or Quattro Professional (Borland International, Scotts Valley, Calif.) programs.

To apply drugs, "puffer" pipettes positioned within several micrometers of the cell under study were used to apply solutions by pressure application. The drugs used for pharmacological characterization were dissolved in a solution identical to the bathing solution. Samples of a 10 mM stock solution of Bay K 8644 (RBI, Natick, Mass.), which was prepared in DMSO, were diluted to a final concentration of 1 μM in 15 mM $Ba^{2+}$-containing bath solution before they were applied.

Twenty-one negative control HEK 293 cells (transiently transfected with the lacZ gene expression vector pCMV$\beta$gal only) were analyzed by the whole-cell variant of the patch clamp method for recording currents. Only one cell displayed a discernable inward barium current; this current was not affected by the presence of 1 μM Bay K 8644. In addition, application of Bay K 8644 to four cells that did not display $Ba^{2+}$ currents did not result in the appearance of any currents.

Two days after transient transfection of HEK 293 cells with $\alpha_1$, $\alpha_2$ and $\beta$ subunit-encoding cDNA and the lacZ gene, individual transfectants were assayed for voltage-dependent barium currents. The currents in nine transfectants were recorded. Because the efficiency of transfection of one cell can vary from the efficiency of transfection of another cell, the degree of expression of heterologous proteins in individual transfectants varies and some cells do not incorporate or express the foreign DNA. Inward barium currents were detected in two of these nine transfectants. In these assays, the holding potential of the membrane was −90 mV. The membrane was depolarized in a series of voltage steps to different test potentials and the current in the presence and absence of 1 μM Bay K 8644 was recorded. The inward barium current was significantly enhanced in magnitude by the addition of Bay K 8644. The largest inward barium current (−160 pA) was recorded when the membrane was depolarized to 0 mV in the presence of 1 μM Bay K 8644. A comparison of the I–V curves, generated by plotting the largest current recorded after each depolarization versus the depolarization voltage, corresponding to recordings conducted in the absence and presence of Bay K 8644 illustrated the enhancement of the voltage-activated current in the presence of Bay K 8644.

Pronounced tail currents were detected in the tracings of currents generated in the presence of Bay K 8644 in HEK 293 cells transfected with $\alpha_1$, $\alpha_2$ and $\beta$ subunit-encoding cDNA and the lacZ gene, indicating that the recombinant calcium channels responsible for the voltage-activated barium currents recorded in this transfected cell appear to be DHP sensitive.

The second of the two transfected cells that displayed inward barium currents expressed a −50 pA current when the membrane was depolarized from −90 mV. This current was nearly completely blocked by 200 μM cadmium, an established calcium channel blocker.

Ten cells that were transiently transfected with the DNA encoding the $\alpha_1$ subunit and the lacZ gene were analyzed by whole-cell patch clamp methods two days after transfection. One of these cells displayed a 30 pA inward barium current. This current amplified 2-fold in the presence of 1 μM Bay K 8644. Furthermore, small tail currents were detected in the presence of Bay K 8644. These data indicate that expression of the human neuronal calcium channel $\alpha_{1D}$ subunit-encoding cDNA in HEK 293 yields a functional DHP-sensitive calcium channel.

3. Analysis of HEK 293 cells stably transfected with DNA encoding human neuronal calcium channel subunits Individual stably transfected HEK 293 cells were assayed electrophysiologically for the presence of voltage-dependent barium currents as described for electrophysiological analysis of transiently transfected HEK 293 cells (see Example VII.B.2.c). In an effort to maximize calcium channel activity via cyclic-AMP-dependent kinase-mediated phosphorylation [Pelzer, et al. (1990) *Rev. Physiol. Biochem. Pharmacol.* 114:107–207], cAMP (Na salt, 250 µM) was added to the pipet solution and forskolin (10 µM) was added to the bath solution in some of the recordings. Qualitatively similar results were obtained whether these compounds were present or not.

Barium currents were recorded from stably transfected cells in the absence and presence of Bay K 8644 (1 µM). When the cell was depolarized to −10 mV from a holding potential of −90 mV in the absence of Bay K 8644, a current of approximately 35pA with a rapidly deactivating tail current was recorded. During application of Bay K 8644, an identical depolarizing protocol elicited a current of approximately 75 pA, accompanied by an augmented and prolonged tail current. The peak magnitude of currents recorded from this same cell as a function of a series of depolarizing voltages were assessed. The responses in the presence of Bay K 8644 not only increased, but the entire current-voltage relation shifted about −10 mV. Thus, three typical hallmarks of Bay K 8644 action, namely increased current magnitude, prolonged tail currents, and negatively shifted activation voltage, were observed, clearly indicating the expression of a DHP-sensitive calcium channel in these stably transfected cells. No such effects of Bay K 8644 were observed in untransfected HEK 293 cells, either with or without cAMP or forskolin.

C. Use of pCMV-based vectors and pcDNA1-based vectors for expression of DNA encoding human neuronal calcium channel subunits 1. Preparation of constructs To determine if the levels of recombinant expression of human calcium channel subunit cDNAs in host cells could be enhanced by using pCMV-based instead of pcDNA1-based expression vectors, additional expression vectors were constructed. The full-length $\alpha_{1D}$ cDNA from pVDCCIII(A) (see Example II.A.3.d), the full-length $\alpha_2$ cDNA, contained on a 3600 bp EcoRI fragment from HBCaCH$\alpha_2$ (see Example IV.B) and a full-length $\beta$ subunit cDNA from pHBCaCH$\beta_1$bA (see Example III.B.3) were separately subcloned into plasmid pCMV$\beta$gal. Plasmid pCMV$\beta$gal was digested with NotI to remove the lacZ gene. The remaining vector portion of the plasmid, referred to as pCMV, was blunt-ended at the NotI sites. The full-length $\alpha_2$ and $\beta$ cDNAs, contained on separate EcoRI fragments, were isolated, blunt-ended and separately ligated to the blunt-ended vector fragment of pCMV locating the cDNAs between the CMV promoter and SV40 polyadenylation sites in pCMV. To ligate the $\alpha_{1D}$-encoding cDNA with pCMV, the restriction sites in the polylinkers immediately 5' of the CMV promoter and immediately 3' of the SV40 polyadenylation site were removed from pCMV. A polylinker was added at the NotI site. The polylinker had the following sequence (Sequence Nos. 27 and 28):

| GGCCGC | EcoRI | SalI | PstI | EcoRV | HindIII | XbaII | GT |
|---|---|---|---|---|---|---|---|
| CG | site | site | site | site | site | site | CACCGG |
| | | | | | | | ↑ |
| NotI | | | | | | | Destroys |
| | | | | | | | NotI |

The $\alpha_{1D}$ cDNA, isolated as a BamHI/XhoI fragment from pVDCCIII(A), was then ligated to XbaII/SalI-digested PCMV to place it between the CMV promoter and SV40 polyadenylation site.

Plasmid pCMV contains the CMV promoter as does pcDNA1, but differs from pcDNA1 in the location of splice donor/splice acceptor sites relative to the inserted subunit-encoding DNA. After inserting the subunit-encoding DNA into pCMV, the splice donor/splice acceptor sites are located 3' of the CMV promoter and 5' of the subunit-encoding DNA start codon. After inserting the subunit-encoding DNA into pcDNA1, the splice donor/splice acceptor sites are located 3' of the subunit cDNA stop codon.

2. Transfection of HEK 293 cells

HEK 293 cells were transiently co-transfected with the $\alpha_{1D}$, $\alpha_2$ and $\beta$ subunit-encoding DNA in PCMV or with the $\alpha_1$ D, $\alpha_2$ and $\beta$ subunit-encoding DNA in pcDNA1, (vectors pVDCCIII(A), pHBCaCH$\alpha_2$A and pHBCaCH$\beta_1$bA) as described in Example VII.B.1.a. Plasmid pCMV$\beta$gal was included in each transfection to as a measure of transfection efficiency. The results of $\beta$-galactosidase assays of the transfectants (see Example VII.B.2.), indicated that HEK 293 cells were transfected equally efficiently with PCMV- and pcDNA1-based plasmids.

3. Northern analysis Total and polyA$^+$ RNA were isolated from the transiently transfected cells as described in Examples VII.A.2 and VII.B.2.b. Northern blots of the RNA were hybridized with the following radiolabeled probes: $\alpha_{1D}$ cDNA, human neuronal calcium channel $\alpha_2$ subunit cDNA and DNA encoding the human neuronal calcium channel $\beta$ subunit. Messenger RNA of sizes expected for $\alpha_{1D}$, $\alpha_2$ and $\beta$ subunit transcripts were detected in all transfectants. A greater amount of the $\alpha_{1D}$ transcript was present in cells that were co-transfected with pCMV-based plasmids than in cells that were co-transfected with pcDNA1-based plasmids. Equivalent amounts of $\alpha_2$ and $\beta$ subunit transcripts were detected in all transfectants.

D. Expression in Xenopus laevis oöcytes of RNA encoding human neuronal calcium channel subunits Various combinations of the transcripts of DNA encoding the human neuronal $\alpha_{1D}$, $\alpha_2$ and $\beta$ subunits prepared in vitro were injected into Xenopus laevis oöcytes. Those injected with combinations that included $\alpha_{1D}$ exhibited voltage-activated barium currents.

1. Preparation of transcripts

Transcripts encoding the human neuronal calcium channel $\alpha_{1D}$, $\alpha_2$ and $\beta$ subunits were synthesized according to the instructions of the mCAP mRNA CAPPING KIT (Strategene, La Jolla, Calif. catalog #200350). Plasmids pVDCC III.RBS(A), containing of pcDNA1 and the $\alpha_{1D}$ cDNA that begins with a ribosome binding site and the eighth ATG codon of the coding sequence (see Example III.A.3.d), plasmid pHBCaCH$\alpha_1$ A containing of pcDNA1 and an $\alpha_2$ subunit cDNA (see Example IV), and plasmid pHBCaCH$\beta_1$bA containing of pcDNA1 and the $\beta$ cDNA lacking intron sequence and containing a ribosome binding site (see Example III), were linearized by restriction digestion. The $\alpha_{1D}$ cDNA- and $\alpha_2$ subunit-encoding plasmids were digested with XhoI, and the $\beta$ subunit-encoding plasmid was digested with EcoRV. The DNA insert was transcribed with T7 RNA polymerase.

2. Injection of oöcytes

Xenopus laevis oöcytes were isolated and defolliculated by collagenase treatment and maintained in 100 mM NaCl, 2 mM KCl, 1.8 mM CaCl$_2$, 1 mM MgCl$_2$, 5 mM HEPES, pH 7.6, 20 µg/ml ampicillin and 25 µg/ml streptomycin at 19°–25° C. for 2 to 5 days after injection and prior to recording. For each transcript that was injected into the oöcyte, 6 ng of the specific mRNA was injected per cell in a total volume of 50 nl.

3. Intracellular voltage recordings

Injected oocytes were examined for voltage-dependent barium currents using two-electrode voltage clamp methods [Dascal, N. (1987) *CRC Crit. Rev. Biochem.* 22:317]. The pClamp (Axon Instruments) software package was used in conjunction with a Labmaster 125 kHz data acquisition interface to generate voltage commands and to acquire and analyze data. Quattro Professional was also used in this analysis. Current signals were digitized at 1–5 kHz, and filtered appropriately. The bath solution contained of the following: 40 mM $BaCl_2$, 36 mM tetraethylammonium chloride (TEA-Cl), 2 mM KCl, 5 mM 4-aminopyridine, 0.15 mM niflumic acid, 5 mM HEPES, pH 7.6.

a. Electrophysiological analysis of oocytes injected with transcripts encoding the human neuronal calcium channel $\alpha_1$, $\alpha_1$ and $\beta$-subunits Uninjected oocytes were examined by two-electrode voltage clamp methods and a very small (25 nA) endogenous inward $Ba^{2+}$ current was detected in only one of seven analyzed cells.

Oocytes coinjected with $\alpha_{1D}$, $\alpha_2$ and $\beta$ subunit transcripts expressed sustained inward barium currents upon depolarization of the membrane from a holding potential of −90 mV or −50 mV (154±129 nA, n=21). These currents typically showed little inactivation when test pulses ranging from 140 to 700 msec were administered. Depolarization to a series of voltages revealed currents that first appeared at approximately −30 mV and peaked at approximately 0 mV.

Application of the dihydropyridine Bay K 8644 increased the magnitude of the currents, prolonged the tail currents present upon repolarization of the cell and induced a hyperpolarizing shift in current activation. Bay K 8644 was prepared fresh from a stock solution in DMSO and introduced as a 10× concentrate directly into the 60 μl bath while the perfusion pump was turned off. The DMSO concentration of the final diluted drug solutions in contact with the cell never exceeded 0.1%. Control experiments showed that 0.1% DMSO had no effect on membrane currents.

Application of the dihydropyridine antagonist nifedipine (stock solution prepared in DMSO and applied to the cell as described for application of Bay K 8644) blocked a substantial fraction (91±6%, n=7) of the inward barium current in oocytes coinjected with transcripts of the $\alpha_{1D}$, $\alpha_2$ and $\beta$ subunits. A residual inactivating component of the inward barium current typically remained after nifedipine application. The inward barium current was blocked completely by 50 μM $Cd^{2+}$, but only approximately 15% by 100 μM $Ni^{2+}$.

The effect of ωCgTX on the inward barium currents in oocytes co-injected with transcripts of the $\alpha_{1D}$, $\alpha_2$, and $\beta$ subunits was investigated. ωCgTX (Bachem, Inc., Torrance Calif.) was prepared in the 15 mM $BaCl_2$ bath solution plus 0.1% cytochrome C (Sigma) to serve as a carrier protein. Control experiments showed that cytochrome C had no effect on currents. A series of voltage pulses from a −90 mV holding potential to 0 mV were recorded at 20 msec. intervals. To reduce the inhibition of ωCgTX binding by divalent cations, recordings were made in 15 mM $BaCl_2$, 73.5 mM tetraethylammonium chloride, and the remaining ingredients identical to the 40 mM $Ba^{2+}$ recording solution. Bay K 8644 was applied to the cell prior to addition of ωCgTX in order to determine the effect of ωCgTX on the DHP-sensitive current component that was distinguished by the prolonged tail currents. The inward barium current was blocked weakly (54±29%, n=7) and reversibly by relatively high concentrations (10–15 μM) of ωCgTX. Both the test currents and the accompanying tail currents were blocked progressively within two to three minutes after application of ωCgTX, but both recovered partially as the ωCgTX was flushed from the bath.

b. Analysis of oocytes injected with only transcripts encoding the human neuronal calcium channel $\alpha_{1D}$ or transcripts encoding an $\alpha_{1D}$ and other subunits The contribution of the $\alpha_2$ and $\beta$ subunits to the inward barium current in oocytes injected with transcripts encoding the $\alpha_{1D}$, $\alpha_2$ and $\beta$ subunits was assessed by expression of the $\alpha_{1D}$ subunit alone or in combination with either the $\beta$ subunit or the $\alpha_2$ subunit. In oocytes injected with only the transcript of a $\alpha_{1D}$ cDNA, no $Ba^{2+}$ currents were detected (n=3). In oocytes injected with transcripts of $\alpha_{1D}$ and $\beta$ cDNAs, small (108±39 nA) $Ba^{2+}$ currents were detected upon depolarization of the membrane from a holding potential of −90 mV that resembled the currents observed in cells injected with transcripts of $\alpha_{1D}$, $\alpha_2$ and $\beta$ cDNAs, although the magnitude of the current was less. In two of the four oocytes injected with transcripts of the $\alpha_{1D}$ and $\beta$ cDNAs, the $Ba^{2+}$ currents exhibited a sensitivity to Bay K 8644 that was similar to the Bay K 8644 sensitivity of $Ba^{2+}$ currents expressed in oocytes injected with transcripts encoding the $\alpha_{1D}$ $\alpha_1$-, $\alpha_2$ and $\beta$-subunits.

Three of five oocytes injected with transcripts encoding the $\alpha_{1D}$ and $\alpha_2$ subunits exhibited very small $Ba^{2+}$ currents (15–30 nA) upon depolarization of the membrane from a holding potential of −90 mV. These barium currents showed little or no response to Bay K 8644.

c. Analysis of oocytes injected with transcripts encoding the human neuronal calcium channel $\alpha_1$ and/or $\beta$ subunit To evaluate the contribution of the $\alpha_{1D}$ $\alpha_1$-subunit to the inward barium currents detected in oocytes co-injected with transcripts encoding the $\alpha_{1D}$, $\alpha_2$ and $\beta$ subunits, oocytes injected with transcripts encoding the human neuronal calcium channel $\alpha_2$ and/or $\beta$ subunits were assayed for barium currents. Oocytes injected with transcripts encoding the $\alpha_2$ subunit displayed no detectable inward barium currents (n=5). Oocytes injected with transcripts encoding a $\beta$ subunit displayed measurable (54±23 nA, n=5) inward barium currents upon depolarization and oocytes injected with transcripts encoding the $\alpha_2$ and $\beta$ subunits displayed inward barium currents that were approximately 50% larger (80±61 nA, n=18) than those detected in oocytes injected with transcripts of the $\beta$ cDNA only.

The inward barium currents in oocytes injected with transcripts encoding the $\beta$ subunit or $\alpha_2$ and $\beta$ subunits typically were first observed when the membrane was depolarized to −30 mV from a holding potential of −90 mV and peaked when the membrane was depolarized to 10 to 20 mV. Macroscopically, the currents in oocytes injected with transcripts encoding the $\alpha_2$ and $\beta$ subunits or with transcripts encoding the $\beta$ subunit were indistinguishable. In contrast to the currents in oocytes co-injected with transcripts of $\alpha_{1D}$, $\alpha_2$ and $\beta$ subunit cDNAs, these currents showed a significant inactivation during the test pulse and a strong sensitivity to the holding potential. The inward barium currents in oocytes co-injected with transcripts encoding the $\alpha_2$ and $\beta$ subunits usually inactivated to 10–60% of the peak magnitude during a 140-msec pulse and were significantly more sensitive to holding potential than hose in oocytes co-injected with transcripts encoding the $\alpha_{1D}$, $\alpha_2$ and $\beta$ subunits. Changing the holding potential of the membranes of oocytes co-injected with transcripts encoding the $\alpha_2$ and $\beta$ subunits from −90 to −50 mV resulted in an approximately 81% (n=11) reduction in the magnitude of the inward barium current of these cells. In contrast, the inward barium current measured in oocytes co-injected with transcripts encoding the $\alpha_{1D}$, $\alpha_2$ and $\beta$ subunits were reduced approximately 24% (n=11) when the holding potential was changed from −90 to −50 mV.

The inward barium currents detected in oocytes injected with transcripts encoding the $\alpha_2$ and $\beta$ subunits were pharmacologically distinct from those observed in oocytes co-injected with transcripts encoding the $\alpha_{1D}$, $\alpha_2$ and $\beta$ subunits. Oocytes injected with transcripts encoding the $\alpha_2$ and $\beta$ subunits displayed inward barium currents that were insensitive to Bay K 8644 (n=11). Nifedipine sensitivity was difficult to measure because of the holding potential sensitivity of nifedipine and the current observed in oocytes injected with transcripts encoding the $\alpha_2$ and $\beta$ subunits. Nevertheless, two oocytes that were co-injected with transcripts encoding the $\alpha_2$ and $\beta$ subunits displayed measurable (25 to 45 nA) inward barium currents when depolarized from a holding potential of −50 mV. These currents were insensitive to nifedipine (5 to 10 μM). The inward barium currents in oocytes injected with transcripts encoding the $\alpha_2$ and $\beta$ subunits showed the same sensitivity to heavy metals as the currents detected in oocytes injected with transcripts encoding the $\alpha_{1D}$, $\alpha_2$ and $\beta$ subunits.

The inward barium current detected in oocytes injected with transcripts encoding the human neuronal $\alpha_2$ and $\beta$ subunits has pharmacological and biophysical properties that resemble calcium currents in uninjected Xenopus oocytes. Because the amino acids of this human neuronal calcium channel $\beta$ subunit lack hydrophobic segments capable of forming transmembrane domains, it is unlikely that recombinant $\beta$ subunits alone can form an ion channel. It is more probable that a homologous endogenous $\alpha_1$ subunit exists in oocytes and that the activity mediated by such an $\alpha_1$ subunit is enhanced by expression of a human neuronal $\beta$ subunit.

While the invention has been described with some specificity, modifications apparent to those with ordinary skill in the art may be made without departing from the scope of the invention. Since such modifications will be apparent to those of skill in the art, it is intended that this invention be limited only by the scope of the appended claims.

What is claimed is:

1. An isolated DNA molecule, comprising a sequence of nucleotides that encodes an $\alpha_{1B}$-subunit of human calcium channel, wherein:

the sequence of nucleotides encoding the $\alpha_{1B}$-subunit is selected from the group consisting of:

(a) a sequence of nucleotides that encodes a naturally-occurring human $\alpha_{1B}$-subunit and comprises the sequence of nucleotides set forth in SEQ ID No. 7 or 8;

(b) a sequence of nucleotides that encodes an $\alpha_{1B}$-subunit, wherein:

the DNA molecule comprising this sequence hybridizes under conditions of high stringency to DNA that if fully complementary to an mRNA transcript native to a human cell; and the transcript: (i) encodes an $\alpha_{1B}$-subunit, (ii) comprises the sequence of nucleotides set forth in SEQ ID No. 8 or 7 in which T residues are replaced by U, and (iii) hybridizes under conditions of high stringency to any probe containing at least about 14 contiguous bases from the coding portion the sequence of nucleotides that encodes the $\alpha_{1B}$-subunit;

(c) a sequence of nucleotides that encodes an $\alpha_1$-subunit that comprises the sequence of amino acids of the $\alpha_1$-subunit set forth in SEQ ID NO. 47 or SEQ ID NO. 48; and (d) a sequence of nucleotides comprising degenerate codons with sequence of (b).

2. A cultured eukaryotic cell, comprising heterologous DNA that encodes a human calcium channel $\alpha_1$-subunit encoded by the DNA of claim 1, wherein the cell is a mammalian cell or yeast cell.

3. The eukaryotic cell of claim 2, further comprising additional DNA encoding at least one subunit selected from the group consisting of a human calcium channel $\beta$-subunit, a human calcium channel $\alpha_2$-subunit and a $\gamma$-subunit of a human calcium channel, wherein:

the $\alpha_2$-subunit is a human calcium channel $\alpha_2$-subunit that has an amino acid sequence set forth in SEQ ID NO. 53, 54, 55 or 56 or is an $\alpha_{2a}$, $\alpha_{2c}$, $\alpha_{2d}$, or an $\alpha_{2e}$ subtype, is encoded by DNA that is capable of hybridizing under conditions of high stringency with DNA that is fully complementary to an mRNA transcript native to a human cell that encodes one of the aforesaid human calcium channel $\alpha_2$ subunits having an amino acid sequence set forth in SEQ ID NO. 53, 54, 55 or 56 such that any probe that contains at least 14 contiguous bases from the coding portion of the DNA that encodes the $\alpha_{2a}$-subunit $\alpha_{2c}$-subunit, or $\alpha_{2e}$-subunit hybridizes under conditions of high stringency to the DNA that is fully complementary to the mRNA transcript native to a human cell that encodes any of the aforesaid subunits; and the $\beta$-subunit is selected from the group consisting of
a $\beta$-subunit comprising the amino acids set forth in SEQ ID NO. 40,
a $\beta$-subunit comprising the amino acids set forth in SEQ ID NO. 41,
a $\beta$-subunit comprising the amino acids set forth in SEQ ID NO. 42,
a $\beta$-subunit comprising the amino acids set forth in SEQ ID NO. 43,
a $\beta$-subunit comprising the amino acids set forth in SEQ ID NO. 44, and a human calcium channel $\beta$ subunit encoded by DNA capable of hybridizing under conditions of high stringency with DNA that is fully complementary to an mRNA transcript native to a human cell that encodes one of the aforesaid $\beta$-subunits such that any probe that contains at least 14 contiguous bases from the coding portion of the DNA that encodes the $\beta$-subunit hybridizes under conditions of high stringency to the DNA that is fully complementary to the mRNA transcript; and the $\gamma$-subunit comprises amino acids set forth in SEQ ID No. 57, or is a human calcium channel $\gamma$-subunit encoded by DNA capable of hybridizing under conditions of high stringency with DNA that is fully complementary to an mRNA transcript native to a human cell that a $\gamma$-subunit, such that any probe that contains at least 14 contiguous bases from the coding portion of the DNA that encodes the $\gamma$-subunit hybridizes under conditions of high stringency to the DNA that is fully complementary to the mRNA transcript.

4. The eukaryotic cell of claim 2, further comprising additional DNA encoding at least one subunit selected from the group consisting of a human calcium channel $\beta$-subunit, a human calcium channel $\alpha_{2b}$-subunit and a $\gamma$-subunit of a human calcium channel, wherein:

the $\alpha_{2b}$-subunit is a human calcium channel $\alpha_2$-subunit that has an amino acid sequence set forth in SEQ ID NO. 52 or is encoded by DNA that is capable of hybridizing under conditions of high stringency with DNA that is fully complementary to an mRNA transcript native to a human cell that encodes the aforesaid human calcium channel $\alpha_{2b}$ subunit, such that any probe that contains at least 14 contiguous bases from the coding portion of the DNA that encodes the $\alpha_{2b}$-subunit hybridizes under conditions of high stringency to the DNA that is fully complementary to the mRNA transcript native to a human cell that encodes any of the aforesaid subunits; and the $\beta$-subunit is selected from the group consisting of
a $\beta$-subunit comprising the amino acids set forth in SEQ ID NO. 40,
a $\beta$-subunit comprising the amino acids set forth in SEQ ID NO. 41,
a $\beta$-subunit comprising the amino acids set forth in SEQ ID NO. 42, a β-subunit comprising the amino acids set forth in SEQ ID NO. 43, a β-subunit comprising the amino acids set forth in SEQ ID NO. 44, and a human calcium channel β subunit encoded by DNA capable of hybridizing under conditions of high stringency with DNA that is fully complementary to an mRNA transcript native to a human cell that encodes one of the aforesaid β-subunits such that any probe that contains at least 14 contiguous bases from the coding portion of the DNA that encodes the β-subunit hybridizes under conditions of high stringency to the DNA that is fully complementary to the mRNA transcript; and the γ-subunit comprises amino acids set forth in SEQ ID No. 57, or is a human calcium channel γ-subunit encoded by DNA capable of hybridizing under conditions of high stringency with DNA that is fully complementary to an mRNA transcript native to a human cell that a γ-subunit, such that any probe that contains at least 14 contiguous bases from the coding portion of the DNA that encodes the γ-subunit hybridizes under conditions of high stringency to the DNA that is fully complementary to the mRNA transcript.

5. The eukaryotic cell of claim 3, wherein the additional DNA comprises DNA encoding an $\alpha_2$-subunit of a human calcium channel selected from an $\alpha_{2a}$, $\alpha_{2c}$, $\alpha_{2d}$ and $\alpha_{2e}$ subunit.

6. The eukaryotic cell of claim 3, wherein the additional DNA comprises DNA encoding a γ-subunit of a human calcium channel.

7. The eukaryotic cell of claim 3, that has a functional heterologous voltage dependent calcium channel that contains at least one subunit encoded by the heterologous DNA, wherein the at least one subunit is an $\alpha_{1B}$-subunit of a human calcium channel.

8. The eukaryotic cell of claim 3 selected from the group consisting of an HEK 293 cell, a Chinese hamster ovary cell, an African green monkey cell, and a mouse L cell.

9. The eukaryotic cell of claim 7 selected from the group consisting of an HEK 293 cell, a Chinese hamster ovary cell, an African green monkey cell, and a mouse L cell.

10. The DNA molecule of claim 1, comprising the sequence of amino acids set forth in SEQ ID NO. 47.

11. The DNA molecule of claim 1, comprising the sequence of amino acids set forth in SEQ ID NO. 48.

12. The DNA molecule of claim 1, comprising the sequence of nucleotides set forth in SEQ ID NO. 7.

13. The DNA molecule of claim 1, comprising the sequence of nucleotides set forth in SEQ ID NO. 8.

14. The eukaryotic cell of claim 2, comprising a heterologous calcium channel receptor.

15. An isolated eukaryotic cell with a functional, heterologous calcium channel, produced by a process, comprising:

introducing into the cell RNA into that is translatable in the cell to afford an $\alpha_1$-subunit of a human calcium channel, wherein the $\alpha_1$-subunit comprises an amino acid sequence encoded by the DNA molecule of claim 1.

16. An isolated eukaryotic cell with a functional, heterologous calcium channel, produced by a process, comprising:

introducing into the cell at least one RNA transcript selected from the group consisting of a first RNA that is translatable in said cell into an $\alpha_{1B}$-subunit of a human calcium channel, a second RNA which is translatable in said cell into a β-subunit of a human calcium channel, a third RNA which is translatable in said cell into an $\alpha_2$-subunit of a human calcium channel, and a fourth RNA which is translatable in said cell into a γ-subunit of a human calcium channel, wherein the cell is a mammalian cell, yeast cell or amphibian oocyte, wherein:

the $\alpha_1$-subunit comprises a sequence of amino acids encoded by the DNA molecule of claim 1;

the $\alpha_2$-subunit is a human calcium channel $\alpha_2$-subunit that has an amino acid sequence set forth in SEQ ID NO. 53, 54, 55 or 56, or is an $\alpha_{2a}$, $\alpha_{2c}$, $\alpha_{2d}$, or an $\alpha_{2e}$ subtype and is encoded by DNA that is capable of hybridizing under conditions of high stringency with DNA that is fully complementary to an mRNA transcript present in a human cell that encodes one of the aforesaid human calcium channel $\alpha_2$-subunits having an amino acid sequence set forth in any of the SEQ ID NOs. 53, 54, 55 or 56, such that any probe that contains at least 14 contiguous bases from the coding portion of the DNA that encodes the $\alpha_2$-subunit hybridizes under conditions of high stringency to the DNA that is fully complementary to the mRNA transcript present in a human cell;

the β-subunit is selected from the group consisting of a β-subunit comprising the amino acids set forth in SEQ ID NO. 40, a β-subunit comprising the amino acids set forth in SEQ ID NO. 41, a β-subunit comprising the amino acids set forth in SEQ ID NO. 42, a β-subunit comprising the amino acids set forth in SEQ ID NO. 43, a β-subunit comprising the amino acids set forth in SEQ ID NO. 44, and a human calcium channel β-subunit, wherein the β-subunit is encoded by DNA capable of hybridizing under conditions of high stringency with DNA that is fully complementary to an mRNA transcript present in a human cell that encodes one of the aforesaid β-subunits such that any probe that contains at least 14 contiguous bases from the coding portion of the DNA that encodes the β-subunit hybridizes under conditions of high stringency to the DNA that is fully complementary to the mRNA transcript present in a human cell that encodes any of the aforesaid β-subunits;

the γ-subunit comprises amino acids set forth in SEQ ID No. 57, or is a human calcium channel γ-subunit encoded by DNA capable of hybridizing under conditions of high stringency with DNA that is complementary to an mRNA transcript present in a human cell that comprises the sequence of nucleotides set forth in SEQ ID NO. 14 such that any probe that contains at least 14 contiguous bases from the coding portion of the DNA that encodes the γ-subunit hybridizes under conditions of high stringency to the DNA that is fully complementary to the mRNA transcript present in a human cell; and the only heterologous ion channels that are expressed by the cell are calcium channels.

17. An isolated eukaryotic cell with a functional, heterologous calcium channel, produced by a process, comprising introducing into the cell at least one RNA transcript selected from the group consisting of a first RNA that is translatable in said cell into an $\alpha_{1B}$-subunit of a human calcium channel, a second RNA which is translatable in said cell into a β-subunit of a human calcium channel, a third RNA which is translatable in said cell into an $\alpha_{2b}$-subunit of a human calcium channel, and a fourth RNA which is translatable in said cell into a γ-subunit of a human calcium channel, wherein the cell is a mammalian cell, yeast cell or amphibian oocyte, wherein:

the $\alpha_1$-subunit comprises a sequence of amino acids encoded by the DNA molecule of claim 52;

the $\alpha_{2b}$-subunit is a human calcium channel $\alpha_2$-subunit that has an amino acid sequence set forth in SEQ ID NO. 52 or is encoded by DNA that is capable of hybridizing under conditions of high stringency with DNA that is fully complementary to an mRNA transcript native to a human cell that encodes the aforesaid human calcium channel $\alpha_{2b}$ subunit, such that any probe that contains at least 14 contiguous bases from the coding portion of the DNA that encodes the $\alpha_{2b}$-subunit hybridizes under conditions of high stringency to the DNA that is fully complementary to the mRNA transcript native to a human cell that encodes any of the aforesaid subunits; and the β-subunit is selected from the group consisting of a β-subunit comprising the amino acids set forth in SEQ ID NO. 40, a β-subunit comprising the amino acids set forth in SEQ ID NO. 41, a β-subunit comprising the amino acids set forth in SEQ ID NO. 42, a β-subunit comprising the amino acids set forth in SEQ ID NO. 43, a β-subunit comprising the amino acids set forth in SEQ ID NO. 44, and a human calcium channel β-subunit, wherein the β-subunit is encoded by DNA capable of hybridizing under conditions of high stringency with DNA that is fully complementary to an mRNA transcript present in a human cell that encodes one of the aforesaid β-subunits such that any probe that contains at least 14 contiguous bases from the coding portion of the DNA that encodes the β-subunit hybridizes under conditions of high stringency to the DNA that is fully complementary to the mRNA transcript present in a human cell that encodes any of the aforesaid β-subunits;

the γ-subunit comprises amino acids set forth in SEQ ID No. 57, or is a human calcium channel γ-subunit encoded by DNA capable of hybridizing under conditions of high stringency with DNA that is complementary to an mRNA transcript present in a human cell that comprises the sequence of nucleotides set forth in SEQ ID NO. 14 such that any probe that contains at least 14 contiguous bases from the coding portion of the DNA that encodes the γ-subunit hybridizes under conditions of high stringency to the DNA that is fully complementary to the mRNA transcript present in a human cell; and the only heterologous ion channels that are expressed by the cell are calcium channels.

18. The eukaryotic cell of claim 4, that has a functional heterologous voltage dependent calcium channel that contains at least one subunit encoded by the heterologous DNA, wherein the at least one subunit is an $\alpha_{1B}$-subunit of a human calcium channel.

19. The eukaryotic cell of claim 4 selected from the group consisting of an HEK 293 cell, a Chinese hamster ovary cell, an African green monkey cell, and a mouse L cell.

20. The eukaryotic cell of claim 18 selected from the group consisting of an HEK 293 cell, a Chinese hamster ovary cell, an African green monkey cell, and a mouse L cell.

21. The eukaryotic cell of claim 4, wherein the additional DNA comprises DNA encoding a γ-subunit of a human calcium channel.

* * * * *

UNITED STATES PATENT AND TRADEMARK OFFICE
CERTIFICATE OF CORRECTION

PATENT NO. : 5,792,846
DATED : August 11, 1998
INVENTOR(S) : Harpold et al.

It is certified that error appears in the above-identified patent and that said Letters Patent is hereby corrected as shown below:

ON THE TITLE PAGE:

The following citations are to be added to Item [56] entitled Other Publications:

"Ruth, *et al.*, "Primary structure of the alpha-subunit of the DHP-sensitive calcium channel from skeletal muscle" Science 245:1115-1118 (1989)."

"Starr *et al.*, "Primary structure of a calcium channel that is highly expressed in the rat cerebellum" P.N.A.S. 88:5621-5625 (1991)."

"Pragnell *et al.*, "Cloning and tissue-specific expression of the brain calcium channel B-subunit." FEBS Letters, 29:253 (1991)."

"DeJongh *et al.*, "Subunits of purified calcium channels" J. Biol. Chem. 265:14738-14741 (1990)."

"Carbone *et al.*, "Ca currents in human neuroblastoma IMR32 cells: kinetics, permeability and pharmacology" Pfluegers Arch. 416:170-179 (1990). "

At column 29, line 8 replace "alc" with $-\alpha_{1c}-$

At Column 35, line 23 insert "Sequence ID No. 19 in which nt. 627 to 885 are not present" after —cells—.

UNITED STATES PATENT AND TRADEMARK OFFICE
CERTIFICATE OF CORRECTION

PATENT NO. : 5,792,846
DATED : August 11, 1998
INVENTOR(S) : Harpold et al.

It is certified that error appears in the above-identified patent and that said Letters Patent is hereby corrected as shown below:

IN THE CLAIMS:

Delete claim 17 and replace with the following claim:

—17. An isolated eukaryotic cell with a functional, heterologous calcium channel, produced by a process, comprising introducing into the cell at least one RNA transcript selected from the group consisting of a first RNA that is translatable in said cell into an $\alpha_{1B}$-subunit of a human calcium channel, a second RNA which is translatable in said cell into a $\beta$-subunit of a human calcium channel, a third RNA which is translatable in said cell into an $\alpha_{2b}$-subunit of a human calcium channel, and a fourth RNA which is translatable in said cell into a $\gamma$-subunit of a human calcium channel, wherein the cell is a mammalian cell, yeast cell or amphibian öocyte, wherein:

the $\alpha_1$-subunit comprises a sequence of amino acids encoded by the DNA molecule of claim 1;

the $\alpha_{2b}$-subunit is a human calcium channel $\alpha_2$-subunit that has an amino acid sequence set forth in SEQ ID NO. 52 or is encoded by DNA that is capable of hybridizing under conditions of high stringency with DNA that is fully complementary to an mRNA transcript native to a human cell and that encodes the aforesaid human calcium channel $\alpha_{2b}$ subunit, such that any probe that contains at least 14 contiguous bases from the coding portion of the DNA that encodes the $\alpha_{2b}$-subunit hybridizes under conditions of high stringency to the DNA that is fully complementary to the mRNA transcript native to a human cell that encodes any of the aforesaid subunits; and

UNITED STATES PATENT AND TRADEMARK OFFICE
CERTIFICATE OF CORRECTION

PATENT NO. : 5,792,846

DATED : August 11, 1998

INVENTOR(S) : Harpold et al.

Page 3 of 4

It is certified that error appears in the above-identified patent and that said Letters Patent is hereby corrected as shown below:

the β-subunit is selected from the group consisting of a β-subunit comprising the amino acids set forth in SEQ ID NO. 40, a β-subunit comprising the amino acids set forth in SEQ ID NO. 41, a β-subunit comprising the amino acids set forth in SEQ ID NO. 42, a β-subunit comprising the amino acids set forth in SEQ ID NO. 43, a β-subunit comprising the amino acids set forth in SEQ ID NO. 44, and a human calcium channel β-subunit, wherein the β-subunit is encoded by DNA capable of hybridizing under conditions of high stringency with DNA that is fully complementary to an mRNA transcript present in a human cell that encodes one of the aforesaid β-subunits such that any probe that contains at least 14 contiguous bases from the coding portion of the DNA that encodes the β-subunit hybridizes under conditions of high stringency to the DNA that is fully complementary to the mRNA transcript present in a human cell that encodes any of the aforesaid β-subunits;

UNITED STATES PATENT AND TRADEMARK OFFICE
CERTIFICATE OF CORRECTION

PATENT NO. : 5,792,846
DATED : August 11, 1998
INVENTOR(S) : Harpold et al.

It is certified that error appears in the above-identified patent and that said Letters Patent is hereby corrected as shown below:

the γ-subunit comprises amino acids set forth in SEQ ID No. 57, or is a human calcium channel γ-subunit encoded by DNA capable of hybridizing under conditions of high stringency with DNA that is complementary to an mRNA transcript present in a human cell that comprises the sequence of nucleotides set forth in SEQ ID NO. 14 such that any probe that contains at least 14 contiguous bases from the coding portion of the DNA that encodes the γ-subunit hybridizes under conditions of high stringency to the DNA that is fully complementary to the mRNA transcript present in a human cell; and the only heterologous ion channels that are expressed by the cell are calcium channels.--

Signed and Sealed this

Twenty-eighth Day of September, 1999

Attest:

Q. TODD DICKINSON

*Attesting Officer*   Acting Commissioner of Patents and Trademarks

SEQUENCE LISTING ( 1 ) GENERAL INFORMATION:

( i i i ) NUMBER OF SEQUENCES: 57

( 2 ) INFORMATION FOR SEQ ID NO:1:

( i ) SEQUENCE CHARACTERISTICS:
        ( A ) LENGTH: 7635 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 511..6996

( i x ) FEATURE:
        ( A ) NAME/KEY: 5'UTR
        ( B ) LOCATION: 1..510

( i x ) FEATURE:
        ( A ) NAME/KEY: 3'UTR
        ( B ) LOCATION: 6994..7635

( x i ) SEQUENCE DESCRIPTION: SEQ ID NO:1:

```
GGGCGAGCGC  CTCCGTCCCC  GGATGTGAGC  TCCGGCTGCC  CGCGGTCCCG  AGCCAGCGGC        60

GCGCGGGCGG  CGGCGGCGGG  CACCGGGCAC  CGCGGCGGGC  GGGCAGACGG  GCGGGCATGG       120

GGGAGCGCC   GAGCGGCCCC  GGCGGCCGGG  CCGGCATCAC  CGCGGCGTCT  CTCCGCTAGA       180

GGAGGGGACA  AGCCAGTTCT  CCTTTGCAGC  AAAAAATTAC  ATGTATATAT  TATTAAGATA       240

ATATATACAT  TGGATTTTAT  TTTTTAAAA   AGTTTATTTT  GCTCCATTTT  TGAAAAAGAG       300

AGAGCTTGGG  TGGCGAGCGG  TTTTTTTTA   AAATCAATTA  TCCTTATTTT  CTGTTATTTG       360

TCCCCGTCCC  TCCCCACCCC  CCTGCTGAAG  CGAGAATAAG  GGCAGGGACC  GCGGCTCCTA       420

CCTCTTGGTG  ATCCCCTTCC  CCATTCCGCC  CCCGCCCCAA  CGCCCAGCAC  AGTGCCCTGC       480

ACACAGTAGT  CGCTCAATAA  ATGTTCGTGG  ATG ATG ATG ATG ATG ATG ATG AAA         534
                                    Met Met Met Met Met Met Met Lys
                                     1               5

AAA ATG CAG CAT CAA CGG CAG CAG CAA GCG GAC CAC GCG AAC GAG GCA             582
```

-continued

| | | | | | | | | | | | | | | | | |
|---|---|---|---|---|---|---|---|---|---|---|---|---|---|---|---|---|
| Lys | Met | Gln | His | Gln | Arg | Gln | Gln | Gln | Ala | Asp | His | Ala | Asn | Glu | Ala | |
| | 10 | | | | 15 | | | | | 20 | | | | | | |
| AAC | TAT | GCA | AGA | GGC | ACC | AGA | CTT | CCT | CTT | TCT | GGT | GAA | GGA | CCA | ACT | 630 |
| Asn | Tyr | Ala | Arg | Gly | Thr | Arg | Leu | Pro | Leu | Ser | Gly | Glu | Gly | Pro | Thr | |
| 25 | | | | | 30 | | | | | 35 | | | | | 40 | |
| TCT | CAG | CCG | AAT | AGC | TCC | AAG | CAA | ACT | GTC | CTG | TCT | TGG | CAA | GCT | GCA | 678 |
| Ser | Gln | Pro | Asn | Ser | Ser | Lys | Gln | Thr | Val | Leu | Ser | Trp | Gln | Ala | Ala | |
| | | | | 45 | | | | | 50 | | | | | 55 | | |
| ATC | GAT | GCT | GCT | AGA | CAG | GCC | AAG | GCT | GCC | CAA | ACT | ATG | AGC | ACC | TCT | 726 |
| Ile | Asp | Ala | Ala | Arg | Gln | Ala | Lys | Ala | Ala | Gln | Thr | Met | Ser | Thr | Ser | |
| | | | 60 | | | | 65 | | | | | 70 | | | | |
| GCA | CCC | CCA | CCT | GTA | GGA | TCT | CTC | TCC | CAA | AGA | AAA | CGT | CAG | CAA | TAC | 774 |
| Ala | Pro | Pro | Pro | Val | Gly | Ser | Leu | Ser | Gln | Arg | Lys | Arg | Gln | Gln | Tyr | |
| | | 75 | | | | | 80 | | | | | 85 | | | | |
| GCC | AAG | AGC | AAA | AAA | CAG | GGT | AAC | TCG | TCC | AAC | AGC | CGA | CCT | GCC | CGC | 822 |
| Ala | Lys | Ser | Lys | Lys | Gln | Gly | Asn | Ser | Ser | Asn | Ser | Arg | Pro | Ala | Arg | |
| | 90 | | | | | 95 | | | | | 100 | | | | | |
| GCC | CTT | TTC | TGT | TTA | TCA | CTC | AAT | AAC | CCC | ATC | CGA | AGA | GCC | TGC | ATT | 870 |
| Ala | Leu | Phe | Cys | Leu | Ser | Leu | Asn | Asn | Pro | Ile | Arg | Arg | Ala | Cys | Ile | |
| 105 | | | | | 110 | | | | | 115 | | | | | 120 | |
| AGT | ATA | GTG | GAA | TGG | AAA | CCA | TTT | GAC | ATA | TTT | ATA | TTA | TTG | GCT | ATT | 918 |
| Ser | Ile | Val | Glu | Trp | Lys | Pro | Phe | Asp | Ile | Phe | Ile | Leu | Leu | Ala | Ile | |
| | | | | 125 | | | | | 130 | | | | | 135 | | |
| TTT | GCC | AAT | TGT | GTG | GCC | TTA | GCT | ATT | TAC | ATC | CCA | TTC | CCT | GAA | GAT | 966 |
| Phe | Ala | Asn | Cys | Val | Ala | Leu | Ala | Ile | Tyr | Ile | Pro | Phe | Pro | Glu | Asp | |
| | | | 140 | | | | | 145 | | | | | 150 | | | |
| GAT | TCT | AAT | TCA | ACA | AAT | CAT | AAC | TTG | GAA | AAA | GTA | GAA | TAT | GCC | TTC | 1014 |
| Asp | Ser | Asn | Ser | Thr | Asn | His | Asn | Leu | Glu | Lys | Val | Glu | Tyr | Ala | Phe | |
| | | 155 | | | | | 160 | | | | | 165 | | | | |
| CTG | ATT | ATT | TTT | ACA | GTC | GAG | ACA | TTT | TTG | AAG | ATT | ATA | GCG | TAT | GGA | 1062 |
| Leu | Ile | Ile | Phe | Thr | Val | Glu | Thr | Phe | Leu | Lys | Ile | Ile | Ala | Tyr | Gly | |
| | 170 | | | | | 175 | | | | | 180 | | | | | |
| TTA | TTG | CTA | CAT | CCT | AAT | GCT | TAT | GTT | AGG | AAT | GGA | TGG | AAT | TTA | CTG | 1110 |
| Leu | Leu | Leu | His | Pro | Asn | Ala | Tyr | Val | Arg | Asn | Gly | Trp | Asn | Leu | Leu | |
| 185 | | | | | 190 | | | | | 195 | | | | | 200 | |
| GAT | TTT | GTT | ATA | GTA | ATA | GTA | GGA | TTG | TTT | AGT | GTA | ATT | TTG | GAA | CAA | 1158 |
| Asp | Phe | Val | Ile | Val | Ile | Val | Gly | Leu | Phe | Ser | Val | Ile | Leu | Glu | Gln | |
| | | | | 205 | | | | | 210 | | | | | 215 | | |
| TTA | ACC | AAA | GAA | ACA | GAA | GGC | GGG | AAC | CAC | TCA | AGC | GGC | AAA | TCT | GGA | 1206 |
| Leu | Thr | Lys | Glu | Thr | Glu | Gly | Gly | Asn | His | Ser | Ser | Gly | Lys | Ser | Gly | |
| | | | 220 | | | | | 225 | | | | | 230 | | | |
| GGC | TTT | GAT | GTC | AAA | GCC | CTC | CGT | GCC | TTT | CGA | GTG | TTG | CGA | CCA | CTT | 1254 |
| Gly | Phe | Asp | Val | Lys | Ala | Leu | Arg | Ala | Phe | Arg | Val | Leu | Arg | Pro | Leu | |
| | | 235 | | | | | 240 | | | | | 245 | | | | |
| CGA | CTA | GTG | TCA | GGA | GTG | CCC | AGT | TTA | CAA | GTT | GTC | CTG | AAC | TCC | ATT | 1302 |
| Arg | Leu | Val | Ser | Gly | Val | Pro | Ser | Leu | Gln | Val | Val | Leu | Asn | Ser | Ile | |
| | 250 | | | | | 255 | | | | | 260 | | | | | |
| ATA | AAA | GCC | ATG | GTT | CCC | CTC | CTT | CAC | ATA | GCC | CTT | TTG | GTA | TTA | TTT | 1350 |
| Ile | Lys | Ala | Met | Val | Pro | Leu | Leu | His | Ile | Ala | Leu | Leu | Val | Leu | Phe | |
| 265 | | | | | 270 | | | | | 275 | | | | | 280 | |
| GTA | ATC | ATA | ATC | TAT | GCT | ATT | ATA | GGA | TTG | GAA | CTT | TTT | ATT | GGA | AAA | 1398 |
| Val | Ile | Ile | Ile | Tyr | Ala | Ile | Ile | Gly | Leu | Glu | Leu | Phe | Ile | Gly | Lys | |
| | | | | 285 | | | | | 290 | | | | | 295 | | |
| ATG | CAC | AAA | ACA | TGT | TTT | TTT | GCT | GAC | TCA | GAT | ATC | GTA | GCT | GAA | GAG | 1446 |
| Met | His | Lys | Thr | Cys | Phe | Phe | Ala | Asp | Ser | Asp | Ile | Val | Ala | Glu | Glu | |
| | | | 300 | | | | | 305 | | | | | 310 | | | |
| GAC | CCA | GCT | CCA | TGT | GCG | TTC | TCA | GGG | AAT | GGA | CGC | CAG | TGT | ACT | GCC | 1494 |
| Asp | Pro | Ala | Pro | Cys | Ala | Phe | Ser | Gly | Asn | Gly | Arg | Gln | Cys | Thr | Ala | |
| | | 315 | | | | | 320 | | | | | 325 | | | | |
| AAT | GGC | ACG | GAA | TGT | AGG | AGT | GGC | TGG | GTT | GGC | CCG | AAC | GGA | GGC | ATC | 1542 |

-continued

| | | | | | | | | | | | | | | | |
|---|---|---|---|---|---|---|---|---|---|---|---|---|---|---|---|
| Asn | Gly | Thr | Glu | Cys | Arg | Ser | Gly | Trp | Val | Gly | Pro | Asn | Gly | Gly | Ile |
| | 330 | | | | | 335 | | | | 340 | | | | | |

| ACC | AAC | TTT | GAT | AAC | TTT | GCC | TTT | GCC | ATG | CTT | ACT | GTG | TTT | CAG | TGC | 1590 |
|---|---|---|---|---|---|---|---|---|---|---|---|---|---|---|---|---|
| Thr | Asn | Phe | Asp | Asn | Phe | Ala | Phe | Ala | Met | Leu | Thr | Val | Phe | Gln | Cys | |
| 345 | | | | | 350 | | | | | 355 | | | | | 360 | |

| ATC | ACC | ATG | GAG | GGC | TGG | ACA | GAC | GTG | CTC | TAC | TGG | ATG | AAT | GAT | GCT | 1638 |
|---|---|---|---|---|---|---|---|---|---|---|---|---|---|---|---|---|
| Ile | Thr | Met | Glu | Gly | Trp | Thr | Asp | Val | Leu | Tyr | Trp | Met | Asn | Asp | Ala | |
| | | | | 365 | | | | | 370 | | | | | 375 | | |

| ATG | GGA | TTT | GAA | TTG | CCC | TGG | GTG | TAT | TTT | GTC | AGT | CTC | GTC | ATC | TTT | 1686 |
|---|---|---|---|---|---|---|---|---|---|---|---|---|---|---|---|---|
| Met | Gly | Phe | Glu | Leu | Pro | Trp | Val | Tyr | Phe | Val | Ser | Leu | Val | Ile | Phe | |
| | | | 380 | | | | | 385 | | | | | 390 | | | |

| GGG | TCA | TTT | TTC | GTA | CTA | AAT | CTT | GTA | CTT | GGT | GTA | TTG | AGC | GGA | GAA | 1734 |
|---|---|---|---|---|---|---|---|---|---|---|---|---|---|---|---|---|
| Gly | Ser | Phe | Phe | Val | Leu | Asn | Leu | Val | Leu | Gly | Val | Leu | Ser | Gly | Glu | |
| | | 395 | | | | | 400 | | | | | 405 | | | | |

| TTC | TCA | AAG | GAA | AGA | GAG | AAG | GCA | AAA | GCA | CGG | GGA | GAT | TTC | CAG | AAG | 1782 |
|---|---|---|---|---|---|---|---|---|---|---|---|---|---|---|---|---|
| Phe | Ser | Lys | Glu | Arg | Glu | Lys | Ala | Lys | Ala | Arg | Gly | Asp | Phe | Gln | Lys | |
| | | 410 | | | | | 415 | | | | | 420 | | | | |

| CTC | CGG | GAG | AAG | CAG | CAG | CTG | GAG | GAG | GAT | CTA | AAG | GGC | TAC | TTG | GAT | 1830 |
|---|---|---|---|---|---|---|---|---|---|---|---|---|---|---|---|---|
| Leu | Arg | Glu | Lys | Gln | Gln | Leu | Glu | Glu | Asp | Leu | Lys | Gly | Tyr | Leu | Asp | |
| 425 | | | | | 430 | | | | | 435 | | | | | 440 | |

| TGG | ATC | ACC | CAA | GCT | GAG | GAC | ATC | GAT | CCG | GAG | AAT | GAG | GAA | GAA | GGA | 1878 |
|---|---|---|---|---|---|---|---|---|---|---|---|---|---|---|---|---|
| Trp | Ile | Thr | Gln | Ala | Glu | Asp | Ile | Asp | Pro | Glu | Asn | Glu | Glu | Glu | Gly | |
| | | | | 445 | | | | | 450 | | | | | 455 | | |

| GGA | GAG | GAA | GGC | AAA | CGA | AAT | ACT | AGC | ATG | CCC | ACC | AGC | GAG | ACT | GAG | 1926 |
|---|---|---|---|---|---|---|---|---|---|---|---|---|---|---|---|---|
| Gly | Glu | Glu | Gly | Lys | Arg | Asn | Thr | Ser | Met | Pro | Thr | Ser | Glu | Thr | Glu | |
| | | | 460 | | | | | 465 | | | | | 470 | | | |

| TCT | GTG | AAC | ACA | GAG | AAC | GTC | AGC | GGT | GAA | GGC | GAG | AAC | CGA | GGC | TGC | 1974 |
|---|---|---|---|---|---|---|---|---|---|---|---|---|---|---|---|---|
| Ser | Val | Asn | Thr | Glu | Asn | Val | Ser | Gly | Glu | Gly | Glu | Asn | Arg | Gly | Cys | |
| | | 475 | | | | | 480 | | | | | 485 | | | | |

| TGT | GGA | AGT | CTC | TGT | CAA | GCC | ATC | TCA | AAA | TCC | AAA | CTC | AGC | CGA | CGC | 2022 |
|---|---|---|---|---|---|---|---|---|---|---|---|---|---|---|---|---|
| Cys | Gly | Ser | Leu | Cys | Gln | Ala | Ile | Ser | Lys | Ser | Lys | Leu | Ser | Arg | Arg | |
| | 490 | | | | | 495 | | | | | 500 | | | | | |

| TGG | CGT | CGC | TGG | AAC | CGA | TTC | AAT | CGC | AGA | AGA | TGT | AGG | GCC | GCC | GTG | 2070 |
|---|---|---|---|---|---|---|---|---|---|---|---|---|---|---|---|---|
| Trp | Arg | Arg | Trp | Asn | Arg | Phe | Asn | Arg | Arg | Arg | Cys | Arg | Ala | Ala | Val | |
| 505 | | | | | 510 | | | | | 515 | | | | | 520 | |

| AAG | TCT | GTC | ACG | TTT | TAC | TGG | CTG | GTT | ATC | GTC | CTG | GTG | TTT | CTG | AAC | 2118 |
|---|---|---|---|---|---|---|---|---|---|---|---|---|---|---|---|---|
| Lys | Ser | Val | Thr | Phe | Tyr | Trp | Leu | Val | Ile | Val | Leu | Val | Phe | Leu | Asn | |
| | | | | 525 | | | | | 530 | | | | | 535 | | |

| ACC | TTA | ACC | ATT | TCC | TCT | GAG | CAC | TAC | AAT | CAG | CCA | GAT | TGG | TTG | ACA | 2166 |
|---|---|---|---|---|---|---|---|---|---|---|---|---|---|---|---|---|
| Thr | Leu | Thr | Ile | Ser | Ser | Glu | His | Tyr | Asn | Gln | Pro | Asp | Trp | Leu | Thr | |
| | | | 540 | | | | | 545 | | | | | 550 | | | |

| CAG | ATT | CAA | GAT | ATT | GCC | AAC | AAA | GTC | CTC | TTG | GCT | CTG | TTC | ACC | TGC | 2214 |
|---|---|---|---|---|---|---|---|---|---|---|---|---|---|---|---|---|
| Gln | Ile | Gln | Asp | Ile | Ala | Asn | Lys | Val | Leu | Leu | Ala | Leu | Phe | Thr | Cys | |
| | | 555 | | | | | 560 | | | | | 565 | | | | |

| GAG | ATG | CTG | GTA | AAA | ATG | TAC | AGC | TTG | GGC | CTC | CAA | GCA | TAT | TTC | GTC | 2262 |
|---|---|---|---|---|---|---|---|---|---|---|---|---|---|---|---|---|
| Glu | Met | Leu | Val | Lys | Met | Tyr | Ser | Leu | Gly | Leu | Gln | Ala | Tyr | Phe | Val | |
| 570 | | | | | 575 | | | | | 580 | | | | | | |

| TCT | CTT | TTC | AAC | CGG | TTT | GAT | TGC | TTC | GTG | GTG | TGT | GGT | GGA | ATC | ACT | 2310 |
|---|---|---|---|---|---|---|---|---|---|---|---|---|---|---|---|---|
| Ser | Leu | Phe | Asn | Arg | Phe | Asp | Cys | Phe | Val | Val | Cys | Gly | Gly | Ile | Thr | |
| 585 | | | | | 590 | | | | | 595 | | | | | 600 | |

| GAG | ACG | ATC | TTG | GTG | GAA | CTG | GAA | ATC | ATG | TCT | CCC | CTG | GGG | ATC | TCT | 2358 |
|---|---|---|---|---|---|---|---|---|---|---|---|---|---|---|---|---|
| Glu | Thr | Ile | Leu | Val | Glu | Leu | Glu | Ile | Met | Ser | Pro | Leu | Gly | Ile | Ser | |
| | | | | 605 | | | | | 610 | | | | | 615 | | |

| GTG | TTT | CGG | TGT | GTG | CGC | CTC | TTA | AGA | ATC | TTC | AAA | GTG | ACC | AGG | CAC | 2406 |
|---|---|---|---|---|---|---|---|---|---|---|---|---|---|---|---|---|
| Val | Phe | Arg | Cys | Val | Arg | Leu | Leu | Arg | Ile | Phe | Lys | Val | Thr | Arg | His | |
| | | | 620 | | | | | 625 | | | | | 630 | | | |

| TGG | ACT | TCC | CTG | AGC | AAC | TTA | GTG | GCA | TCC | TTA | TTA | AAC | TCC | ATG | AAG | 2454 |
|---|---|---|---|---|---|---|---|---|---|---|---|---|---|---|---|---|
| Trp | Thr | Ser | Leu | Ser | Asn | Leu | Val | Ala | Ser | Leu | Leu | Asn | Ser | Met | Lys | |
| | | 635 | | | | | 640 | | | | | 645 | | | | |

| TCC | ATC | GCT | TCG | CTG | TTG | CTT | CTG | CTT | TTT | CTC | TTC | ATT | ATC | ATC | TTT | 2502 |

| | | | | | | | | | | | | | | | | |
|---|---|---|---|---|---|---|---|---|---|---|---|---|---|---|---|---|
| Ser | Ile | Ala | Ser | Leu | Leu | Leu | Leu | Leu | Phe | Leu | Phe | Ile | Ile | Ile | Phe | |
| 650 | | | | | 655 | | | | | 660 | | | | | | |
| TCC | TTG | CTT | GGG | ATG | CAG | CTG | TTT | GGC | GGC | AAG | TTT | AAT | TTT | GAT | GAA | 2550 |
| Ser | Leu | Leu | Gly | Met | Gln | Leu | Phe | Gly | Gly | Lys | Phe | Asn | Phe | Asp | Glu | |
| 665 | | | | 670 | | | | | 675 | | | | | | 680 | |
| ACG | CAA | ACC | AAG | CGG | AGC | ACC | TTT | GAC | AAT | TTC | CCT | CAA | GCA | CTT | CTC | 2598 |
| Thr | Gln | Thr | Lys | Arg | Ser | Thr | Phe | Asp | Asn | Phe | Pro | Gln | Ala | Leu | Leu | |
| | | | | 685 | | | | | 690 | | | | | 695 | | |
| ACA | GTG | TTC | CAG | ATC | CTG | ACA | GGC | GAA | GAC | TGG | AAT | GCT | GTG | ATG | TAC | 2646 |
| Thr | Val | Phe | Gln | Ile | Leu | Thr | Gly | Glu | Asp | Trp | Asn | Ala | Val | Met | Tyr | |
| | | | 700 | | | | | 705 | | | | | 710 | | | |
| GAT | GGC | ATC | ATG | GCT | TAC | GGG | GGC | CCA | TCC | TCT | TCA | GGA | ATG | ATC | GTC | 2694 |
| Asp | Gly | Ile | Met | Ala | Tyr | Gly | Gly | Pro | Ser | Ser | Ser | Gly | Met | Ile | Val | |
| | | 715 | | | | | 720 | | | | | 725 | | | | |
| TGC | ATC | TAC | TTC | ATC | ATC | CTC | TTC | ATT | TGT | GGT | AAC | TAT | ATT | CTA | CTG | 2742 |
| Cys | Ile | Tyr | Phe | Ile | Ile | Leu | Phe | Ile | Cys | Gly | Asn | Tyr | Ile | Leu | Leu | |
| | 730 | | | | | 735 | | | | | 740 | | | | | |
| AAT | GTC | TTC | TTG | GCC | ATC | GCT | GTA | GAC | AAT | TTG | GCT | GAT | GCT | GAA | AGT | 2790 |
| Asn | Val | Phe | Leu | Ala | Ile | Ala | Val | Asp | Asn | Leu | Ala | Asp | Ala | Glu | Ser | |
| 745 | | | | | 750 | | | | | 755 | | | | | 760 | |
| CTG | AAC | ACT | GCT | CAG | AAA | GAA | GAA | GCG | GAA | GAA | AAG | GAG | AGG | AAA | AAG | 2838 |
| Leu | Asn | Thr | Ala | Gln | Lys | Glu | Glu | Ala | Glu | Glu | Lys | Glu | Arg | Lys | Lys | |
| | | | | 765 | | | | | 770 | | | | | 775 | | |
| ATT | GCC | AGA | AAA | GAG | AGC | CTA | GAA | AAT | AAA | AAG | AAC | AAC | AAA | CCA | GAA | 2886 |
| Ile | Ala | Arg | Lys | Glu | Ser | Leu | Glu | Asn | Lys | Lys | Asn | Asn | Lys | Pro | Glu | |
| | | | 780 | | | | | 785 | | | | | 790 | | | |
| GTC | AAC | CAG | ATA | GCC | AAC | AGT | GAC | AAC | AAG | GTT | ACA | ATT | GAT | GAC | TAT | 2934 |
| Val | Asn | Gln | Ile | Ala | Asn | Ser | Asp | Asn | Lys | Val | Thr | Ile | Asp | Asp | Tyr | |
| | | | 795 | | | | | 800 | | | | | 805 | | | |
| AGA | GAA | GAG | GAT | GAA | GAC | AAG | GAC | CCC | TAT | CCG | CCT | TGC | GAT | GTG | CCA | 2982 |
| Arg | Glu | Glu | Asp | Glu | Asp | Lys | Asp | Pro | Tyr | Pro | Pro | Cys | Asp | Val | Pro | |
| | | 810 | | | | | 815 | | | | | 820 | | | | |
| GTA | GGG | GAA | GAG | GAA | GAG | GAA | GAG | GAG | GAG | GAT | GAA | CCT | GAG | GTT | CCT | 3030 |
| Val | Gly | Glu | Glu | Glu | Glu | Glu | Glu | Glu | Glu | Asp | Glu | Pro | Glu | Val | Pro | |
| 825 | | | | | 830 | | | | | 835 | | | | | 840 | |
| GCC | GGA | CCC | CGT | CCT | CGA | AGG | ATC | TCG | GAG | TTG | AAC | ATG | AAG | GAA | AAA | 3078 |
| Ala | Gly | Pro | Arg | Pro | Arg | Arg | Ile | Ser | Glu | Leu | Asn | Met | Lys | Glu | Lys | |
| | | | | 845 | | | | | 850 | | | | | 855 | | |
| ATT | GCC | CCC | ATC | CCT | GAA | GGG | AGC | GCT | TTC | TTC | ATT | CTT | AGC | AAG | ACC | 3126 |
| Ile | Ala | Pro | Ile | Pro | Glu | Gly | Ser | Ala | Phe | Phe | Ile | Leu | Ser | Lys | Thr | |
| | | | 860 | | | | | 865 | | | | | 870 | | | |
| AAC | CCG | ATC | CGC | GTA | GGC | TGC | CAC | AAG | CTC | ATC | AAC | CAC | CAC | ATC | TTC | 3174 |
| Asn | Pro | Ile | Arg | Val | Gly | Cys | His | Lys | Leu | Ile | Asn | His | His | Ile | Phe | |
| | | 875 | | | | | 880 | | | | | 885 | | | | |
| ACC | AAC | CTC | ATC | CTT | GTC | TTC | ATC | ATG | CTG | AGC | AGT | GCT | GCC | CTG | GCC | 3222 |
| Thr | Asn | Leu | Ile | Leu | Val | Phe | Ile | Met | Leu | Ser | Ser | Ala | Ala | Leu | Ala | |
| | 890 | | | | | 895 | | | | | 900 | | | | | |
| GCA | GAG | GAC | CCC | ATC | CGC | AGC | CAC | TCC | TTC | CGG | AAC | ACG | ATA | CTG | GGT | 3270 |
| Ala | Glu | Asp | Pro | Ile | Arg | Ser | His | Ser | Phe | Arg | Asn | Thr | Ile | Leu | Gly | |
| 905 | | | | | 910 | | | | | 915 | | | | | 920 | |
| TAC | TTT | GAC | TAT | GCC | TTC | ACA | GCC | ATC | TTT | ACT | GTT | GAG | ATC | CTG | TTG | 3318 |
| Tyr | Phe | Asp | Tyr | Ala | Phe | Thr | Ala | Ile | Phe | Thr | Val | Glu | Ile | Leu | Leu | |
| | | | | 925 | | | | | 930 | | | | | 935 | | |
| AAG | ATG | ACA | ACT | TTT | GGA | GCT | TTC | CTC | CAC | AAA | GGG | GCC | TTC | TGC | AGG | 3366 |
| Lys | Met | Thr | Thr | Phe | Gly | Ala | Phe | Leu | His | Lys | Gly | Ala | Phe | Cys | Arg | |
| | | | | 940 | | | | | 945 | | | | | 950 | | |
| AAC | TAC | TTC | AAT | TTG | CTG | GAT | ATG | CTG | GTG | GTT | GGG | GTG | TCT | CTG | GTG | 3414 |
| Asn | Tyr | Phe | Asn | Leu | Leu | Asp | Met | Leu | Val | Val | Gly | Val | Ser | Leu | Val | |
| | | 955 | | | | | 960 | | | | | 965 | | | | |
| TCA | TTT | GGG | ATT | CAA | TCC | AGT | GCC | ATC | TCC | GTT | GTG | AAG | ATT | CTG | AGG | 3462 |

-continued

```
                Ser Phe Gly Ile Gln Ser Ser Ala Ile Ser Val Val Lys Ile Leu Arg
                    970             975             980

GTC TTA AGG GTC CTG CGT CCC CTC AGG GCC ATC AAC AGA GCA AAA GGA            3510
Val Leu Arg Val Leu Arg Pro Leu Arg Ala Ile Asn Arg Ala Lys Gly
985             990             995             1000

CTT AAG CAC GTG GTC CAG TGC GTC TTC GTG GCC ATC CGG ACC ATC GGC            3558
Leu Lys His Val Val Gln Cys Val Phe Val Ala Ile Arg Thr Ile Gly
                1005            1010            1015

AAC ATC ATG ATC GTC ACC ACC CTC CTG CAG TTC ATG TTT GCC TGT ATC            3606
Asn Ile Met Ile Val Thr Thr Leu Leu Gln Phe Met Phe Ala Cys Ile
                1020            1025            1030

GGG GTC CAG TTG TTC AAG GGG AAG TTC TAT CGC TGT ACG GAT GAA GCC            3654
Gly Val Gln Leu Phe Lys Gly Lys Phe Tyr Arg Cys Thr Asp Glu Ala
            1035            1040            1045

AAA AGT AAC CCT GAA GAA TGC AGG GGA CTT TTC ATC CTC TAC AAG GAT            3702
Lys Ser Asn Pro Glu Glu Cys Arg Gly Leu Phe Ile Leu Tyr Lys Asp
            1050            1055            1060

GGG GAT GTT GAC AGT CCT GTG GTC CGT GAA CGG ATC TGG CAA AAC AGT            3750
Gly Asp Val Asp Ser Pro Val Val Arg Glu Arg Ile Trp Gln Asn Ser
1065            1070            1075            1080

GAT TTC AAC TTC GAC AAC GTC CTC TCT GCT ATG ATG GCG CTC TTC ACA            3798
Asp Phe Asn Phe Asp Asn Val Leu Ser Ala Met Met Ala Leu Phe Thr
                1085            1090            1095

GTC TCC ACG TTT GAG GGC TGG CCT GCG TTG CTG TAT AAA GCC ATC GAC            3846
Val Ser Thr Phe Glu Gly Trp Pro Ala Leu Leu Tyr Lys Ala Ile Asp
            1100            1105            1110

TCG AAT GGA GAG AAC ATC GGC CCA ATC TAC AAC CAC CGC GTG GAG ATC            3894
Ser Asn Gly Glu Asn Ile Gly Pro Ile Tyr Asn His Arg Val Glu Ile
            1115            1120            1125

TCC ATC TTC TTC ATC ATC TAC ATC ATC ATT GTA GCT TTC TTC ATG ATG            3942
Ser Ile Phe Phe Ile Ile Tyr Ile Ile Ile Val Ala Phe Phe Met Met
            1130            1135            1140

AAC ATC TTT GTG GGC TTT GTC ATC GTT ACA TTT CAG GAA CAA GGA GAA            3990
Asn Ile Phe Val Gly Phe Val Ile Val Thr Phe Gln Glu Gln Gly Glu
1145            1150            1155            1160

AAA GAG TAT AAG AAC TGT GAG CTG GAC AAA AAT CAG CGT CAG TGT GTT            4038
Lys Glu Tyr Lys Asn Cys Glu Leu Asp Lys Asn Gln Arg Gln Cys Val
                1165            1170            1175

GAA TAC GCC TTG AAA GCA CGT CCC TTG CGG AGA TAC ATC CCC AAA AAC            4086
Glu Tyr Ala Leu Lys Ala Arg Pro Leu Arg Arg Tyr Ile Pro Lys Asn
            1180            1185            1190

CCC TAC CAG TAC AAG TTC TGG TAC GTG GTG AAC TCT TCG CCT TTC GAA            4134
Pro Tyr Gln Tyr Lys Phe Trp Tyr Val Val Asn Ser Ser Pro Phe Glu
            1195            1200            1205

TAC ATG ATG TTT GTC CTC ATC ATG CTC AAC ACA CTC TGC TTG GCC ATG            4182
Tyr Met Met Phe Val Leu Ile Met Leu Asn Thr Leu Cys Leu Ala Met
1210            1215            1220

CAG CAC TAC GAG CAG TCC AAG ATG TTC AAT GAT GCC ATG GAC ATT CTG            4230
Gln His Tyr Glu Gln Ser Lys Met Phe Asn Asp Ala Met Asp Ile Leu
1225            1230            1235            1240

AAC ATG GTC TTC ACC GGG GTG TTC ACC GTC GAG ATG GTT TTG AAA GTC            4278
Asn Met Val Phe Thr Gly Val Phe Thr Val Glu Met Val Leu Lys Val
                1245            1250            1255

ATC GCA TTT AAG CCT AAG GGG TAT TTT AGT GAC GCC TGG AAC ACG TTT            4326
Ile Ala Phe Lys Pro Lys Gly Tyr Phe Ser Asp Ala Trp Asn Thr Phe
            1260            1265            1270

GAC TCC CTC ATC GTA ATC GGC AGC ATT ATA GAC GTG GCC CTC AGC GAA            4374
Asp Ser Leu Ile Val Ile Gly Ser Ile Ile Asp Val Ala Leu Ser Glu
            1275            1280            1285

GCA GAC CCA ACT GAA AGT GAA AAT GTC CCT GTC CCA ACT GCT ACA CCT            4422
```

|     |     |
| --- | --- |
| Ala Asp Pro Thr Glu Ser Glu Asn Val Pro Val Pro Thr Ala Thr Pro<br>1290                        1295                      1300 | |
| GGG AAC TCT GAA GAG AGC AAT AGA ATC TCC ATC ACC TTT TTC CGT CTT<br>Gly Asn Ser Glu Glu Ser Asn Arg Ile Ser Ile Thr Phe Phe Arg Leu<br>1305                       1310                    1315                  1320 | 4470 |
| TTC CGA GTG ATG CGA TTG GTG AAG CTT CTC AGC AGG GGG GAA GGC ATC<br>Phe Arg Val Met Arg Leu Val Lys Leu Leu Ser Arg Gly Glu Gly Ile<br>                        1325                   1330                   1335 | 4518 |
| CGG ACA TTG CTG TGG ACT TTT ATT AAG TTC TTT CAG GCG CTC CCG TAT<br>Arg Thr Leu Leu Trp Thr Phe Ile Lys Phe Phe Gln Ala Leu Pro Tyr<br>1340                          1345                      1350 | 4566 |
| GTG GCC CTC CTC ATA GCC ATG CTG TTC TTC ATC TAT GCG GTC ATT GGC<br>Val Ala Leu Leu Ile Ala Met Leu Phe Phe Ile Tyr Ala Val Ile Gly<br>                        1355                   1360                   1365 | 4614 |
| ATG CAG ATG TTT GGG AAA GTT GCC ATG AGA GAT AAC AAC CAG ATC AAT<br>Met Gln Met Phe Gly Lys Val Ala Met Arg Asp Asn Asn Gln Ile Asn<br>1370                          1375                      1380 | 4662 |
| AGG AAC AAT AAC TTC CAG ACG TTT CCC CAG GCG GTG CTG CTG CTC TTC<br>Arg Asn Asn Asn Phe Gln Thr Phe Pro Gln Ala Val Leu Leu Leu Phe<br>1385                        1390                    1395                  1400 | 4710 |
| AGG TGT GCA ACA GGT GAG GCC TGG CAG GAG ATC ATG CTG GCC TGT CTC<br>Arg Cys Ala Thr Gly Glu Ala Trp Gln Glu Ile Met Leu Ala Cys Leu<br>                        1405                   1410                   1415 | 4758 |
| CCA GGG AAG CTC TGT GAC CCT GAG TCA GAT TAC AAC CCC GGG GAG GAG<br>Pro Gly Lys Leu Cys Asp Pro Glu Ser Asp Tyr Asn Pro Gly Glu Glu<br>                        1420                   1425                   1430 | 4806 |
| CAT ACA TGT GGG AGC AAC TTT GCC ATT GTC TAT TTC ATC AGT TTT TAC<br>His Thr Cys Gly Ser Asn Phe Ala Ile Val Tyr Phe Ile Ser Phe Tyr<br>                        1435                   1440                   1445 | 4854 |
| ATG CTC TGT GCA TTT CTG ATC ATC AAT CTG TTT GTG GCT GTC ATC ATG<br>Met Leu Cys Ala Phe Leu Ile Ile Asn Leu Phe Val Ala Val Ile Met<br>1450                          1455                      1460 | 4902 |
| GAT AAT TTC GAC TAT CTG ACC CGG GAC TGG TCT ATT TTG GGG CCT CAC<br>Asp Asn Phe Asp Tyr Leu Thr Arg Asp Trp Ser Ile Leu Gly Pro His<br>1465                          1470                      1475                   1480 | 4950 |
| CAT TTA GAT GAA TTC AAA AGA ATA TGG TCA GAA TAT GAC CCT GAG GCA<br>His Leu Asp Glu Phe Lys Arg Ile Trp Ser Glu Tyr Asp Pro Glu Ala<br>                        1485                    1490                   1495 | 4998 |
| AAG GGA AGG ATA AAA CAC CTT GAT GTG GTC ACT CTG CTT CGA CGC ATC<br>Lys Gly Arg Ile Lys His Leu Asp Val Val Thr Leu Leu Arg Arg Ile<br>                        1500                    1505                  1510 | 5046 |
| CAG CCT CCC CTG GGG TTT GGG AAG TTA TGT CCA CAC AGG GTA GCG TGC<br>Gln Pro Pro Leu Gly Phe Gly Lys Leu Cys Pro His Arg Val Ala Cys<br>                        1515                    1520                  1525 | 5094 |
| AAG AGA TTA GTT GCC ATG AAC ATG CCT CTC AAC AGT GAC GGG ACA GTC<br>Lys Arg Leu Val Ala Met Asn Met Pro Leu Asn Ser Asp Gly Thr Val<br>1530                          1535                    1540 | 5142 |
| ATG TTT AAT GCA ACC CTG TTT GCT TTG GTT CGA ACG GCT CTT AAG ATC<br>Met Phe Asn Ala Thr Leu Phe Ala Leu Val Arg Thr Ala Leu Lys Ile<br>1545                          1550                      1555                  1560 | 5190 |
| AAG ACC GAA GGG AAC CTG GAG CAA GCT AAT GAA GAA CTT CGG GCT GTG<br>Lys Thr Glu Gly Asn Leu Glu Gln Ala Asn Glu Glu Leu Arg Ala Val<br>                        1565                    1570                   1575 | 5238 |
| ATA AAG AAA ATT TGG AAG AAA ACC AGC ATG AAA TTA CTT GAC CAA GTT<br>Ile Lys Lys Ile Trp Lys Lys Thr Ser Met Lys Leu Leu Asp Gln Val<br>                        1580                    1585                  1590 | 5286 |
| GTC CCT CCA GCT GGT GAT GAT GAG GTA ACC GTG GGG AAG TTC TAT GCC<br>Val Pro Pro Ala Gly Asp Asp Glu Val Thr Val Gly Lys Phe Tyr Ala<br>                        1595                    1600                   1605 | 5334 |
| ACT TTC CTG ATA CAG GAC TAC TTT AGG AAA TTC AAG AAA CGG AAA GAA | 5382 |

```
Thr Phe Leu Ile Gln Asp Tyr Phe Arg Lys Phe Lys Lys Arg Lys Glu
     1610                1615                1620

CAA GGA CTG GTG GGA AAG TAC CCT GCG AAG AAC ACC ACA ATT GCC CTA                5430
Gln Gly Leu Val Gly Lys Tyr Pro Ala Lys Asn Thr Thr Ile Ala Leu
1625                1630                1635                1640

CAG GCG GGA TTA AGG ACA CTG CAT GAC ATT GGG CCA GAA ATC CGG CGT                5478
Gln Ala Gly Leu Arg Thr Leu His Asp Ile Gly Pro Glu Ile Arg Arg
                1645                1650                1655

GCT ATA TCG TGT GAT TTG CAA GAT GAC GAG CCT GAG GAA ACA AAA CGA                5526
Ala Ile Ser Cys Asp Leu Gln Asp Asp Glu Pro Glu Glu Thr Lys Arg
1660                1665                1670

GAA GAA GAA GAT GAT GTG TTC AAA AGA AAT GGT GCC CTG CTT GGA AAC                5574
Glu Glu Glu Asp Asp Val Phe Lys Arg Asn Gly Ala Leu Leu Gly Asn
1675                1680                1685

CAT GTC AAT CAT GTT AAT AGT GAT AGG AGA GAT TCC CTT CAG CAG ACC                5622
His Val Asn His Val Asn Ser Asp Arg Arg Asp Ser Leu Gln Gln Thr
1690                1695                1700

AAT ACC ACC CAC CGT CCC CTG CAT GTC CAA AGG CCT TCA ATT CCA CCT                5670
Asn Thr Thr His Arg Pro Leu His Val Gln Arg Pro Ser Ile Pro Pro
1705                1710                1715                1720

GCA AGT GAT ACT GAG AAA CCG CTG TTT CCT CCA GCA GGA AAT TCG GTG                5718
Ala Ser Asp Thr Glu Lys Pro Leu Phe Pro Pro Ala Gly Asn Ser Val
                1725                1730                1735

TGT CAT AAC CAT CAT AAC CAT AAT TCC ATA GGA AAG CAA GTT CCC ACC                5766
Cys His Asn His His Asn His Asn Ser Ile Gly Lys Gln Val Pro Thr
                1740                1745                1750

TCA ACA AAT GCC AAT CTC AAT AAT GCC AAT ATG TCC AAA GCT GCC CAT                5814
Ser Thr Asn Ala Asn Leu Asn Asn Ala Asn Met Ser Lys Ala Ala His
                1755                1760                1765

GGA AAG CGG CCC AGC ATT GGG AAC CTT GAG CAT GTG TCT GAA AAT GGG                5862
Gly Lys Arg Pro Ser Ile Gly Asn Leu Glu His Val Ser Glu Asn Gly
1770                1775                1780

CAT CAT TCT TCC CAC AAG CAT GAC CGG GAG CCT CAG AGA AGG TCC AGT                5910
His His Ser Ser His Lys His Asp Arg Glu Pro Gln Arg Arg Ser Ser
1785                1790                1795                1800

GTG AAA AGA ACC CGC TAT TAT GAA ACT TAC ATT AGG TCC GAC TCA GGA                5958
Val Lys Arg Thr Arg Tyr Tyr Glu Thr Tyr Ile Arg Ser Asp Ser Gly
                1805                1810                1815

GAT GAA CAG CTC CCA ACT ATT TGC CGG GAA GAC CCA GAG ATA CAT GGC                6006
Asp Glu Gln Leu Pro Thr Ile Cys Arg Glu Asp Pro Glu Ile His Gly
                1820                1825                1830

TAT TTC AGG GAC CCC CAC TGC TTG GGG GAG CAG GAG TAT TTC AGT AGT                6054
Tyr Phe Arg Asp Pro His Cys Leu Gly Glu Gln Glu Tyr Phe Ser Ser
                1835                1840                1845

GAG GAA TGC TAC GAG GAT GAC AGC TCG CCC ACC TGG AGC AGG CAA AAC                6102
Glu Glu Cys Tyr Glu Asp Asp Ser Ser Pro Thr Trp Ser Arg Gln Asn
1850                1855                1860

TAT GGC TAC TAC AGC AGA TAC CCA GGC AGA AAC ATC GAC TCT GAG AGG                6150
Tyr Gly Tyr Tyr Ser Arg Tyr Pro Gly Arg Asn Ile Asp Ser Glu Arg
1865                1870                1875                1880

CCC CGA GGC TAC CAT CAT CCC CAA GGA TTC TTG GAG GAC GAT GAC TCG                6198
Pro Arg Gly Tyr His His Pro Gln Gly Phe Leu Glu Asp Asp Asp Ser
                1885                1890                1895

CCC GTT TGC TAT GAT TCA CGG AGA TCT CCA AGG AGA CGC CTA CTA CCT                6246
Pro Val Cys Tyr Asp Ser Arg Arg Ser Pro Arg Arg Arg Leu Leu Pro
                1900                1905                1910

CCC ACC CCA GCA TCC CAC CGG AGA TCC TCC TTC AAC TTT GAG TGC CTG                6294
Pro Thr Pro Ala Ser His Arg Arg Ser Ser Phe Asn Phe Glu Cys Leu
                1915                1920                1925

CGC CGG CAG AGC AGC CAG GAA GAG GTC CCG TCG TCT CCC ATC TTC CCC                6342
```

| | | |
|---|---|---|
| Arg Arg Gln Ser Ser Gln Glu Glu Val Pro Ser Ser Pro Ile Phe Pro<br>1930                         1935                    1940 | | |
| CAT CGC ACG GCC CTG CCT CTG CAT CTA ATG CAG CAA CAG ATC ATG GCA<br>His Arg Thr Ala Leu Pro Leu His Leu Met Gln Gln Gln Ile Met Ala<br>1945                         1950                         1955                  1960 | | 6390 |
| GTT GCC GGC CTA GAT TCA AGT AAA GCC CAG AAG TAC TCA CCG AGT CAC<br>Val Ala Gly Leu Asp Ser Ser Lys Ala Gln Lys Tyr Ser Pro Ser His<br>                       1965                     1970                     1975 | | 6438 |
| TCG ACC CGG TCG TGG GCC ACC CCT CCA GCA ACC CCT CCC TAC CGG GAC<br>Ser Thr Arg Ser Trp Ala Thr Pro Pro Ala Thr Pro Pro Tyr Arg Asp<br>         1980                     1985                     1990 | | 6486 |
| TGG ACA CCG TGC TAC ACC CCC CTG ATC CAA GTG GAG CAG TCA GAG GCC<br>Trp Thr Pro Cys Tyr Thr Pro Leu Ile Gln Val Glu Gln Ser Glu Ala<br>        1995                     2000                     2005 | | 6534 |
| CTG GAC CAG GTG AAC GGC AGC CTG CCG TCC CTG CAC CGC AGC TCC TGG<br>Leu Asp Gln Val Asn Gly Ser Leu Pro Ser Leu His Arg Ser Ser Trp<br>        2010                     2015                     2020 | | 6582 |
| TAC ACA GAC GAG CCC GAC ATC TCC TAC CGG ACT TTC ACA CCA GCC AGC<br>Tyr Thr Asp Glu Pro Asp Ile Ser Tyr Arg Thr Phe Thr Pro Ala Ser<br>2025                         2030                     2035                  2040 | | 6630 |
| CTG ACT GTC CCC AGC AGC TTC CGG AAC AAA AAC AGC GAC AAG CAG AGG<br>Leu Thr Val Pro Ser Ser Phe Arg Asn Lys Asn Ser Asp Lys Gln Arg<br>                   2045                     2050                     2055 | | 6678 |
| AGT GCG GAC AGC TTG GTG GAG GCA GTC CTG ATA TCC GAA GGC TTG GGA<br>Ser Ala Asp Ser Leu Val Glu Ala Val Leu Ile Ser Glu Gly Leu Gly<br>              2060                     2065                     2070 | | 6726 |
| CGC TAT GCA AGG GAC CCA AAA TTT GTG TCA GCA ACA AAA CAC GAA ATC<br>Arg Tyr Ala Arg Asp Pro Lys Phe Val Ser Ala Thr Lys His Glu Ile<br>2075                         2080                     2085 | | 6774 |
| GCT GAT GCC TGT GAC CTC ACC ATC GAC GAG ATG GAG AGT GCA GCC AGC<br>Ala Asp Ala Cys Asp Leu Thr Ile Asp Glu Met Glu Ser Ala Ala Ser<br>2090                         2095                     2100 | | 6822 |
| ACC CTG CTT AAT GGG AAC GTG CGT CCC CGA GCC AAC GGG GAT GTG GGC<br>Thr Leu Leu Asn Gly Asn Val Arg Pro Arg Ala Asn Gly Asp Val Gly<br>2105                         2110                     2115                  2120 | | 6870 |
| CCC CTC TCA CAC CGG CAG GAC TAT GAG CTA CAG GAC TTT GGT CCT GGC<br>Pro Leu Ser His Arg Gln Asp Tyr Glu Leu Gln Asp Phe Gly Pro Gly<br>                   2125                     2130                  2135 | | 6918 |
| TAC AGC GAC GAA GAG CCA GAC CCT GGG AGG GAT GAG GAG GAC CTG GCG<br>Tyr Ser Asp Glu Glu Pro Asp Pro Gly Arg Asp Glu Glu Asp Leu Ala<br>              2140                     2145                     2150 | | 6966 |
| GAT GAA ATG ATA TGC ATC ACC ACC TTG TAGCCCCCAG CGAGGGGCAG<br>Asp Glu Met Ile Cys Ile Thr Thr Leu<br>             2155                     2160 | | 7013 |
| ACTGGCTCTG GCCTCAGGTG GGGCGCAGGA GAGCCAGGGG AAAAGTGCCT CATAGTTAGG | | 7073 |
| AAAGTTTAGG CACTAGTTGG GAGTAATATT CAATTAATTA GACTTTTGTA TAAGAGATGT | | 7133 |
| CATGCCTCAA GAAAGCCATA AACCTGGTAG GAACAGGTCC CAAGCGGTTG AGCCTGGCAG | | 7193 |
| AGTACCATGC GCTCGGCCCC AGCTGCAGGA AACAGCAGGC CCGCCCTCT CACAGAGGAT | | 7253 |
| GGGTGAGGAG GCCAGACCTG CCCTGCCCCA TTGTCCAGAT GGGCACTGCT GTGGAGTCTG | | 7313 |
| CTTCTCCCAT GTACCAGGGC ACCAGGCCCA CCCAACTGAA GGCATGGCGG CGGGGTGCAG | | 7373 |
| GGGAAAGTTA AAGGTGATGA CGATCATCAC ACCTGTGTCG TTACCTCAGC CATCGGTCTA | | 7433 |
| GCATATCAGT CACTGGGCCC AACATATCCA TTTTAAACC CTTTCCCCCA AATACACTGC | | 7493 |
| GTCCTGGTTC CTGTTTAGCT GTTCTGAAAT ACGGTGTGTA AGTAAGTCAG AACCCAGCTA | | 7553 |
| CCAGTGATTA TTGCGAGGGC AATGGGACCT CATAAATAAG GTTTTCTGTG ATGTGACGCC | | 7613 |
| AGTTTACATA AGAGAATATC AC | | 7635 |

( 2 ) INFORMATION FOR SEQ ID NO:2:

( i ) SEQUENCE CHARACTERISTICS:
        ( A ) LENGTH: 104 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 1..102

( i x ) FEATURE:
        ( A ) NAME/KEY: misc_feature
        ( B ) LOCATION: 1..104
        ( D ) OTHER INFORMATION: /note="A 104-nucleotide
                alternative exon of alpha-1D."

( x i ) SEQUENCE DESCRIPTION: SEQ ID NO:2:

```
GTA  AAT  GAT  GCG  ATA  GGA  TGG  GAA  TGG  CCA  TGG  GTG  TAT  TTT  GTT  AGT     48
Val  Asn  Asp  Ala  Ile  Gly  Trp  Glu  Trp  Pro  Trp  Val  Tyr  Phe  Val  Ser
 1              5                        10                       15

CTG  ATC  ATC  CTT  GGC  TCA  TTT  TTC  GTC  CTT  AAC  CTG  GTT  CTT  GGT  GTC     96
Leu  Ile  Ile  Leu  Gly  Ser  Phe  Phe  Val  Leu  Asn  Leu  Val  Leu  Gly  Val
              20                        25                       30

CTT  AGT  GG                                                                       104
Leu  Ser
```

( 2 ) INFORMATION FOR SEQ ID NO:3:

( i ) SEQUENCE CHARACTERISTICS:
        ( A ) LENGTH: 5904 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..5904

( x i ) SEQUENCE DESCRIPTION: SEQ ID NO:3:

```
ATG  GTC  AAT  GAG  AAT  ACG  AGG  ATG  TAC  ATT  CCA  GAG  GAA  AAC  CAC  CAA     48
Met  Val  Asn  Glu  Asn  Thr  Arg  Met  Tyr  Ile  Pro  Glu  Glu  Asn  His  Gln
 1              5                        10                       15

GGT  TCC  AAC  TAT  GGG  AGC  CCA  CGC  CCC  GCC  CAT  GCC  AAC  ATG  AAT  GCC     96
Gly  Ser  Asn  Tyr  Gly  Ser  Pro  Arg  Pro  Ala  His  Ala  Asn  Met  Asn  Ala
              20                        25                       30

AAT  GCG  GCA  GCG  GGG  CTG  GCC  CCT  GAG  CAC  ATC  CCC  ACC  CCG  GGG  GCT    144
Asn  Ala  Ala  Ala  Gly  Leu  Ala  Pro  Glu  His  Ile  Pro  Thr  Pro  Gly  Ala
         35                       40                       45

GCC  CTG  TCG  TGG  CAG  GCG  GCC  ATC  GAC  GCA  GCC  CGG  CAG  GCT  AAG  CTG    192
Ala  Leu  Ser  Trp  Gln  Ala  Ala  Ile  Asp  Ala  Ala  Arg  Gln  Ala  Lys  Leu
     50                       55                       60

ATG  GGC  AGC  GCT  GGC  AAT  GCG  ACC  ATC  TCC  ACA  GTC  AGC  TCC  ACG  CAG    240
Met  Gly  Ser  Ala  Gly  Asn  Ala  Thr  Ile  Ser  Thr  Val  Ser  Ser  Thr  Gln
65                        70                       75                       80

CGG  AAG  CGC  CAG  CAA  TAT  GGG  AAA  CCC  AAG  AAG  CAG  GGC  AGC  ACC  ACG    288
Arg  Lys  Arg  Gln  Gln  Tyr  Gly  Lys  Pro  Lys  Lys  Gln  Gly  Ser  Thr  Thr
                     85                       90                       95

GCC  ACA  CGC  CCG  CCC  CGA  GCC  CTG  CTC  TGC  CTG  ACC  CTG  AAG  AAC  CCC    336
Ala  Thr  Arg  Pro  Pro  Arg  Ala  Leu  Leu  Cys  Leu  Thr  Leu  Lys  Asn  Pro
              100                      105                      110
```

```
ATC CGG AGG GCC TGC ATC AGC ATT GTC GAA TGG AAA CCA TTT GAA ATA        384
Ile Arg Arg Ala Cys Ile Ser Ile Val Glu Trp Lys Pro Phe Glu Ile
    115             120                 125

ATT ATT TTA CTG ACT ATT TTT GCC AAT TGT GTG GCC TTA GCG ATC TAT        432
Ile Ile Leu Leu Thr Ile Phe Ala Asn Cys Val Ala Leu Ala Ile Tyr
130                 135                 140

ATT CCC TTT CCA GAA GAT GAT TCC AAC GCC ACC AAT TCC AAC CTG GAA        480
Ile Pro Phe Pro Glu Asp Asp Ser Asn Ala Thr Asn Ser Asn Leu Glu
145                 150                 155                 160

CGA GTG GAA TAT CTC TTT CTC ATA ATT TTT ACG GTG GAA GCG TTT TTA        528
Arg Val Glu Tyr Leu Phe Leu Ile Ile Phe Thr Val Glu Ala Phe Leu
                165                 170                 175

AAA GTA ATC GCC TAT GGA CTC CTC TTT CAC CCC AAT GCC TAC CTC CGC        576
Lys Val Ile Ala Tyr Gly Leu Leu Phe His Pro Asn Ala Tyr Leu Arg
                180                 185                 190

AAC GGC TGG AAC CTA CTA GAT TTT ATA ATT GTG GTT GTG GGG CTT TTT        624
Asn Gly Trp Asn Leu Leu Asp Phe Ile Ile Val Val Val Gly Leu Phe
            195                 200                 205

AGT GCA ATT TTA GAA CAA GCA ACC AAA GCA GAT GGG GCA AAC GCT CTC        672
Ser Ala Ile Leu Glu Gln Ala Thr Lys Ala Asp Gly Ala Asn Ala Leu
        210                 215                 220

GGA GGG AAA GGG GCC GGA TTT GAT GTG AAG GCG CTG AGG GCC TTC CGC        720
Gly Gly Lys Gly Ala Gly Phe Asp Val Lys Ala Leu Arg Ala Phe Arg
225                 230                 235                 240

GTG CTG CGC CCC CTG CGG CTG GTG TCC GGA GTC CCA AGT CTC CAG GTG        768
Val Leu Arg Pro Leu Arg Leu Val Ser Gly Val Pro Ser Leu Gln Val
                245                 250                 255

GTC CTG AAT TCC ATC ATC AAG GCC ATG GTC CCC CTG CTG CAC ATC GCC        816
Val Leu Asn Ser Ile Ile Lys Ala Met Val Pro Leu Leu His Ile Ala
            260                 265                 270

CTG CTT GTG CTG TTT GTC ATC ATC ATC TAC GCC ATC ATC GGC TTG GAG        864
Leu Leu Val Leu Phe Val Ile Ile Ile Tyr Ala Ile Ile Gly Leu Glu
        275                 280                 285

CTC TTC ATG GGG AAG ATG CAC AAG ACC TGC TAC AAC CAG GAG GGC ATA        912
Leu Phe Met Gly Lys Met His Lys Thr Cys Tyr Asn Gln Glu Gly Ile
        290                 295                 300

GCA GAT GTT CCA GCA GAA GAT GAC CCT TCC CCT TGT GCG CTG GAA ACG        960
Ala Asp Val Pro Ala Glu Asp Asp Pro Ser Pro Cys Ala Leu Glu Thr
305                 310                 315                 320

GGC CAC GGG CGG CAG TGC CAG AAC GGC ACG GTG TGC AAG CCC GGC TGG       1008
Gly His Gly Arg Gln Cys Gln Asn Gly Thr Val Cys Lys Pro Gly Trp
                325                 330                 335

GAT GGT CCC AAG CAC GGC ATC ACC AAC TTT GAC AAC TTT GCC TTC GCC       1056
Asp Gly Pro Lys His Gly Ile Thr Asn Phe Asp Asn Phe Ala Phe Ala
            340                 345                 350

ATG CTC ACG GTG TTC CAG TGC ATC ACC ATG GAG GGC TGG ACG GAC GTG       1104
Met Leu Thr Val Phe Gln Cys Ile Thr Met Glu Gly Trp Thr Asp Val
        355                 360                 365

CTG TAC TGG GTC AAT GAT GCC GTA GGA AGG GAC TGG CCC TGG ATC TAT       1152
Leu Tyr Trp Val Asn Asp Ala Val Gly Arg Asp Trp Pro Trp Ile Tyr
        370                 375                 380

TTT GTT ACA CTA ATC ATC ATA GGG TCA TTT TTT GTA CTT AAC TTG GTT       1200
Phe Val Thr Leu Ile Ile Ile Gly Ser Phe Phe Val Leu Asn Leu Val
385                 390                 395                 400

CTC GGT GTG CTT AGC GGA GAG TTT TCC AAA GAG AGG GAG AAG GCC AAG       1248
Leu Gly Val Leu Ser Gly Glu Phe Ser Lys Glu Arg Glu Lys Ala Lys
                405                 410                 415

GCC CGG GGA GAT TTC CAG AAG CTG CGG GAG AAG CAG CAG CTA GAA GAG       1296
Ala Arg Gly Asp Phe Gln Lys Leu Arg Glu Lys Gln Gln Leu Glu Glu
            420                 425                 430
```

| | | | | | | | | | | | | | | | | |
|---|---|---|---|---|---|---|---|---|---|---|---|---|---|---|---|---|
| GAT | CTC | AAA | GGC | TAC | CTG | GAT | TGG | ATC | ACT | CAG | GCC | GAA | GAC | ATC | GNT | 1344 |
| Asp | Leu | Lys 435 | Gly | Tyr | Leu | Asp | Trp 440 | Ile | Thr | Gln | Ala | Glu | Asp 445 | Ile | Xaa | |
| CCT | GAG | AAT | GAG | GAC | GAA | GGC | ATG | GAT | GAG | GAG | AAG | CCC | CGA | AAC | AGA | 1392 |
| Pro | Glu | Asn 450 | Glu | Asp | Glu | Gly | Met 455 | Asp | Glu | Glu | Lys | Pro 460 | Arg | Asn | Arg | |
| GGC | ACT | CCG | GCG | GGC | ATG | CTT | GAT | CAG | AAG | AAA | GGG | AAG | TTT | GCT | TGG | 1440 |
| Gly | Thr | Pro 465 | Ala | Gly | Met | Leu | Asp 470 | Gln | Lys | Lys | Gly | Lys 475 | Phe | Ala | Trp 480 | |
| TTT | AGT | CAC | TCC | ACA | GAA | ACC | CAT | GTG | AGC | ATG | CCC | ACC | AGT | GAG | ACC | 1488 |
| Phe | Ser | His | Ser | Thr 485 | Glu | Thr | His | Val | Ser 490 | Met | Pro | Thr | Ser | Glu 495 | Thr | |
| GAG | TCC | GTC | AAC | ACC | GAA | AAC | GTG | GCT | GGA | GGT | GAC | ATC | GAG | GGA | GAA | 1536 |
| Glu | Ser | Val | Asn 500 | Thr | Glu | Asn | Val | Ala 505 | Gly | Gly | Asp | Ile | Glu 510 | Gly | Glu | |
| AAC | TGC | GGG | GCC | AGG | CTG | GCC | CAC | CGG | ATC | TCC | AAG | TCA | AAG | TTC | AGC | 1584 |
| Asn | Cys | Gly | Ala | Arg 515 | Leu | Ala | His | Arg | Ile 520 | Ser | Lys | Ser | Lys 525 | Phe | Ser | |
| CGC | TAC | TGG | CGC | CGG | TGG | AAT | CGG | TTC | TGC | AGA | AGG | AAG | TGC | CGC | GCC | 1632 |
| Arg | Tyr | Trp | Arg 530 | Arg | Trp | Asn | Arg | Phe 535 | Cys | Arg | Arg | Lys 540 | Cys | Arg | Ala | |
| GCA | GTC | AAG | TCT | AAT | GTC | TTC | TAC | TGG | CTG | GTG | ATT | TTC | CTG | GTG | TTC | 1680 |
| Ala | Val 545 | Lys | Ser | Asn | Val | Phe 550 | Tyr | Trp | Leu | Val | Ile 555 | Phe | Leu | Val | Phe 560 | |
| CTC | AAC | ACG | CTC | ACC | ATT | GCC | TCT | GAG | CAC | TAC | AAC | CAG | CCC | AAC | TGG | 1728 |
| Leu | Asn | Thr | Leu | Thr 565 | Ile | Ala | Ser | Glu | His 570 | Tyr | Asn | Gln | Pro | Asn 575 | Trp | |
| CTC | ACA | GAA | GTC | CAA | GAC | ACG | GCA | AAC | AAG | GCC | CTG | CTG | GCC | CTG | TTC | 1776 |
| Leu | Thr | Glu | Val | Gln 580 | Asp | Thr | Ala | Asn | Lys 585 | Ala | Leu | Leu | Ala | Leu 590 | Phe | |
| ACG | GCA | GAG | ATG | CTC | CTG | AAG | ATG | TAC | AGC | CTG | GGC | CTG | CAG | GCC | TAC | 1824 |
| Thr | Ala | Glu 595 | Met | Leu | Leu | Lys | Met 600 | Tyr | Ser | Leu | Gly | Leu 605 | Gln | Ala | Tyr | |
| TTC | GTG | TCC | CTC | TTC | AAC | CGC | TTT | GAC | TGC | TTC | GTC | GTG | TGT | GGC | GGC | 1872 |
| Phe | Val 610 | Ser | Leu | Phe | Asn | Arg 615 | Phe | Asp | Cys | Phe | Val 620 | Val | Cys | Gly | Gly | |
| ATC | CTG | GAG | ACC | ATC | CTG | GTG | GAG | ACC | AAG | ATC | ATG | TCC | CCA | CTG | GGC | 1920 |
| Ile | Leu | Glu | Thr | Ile 625 | Leu | Val | Glu | Thr | Lys 630 | Ile | Met | Ser | Pro | Leu 635 | Gly 640 | |
| ATC | TCC | GTG | CTC | AGA | TGC | GTC | CGG | CTG | CTG | AGG | ATT | TTC | AAG | ATC | ACG | 1968 |
| Ile | Ser | Val | Leu | Arg 645 | Cys | Val | Arg | Leu | Leu 650 | Arg | Ile | Phe | Lys | Ile 655 | Thr | |
| AGG | TAC | TGG | AAC | TCC | TTG | AGC | AAC | CTG | GTG | GCA | TCC | TTG | CTG | AAC | TCT | 2016 |
| Arg | Tyr | Trp | Asn | Ser 660 | Leu | Ser | Asn | Leu | Val 665 | Ala | Ser | Leu | Leu | Asn 670 | Ser | |
| GTG | CGC | TCC | ATC | GCC | TCC | CTG | CTC | CTC | CTC | TTC | CTC | TTC | ATC | ATC | | 2064 |
| Val | Arg | Ser 675 | Ile | Ala | Ser | Leu | Leu 680 | Leu | Leu | Phe | Leu | Phe 685 | Ile | Ile | | |
| ATC | TTC | TCC | CTC | CTG | GGG | ATG | CAG | CTC | TTT | GGA | GGA | AAG | TTC | AAC | TTT | 2112 |
| Ile | Phe | Ser | Leu | Leu 690 | Gly | Met | Gln | Leu | Phe 695 | Gly | Gly | Lys | Phe | Asn 700 | Phe | |
| GAT | GAG | ATG | CAG | ACC | CGG | AGG | AGC | ACA | TTC | GAT | AAC | TTC | CCC | CAG | TCC | 2160 |
| Asp | Glu | Met | Gln | Thr 705 | Arg | Arg | Ser | Thr | Phe 710 | Asp | Asn | Phe | Pro | Gln 715 | Ser 720 | |
| CTC | CTC | ACT | GTG | TTT | CAG | ATC | CTG | ACC | GGG | GAG | GAC | TGG | AAT | TCG | GTG | 2208 |
| Leu | Leu | Thr | Val | Phe 725 | Gln | Ile | Leu | Thr | Gly 730 | Glu | Asp | Trp | Asn | Ser 735 | Val | |
| ATG | TAT | GAT | GGG | ATC | ATG | GCT | TAT | GGG | GGC | CCC | TCT | TTT | CCA | GGG | ATG | 2256 |
| Met | Tyr | Asp | Gly | Ile 740 | Met | Ala | Tyr | Gly | Gly 745 | Pro | Ser | Phe | Pro | Gly 750 | Met | |

-continued

| | | | | | | | | | | | | | | | | |
|---|---|---|---|---|---|---|---|---|---|---|---|---|---|---|---|---|
| TTA | GTC | TGT | ATT | TAC | TTC | ATC | ATC | CTC | TTC | ATC | TCT | GGA | AAC | TAT | ATC | 2304 |
| Leu | Val | Cys | Ile | Tyr | Phe | Ile | Ile | Leu | Phe | Ile | Ser | Gly | Asn | Tyr | Ile | |
| | | 755 | | | | 760 | | | | | 765 | | | | | |
| CTA | CTG | AAT | GTG | TTC | TTG | GCC | ATT | GCT | GTG | GAC | AAC | CTG | GCT | GAT | GCT | 2352 |
| Leu | Leu | Asn | Val | Phe | Leu | Ala | Ile | Ala | Val | Asp | Asn | Leu | Ala | Asp | Ala | |
| | 770 | | | | 775 | | | | | 780 | | | | | | |
| GAG | AGC | CTC | ACA | TCT | GCC | CTA | AAG | GAG | GAG | GAA | GAG | GAG | AAG | GAG | AGA | 2400 |
| Glu | Ser | Leu | Thr | Ser | Ala | Leu | Lys | Glu | Glu | Glu | Glu | Glu | Lys | Glu | Arg | |
| 785 | | | | | 790 | | | | | 795 | | | | | 800 | |
| AAG | AAG | CTG | GCC | AGG | ACT | GCC | AGC | CCA | GAG | AAG | AAA | CAA | GAG | TTG | GTG | 2448 |
| Lys | Lys | Leu | Ala | Arg | Thr | Ala | Ser | Pro | Glu | Lys | Lys | Gln | Glu | Leu | Val | |
| | | | | 805 | | | | | 810 | | | | | 815 | | |
| GAG | AAG | CCG | GCA | GTG | GGG | GAA | TCC | AAG | GAG | GAG | AAG | ATT | GAG | CTG | AAA | 2496 |
| Glu | Lys | Pro | Ala | Val | Gly | Glu | Ser | Lys | Glu | Glu | Lys | Ile | Glu | Leu | Lys | |
| | | | 820 | | | | | 825 | | | | | 830 | | | |
| TCC | ATC | ACG | GCT | GAC | GGA | GAG | TCT | CCA | CCC | GCC | ACC | AAG | ATC | AAC | ATG | 2544 |
| Ser | Ile | Thr | Ala | Asp | Gly | Glu | Ser | Pro | Pro | Ala | Thr | Lys | Ile | Asn | Met | |
| | | 835 | | | | | 840 | | | | | 845 | | | | |
| GAT | GAC | CTC | CAG | CCC | AAT | GAA | AAT | GAG | GAT | AAG | AGC | CCC | TAC | CCC | AAC | 2592 |
| Asp | Asp | Leu | Gln | Pro | Asn | Glu | Asn | Glu | Asp | Lys | Ser | Pro | Tyr | Pro | Asn | |
| 850 | | | | | 855 | | | | | 860 | | | | | | |
| CCA | GAA | ACT | ACA | GGA | GAA | GAG | GAT | GAG | GAG | GAG | CCA | GAG | ATG | CCT | GTC | 2640 |
| Pro | Glu | Thr | Thr | Gly | Glu | Glu | Asp | Glu | Glu | Glu | Pro | Glu | Met | Pro | Val | |
| 865 | | | | | 870 | | | | | 875 | | | | | 880 | |
| GGC | CCT | CGC | CCA | CGA | CCA | CTC | TCT | GAG | CTT | CAC | CTT | AAG | GAA | AAG | GCA | 2688 |
| Gly | Pro | Arg | Pro | Arg | Pro | Leu | Ser | Glu | Leu | His | Leu | Lys | Glu | Lys | Ala | |
| | | | | 885 | | | | | 890 | | | | | 895 | | |
| GTG | CCC | ATG | CCA | GAA | GCC | AGC | GCG | TTT | TTC | ATC | TTC | AGC | TCT | AAC | AAC | 2736 |
| Val | Pro | Met | Pro | Glu | Ala | Ser | Ala | Phe | Phe | Ile | Phe | Ser | Ser | Asn | Asn | |
| | | | 900 | | | | | 905 | | | | | 910 | | | |
| AGG | TTT | CGC | CTC | CAG | TGC | CAC | CGC | ATT | GTC | AAT | GAC | ACG | ATC | TTC | ACC | 2784 |
| Arg | Phe | Arg | Leu | Gln | Cys | His | Arg | Ile | Val | Asn | Asp | Thr | Ile | Phe | Thr | |
| | | 915 | | | | | 920 | | | | | 925 | | | | |
| AAC | CTG | ATC | CTC | TTC | TTC | ATT | CTG | CTC | AGC | AGC | ATT | TCC | CTG | GCT | GCT | 2832 |
| Asn | Leu | Ile | Leu | Phe | Phe | Ile | Leu | Leu | Ser | Ser | Ile | Ser | Leu | Ala | Ala | |
| | 930 | | | | | 935 | | | | | 940 | | | | | |
| GAG | GAC | CCG | GTC | CAG | CAC | ACC | TCC | TTC | AGG | AAC | CAT | ATT | CTG | TTT | TAT | 2880 |
| Glu | Asp | Pro | Val | Gln | His | Thr | Ser | Phe | Arg | Asn | His | Ile | Leu | Phe | Tyr | |
| 945 | | | | | 950 | | | | | 955 | | | | | 960 | |
| TTT | GAT | ATT | GTT | TTT | ACC | ACC | ATT | TTC | ACC | ATT | GAA | ATT | GCT | CTG | AAG | 2928 |
| Phe | Asp | Ile | Val | Phe | Thr | Thr | Ile | Phe | Thr | Ile | Glu | Ile | Ala | Leu | Lys | |
| | | | | 965 | | | | | 970 | | | | | 975 | | |
| ATG | ACT | GCT | TAT | GGG | GCT | TTC | TTG | CAC | AAG | GGT | TCT | TTC | TGC | CGG | AAC | 2976 |
| Met | Thr | Ala | Tyr | Gly | Ala | Phe | Leu | His | Lys | Gly | Ser | Phe | Cys | Arg | Asn | |
| | | | 980 | | | | | 985 | | | | | 990 | | | |
| TAC | TTC | AAC | ATC | CTG | GAC | CTG | CTG | GTG | GTC | AGC | GTG | TCC | CTC | ATC | TCC | 3024 |
| Tyr | Phe | Asn | Ile | Leu | Asp | Leu | Leu | Val | Val | Ser | Val | Ser | Leu | Ile | Ser | |
| | | 995 | | | | | 1000 | | | | | 1005 | | | | |
| TTT | GGC | ATC | CAG | TCC | AGT | GCA | ATC | AAT | GTC | GTG | AAG | ATC | TTG | CGA | GTC | 3072 |
| Phe | Gly | Ile | Gln | Ser | Ser | Ala | Ile | Asn | Val | Val | Lys | Ile | Leu | Arg | Val | |
| | 1010 | | | | | 1015 | | | | | 1020 | | | | | |
| CTG | CGA | GTA | CTC | AGG | CCC | CTG | AGG | GCC | ATC | AAC | AGG | GCC | AAG | GGG | CTA | 3120 |
| Leu | Arg | Val | Leu | Arg | Pro | Leu | Arg | Ala | Ile | Asn | Arg | Ala | Lys | Gly | Leu | |
| 1025 | | | | | 1030 | | | | | 1035 | | | | | 1040 | |
| AAG | CAT | GTG | GTT | CAG | TGT | GTG | TTT | GTC | GCC | ATC | CGG | ACC | ATC | GGG | AAC | 3168 |
| Lys | His | Val | Val | Gln | Cys | Val | Phe | Val | Ala | Ile | Arg | Thr | Ile | Gly | Asn | |
| | | | | 1045 | | | | | 1050 | | | | | 1055 | | |
| ATC | GTG | ATT | GTC | ACC | ACC | CTG | CTG | CAG | TTC | ATG | TTT | GCC | TGC | ATC | GGG | 3216 |
| Ile | Val | Ile | Val | Thr | Thr | Leu | Leu | Gln | Phe | Met | Phe | Ala | Cys | Ile | Gly | |
| | | | | 1060 | | | | | 1065 | | | | | 1070 | | |

| | | | | | | | | | | | | | | | | |
|---|---|---|---|---|---|---|---|---|---|---|---|---|---|---|---|---|
| GTC | CAG | CTC | TTC | AAG | GGA | AAG | CTG | TAC | ACC | TGT | TCA | GAC | AGT | TCC | AAG | 3264 |
| Val | Gln | Leu | Phe | Lys | Gly | Lys | Leu | Tyr | Thr | Cys | Ser | Asp | Ser | Ser | Lys | |
| | | | 1075 | | | | 1080 | | | | 1085 | | | | | |
| CAG | ACA | GAG | GCG | GAA | TGC | AAG | GGC | AAC | TAC | ATC | ACG | TAC | AAA | GAC | GGG | 3312 |
| Gln | Thr | Glu | Ala | Glu | Cys | Lys | Gly | Asn | Tyr | Ile | Thr | Tyr | Lys | Asp | Gly | |
| | 1090 | | | | | 1095 | | | | | 1100 | | | | | |
| GAG | GTT | GAC | CAC | CCC | ATC | ATC | CAA | CCC | CGC | AGC | TGG | GAG | AAC | AGC | AAG | 3360 |
| Glu | Val | Asp | His | Pro | Ile | Ile | Gln | Pro | Arg | Ser | Trp | Glu | Asn | Ser | Lys | |
| 1105 | | | | | | 1110 | | | | | 1115 | | | | 1120 | |
| TTT | GAC | TTT | GAC | AAT | GTT | CTG | GCA | GCC | ATG | ATG | GCC | CTC | TTC | ACC | GTC | 3408 |
| Phe | Asp | Phe | Asp | Asn | Val | Leu | Ala | Ala | Met | Met | Ala | Leu | Phe | Thr | Val | |
| | | | | 1125 | | | | | 1130 | | | | | 1135 | | |
| TCC | ACC | TTC | GAA | GGG | TGG | CCA | GAG | CTG | CTG | TAC | CGC | TCC | ATC | GAC | TCC | 3456 |
| Ser | Thr | Phe | Glu | Gly | Trp | Pro | Glu | Leu | Leu | Tyr | Arg | Ser | Ile | Asp | Ser | |
| | | 1140 | | | | | 1145 | | | | | 1150 | | | | |
| CAC | ACG | GAA | GAC | AAG | GGC | CCC | ATC | TAC | AAC | TAC | CGT | GTG | GAG | ATC | TCC | 3504 |
| His | Thr | Glu | Asp | Lys | Gly | Pro | Ile | Tyr | Asn | Tyr | Arg | Val | Glu | Ile | Ser | |
| | 1155 | | | | | 1160 | | | | | 1165 | | | | | |
| ATC | TTC | TTC | ATC | ATC | TAC | ATC | ATC | ATC | GCC | TTC | TTC | ATG | ATG | AAC | | 3552 |
| Ile | Phe | Phe | Ile | Ile | Tyr | Ile | Ile | Ile | Ala | Phe | Phe | Met | Met | Asn | | |
| 1170 | | | | | 1175 | | | | | 1180 | | | | | | |
| ATC | TTC | GTG | GGC | TTC | GTC | ATC | GTC | ACC | TTT | CAG | GAG | CAG | GGG | GAG | CAG | 3600 |
| Ile | Phe | Val | Gly | Phe | Val | Ile | Val | Thr | Phe | Gln | Glu | Gln | Gly | Glu | Gln | |
| 1185 | | | | 1190 | | | | | 1195 | | | | 1200 | | | |
| GAG | TAC | AAG | AAC | TGT | GAG | CTG | GAC | AAG | AAC | CAG | CGA | CAG | TGC | GTG | GAA | 3648 |
| Glu | Tyr | Lys | Asn | Cys | Glu | Leu | Asp | Lys | Asn | Gln | Arg | Gln | Cys | Val | Glu | |
| | | | 1205 | | | | | 1210 | | | | | 1215 | | | |
| TAC | GCC | CTC | AAG | GCC | CGG | CCC | CTG | CGG | AGG | TAC | ATC | CCC | AAG | AAC | CAG | 3696 |
| Tyr | Ala | Leu | Lys | Ala | Arg | Pro | Leu | Arg | Arg | Tyr | Ile | Pro | Lys | Asn | Gln | |
| | | | 1220 | | | | | 1225 | | | | | 1230 | | | |
| CAC | CAG | TAC | AAA | GTG | TGG | TAC | GTG | GTC | AAC | TCC | ACC | TAC | TTC | GAG | TAC | 3744 |
| His | Gln | Tyr | Lys | Val | Trp | Tyr | Val | Val | Asn | Ser | Thr | Tyr | Phe | Glu | Tyr | |
| | 1235 | | | | | 1240 | | | | | 1245 | | | | | |
| CTG | ATG | TTC | GTC | CTC | ATC | CTG | CTC | AAC | ACC | ATC | TGC | CTG | GCC | ATG | CAG | 3792 |
| Leu | Met | Phe | Val | Leu | Ile | Leu | Leu | Asn | Thr | Ile | Cys | Leu | Ala | Met | Gln | |
| | | 1250 | | | | | 1255 | | | | | 1260 | | | | |
| CAC | TAC | GGC | CAG | AGC | TGC | CTG | TTC | AAA | ATC | GCC | ATG | AAC | ATC | CTC | AAC | 3840 |
| His | Tyr | Gly | Gln | Ser | Cys | Leu | Phe | Lys | Ile | Ala | Met | Asn | Ile | Leu | Asn | |
| 1265 | | | | | 1270 | | | | | 1275 | | | | | 1280 | |
| ATG | CTC | TTC | ACT | GGC | CTC | TTC | ACC | GTG | GAG | ATG | ATC | CTG | AAG | CTC | ATT | 3888 |
| Met | Leu | Phe | Thr | Gly | Leu | Phe | Thr | Val | Glu | Met | Ile | Leu | Lys | Leu | Ile | |
| | | | | 1285 | | | | | 1290 | | | | | 1295 | | |
| GCC | TTC | AAA | CCC | AAG | GGT | TAC | TTT | AGT | GAT | CCC | TGG | AAT | GTT | TTT | GAC | 3936 |
| Ala | Phe | Lys | Pro | Lys | Gly | Tyr | Phe | Ser | Asp | Pro | Trp | Asn | Val | Phe | Asp | |
| | | | 1300 | | | | | 1305 | | | | | 1310 | | | |
| TTC | CTC | ATC | GTA | ATT | GGC | AGC | ATA | ATT | GAC | GTC | ATT | CTC | AGT | GAG | ACT | 3984 |
| Phe | Leu | Ile | Val | Ile | Gly | Ser | Ile | Ile | Asp | Val | Ile | Leu | Ser | Glu | Thr | |
| | | | 1315 | | | | | 1320 | | | | | 1325 | | | |
| AAT | CCA | GCT | GAA | CAT | ACC | CAA | TGC | TCT | CCC | TCT | ATG | AAC | GCA | GAG | GAA | 4032 |
| Asn | Pro | Ala | Glu | His | Thr | Gln | Cys | Ser | Pro | Ser | Met | Asn | Ala | Glu | Glu | |
| | 1330 | | | | | 1335 | | | | | 1340 | | | | | |
| AAC | TCC | CGC | ATC | TCC | ATC | ACC | TTC | TTC | CGC | CTG | TTC | CGG | GTC | ATG | CGT | 4080 |
| Asn | Ser | Arg | Ile | Ser | Ile | Thr | Phe | Phe | Arg | Leu | Phe | Arg | Val | Met | Arg | |
| 1345 | | | | | 1350 | | | | | 1355 | | | | | 1360 | |
| CTG | GTG | AAG | CTG | CTG | AGC | CGT | GGG | GAG | GGC | ATC | CGG | ACG | CTG | CTG | TGG | 4128 |
| Leu | Val | Lys | Leu | Leu | Ser | Arg | Gly | Glu | Gly | Ile | Arg | Thr | Leu | Leu | Trp | |
| | | | | 1365 | | | | | 1370 | | | | | 1375 | | |
| ACC | TTC | ATC | AAG | TCC | TTC | CAG | GCC | CTG | CCC | TAT | GTG | GCC | CTC | CTG | ATC | 4176 |
| Thr | Phe | Ile | Lys | Ser | Phe | Gln | Ala | Leu | Pro | Tyr | Val | Ala | Leu | Leu | Ile | |
| | | | 1380 | | | | | 1385 | | | | | 1390 | | | |

| | |
|---|---|
| GTG ATG CTG TTC TTC ATC TAC GCG GTG ATC GGG ATG CAG GTG TTT GGG<br>Val Met Leu Phe Phe Ile Tyr Ala Val Ile Gly Met Gln Val Phe Gly<br>           1395                           1400                     1405 | 4224 |
| AAA ATT GCC CTG AAT GAT ACC ACA GAG ATC AAC CGG AAC AAC AAC TTT<br>Lys Ile Ala Leu Asn Asp Thr Thr Glu Ile Asn Arg Asn Asn Asn Phe<br>1410                           1415                         1420 | 4272 |
| CAG ACC TTC CCC CAG GCC GTG CTG CTC CTC TTC AGG TGT GCC ACC GGG<br>Gln Thr Phe Pro Gln Ala Val Leu Leu Leu Phe Arg Cys Ala Thr Gly<br>1425                     1430                     1435                 1440 | 4320 |
| GAG GCC TGG CAG GAC ATC ATG CTG GCC TGC ATG CCA GGC AAG AAG TGT<br>Glu Ala Trp Gln Asp Ile Met Leu Ala Cys Met Pro Gly Lys Lys Cys<br>                   1445                     1450                 1455 | 4368 |
| GCC CCA GAG TCC GAG CCC AGC AAC AGC ACG GAG GGT GAA ACA CCC TGT<br>Ala Pro Glu Ser Glu Pro Ser Asn Ser Thr Glu Gly Glu Thr Pro Cys<br>                   1460                     1465                 1470 | 4416 |
| GGT AGC AGC TTT GCT GTC TTC TAC TTC ATC AGC TTC TAC ATG CGC TGT<br>Gly Ser Ser Phe Ala Val Phe Tyr Phe Ile Ser Phe Tyr Met Arg Cys<br>                   1475                     1480                 1485 | 4464 |
| GCC TTC CTG ATC ATC AAC CTC TTT GTA GCT GTC ATC ATG GAC AAC TTT<br>Ala Phe Leu Ile Ile Asn Leu Phe Val Ala Val Ile Met Asp Asn Phe<br>1490                           1495                         1500 | 4512 |
| GAC TAC CTG ACA AGG GAC TGG TCC ATC CTT GGT CCC CAC CAC CTG GAT<br>Asp Tyr Leu Thr Arg Asp Trp Ser Ile Leu Gly Pro His His Leu Asp<br>1505                   1510                     1515                 1520 | 4560 |
| GAG TTT AAA AGA ATC TGG GCA GAG TAT GAC CCT GAA GCC AAG GGT CGT<br>Glu Phe Lys Arg Ile Trp Ala Glu Tyr Asp Pro Glu Ala Lys Gly Arg<br>                   1525                     1530                 1535 | 4608 |
| ATC AAA CAC CTG GAT GTG GTG ACC CTC CTC CGG CGG ATT CAG CCG CCA<br>Ile Lys His Leu Asp Val Val Thr Leu Leu Arg Arg Ile Gln Pro Pro<br>               1540                     1545                 1550 | 4656 |
| CTA GGT TTT GGG AAG CTG TGC CCT CAC CGC GTG GCT TGC AAA CGC CTG<br>Leu Gly Phe Gly Lys Leu Cys Pro His Arg Val Ala Cys Lys Arg Leu<br>               1555                     1560                 1565 | 4704 |
| GTC TCC ATG AAC ATG CCT CTG AAC AGC GAC GGG ACA GTC ATG TTC AAT<br>Val Ser Met Asn Met Pro Leu Asn Ser Asp Gly Thr Val Met Phe Asn<br>1570                           1575                         1580 | 4752 |
| GCC ACC CTG TTT GCC CTG GTC AGG ACG GCC CTG AGG ATC AAA ACA GAA<br>Ala Thr Leu Phe Ala Leu Val Arg Thr Ala Leu Arg Ile Lys Thr Glu<br>1585                   1590                     1595                 1600 | 4800 |
| GGG AAC CTA GAA CAA GCC AAT GAG GAG CTG CGG GCG ATC ATC AAG AAG<br>Gly Asn Leu Glu Gln Ala Asn Glu Glu Leu Arg Ala Ile Ile Lys Lys<br>                   1605                     1610                 1615 | 4848 |
| ATC TGG AAG CGG ACC AGC ATG AAG CTG CTG GAC CAG GTG GTG CCC CCT<br>Ile Trp Lys Arg Thr Ser Met Lys Leu Leu Asp Gln Val Val Pro Pro<br>               1620                     1625                 1630 | 4896 |
| GCA GGT GAT GAT GAG GTC ACC GTT GGC AAG TTC TAC GCC ACG TTC CTG<br>Ala Gly Asp Asp Glu Val Thr Val Gly Lys Phe Tyr Ala Thr Phe Leu<br>               1635                     1640                 1645 | 4944 |
| ATC CAG GAG TAC TTC CGG AAG TTC AAG AAG CGC AAA GAG CAG GGC CTT<br>Ile Gln Glu Tyr Phe Arg Lys Phe Lys Lys Arg Lys Glu Gln Gly Leu<br>1650                           1655                         1660 | 4992 |
| GTG GGC AAG CCC TCC CAG AGG AAC GCG CTG TCT CTG CAG GCT GGC TTG<br>Val Gly Lys Pro Ser Gln Arg Asn Ala Leu Ser Leu Gln Ala Gly Leu<br>1665                   1670                     1675                 1680 | 5040 |
| CGC ACA CTG CAT GAC ATC GGG CCT GAG ATC CGA CGG GCC ATC TCT GGA<br>Arg Thr Leu His Asp Ile Gly Pro Glu Ile Arg Arg Ala Ile Ser Gly<br>                   1685                     1690                 1695 | 5088 |
| GAT CTC ACC GCT GAG GAG GAG CTG GAC AAG GCC ATG AAG GAG GCT GTG<br>Asp Leu Thr Ala Glu Glu Glu Leu Asp Lys Ala Met Lys Glu Ala Val<br>               1700                     1705                 1710 | 5136 |

| | | | | | | | | | | | | | | | | |
|---|---|---|---|---|---|---|---|---|---|---|---|---|---|---|---|---|
| TCC | GCT | GCT | TCT | GAA | GAT | GAC | ATC | TTC | AGG | AGG | GCC | GGT | GGC | CTG | TTC | 5184 |
| Ser | Ala | Ala | Ser | Glu | Asp | Asp | Ile | Phe | Arg | Arg | Ala | Gly | Gly | Leu | Phe | |
| | | 1715 | | | 1720 | | | | | | | 1725 | | | | |
| GGC | AAC | CAC | GTC | AGC | TAC | TAC | CAA | AGC | GAC | GGC | AGG | AGC | GCC | TTC | CCC | 5232 |
| Gly | Asn | His | Val | Ser | Tyr | Tyr | Gln | Ser | Asp | Gly | Arg | Ser | Ala | Phe | Pro | |
| | 1730 | | | | | 1735 | | | | | 1740 | | | | | |
| CAG | ACC | TTC | ACC | ACT | CAG | CGC | CCG | CTG | CAC | ATC | AAC | AAG | GCG | GGC | AGC | 5280 |
| Gln | Thr | Phe | Thr | Thr | Gln | Arg | Pro | Leu | His | Ile | Asn | Lys | Ala | Gly | Ser | |
| 1745 | | | | | 1750 | | | | 1755 | | | | | | 1760 | |
| AGC | CAG | GGC | GAC | ACT | GAG | TCG | CCA | TCC | CAC | GAG | AAG | CTG | GTG | GAC | TCC | 5328 |
| Ser | Gln | Gly | Asp | Thr | Glu | Ser | Pro | Ser | His | Glu | Lys | Leu | Val | Asp | Ser | |
| | | | | 1765 | | | | | 1770 | | | | | 1775 | | |
| ACC | TTC | ACC | CCG | AGC | AGC | TAC | TCG | TCC | ACC | GGC | TCC | AAC | GCC | AAC | ATC | 5376 |
| Thr | Phe | Thr | Pro | Ser | Ser | Tyr | Ser | Ser | Thr | Gly | Ser | Asn | Ala | Asn | Ile | |
| | | | 1780 | | | | | 1785 | | | | | 1790 | | | |
| AAC | AAC | GCC | AAC | AAC | ACC | GCC | CTG | GGT | CGC | CTC | CCT | CGC | CCC | GCC | GGC | 5424 |
| Asn | Asn | Ala | Asn | Asn | Thr | Ala | Leu | Gly | Arg | Leu | Pro | Arg | Pro | Ala | Gly | |
| | | | 1795 | | | | 1800 | | | | | 1805 | | | | |
| TAC | CCC | AGC | ACA | GTC | AGC | ACT | GTG | GAG | GGC | CAC | GGG | CCC | CCC | TTG | TCC | 5472 |
| Tyr | Pro | Ser | Thr | Val | Ser | Thr | Val | Glu | Gly | His | Gly | Pro | Pro | Leu | Ser | |
| | 1810 | | | | | 1815 | | | | | 1820 | | | | | |
| CCT | GCC | ATC | CGG | GTG | CAG | GAG | GTG | GCG | TGG | AAG | CTC | AGC | TCC | AAC | AGG | 5520 |
| Pro | Ala | Ile | Arg | Val | Gln | Glu | Val | Ala | Trp | Lys | Leu | Ser | Ser | Asn | Arg | |
| 1825 | | | | | 1830 | | | | | 1835 | | | | | 1840 | |
| TGC | CAC | TCC | CGG | GAG | AGC | CAG | GCA | GCC | ATG | GCG | CGT | CAG | GAG | GAG | ACG | 5568 |
| Cys | His | Ser | Arg | Glu | Ser | Gln | Ala | Ala | Met | Ala | Arg | Gln | Glu | Glu | Thr | |
| | | | | 1845 | | | | | 1850 | | | | | 1855 | | |
| TCT | CAG | GAT | GAG | ACC | TAT | GAA | GTG | AAG | ATG | AAC | CAT | GAC | ACG | GAG | GCC | 5616 |
| Ser | Gln | Asp | Glu | Thr | Tyr | Glu | Val | Lys | Met | Asn | His | Asp | Thr | Glu | Ala | |
| | | | 1860 | | | | | 1865 | | | | | 1870 | | | |
| TGC | AGT | GAG | CCC | AGC | CTG | CTC | TCC | ACA | GAG | ATG | CTC | TCC | TAC | CAG | GAT | 5664 |
| Cys | Ser | Glu | Pro | Ser | Leu | Leu | Ser | Thr | Glu | Met | Leu | Ser | Tyr | Gln | Asp | |
| | | 1875 | | | | | 1880 | | | | | 1885 | | | | |
| GAC | GAA | AAT | CGG | CAA | CTG | ACG | CTC | CCA | GAG | GAG | GAC | AAG | AGG | GAC | ATC | 5712 |
| Asp | Glu | Asn | Arg | Gln | Leu | Thr | Leu | Pro | Glu | Glu | Asp | Lys | Arg | Asp | Ile | |
| | | 1890 | | | | | 1895 | | | | | 1900 | | | | |
| CGG | CAA | TCT | CCG | AAG | AGG | GGT | TTC | CTC | CGC | TCT | TCC | TCA | CTA | GGT | CGA | 5760 |
| Arg | Gln | Ser | Pro | Lys | Arg | Gly | Phe | Leu | Arg | Ser | Ser | Ser | Leu | Gly | Arg | |
| 1905 | | | | | 1910 | | | | | 1915 | | | | | 1920 | |
| AGG | GCC | TCC | TTC | CAC | CTG | GAA | TGT | CTG | AAG | CGA | CAG | AAG | GAC | CGA | GGG | 5808 |
| Arg | Ala | Ser | Phe | His | Leu | Glu | Cys | Leu | Lys | Arg | Gln | Lys | Asp | Arg | Gly | |
| | | | | 1925 | | | | | 1930 | | | | | 1935 | | |
| GGA | GAC | ATC | TCT | CAG | AAG | ACA | GTC | CTG | CCC | TTG | CAT | CTG | GTT | CAT | CAT | 5856 |
| Gly | Asp | Ile | Ser | Gln | Lys | Thr | Val | Leu | Pro | Leu | His | Leu | Val | His | His | |
| | | | 1940 | | | | | 1945 | | | | | 1950 | | | |
| CAG | GCA | TTG | GCA | GTG | GCA | GGC | CTG | AGC | CCC | CTC | CTC | CAG | AGA | AGC | CAT | 5904 |
| Gln | Ala | Leu | Ala | Val | Ala | Gly | Leu | Ser | Pro | Leu | Leu | Gln | Arg | Ser | His | |
| | | | 1955 | | | | | 1960 | | | | | 1965 | | | |

( 2 ) INFORMATION FOR SEQ ID NO:4:

( i ) SEQUENCE CHARACTERISTICS:
        ( A ) LENGTH: 132 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:4:

| | | | | | |
|---|---|---|---|---|---|
| AGACCACGGC | TTCCTCGAAT | CTTGCGCGAA | GCCGCCGGCC | TCGGAGGAGG | GATTAATCCA | 60 |
| GACCCGCCGG | GGGGTGTTTT | CACATTTCTT | CCTCTTCGTG | GCTGCTCCTC | CTATTAAAAC | 120 |

CATTTTTGGT CC                                                                                        132

( 2 ) INFORMATION FOR SEQ ID NO:5:

( i ) SEQUENCE CHARACTERISTICS:
        ( A ) LENGTH: 89 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:5:

```
CGCTGAGGGC  CTTCCGCGTG  CTGCGCCCCC  TGCGGCTGGT  GTCCGGAGTC  CCAAGTCTCC       60

AGGTGGTCCT  GAATTCCATC  ATCAAGGCC                                           89
```

( 2 ) INFORMATION FOR SEQ ID NO:6:

( i ) SEQUENCE CHARACTERISTICS:
        ( A ) LENGTH: 84 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 1..84
        ( D ) OTHER INFORMATION: /note="An alternative exon of
            alpha-1C."

( x i ) SEQUENCE DESCRIPTION: SEQ ID NO:6:

```
CAC  TAT  TTC  TGT  GAT  GCA  TGG  AAT  ACA  TTT  GAC  GCC  TTG  ATT  GTT  GTG    48
His  Tyr  Phe  Cys  Asp  Ala  Trp  Asn  Thr  Phe  Asp  Ala  Leu  Ile  Val  Val
 1                  5                        10                       15

GGT  AGC  ATT  GTT  GAT  ATA  GCA  ATC  ACC  GAG  GTA  AAC                        84
Gly  Ser  Ile  Val  Asp  Ile  Ala  Ile  Thr  Glu  Val  Asn
           20                       25
```

( 2 ) INFORMATION FOR SEQ ID NO:7:

( i ) SEQUENCE CHARACTERISTICS:
        ( A ) LENGTH: 7362 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 144..7163

( i x ) FEATURE:
        ( A ) NAME/KEY: 5'UTR
        ( B ) LOCATION: 1..143

( i x ) FEATURE:
        ( A ) NAME/KEY: 3'UTR
        ( B ) LOCATION: 7161..7362

( x i ) SEQUENCE DESCRIPTION: SEQ ID NO:7:

```
GCGGCGGCGG  CTGCGGCGGT  GGGGCCGGGC  GAGGTCCGTG  CGGTCCCGGC  GGCTCCGTGG        60

CTGCTCCGCT  CTGAGCGCCT  GCGCGCCCCG  CGCCCTCCCT  GCCGGGGCCG  CTGGGCCGGG       120

GATGCACGCG  GGGCCCGGGA  GCC  ATG  GTC  CGC  TTC  GGG  GAC  GAG  CTG  GGC     170
                             Met  Val  Arg  Phe  Gly  Asp  Glu  Leu  Gly
                              1                  5
```

| | | | | | | | | | | | | | | | | |
|---|---|---|---|---|---|---|---|---|---|---|---|---|---|---|---|---|
| GGC | CGC | TAT | GGA | GGC | CCC | GGC | GGC | GGA | GAG | CGG | GCC | CGG | GGC | GGC | GGG | 218 |
| Gly | Arg | Tyr | Gly | Gly | Pro | Gly | Gly | Gly | Glu | Arg | Ala | Arg | Gly | Gly | Gly | |
| 10 | | | | 15 | | | | | 20 | | | | | | 25 | |
| GCC | GGC | GGG | GCG | GGG | GGC | CCG | GGT | CCC | GGG | GGG | CTG | CAG | CCC | GGC | CAG | 266 |
| Ala | Gly | Gly | Ala | Gly | Gly | Pro | Gly | Pro | Gly | Gly | Leu | Gln | Pro | Gly | Gln | |
| | | | 30 | | | | | 35 | | | | | 40 | | | |
| CGG | GTC | CTC | TAC | AAG | CAA | TCG | ATC | GCG | CAG | CGC | GCG | CGG | ACC | ATG | GCG | 314 |
| Arg | Val | Leu | Tyr | Lys | Gln | Ser | Ile | Ala | Gln | Arg | Ala | Arg | Thr | Met | Ala | |
| | | | 45 | | | | | 50 | | | | | 55 | | | |
| CTG | TAC | AAC | CCC | ATC | CCG | GTC | AAG | CAG | AAC | TGC | TTC | ACC | GTC | AAC | CGC | 362 |
| Leu | Tyr | Asn | Pro | Ile | Pro | Val | Lys | Gln | Asn | Cys | Phe | Thr | Val | Asn | Arg | |
| | | | 60 | | | | | 65 | | | | | 70 | | | |
| TCG | CTC | TTC | GTC | TTC | AGC | GAG | GAC | AAC | GTC | GTC | CGC | AAA | TAC | GCG | AAG | 410 |
| Ser | Leu | Phe | Val | Phe | Ser | Glu | Asp | Asn | Val | Val | Arg | Lys | Tyr | Ala | Lys | |
| | | 75 | | | | | 80 | | | | | 85 | | | | |
| CGC | ATC | ACC | GAG | TGG | CCT | CCA | TTC | GAG | AAT | ATG | ATC | CTG | GCC | ACC | ATC | 458 |
| Arg | Ile | Thr | Glu | Trp | Pro | Pro | Phe | Glu | Asn | Met | Ile | Leu | Ala | Thr | Ile | |
| 90 | | | | | 95 | | | | | 100 | | | | | 105 | |
| ATC | GCC | AAC | TGC | ATC | GTG | CTG | GCC | CTG | GAG | CAG | CAC | CTC | CCT | GAT | GGG | 506 |
| Ile | Ala | Asn | Cys | Ile | Val | Leu | Ala | Leu | Glu | Gln | His | Leu | Pro | Asp | Gly | |
| | | | | 110 | | | | | 115 | | | | | 120 | | |
| GAC | AAA | ACG | CCC | ATG | TCC | GAG | CGG | CTG | GAC | GAC | ACG | GAG | CCC | TAT | TTC | 554 |
| Asp | Lys | Thr | Pro | Met | Ser | Glu | Arg | Leu | Asp | Asp | Thr | Glu | Pro | Tyr | Phe | |
| | | | 125 | | | | | 130 | | | | | 135 | | | |
| ATC | GGG | ATC | TTT | TGC | TTC | GAG | GCA | GGG | ATC | AAA | ATC | ATC | GCT | CTG | GGC | 602 |
| Ile | Gly | Ile | Phe | Cys | Phe | Glu | Ala | Gly | Ile | Lys | Ile | Ile | Ala | Leu | Gly | |
| | | | 140 | | | | | 145 | | | | | 150 | | | |
| TTT | GTC | TTC | CAC | AAG | GGC | TCT | TAC | CTG | CGG | AAC | GGC | TGG | AAC | GTC | ATG | 650 |
| Phe | Val | Phe | His | Lys | Gly | Ser | Tyr | Leu | Arg | Asn | Gly | Trp | Asn | Val | Met | |
| | | 155 | | | | | 160 | | | | | 165 | | | | |
| GAC | TTC | GTG | GTC | GTC | CTC | ACA | GGG | ATC | CTT | GCC | ACG | GCT | GGA | ACT | GAC | 698 |
| Asp | Phe | Val | Val | Val | Leu | Thr | Gly | Ile | Leu | Ala | Thr | Ala | Gly | Thr | Asp | |
| 170 | | | | | 175 | | | | | 180 | | | | | 185 | |
| TTC | GAC | CTG | CGA | ACA | CTG | AGG | GCT | GTG | CGT | GTG | CTG | AGG | CCC | CTG | AAG | 746 |
| Phe | Asp | Leu | Arg | Thr | Leu | Arg | Ala | Val | Arg | Val | Leu | Arg | Pro | Leu | Lys | |
| | | | | 190 | | | | | 195 | | | | | 200 | | |
| CTG | GTG | TCT | GGG | ATT | CCA | AGT | TTG | CAG | GTG | GTG | CTC | AAG | TCC | ATC | ATG | 794 |
| Leu | Val | Ser | Gly | Ile | Pro | Ser | Leu | Gln | Val | Val | Leu | Lys | Ser | Ile | Met | |
| | | | 205 | | | | | 210 | | | | | 215 | | | |
| AAG | GCC | ATG | GTT | CCA | CTC | CTG | CAG | ATT | GGG | CTG | CTT | CTC | TTC | TTT | GCC | 842 |
| Lys | Ala | Met | Val | Pro | Leu | Leu | Gln | Ile | Gly | Leu | Leu | Leu | Phe | Phe | Ala | |
| | | 220 | | | | | 225 | | | | | 230 | | | | |
| ATC | CTC | ATG | TTT | GCC | ATC | ATT | GGC | CTG | GAG | TTC | TAC | ATG | GGC | AAG | TTC | 890 |
| Ile | Leu | Met | Phe | Ala | Ile | Ile | Gly | Leu | Glu | Phe | Tyr | Met | Gly | Lys | Phe | |
| | 235 | | | | | 240 | | | | | 245 | | | | | |
| CAC | AAG | GCC | TGT | TTC | CCC | AAC | AGC | ACA | GAT | GCG | GAG | CCC | GTG | GGT | GAC | 938 |
| His | Lys | Ala | Cys | Phe | Pro | Asn | Ser | Thr | Asp | Ala | Glu | Pro | Val | Gly | Asp | |
| 250 | | | | | 255 | | | | | 260 | | | | | 265 | |
| TTC | CCC | TGT | GGC | AAG | GAG | GCC | CCA | GCC | CGG | CTG | TGC | GAG | GGC | GAC | ACT | 986 |
| Phe | Pro | Cys | Gly | Lys | Glu | Ala | Pro | Ala | Arg | Leu | Cys | Glu | Gly | Asp | Thr | |
| | | | 270 | | | | | 275 | | | | | 280 | | | |
| GAG | TGC | CGG | GAG | TAC | TGG | CCA | GGA | CCC | AAC | TTT | GGC | ATC | ACC | AAC | TTT | 1034 |
| Glu | Cys | Arg | Glu | Tyr | Trp | Pro | Gly | Pro | Asn | Phe | Gly | Ile | Thr | Asn | Phe | |
| | | | 285 | | | | | 290 | | | | | 295 | | | |
| GAC | AAT | ATC | CTG | TTT | GCC | ATC | TTG | ACG | GTG | TTC | CAG | TGC | ATC | ACC | ATG | 1082 |
| Asp | Asn | Ile | Leu | Phe | Ala | Ile | Leu | Thr | Val | Phe | Gln | Cys | Ile | Thr | Met | |
| | | | 300 | | | | | 305 | | | | | 310 | | | |
| GAG | GGC | TGG | ACT | GAC | ATC | CTC | TAT | AAT | ACA | AAC | GAT | GCG | GCC | GGC | AAC | 1130 |
| Glu | Gly | Trp | Thr | Asp | Ile | Leu | Tyr | Asn | Thr | Asn | Asp | Ala | Ala | Gly | Asn | |
| | | 315 | | | | | 320 | | | | | 325 | | | | |

-continued

| | | | | | | | | | | | | | | | | |
|---|---|---|---|---|---|---|---|---|---|---|---|---|---|---|---|---|
| ACC | TGG | AAC | TGG | CTC | TAC | TTC | ATC | CCT | CTC | ATC | ATC | ATC | GGC | TCC | TTC | 1178 |
| Thr | Trp | Asn | Trp | Leu | Tyr | Phe | Ile | Pro | Leu | Ile | Ile | Ile | Gly | Ser | Phe | |
| 330 | | | | 335 | | | | | 340 | | | | | 345 | | |
| TTC | ATG | CTC | AAC | CTG | GTG | CTG | GGC | GTG | CTC | TCG | GGG | GAG | TTT | GCC | AAG | 1226 |
| Phe | Met | Leu | Asn | Leu | Val | Leu | Gly | Val | Leu | Ser | Gly | Glu | Phe | Ala | Lys | |
| | | | 350 | | | | | 355 | | | | | 360 | | | |
| GAG | CGA | GAG | AGG | GTG | GAG | AAC | CGC | CGC | GCC | TTC | CTG | AAG | CTG | CGC | CGG | 1274 |
| Glu | Arg | Glu | Arg | Val | Glu | Asn | Arg | Arg | Ala | Phe | Leu | Lys | Leu | Arg | Arg | |
| | | 365 | | | | | 370 | | | | | 375 | | | | |
| CAG | CAG | CAG | ATC | GAG | CGA | GAG | CTC | AAC | GGG | TAC | CTG | GAG | TGG | ATC | TTC | 1322 |
| Gln | Gln | Gln | Ile | Glu | Arg | Glu | Leu | Asn | Gly | Tyr | Leu | Glu | Trp | Ile | Phe | |
| | | 380 | | | | | 385 | | | | | 390 | | | | |
| AAG | GCG | GAG | GAA | GTC | ATG | CTG | GCC | GAG | GAG | GAC | AGG | AAT | GCA | GAG | GAG | 1370 |
| Lys | Ala | Glu | Glu | Val | Met | Leu | Ala | Glu | Glu | Asp | Arg | Asn | Ala | Glu | Glu | |
| 395 | | | | | 400 | | | | | 405 | | | | | | |
| AAG | TCC | CCT | TTG | GAC | GTG | CTG | AAG | AGA | GCG | GCC | ACC | AAG | AAG | AGC | AGA | 1418 |
| Lys | Ser | Pro | Leu | Asp | Val | Leu | Lys | Arg | Ala | Ala | Thr | Lys | Lys | Ser | Arg | |
| 410 | | | | 415 | | | | | 420 | | | | | 425 | | |
| AAT | GAC | CTG | ATC | CAC | GCA | GAG | GAG | GGA | GAG | GAC | CGG | TTT | GCA | GAT | CTC | 1466 |
| Asn | Asp | Leu | Ile | His | Ala | Glu | Glu | Gly | Glu | Asp | Arg | Phe | Ala | Asp | Leu | |
| | | | 430 | | | | | 435 | | | | | 440 | | | |
| TGT | GCT | GTT | GGA | TCC | CCC | TTC | GCC | CGC | GCC | AGC | CTC | AAG | AGC | GGG | AAG | 1514 |
| Cys | Ala | Val | Gly | Ser | Pro | Phe | Ala | Arg | Ala | Ser | Leu | Lys | Ser | Gly | Lys | |
| | | | 445 | | | | | 450 | | | | | 455 | | | |
| ACA | GAG | AGC | TCG | TCA | TAC | TTC | CGG | AGG | AAG | GAG | AAG | ATG | TTC | CGG | TTT | 1562 |
| Thr | Glu | Ser | Ser | Ser | Tyr | Phe | Arg | Arg | Lys | Glu | Lys | Met | Phe | Arg | Phe | |
| | | 460 | | | | | 465 | | | | | 470 | | | | |
| TTT | ATC | CGG | CGC | ATG | GTG | AAG | GCT | CAG | AGC | TTC | TAC | TGG | GTG | GTG | CTG | 1610 |
| Phe | Ile | Arg | Arg | Met | Val | Lys | Ala | Gln | Ser | Phe | Tyr | Trp | Val | Val | Leu | |
| | 475 | | | | | 480 | | | | | 485 | | | | | |
| TGC | GTG | GTG | GCC | CTG | AAC | ACA | CTG | TGT | GTG | GCC | ATG | GTG | CAT | TAC | AAC | 1658 |
| Cys | Val | Val | Ala | Leu | Asn | Thr | Leu | Cys | Val | Ala | Met | Val | His | Tyr | Asn | |
| 490 | | | | | 495 | | | | | 500 | | | | | 505 | |
| CAG | CCG | CGG | CGG | CTT | ACC | ACG | ACC | CTG | TAT | TTT | GCA | GAG | TTT | GTT | TTC | 1706 |
| Gln | Pro | Arg | Arg | Leu | Thr | Thr | Thr | Leu | Tyr | Phe | Ala | Glu | Phe | Val | Phe | |
| | | | | 510 | | | | | 515 | | | | | 520 | | |
| CTG | GGT | CTC | TTC | CTC | ACA | GAG | ATG | TCC | CTG | AAG | ATG | TAT | GGC | CTG | GGG | 1754 |
| Leu | Gly | Leu | Phe | Leu | Thr | Glu | Met | Ser | Leu | Lys | Met | Tyr | Gly | Leu | Gly | |
| | | | 525 | | | | | 530 | | | | | 535 | | | |
| CCC | AGA | AGC | TAC | TTC | CGG | TCC | TCC | TTC | AAC | TGC | TTC | GAC | TTT | GGG | GTC | 1802 |
| Pro | Arg | Ser | Tyr | Phe | Arg | Ser | Ser | Phe | Asn | Cys | Phe | Asp | Phe | Gly | Val | |
| | | 540 | | | | | 545 | | | | | 550 | | | | |
| ATC | GTG | GGG | AGC | GTC | TTT | GAA | GTG | GTC | TGG | GCG | GCC | ATC | AAG | CCG | GGA | 1850 |
| Ile | Val | Gly | Ser | Val | Phe | Glu | Val | Val | Trp | Ala | Ala | Ile | Lys | Pro | Gly | |
| | 555 | | | | | 560 | | | | | 565 | | | | | |
| AGC | TCC | TTT | GGG | ATC | AGT | GTG | CTG | CGG | GCC | CTC | CGC | CTG | CTG | AGG | ATC | 1898 |
| Ser | Ser | Phe | Gly | Ile | Ser | Val | Leu | Arg | Ala | Leu | Arg | Leu | Leu | Arg | Ile | |
| 570 | | | | | 575 | | | | | 580 | | | | | 585 | |
| TTC | AAA | GTC | ACG | AAG | TAC | TGG | AGC | TCC | CTG | CGG | AAC | CTG | GTG | GTG | TCC | 1946 |
| Phe | Lys | Val | Thr | Lys | Tyr | Trp | Ser | Ser | Leu | Arg | Asn | Leu | Val | Val | Ser | |
| | | | | 590 | | | | | 595 | | | | | 600 | | |
| CTG | CTG | AAC | TCC | ATG | AAG | TCC | ATC | ATC | AGC | CTC | TTC | TTG | CTC | TTC | 1994 |
| Leu | Leu | Asn | Ser | Met | Lys | Ser | Ile | Ile | Ser | Leu | Leu | Phe | Leu | Phe | |
| | | | 605 | | | | | 610 | | | | | 615 | | | |
| CTG | TTC | ATT | GTG | GTC | TTC | GCC | CTG | CTG | GGG | ATG | CAG | CTG | TTT | GGG | GGA | 2042 |
| Leu | Phe | Ile | Val | Val | Phe | Ala | Leu | Leu | Gly | Met | Gln | Leu | Phe | Gly | Gly | |
| | | 620 | | | | | 625 | | | | | 630 | | | | |
| CAG | TTC | AAC | TTC | CAG | GAT | GAG | ACT | CCC | ACA | ACC | AAC | TTC | GAC | ACC | TTC | 2090 |
| Gln | Phe | Asn | Phe | Gln | Asp | Glu | Thr | Pro | Thr | Thr | Asn | Phe | Asp | Thr | Phe | |
| | 635 | | | | | 640 | | | | | 645 | | | | | |

```
CCT GCC GCC ATC CTC ACT GTC TTC CAG ATC CTG ACG GGA GAG GAC TGG         2138
Pro Ala Ala Ile Leu Thr Val Phe Gln Ile Leu Thr Gly Glu Asp Trp
650             655                 660                 665

AAT GCA GTG ATG TAT CAC GGG ATC GAA TCG CAA GGC GGC GTC AGC AAA         2186
Asn Ala Val Met Tyr His Gly Ile Glu Ser Gln Gly Gly Val Ser Lys
                670                 675                 680

GGC ATG TTC TCG TCC TTT TAC TTC ATT GTC CTG ACA CTG TTC GGA AAC         2234
Gly Met Phe Ser Ser Phe Tyr Phe Ile Val Leu Thr Leu Phe Gly Asn
            685                 690                 695

TAC ACT CTG CTG AAT GTC TTT CTG GCC ATC GCT GTG GAC AAC CTG GCC         2282
Tyr Thr Leu Leu Asn Val Phe Leu Ala Ile Ala Val Asp Asn Leu Ala
        700                 705                 710

AAC GCC CAA GAG CTG ACC AAG GAT GAA GAG GAG ATG GAA GAA GCA GCC         2330
Asn Ala Gln Glu Leu Thr Lys Asp Glu Glu Glu Met Glu Glu Ala Ala
    715                 720                 725

AAT CAG AAG CTT GCT CTG CAA AAG GCC AAA GAA GTG GCT GAA GTC AGC         2378
Asn Gln Lys Leu Ala Leu Gln Lys Ala Lys Glu Val Ala Glu Val Ser
730                 735                 740                 745

CCC ATG TCT GCC GCG AAC ATC TCC ATC GCC GCC AGG CAG CAG AAC TCG         2426
Pro Met Ser Ala Ala Asn Ile Ser Ile Ala Ala Arg Gln Gln Asn Ser
                750                 755                 760

GCC AAG GCG CGC TCG GTG TGG GAG CAG CGG GCC AGC CAG CTA CGG CTG         2474
Ala Lys Ala Arg Ser Val Trp Glu Gln Arg Ala Ser Gln Leu Arg Leu
            765                 770                 775

CAG AAC CTG CGG GCC AGC TGC GAG GCG CTG TAC AGC GAG ATG GAC CCC         2522
Gln Asn Leu Arg Ala Ser Cys Glu Ala Leu Tyr Ser Glu Met Asp Pro
        780                 785                 790

GAG GAG CGG CTG CGC TTC GCC ACT ACG CGC CAC CTG CGG CCC GAC ATG         2570
Glu Glu Arg Leu Arg Phe Ala Thr Thr Arg His Leu Arg Pro Asp Met
    795                 800                 805

AAG ACG CAC CTG GAC CGG CCG CTG GTG GTG GAG CTG GGC CGC GAC GGC         2618
Lys Thr His Leu Asp Arg Pro Leu Val Val Glu Leu Gly Arg Asp Gly
810                 815                 820                 825

GCG CGG GGG CCC GTG GGA GGC AAA GCC CGA CCT GAG GCT GCG GAG GCC         2666
Ala Arg Gly Pro Val Gly Gly Lys Ala Arg Pro Glu Ala Ala Glu Ala
                830                 835                 840

CCC GAG GGC GTC GAC CCT CCG CGC AGG CAC CAC CGG CAC CGC GAC AAG         2714
Pro Glu Gly Val Asp Pro Pro Arg Arg His His Arg His Arg Asp Lys
            845                 850                 855

GAC AAG ACC CCC GCG GCG GGG GAC CAG GAC CGA GCA GAG GCC CCG AAG         2762
Asp Lys Thr Pro Ala Ala Gly Asp Gln Asp Arg Ala Glu Ala Pro Lys
        860                 865                 870

GCG GAG AGC GGG GAG CCC GGT GCC CGG GAG GAG CGG CCG CGG CCG CAC         2810
Ala Glu Ser Gly Glu Pro Gly Ala Arg Glu Glu Arg Pro Arg Pro His
    875                 880                 885

CGC AGC CAC AGC AAG GAG GCC GCG GGG CCC CCG GAG GCG CGG AGC GAG         2858
Arg Ser His Ser Lys Glu Ala Ala Gly Pro Pro Glu Ala Arg Ser Glu
890                 895                 900                 905

CGC GGC CGA GGC CCA GGC CCC GAG GGC GGC CGG CGG CAC CAC CGG CGC         2906
Arg Gly Arg Gly Pro Gly Pro Glu Gly Gly Arg Arg His His Arg Arg
                910                 915                 920

GGC TCC CCG GAG GAG GCG GCC GAG CGG GAG CCC CGA CGC CAC CGC GCG         2954
Gly Ser Pro Glu Glu Ala Ala Glu Arg Glu Pro Arg Arg His Arg Ala
            925                 930                 935

CAC CGG CAC CAG GAT CCG AGC AAG GAG TGC GCC GGC GCC AAG GGC GAG         3002
His Arg His Gln Asp Pro Ser Lys Glu Cys Ala Gly Ala Lys Gly Glu
        940                 945                 950

CGG CGC GCG CGG CAC CGC GGC GGC CCC CGA GCG GGG CCC CGG GAG GCG         3050
Arg Arg Ala Arg His Arg Gly Gly Pro Arg Ala Gly Pro Arg Glu Ala
    955                 960                 965
```

|  |  |  |  |  |  |  |  |  |  |  |  |  |  |  |  |
|---|---|---|---|---|---|---|---|---|---|---|---|---|---|---|---|
| GAG | AGC | GGG | GAG | GAG | CCG | GCG | CGG | CGG | CAC | CGG | GCC | CGG | CAC | AAG | GCG |
| Glu | Ser | Gly | Glu | Glu | Pro | Ala | Arg | Arg | His | Arg | Ala | Arg | His | Lys | Ala |
| 970 |  |  |  |  | 975 |  |  |  | 980 |  |  |  |  |  | 985 |

3098

|  |  |  |  |  |  |  |  |  |  |  |  |  |  |  |  |
|---|---|---|---|---|---|---|---|---|---|---|---|---|---|---|---|
| CAG | CCT | GCT | CAC | GAG | GCT | GTG | GAG | AAG | GAG | ACC | ACG | GAG | AAG | GAG | GCC |
| Gln | Pro | Ala | His | Glu | Ala | Val | Glu | Lys | Glu | Thr | Thr | Glu | Lys | Glu | Ala |
|  |  |  |  |  | 990 |  |  |  | 995 |  |  |  |  |  | 1000 |

3146

|  |  |  |  |  |  |  |  |  |  |  |  |  |  |  |  |
|---|---|---|---|---|---|---|---|---|---|---|---|---|---|---|---|
| ACG | GAG | AAG | GAG | GCT | GAG | ATA | GTG | GAA | GCC | GAC | AAG | GAA | AAG | GAG | CTC |
| Thr | Glu | Lys | Glu | Ala | Glu | Ile | Val | Glu | Ala | Asp | Lys | Glu | Lys | Glu | Leu |
|  |  |  |  | 1005 |  |  |  | 1010 |  |  |  |  | 1015 |  |  |

3194

|  |  |  |  |  |  |  |  |  |  |  |  |  |  |  |  |
|---|---|---|---|---|---|---|---|---|---|---|---|---|---|---|---|
| CGG | AAC | CAC | CAG | CCC | CGG | GAG | CCA | CAC | TGT | GAC | CTG | GAG | ACC | AGT | GGG |
| Arg | Asn | His | Gln | Pro | Arg | Glu | Pro | His | Cys | Asp | Leu | Glu | Thr | Ser | Gly |
|  |  |  | 1020 |  |  |  |  | 1025 |  |  |  |  | 1030 |  |  |

3242

|  |  |  |  |  |  |  |  |  |  |  |  |  |  |  |  |
|---|---|---|---|---|---|---|---|---|---|---|---|---|---|---|---|
| ACT | GTG | ACT | GTG | GGT | CCC | ATG | CAC | ACA | CTG | CCC | AGC | ACC | TGT | CTC | CAG |
| Thr | Val | Thr | Val | Gly | Pro | Met | His | Thr | Leu | Pro | Ser | Thr | Cys | Leu | Gln |
|  |  | 1035 |  |  |  |  | 1040 |  |  |  |  | 1045 |  |  |  |

3290

|  |  |  |  |  |  |  |  |  |  |  |  |  |  |  |  |
|---|---|---|---|---|---|---|---|---|---|---|---|---|---|---|---|
| AAG | GTG | GAG | GAA | CAG | CCA | GAG | GAT | GCA | GAC | AAT | CAG | CGG | AAC | GTC | ACT |
| Lys | Val | Glu | Glu | Gln | Pro | Glu | Asp | Ala | Asp | Asn | Gln | Arg | Asn | Val | Thr |
| 1050 |  |  |  |  | 1055 |  |  |  | 1060 |  |  |  |  |  | 1065 |

3338

|  |  |  |  |  |  |  |  |  |  |  |  |  |  |  |  |
|---|---|---|---|---|---|---|---|---|---|---|---|---|---|---|---|
| CGC | ATG | GGC | AGT | CAG | CCC | CCA | GAC | CCG | AAC | ACT | ATT | GTA | CAT | ATC | CCA |
| Arg | Met | Gly | Ser | Gln | Pro | Pro | Asp | Pro | Asn | Thr | Ile | Val | His | Ile | Pro |
|  |  |  | 1070 |  |  |  |  | 1075 |  |  |  |  | 1080 |  |  |

3386

|  |  |  |  |  |  |  |  |  |  |  |  |  |  |  |  |
|---|---|---|---|---|---|---|---|---|---|---|---|---|---|---|---|
| GTG | ATG | CTG | ACG | GGC | CCT | CTT | GGG | GAA | GCC | ACG | GTC | GTT | CCC | AGT | GGT |
| Val | Met | Leu | Thr | Gly | Pro | Leu | Gly | Glu | Ala | Thr | Val | Val | Pro | Ser | Gly |
|  |  |  |  | 1085 |  |  |  |  | 1090 |  |  |  |  | 1095 |  |

3434

|  |  |  |  |  |  |  |  |  |  |  |  |  |  |  |  |
|---|---|---|---|---|---|---|---|---|---|---|---|---|---|---|---|
| AAC | GTG | GAC | CTG | GAA | AGC | CAA | GCA | GAG | GGG | AAG | AAG | GAG | GTG | GAA | GCG |
| Asn | Val | Asp | Leu | Glu | Ser | Gln | Ala | Glu | Gly | Lys | Lys | Glu | Val | Glu | Ala |
|  |  |  | 1100 |  |  |  |  | 1105 |  |  |  |  | 1110 |  |  |

3482

|  |  |  |  |  |  |  |  |  |  |  |  |  |  |  |  |
|---|---|---|---|---|---|---|---|---|---|---|---|---|---|---|---|
| GAT | GAC | GTG | ATG | AGG | AGC | GGC | CCC | CGG | CCT | ATC | GTC | CCA | TAC | AGC | TCC |
| Asp | Asp | Val | Met | Arg | Ser | Gly | Pro | Arg | Pro | Ile | Val | Pro | Tyr | Ser | Ser |
|  |  | 1115 |  |  |  |  | 1120 |  |  |  |  | 1125 |  |  |  |

3530

|  |  |  |  |  |  |  |  |  |  |  |  |  |  |  |  |
|---|---|---|---|---|---|---|---|---|---|---|---|---|---|---|---|
| ATG | TTC | TGT | TTA | AGC | CCC | ACC | AAC | CTG | CTC | CGC | CGC | TTC | TGC | CAC | TAC |
| Met | Phe | Cys | Leu | Ser | Pro | Thr | Asn | Leu | Leu | Arg | Arg | Phe | Cys | His | Tyr |
| 1130 |  |  |  |  | 1135 |  |  |  | 1140 |  |  |  |  |  | 1145 |

3578

|  |  |  |  |  |  |  |  |  |  |  |  |  |  |  |  |
|---|---|---|---|---|---|---|---|---|---|---|---|---|---|---|---|
| ATC | GTG | ACC | ATG | AGG | TAC | TTC | GAG | GTG | GTC | ATT | CTC | GTG | GTC | ATC | GCC |
| Ile | Val | Thr | Met | Arg | Tyr | Phe | Glu | Val | Val | Ile | Leu | Val | Val | Ile | Ala |
|  |  |  |  | 1150 |  |  |  |  | 1155 |  |  |  |  | 1160 |  |

3626

|  |  |  |  |  |  |  |  |  |  |  |  |  |  |  |  |
|---|---|---|---|---|---|---|---|---|---|---|---|---|---|---|---|
| TTG | AGC | AGC | ATC | GCC | CTG | GCT | GCT | GAG | GAC | CCA | GTG | CGC | ACA | GAC | TCG |
| Leu | Ser | Ser | Ile | Ala | Leu | Ala | Ala | Glu | Asp | Pro | Val | Arg | Thr | Asp | Ser |
|  |  |  | 1165 |  |  |  |  | 1170 |  |  |  |  | 1175 |  |  |

3674

|  |  |  |  |  |  |  |  |  |  |  |  |  |  |  |  |
|---|---|---|---|---|---|---|---|---|---|---|---|---|---|---|---|
| CCC | AGG | AAC | AAC | GCT | CTG | AAA | TAC | CTG | GAT | TAC | ATT | TTC | ACT | GGT | GTC |
| Pro | Arg | Asn | Asn | Ala | Leu | Lys | Tyr | Leu | Asp | Tyr | Ile | Phe | Thr | Gly | Val |
|  |  |  | 1180 |  |  |  |  | 1185 |  |  |  |  | 1190 |  |  |

3722

|  |  |  |  |  |  |  |  |  |  |  |  |  |  |  |  |
|---|---|---|---|---|---|---|---|---|---|---|---|---|---|---|---|
| TTT | ACC | TTT | GAG | ATG | GTG | ATA | AAG | ATG | ATC | GAC | TTG | GGA | CTG | CTG | CTT |
| Phe | Thr | Phe | Glu | Met | Val | Ile | Lys | Met | Ile | Asp | Leu | Gly | Leu | Leu | Leu |
| 1195 |  |  |  |  | 1200 |  |  |  | 1205 |  |  |  |  |  |  |

3770

|  |  |  |  |  |  |  |  |  |  |  |  |  |  |  |  |
|---|---|---|---|---|---|---|---|---|---|---|---|---|---|---|---|
| CAC | CCT | GGA | GCC | TAT | TTC | CGG | GAC | TTG | TGG | AAC | ATT | CTG | GAC | TTC | ATT |
| His | Pro | Gly | Ala | Tyr | Phe | Arg | Asp | Leu | Trp | Asn | Ile | Leu | Asp | Phe | Ile |
| 1210 |  |  |  |  | 1215 |  |  |  | 1220 |  |  |  |  |  | 1225 |

3818

|  |  |  |  |  |  |  |  |  |  |  |  |  |  |  |  |
|---|---|---|---|---|---|---|---|---|---|---|---|---|---|---|---|
| GTG | GTC | AGT | GGC | GCC | CTG | GTG | GCG | TTT | GCT | TTC | TCA | GGA | TCC | AAA | GGG |
| Val | Val | Ser | Gly | Ala | Leu | Val | Ala | Phe | Ala | Phe | Ser | Gly | Ser | Lys | Gly |
|  |  |  | 1230 |  |  |  |  | 1235 |  |  |  |  | 1240 |  |  |

3866

|  |  |  |  |  |  |  |  |  |  |  |  |  |  |  |  |
|---|---|---|---|---|---|---|---|---|---|---|---|---|---|---|---|
| AAA | GAC | ATC | AAT | ACC | ATC | AAG | TCT | CTG | AGA | GTC | CTT | CGT | GTC | CTG | CGG |
| Lys | Asp | Ile | Asn | Thr | Ile | Lys | Ser | Leu | Arg | Val | Leu | Arg | Val | Leu | Arg |
|  |  |  | 1245 |  |  |  |  | 1250 |  |  |  |  | 1255 |  |  |

3914

|  |  |  |  |  |  |  |  |  |  |  |  |  |  |  |  |
|---|---|---|---|---|---|---|---|---|---|---|---|---|---|---|---|
| CCC | CTC | AAG | ACC | ATC | AAA | CGG | CTG | CCC | AAG | CTC | AAG | GCT | GTG | TTT | GAC |
| Pro | Leu | Lys | Thr | Ile | Lys | Arg | Leu | Pro | Lys | Leu | Lys | Ala | Val | Phe | Asp |
|  |  |  | 1260 |  |  |  |  | 1265 |  |  |  |  | 1270 |  |  |

3962

|  |  |  |  |  |  |  |  |  |  |  |  |  |  |  |  |
|---|---|---|---|---|---|---|---|---|---|---|---|---|---|---|---|
| TGT | GTG | GTG | AAC | TCC | CTG | AAG | AAT | GTC | CTC | AAC | ATC | TTG | ATT | GTC | TAC |
| Cys | Val | Val | Asn | Ser | Leu | Lys | Asn | Val | Leu | Asn | Ile | Leu | Ile | Val | Tyr |
| 1275 |  |  |  |  | 1280 |  |  |  | 1285 |  |  |  |  |  |  |

4010

```
ATG CTC TTC ATG TTC ATA TTT GCC GTC ATT GCG GTG CAG CTC TTC AAA    4058
Met Leu Phe Met Phe Ile Phe Ala Val Ile Ala Val Gln Leu Phe Lys
1290            1295            1300            1305

GGG AAG TTT TTC TAC TGC ACA GAT GAA TCC AAG GAG CTG GAG AGG GAC    4106
Gly Lys Phe Phe Tyr Cys Thr Asp Glu Ser Lys Glu Leu Glu Arg Asp
        1310            1315            1320

TGC AGG GGT CAG TAT TTG GAT TAT GAG AAG GAG GAA GTG GAA GCT CAG    4154
Cys Arg Gly Gln Tyr Leu Asp Tyr Glu Lys Glu Glu Val Glu Ala Gln
1325            1330            1335

CCC AGG CAG TGG AAG AAA TAC GAC TTT CAC TAC GAC AAT GTG CTC TGG    4202
Pro Arg Gln Trp Lys Lys Tyr Asp Phe His Tyr Asp Asn Val Leu Trp
        1340            1345            1350

GCT CTG CTG ACG CTG TTC ACA GTG TCC ACG GGA GAA GGC TGG CCC ATG    4250
Ala Leu Leu Thr Leu Phe Thr Val Ser Thr Gly Glu Gly Trp Pro Met
1355            1360            1365

GTG CTG AAA CAC TCC GTG GAT GCC ACC TAT GAG GAG CAG GGT CCA AGC    4298
Val Leu Lys His Ser Val Asp Ala Thr Tyr Glu Glu Gln Gly Pro Ser
1370            1375            1380            1385

CCT GGG TAC CGC ATG GAG CTG TCC ATC TTC TAC GTG GTC TAC TTT GTG    4346
Pro Gly Tyr Arg Met Glu Leu Ser Ile Phe Tyr Val Val Tyr Phe Val
        1390            1395            1400

GTC TTT CCC TTC TTC TTC GTC AAC ATC TTT GTG GCT TTG ATC ATC ATC    4394
Val Phe Pro Phe Phe Phe Val Asn Ile Phe Val Ala Leu Ile Ile Ile
        1405            1410            1415

ACC TTC CAG GAG CAG GGG GAC AAG GTG ATG TCT GAA TGC AGC CTG GAG    4442
Thr Phe Gln Glu Gln Gly Asp Lys Val Met Ser Glu Cys Ser Leu Glu
        1420            1425            1430

AAG AAC GAG AGG GCT TGC ATT GAC TTC GCC ATC AGC GCC AAA CCC CTG    4490
Lys Asn Glu Arg Ala Cys Ile Asp Phe Ala Ile Ser Ala Lys Pro Leu
        1435            1440            1445

ACA CGG TAC ATG CCC CAA AAC CGG CAG TCG TTC CAG TAT AAG ACG TGG    4538
Thr Arg Tyr Met Pro Gln Asn Arg Gln Ser Phe Gln Tyr Lys Thr Trp
1450            1455            1460            1465

ACA TTT GTG GTC TCC CCG CCC TTT GAA TAC TTC ATC ATG GCC ATG ATA    4586
Thr Phe Val Val Ser Pro Pro Phe Glu Tyr Phe Ile Met Ala Met Ile
                1470            1475            1480

GCC CTC AAC ACT GTG GTG CTG ATG ATG AAG TTC TAT GAT GCA CCC TAT    4634
Ala Leu Asn Thr Val Val Leu Met Met Lys Phe Tyr Asp Ala Pro Tyr
        1485            1490            1495

GAG TAC GAG CTG ATG CTG AAA TGC CTG AAC ATC GTG TTC ACA TCC ATG    4682
Glu Tyr Glu Leu Met Leu Lys Cys Leu Asn Ile Val Phe Thr Ser Met
        1500            1505            1510

TTC TCC ATG GAA TGC GTG CTG AAG ATC ATC GCC TTT GGG GTG CTG AAC    4730
Phe Ser Met Glu Cys Val Leu Lys Ile Ile Ala Phe Gly Val Leu Asn
        1515            1520            1525

TAT TTC AGA GAT GCC TGG AAT GTC TTT GAC TTT GTC ACT GTG TTG GGA    4778
Tyr Phe Arg Asp Ala Trp Asn Val Phe Asp Phe Val Thr Val Leu Gly
1530            1535            1540            1545

AGT ATT ACT GAT ATT TTA GTA ACA GAG ATT GCG GAA ACG AAC AAT TTC    4826
Ser Ile Thr Asp Ile Leu Val Thr Glu Ile Ala Glu Thr Asn Asn Phe
                1550            1555            1560

ATC AAC CTC AGC TTC CTC CGC CTC TTT CGA GCT GCG CGG CTG ATC AAG    4874
Ile Asn Leu Ser Phe Leu Arg Leu Phe Arg Ala Ala Arg Leu Ile Lys
        1565            1570            1575

CTG CTC CGC CAG GGC TAC ACC ATC CGC ATC CTG CTG TGG ACC TTT GTC    4922
Leu Leu Arg Gln Gly Tyr Thr Ile Arg Ile Leu Leu Trp Thr Phe Val
        1580            1585            1590

CAG TCC TTC AAG GCC CTG CCC TAC GTG TGT CTG CTC ATT GCC ATG CTG    4970
Gln Ser Phe Lys Ala Leu Pro Tyr Val Cys Leu Leu Ile Ala Met Leu
        1595            1600            1605
```

| | | | | | | | | | | | | | | | | |
|---|---|---|---|---|---|---|---|---|---|---|---|---|---|---|---|---|
| TTC | TTC | ATC | TAC | GCC | ATC | ATC | GGC | ATG | CAG | GTG | TTT | GGG | AAT | ATT | GCC | 5018 |
| Phe 1610 | Phe | Ile | Tyr | Ala | Ile 1615 | Ile | Gly | Met | Gln 1620 | Val | Phe | Gly | Asn | Ile 1625 | Ala | |
| CTG | GAT | GAT | GAC | ACC | AGC | ATC | AAC | CGC | CAC | AAC | AAC | TTC | CGG | ACG | TTT | 5066 |
| Leu | Asp | Asp | Asp | Thr | Ser 1630 | Ile | Asn | Arg | His 1635 | Asn | Asn | Phe | Arg | Thr 1640 | Phe | |
| TTG | CAA | GCC | CTG | ATG | CTG | CTG | TTC | AGG | AGC | GCC | ACG | GGG | GAG | GCC | TGG | 5114 |
| Leu | Gln | Ala | Leu | Met 1645 | Leu | Leu | Phe | Arg | Ser 1650 | Ala | Thr | Gly | Glu | Ala 1655 | Trp | |
| CAC | GAG | ATC | ATG | CTG | TCC | TGC | CTG | AGC | AAC | CAG | GCC | TGT | GAT | GAG | CAG | 5162 |
| His | Glu | Ile | Met 1660 | Leu | Ser | Cys | Leu | Ser 1665 | Asn | Gln | Ala | Cys | Asp 1670 | Glu | Gln | |
| GCC | AAT | GCC | ACC | GAG | TGT | GGA | AGT | GAC | TTT | GCC | TAC | TTC | TAC | TTC | GTC | 5210 |
| Ala | Asn | Ala | Thr 1675 | Glu | Cys | Gly | Ser | Asp 1680 | Phe | Ala | Tyr | Phe | Tyr 1685 | Phe | Val | |
| TCC | TTC | ATC | TTC | CTG | TGC | TCC | TTT | CTG | ATG | TTG | AAC | CTC | TTT | GTG | GCT | 5258 |
| Ser | Phe | Ile | Phe 1690 | Leu | Cys | Ser | Phe | Leu 1695 | Met | Leu | Asn | Leu | Phe 1700 | Val | Ala 1705 | |
| GTG | ATC | ATG | GAC | AAT | TTT | GAG | TAC | CTC | ACG | CGG | GAC | TCT | TCC | ATC | CTA | 5306 |
| Val | Ile | Met | Asp | Asn 1710 | Phe | Glu | Tyr | Leu | Thr 1715 | Arg | Asp | Ser | Ser | Ile 1720 | Leu | |
| GGT | CCT | CAC | CAC | TTG | GAT | GAG | TTC | ATC | CGG | GTC | TGG | GCT | GAA | TAC | GAC | 5354 |
| Gly | Pro | His | His | Leu 1725 | Asp | Glu | Phe | Ile | Arg 1730 | Val | Trp | Ala | Glu | Tyr 1735 | Asp | |
| CCG | GCT | GCG | TGT | GGG | CGC | ATC | AGT | TAC | AAT | GAC | ATG | TTT | GAG | ATG | CTG | 5402 |
| Pro | Ala | Ala | Cys | Gly 1740 | Arg | Ile | Ser | Tyr | Asn 1745 | Asp | Met | Phe | Glu | Met 1750 | Leu | |
| AAA | CAC | ATG | TCC | CCG | CCT | CTG | GGG | CTG | GGG | AAG | AAA | TGC | CCT | GCT | CGA | 5450 |
| Lys | His | Met | Ser 1755 | Pro | Pro | Leu | Gly | Leu 1760 | Gly | Lys | Lys | Cys | Pro 1765 | Ala | Arg | |
| GTT | GCT | TAC | AAG | CGC | CTG | GTT | CGC | ATG | AAC | ATG | CCC | ATC | TCC | AAC | GAG | 5498 |
| Val | Ala | Tyr | Lys | Arg 1770 | Leu | Val | Arg | Met | Asn 1775 | Met | Pro | Ile | Ser | Asn 1780 | Glu 1785 | |
| GAC | ATG | ACT | GTT | CAC | TTC | ACG | TCC | ACG | CTG | ATG | GCC | CTC | ATC | CGG | ACG | 5546 |
| Asp | Met | Thr | Val | His 1790 | Phe | Thr | Ser | Thr | Leu 1795 | Met | Ala | Leu | Ile | Arg 1800 | Thr | |
| GCA | CTG | GAG | ATC | AAG | CTG | GCC | CCA | GCT | GGG | ACA | AAG | CAG | CAT | CAG | TGT | 5594 |
| Ala | Leu | Glu | Ile | Lys 1805 | Leu | Ala | Pro | Ala | Gly 1810 | Thr | Lys | Gln | His | Gln 1815 | Cys | |
| GAC | GCG | GAG | TTG | AGG | AAG | GAG | ATT | TCC | GTT | GTG | TGG | GCC | AAT | CTG | CCC | 5642 |
| Asp | Ala | Glu | Leu | Arg 1820 | Lys | Glu | Ile | Ser | Val 1825 | Val | Trp | Ala | Asn | Leu 1830 | Pro | |
| CAG | AAG | ACT | TTG | GAC | TTG | CTG | GTA | CCA | CCC | CAT | AAG | CCT | GAT | GAG | ATG | 5690 |
| Gln | Lys | Thr | Leu | Asp 1835 | Leu | Leu | Val | Pro | Pro 1840 | His | Lys | Pro | Asp | Glu 1845 | Met | |
| ACA | GTG | GGG | AAG | GTT | TAT | GCA | GCT | CTG | ATG | ATA | TTT | GAC | TTC | TAC | AAG | 5738 |
| Thr | Val | Gly | Lys | Val 1855 | Tyr | Ala | Ala | Leu | Met 1860 | Ile | Phe | Asp | Phe | Tyr 1865 | Lys | |
| | | | | | | | | | | | | | | | | |
| Thr 1850 | | | | | | | | | | | | | | | | |
| CAG | AAC | AAA | ACC | ACC | AGA | GAC | CAG | ATG | CAG | CAG | GCT | CCT | GGA | GGC | CTC | 5786 |
| Gln | Asn | Lys | Thr | Thr 1870 | Arg | Asp | Gln | Met | Gln 1875 | Gln | Ala | Pro | Gly | Gly 1880 | Leu | |
| TCC | CAG | ATG | GGT | CCT | GTG | TCC | CTG | TTC | CAC | CCT | CTG | AAG | GCC | ACC | CTG | 5834 |
| Ser | Gln | Met | Gly | Pro 1885 | Val | Ser | Leu | Phe | His 1890 | Pro | Leu | Lys | Ala | Thr 1895 | Leu | |
| GAG | CAG | ACA | CAG | CCG | GCT | GTG | CTC | CGA | GGA | GCC | CGG | GTT | TTC | CTT | CGA | 5882 |
| Glu | Gln | Thr | Gln 1900 | Pro | Ala | Val | Leu | Arg 1905 | Gly | Ala | Arg | Val | Phe 1910 | Leu | Arg | |
| CAG | AAG | AGT | TCC | ACC | TCC | CTC | AGC | AAT | GGC | GGG | GCC | ATA | CAA | AAC | CAA | 5930 |
| Gln | Lys | Ser | Ser | Thr 1915 | Ser | Leu | Ser | Asn | Gly 1920 | Gly | Ala | Ile | Gln | Asn 1925 | Gln | |

```
GAG AGT GGC ATC AAA GAG TCT GTC TCC TGG GGC ACT CAA AGG ACC CAG      5978
Glu Ser Gly Ile Lys Glu Ser Val Ser Trp Gly Thr Gln Arg Thr Gln
1930            1935            1940            1945

GAT GCA CCC CAT GAG GCC AGG CCA CCC CTG GAG CGT GGC CAC TCC ACA      6026
Asp Ala Pro His Glu Ala Arg Pro Pro Leu Glu Arg Gly His Ser Thr
        1950            1955            1960

GAG ATC CCT GTG GGG CGG TCA GGA GCA CTG GCT GTG GAC GTT CAG ATG      6074
Glu Ile Pro Val Gly Arg Ser Gly Ala Leu Ala Val Asp Val Gln Met
1965            1970            1975

CAG AGC ATA ACC CGG AGG GGC CCT GAT GGG GAG CCC CAG CCT GGG CTG      6122
Gln Ser Ile Thr Arg Arg Gly Pro Asp Gly Glu Pro Gln Pro Gly Leu
        1980            1985            1990

GAG AGC CAG GGT CGA GCG GCC TCC ATG CCC CGC CTT GCG GCC GAG ACT      6170
Glu Ser Gln Gly Arg Ala Ala Ser Met Pro Arg Leu Ala Ala Glu Thr
1995            2000            2005

CAG CCC GTC ACA GAT GCC AGC CCC ATG AAG CGC TCC ATC TCC ACG CTG      6218
Gln Pro Val Thr Asp Ala Ser Pro Met Lys Arg Ser Ile Ser Thr Leu
2010            2015            2020            2025

GCC CAG CGG CCC CGT GGG ACT CAT CTT TGC AGC ACC ACC CCG GAC CGC      6266
Ala Gln Arg Pro Arg Gly Thr His Leu Cys Ser Thr Thr Pro Asp Arg
        2030            2035            2040

CCA CCC CCT AGC CAG GCG TCG TCG CAC CAC CAC CAC CAC CGC TGC CAC      6314
Pro Pro Pro Ser Gln Ala Ser Ser His His His His His Arg Cys His
2045            2050            2055

CGC CGC AGG GAC AGG AAG CAG AGG TCC CTG GAG AAG GGG CCC AGC CTG      6362
Arg Arg Arg Asp Arg Lys Gln Arg Ser Leu Glu Lys Gly Pro Ser Leu
2060            2065            2070

TCT GCC GAT ATG GAT GGC GCA CCA AGC AGT GCT GTG GGG CCG GGG CTG      6410
Ser Ala Asp Met Asp Gly Ala Pro Ser Ser Ala Val Gly Pro Gly Leu
2075            2080            2085

CCC CCG GGA GAG GGG CCT ACA GGC TGC CGG CGG GAA CGA GAG CGC CGG      6458
Pro Pro Gly Glu Gly Pro Thr Gly Cys Arg Arg Glu Arg Glu Arg Arg
2090            2095            2100            2105

CAG GAG CGG GGC CGG TCC CAG GAG CGG AGG CAG CCC TCA TCC TCC TCC      6506
Gln Glu Arg Gly Arg Ser Gln Glu Arg Arg Gln Pro Ser Ser Ser Ser
        2110            2115            2120

TCG GAG AAG CAG CGC TTC TAC TCC TGC GAC CGC TTT GGG GGC CGT GAG      6554
Ser Glu Lys Gln Arg Phe Tyr Ser Cys Asp Arg Phe Gly Gly Arg Glu
2125            2130            2135

CCC CCG AAG CCC AAG CCC TCC CTC AGC AGC CAC CCA ACG TCG CCA ACA      6602
Pro Pro Lys Pro Lys Pro Ser Leu Ser Ser His Pro Thr Ser Pro Thr
        2140            2145            2150

GCT GGC CAG GAG CCG GGA CCC CAC CCA CAG GGC AGT GGT TCC GTG AAT      6650
Ala Gly Gln Glu Pro Gly Pro His Pro Gln Gly Ser Gly Ser Val Asn
2155            2160            2165

GGG AGC CCC TTG CTG TCA ACA TCT GGT GCT AGC ACC CCC GGC CGC GGT      6698
Gly Ser Pro Leu Leu Ser Thr Ser Gly Ala Ser Thr Pro Gly Arg Gly
2170            2175            2180            2185

GGG CGG AGG CAG CTC CCC CAG ACG CCC CTG ACT CCC CGC CCC AGC ATC      6746
Gly Arg Arg Gln Leu Pro Gln Thr Pro Leu Thr Pro Arg Pro Ser Ile
        2190            2195            2200

ACC TAC AAG ACG GCC AAC TCC TCA CCC ATC CAC TTC GCC GGG GCT CAG      6794
Thr Tyr Lys Thr Ala Asn Ser Ser Pro Ile His Phe Ala Gly Ala Gln
        2205            2210            2215

ACC AGC CTC CCT GCC TTC TCC CCA GGC CGG CTC AGC CGT GGG CTT TCC      6842
Thr Ser Leu Pro Ala Phe Ser Pro Gly Arg Leu Ser Arg Gly Leu Ser
        2220            2225            2230

GAA CAC AAC GCC CTG CTG CAG AGA GAC CCC CTC AGC CAG CCC CTG GCC      6890
Glu His Asn Ala Leu Leu Gln Arg Asp Pro Leu Ser Gln Pro Leu Ala
2235            2240            2245
```

| | | | | | | | | | | | | | | | | |
|---|---|---|---|---|---|---|---|---|---|---|---|---|---|---|---|---|
| CCT | GGC | TCT | CGA | ATT | GGC | TCT | GAC | CCT | TAC | CTG | GGG | CAG | CGT | CTG | GAC | 6938 |
| Pro | Gly | Ser | Arg | Ile | Gly | Ser | Asp | Pro | Tyr | Leu | Gly | Gln | Arg | Leu | Asp | |
| 2250 | | | | 2255 | | | | | 2260 | | | | | | 2265 | |

```
AGT GAG GCC TCT GTC CAC GCC CTG CCT GAG GAC ACG CTC ACT TTC GAG      6986
Ser Glu Ala Ser Val His Ala Leu Pro Glu Asp Thr Leu Thr Phe Glu
            2270                    2275                2280

GAG GCT GTG GCC ACC AAC TCG GGC CGC TCC TCC AGG ACT TCC TAC GTG      7034
Glu Ala Val Ala Thr Asn Ser Gly Arg Ser Ser Arg Thr Ser Tyr Val
                2285                2290                2295

TCC TCC CTG ACC TCC CAG TCT CAC CCT CTC CGC CGC GTG CCC AAC GGT      7082
Ser Ser Leu Thr Ser Gln Ser His Pro Leu Arg Arg Val Pro Asn Gly
            2300                    2305                2310

TAC CAC TGC ACC CTG GGA CTC AGC TCG GGT GGC CGA GCA CGG CAC AGC      7130
Tyr His Cys Thr Leu Gly Leu Ser Ser Gly Gly Arg Ala Arg His Ser
    2315                    2320                2325

TAC CAC CAC CCT GAC CAA GAC CAC TGG TGC TAGCTGCACC GTGACCGCTC        7180
Tyr His His Pro Asp Gln Asp His Trp Cys
2330                    2335
```

| | | | | |
|---|---|---|---|---|
| AGACGCCTGC | ATGCAGCAGG | CGTGTGTTCC | AGTGGATGAG | TTTTATCATC | CACACGGGGC | 7240 |
| AGTCGGCCCT | CGGGGGAGGC | CTTGCCCACC | TTGGTGAGGC | TCCTGTGGCC | CCTCCCTCCC | 7300 |
| CCTCCTCCCC | TCTTTTACTC | TAGACGACGA | ATAAAGCCCT | GTTGCTTGAG | TGTACGTACC | 7360 |
| GC | | | | | | 7362 |

( 2 ) INFORMATION FOR SEQ ID NO:8:

( i ) SEQUENCE CHARACTERISTICS:
        ( A ) LENGTH: 7175 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 144..6857

( i x ) FEATURE:
        ( A ) NAME/KEY: 5'UTR
        ( B ) LOCATION: 1..143

( i x ) FEATURE:
        ( A ) NAME/KEY: 3'UTR
        ( B ) LOCATION: 6855..7175

( x i ) SEQUENCE DESCRIPTION: SEQ ID NO:8:

| | | | | |
|---|---|---|---|---|
| GCGGCGGCGG | CTGCGGCGGT | GGGGCCGGGC | GAGGTCCGTG | CGGTCCCGGC | GGCTCCGTGG | 60 |
| CTGCTCCGCT | CTGAGCGCCT | GCGCGCCCCG | CGCCCTCCCT | GCCGGGGCCG | CTGGGCCGGG | 120 |

```
GATGCACGCG GGGCCCGGGA GCC ATG GTC CGC TTC GGG GAC GAG CTG GGC        170
                         Met Val Arg Phe Gly Asp Glu Leu Gly
                           1               5

GGC CGC TAT GGA GGC CCC GGC GGC GGA GAG CGG GCC CGG GGC GGC GGG      218
Gly Arg Tyr Gly Gly Pro Gly Gly Gly Glu Arg Ala Arg Gly Gly Gly
    10              15                  20                  25

GCC GGC GGG GCG GGG GGC CCG GGT CCC GGG GGG CTG CAG CCC GGC CAG      266
Ala Gly Gly Ala Gly Gly Pro Gly Pro Gly Gly Leu Gln Pro Gly Gln
                30              35                  40

CGG GTC CTC TAC AAG CAA TCG ATC GCG CAG CGC GCG CGG ACC ATG GCG      314
Arg Val Leu Tyr Lys Gln Ser Ile Ala Gln Arg Ala Arg Thr Met Ala
                    45                  50                  55

CTG TAC AAC CCC ATC CCG GTC AAG CAG AAC TGC TTC ACC GTC AAC CGC      362
Leu Tyr Asn Pro Ile Pro Val Lys Gln Asn Cys Phe Thr Val Asn Arg
            60                  65                      70
```

-continued

| | | | | | | | | | | | | | | | | |
|---|---|---|---|---|---|---|---|---|---|---|---|---|---|---|---|---|
| TCG | CTC | TTC | GTC | TTC | AGC | GAG | GAC | AAC | GTC | GTC | CGC | AAA | TAC | GCG | AAG | 410 |
| Ser | Leu | Phe | Val | Phe | Ser | Glu | Asp | Asn | Val | Val | Arg | Lys | Tyr | Ala | Lys | |
| | 75 | | | | | 80 | | | | | 85 | | | | | |
| CGC | ATC | ACC | GAG | TGG | CCT | CCA | TTC | GAG | AAT | ATG | ATC | CTG | GCC | ACC | ATC | 458 |
| Arg | Ile | Thr | Glu | Trp | Pro | Pro | Phe | Glu | Asn | Met | Ile | Leu | Ala | Thr | Ile | |
| 90 | | | | | 95 | | | | | 100 | | | | | 105 | |
| ATC | GCC | AAC | TGC | ATC | GTG | CTG | GCC | CTG | GAG | CAG | CAC | CTC | CCT | GAT | GGG | 506 |
| Ile | Ala | Asn | Cys | Ile | Val | Leu | Ala | Leu | Glu | Gln | His | Leu | Pro | Asp | Gly | |
| | | | | 110 | | | | | 115 | | | | | 120 | | |
| GAC | AAA | ACG | CCC | ATG | TCC | GAG | CGG | CTG | GAC | GAC | ACG | GAG | CCC | TAT | TTC | 554 |
| Asp | Lys | Thr | Pro | Met | Ser | Glu | Arg | Leu | Asp | Asp | Thr | Glu | Pro | Tyr | Phe | |
| | | | 125 | | | | | 130 | | | | | 135 | | | |
| ATC | GGG | ATC | TTT | TGC | TTC | GAG | GCA | GGG | ATC | AAA | ATC | ATC | GCT | CTG | GGC | 602 |
| Ile | Gly | Ile | Phe | Cys | Phe | Glu | Ala | Gly | Ile | Lys | Ile | Ile | Ala | Leu | Gly | |
| | | 140 | | | | | 145 | | | | | | 150 | | | |
| TTT | GTC | TTC | CAC | AAG | GGC | TCT | TAC | CTG | CGG | AAC | GGC | TGG | AAC | GTC | ATG | 650 |
| Phe | Val | Phe | His | Lys | Gly | Ser | Tyr | Leu | Arg | Asn | Gly | Trp | Asn | Val | Met | |
| | 155 | | | | | 160 | | | | | 165 | | | | | |
| GAC | TTC | GTG | GTC | GTC | CTC | ACA | GGG | ATC | CTT | GCC | ACG | GCT | GGA | ACT | GAC | 698 |
| Asp | Phe | Val | Val | Val | Leu | Thr | Gly | Ile | Leu | Ala | Thr | Ala | Gly | Thr | Asp | |
| 170 | | | | | 175 | | | | | 180 | | | | | 185 | |
| TTC | GAC | CTG | CGA | ACA | CTG | AGG | GCT | GTG | CGT | GTG | CTG | AGG | CCC | CTG | AAG | 746 |
| Phe | Asp | Leu | Arg | Thr | Leu | Arg | Ala | Val | Arg | Val | Leu | Arg | Pro | Leu | Lys | |
| | | | | 190 | | | | | 195 | | | | | 200 | | |
| CTG | GTG | TCT | GGG | ATT | CCA | AGT | TTG | CAG | GTG | GTG | CTC | AAG | TCC | ATC | ATG | 794 |
| Leu | Val | Ser | Gly | Ile | Pro | Ser | Leu | Gln | Val | Val | Leu | Lys | Ser | Ile | Met | |
| | | | 205 | | | | | 210 | | | | | 215 | | | |
| AAG | GCC | ATG | GTT | CCA | CTC | CTG | CAG | ATT | GGG | CTG | CTT | CTC | TTC | TTT | GCC | 842 |
| Lys | Ala | Met | Val | Pro | Leu | Leu | Gln | Ile | Gly | Leu | Leu | Leu | Phe | Phe | Ala | |
| | | 220 | | | | | 225 | | | | | 230 | | | | |
| ATC | CTC | ATG | TTT | GCC | ATC | ATT | GGC | CTG | GAG | TTC | TAC | ATG | GGC | AAG | TTC | 890 |
| Ile | Leu | Met | Phe | Ala | Ile | Ile | Gly | Leu | Glu | Phe | Tyr | Met | Gly | Lys | Phe | |
| | 235 | | | | | 240 | | | | | 245 | | | | | |
| CAC | AAG | GCC | TGT | TTC | CCC | AAC | AGC | ACA | GAT | GCG | GAG | CCC | GTG | GGT | GAC | 938 |
| His | Lys | Ala | Cys | Phe | Pro | Asn | Ser | Thr | Asp | Ala | Glu | Pro | Val | Gly | Asp | |
| 250 | | | | | 255 | | | | | 260 | | | | | 265 | |
| TTC | CCC | TGT | GGC | AAG | GAG | GCC | CCA | GCC | CGG | CTG | TGC | GAG | GGC | GAC | ACT | 986 |
| Phe | Pro | Cys | Gly | Lys | Glu | Ala | Pro | Ala | Arg | Leu | Cys | Glu | Gly | Asp | Thr | |
| | | | | 270 | | | | | 275 | | | | | 280 | | |
| GAG | TGC | CGG | GAG | TAC | TGG | CCA | GGA | CCC | AAC | TTT | GGC | ATC | ACC | AAC | TTT | 1034 |
| Glu | Cys | Arg | Glu | Tyr | Trp | Pro | Gly | Pro | Asn | Phe | Gly | Ile | Thr | Asn | Phe | |
| | | | 285 | | | | | 290 | | | | | 295 | | | |
| GAC | AAT | ATC | CTG | TTT | GCC | ATC | TTG | ACG | GTG | TTC | CAG | TGC | ATC | ACC | ATG | 1082 |
| Asp | Asn | Ile | Leu | Phe | Ala | Ile | Leu | Thr | Val | Phe | Gln | Cys | Ile | Thr | Met | |
| | | 300 | | | | | 305 | | | | | 310 | | | | |
| GAG | GGC | TGG | ACT | GAC | ATC | CTC | TAT | AAT | ACA | AAC | GAT | GCG | GCC | GGC | AAC | 1130 |
| Glu | Gly | Trp | Thr | Asp | Ile | Leu | Tyr | Asn | Thr | Asn | Asp | Ala | Ala | Gly | Asn | |
| | 315 | | | | | 320 | | | | | 325 | | | | | |
| ACC | TGG | AAC | TGG | CTC | TAC | TTC | ATC | CCT | CTC | ATC | ATC | ATC | GGC | TCC | TTC | 1178 |
| Thr | Trp | Asn | Trp | Leu | Tyr | Phe | Ile | Pro | Leu | Ile | Ile | Ile | Gly | Ser | Phe | |
| 330 | | | | | 335 | | | | | 340 | | | | | 345 | |
| TTC | ATG | CTC | AAC | CTG | GTG | CTC | GGC | GTG | CTC | TCG | GGG | GAG | TTT | GCC | AAG | 1226 |
| Phe | Met | Leu | Asn | Leu | Val | Leu | Gly | Val | Leu | Ser | Gly | Glu | Phe | Ala | Lys | |
| | | | | 350 | | | | | 355 | | | | | 360 | | |
| GAG | CGA | GAG | AGG | GTG | GAG | AAC | CGC | CGC | GCC | TTC | CTG | AAG | CTG | CGC | CGG | 1274 |
| Glu | Arg | Glu | Arg | Val | Glu | Asn | Arg | Arg | Ala | Phe | Leu | Lys | Leu | Arg | Arg | |
| | | | 365 | | | | | 370 | | | | | 375 | | | |
| CAG | CAG | CAG | ATC | GAG | CGA | GAG | CTC | AAC | GGG | TAC | CTG | GAG | TGG | ATC | TTC | 1322 |
| Gln | Gln | Gln | Ile | Glu | Arg | Glu | Leu | Asn | Gly | Tyr | Leu | Glu | Trp | Ile | Phe | |
| | | 380 | | | | | 385 | | | | | 390 | | | | |

| | | | | | | | | | | | | | | | |
|---|---|---|---|---|---|---|---|---|---|---|---|---|---|---|---|
| AAG | GCG | GAG | GAA | GTC | ATG | CTG | GCC | GAG | GAG | GAC | AGG | AAT | GCA | GAG | GAG | 1370 |
| Lys | Ala | Glu | Glu | Val | Met | Leu | Ala | Glu | Glu | Asp | Arg | Asn | Ala | Glu | Glu | |
| | 395 | | | | 400 | | | | | 405 | | | | | | |
| AAG | TCC | CCT | TTG | GAC | GTG | CTG | AAG | AGA | GCG | GCC | ACC | AAG | AAG | AGC | AGA | 1418 |
| Lys | Ser | Pro | Leu | Asp | Val | Leu | Lys | Arg | Ala | Ala | Thr | Lys | Lys | Ser | Arg | |
| 410 | | | | | 415 | | | | | 420 | | | | | 425 | |
| AAT | GAC | CTG | ATC | CAC | GCA | GAG | GAG | GGA | GAG | GAC | CGG | TTT | GCA | GAT | CTC | 1466 |
| Asn | Asp | Leu | Ile | His | Ala | Glu | Glu | Gly | Glu | Asp | Arg | Phe | Ala | Asp | Leu | |
| | | | | 430 | | | | | 435 | | | | | 440 | | |
| TGT | GCT | GTT | GGA | TCC | CCC | TTC | GCC | CGC | GCC | AGC | CTC | AAG | AGC | GGG | AAG | 1514 |
| Cys | Ala | Val | Gly | Ser | Pro | Phe | Ala | Arg | Ala | Ser | Leu | Lys | Ser | Gly | Lys | |
| | | | 445 | | | | | 450 | | | | | 455 | | | |
| ACA | GAG | AGC | TCG | TCA | TAC | TTC | CGG | AGG | AAG | GAG | AAG | ATG | TTC | CGG | TTT | 1562 |
| Thr | Glu | Ser | Ser | Ser | Tyr | Phe | Arg | Arg | Lys | Glu | Lys | Met | Phe | Arg | Phe | |
| | | 460 | | | | | 465 | | | | | 470 | | | | |
| TTT | ATC | CGG | CGC | ATG | GTG | AAG | GCT | CAG | AGC | TTC | TAC | TGG | GTG | GTG | CTG | 1610 |
| Phe | Ile | Arg | Arg | Met | Val | Lys | Ala | Gln | Ser | Phe | Tyr | Trp | Val | Val | Leu | |
| | 475 | | | | | 480 | | | | | 485 | | | | | |
| TGC | GTG | GTG | GCC | CTG | AAC | ACA | CTG | TGT | GTG | GCC | ATG | GTG | CAT | TAC | AAC | 1658 |
| Cys | Val | Val | Ala | Leu | Asn | Thr | Leu | Cys | Val | Ala | Met | Val | His | Tyr | Asn | |
| 490 | | | | | 495 | | | | | 500 | | | | | 505 | |
| CAG | CCG | CGG | CGG | CTT | ACC | ACG | ACC | CTG | TAT | TTT | GCA | GAG | TTT | GTT | TTC | 1706 |
| Gln | Pro | Arg | Arg | Leu | Thr | Thr | Thr | Leu | Tyr | Phe | Ala | Glu | Phe | Val | Phe | |
| | | | | 510 | | | | | 515 | | | | | 520 | | |
| CTG | GGT | CTC | TTC | CTC | ACA | GAG | ATG | TCC | CTG | AAG | ATG | TAT | GGC | CTG | GGG | 1754 |
| Leu | Gly | Leu | Phe | Leu | Thr | Glu | Met | Ser | Leu | Lys | Met | Tyr | Gly | Leu | Gly | |
| | | | 525 | | | | | 530 | | | | | 535 | | | |
| CCC | AGA | AGC | TAC | TTC | CGG | TCC | TCC | TTC | AAC | TGC | TTC | GAC | TTT | GGG | GTC | 1802 |
| Pro | Arg | Ser | Tyr | Phe | Arg | Ser | Ser | Phe | Asn | Cys | Phe | Asp | Phe | Gly | Val | |
| | | 540 | | | | | 545 | | | | | 550 | | | | |
| ATC | GTG | GGG | AGC | GTC | TTT | GAA | GTG | GTC | TGG | GCG | GCC | ATC | AAG | CCG | GGA | 1850 |
| Ile | Val | Gly | Ser | Val | Phe | Glu | Val | Val | Trp | Ala | Ala | Ile | Lys | Pro | Gly | |
| | 555 | | | | | 560 | | | | | 565 | | | | | |
| AGC | TCC | TTT | GGG | ATC | AGT | GTG | CTG | CGG | GCC | CTC | CGC | CTG | CTG | AGG | ATC | 1898 |
| Ser | Ser | Phe | Gly | Ile | Ser | Val | Leu | Arg | Ala | Leu | Arg | Leu | Leu | Arg | Ile | |
| 570 | | | | | 575 | | | | | 580 | | | | | 585 | |
| TTC | AAA | GTC | ACG | AAG | TAC | TGG | AGC | TCC | CTG | CGG | AAC | CTG | GTG | GTG | TCC | 1946 |
| Phe | Lys | Val | Thr | Lys | Tyr | Trp | Ser | Ser | Leu | Arg | Asn | Leu | Val | Val | Ser | |
| | | | | 590 | | | | | 595 | | | | | 600 | | |
| CTG | CTG | AAC | TCC | ATG | AAG | TCC | ATC | ATC | AGC | CTG | CTC | TTC | TTG | CTC | TTC | 1994 |
| Leu | Leu | Asn | Ser | Met | Lys | Ser | Ile | Ile | Ser | Leu | Leu | Phe | Leu | Leu | Phe | |
| | | | 605 | | | | | 610 | | | | | 615 | | | |
| CTG | TTC | ATT | GTG | GTC | TTC | GCC | CTG | CTG | GGG | ATG | CAG | CTG | TTT | GGG | GGA | 2042 |
| Leu | Phe | Ile | Val | Val | Phe | Ala | Leu | Leu | Gly | Met | Gln | Leu | Phe | Gly | Gly | |
| | | 620 | | | | | 625 | | | | | 630 | | | | |
| CAG | TTC | AAC | TTC | CAG | GAT | GAG | ACT | CCC | ACA | ACC | AAC | TTC | GAC | ACC | TTC | 2090 |
| Gln | Phe | Asn | Phe | Gln | Asp | Glu | Thr | Pro | Thr | Thr | Asn | Phe | Asp | Thr | Phe | |
| | 635 | | | | | 640 | | | | | 645 | | | | | |
| CCT | GCC | GCC | ATC | CTC | ACT | GTC | TTC | CAG | ATC | CTG | ACG | GGA | GAG | GAC | TGG | 2138 |
| Pro | Ala | Ala | Ile | Leu | Thr | Val | Phe | Gln | Ile | Leu | Thr | Gly | Glu | Asp | Trp | |
| 650 | | | | | 655 | | | | | 660 | | | | | 665 | |
| AAT | GCA | GTG | ATG | TAT | CAC | GGG | ATC | GAA | TCG | CAA | GGC | GGC | GTC | AGC | AAA | 2186 |
| Asn | Ala | Val | Met | Tyr | His | Gly | Ile | Glu | Ser | Gln | Gly | Gly | Val | Ser | Lys | |
| | | | | 670 | | | | | 675 | | | | | 680 | | |
| GGC | ATG | TTC | TCG | TCC | TTT | TAC | TTC | ATT | GTC | CTG | ACA | CTG | TTC | GGA | AAC | 2234 |
| Gly | Met | Phe | Ser | Ser | Phe | Tyr | Phe | Ile | Val | Leu | Thr | Leu | Phe | Gly | Asn | |
| | | | 685 | | | | | 690 | | | | | 695 | | | |
| TAC | ACT | CTG | CTG | AAT | GTC | TTT | CTG | GCC | ATC | GCT | GTG | GAC | AAC | CTG | GCC | 2282 |
| Tyr | Thr | Leu | Leu | Asn | Val | Phe | Leu | Ala | Ile | Ala | Val | Asp | Asn | Leu | Ala | |
| | | 700 | | | | | 705 | | | | | 710 | | | | |

| | | | | | | | | | | | | | | | |
|---|---|---|---|---|---|---|---|---|---|---|---|---|---|---|---|
| AAC | GCC | CAA | GAG | CTG | ACC | AAG | GAT | GAA | GAG | GAG | ATG | GAA | GAA | GCA | GCC |
| Asn | Ala | Gln | Glu | Leu | Thr | Lys | Asp | Glu | Glu | Glu | Met | Glu | Glu | Ala | Ala |
| | 715 | | | | | 720 | | | | | 725 | | | | |

2330

| | | | | | | | | | | | | | | | |
|---|---|---|---|---|---|---|---|---|---|---|---|---|---|---|---|
| AAT | CAG | AAG | CTT | GCT | CTG | CAA | AAG | GCC | AAA | GAA | GTG | GCT | GAA | GTC | AGC |
| Asn | Gln | Lys | Leu | Ala | Leu | Gln | Lys | Ala | Lys | Glu | Val | Ala | Glu | Val | Ser |
| 730 | | | | | 735 | | | | | 740 | | | | | 745 |

2378

| | | | | | | | | | | | | | | | |
|---|---|---|---|---|---|---|---|---|---|---|---|---|---|---|---|
| CCC | ATG | TCT | GCC | GCG | AAC | ATC | TCC | ATC | GCC | GCC | AGG | CAG | CAG | AAC | TCG |
| Pro | Met | Ser | Ala | Ala | Asn | Ile | Ser | Ile | Ala | Ala | Arg | Gln | Gln | Asn | Ser |
| | | | | 750 | | | | | 755 | | | | | 760 | |

2426

| | | | | | | | | | | | | | | | |
|---|---|---|---|---|---|---|---|---|---|---|---|---|---|---|---|
| GCC | AAG | GCG | CGC | TCG | GTG | TGG | GAG | CAG | CGG | GCC | AGC | CAG | CTA | CGG | CTG |
| Ala | Lys | Ala | Arg | Ser | Val | Trp | Glu | Gln | Arg | Ala | Ser | Gln | Leu | Arg | Leu |
| | | | 765 | | | | | 770 | | | | | 775 | | |

2474

| | | | | | | | | | | | | | | | |
|---|---|---|---|---|---|---|---|---|---|---|---|---|---|---|---|
| CAG | AAC | CTG | CGG | GCC | AGC | TGC | GAG | GCG | CTG | TAC | AGC | GAG | ATG | GAC | CCC |
| Gln | Asn | Leu | Arg | Ala | Ser | Cys | Glu | Ala | Leu | Tyr | Ser | Glu | Met | Asp | Pro |
| | | 780 | | | | | 785 | | | | | 790 | | | |

2522

| | | | | | | | | | | | | | | | |
|---|---|---|---|---|---|---|---|---|---|---|---|---|---|---|---|
| GAG | GAG | CGG | CTG | CGC | TTC | GCC | ACT | ACG | CGC | CAC | CTG | CGG | CCC | GAC | ATG |
| Glu | Glu | Arg | Leu | Arg | Phe | Ala | Thr | Thr | Arg | His | Leu | Arg | Pro | Asp | Met |
| | 795 | | | | | 800 | | | | | 805 | | | | |

2570

| | | | | | | | | | | | | | | | |
|---|---|---|---|---|---|---|---|---|---|---|---|---|---|---|---|
| AAG | ACG | CAC | CTG | GAC | CGG | CCG | CTG | GTG | GTG | GAG | CTG | GGC | CGC | GAC | GGC |
| Lys | Thr | His | Leu | Asp | Arg | Pro | Leu | Val | Val | Glu | Leu | Gly | Arg | Asp | Gly |
| 810 | | | | | 815 | | | | | 820 | | | | | 825 |

2618

| | | | | | | | | | | | | | | | |
|---|---|---|---|---|---|---|---|---|---|---|---|---|---|---|---|
| GCG | CGG | GGG | CCC | GTG | GGA | GGC | AAA | GCC | CGA | CCT | GAG | GCT | GCG | GAG | GCC |
| Ala | Arg | Gly | Pro | Val | Gly | Gly | Lys | Ala | Arg | Pro | Glu | Ala | Ala | Glu | Ala |
| | | | | 830 | | | | | 835 | | | | | 840 | |

2666

| | | | | | | | | | | | | | | | |
|---|---|---|---|---|---|---|---|---|---|---|---|---|---|---|---|
| CCC | GAG | GGC | GTC | GAC | CCT | CCG | CGC | AGG | CAC | CAC | CGG | CAC | CGC | GAC | AAG |
| Pro | Glu | Gly | Val | Asp | Pro | Pro | Arg | Arg | His | His | Arg | His | Arg | Asp | Lys |
| | | | 845 | | | | | 850 | | | | | 855 | | |

2714

| | | | | | | | | | | | | | | | |
|---|---|---|---|---|---|---|---|---|---|---|---|---|---|---|---|
| GAC | AAG | ACC | CCC | GCG | GCG | GGG | GAC | CAG | GAC | CGA | GCA | GAG | GCC | CCG | AAG |
| Asp | Lys | Thr | Pro | Ala | Ala | Gly | Asp | Gln | Asp | Arg | Ala | Glu | Ala | Pro | Lys |
| | | 860 | | | | | 865 | | | | | 870 | | | |

2762

| | | | | | | | | | | | | | | | |
|---|---|---|---|---|---|---|---|---|---|---|---|---|---|---|---|
| GCG | GAG | AGC | GGG | GAG | CCC | GGT | GCC | CGG | GAG | GAG | CGG | CCG | CGG | CCG | CAC |
| Ala | Glu | Ser | Gly | Glu | Pro | Gly | Ala | Arg | Glu | Glu | Arg | Pro | Arg | Pro | His |
| | 875 | | | | | 880 | | | | | 885 | | | | |

2810

| | | | | | | | | | | | | | | | |
|---|---|---|---|---|---|---|---|---|---|---|---|---|---|---|---|
| CGC | AGC | CAC | AGC | AAG | GAG | GCC | GCG | GGG | CCC | CCG | GAG | GCG | CGG | AGC | GAG |
| Arg | Ser | His | Ser | Lys | Glu | Ala | Ala | Gly | Pro | Pro | Glu | Ala | Arg | Ser | Glu |
| 890 | | | | | 895 | | | | | 900 | | | | | 905 |

2858

| | | | | | | | | | | | | | | | |
|---|---|---|---|---|---|---|---|---|---|---|---|---|---|---|---|
| CGC | GGC | CGA | GGC | CCA | GGC | CCC | GAG | GGC | GGC | CGG | CGG | CAC | CAC | CGG | CGC |
| Arg | Gly | Arg | Gly | Pro | Gly | Pro | Glu | Gly | Gly | Arg | Arg | His | His | Arg | Arg |
| | | | | 910 | | | | | 915 | | | | | 920 | |

2906

| | | | | | | | | | | | | | | | |
|---|---|---|---|---|---|---|---|---|---|---|---|---|---|---|---|
| GGC | TCC | CCG | GAG | GAG | GCG | GCC | GAG | CGG | GAG | CCC | CGA | CGC | CAC | CGC | GCG |
| Gly | Ser | Pro | Glu | Glu | Ala | Ala | Glu | Arg | Glu | Pro | Arg | Arg | His | Arg | Ala |
| | | | 925 | | | | | 930 | | | | | 935 | | |

2954

| | | | | | | | | | | | | | | | |
|---|---|---|---|---|---|---|---|---|---|---|---|---|---|---|---|
| CAC | CGG | CAC | CAG | GAT | CCG | AGC | AAG | GAG | TGC | GCC | GGC | GCC | AAG | GGC | GAG |
| His | Arg | His | Gln | Asp | Pro | Ser | Lys | Glu | Cys | Ala | Gly | Ala | Lys | Gly | Glu |
| | | 940 | | | | | 945 | | | | | 950 | | | |

3002

| | | | | | | | | | | | | | | | |
|---|---|---|---|---|---|---|---|---|---|---|---|---|---|---|---|
| CGG | CGC | GCG | CGG | CAC | CGC | GGC | GGC | CCC | CGA | GCG | GGG | CCC | CGG | GAG | GCG |
| Arg | Arg | Ala | Arg | His | Arg | Gly | Gly | Pro | Arg | Ala | Gly | Pro | Arg | Glu | Ala |
| | 955 | | | | | 960 | | | | | 965 | | | | |

3050

| | | | | | | | | | | | | | | | |
|---|---|---|---|---|---|---|---|---|---|---|---|---|---|---|---|
| GAG | AGC | GGG | GAG | GAG | CCG | GCG | CGG | CGG | CAC | CGG | GCC | CGG | CAC | AAG | GCG |
| Glu | Ser | Gly | Glu | Glu | Pro | Ala | Arg | Arg | His | Arg | Ala | Arg | His | Lys | Ala |
| 970 | | | | | 975 | | | | | 980 | | | | | 985 |

3098

| | | | | | | | | | | | | | | | |
|---|---|---|---|---|---|---|---|---|---|---|---|---|---|---|---|
| CAG | CCT | GCT | CAC | GAG | GCT | GTG | GAG | AAG | GAG | ACC | ACG | GAG | AAG | GAG | GCC |
| Gln | Pro | Ala | His | Glu | Ala | Val | Glu | Lys | Glu | Thr | Thr | Glu | Lys | Glu | Ala |
| | | | | 990 | | | | | 995 | | | | | 1000 | |

3146

| | | | | | | | | | | | | | | | |
|---|---|---|---|---|---|---|---|---|---|---|---|---|---|---|---|
| ACG | GAG | AAG | GAG | GCT | GAG | ATA | GTG | GAA | GCC | GAC | AAG | GAA | AAG | GAG | CTC |
| Thr | Glu | Lys | Glu | Ala | Glu | Ile | Val | Glu | Ala | Asp | Lys | Glu | Lys | Glu | Leu |
| | | | | 1005 | | | | | 1010 | | | | | 1015 | |

3194

| | | | | | | | | | | | | | | | |
|---|---|---|---|---|---|---|---|---|---|---|---|---|---|---|---|
| CGG | AAC | CAC | CAG | CCC | CGG | GAG | CCA | CAC | TGT | GAC | CTG | GAG | ACC | AGT | GGG |
| Arg | Asn | His | Gln | Pro | Arg | Glu | Pro | His | Cys | Asp | Leu | Glu | Thr | Ser | Gly |
| | | 1020 | | | | | 1025 | | | | | 1030 | | | |

3242

```
ACT GTG ACT GTG GGT CCC ATG CAC ACA CTG CCC AGC ACC TGT CTC CAG     3290
Thr Val Thr Val Gly Pro Met His Thr Leu Pro Ser Thr Cys Leu Gln
    1035                1040                1045

AAG GTG GAG GAA CAG CCA GAG GAT GCA GAC AAT CAG CGG AAC GTC ACT     3338
Lys Val Glu Glu Gln Pro Glu Asp Ala Asp Asn Gln Arg Asn Val Thr
1050                1055                1060                1065

CGC ATG GGC AGT CAG CCC CCA GAC CCG AAC ACT ATT GTA CAT ATC CCA     3386
Arg Met Gly Ser Gln Pro Pro Asp Pro Asn Thr Ile Val His Ile Pro
                1070                1075                1080

GTG ATG CTG ACG GGC CCT CTT GGG GAA GCC ACG GTC GTT CCC AGT GGT     3434
Val Met Leu Thr Gly Pro Leu Gly Glu Ala Thr Val Val Pro Ser Gly
            1085                1090                1095

AAC GTG GAC CTG GAA AGC CAA GCA GAG GGG AAG AAG GAG GTG GAA GCG     3482
Asn Val Asp Leu Glu Ser Gln Ala Glu Gly Lys Lys Glu Val Glu Ala
        1100                1105                1110

GAT GAC GTG ATG AGG AGC GGC CCC CGG CCT ATC GTC CCA TAC AGC TCC     3530
Asp Asp Val Met Arg Ser Gly Pro Arg Pro Ile Val Pro Tyr Ser Ser
    1115                1120                1125

ATG TTC TGT TTA AGC CCC ACC AAC CTG CTC CGC CGC TTC TGC CAC TAC     3578
Met Phe Cys Leu Ser Pro Thr Asn Leu Leu Arg Arg Phe Cys His Tyr
1130                1135                1140                1145

ATC GTG ACC ATG AGG TAC TTC GAG GTG GTC ATT CTC GTG GTC ATC GCC     3626
Ile Val Thr Met Arg Tyr Phe Glu Val Val Ile Leu Val Val Ile Ala
                1150                1155                1160

TTG AGC AGC ATC GCC CTG GCT GCT GAG GAC CCA GTG CGC ACA GAC TCG     3674
Leu Ser Ser Ile Ala Leu Ala Ala Glu Asp Pro Val Arg Thr Asp Ser
            1165                1170                1175

CCC AGG AAC AAC GCT CTG AAA TAC CTG GAT TAC ATT TTC ACT GGT GTC     3722
Pro Arg Asn Asn Ala Leu Lys Tyr Leu Asp Tyr Ile Phe Thr Gly Val
        1180                1185                1190

TTT ACC TTT GAG ATG GTG ATA AAG ATG ATC GAC TTG GGA CTG CTG CTT     3770
Phe Thr Phe Glu Met Val Ile Lys Met Ile Asp Leu Gly Leu Leu Leu
    1195                1200                1205

CAC CCT GGA GCC TAT TTC CGG GAC TTG TGG AAC ATT CTG GAC TTC ATT     3818
His Pro Gly Ala Tyr Phe Arg Asp Leu Trp Asn Ile Leu Asp Phe Ile
1210                1215                1220                1225

GTG GTC AGT GGC GCC CTG GTG GCG TTT GCT TTC TCA GGA TCC AAA GGG     3866
Val Val Ser Gly Ala Leu Val Ala Phe Ala Phe Ser Gly Ser Lys Gly
                1230                1235                1240

AAA GAC ATC AAT ACC ATC AAG TCT CTG AGA GTC CTT CGT GTC CTG CGG     3914
Lys Asp Ile Asn Thr Ile Lys Ser Leu Arg Val Leu Arg Val Leu Arg
            1245                1250                1255

CCC CTC AAG ACC ATC AAA CGG CTG CCC AAG CTC AAG GCT GTG TTT GAC     3962
Pro Leu Lys Thr Ile Lys Arg Leu Pro Lys Leu Lys Ala Val Phe Asp
        1260                1265                1270

TGT GTG GTG AAC TCC CTG AAG AAT GTC CTC AAC ATC TTG ATT GTC TAC     4010
Cys Val Val Asn Ser Leu Lys Asn Val Leu Asn Ile Leu Ile Val Tyr
    1275                1280                1285

ATG CTC TTC ATG TTC ATA TTT GCC GTC ATT GCG GTG CAG CTC TTC AAA     4058
Met Leu Phe Met Phe Ile Phe Ala Val Ile Ala Val Gln Leu Phe Lys
1290                1295                1300                1305

GGG AAG TTT TTC TAC TGC ACA GAT GAA TCC AAG GAG CTG GAG AGG GAC     4106
Gly Lys Phe Phe Tyr Cys Thr Asp Glu Ser Lys Glu Leu Glu Arg Asp
                1310                1315                1320

TGC AGG GGT CAG TAT TTG GAT TAT GAG AAG GAG GAA GTG GAA GCT CAG     4154
Cys Arg Gly Gln Tyr Leu Asp Tyr Glu Lys Glu Glu Val Glu Ala Gln
            1325                1330                1335

CCC AGG CAG TGG AAG AAA TAC GAC TTT CAC TAC GAC AAT GTG CTC TGG     4202
Pro Arg Gln Trp Lys Lys Tyr Asp Phe His Tyr Asp Asn Val Leu Trp
        1340                1345                1350
```

```
GCT CTG CTG ACG CTG TTC ACA GTG TCC ACG GGA GAA GGC TGG CCC ATG        4250
Ala Leu Leu Thr Leu Phe Thr Val Ser Thr Gly Glu Gly Trp Pro Met
    1355                1360                1365

GTG CTG AAA CAC TCC GTG GAT GCC ACC TAT GAG GAG CAG GGT CCA AGC        4298
Val Leu Lys His Ser Val Asp Ala Thr Tyr Glu Glu Gln Gly Pro Ser
1370                1375                1380                1385

CCT GGG TAC CGC ATG GAG CTG TCC ATC TTC TAC GTG GTC TAC TTT GTG        4346
Pro Gly Tyr Arg Met Glu Leu Ser Ile Phe Tyr Val Val Tyr Phe Val
        1390                1395                1400

GTC TTT CCC TTC TTC TTC GTC AAC ATC TTT GTG GCT TTG ATC ATC ATC        4394
Val Phe Pro Phe Phe Phe Val Asn Ile Phe Val Ala Leu Ile Ile Ile
            1405                1410                1415

ACC TTC CAG GAG CAG GGG GAC AAG GTG ATG TCT GAA TGC AGC CTG GAG        4442
Thr Phe Gln Glu Gln Gly Asp Lys Val Met Ser Glu Cys Ser Leu Glu
        1420                1425                1430

AAG AAC GAG AGG GCT TGC ATT GAC TTC GCC ATC AGC GCC AAA CCC CTG        4490
Lys Asn Glu Arg Ala Cys Ile Asp Phe Ala Ile Ser Ala Lys Pro Leu
    1435                1440                1445

ACA CGG TAC ATG CCC CAA AAC CGG CAG TCG TTC CAG TAT AAG ACG TGG        4538
Thr Arg Tyr Met Pro Gln Asn Arg Gln Ser Phe Gln Tyr Lys Thr Trp
1450                1455                1460                1465

ACA TTT GTG GTC TCC CCG CCC TTT GAA TAC TTC ATC ATG GCC ATG ATA        4586
Thr Phe Val Val Ser Pro Pro Phe Glu Tyr Phe Ile Met Ala Met Ile
            1470                1475                1480

GCC CTC AAC ACT GTG GTG CTG ATG ATG AAG TTC TAT GAT GCA CCC TAT        4634
Ala Leu Asn Thr Val Val Leu Met Met Lys Phe Tyr Asp Ala Pro Tyr
        1485                1490                1495

GAG TAC GAG CTG ATG CTG AAA TGC CTG AAC ATC GTG TTC ACA TCC ATG        4682
Glu Tyr Glu Leu Met Leu Lys Cys Leu Asn Ile Val Phe Thr Ser Met
        1500                1505                1510

TTC TCC ATG GAA TGC GTG CTG AAG ATC ATC GCC TTT GGG GTG CTG AAC        4730
Phe Ser Met Glu Cys Val Leu Lys Ile Ile Ala Phe Gly Val Leu Asn
    1515                1520                1525

TAT TTC AGA GAT GCC TGG AAT GTC TTT GAC TTT GTC ACT GTG TTG GGA        4778
Tyr Phe Arg Asp Ala Trp Asn Val Phe Asp Phe Val Thr Val Leu Gly
1530                1535                1540                1545

AGT ATT ACT GAT ATT TTA GTA ACA GAG ATT GCG GAA ACG AAC AAT TTC        4826
Ser Ile Thr Asp Ile Leu Val Thr Glu Ile Ala Glu Thr Asn Asn Phe
            1550                1555                1560

ATC AAC CTC AGC TTC CTC CGC CTC TTT CGA GCT GCG CGG CTG ATC AAG        4874
Ile Asn Leu Ser Phe Leu Arg Leu Phe Arg Ala Ala Arg Leu Ile Lys
        1565                1570                1575

CTG CTC CGC CAG GGC TAC ACC ATC CGC ATC CTG CTG TGG ACC TTT GTC        4922
Leu Leu Arg Gln Gly Tyr Thr Ile Arg Ile Leu Leu Trp Thr Phe Val
        1580                1585                1590

CAG TCC TTC AAG GCC CTG CCC TAC GTG TGT CTG CTC ATT GCC ATG CTG        4970
Gln Ser Phe Lys Ala Leu Pro Tyr Val Cys Leu Leu Ile Ala Met Leu
    1595                1600                1605

TTC TTC ATC TAC GCC ATC ATC GGC ATG CAG GTG TTT GGG AAT ATT GCC        5018
Phe Phe Ile Tyr Ala Ile Ile Gly Met Gln Val Phe Gly Asn Ile Ala
1610                1615                1620                1625

CTG GAT GAT GAC ACC AGC ATC AAC CGC CAC AAC AAC TTC CGG ACG TTT        5066
Leu Asp Asp Asp Thr Ser Ile Asn Arg His Asn Asn Phe Arg Thr Phe
            1630                1635                1640

TTG CAA GCC CTG ATG CTG CTG TTC AGG AGC GCC ACG GGG GAG GCC TGG        5114
Leu Gln Ala Leu Met Leu Leu Phe Arg Ser Ala Thr Gly Glu Ala Trp
        1645                1650                1655

CAC GAG ATC ATG CTG TCC TGC CTG AGC AAC CAG GCC TGT GAT GAG CAG        5162
His Glu Ile Met Leu Ser Cys Leu Ser Asn Gln Ala Cys Asp Glu Gln
        1660                1665                1670
```

-continued

| | | | | | | | | | | | | | | | | |
|---|---|---|---|---|---|---|---|---|---|---|---|---|---|---|---|---|
| GCC | AAT | GCC | ACC | GAG | TGT | GGA | AGT | GAC | TTT | GCC | TAC | TTC | TAC | TTC | GTC | 5210 |
| Ala | Asn | Ala | Thr | Glu | Cys | Gly | Ser | Asp | Phe | Ala | Tyr | Phe | Tyr | Phe | Val | |
| | | | 1675 | | | | 1680 | | | | | 1685 | | | | |
| TCC | TTC | ATC | TTC | CTG | TGC | TCC | TTT | CTG | ATG | TTG | AAC | CTC | TTT | GTG | GCT | 5258 |
| Ser | Phe | Ile | Phe | Leu | Cys | Ser | Phe | Leu | Met | Leu | Asn | Leu | Phe | Val | Ala | |
| 1690 | | | | | 1695 | | | | 1700 | | | | | 1705 | | |
| GTG | ATC | ATG | GAC | AAT | TTT | GAG | TAC | CTC | ACG | CGG | GAC | TCT | TCC | ATC | CTA | 5306 |
| Val | Ile | Met | Asp | Asn | Phe | Glu | Tyr | Leu | Thr | Arg | Asp | Ser | Ser | Ile | Leu | |
| | | | | 1710 | | | | 1715 | | | | | 1720 | | | |
| GGT | CCT | CAC | CAC | TTG | GAT | GAG | TTC | ATC | CGG | GTC | TGG | GCT | GAA | TAC | GAC | 5354 |
| Gly | Pro | His | His | Leu | Asp | Glu | Phe | Ile | Arg | Val | Trp | Ala | Glu | Tyr | Asp | |
| | | | 1725 | | | | 1730 | | | | | 1735 | | | | |
| CCG | GCT | GCG | TGT | GGG | CGC | ATC | AGT | TAC | AAT | GAC | ATG | TTT | GAG | ATG | CTG | 5402 |
| Pro | Ala | Ala | Cys | Gly | Arg | Ile | Ser | Tyr | Asn | Asp | Met | Phe | Glu | Met | Leu | |
| | | | 1740 | | | | 1745 | | | | | 1750 | | | | |
| AAA | CAC | ATG | TCC | CCG | CCT | CTG | GGG | CTG | GGG | AAG | AAA | TGC | CCT | GCT | CGA | 5450 |
| Lys | His | Met | Ser | Pro | Pro | Leu | Gly | Leu | Gly | Lys | Lys | Cys | Pro | Ala | Arg | |
| | 1755 | | | | 1760 | | | | | 1765 | | | | | | |
| GTT | GCT | TAC | AAG | CGC | CTG | GTT | CGC | ATG | AAC | ATG | CCC | ATC | TCC | AAC | GAG | 5498 |
| Val | Ala | Tyr | Lys | Arg | Leu | Val | Arg | Met | Asn | Met | Pro | Ile | Ser | Asn | Glu | |
| 1770 | | | | | 1775 | | | | | 1780 | | | | | 1785 | |
| GAC | ATG | ACT | GTT | CAC | TTC | ACG | TCC | ACG | CTG | ATG | GCC | CTC | ATC | CGG | ACG | 5546 |
| Asp | Met | Thr | Val | His | Phe | Thr | Ser | Thr | Leu | Met | Ala | Leu | Ile | Arg | Thr | |
| | | | | 1790 | | | | 1795 | | | | | | 1800 | | |
| GCA | CTG | GAG | ATC | AAG | CTG | GCC | CCA | GCT | GGG | ACA | AAG | CAG | CAT | CAG | TGT | 5594 |
| Ala | Leu | Glu | Ile | Lys | Leu | Ala | Pro | Ala | Gly | Thr | Lys | Gln | His | Gln | Cys | |
| | | | 1805 | | | | 1810 | | | | | 1815 | | | | |
| GAC | GCG | GAG | TTG | AGG | AAG | GAG | ATT | TCC | GTT | GTG | TGG | GCC | AAT | CTG | CCC | 5642 |
| Asp | Ala | Glu | Leu | Arg | Lys | Glu | Ile | Ser | Val | Val | Trp | Ala | Asn | Leu | Pro | |
| | | 1820 | | | | | 1825 | | | | | | 1830 | | | |
| CAG | AAG | ACT | TTG | GAC | TTG | CTG | GTA | CCA | CCC | CAT | AAG | CCT | GAT | GAG | ATG | 5690 |
| Gln | Lys | Thr | Leu | Asp | Leu | Leu | Val | Pro | Pro | His | Lys | Pro | Asp | Glu | Met | |
| | 1835 | | | | | 1840 | | | | | 1845 | | | | | |
| ACA | GTG | GGG | AAG | GTT | TAT | GCA | GCT | CTG | ATG | ATA | TTT | GAC | TTC | TAC | AAG | 5738 |
| Thr | Val | Gly | Lys | Val | Tyr | Ala | Ala | Leu | Met | Ile | Phe | Asp | Phe | Tyr | Lys | |
| 1850 | | | | | 1855 | | | | | 1860 | | | | | 1865 | |
| CAG | AAC | AAA | ACC | ACC | AGA | GAC | CAG | ATG | CAG | CAG | GCT | CCT | GGA | GGC | CTC | 5786 |
| Gln | Asn | Lys | Thr | Thr | Arg | Asp | Gln | Met | Gln | Gln | Ala | Pro | Gly | Gly | Leu | |
| | | | | 1870 | | | | 1875 | | | | | | 1880 | | |
| TCC | CAG | ATG | GGT | CCT | GTG | TCC | CTG | TTC | CAC | CCT | CTG | AAG | GCC | ACC | CTG | 5834 |
| Ser | Gln | Met | Gly | Pro | Val | Ser | Leu | Phe | His | Pro | Leu | Lys | Ala | Thr | Leu | |
| | | | 1885 | | | | 1890 | | | | | 1895 | | | | |
| GAG | CAG | ACA | CAG | CCG | GCT | GTG | CTC | CGA | GGA | GCC | CGG | GTT | TTC | CTT | CGA | 5882 |
| Glu | Gln | Thr | Gln | Pro | Ala | Val | Leu | Arg | Gly | Ala | Arg | Val | Phe | Leu | Arg | |
| | 1900 | | | | | 1905 | | | | | | 1910 | | | | |
| CAG | AAG | AGT | TCC | ACC | TCC | CTC | AGC | AAT | GGC | GGG | GCC | ATA | CAA | AAC | CAA | 5930 |
| Gln | Lys | Ser | Ser | Thr | Ser | Leu | Ser | Asn | Gly | Gly | Ala | Ile | Gln | Asn | Gln | |
| | 1915 | | | | 1920 | | | | | 1925 | | | | | | |
| GAG | AGT | GGC | ATC | AAA | GAG | TCT | GTC | TCC | TGG | GGC | ACT | CAA | AGG | ACC | CAG | 5978 |
| Glu | Ser | Gly | Ile | Lys | Glu | Ser | Val | Ser | Trp | Gly | Thr | Gln | Arg | Thr | Gln | |
| 1930 | | | | | 1935 | | | | | 1940 | | | | | 1945 | |
| GAT | GCA | CCC | CAT | GAG | GCC | AGG | CCA | CCC | CTG | GAG | CGT | GGC | CAC | TCC | ACA | 6026 |
| Asp | Ala | Pro | His | Glu | Ala | Arg | Pro | Pro | Leu | Glu | Arg | Gly | His | Ser | Thr | |
| | | | | 1950 | | | | 1955 | | | | | | 1960 | | |
| GAG | ATC | CCT | GTG | GGG | CGG | TCA | GGA | GCA | CTG | GCT | GTG | GAC | GTT | CAG | ATG | 6074 |
| Glu | Ile | Pro | Val | Gly | Arg | Ser | Gly | Ala | Leu | Ala | Val | Asp | Val | Gln | Met | |
| | | | 1965 | | | | 1970 | | | | | 1975 | | | | |
| CAG | AGC | ATA | ACC | CGG | AGG | GGC | CCT | GAT | GGG | GAG | CCC | CAG | CCT | GGG | CTG | 6122 |
| Gln | Ser | Ile | Thr | Arg | Arg | Gly | Pro | Asp | Gly | Glu | Pro | Gln | Pro | Gly | Leu | |
| | | | 1980 | | | | 1985 | | | | | 1990 | | | | |

| | | | | | | | | | | | | | | | | |
|---|---|---|---|---|---|---|---|---|---|---|---|---|---|---|---|---|
| GAG | AGC | CAG | GGT | CGA | GCG | GCC | TCC | ATG | CCC | CGC | CTT | GCG | GCC | GAG | ACT | 6170 |
| Glu | Ser | Gln | Gly | Arg | Ala | Ala | Ser | Met | Pro | Arg | Leu | Ala | Ala | Glu | Thr | |
| | 1995 | | | | | 2000 | | | | | 2005 | | | | | |
| CAG | CCC | GTC | ACA | GAT | GCC | AGC | CCC | ATG | AAG | CGC | TCC | ATC | TCC | ACG | CTG | 6218 |
| Gln | Pro | Val | Thr | Asp | Ala | Ser | Pro | Met | Lys | Arg | Ser | Ile | Ser | Thr | Leu | |
| 2010 | | | | | 2015 | | | | | 2020 | | | | | 2025 | |
| GCC | CAG | CGG | CCC | CGT | GGG | ACT | CAT | CTT | TGC | AGC | ACC | ACC | CCG | GAC | CGC | 6266 |
| Ala | Gln | Arg | Pro | Arg | Gly | Thr | His | Leu | Cys | Ser | Thr | Thr | Pro | Asp | Arg | |
| | | | 2030 | | | | | 2035 | | | | | 2040 | | | |
| CCA | CCC | CCT | AGC | CAG | GCG | TCG | TCG | CAC | CAC | CAC | CAC | CAC | CGC | TGC | CAC | 6314 |
| Pro | Pro | Pro | Ser | Gln | Ala | Ser | Ser | His | His | His | His | His | Arg | Cys | His | |
| | | | 2045 | | | | | 2050 | | | | | 2055 | | | |
| CGC | CGC | AGG | GAC | AGG | AAG | CAG | AGG | TCC | CTG | GAG | AAG | GGG | CCC | AGC | CTG | 6362 |
| Arg | Arg | Arg | Asp | Arg | Lys | Gln | Arg | Ser | Leu | Glu | Lys | Gly | Pro | Ser | Leu | |
| | | 2060 | | | | | 2065 | | | | | 2070 | | | | |
| TCT | GCC | GAT | ATG | GAT | GGC | GCA | CCA | AGC | AGT | GCT | GTG | GGG | CCG | GGG | CTG | 6410 |
| Ser | Ala | Asp | Met | Asp | Gly | Ala | Pro | Ser | Ser | Ala | Val | Gly | Pro | Gly | Leu | |
| | | 2075 | | | | | 2080 | | | | | 2085 | | | | |
| CCC | CCG | GGA | GAG | GGG | CCT | ACA | GGC | TGC | CGG | CGG | GAA | CGA | GAG | CGC | CGG | 6458 |
| Pro | Pro | Gly | Glu | Gly | Pro | Thr | Gly | Cys | Arg | Arg | Glu | Arg | Glu | Arg | Arg | |
| 2090 | | | | | 2095 | | | | | 2100 | | | | | 2105 | |
| CAG | GAG | CGG | GGC | CGG | TCC | CAG | GAG | CGG | AGG | CAG | CCC | TCA | TCC | TCC | TCC | 6506 |
| Gln | Glu | Arg | Gly | Arg | Ser | Gln | Glu | Arg | Arg | Gln | Pro | Ser | Ser | Ser | Ser | |
| | | | 2110 | | | | | 2115 | | | | | 2120 | | | |
| TCG | GAG | AAG | CAG | CGC | TTC | TAC | TCC | TGC | GAC | CGC | TTT | GGG | GGC | CGT | GAG | 6554 |
| Ser | Glu | Lys | Gln | Arg | Phe | Tyr | Ser | Cys | Asp | Arg | Phe | Gly | Gly | Arg | Glu | |
| | | | 2125 | | | | | 2130 | | | | | 2135 | | | |
| CCC | CCG | AAG | CCC | AAG | CCC | TCC | CTC | AGC | AGC | CAC | CCA | ACG | TCG | CCA | ACA | 6602 |
| Pro | Pro | Lys | Pro | Lys | Pro | Ser | Leu | Ser | Ser | His | Pro | Thr | Ser | Pro | Thr | |
| | | 2140 | | | | | 2145 | | | | | 2150 | | | | |
| GCT | GGC | CAG | GAG | CCG | GGA | CCC | CAC | CCA | CAG | GCC | GGC | TCA | GCC | GTG | GGC | 6650 |
| Ala | Gly | Gln | Glu | Pro | Gly | Pro | His | Pro | Gln | Ala | Gly | Ser | Ala | Val | Gly | |
| | | 2155 | | | | | 2160 | | | | | 2165 | | | | |
| TTT | CCG | AAC | ACA | ACG | CCC | TGC | TGC | AGA | GAG | ACC | CCC | TCA | GCC | AGC | CCC | 6698 |
| Phe | Pro | Asn | Thr | Thr | Pro | Cys | Cys | Arg | Glu | Thr | Pro | Ser | Ala | Ser | Pro | |
| 2170 | | | | | 2175 | | | | | 2180 | | | | | 2185 | |
| TGG | CCC | CTG | GCT | CTC | GAA | TTG | GCT | CTG | ACC | CTT | ACC | TGG | GGC | AGC | GTC | 6746 |
| Trp | Pro | Leu | Ala | Leu | Glu | Leu | Ala | Leu | Thr | Leu | Thr | Trp | Gly | Ser | Val | |
| | | | 2190 | | | | | 2195 | | | | | 2200 | | | |
| TGG | ACA | GTG | AGG | CCT | CTG | TCC | ACG | CCC | TGC | CTG | AGG | ACA | CGC | TCA | CTT | 6794 |
| Trp | Thr | Val | Arg | Pro | Leu | Ser | Thr | Pro | Cys | Leu | Arg | Thr | Arg | Ser | Leu | |
| | | | 2205 | | | | | 2210 | | | | | 2215 | | | |
| TCG | AGG | AGG | CTG | TGG | CCA | CCA | ACT | CGG | GCC | GCT | CCT | CCA | GGA | CTT | CCT | 6842 |
| Ser | Arg | Arg | Leu | Trp | Pro | Pro | Thr | Arg | Ala | Ala | Pro | Pro | Gly | Leu | Pro | |
| | | 2220 | | | | | 2225 | | | | | 2230 | | | | |
| ACG | TGT | CCT | CCC | TGACCTCCCA | | GTCTCACCCT | | CTCCGCCGCG | | TGCCCAACGG | | | | | | 6894 |
| Thr | Cys | Pro | Pro | | | | | | | | | | | | | |
| | | 2235 | | | | | | | | | | | | | | |

```
TTACCACTGC  ACCCTGGGAC  TCAGCTCGGG  TGGCCGAGCA  CGGCACAGCT  ACCACCACCC       6954

TGACCAAGAC  CACTGGTGCT  AGCTGCACCG  TGACCGCTCA  GACGCCTGCA  TGCAGCAGGC       7014

GTGTGTTCCA  GTGGATGAGT  TTTATCATCC  ACACGGGGCA  GTCGGCCCTC  GGGGGAGGCC       7074

TTGCCCACCT  TGGTGAGGCT  CCTGTGGCCC  CTCCCTCCCC  CTCCTCCCCT  CTTTTACTCT       7134

AGACGACGAA  TAAAGCCCTG  TTGCTTGAGT  GTACGTACCG  C                            7175
```

( 2 ) INFORMATION FOR SEQ ID NO:9:

( i ) SEQUENCE CHARACTERISTICS:
( A ) LENGTH: 1546 base pairs (B) TYPE: nucleic acid
(C) STRANDEDNESS: double
(D) TOPOLOGY: linear (ii) MOLECULE TYPE: DNA (genomic)

(ix) FEATURE:
(A) NAME/KEY: CDS
(B) LOCATION: 1..1437

(ix) FEATURE:
(A) NAME/KEY: 3'UTR
(B) LOCATION: 1435..1546

(xi) SEQUENCE DESCRIPTION: SEQ ID NO:9:

| ATG | GTC | CAG | AAG | ACC | AGC | ATG | TCC | CGG | GGC | CCT | TAC | CCA | CCC | TCC | CAG | 48 |
|---|---|---|---|---|---|---|---|---|---|---|---|---|---|---|---|---|
| Met | Val | Gln | Lys | Thr | Ser | Met | Ser | Arg | Gly | Pro | Tyr | Pro | Pro | Ser | Gln | |
| 1 | | | | 5 | | | | | 10 | | | | | 15 | | |

| GAG | ATC | CCC | ATG | GAG | GTC | TTC | GAC | CCC | AGC | CCG | CAG | GGC | AAA | TAC | AGC | 96 |
|---|---|---|---|---|---|---|---|---|---|---|---|---|---|---|---|---|
| Glu | Ile | Pro | Met | Glu | Val | Phe | Asp | Pro | Ser | Pro | Gln | Gly | Lys | Tyr | Ser | |
| | | | 20 | | | | | 25 | | | | | 30 | | | |

| AAG | AGG | AAA | GGG | CGA | TTC | AAA | CGG | TCA | GAT | GGG | AGC | ACG | TCC | TCG | GAT | 144 |
|---|---|---|---|---|---|---|---|---|---|---|---|---|---|---|---|---|
| Lys | Arg | Lys | Gly | Arg | Phe | Lys | Arg | Ser | Asp | Gly | Ser | Thr | Ser | Ser | Asp | |
| | | 35 | | | | | 40 | | | | | 45 | | | | |

| ACC | ACA | TCC | AAC | AGC | TTT | GTC | CGC | CAG | GGC | TCA | GCG | GAG | TCC | TAC | ACC | 192 |
|---|---|---|---|---|---|---|---|---|---|---|---|---|---|---|---|---|
| Thr | Thr | Ser | Asn | Ser | Phe | Val | Arg | Gln | Gly | Ser | Ala | Glu | Ser | Tyr | Thr | |
| | 50 | | | | | 55 | | | | | 60 | | | | | |

| AGC | CGT | CCA | TCA | GAC | TCT | GAT | GTA | TCT | CTG | GAG | GAG | GAC | CGG | GAA | GCC | 240 |
|---|---|---|---|---|---|---|---|---|---|---|---|---|---|---|---|---|
| Ser | Arg | Pro | Ser | Asp | Ser | Asp | Val | Ser | Leu | Glu | Glu | Asp | Arg | Glu | Ala | |
| 65 | | | | | 70 | | | | | 75 | | | | | 80 | |

| TTA | AGG | AAG | GAA | GCA | GAG | CGC | CAG | GCA | TTA | GCG | CAG | CTC | GAG | AAG | GCC | 288 |
|---|---|---|---|---|---|---|---|---|---|---|---|---|---|---|---|---|
| Leu | Arg | Lys | Glu | Ala | Glu | Arg | Gln | Ala | Leu | Ala | Gln | Leu | Glu | Lys | Ala | |
| | | | | 85 | | | | | 90 | | | | | 95 | | |

| AAG | ACC | AAG | CCA | GTG | GCA | TTT | GCT | GTG | CGG | ACA | AAT | GTT | GGC | TAC | AAT | 336 |
|---|---|---|---|---|---|---|---|---|---|---|---|---|---|---|---|---|
| Lys | Thr | Lys | Pro | Val | Ala | Phe | Ala | Val | Arg | Thr | Asn | Val | Gly | Tyr | Asn | |
| | | | 100 | | | | | 105 | | | | | 110 | | | |

| CCG | TCT | CCA | GGG | GAT | GAG | GTG | CCT | GTG | CAG | GGA | GTG | GCC | ATC | ACC | TTC | 384 |
|---|---|---|---|---|---|---|---|---|---|---|---|---|---|---|---|---|
| Pro | Ser | Pro | Gly | Asp | Glu | Val | Pro | Val | Gln | Gly | Val | Ala | Ile | Thr | Phe | |
| | | 115 | | | | | 120 | | | | | 125 | | | | |

| GAG | CCC | AAA | GAC | TTC | CTG | CAC | ATC | AAG | GAG | AAA | TAC | AAT | AAT | GAC | TGG | 432 |
|---|---|---|---|---|---|---|---|---|---|---|---|---|---|---|---|---|
| Glu | Pro | Lys | Asp | Phe | Leu | His | Ile | Lys | Glu | Lys | Tyr | Asn | Asn | Asp | Trp | |
| | 130 | | | | | 135 | | | | | 140 | | | | | |

| TGG | ATC | GGG | CGG | CTG | GTG | AAG | GAG | GGC | TGT | GAG | GTT | GGC | TTC | ATT | CCC | 480 |
|---|---|---|---|---|---|---|---|---|---|---|---|---|---|---|---|---|
| Trp | Ile | Gly | Arg | Leu | Val | Lys | Glu | Gly | Cys | Glu | Val | Gly | Phe | Ile | Pro | |
| 145 | | | | | 150 | | | | | 155 | | | | | 160 | |

| AGC | CCC | GTC | AAA | CTG | GAC | AGC | CTT | CGC | CTG | CTG | CAG | GAA | CAG | AAG | CTG | 528 |
|---|---|---|---|---|---|---|---|---|---|---|---|---|---|---|---|---|
| Ser | Pro | Val | Lys | Leu | Asp | Ser | Leu | Arg | Leu | Leu | Gln | Glu | Gln | Lys | Leu | |
| | | | | 165 | | | | | 170 | | | | | 175 | | |

| CGC | CAG | AAC | CGC | CTC | GGC | TCC | AGC | AAA | TCA | GGC | GAT | AAC | TCC | AGT | TCC | 576 |
|---|---|---|---|---|---|---|---|---|---|---|---|---|---|---|---|---|
| Arg | Gln | Asn | Arg | Leu | Gly | Ser | Ser | Lys | Ser | Gly | Asp | Asn | Ser | Ser | Ser | |
| | | | 180 | | | | | 185 | | | | | 190 | | | |

| AGT | CTG | GGA | GAT | GTG | GTG | ACT | GGC | ACC | CGC | CGC | CCC | ACA | CCC | CCT | GCC | 624 |
|---|---|---|---|---|---|---|---|---|---|---|---|---|---|---|---|---|
| Ser | Leu | Gly | Asp | Val | Val | Thr | Gly | Thr | Arg | Arg | Pro | Thr | Pro | Pro | Ala | |
| | | 195 | | | | | 200 | | | | | 205 | | | | |

| AGT | GCC | AAA | CAG | AAG | CAG | AAG | TCG | ACA | GAG | CAT | GTG | CCC | CCC | TAT | GAC | 672 |
|---|---|---|---|---|---|---|---|---|---|---|---|---|---|---|---|---|
| Ser | Ala | Lys | Gln | Lys | Gln | Lys | Ser | Thr | Glu | His | Val | Pro | Pro | Tyr | Asp | |
| | 210 | | | | | 215 | | | | | 220 | | | | | |

| GTG | GTG | CCT | TCC | ATG | AGG | CCC | ATC | ATC | CTG | GTG | GGA | CCG | TCG | CTC | AAG | 720 |
|---|---|---|---|---|---|---|---|---|---|---|---|---|---|---|---|---|
| Val | Val | Pro | Ser | Met | Arg | Pro | Ile | Ile | Leu | Val | Gly | Pro | Ser | Leu | Lys | |
| 225 | | | | | 230 | | | | | 235 | | | | | 240 | |

| GGC | TAC | GAG | GTT | ACA | GAC | ATG | ATG | CAG | AAA | GCT | TTA | TTT | GAC | TTC | TTG | 768 |
|---|---|---|---|---|---|---|---|---|---|---|---|---|---|---|---|---|
| Gly | Tyr | Glu | Val | Thr | Asp | Met | Met | Gln | Lys | Ala | Leu | Phe | Asp | Phe | Leu | |
| | | | | 245 | | | | | 250 | | | | | 255 | | |

```
AAG  CAT  CGG  TTT  GAT  GGC  AGG  ATC  TCC  ATC  ACT  CGT  GTG  ACG  GCA  GAT       816
Lys  His  Arg  Phe  Asp  Gly  Arg  Ile  Ser  Ile  Thr  Arg  Val  Thr  Ala  Asp
               260                      265                     270

ATT  TCC  CTG  GCT  AAG  CGC  TCA  GTT  CTC  AAC  AAC  CCC  AGC  AAA  CAC  ATC       864
Ile  Ser  Leu  Ala  Lys  Arg  Ser  Val  Leu  Asn  Asn  Pro  Ser  Lys  His  Ile
               275                      280                     285

ATC  ATT  GAG  CGC  TCC  AAC  ACA  CGC  TCC  AGC  CTG  GCT  GAG  GTG  CAG  AGT       912
Ile  Ile  Glu  Arg  Ser  Asn  Thr  Arg  Ser  Ser  Leu  Ala  Glu  Val  Gln  Ser
          290                      295                     300

GAA  ATC  GAG  CGA  ATC  TTC  GAG  CTG  GCC  CGG  ACC  CTT  CAG  TTG  GTC  GCT       960
Glu  Ile  Glu  Arg  Ile  Phe  Glu  Leu  Ala  Arg  Thr  Leu  Gln  Leu  Val  Ala
305                      310                     315                     320

CTG  GAT  GCT  GAC  ACC  ATC  AAT  CAC  CCA  GCC  CAG  CTG  TCC  AAG  ACC  TCG      1008
Leu  Asp  Ala  Asp  Thr  Ile  Asn  His  Pro  Ala  Gln  Leu  Ser  Lys  Thr  Ser
                    325                     330                     335

CTG  GCC  CCC  ATC  ATT  GTT  TAC  ATC  AAG  ATC  ACC  TCT  CCC  AAG  GTA  CTT      1056
Leu  Ala  Pro  Ile  Ile  Val  Tyr  Ile  Lys  Ile  Thr  Ser  Pro  Lys  Val  Leu
               340                      345                     350

CAA  AGG  CTC  ATC  AAG  TCC  CGA  GGA  AAG  TCT  CAG  TCC  AAA  CAC  CTC  AAT      1104
Gln  Arg  Leu  Ile  Lys  Ser  Arg  Gly  Lys  Ser  Gln  Ser  Lys  His  Leu  Asn
               355                      360                     365

GTC  CAA  ATA  GCG  GCC  TCG  GAA  AAG  CTG  GCA  CAG  TGC  CCC  CCT  GAA  ATG      1152
Val  Gln  Ile  Ala  Ala  Ser  Glu  Lys  Leu  Ala  Gln  Cys  Pro  Pro  Glu  Met
     370                      375                     380

TTT  GAC  ATC  ATC  CTG  GAT  GAG  AAC  CAA  TTG  GAG  GAT  GCC  TGC  GAG  CAT      1200
Phe  Asp  Ile  Ile  Leu  Asp  Glu  Asn  Gln  Leu  Glu  Asp  Ala  Cys  Glu  His
385                      390                     395                     400

CTG  GCG  GAG  TAC  TTG  GAA  GCC  TAT  TGG  AAG  GCC  ACA  CAC  CCG  CCC  AGC      1248
Leu  Ala  Glu  Tyr  Leu  Glu  Ala  Tyr  Trp  Lys  Ala  Thr  His  Pro  Pro  Ser
                    405                     410                     415

AGC  ACG  CCA  CCC  AAT  CCG  CTG  CTG  AAC  CGC  ACC  ATG  GCT  ACC  GCA  GCC      1296
Ser  Thr  Pro  Pro  Asn  Pro  Leu  Leu  Asn  Arg  Thr  Met  Ala  Thr  Ala  Ala
               420                      425                     430

CTG  GCT  GCC  AGC  CCT  GCC  CCT  GTC  TCC  AAC  CTC  CAG  GTA  CAG  GTG  CTC      1344
Leu  Ala  Ala  Ser  Pro  Ala  Pro  Val  Ser  Asn  Leu  Gln  Val  Gln  Val  Leu
               435                      440                     445

ACC  TCG  CTC  AGG  AGA  AAC  CTC  GGC  TTC  TGG  GGC  GGG  CTG  GAG  TCC  TCA      1392
Thr  Ser  Leu  Arg  Arg  Asn  Leu  Gly  Phe  Trp  Gly  Gly  Leu  Glu  Ser  Ser
     450                      455                     460

CAG  CGG  GGC  AGT  GTG  GTG  CCC  CAG  GAG  CAG  GAA  CAT  GCC  ATG  TAGTGGGCGC     1444
Gln  Arg  Gly  Ser  Val  Val  Pro  Gln  Glu  Gln  Glu  His  Ala  Met
465                      470                     475

CCTGCCCGTC  TTCCCTCCTG  CTCTGGGGTC  GGAACTGGAG  TGCAGGGAAC  ATGGAGGAGG              1504

AAGGGAAGAG  CTTTATTTTG  TAAAAAAATA  AGATGAGCGG  CA                                   1546
```

( 2 ) INFORMATION FOR SEQ ID NO:10:

( i ) SEQUENCE CHARACTERISTICS:
        ( A ) LENGTH: 1851 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 1..1797
        ( D ) OTHER INFORMATION: /standard_name="Beta-3"

( i x ) FEATURE:
        ( A ) NAME/KEY: 3'UTR
        ( B ) LOCATION: 1795..1851

( x i ) SEQUENCE DESCRIPTION: SEQ ID NO:10:

| | | | | | | | | | | | | | | | | |
|---|---|---|---|---|---|---|---|---|---|---|---|---|---|---|---|---|
| ATG | GTC | CAG | AAG | ACC | AGC | ATG | TCC | CGG | GAG | CCT | TAC | CCA | CCC | TCC | CAG | 48 |
| Met | Val | Gln | Lys | Thr | Ser | Met | Ser | Arg | Glu | Pro | Tyr | Pro | Pro | Ser | Gln | |
| 1 | | | | 5 | | | | | 10 | | | | | 15 | | |
| GAG | ATC | CCC | ATG | GAG | GTC | TTC | GAC | CCC | AGC | CCG | CAG | GGC | AAA | TAC | AGC | 96 |
| Glu | Ile | Pro | Met | Glu | Val | Phe | Asp | Pro | Ser | Pro | Gln | Gly | Lys | Tyr | Ser | |
| | | | 20 | | | | | 25 | | | | | 30 | | | |
| AAG | AGG | AAA | GGG | CGA | TTC | AAA | CGG | TCA | GAT | GGG | AGC | ACG | TCC | TCG | GAT | 144 |
| Lys | Arg | Lys | Gly | Arg | Phe | Lys | Arg | Ser | Asp | Gly | Ser | Thr | Ser | Ser | Asp | |
| | | 35 | | | | | 40 | | | | | 45 | | | | |
| ACC | ACA | TCC | AAC | AGC | TTT | GTC | CGC | CAG | GGC | TCA | GCG | GAG | TCC | TAC | ACC | 192 |
| Thr | Thr | Ser | Asn | Ser | Phe | Val | Arg | Gln | Gly | Ser | Ala | Glu | Ser | Tyr | Thr | |
| | 50 | | | | | 55 | | | | | 60 | | | | | |
| AGC | CGT | CCA | TCA | GAC | TCT | GAT | GTA | TCT | CTG | GAG | GAG | GAC | CGG | GAA | GCC | 240 |
| Ser | Arg | Pro | Ser | Asp | Ser | Asp | Val | Ser | Leu | Glu | Glu | Asp | Arg | Glu | Ala | |
| 65 | | | | | 70 | | | | | 75 | | | | | 80 | |
| TTA | AGG | AAG | GAA | GCA | GAG | CGC | CAG | GCA | TTA | GCG | CAG | CTC | GAG | AAG | GCC | 288 |
| Leu | Arg | Lys | Glu | Ala | Glu | Arg | Gln | Ala | Leu | Ala | Gln | Leu | Glu | Lys | Ala | |
| | | | | 85 | | | | | 90 | | | | | 95 | | |
| AAG | ACC | AAG | CCA | GTG | GCA | TTT | GCT | GTG | CGG | ACA | AAT | GTT | GGC | TAC | AAT | 336 |
| Lys | Thr | Lys | Pro | Val | Ala | Phe | Ala | Val | Arg | Thr | Asn | Val | Gly | Tyr | Asn | |
| | | | 100 | | | | | 105 | | | | | 110 | | | |
| CCG | TCT | CCA | GGG | GAT | GAG | GTG | CCT | GTG | CAG | GGA | GTG | GCC | ATC | ACC | TTC | 384 |
| Pro | Ser | Pro | Gly | Asp | Glu | Val | Pro | Val | Gln | Gly | Val | Ala | Ile | Thr | Phe | |
| | | 115 | | | | | 120 | | | | | 125 | | | | |
| GAG | CCC | AAA | GAC | TTC | CTG | CAC | ATC | AAG | GAG | AAA | TAC | AAT | AAT | GAC | TGG | 432 |
| Glu | Pro | Lys | Asp | Phe | Leu | His | Ile | Lys | Glu | Lys | Tyr | Asn | Asn | Asp | Trp | |
| | 130 | | | | | 135 | | | | | 140 | | | | | |
| TGG | ATC | GGG | CGG | CTG | GTG | AAG | GAG | GGC | TGT | GAG | GTT | GGC | TTC | ATT | CCC | 480 |
| Trp | Ile | Gly | Arg | Leu | Val | Lys | Glu | Gly | Cys | Glu | Val | Gly | Phe | Ile | Pro | |
| 145 | | | | | 150 | | | | | 155 | | | | | 160 | |
| AGC | CCC | GTC | AAA | CTG | GAC | AGC | CTT | CGC | CTG | CTG | CAG | GAA | CAG | AAG | CTG | 528 |
| Ser | Pro | Val | Lys | Leu | Asp | Ser | Leu | Arg | Leu | Leu | Gln | Glu | Gln | Lys | Leu | |
| | | | | 165 | | | | | 170 | | | | | 175 | | |
| CGC | CAG | AAC | CGC | CTC | GGC | TCC | AGC | AAA | TCA | GGC | GAT | AAC | TCC | AGT | TCC | 576 |
| Arg | Gln | Asn | Arg | Leu | Gly | Ser | Ser | Lys | Ser | Gly | Asp | Asn | Ser | Ser | Ser | |
| | | | 180 | | | | | 185 | | | | | 190 | | | |
| AGT | CTG | GGA | GAT | GTG | GTG | ACT | GGC | ACC | CGC | CGC | CCC | ACA | CCC | CCT | GCC | 624 |
| Ser | Leu | Gly | Asp | Val | Val | Thr | Gly | Thr | Arg | Arg | Pro | Thr | Pro | Pro | Ala | |
| | | 195 | | | | | 200 | | | | | 205 | | | | |
| AGT | GCC | AAA | CAG | AAG | CAG | AAG | TCG | ACA | GAG | CAT | GTG | CCC | CCC | TAT | GAC | 672 |
| Ser | Ala | Lys | Gln | Lys | Gln | Lys | Ser | Thr | Glu | His | Val | Pro | Pro | Tyr | Asp | |
| | 210 | | | | | 215 | | | | | 220 | | | | | |
| GTG | GTG | CCT | TCC | ATG | AGG | CCC | ATC | ATC | CTG | GTG | GGA | CCG | TCG | CTC | AAG | 720 |
| Val | Val | Pro | Ser | Met | Arg | Pro | Ile | Ile | Leu | Val | Gly | Pro | Ser | Leu | Lys | |
| 225 | | | | | 230 | | | | | 235 | | | | | 240 | |
| GGC | TAC | GAG | GTT | ACA | GAC | ATG | ATG | CAG | AAA | GCT | TTA | TTT | GAC | TTC | TTG | 768 |
| Gly | Tyr | Glu | Val | Thr | Asp | Met | Met | Gln | Lys | Ala | Leu | Phe | Asp | Phe | Leu | |
| | | | | 245 | | | | | 250 | | | | | 255 | | |
| AAG | CAT | CGG | TTT | GAT | GGC | AGG | ATC | TCC | ATC | ACT | CGT | GTG | ACG | GCA | GAT | 816 |
| Lys | His | Arg | Phe | Asp | Gly | Arg | Ile | Ser | Ile | Thr | Arg | Val | Thr | Ala | Asp | |
| | | | 260 | | | | | 265 | | | | | 270 | | | |
| ATT | TCC | CTG | GCT | AAG | CGC | TCA | GTT | CTC | AAC | AAC | CCC | AGC | AAA | CAC | ATC | 864 |
| Ile | Ser | Leu | Ala | Lys | Arg | Ser | Val | Leu | Asn | Asn | Pro | Ser | Lys | His | Ile | |
| | | 275 | | | | | 280 | | | | | 285 | | | | |
| ATC | ATT | GAG | CGC | TCC | AAC | ACA | CGC | TCC | AGC | CTG | GCT | GAG | GTG | CAG | AGT | 912 |
| Ile | Ile | Glu | Arg | Ser | Asn | Thr | Arg | Ser | Ser | Leu | Ala | Glu | Val | Gln | Ser | |
| | 290 | | | | | 295 | | | | | 300 | | | | | |
| GAA | ATC | GAG | CGA | ATC | TTC | GAG | CTG | GCC | CGG | ACC | CTT | CAG | TTG | GTC | GCT | 960 |
| Glu | Ile | Glu | Arg | Ile | Phe | Glu | Leu | Ala | Arg | Thr | Leu | Gln | Leu | Val | Ala | |

```
    305                          310                          315                          320
CTG GAT GCT GAC ACC ATC AAT CAC CCA GCC CAG CTG TCC AAG ACC TCG                                    1008
Leu Asp Ala Asp Thr Ile Asn His Pro Ala Gln Leu Ser Lys Thr Ser
                    325                      330                      335

CTG GCC CCC ATC ATT GTT TAC ATC AAG ATC ACC TCT CCC AAG GTA CTT                                    1056
Leu Ala Pro Ile Ile Val Tyr Ile Lys Ile Thr Ser Pro Lys Val Leu
                340                      345                      350

CAA AGG CTC ATC AAG TCC CGA GGA AAG TCT CAG TCC AAA CAC CTC AAT                                    1104
Gln Arg Leu Ile Lys Ser Arg Gly Lys Ser Gln Ser Lys His Leu Asn
            355                      360                      365

GTC CAA ATA GCG GCC TCG GAA AAG CTG GCA CAG TGC CCC CCT GAA ATG                                    1152
Val Gln Ile Ala Ala Ser Glu Lys Leu Ala Gln Cys Pro Pro Glu Met
        370                      375                      380

TTT GAC ATC ATC CTG GAT GAG AAC CAA TTG GAG GAT GCC TGC GAG CAT                                    1200
Phe Asp Ile Ile Leu Asp Glu Asn Gln Leu Glu Asp Ala Cys Glu His
385                      390                      395                      400

CTG GCG GAG TAC TTG GAA GCC TAT TGG AAG GCC ACA CAC CCG CCC AGC                                    1248
Leu Ala Glu Tyr Leu Glu Ala Tyr Trp Lys Ala Thr His Pro Pro Ser
                    405                      410                      415

AGC ACG CCA CCC AAT CCG CTG CTG AAC CGC ACC ATG GCT ACC GCA GCC                                    1296
Ser Thr Pro Pro Asn Pro Leu Leu Asn Arg Thr Met Ala Thr Ala Ala
                420                      425                      430

CTG GCT GCC AGC CCT GCC CCT GTC TCC AAC CTC CAG GGA CCC TAC CTT                                    1344
Leu Ala Ala Ser Pro Ala Pro Val Ser Asn Leu Gln Gly Pro Tyr Leu
            435                      440                      445

GCT TCC GGG GAC CAG CCA CTG GAA CGG GCC ACC GGG GAG CAC GCC AGC                                    1392
Ala Ser Gly Asp Gln Pro Leu Glu Arg Ala Thr Gly Glu His Ala Ser
        450                      455                      460

ATG CAC GAG TAC CCA GGG GAG CTG GGC CAG CCC CCA GGC CTT TAC CCC                                    1440
Met His Glu Tyr Pro Gly Glu Leu Gly Gln Pro Pro Gly Leu Tyr Pro
465                      470                      475                      480

AGC AGC CAC CCA CCA GGC CGG GCA GGC ACG CTA CGG GCA CTG TCC CGC                                    1488
Ser Ser His Pro Pro Gly Arg Ala Gly Thr Leu Arg Ala Leu Ser Arg
                    485                      490                      495

CAA GAC ACT TTT GAT GCC GAC ACC CCC GGC AGC CGA AAC TCT GCC TAC                                    1536
Gln Asp Thr Phe Asp Ala Asp Thr Pro Gly Ser Arg Asn Ser Ala Tyr
                500                      505                      510

ACG GAG CTG GGA GAC TCA TGT GTG GAC ATG GAG ACT GAC CCC TCA GAG                                    1584
Thr Glu Leu Gly Asp Ser Cys Val Asp Met Glu Thr Asp Pro Ser Glu
            515                      520                      525

GGG CCA GGG CTT GGA GAC CCT GCA GGG GGC ACG CCC CCA GCC CGA                                        1632
Gly Pro Gly Leu Gly Asp Pro Ala Gly Gly Gly Thr Pro Pro Ala Arg
        530                      535                      540

CAG GGA TCC TGG GAG GAC GAG GAA GAA GAC TAT GAG GAA GAG CTG ACC                                    1680
Gln Gly Ser Trp Glu Asp Glu Glu Glu Asp Tyr Glu Glu Glu Leu Thr
545                      550                      555                      560

GAC AAC CGG AAC CGG GGC CGG AAT AAG GCC CGC TAC TGC GCT GAG GGT                                    1728
Asp Asn Arg Asn Arg Gly Arg Asn Lys Ala Arg Tyr Cys Ala Glu Gly
                    565                      570                      575

GGG GGT CCA GTT TTG GGG CGC AAC AAG AAT GAG CTG GAG GGC TGG GGA                                    1776
Gly Gly Pro Val Leu Gly Arg Asn Lys Asn Glu Leu Glu Gly Trp Gly
                580                      585                      590

CGA GGC GTC TAC ATT CGC TGAGAGGCAG GGGCCACACG GCGGGAGGAA                                           1824
Arg Gly Val Tyr Ile Arg
            595

GGGCTCTGAG CCCAGGGGAG GGGAGGG                                                                      1851
```

( 2 ) INFORMATION FOR SEQ ID NO:11:

( i ) SEQUENCE CHARACTERISTICS:

( A ) LENGTH: 3600 base pairs
( B ) TYPE: nucleic acid
( C ) STRANDEDNESS: double
( D ) TOPOLOGY: linear ( i i ) MOLECULE TYPE: DNA (genomic)

( i x ) FEATURE:
( A ) NAME/KEY: CDS
( B ) LOCATION: 35..3310
( D ) OTHER INFORMATION: /standard_name="Alpha-2"

( i x ) FEATURE:
( A ) NAME/KEY: 5'UTR
( B ) LOCATION: 1..34

( i x ) FEATURE:
( A ) NAME/KEY: 3'UTR
( B ) LOCATION: 3308..3600

( x i ) SEQUENCE DESCRIPTION: SEQ ID NO:11:

| | | |
|---|---|---|
| GCGGGGGAGG GGGCATTGAT CTTCGATCGC GAAG ATG GCT GCT GGC TGC CTG<br>                                       Met Ala Ala Gly Cys Leu<br>                                        1                 5 | 52 |
| CTG GCC TTG ACT CTG ACA CTT TTC CAA TCT TTG CTC ATC GGC CCC TCG<br>Leu Ala Leu Thr Leu Thr Leu Phe Gln Ser Leu Leu Ile Gly Pro Ser<br>         10              15              20 | 100 |
| TCG GAG GAG CCG TTC CCT TCG GCC GTC ACT ATC AAA TCA TGG GTG GAT<br>Ser Glu Glu Pro Phe Pro Ser Ala Val Thr Ile Lys Ser Trp Val Asp<br>     25              30              35 | 148 |
| AAG ATG CAA GAA GAC CTT GTC ACA CTG GCA AAA ACA GCA AGT GGA GTC<br>Lys Met Gln Glu Asp Leu Val Thr Leu Ala Lys Thr Ala Ser Gly Val<br>     40              45              50 | 196 |
| AAT CAG CTT GTT GAT ATT TAT GAG AAA TAT CAA GAT TTG TAT ACT GTG<br>Asn Gln Leu Val Asp Ile Tyr Glu Lys Tyr Gln Asp Leu Tyr Thr Val<br>55              60              65              70 | 244 |
| GAA CCA AAT AAT GCA CGC CAG CTG GTA GAA ATT GCA GCC AGG GAT ATT<br>Glu Pro Asn Asn Ala Arg Gln Leu Val Glu Ile Ala Ala Arg Asp Ile<br>             75              80              85 | 292 |
| GAG AAA CTT CTG AGC AAC AGA TCT AAA GCC CTG GTG AGC CTG GCA TTG<br>Glu Lys Leu Leu Ser Asn Arg Ser Lys Ala Leu Val Ser Leu Ala Leu<br>         90              95              100 | 340 |
| GAA GCG GAG AAA GTT CAA GCA GCT CAC CAG TGG AGA GAA GAT TTT GCA<br>Glu Ala Glu Lys Val Gln Ala Ala His Gln Trp Arg Glu Asp Phe Ala<br>     105             110             115 | 388 |
| AGC AAT GAA GTT GTC TAC TAC AAT GCA AAG GAT GAT CTC GAT CCT GAG<br>Ser Asn Glu Val Val Tyr Tyr Asn Ala Lys Asp Asp Leu Asp Pro Glu<br>     120             125             130 | 436 |
| AAA AAT GAC AGT GAG CCA GGC AGC CAG AGG ATA AAA CCT GTT TTC ATT<br>Lys Asn Asp Ser Glu Pro Gly Ser Gln Arg Ile Lys Pro Val Phe Ile<br>135             140             145             150 | 484 |
| GAA GAT GCT AAT TTT GGA CGA CAA ATA TCT TAT CAG CAC GCA GCA GTC<br>Glu Asp Ala Asn Phe Gly Arg Gln Ile Ser Tyr Gln His Ala Ala Val<br>             155             160             165 | 532 |
| CAT ATT CCT ACT GAC ATC TAT GAG GGC TCA ACA ATT GTG TTA AAT GAA<br>His Ile Pro Thr Asp Ile Tyr Glu Gly Ser Thr Ile Val Leu Asn Glu<br>         170             175             180 | 580 |
| CTC AAC TGG ACA AGT GCC TTA GAT GAA GTT TTC AAA AAG AAT CGC GAG<br>Leu Asn Trp Thr Ser Ala Leu Asp Glu Val Phe Lys Lys Asn Arg Glu<br>         185             190             195 | 628 |
| GAA GAC CCT TCA TTA TTG TGG CAG GTT TTT GGC AGT GCC ACT GGC CTA<br>Glu Asp Pro Ser Leu Leu Trp Gln Val Phe Gly Ser Ala Thr Gly Leu<br>     200             205             210 | 676 |
| GCT CGA TAT TAT CCA GCT TCA CCA TGG GTT GAT AAT AGT AGA ACT CCA<br>Ala Arg Tyr Tyr Pro Ala Ser Pro Trp Val Asp Asn Ser Arg Thr Pro | 724 |

| | | | | | | | | | | | | | | | | |
|---|---|---|---|---|---|---|---|---|---|---|---|---|---|---|---|---|
| AAT | AAG | ATT | GAC | CTT | TAT | GAT | GTA | CGC | AGA | AGA | CCA | TGG | TAC | ATC | CAA | 772 |
| Asn | Lys | Ile | Asp | Leu | Tyr | Asp | Val | Arg | Arg | Arg | Pro | Trp | Tyr | Ile | Gln | |
| | | | | 235 | | | | 240 | | | | | | 245 | | |
| GGA | GCT | GCA | TCT | CCT | AAA | GAC | ATG | CTT | ATT | CTG | GTG | GAT | GTG | AGT | GGA | 820 |
| Gly | Ala | Ala | Ser | Pro | Lys | Asp | Met | Leu | Ile | Leu | Val | Asp | Val | Ser | Gly | |
| | | | 250 | | | | 255 | | | | | 260 | | | | |
| AGT | GTT | AGT | GGA | TTG | ACA | CTT | AAA | CTG | ATC | CGA | ACA | TCT | GTC | TCC | GAA | 868 |
| Ser | Val | Ser | Gly | Leu | Thr | Leu | Lys | Leu | Ile | Arg | Thr | Ser | Val | Ser | Glu | |
| | | 265 | | | | 270 | | | | | | 275 | | | | |
| ATG | TTA | GAA | ACC | CTC | TCA | GAT | GAT | GAT | TTC | GTG | AAT | GTA | GCT | TCA | TTT | 916 |
| Met | Leu | Glu | Thr | Leu | Ser | Asp | Asp | Asp | Phe | Val | Asn | Val | Ala | Ser | Phe | |
| | 280 | | | | | 285 | | | | | 290 | | | | | |
| AAC | AGC | AAT | GCT | CAG | GAT | GTA | AGC | TGT | TTT | CAG | CAC | CTT | GTC | CAA | GCA | 964 |
| Asn | Ser | Asn | Ala | Gln | Asp | Val | Ser | Cys | Phe | Gln | His | Leu | Val | Gln | Ala | |
| 295 | | | | 300 | | | | | 305 | | | | | 310 | | |
| AAT | GTA | AGA | AAT | AAA | AAA | GTG | TTG | AAA | GAC | GCG | GTG | AAT | AAT | ATC | ACA | 1012 |
| Asn | Val | Arg | Asn | Lys | Lys | Val | Leu | Lys | Asp | Ala | Val | Asn | Asn | Ile | Thr | |
| | | | | 315 | | | | | 320 | | | | | 325 | | |
| GCC | AAA | GGA | ATT | ACA | GAT | TAT | AAG | AAG | GGC | TTT | AGT | TTT | GCT | TTT | GAA | 1060 |
| Ala | Lys | Gly | Ile | Thr | Asp | Tyr | Lys | Lys | Gly | Phe | Ser | Phe | Ala | Phe | Glu | |
| | | | 330 | | | | | 335 | | | | | 340 | | | |
| CAG | CTG | CTT | AAT | TAT | AAT | GTT | TCC | AGA | GCA | AAC | TGC | AAT | AAG | ATT | ATT | 1108 |
| Gln | Leu | Leu | Asn | Tyr | Asn | Val | Ser | Arg | Ala | Asn | Cys | Asn | Lys | Ile | Ile | |
| | | 345 | | | | | 350 | | | | | 355 | | | | |
| ATG | CTA | TTC | ACG | GAT | GGA | GGA | GAA | GAG | AGA | GCC | CAG | GAG | ATA | TTT | AAC | 1156 |
| Met | Leu | Phe | Thr | Asp | Gly | Gly | Glu | Glu | Arg | Ala | Gln | Glu | Ile | Phe | Asn | |
| | 360 | | | | | 365 | | | | | 370 | | | | | |
| AAA | TAC | AAT | AAA | GAT | AAA | AAA | GTA | CGT | GTA | TTC | AGG | TTT | TCA | GTT | GGT | 1204 |
| Lys | Tyr | Asn | Lys | Asp | Lys | Lys | Val | Arg | Val | Phe | Arg | Phe | Ser | Val | Gly | |
| 375 | | | | 380 | | | | | 385 | | | | | 390 | | |
| CAA | CAC | AAT | TAT | GAG | AGA | GGA | CCT | ATT | CAG | TGG | ATG | GCC | TGT | GAA | AAC | 1252 |
| Gln | His | Asn | Tyr | Glu | Arg | Gly | Pro | Ile | Gln | Trp | Met | Ala | Cys | Glu | Asn | |
| | | | | 395 | | | | 400 | | | | | 405 | | | |
| AAA | GGT | TAT | TAT | TAT | GAA | ATT | CCT | TCC | ATT | GGT | GCA | ATA | AGA | ATC | AAT | 1300 |
| Lys | Gly | Tyr | Tyr | Tyr | Glu | Ile | Pro | Ser | Ile | Gly | Ala | Ile | Arg | Ile | Asn | |
| | | | 410 | | | | 415 | | | | | 420 | | | | |
| ACT | CAG | GAA | TAT | TTG | GAT | GTT | TTG | GGA | AGA | CCA | ATG | GTT | TTA | GCA | GGA | 1348 |
| Thr | Gln | Glu | Tyr | Leu | Asp | Val | Leu | Gly | Arg | Pro | Met | Val | Leu | Ala | Gly | |
| | | 425 | | | | 430 | | | | | 435 | | | | | |
| GAC | AAA | GCT | AAG | CAA | GTC | CAA | TGG | ACA | AAT | GTG | TAC | CTG | GAT | GCA | TTG | 1396 |
| Asp | Lys | Ala | Lys | Gln | Val | Gln | Trp | Thr | Asn | Val | Tyr | Leu | Asp | Ala | Leu | |
| | 440 | | | | 445 | | | | | 450 | | | | | | |
| GAA | CTG | GGA | CTT | GTC | ATT | ACT | GGA | ACT | CTT | CCG | GTC | TTC | AAC | ATA | ACC | 1444 |
| Glu | Leu | Gly | Leu | Val | Ile | Thr | Gly | Thr | Leu | Pro | Val | Phe | Asn | Ile | Thr | |
| 455 | | | | 460 | | | | | 465 | | | | | 470 | | |
| GGC | CAA | TTT | GAA | AAT | AAG | ACA | AAC | TTA | AAG | AAC | CAG | CTG | ATT | CTT | GGT | 1492 |
| Gly | Gln | Phe | Glu | Asn | Lys | Thr | Asn | Leu | Lys | Asn | Gln | Leu | Ile | Leu | Gly | |
| | | | 475 | | | | 480 | | | | | 485 | | | | |
| GTG | ATG | GGA | GTA | GAT | GTG | TCT | TTG | GAA | GAT | ATT | AAA | AGA | CTG | ACA | CCA | 1540 |
| Val | Met | Gly | Val | Asp | Val | Ser | Leu | Glu | Asp | Ile | Lys | Arg | Leu | Thr | Pro | |
| | | | 490 | | | | 495 | | | | | 500 | | | | |
| CGT | TTT | ACA | CTG | TGC | CCC | AAT | GGG | TAT | TAC | TTT | GCA | ATC | GAT | CCT | AAT | 1588 |
| Arg | Phe | Thr | Leu | Cys | Pro | Asn | Gly | Tyr | Tyr | Phe | Ala | Ile | Asp | Pro | Asn | |
| | | 505 | | | | | 510 | | | | | 515 | | | | |
| GGT | TAT | GTT | TTA | TTA | CAT | CCA | AAT | CTT | CAG | CCA | AAG | AAC | CCC | AAA | TCT | 1636 |
| Gly | Tyr | Val | Leu | Leu | His | Pro | Asn | Leu | Gln | Pro | Lys | Asn | Pro | Lys | Ser | |
| | | 520 | | | | 525 | | | | | 530 | | | | | |
| CAG | GAG | CCA | GTA | ACA | TTG | GAT | TTC | CTT | GAT | GCA | GAG | TTA | GAG | AAT | GAT | 1684 |
| Gln | Glu | Pro | Val | Thr | Leu | Asp | Phe | Leu | Asp | Ala | Glu | Leu | Glu | Asn | Asp | |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| 535 |     |     |     | 540 |     |     |     | 545 |     |     |     | 550 |     |     |     |      |
| ATT | AAA | GTG | GAG | ATT | CGA | AAT | AAG | ATG | ATT | GAT | GGG | GAA | AGT | GGA | GAA | 1732 |
| Ile | Lys | Val | Glu | Ile | Arg | Asn | Lys | Met | Ile | Asp | Gly | Glu | Ser | Gly | Glu |      |
|     |     |     |     | 555 |     |     |     | 560 |     |     |     |     | 565 |     |     |      |
| AAA | ACA | TTC | AGA | ACT | CTG | GTT | AAA | TCT | CAA | GAT | GAG | AGA | TAT | ATT | GAC | 1780 |
| Lys | Thr | Phe | Arg | Thr | Leu | Val | Lys | Ser | Gln | Asp | Glu | Arg | Tyr | Ile | Asp |      |
|     |     |     | 570 |     |     |     |     | 575 |     |     |     | 580 |     |     |     |      |
| AAA | GGA | AAC | AGG | ACA | TAC | ACA | TGG | ACA | CCT | GTC | AAT | GGC | ACA | GAT | TAC | 1828 |
| Lys | Gly | Asn | Arg | Thr | Tyr | Thr | Trp | Thr | Pro | Val | Asn | Gly | Thr | Asp | Tyr |      |
|     |     | 585 |     |     |     |     | 590 |     |     |     |     | 595 |     |     |     |      |
| AGT | TTG | GCC | TTG | GTA | TTA | CCA | ACC | TAC | AGT | TTT | TAC | TAT | ATA | AAA | GCC | 1876 |
| Ser | Leu | Ala | Leu | Val | Leu | Pro | Thr | Tyr | Ser | Phe | Tyr | Tyr | Ile | Lys | Ala |      |
|     |     | 600 |     |     |     | 605 |     |     |     | 610 |     |     |     |     |     |      |
| AAA | CTA | GAA | GAG | ACA | ATA | ACT | CAG | GCC | AGA | TCA | AAA | AAG | GGC | AAA | ATG | 1924 |
| Lys | Leu | Glu | Glu | Thr | Ile | Thr | Gln | Ala | Arg | Ser | Lys | Lys | Gly | Lys | Met |      |
| 615 |     |     |     |     | 620 |     |     |     | 625 |     |     |     |     |     | 630 |      |
| AAG | GAT | TCG | GAA | ACC | CTG | AAG | CCA | GAT | AAT | TTT | GAA | GAA | TCT | GGC | TAT | 1972 |
| Lys | Asp | Ser | Glu | Thr | Leu | Lys | Pro | Asp | Asn | Phe | Glu | Glu | Ser | Gly | Tyr |      |
|     |     |     |     | 635 |     |     |     |     | 640 |     |     |     |     | 645 |     |      |
| ACA | TTC | ATA | GCA | CCA | AGA | GAT | TAC | TGC | AAT | GAC | CTG | AAA | ATA | TCG | GAT | 2020 |
| Thr | Phe | Ile | Ala | Pro | Arg | Asp | Tyr | Cys | Asn | Asp | Leu | Lys | Ile | Ser | Asp |      |
|     |     |     | 650 |     |     |     |     | 655 |     |     |     |     | 660 |     |     |      |
| AAT | AAC | ACT | GAA | TTT | CTT | TTA | AAT | TTC | AAC | GAG | TTT | ATT | GAT | AGA | AAA | 2068 |
| Asn | Asn | Thr | Glu | Phe | Leu | Leu | Asn | Phe | Asn | Glu | Phe | Ile | Asp | Arg | Lys |      |
|     |     | 665 |     |     |     |     | 670 |     |     |     |     | 675 |     |     |     |      |
| ACT | CCA | AAC | AAC | CCA | TCA | TGT | AAC | GCG | GAT | TTG | ATT | AAT | AGA | GTC | TTG | 2116 |
| Thr | Pro | Asn | Asn | Pro | Ser | Cys | Asn | Ala | Asp | Leu | Ile | Asn | Arg | Val | Leu |      |
|     |     | 680 |     |     |     | 685 |     |     |     | 690 |     |     |     |     |     |      |
| CTT | GAT | GCA | GGC | TTT | ACA | AAT | GAA | CTT | GTC | CAA | AAT | TAC | TGG | AGT | AAG | 2164 |
| Leu | Asp | Ala | Gly | Phe | Thr | Asn | Glu | Leu | Val | Gln | Asn | Tyr | Trp | Ser | Lys |      |
| 695 |     |     |     |     | 700 |     |     |     | 705 |     |     |     |     |     | 710 |      |
| CAG | AAA | AAT | ATC | AAG | GGA | GTG | AAA | GCA | CGA | TTT | GTT | GTG | ACT | GAT | GGT | 2212 |
| Gln | Lys | Asn | Ile | Lys | Gly | Val | Lys | Ala | Arg | Phe | Val | Val | Thr | Asp | Gly |      |
|     |     |     |     | 715 |     |     |     |     | 720 |     |     |     |     | 725 |     |      |
| GGG | ATT | ACC | AGA | GTT | TAT | CCC | AAA | GAG | GCT | GGA | GAA | AAT | TGG | CAA | GAA | 2260 |
| Gly | Ile | Thr | Arg | Val | Tyr | Pro | Lys | Glu | Ala | Gly | Glu | Asn | Trp | Gln | Glu |      |
|     |     |     | 730 |     |     |     |     | 735 |     |     |     |     | 740 |     |     |      |
| AAC | CCA | GAG | ACA | TAT | GAG | GAC | AGC | TTC | TAT | AAA | AGG | AGC | CTA | GAT | AAT | 2308 |
| Asn | Pro | Glu | Thr | Tyr | Glu | Asp | Ser | Phe | Tyr | Lys | Arg | Ser | Leu | Asp | Asn |      |
|     |     | 745 |     |     |     |     | 750 |     |     |     |     | 755 |     |     |     |      |
| GAT | AAC | TAT | GTT | TTC | ACT | GCT | CCC | TAC | TTT | AAC | AAA | AGT | GGA | CCT | GGT | 2356 |
| Asp | Asn | Tyr | Val | Phe | Thr | Ala | Pro | Tyr | Phe | Asn | Lys | Ser | Gly | Pro | Gly |      |
|     | 760 |     |     |     |     | 765 |     |     |     |     | 770 |     |     |     |     |      |
| GCC | TAT | GAA | TCG | GGC | ATT | ATG | GTA | AGC | AAA | GCT | GTA | GAA | ATA | TAT | ATT | 2404 |
| Ala | Tyr | Glu | Ser | Gly | Ile | Met | Val | Ser | Lys | Ala | Val | Glu | Ile | Tyr | Ile |      |
| 775 |     |     |     |     | 780 |     |     |     | 785 |     |     |     |     |     | 790 |      |
| CAA | GGG | AAA | CTT | CTT | AAA | CCT | GCA | GTT | GTT | GGA | ATT | AAA | ATT | GAT | GTA | 2452 |
| Gln | Gly | Lys | Leu | Leu | Lys | Pro | Ala | Val | Val | Gly | Ile | Lys | Ile | Asp | Val |      |
|     |     |     |     | 795 |     |     |     |     | 800 |     |     |     |     | 805 |     |      |
| AAT | TCC | TGG | ATA | GAG | AAT | TTC | ACC | AAA | ACC | TCA | ATC | AGA | GAT | CCG | TGT | 2500 |
| Asn | Ser | Trp | Ile | Glu | Asn | Phe | Thr | Lys | Thr | Ser | Ile | Arg | Asp | Pro | Cys |      |
|     |     |     | 810 |     |     |     |     | 815 |     |     |     | 820 |     |     |     |      |
| GCT | GGT | CCA | GTT | TGT | GAC | TGC | AAA | AGA | AAC | AGT | GAC | GTA | ATG | GAT | TGT | 2548 |
| Ala | Gly | Pro | Val | Cys | Asp | Cys | Lys | Arg | Asn | Ser | Asp | Val | Met | Asp | Cys |      |
|     |     | 825 |     |     |     |     | 830 |     |     |     |     | 835 |     |     |     |      |
| GTG | ATT | CTG | GAT | GAT | GGT | GGG | TTT | CTT | CTG | ATG | GCA | AAT | CAT | GAT | GAT | 2596 |
| Val | Ile | Leu | Asp | Asp | Gly | Gly | Phe | Leu | Leu | Met | Ala | Asn | His | Asp | Asp |      |
|     | 840 |     |     |     |     | 845 |     |     |     |     | 850 |     |     |     |     |      |
| TAT | ACT | AAT | CAG | ATT | GGA | AGA | TTT | TTT | GGA | GAG | ATT | GAT | CCC | AGC | TTG | 2644 |
| Tyr | Thr | Asn | Gln | Ile | Gly | Arg | Phe | Phe | Gly | Glu | Ile | Asp | Pro | Ser | Leu |      |

```
855                        860                        865                        870
ATG AGA CAC CTG GTT AAT ATA TCA GTT TAT GCT TTT AAC AAA TCT TAT         2692
Met Arg His Leu Val Asn Ile Ser Val Tyr Ala Phe Asn Lys Ser Tyr
            875                 880                 885

GAT TAT CAG TCA GTA TGT GAG CCC GGT GCT GCA CCA AAA CAA GGA GCA         2740
Asp Tyr Gln Ser Val Cys Glu Pro Gly Ala Ala Pro Lys Gln Gly Ala
            890                 895                 900

GGA CAT CGC TCA GCA TAT GTG CCA TCA GTA GCA GAC ATA TTA CAA ATT         2788
Gly His Arg Ser Ala Tyr Val Pro Ser Val Ala Asp Ile Leu Gln Ile
        905                 910                 915

GGC TGG TGG GCC ACT GCT GCT GCC TGG TCT ATT CTA CAG CAG TTT CTC         2836
Gly Trp Trp Ala Thr Ala Ala Ala Trp Ser Ile Leu Gln Gln Phe Leu
920                 925                 930

TTG AGT TTG ACC TTT CCA CGA CTC CTT GAG GCA GTT GAG ATG GAG GAT         2884
Leu Ser Leu Thr Phe Pro Arg Leu Leu Glu Ala Val Glu Met Glu Asp
935                 940                 945                 950

GAT GAC TTC ACG GCC TCC CTG TCC AAG CAG AGC TGC ATT ACT GAA CAA         2932
Asp Asp Phe Thr Ala Ser Leu Ser Lys Gln Ser Cys Ile Thr Glu Gln
            955                 960                 965

ACC CAG TAT TTC TTC GAT AAC GAC AGT AAA TCA TTC AGT GGT GTA TTA         2980
Thr Gln Tyr Phe Phe Asp Asn Asp Ser Lys Ser Phe Ser Gly Val Leu
            970                 975                 980

GAC TGT GGA AAC TGT TCC AGA ATC TTT CAT GGA GAA AAG CTT ATG AAC         3028
Asp Cys Gly Asn Cys Ser Arg Ile Phe His Gly Glu Lys Leu Met Asn
        985                 990                 995

ACC AAC TTA ATA TTC ATA ATG GTT GAG AGC AAA GGG ACA TGT CCA TGT         3076
Thr Asn Leu Ile Phe Ile Met Val Glu Ser Lys Gly Thr Cys Pro Cys
    1000                1005                1010

GAC ACA CGA CTG CTC ATA CAA GCG GAG CAG ACT TCT GAC GGT CCA AAT         3124
Asp Thr Arg Leu Leu Ile Gln Ala Glu Gln Thr Ser Asp Gly Pro Asn
1015                1020                1025                1030

CCT TGT GAC ATG GTT AAG CAA CCT AGA TAC CGA AAA GGG CCT GAT GTC         3172
Pro Cys Asp Met Val Lys Gln Pro Arg Tyr Arg Lys Gly Pro Asp Val
            1035                1040                1045

TGC TTT GAT AAC AAT GTC TTG GAG GAT TAT ACT GAC TGT GGT GGT GTT         3220
Cys Phe Asp Asn Asn Val Leu Glu Asp Tyr Thr Asp Cys Gly Gly Val
            1050                1055                1060

TCT GGA TTA AAT CCC TCC CTG TGG TAT ATC ATT GGA ATC CAG TTT CTA         3268
Ser Gly Leu Asn Pro Ser Leu Trp Tyr Ile Ile Gly Ile Gln Phe Leu
        1065                1070                1075

CTA CTT TGG CTG GTA TCT GGC AGC ACA CAC CGG CTG TTA TGACCTTCTA         3317
Leu Leu Trp Leu Val Ser Gly Ser Thr His Arg Leu Leu
1080                1085                1090

AAAACCAAAT CTGCATAGTT AAACTCCAGA CCCTGCCAAA ACATGAGCCC TGCCCTCAAT      3377

TACAGTAACG TAGGGTCAGC TATAAAATCA GACAAACATT AGCTGGGCCT GTTCCATGGC      3437

ATAACACTAA GGCGCAGACT CCTAAGGCAC CCACTGGCTG CATGTCAGGG TGTCAGATCC      3497

TTAAACGTGT GTGAATGCTG CATCATCTAT GTGTAACATC AAAGCAAAAT CCTATACGTG      3557

TCCTCTATTG GAAAATTTGG GCGTTTGTTG TTGCATTGTT GGT                        3600
```

( 2 ) INFORMATION FOR SEQ ID NO:12:

( i ) SEQUENCE CHARACTERISTICS:
        ( A ) LENGTH: 323 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:12:

```
CCCCCTGCCA GTGGCCAAAC AGAAGCAGAA GTCGGGTAAT GAAATGACTA ACTTAGCCTT      60

TGAACTAGAC CCCCTAGAGT TAGAGGAGGA AGAGGCTGAG CTTGGTGAGC AGAGTGGCTC     120

TGCCAAGACT AGTGTTAGCA GTGTCACCAC CCCGCCACCC CATGGCAAAC GCATCCCCTT     180

CTTTAAGAAG ACAGAGCATG TGCCCCCCTA TGACGTGGTG CCTTCCATGA GGCCCATCAT     240

CCTGGTGGGA CCGTCGCTCA AGGGCTACGA GGTTACAGAC ATGATGCAGA AAGCTTTATT     300

TGACTTCTTG AAGCATCGGT TTG                                             323
```

( 2 ) INFORMATION FOR SEQ ID NO:13:

( i ) SEQUENCE CHARACTERISTICS:
        ( A ) LENGTH: 57 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:13:

```
CCTATTGGTG TAGGTATACC AACAATTAAT TTAAGAAAAA GGAGACCCAA TATCCAG        57
```

( 2 ) INFORMATION FOR SEQ ID NO:14:

( i ) SEQUENCE CHARACTERISTICS:
        ( A ) LENGTH: 180 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 1..132

( x i ) SEQUENCE DESCRIPTION: SEQ ID NO:14:

```
TGG TCC TTT GCC TGC GCC TGT GCC GCC TTC ATC CTC CTC TTT CTC GGC       48
Trp Ser Phe Ala Cys Ala Cys Ala Ala Phe Ile Leu Leu Phe Leu Gly
 1               5                  10                  15

GGT CTC GCC CTC CTG CTG TTC TCC CTG CCT CGA ATG CCC CGG AAC CCA       96
Gly Leu Ala Leu Leu Leu Phe Ser Leu Pro Arg Met Pro Arg Asn Pro
             20                  25                  30

TGG GAG TCC TGC ATG GAT GCT GAG CCC GAG CAC TAACCCTCCT GCGGCCCTAG    149
Trp Glu Ser Cys Met Asp Ala Glu Pro Glu His
         35                  40

CGACCCTCAG GCTTCTTCCC AGGAAGCGGG G                                    180
```

( 2 ) INFORMATION FOR SEQ ID NO:15:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: Other nucleic acid;
        ( A ) DESCRIPTION: Oligonucleotide ( x i ) SEQUENCE DESCRIPTION: SEQ ID NO:15:

```
AATTCGGTAC GTACACTCGA GC                                              22
```

( 2 ) INFORMATION FOR SEQ ID NO:16:

( i ) SEQUENCE CHARACTERISTICS:
        ( A ) LENGTH: 18 base pairs ( B ) TYPE: nucleic acid
                    ( C ) STRANDEDNESS: single
                    ( D ) TOPOLOGY: linear ( i i ) MOLECULE TYPE: Other nucleic acid;
                    ( A ) DESCRIPTION: Oligonucleotide ( x i ) SEQUENCE DESCRIPTION: SEQ ID NO:16:

GCTCGAGTGT ACGTACCG                                                                            18

( 2 ) INFORMATION FOR SEQ ID NO:17:

( i ) SEQUENCE CHARACTERISTICS:
                    ( A ) LENGTH: 20 base pairs
                    ( B ) TYPE: nucleic acid
                    ( C ) STRANDEDNESS: single
                    ( D ) TOPOLOGY: linear ( i i ) MOLECULE TYPE: Other nucleic acid;
                    ( A ) DESCRIPTION: Oligonucleotide ( x i ) SEQUENCE DESCRIPTION: SEQ ID NO:17:

CCATGGTACC TTCGTTGACG                                                                          20

( 2 ) INFORMATION FOR SEQ ID NO:18:

( i ) SEQUENCE CHARACTERISTICS:
                    ( A ) LENGTH: 24 base pairs
                    ( B ) TYPE: nucleic acid
                    ( C ) STRANDEDNESS: single
                    ( D ) TOPOLOGY: linear ( i i ) MOLECULE TYPE: Other nucleic acid;
                    ( A ) DESCRIPTION: Oligonucleotide ( x i ) SEQUENCE DESCRIPTION: SEQ ID NO:18:

AATTCGTCAA CGAAGGTACC ATGG                                                                     24

( 2 ) INFORMATION FOR SEQ ID NO:19:

( i ) SEQUENCE CHARACTERISTICS:
                    ( A ) LENGTH: 1702 base pairs
                    ( B ) TYPE: nucleic acid
                    ( C ) STRANDEDNESS: double
                    ( D ) TOPOLOGY: linear ( i i ) MOLECULE TYPE: Genomic DNA ( i i i ) HYPOTHETICAL: NO ( i v ) ANTI-SENSE: NO ( v ) FRAGMENT TYPE:

( v i ) ORIGINAL SOURCE:

( i x ) FEATURE:
                    ( A ) NAME/KEY: Coding Sequence
                    ( B ) LOCATION: 1...1590
                    ( D ) OTHER INFORMATION:
                    ( A ) NAME/KEY: 3'UTR
                    ( B ) LOCATION: 1591...1702
                    ( D ) OTHER INFORMATION:

( x i ) SEQUENCE DESCRIPTION: SEQ ID NO:19:

| ATG | GTC | CAG | AAG | ACC | AGC | ATG | TCC | CGG | GGC | CCT | TAC | CCA | CCC | TCC | CAG | 48 |
| Met | Val | Gln | Lys | Thr | Ser | Met | Ser | Arg | Gly | Pro | Tyr | Pro | Pro | Ser | Gln | |
| 1 | | | | 5 | | | | | 10 | | | | | 15 | | |

| GAG | ATC | CCC | ATG | GAG | GTC | TTC | GAC | CCC | AGC | CCG | CAG | GGC | AAA | TAC | AGC | 96 |
| Glu | Ile | Pro | Met | Glu | Val | Phe | Asp | Pro | Ser | Pro | Gln | Gly | Lys | Tyr | Ser | |
| | | | 20 | | | | | 25 | | | | | 30 | | | |

-continued

| | | | | | | | | | | | | | | | | |
|---|---|---|---|---|---|---|---|---|---|---|---|---|---|---|---|---|
| AAG | AGG | AAA | GGG | CGA | TTC | AAA | CGG | TCA | GAT | GGG | AGC | ACG | TCC | TCG | GAT | 144 |
| Lys | Arg | Lys 35 | Gly | Arg | Phe | Lys 40 | Arg | Ser | Asp | Gly | Ser 45 | Thr | Ser | Ser | Asp | |
| ACC | ACA | TCC | AAC | AGC | TTT | GTC | CGC | CAG | GGC | TCA | GCG | GAG | TCC | TAC | ACC | 192 |
| Thr | Thr 50 | Ser | Asn | Ser | Phe | Val 55 | Arg | Gln | Gly | Ser | Ala 60 | Glu | Ser | Tyr | Thr | |
| AGC | CGT | CCA | TCA | GAC | TCT | GAT | GTA | TCT | CTG | GAG | GAG | GAC | CGG | GAA | GCC | 240 |
| Ser 65 | Arg | Pro | Ser | Asp | Ser 70 | Asp | Val | Ser | Leu | Glu 75 | Glu | Asp | Arg | Glu | Ala 80 | |
| TTA | AGG | AAG | GAA | GCA | GAG | CGC | CAG | GCA | TTA | GCG | CAG | CTC | GAG | AAG | GCC | 288 |
| Leu | Arg | Lys | Glu | Ala 85 | Glu | Arg | Gln | Ala | Leu 90 | Ala | Gln | Leu | Glu | Lys 95 | Ala | |
| AAG | ACC | AAG | CCA | GTG | GCA | TTT | GCT | GTG | CGG | ACA | AAT | GTT | GGC | TAC | AAT | 336 |
| Lys | Thr | Lys | Pro 100 | Val | Ala | Phe | Ala | Val 105 | Arg | Thr | Asn | Val | Gly 110 | Tyr | Asn | |
| CCG | TCT | CCA | GGG | GAT | GAG | GTG | CCT | GTG | CAG | GGA | GTG | GCC | ATC | ACC | TTC | 384 |
| Pro | Ser | Pro 115 | Gly | Asp | Glu | Val | Pro 120 | Val | Gln | Gly | Val | Ala 125 | Ile | Thr | Phe | |
| GAG | CCC | AAA | GAC | TTC | CTG | CAC | ATC | AAG | GAG | AAA | TAC | AAT | AAT | GAC | TGG | 432 |
| Glu | Pro | Lys 130 | Asp | Phe | Leu | His 135 | Ile | Lys | Glu | Lys | Tyr 140 | Asn | Asn | Asp | Trp | |
| TGG | ATC | GGG | CGG | CTG | GTG | AAG | GAG | GGC | TGT | GAG | GTT | GGC | TTC | ATT | CCC | 480 |
| Trp 145 | Ile | Gly | Arg | Leu | Val 150 | Lys | Glu | Gly | Cys | Glu 155 | Val | Gly | Phe | Ile | Pro 160 | |
| AGC | CCC | GTC | AAA | CTG | GAC | AGC | CTT | CGC | CTG | CTG | CAG | GAA | CAG | AAG | CTG | 528 |
| Ser | Pro | Val | Lys 165 | Leu | Asp | Ser | Leu | Arg 170 | Leu | Leu | Gln | Glu | Gln 175 | Lys | Leu | |
| CGC | CAG | AAC | CGC | CTC | GGC | TCC | AGC | AAA | TCA | GGC | GAT | AAC | TCC | AGT | TCC | 576 |
| Arg | Gln | Asn | Arg 180 | Leu | Gly | Ser | Ser | Lys 185 | Ser | Gly | Asp | Asn | Ser 190 | Ser | Ser | |
| AGT | CTG | GGA | GAT | GTG | GTG | ACT | GGC | ACC | CGC | CGC | CCC | ACC | CCC | CTG | CCA | 624 |
| Ser | Leu | Gly 195 | Asp | Val | Val | Thr | Gly 200 | Thr | Arg | Arg | Pro | Thr 205 | Pro | Leu | Pro | |
| GTG | GCC | AAA | CAG | AAG | CAG | AAG | TCG | GGT | AAT | GAA | ATG | ACT | AAC | TTA | GCC | 672 |
| Val | Ala | Lys 210 | Gln | Lys | Gln | Lys | Ser 215 | Gly | Asn | Glu | Met | Thr 220 | Asn | Leu | Ala | |
| TTT | GAA | CTA | GAC | CCC | CTA | GAG | TTA | GAG | GAG | GAA | GAG | GCT | GAG | CTT | GGT | 720 |
| Phe | Glu | Leu | Asp 225 | Pro | Leu | Glu | Leu | Glu 230 | Glu | Glu | Glu | Ala | Glu 235 | Leu | Gly 240 | |
| GAG | CAG | AGT | GGC | TCT | GCC | AAG | ACT | AGT | GTT | AGC | AGT | GTC | ACC | ACC | CCG | 768 |
| Glu | Gln | Ser | Gly | Ser 245 | Ala | Lys | Thr | Ser | Val 250 | Ser | Ser | Val | Thr | Thr 255 | Pro | |
| CCA | CCC | CAT | GGC | AAA | CGC | ATC | CCC | TTC | TTT | AAG | AAG | ACA | GAG | CAT | GTG | 816 |
| Pro | Pro | His | Gly 260 | Lys | Arg | Ile | Pro | Phe 265 | Phe | Lys | Lys | Thr | Glu 270 | His | Val | |
| CCC | CCC | TAT | GAC | GTG | GTG | CCT | TCC | ATG | AGG | CCC | ATC | ATC | CTG | GTG | GGA | 864 |
| Pro | Pro | Tyr 275 | Asp | Val | Val | Pro | Ser 280 | Met | Arg | Pro | Ile | Ile 285 | Leu | Val | Gly | |
| CCG | TCG | CTC | AAG | GGC | TAC | GAG | GTT | ACA | GAC | ATG | ATG | CAG | AAA | GCT | TTA | 912 |
| Pro | Ser | Leu | Lys | Gly 290 | Tyr | Glu | Val | Thr | Asp 295 | Met | Met | Gln | Lys | Ala 300 | Leu | |
| TTT | GAC | TTC | TTG | AAG | CAT | CGG | TTT | GAT | GGC | AGG | ATC | TCC | ATC | ACT | CGT | 960 |
| Phe 305 | Asp | Phe | Leu | Lys | His 310 | Arg | Phe | Asp | Gly | Arg 315 | Ile | Ser | Ile | Thr | Arg 320 | |
| GTG | ACG | GCA | GAT | ATT | TCC | CTG | GCT | AAG | CGC | TCA | GTT | CTC | AAC | AAC | CCC | 1008 |
| Val | Thr | Ala | Asp | Ile 325 | Ser | Leu | Ala | Lys | Arg 330 | Ser | Val | Leu | Asn | Asn 335 | Pro | |
| AGC | AAA | CAC | ATC | ATC | ATT | GAG | CGC | TCC | AAC | ACA | CGC | TCC | AGC | CTG | GCT | 1056 |
| Ser | Lys | His | Ile | Ile 340 | Ile | Glu | Arg | Ser | Asn 345 | Thr | Arg | Ser | Ser 350 | Leu | Ala | |

```
GAG GTG CAG AGT GAA ATC GAG CGA ATC TTC GAG CTG GCC CGG ACC CTT    1104
Glu Val Gln Ser Glu Ile Glu Arg Ile Phe Glu Leu Ala Arg Thr Leu
        355                 360                 365

CAG TTG GTC GCT CTG GAT GCT GAC ACC ATC AAT CAC CCA GCC CAG CTG    1152
Gln Leu Val Ala Leu Asp Ala Asp Thr Ile Asn His Pro Ala Gln Leu
    370                 375                 380

TCC AAG ACC TCG CTG GCC CCC ATC ATT GTT TAC ATC AAG ATC ACC TCT    1200
Ser Lys Thr Ser Leu Ala Pro Ile Ile Val Tyr Ile Lys Ile Thr Ser
385                 390                 395                 400

CCC AAG GTA CTT CAA AGG CTC ATC AAG TCC CGA GGA AAG TCT CAG TCC    1248
Pro Lys Val Leu Gln Arg Leu Ile Lys Ser Arg Gly Lys Ser Gln Ser
                405                 410                 415

AAA CAC CTC AAT GTC CAA ATA GCG GCC TCG GAA AAG CTG GCA CAG TGC    1296
Lys His Leu Asn Val Gln Ile Ala Ala Ser Glu Lys Leu Ala Gln Cys
            420                 425                 430

CCC CCT GAA ATG TTT GAC ATC ATC CTG GAT GAG AAC CAA TTG GAG GAT    1344
Pro Pro Glu Met Phe Asp Ile Ile Leu Asp Glu Asn Gln Leu Glu Asp
        435                 440                 445

GCC TGC GAG CAT CTG GCG GAG TAC TTG GAA GCC TAT TGG AAG GCC ACA    1392
Ala Cys Glu His Leu Ala Glu Tyr Leu Glu Ala Tyr Trp Lys Ala Thr
    450                 455                 460

CAC CCG CCC AGC AGC ACG CCA CCC AAT CCG CTG CTG AAC CGC ACC ATG    1440
His Pro Pro Ser Ser Thr Pro Pro Asn Pro Leu Leu Asn Arg Thr Met
465                 470                 475                 480

GCT ACC GCA GCC CTG GCT GCC AGC CCT GCC CCT GTC TCC AAC CTC CAG    1488
Ala Thr Ala Ala Leu Ala Ala Ser Pro Ala Pro Val Ser Asn Leu Gln
                485                 490                 495

GTA CAG GTG CTC ACC TCG CTC AGG AGA AAC CTC GGC TTC TGG GGC GGG    1536
Val Gln Val Leu Thr Ser Leu Arg Arg Asn Leu Gly Phe Trp Gly Gly
            500                 505                 510

CTG GAG TCC TCA CAG CGG GGC AGT GTG GTG CCC CAG GAG CAG GAA CAT    1584
Leu Glu Ser Ser Gln Arg Gly Ser Val Val Pro Gln Glu Gln Glu His
        515                 520                 525

GCC ATG TAGTGGGCGC CTGCCCGTC TTCCCTCCTG CTCTGGGGTC GGAACTGGAG TGC   1643
Ala Met
530

AGGGAACATG GAGGAGGAAG GGAAGAGCTT TATTTTGTAA AAAAATAAGA TGAGCGGCA    1702
```

( 2 ) INFORMATION FOR SEQ ID NO:20:

( i ) SEQUENCE CHARACTERISTICS:
        ( A ) LENGTH: 3657 base pairs
        ( B ) TYPE: nucleic acid
        ( C ) STRANDEDNESS: double
        ( D ) TOPOLOGY: linear ( i i ) MOLECULE TYPE: Genomic DNA ( i i i ) HYPOTHETICAL: NO ( i v ) ANTI-SENSE: NO ( v ) FRAGMENT TYPE:

( v i ) ORIGINAL SOURCE:

( i x ) FEATURE:
        ( A ) NAME/KEY: Coding Sequence
        ( B ) LOCATION: 35...3364
        ( D ) OTHER INFORMATION: Standard name "alpha2"
        ( A ) NAME/KEY: 5'UTR
        ( B ) LOCATION: 1...34
        ( D ) OTHER INFORMATION:
        ( A ) NAME/KEY: 3'UTR
        ( B ) LOCATION: 3365...3657
        ( D ) OTHER INFORMATION:

( x i ) SEQUENCE DESCRIPTION: SEQ ID NO:20:

| | | | | | | | | | | | | | | | | | |
|---|---|---|---|---|---|---|---|---|---|---|---|---|---|---|---|---|---|
| GCGGGGGAGG | GGGCATTGAT | CTTCGATCGC | GAAG | ATG | GCT | GCT | GGC | TGC | CTG | CTG | | | | | | | 55 |
| | | | | Met | Ala | Ala | Gly | Cys | Leu | Leu | | | | | | | |
| | | | | 1 | | | | 5 | | | | | | | | | |
| GCC | TTG | ACT | CTG | ACA | CTT | TTC | CAA | TCT | TTG | CTC | ATC | GGC | CCC | TCG | TCG | | 103 |
| Ala | Leu | Thr | Leu | Thr | Leu | Phe | Gln | Ser | Leu | Leu | Ile | Gly | Pro | Ser | Ser | | |
| | | 10 | | | | 15 | | | | | 20 | | | | | | |
| GAG | GAG | CCG | TTC | CCT | TCG | GCC | GTC | ACT | ATC | AAA | TCA | TGG | GTG | GAT | AAG | | 151 |
| Glu | Glu | Pro | Phe | Pro | Ser | Ala | Val | Thr | Ile | Lys | Ser | Trp | Val | Asp | Lys | | |
| | 25 | | | | | 30 | | | | | 35 | | | | | | |
| ATG | CAA | GAA | GAC | CTT | GTC | ACA | CTG | GCA | AAA | ACA | GCA | AGT | GGA | GTC | AAT | | 199 |
| Met | Gln | Glu | Asp | Leu | Val | Thr | Leu | Ala | Lys | Thr | Ala | Ser | Gly | Val | Asn | | |
| 40 | | | | 45 | | | | 50 | | | | | | | 55 | | |
| CAG | CTT | GTT | GAT | ATT | TAT | GAG | AAA | TAT | CAA | GAT | TTG | TAT | ACT | GTG | GAA | | 247 |
| Gln | Leu | Val | Asp | Ile | Tyr | Glu | Lys | Tyr | Gln | Asp | Leu | Tyr | Thr | Val | Glu | | |
| | | | | 60 | | | | | 65 | | | | | 70 | | | |
| CCA | AAT | AAT | GCA | CGC | CAG | CTG | GTA | GAA | ATT | GCA | GCC | AGG | GAT | ATT | GAG | | 295 |
| Pro | Asn | Asn | Ala | Arg | Gln | Leu | Val | Glu | Ile | Ala | Ala | Arg | Asp | Ile | Glu | | |
| | | | 75 | | | | 80 | | | | | 85 | | | | | |
| AAA | CTT | CTG | AGC | AAC | AGA | TCT | AAA | GCC | CTG | GTG | AGC | CTG | GCA | TTG | GAA | | 343 |
| Lys | Leu | Leu | Ser | Asn | Arg | Ser | Lys | Ala | Leu | Val | Ser | Leu | Ala | Leu | Glu | | |
| | | 90 | | | | 95 | | | | | 100 | | | | | | |
| GCG | GAG | AAA | GTT | CAA | GCA | GCT | CAC | CAG | TGG | AGA | GAA | GAT | TTT | GCA | AGC | | 391 |
| Ala | Glu | Lys | Val | Gln | Ala | Ala | His | Gln | Trp | Arg | Glu | Asp | Phe | Ala | Ser | | |
| | 105 | | | | | 110 | | | | | 115 | | | | | | |
| AAT | GAA | GTT | GTC | TAC | TAC | AAT | GCA | AAG | GAT | GAT | CTC | GAT | CCT | GAG | AAA | | 439 |
| Asn | Glu | Val | Val | Tyr | Tyr | Asn | Ala | Lys | Asp | Asp | Leu | Asp | Pro | Glu | Lys | | |
| 120 | | | | | 125 | | | | | 130 | | | | | 135 | | |
| AAT | GAC | AGT | GAG | CCA | GGC | AGC | CAG | AGG | ATA | AAA | CCT | GTT | TTC | ATT | GAA | | 487 |
| Asn | Asp | Ser | Glu | Pro | Gly | Ser | Gln | Arg | Ile | Lys | Pro | Val | Phe | Ile | Glu | | |
| | | | | 140 | | | | 145 | | | | | 150 | | | | |
| GAT | GCT | AAT | TTT | GGA | CGA | CAA | ATA | TCT | TAT | CAG | CAC | GCA | GCA | GTC | CAT | | 535 |
| Asp | Ala | Asn | Phe | Gly | Arg | Gln | Ile | Ser | Tyr | Gln | His | Ala | Ala | Val | His | | |
| | | | 155 | | | | | 160 | | | | | 165 | | | | |
| ATT | CCT | ACT | GAC | ATC | TAT | GAG | GGC | TCA | ACA | ATT | GTG | TTA | AAT | GAA | CTC | | 583 |
| Ile | Pro | Thr | Asp | Ile | Tyr | Glu | Gly | Ser | Thr | Ile | Val | Leu | Asn | Glu | Leu | | |
| | | 170 | | | | 175 | | | | | 180 | | | | | | |
| AAC | TGG | ACA | AGT | GCC | TTA | GAT | GAA | GTT | TTC | AAA | AAG | AAT | CGC | GAG | GAA | | 631 |
| Asn | Trp | Thr | Ser | Ala | Leu | Asp | Glu | Val | Phe | Lys | Lys | Asn | Arg | Glu | Glu | | |
| | 185 | | | | | 190 | | | | | 195 | | | | | | |
| GAC | CCT | TCA | TTA | TTG | TGG | CAG | GTT | TTT | GGC | AGT | GCC | ACT | GGC | CTA | GCT | | 679 |
| Asp | Pro | Ser | Leu | Leu | Trp | Gln | Val | Phe | Gly | Ser | Ala | Thr | Gly | Leu | Ala | | |
| 200 | | | | | 205 | | | | | 210 | | | | | 215 | | |
| CGA | TAT | TAT | CCA | GCT | TCA | CCA | TGG | GTT | GAT | AAT | AGT | AGA | ACT | CCA | AAT | | 727 |
| Arg | Tyr | Tyr | Pro | Ala | Ser | Pro | Trp | Val | Asp | Asn | Ser | Arg | Thr | Pro | Asn | | |
| | | | | 220 | | | | 225 | | | | | 230 | | | | |
| AAG | ATT | GAC | CTT | TAT | GAT | GTA | CGC | AGA | AGA | CCA | TGG | TAC | ATC | CAA | GGA | | 775 |
| Lys | Ile | Asp | Leu | Tyr | Asp | Val | Arg | Arg | Arg | Pro | Trp | Tyr | Ile | Gln | Gly | | |
| | | | 235 | | | | | 240 | | | | | 245 | | | | |
| GCT | GCA | TCT | CCT | AAA | GAC | ATG | CTT | ATT | CTG | GTG | GAT | GTG | AGT | GGA | AGT | | 823 |
| Ala | Ala | Ser | Pro | Lys | Asp | Met | Leu | Ile | Leu | Val | Asp | Val | Ser | Gly | Ser | | |
| | | 250 | | | | 255 | | | | | 260 | | | | | | |
| GTT | AGT | GGA | TTG | ACA | CTT | AAA | CTG | ATC | CGA | ACA | TCT | GTC | TCC | GAA | ATG | | 871 |
| Val | Ser | Gly | Leu | Thr | Leu | Lys | Leu | Ile | Arg | Thr | Ser | Val | Ser | Glu | Met | | |
| | 265 | | | | | 270 | | | | | 275 | | | | | | |
| TTA | GAA | ACC | CTC | TCA | GAT | GAT | GAT | TTC | GTG | AAT | GTA | GCT | TCA | TTT | AAC | | 919 |
| Leu | Glu | Thr | Leu | Ser | Asp | Asp | Asp | Phe | Val | Asn | Val | Ala | Ser | Phe | Asn | | |
| 280 | | | | | 285 | | | | | 290 | | | | | 295 | | |
| AGC | AAT | GCT | CAG | GAT | GTA | AGC | TGT | TTT | CAG | CAC | CTT | GTC | CAA | GCA | AAT | | 967 |
| Ser | Asn | Ala | Gln | Asp | Val | Ser | Cys | Phe | Gln | His | Leu | Val | Gln | Ala | Asn | | |

|     |     |     |     |     |     |     |     |     |     |     |     |     |     |     |      |
| --- | --- | --- | --- | --- | --- | --- | --- | --- | --- | --- | --- | --- | --- | --- | ---- |
|     |     |     |     | 300 |     |     |     |     | 305 |     |     |     |     | 310 |      |
| GTA | AGA | AAT | AAA | AAA | GTG | TTG | AAA | GAC | GCG | GTG | AAT | AAT | ATC | ACA | GCC  | 1015 |
| Val | Arg | Asn | Lys | Lys | Val | Leu | Lys | Asp | Ala | Val | Asn | Asn | Ile | Thr | Ala  |
|     |     |     | 315 |     |     |     | 320 |     |     |     |     |     | 325 |     |      |
| AAA | GGA | ATT | ACA | GAT | TAT | AAG | AAG | GGC | TTT | AGT | TTT | GCT | TTT | GAA | CAG  | 1063 |
| Lys | Gly | Ile | Thr | Asp | Tyr | Lys | Lys | Gly | Phe | Ser | Phe | Ala | Phe | Glu | Gln  |
|     |     |     | 330 |     |     |     | 335 |     |     |     |     |     | 340 |     |      |
| CTG | CTT | AAT | TAT | AAT | GTT | TCC | AGA | GCA | AAC | TGC | AAT | AAG | ATT | ATT | ATG  | 1111 |
| Leu | Leu | Asn | Tyr | Asn | Val | Ser | Arg | Ala | Asn | Cys | Asn | Lys | Ile | Ile | Met  |
|     | 345 |     |     |     |     | 350 |     |     |     |     | 355 |     |     |     |      |
| CTA | TTC | ACG | GAT | GGA | GGA | GAA | GAG | AGA | GCC | CAG | GAG | ATA | TTT | AAC | AAA  | 1159 |
| Leu | Phe | Thr | Asp | Gly | Gly | Glu | Glu | Arg | Ala | Gln | Glu | Ile | Phe | Asn | Lys  |
| 360 |     |     |     |     | 365 |     |     |     |     | 370 |     |     |     |     | 375  |
| TAC | AAT | AAA | GAT | AAA | AAA | GTA | CGT | GTA | TTC | AGG | TTT | TCA | GTT | GGT | CAA  | 1207 |
| Tyr | Asn | Lys | Asp | Lys | Lys | Val | Arg | Val | Phe | Arg | Phe | Ser | Val | Gly | Gln  |
|     |     |     |     | 380 |     |     |     |     | 385 |     |     |     |     | 390 |      |
| CAC | AAT | TAT | GAG | AGA | GGA | CCT | ATT | CAG | TGG | ATG | GCC | TGT | GAA | AAC | AAA  | 1255 |
| His | Asn | Tyr | Glu | Arg | Gly | Pro | Ile | Gln | Trp | Met | Ala | Cys | Glu | Asn | Lys  |
|     |     |     | 395 |     |     |     | 400 |     |     |     |     |     | 405 |     |      |
| GGT | TAT | TAT | TAT | GAA | ATT | CCT | TCC | ATT | GGT | GCA | ATA | AGA | ATC | AAT | ACT  | 1303 |
| Gly | Tyr | Tyr | Tyr | Glu | Ile | Pro | Ser | Ile | Gly | Ala | Ile | Arg | Ile | Asn | Thr  |
|     |     | 410 |     |     |     |     | 415 |     |     |     |     | 420 |     |     |      |
| CAG | GAA | TAT | TTG | GAT | GTT | TTG | GGA | AGA | CCA | ATG | GTT | TTA | GCA | GGA | GAC  | 1351 |
| Gln | Glu | Tyr | Leu | Asp | Val | Leu | Gly | Arg | Pro | Met | Val | Leu | Ala | Gly | Asp  |
|     | 425 |     |     |     |     | 430 |     |     |     |     | 435 |     |     |     |      |
| AAA | GCT | AAG | CAA | GTC | CAA | TGG | ACA | AAT | GTG | TAC | CTG | GAT | GCA | TTG | GAA  | 1399 |
| Lys | Ala | Lys | Gln | Val | Gln | Trp | Thr | Asn | Val | Tyr | Leu | Asp | Ala | Leu | Glu  |
| 440 |     |     |     |     | 445 |     |     |     |     | 450 |     |     |     |     | 455  |
| CTG | GGA | CTT | GTC | ATT | ACT | GGA | ACT | CTT | CCG | GTC | TTC | AAC | ATA | ACC | GGC  | 1447 |
| Leu | Gly | Leu | Val | Ile | Thr | Gly | Thr | Leu | Pro | Val | Phe | Asn | Ile | Thr | Gly  |
|     |     |     |     | 460 |     |     |     |     | 465 |     |     |     |     | 470 |      |
| CAA | TTT | GAA | AAT | AAG | ACA | AAC | TTA | AAG | AAC | CAG | CTG | ATT | CTT | GGT | GTG  | 1495 |
| Gln | Phe | Glu | Asn | Lys | Thr | Asn | Leu | Lys | Asn | Gln | Leu | Ile | Leu | Gly | Val  |
|     |     |     | 475 |     |     |     |     | 480 |     |     |     |     | 485 |     |      |
| ATG | GGA | GTA | GAT | GTG | TCT | TTG | GAA | GAT | ATT | AAA | AGA | CTG | ACA | CCA | CGT  | 1543 |
| Met | Gly | Val | Asp | Val | Ser | Leu | Glu | Asp | Ile | Lys | Arg | Leu | Thr | Pro | Arg  |
|     |     | 490 |     |     |     |     | 495 |     |     |     |     | 500 |     |     |      |
| TTT | ACA | CTG | TGC | CCC | AAT | GGG | TAT | TAC | TTT | GCA | ATC | GAT | CCT | AAT | GGT  | 1591 |
| Phe | Thr | Leu | Cys | Pro | Asn | Gly | Tyr | Tyr | Phe | Ala | Ile | Asp | Pro | Asn | Gly  |
|     | 505 |     |     |     |     | 510 |     |     |     |     | 515 |     |     |     |      |
| TAT | GTT | TTA | TTA | CAT | CCA | AAT | CTT | CAG | CCA | AAG | CCT | ATT | GGT | GTA | GGT  | 1639 |
| Tyr | Val | Leu | Leu | His | Pro | Asn | Leu | Gln | Pro | Lys | Pro | Ile | Gly | Val | Gly  |
| 520 |     |     |     |     | 525 |     |     |     |     | 530 |     |     |     |     | 535  |
| ATA | CCA | ACA | ATT | AAT | TTA | AGA | AAA | AGG | AGA | CCC | AAT | ATC | CAG | AAC | CCC  | 1687 |
| Ile | Pro | Thr | Ile | Asn | Leu | Arg | Lys | Arg | Arg | Pro | Asn | Ile | Gln | Asn | Pro  |
|     |     |     |     | 540 |     |     |     |     | 545 |     |     |     |     | 550 |      |
| AAA | TCT | CAG | GAG | CCA | GTA | ACA | TTG | GAT | TTC | CTT | GAT | GCA | GAG | TTA | GAG  | 1735 |
| Lys | Ser | Gln | Glu | Pro | Val | Thr | Leu | Asp | Phe | Leu | Asp | Ala | Glu | Leu | Glu  |
|     |     | 555 |     |     |     |     | 560 |     |     |     |     | 565 |     |     |      |
| AAT | GAT | ATT | AAA | GTG | GAG | ATT | CGA | AAT | AAG | ATG | ATT | GAT | GGG | GAA | AGT  | 1783 |
| Asn | Asp | Ile | Lys | Val | Glu | Ile | Arg | Asn | Lys | Met | Ile | Asp | Gly | Glu | Ser  |
|     |     | 570 |     |     |     |     | 575 |     |     |     |     | 580 |     |     |      |
| GGA | GAA | AAA | ACA | TTC | AGA | ACT | CTG | GTT | AAA | TCT | CAA | GAT | GAG | AGA | TAT  | 1831 |
| Gly | Glu | Lys | Thr | Phe | Arg | Thr | Leu | Val | Lys | Ser | Gln | Asp | Glu | Arg | Tyr  |
|     | 585 |     |     |     |     | 590 |     |     |     |     | 595 |     |     |     |      |
| ATT | GAC | AAA | GGA | AAC | AGG | ACA | TAC | ACA | TGG | ACA | CCT | GTC | AAT | GGC | ACA  | 1879 |
| Ile | Asp | Lys | Gly | Asn | Arg | Thr | Tyr | Thr | Trp | Thr | Pro | Val | Asn | Gly | Thr  |
| 600 |     |     |     |     | 605 |     |     |     |     | 610 |     |     |     |     | 615  |
| GAT | TAC | AGT | TTG | GCC | TTG | GTA | TTA | CCA | ACC | TAC | AGT | TTT | TAC | TAT | ATA  | 1927 |
| Asp | Tyr | Ser | Leu | Ala | Leu | Val | Leu | Pro | Thr | Tyr | Ser | Phe | Tyr | Tyr | Ile  |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     |     |     | 620 |     |     |     | 625 |     |     |     |     |     | 630 |     |      |
| AAA | GCC | AAA | CTA | GAA | GAG | ACA | ATA | ACT | CAG | GCC | AGA | TCA | AAA | AAG | GGC | 1975 |
| Lys | Ala | Lys | Leu<br>635 | Glu | Glu | Thr | Ile | Thr<br>640 | Gln | Ala | Arg | Ser | Lys<br>645 | Lys | Gly |      |
| AAA | ATG | AAG | GAT | TCG | GAA | ACC | CTG | AAG | CCA | GAT | AAT | TTT | GAA | GAA | TCT | 2023 |
| Lys | Met | Lys<br>650 | Asp | Ser | Glu | Thr | Leu<br>655 | Lys | Pro | Asp | Asn | Phe<br>660 | Glu | Glu | Ser |      |
| GGC | TAT | ACA | TTC | ATA | GCA | CCA | AGA | GAT | TAC | TGC | AAT | GAC | CTG | AAA | ATA | 2071 |
| Gly | Tyr<br>665 | Thr | Phe | Ile | Ala | Pro<br>670 | Arg | Asp | Tyr | Cys | Asn<br>675 | Asp | Leu | Lys | Ile |      |
| TCG | GAT | AAT | AAC | ACT | GAA | TTT | CTT | TTA | AAT | TTC | AAC | GAG | TTT | ATT | GAT | 2119 |
| Ser<br>680 | Asp | Asn | Asn | Thr | Glu<br>685 | Phe | Leu | Leu | Asn | Phe<br>690 | Asn | Glu | Phe | Ile | Asp<br>695 |      |
| AGA | AAA | ACT | CCA | AAC | AAC | CCA | TCA | TGT | AAC | GCG | GAT | TTG | ATT | AAT | AGA | 2167 |
| Arg | Lys | Thr | Pro | Asn<br>700 | Asn | Pro | Ser | Cys | Asn<br>705 | Ala | Asp | Leu | Ile | Asn<br>710 | Arg |      |
| GTC | TTG | CTT | GAT | GCA | GGC | TTT | ACA | AAT | GAA | CTT | GTC | CAA | AAT | TAC | TGG | 2215 |
| Val | Leu | Leu | Asp<br>715 | Ala | Gly | Phe | Thr | Asn<br>720 | Glu | Leu | Val | Gln | Asn<br>725 | Tyr | Trp |      |
| AGT | AAG | CAG | AAA | AAT | ATC | AAG | GGA | GTG | AAA | GCA | CGA | TTT | GTT | GTG | ACT | 2263 |
| Ser | Lys | Gln | Lys<br>730 | Asn | Ile | Lys | Gly | Val<br>735 | Lys | Ala | Arg | Phe<br>740 | Val | Val | Thr |      |
| GAT | GGT | GGG | ATT | ACC | AGA | GTT | TAT | CCC | AAA | GAG | GCT | GGA | GAA | AAT | TGG | 2311 |
| Asp | Gly | Gly | Ile | Thr<br>745 | Arg | Val | Tyr | Pro<br>750 | Lys | Glu | Ala | Gly | Glu<br>755 | Asn | Trp |      |
| CAA | GAA | AAC | CCA | GAG | ACA | TAT | GAG | GAC | AGC | TTC | TAT | AAA | AGG | AGC | CTA | 2359 |
| Gln<br>760 | Glu | Asn | Pro | Glu | Thr<br>765 | Tyr | Glu | Asp | Ser | Phe<br>770 | Tyr | Lys | Arg | Ser | Leu<br>775 |      |
| GAT | AAT | GAT | AAC | TAT | GTT | TTC | ACT | GCT | CCC | TAC | TTT | AAC | AAA | AGT | GGA | 2407 |
| Asp | Asn | Asp | Asn | Tyr<br>780 | Val | Phe | Thr | Ala | Pro<br>785 | Tyr | Phe | Asn | Lys | Ser<br>790 | Gly |      |
| CCT | GGT | GCC | TAT | GAA | TCG | GGC | ATT | ATG | GTA | AGC | AAA | GCT | GTA | GAA | ATA | 2455 |
| Pro | Gly | Ala | Tyr<br>795 | Glu | Ser | Gly | Ile | Met<br>800 | Val | Ser | Lys | Ala | Val<br>805 | Glu | Ile |      |
| TAT | ATT | CAA | GGG | AAA | CTT | CTT | AAA | CCT | GCA | GTT | GTT | GGA | ATT | AAA | ATT | 2503 |
| Tyr | Ile | Gln | Gly | Lys<br>810 | Leu | Leu | Lys | Pro | Ala<br>815 | Val | Val | Gly | Ile<br>820 | Lys | Ile |      |
| GAT | GTA | AAT | TCC | TGG | ATA | GAG | AAT | TTC | ACC | AAA | ACC | TCA | ATC | AGA | GAT | 2551 |
| Asp | Val | Asn | Ser | Trp<br>825 | Ile | Glu | Asn | Phe<br>830 | Thr | Lys | Thr | Ser | Ile<br>835 | Arg | Asp |      |
| CCG | TGT | GCT | GGT | CCA | GTT | TGT | GAC | TGC | AAA | AGA | AAC | AGT | GAC | GTA | ATG | 2599 |
| Pro<br>840 | Cys | Ala | Gly | Pro | Val<br>845 | Cys | Asp | Cys | Lys | Arg<br>850 | Asn | Ser | Asp | Val | Met<br>855 |      |
| GAT | TGT | GTG | ATT | CTG | GAT | GAT | GGT | GGG | TTT | CTT | CTG | ATG | GCA | AAT | CAT | 2647 |
| Asp | Cys | Val | Ile | Leu<br>860 | Asp | Asp | Gly | Gly | Phe<br>865 | Leu | Leu | Met | Ala | Asn<br>870 | His |      |
| GAT | GAT | TAT | ACT | AAT | CAG | ATT | GGA | AGA | TTT | TTT | GGA | GAG | ATT | GAT | CCC | 2695 |
| Asp | Asp | Tyr | Thr<br>875 | Asn | Gln | Ile | Gly | Arg<br>880 | Phe | Phe | Gly | Glu | Ile<br>885 | Asp | Pro |      |
| AGC | TTG | ATG | AGA | CAC | CTG | GTT | AAT | ATA | TCA | GTT | TAT | GCT | TTT | AAC | AAA | 2743 |
| Ser | Leu | Met<br>890 | Arg | His | Leu | Val | Asn<br>895 | Ile | Ser | Val | Tyr | Ala<br>900 | Phe | Asn | Lys |      |
| TCT | TAT | GAT | TAT | CAG | TCA | GTA | TGT | GAG | CCC | GGT | GCT | GCA | CCA | AAA | CAA | 2791 |
| Ser | Tyr<br>905 | Asp | Tyr | Gln | Ser | Val<br>910 | Cys | Glu | Pro | Gly | Ala<br>915 | Ala | Pro | Lys | Gln |      |
| GGA | GCA | GGA | CAT | CGC | TCA | GCA | TAT | GTG | CCA | TCA | GTA | GCA | GAC | ATA | TTA | 2839 |
| Gly<br>920 | Ala | Gly | His | Arg | Ser<br>925 | Ala | Tyr | Val | Pro | Ser<br>930 | Val | Ala | Asp | Ile | Leu<br>935 |      |
| CAA | ATT | GGC | TGG | TGG | GCC | ACT | GCT | GCT | GCC | TGG | TCT | ATT | CTA | CAG | CAG | 2887 |
| Gln | Ile | Gly | Trp | Trp | Ala | Thr | Ala | Ala | Ala | Trp | Ser | Ile | Leu | Gln | Gln |      |

|  |  |  |  |  |  |  |  |  |  |  |  |  |  |  |  |
|---|---|---|---|---|---|---|---|---|---|---|---|---|---|---|---|
|  |  |  |  | 940 |  |  |  | 945 |  |  |  |  | 950 |  |  |
| TTT | CTC | TTG | AGT | TTG | ACC | TTT | CCA | CGA | CTC | CTT | GAG | GCA | GTT | GAG | ATG | 2935 |
| Phe | Leu | Leu | Ser | Leu | Thr | Phe | Pro | Arg | Leu | Leu | Glu | Ala | Val | Glu | Met |  |
|  |  |  | 955 |  |  |  | 960 |  |  |  |  | 965 |  |  |  |  |
| GAG | GAT | GAT | GAC | TTC | ACG | GCC | TCC | CTG | TCC | AAG | CAG | AGC | TGC | ATT | ACT | 2983 |
| Glu | Asp | Asp | Asp | Phe | Thr | Ala | Ser | Leu | Ser | Lys | Gln | Ser | Cys | Ile | Thr |  |
|  |  | 970 |  |  |  |  | 975 |  |  |  |  | 980 |  |  |  |  |
| GAA | CAA | ACC | CAG | TAT | TTC | TTC | GAT | AAC | GAC | AGT | AAA | TCA | TTC | AGT | GGT | 3031 |
| Glu | Gln | Thr | Gln | Tyr | Phe | Phe | Asp | Asn | Asp | Ser | Lys | Ser | Phe | Ser | Gly |  |
| 985 |  |  |  |  |  | 990 |  |  |  |  | 995 |  |  |  |  |  |
| GTA | TTA | GAC | TGT | GGA | AAC | TGT | TCC | AGA | ATC | TTT | CAT | GGA | GAA | AAG | CTT | 3079 |
| Val | Leu | Asp | Cys | Gly | Asn | Cys | Ser | Arg | Ile | Phe | His | Gly | Glu | Lys | Leu |  |
| 1000 |  |  |  |  | 1005 |  |  |  |  | 1010 |  |  |  |  | 1015 |  |
| ATG | AAC | ACC | AAC | TTA | ATA | TTC | ATA | ATG | GTT | GAG | AGC | AAA | GGG | ACA | TGT | 3127 |
| Met | Asn | Thr | Asn | Leu | Ile | Phe | Ile | Met | Val | Glu | Ser | Lys | Gly | Thr | Cys |  |
|  |  |  |  | 1020 |  |  |  |  | 1025 |  |  |  |  | 1030 |  |  |
| CCA | TGT | GAC | ACA | CGA | CTG | CTC | ATA | CAA | GCG | GAG | CAG | ACT | TCT | GAC | GGT | 3175 |
| Pro | Cys | Asp | Thr | Arg | Leu | Leu | Ile | Gln | Ala | Glu | Gln | Thr | Ser | Asp | Gly |  |
|  |  |  | 1035 |  |  |  |  | 1040 |  |  |  |  | 1045 |  |  |  |
| CCA | AAT | CCT | TGT | GAC | ATG | GTT | AAG | CAA | CCT | AGA | TAC | CGA | AAA | GGG | CCT | 3223 |
| Pro | Asn | Pro | Cys | Asp | Met | Val | Lys | Gln | Pro | Arg | Tyr | Arg | Lys | Gly | Pro |  |
|  |  | 1050 |  |  |  |  | 1055 |  |  |  |  | 1060 |  |  |  |  |
| GAT | GTC | TGC | TTT | GAT | AAC | AAT | GTC | TTG | GAG | GAT | TAT | ACT | GAC | TGT | GGT | 3271 |
| Asp | Val | Cys | Phe | Asp | Asn | Asn | Val | Leu | Glu | Asp | Tyr | Thr | Asp | Cys | Gly |  |
|  | 1065 |  |  |  |  | 1070 |  |  |  |  | 1075 |  |  |  |  |  |
| GGT | GTT | TCT | GGA | TTA | AAT | CCC | TCC | CTG | TGG | TAT | ATC | ATT | GGA | ATC | CAG | 3319 |
| Gly | Val | Ser | Gly | Leu | Asn | Pro | Ser | Leu | Trp | Tyr | Ile | Ile | Gly | Ile | Gln |  |
| 1080 |  |  |  |  | 1085 |  |  |  |  | 1090 |  |  |  |  | 1095 |  |
| TTT | CTA | CTA | CTT | TGG | CTG | GTA | TCT | GGC | AGC | ACA | CAC | CGG | CTG | TTA | TGACCT | 3370 |
| Phe | Leu | Leu | Leu | Trp | Leu | Val | Ser | Gly | Ser | Thr | His | Arg | Leu | Leu |  |  |
|  |  |  |  | 1100 |  |  |  |  | 1105 |  |  |  |  | 1110 |  |  |

| | | | | |
|---|---|---|---|---|
| TCTAAAAACC | AAATCTGCAT | AGTTAAACTC | CAGACCCTGC | CAAAACATGA | GCCCTGCCCT | 3430 |
| CAATTACAGT | AACGTAGGGT | CAGCTATAAA | ATCAGACAAA | CATTAGCTGG | GCCTGTTCCA | 3490 |
| TGGCATAACA | CTAAGGCGCA | GACTCCTAAG | GCACCCACTG | GCTGCATGTC | AGGGTGTCAG | 3550 |
| ATCCTTAAAC | GTGTGTGAAT | GCTGCATCAT | CTATGTGTAA | CATCAAAGCA | AAATCCTATA | 3610 |
| CGTGTCCTCT | ATTGGAAAAT | TTGGGCGTTT | GTTGTTGCAT | TGTTGGT |  | 3657 |

( 2 ) INFORMATION FOR SEQ ID NO:21:

( i ) SEQUENCE CHARACTERISTICS:
        ( A ) LENGTH: 15 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:21:

AACCCCAAAT CTCAG         15

( 2 ) INFORMATION FOR SEQ ID NO:22:

( i ) SEQUENCE CHARACTERISTICS:
        ( A ) LENGTH: 21 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:22:

| CAAAAAAGGG CAAAATGAAG G | | | | | | | | | | | | | | | 21 |
|---|---|---|---|---|---|---|---|---|---|---|---|---|---|---|---|

( 2 ) INFORMATION FOR SEQ ID NO:23:

( i ) SEQUENCE CHARACTERISTICS:
        ( A ) LENGTH: 7635 base pairs
        ( B ) TYPE: nucleic acid
        ( C ) STRANDEDNESS: double
        ( D ) TOPOLOGY: linear ( i i ) MOLECULE TYPE: Genomic DNA ( i i i ) HYPOTHETICAL: NO ( i v ) ANTI-SENSE: NO ( v ) FRAGMENT TYPE:

( v i ) ORIGINAL SOURCE:

( i x ) FEATURE:
        ( A ) NAME/KEY: Coding Sequence
        ( B ) LOCATION: 511...6996
        ( D ) OTHER INFORMATION:
        ( A ) NAME/KEY: 5'UTR
        ( B ) LOCATION: 1...510
        ( D ) OTHER INFORMATION:
        ( A ) NAME/KEY: 3'UTR
        ( B ) LOCATION: 6994...7635
        ( D ) OTHER INFORMATION:

( x i ) SEQUENCE DESCRIPTION: SEQ ID NO:23:

```
GGGCGAGCGC  CTCCGTCCCC  GGATGTGAGC  TCCGGCTGCC  CGCGGTCCCG  AGCCAGCGGC      60

GCGCGGGCGG  CGGCGGCGGG  CACCGGGCAC  CGCGGCGGGC  GGGCAGACGG  GCGGGCATGG     120

GGGGAGCGCC  GAGCGGCCCC  GGCGGCCGGG  CCGGCATCAC  CGCGGCGTCT  CTCCGCTAGA     180

GGAGGGGACA  AGCCAGTTCT  CCTTTGCAGC  AAAAAATTAC  ATGTATATAT  TATTAAGATA     240

ATATATACAT  TGGATTTTAT  TTTTTAAAA   AGTTTATTTT  GCTCCATTTT  TGAAAAGAG      300

AGAGCTTGGG  TGGCGAGCGG  TTTTTTTTA   AAATCAATTA  TCCTTATTTT  CTGTTATTTG     360

TCCCCGTCCC  TCCCCACCCC  CCTGCTGAAG  CGAGAATAAG  GGCAGGGACC  GCGGCTCCTA     420

CCTCTTGGTG  ATCCCCTTCC  CCATTCCGCC  CCCGCCCCAA  CGCCCAGCAC  AGTGCCCTGC     480

ACACAGTAGT  CGCTCAATAA  ATGTTCGTGG   ATG ATG ATG ATG ATG ATG ATG AAA      534
                                     Met Met Met Met Met Met Met Lys
                                      1                   5

AAA ATG CAG CAT CAA CGG CAG CAG CAA GCG GAC CAC GCG AAC GAG GCA            582
Lys Met Gln His Gln Arg Gln Gln Gln Ala Asp His Ala Asn Glu Ala
     10              15              20

AAC TAT GCA AGA GGC ACC AGA CTT CCT CTT TCT GGT GAA GGA CCA ACT            630
Asn Tyr Ala Arg Gly Thr Arg Leu Pro Leu Ser Gly Glu Gly Pro Thr
 25              30              35              40

TCT CAG CCG AAT AGC TCC AAG CAA ACT GTC CTG TCT TGG CAA GCT GCA            678
Ser Gln Pro Asn Ser Ser Lys Gln Thr Val Leu Ser Trp Gln Ala Ala
             45              50              55

ATC GAT GCT GCT AGA CAG GCC AAG GCT GCC CAA ACT ATG AGC ACC TCT            726
Ile Asp Ala Ala Arg Gln Ala Lys Ala Ala Gln Thr Met Ser Thr Ser
             60              65              70

GCA CCC CCA CCT GTA GGA TCT CTC TCC CAA AGA AAA CGT CAG CAA TAC            774
Ala Pro Pro Pro Val Gly Ser Leu Ser Gln Arg Lys Arg Gln Gln Tyr
         75              80              85

GCC AAG AGC AAA AAA CAG GGT AAC TCG TCC AAC AGC CGA CCT GCC CGC            822
Ala Lys Ser Lys Lys Gln Gly Asn Ser Ser Asn Ser Arg Pro Ala Arg
 90              95              100

GCC CTT TTC TGT TTA TCA CTC AAT AAC CCC ATC CGA AGA GCC TGC ATT            870
Ala Leu Phe Cys Leu Ser Leu Asn Asn Pro Ile Arg Arg Ala Cys Ile
```

-continued

| | | | | | | | | | | | | | | | |
|---|---|---|---|---|---|---|---|---|---|---|---|---|---|---|---|
| | 105 | | | | 110 | | | | 115 | | | | 120 | | |
| AGT | ATA | GTG | GAA | TGG | AAA | CCA | TTT | GAC | ATA | TTT | ATA | TTA | TTG | GCT | ATT | 918
| Ser | Ile | Val | Glu | Trp | Lys | Pro | Phe | Asp | Ile | Phe | Ile | Leu | Leu | Ala | Ile |
| | | | | 125 | | | | 130 | | | | | 135 | | |
| TTT | GCC | AAT | TGT | GTG | GCC | TTA | GCT | ATT | TAC | ATC | CCA | TTC | CCT | GAA | GAT | 966
| Phe | Ala | Asn | Cys | Val | Ala | Leu | Ala | Ile | Tyr | Ile | Pro | Phe | Pro | Glu | Asp |
| | | | 140 | | | | | 145 | | | | | 150 | | |
| GAT | TCT | AAT | TCA | ACA | AAT | CAT | AAC | TTG | GAA | AAA | GTA | GAA | TAT | GCC | TTC | 1014
| Asp | Ser | Asn | Ser | Thr | Asn | His | Asn | Leu | Glu | Lys | Val | Glu | Tyr | Ala | Phe |
| | | | 155 | | | | | 160 | | | | 165 | | | |
| CTG | ATT | ATT | TTT | ACA | GTC | GAG | ACA | TTT | TTG | AAG | ATT | ATA | GCG | TAT | GGA | 1062
| Leu | Ile | Ile | Phe | Thr | Val | Glu | Thr | Phe | Leu | Lys | Ile | Ile | Ala | Tyr | Gly |
| | | 170 | | | | | 175 | | | | 180 | | | | |
| TTA | TTG | CTA | CAT | CCT | AAT | GCT | TAT | GTT | AGG | AAT | GGA | TGG | AAT | TTA | CTG | 1110
| Leu | Leu | Leu | His | Pro | Asn | Ala | Tyr | Val | Arg | Asn | Gly | Trp | Asn | Leu | Leu |
| 185 | | | | | 190 | | | | | 195 | | | | 200 | |
| GAT | TTT | GTT | ATA | GTA | ATA | GTA | GGA | TTG | TTT | AGT | GTA | ATT | TTG | GAA | CAA | 1158
| Asp | Phe | Val | Ile | Val | Ile | Val | Gly | Leu | Phe | Ser | Val | Ile | Leu | Glu | Gln |
| | | | | | 205 | | | | 210 | | | | | 215 | |
| TTA | ACC | AAA | GAA | ACA | GAA | GGC | GGG | AAC | CAC | TCA | AGC | GGC | AAA | TCT | GGA | 1206
| Leu | Thr | Lys | Glu | Thr | Glu | Gly | Gly | Asn | His | Ser | Ser | Gly | Lys | Ser | Gly |
| | | | 220 | | | | | 225 | | | | | 230 | | |
| GGC | TTT | GAT | GTC | AAA | GCC | CTC | CGT | GCC | TTT | CGA | GTG | TTG | CGA | CCA | CTT | 1254
| Gly | Phe | Asp | Val | Lys | Ala | Leu | Arg | Ala | Phe | Arg | Val | Leu | Arg | Pro | Leu |
| | | | 235 | | | | | 240 | | | | 245 | | | |
| CGA | CTA | GTG | TCA | GGA | GTG | CCC | AGT | TTA | CAA | GTT | GTC | CTG | AAC | TCC | ATT | 1302
| Arg | Leu | Val | Ser | Gly | Val | Pro | Ser | Leu | Gln | Val | Val | Leu | Asn | Ser | Ile |
| | 250 | | | | | 255 | | | | | 260 | | | | |
| ATA | AAA | GCC | ATG | GTT | CCC | CTC | CTT | CAC | ATA | GCC | CTT | TTG | GTA | TTA | TTT | 1350
| Ile | Lys | Ala | Met | Val | Pro | Leu | Leu | His | Ile | Ala | Leu | Leu | Val | Leu | Phe |
| 265 | | | | | 270 | | | | | 275 | | | | 280 | |
| GTA | ATC | ATA | ATC | TAT | GCT | ATT | ATA | GGA | TTG | GAA | CTT | TTT | ATT | GGA | AAA | 1398
| Val | Ile | Ile | Ile | Tyr | Ala | Ile | Ile | Gly | Leu | Glu | Leu | Phe | Ile | Gly | Lys |
| | | | | 285 | | | | 290 | | | | | 295 | | |
| ATG | CAC | AAA | ACA | TGT | TTT | TTT | GCT | GAC | TCA | GAT | ATC | GTA | GCT | GAA | GAG | 1446
| Met | His | Lys | Thr | Cys | Phe | Phe | Ala | Asp | Ser | Asp | Ile | Val | Ala | Glu | Glu |
| | | | 300 | | | | 305 | | | | | 310 | | | |
| GAC | CCA | GCT | CCA | TGT | GCG | TTC | TCA | GGG | AAT | GGA | CGC | CAG | TGT | ACT | GCC | 1494
| Asp | Pro | Ala | Pro | Cys | Ala | Phe | Ser | Gly | Asn | Gly | Arg | Gln | Cys | Thr | Ala |
| | | 315 | | | | | 320 | | | | 325 | | | | |
| AAT | GGC | ACG | GAA | TGT | AGG | AGT | GGC | TGG | GTT | GGC | CCG | AAC | GGA | GGC | ATC | 1542
| Asn | Gly | Thr | Glu | Cys | Arg | Ser | Gly | Trp | Val | Gly | Pro | Asn | Gly | Gly | Ile |
| | 330 | | | | | 335 | | | | | 340 | | | | |
| ACC | AAC | TTT | GAT | AAC | TTT | GCC | TTT | GCC | ATG | CTT | ACT | GTG | TTT | CAG | TGC | 1590
| Thr | Asn | Phe | Asp | Asn | Phe | Ala | Phe | Ala | Met | Leu | Thr | Val | Phe | Gln | Cys |
| 345 | | | | | 350 | | | | | 355 | | | | 360 | |
| ATC | ACC | ATG | GAG | GGC | TGG | ACA | GAC | GTG | CTC | TAC | TGG | GTA | AAT | GAT | GCG | 1638
| Ile | Thr | Met | Glu | Gly | Trp | Thr | Asp | Val | Leu | Tyr | Trp | Val | Asn | Asp | Ala |
| | | | | 365 | | | | 370 | | | | | 375 | | |
| ATA | GGA | TGG | GAA | TGG | CCA | TGG | GTG | TAT | TTT | GTT | AGT | CTG | ATC | ATC | CTT | 1686
| Ile | Gly | Trp | Glu | Trp | Pro | Trp | Val | Tyr | Phe | Val | Ser | Leu | Ile | Ile | Leu |
| | | | 380 | | | | 385 | | | | | 390 | | | |
| GGC | TCA | TTT | TTC | GTC | CTT | AAC | CTG | GTT | CTT | GGT | GTC | CTT | AGT | GGA | GAA | 1734
| Gly | Ser | Phe | Phe | Val | Leu | Asn | Leu | Val | Leu | Gly | Val | Leu | Ser | Gly | Glu |
| | | 395 | | | | | 400 | | | | | 405 | | | |
| TTC | TCA | AAG | GAA | AGA | GAG | AAG | GCA | AAA | GCA | CGG | GGA | GAT | TTC | CAG | AAG | 1782
| Phe | Ser | Lys | Glu | Arg | Glu | Lys | Ala | Lys | Ala | Arg | Gly | Asp | Phe | Gln | Lys |
| | 410 | | | | | 415 | | | | | 420 | | | | |
| CTC | CGG | GAG | AAG | CAG | CAG | CTG | GAG | GAG | GAT | CTA | AAG | GGC | TAC | TTG | GAT | 1830
| Leu | Arg | Glu | Lys | Gln | Gln | Leu | Glu | Glu | Asp | Leu | Lys | Gly | Tyr | Leu | Asp |

|     |     |     |     |     |     |     |     |     |     |     |     |     |     |     |     |
|-----|-----|-----|-----|-----|-----|-----|-----|-----|-----|-----|-----|-----|-----|-----|-----|
| 425 |     |     |     |     | 430 |     |     |     |     | 435 |     |     |     | 440 |     |

| TGG | ATC | ACC | CAA | GCT | GAG | GAC | ATC | GAT | CCG | GAG | AAT | GAG | GAA | GAA | GGA | 1878 |
|-----|-----|-----|-----|-----|-----|-----|-----|-----|-----|-----|-----|-----|-----|-----|-----|------|
| Trp | Ile | Thr | Gln | Ala | Glu | Asp | Ile | Asp | Pro | Glu | Asn | Glu | Glu | Glu | Gly |      |
|     |     |     |     | 445 |     |     |     | 450 |     |     |     |     | 455 |     |     |      |

| GGA | GAG | GAA | GGC | AAA | CGA | AAT | ACT | AGC | ATG | CCC | ACC | AGC | GAG | ACT | GAG | 1926 |
| Gly | Glu | Glu | Gly | Lys | Arg | Asn | Thr | Ser | Met | Pro | Thr | Ser | Glu | Thr | Glu |      |
|     |     |     | 460 |     |     |     |     | 465 |     |     |     | 470 |     |     |     |      |

| TCT | GTG | AAC | ACA | GAG | AAC | GTC | AGC | GGT | GAA | GGC | GAG | AAC | CGA | GGC | TGC | 1974 |
| Ser | Val | Asn | Thr | Glu | Asn | Val | Ser | Gly | Glu | Gly | Glu | Asn | Arg | Gly | Cys |      |
|     |     | 475 |     |     |     |     | 480 |     |     |     | 485 |     |     |     |     |      |

| TGT | GGA | AGT | CTC | TGT | CAA | GCC | ATC | TCA | AAA | TCC | AAA | CTC | AGC | CGA | CGC | 2022 |
| Cys | Gly | Ser | Leu | Cys | Gln | Ala | Ile | Ser | Lys | Ser | Lys | Leu | Ser | Arg | Arg |      |
|     | 490 |     |     |     |     | 495 |     |     |     | 500 |     |     |     |     |     |      |

| TGG | CGT | CGC | TGG | AAC | CGA | TTC | AAT | CGC | AGA | AGA | TGT | AGG | GCC | GCC | GTG | 2070 |
| Trp | Arg | Arg | Trp | Asn | Arg | Phe | Asn | Arg | Arg | Arg | Cys | Arg | Ala | Ala | Val |      |
| 505 |     |     |     |     | 510 |     |     |     |     | 515 |     |     |     | 520 |     |      |

| AAG | TCT | GTC | ACG | TTT | TAC | TGG | CTG | GTT | ATC | GTC | CTG | GTG | TTT | CTG | AAC | 2118 |
| Lys | Ser | Val | Thr | Phe | Tyr | Trp | Leu | Val | Ile | Val | Leu | Val | Phe | Leu | Asn |      |
|     |     |     |     | 525 |     |     |     |     | 530 |     |     |     |     | 535 |     |      |

| ACC | TTA | ACC | ATT | TCC | TCT | GAG | CAC | TAC | AAT | CAG | CCA | GAT | TGG | TTG | ACA | 2166 |
| Thr | Leu | Thr | Ile | Ser | Ser | Glu | His | Tyr | Asn | Gln | Pro | Asp | Trp | Leu | Thr |      |
|     |     |     | 540 |     |     |     |     | 545 |     |     |     |     | 550 |     |     |      |

| CAG | ATT | CAA | GAT | ATT | GCC | AAC | AAA | GTC | CTC | TTG | GCT | CTG | TTC | ACC | TGC | 2214 |
| Gln | Ile | Gln | Asp | Ile | Ala | Asn | Lys | Val | Leu | Leu | Ala | Leu | Phe | Thr | Cys |      |
|     |     | 555 |     |     |     |     | 560 |     |     |     | 565 |     |     |     |     |      |

| GAG | ATG | CTG | GTA | AAA | ATG | TAC | AGC | TTG | GGC | CTC | CAA | GCA | TAT | TTC | GTC | 2262 |
| Glu | Met | Leu | Val | Lys | Met | Tyr | Ser | Leu | Gly | Leu | Gln | Ala | Tyr | Phe | Val |      |
|     | 570 |     |     |     |     | 575 |     |     |     | 580 |     |     |     |     |     |      |

| TCT | CTT | TTC | AAC | CGG | TTT | GAT | TGC | TTC | GTG | GTG | TGT | GGT | GGA | ATC | ACT | 2310 |
| Ser | Leu | Phe | Asn | Arg | Phe | Asp | Cys | Phe | Val | Val | Cys | Gly | Gly | Ile | Thr |      |
| 585 |     |     |     |     | 590 |     |     |     |     | 595 |     |     |     | 600 |     |      |

| GAG | ACG | ATC | TTG | GTG | GAA | CTG | GAA | ATC | ATG | TCT | CCC | CTG | GGG | ATC | TCT | 2358 |
| Glu | Thr | Ile | Leu | Val | Glu | Leu | Glu | Ile | Met | Ser | Pro | Leu | Gly | Ile | Ser |      |
|     |     |     |     | 605 |     |     |     | 610 |     |     |     |     | 615 |     |     |      |

| GTG | TTT | CGG | TGT | GTG | CGC | CTC | TTA | AGA | ATC | TTC | AAA | GTG | ACC | AGG | CAC | 2406 |
| Val | Phe | Arg | Cys | Val | Arg | Leu | Leu | Arg | Ile | Phe | Lys | Val | Thr | Arg | His |      |
|     |     |     | 620 |     |     |     |     | 625 |     |     |     |     | 630 |     |     |      |

| TGG | ACT | TCC | CTG | AGC | AAC | TTA | GTG | GCA | TCC | TTA | TTA | AAC | TCC | ATG | AAG | 2454 |
| Trp | Thr | Ser | Leu | Ser | Asn | Leu | Val | Ala | Ser | Leu | Leu | Asn | Ser | Met | Lys |      |
|     |     | 635 |     |     |     |     | 640 |     |     |     | 645 |     |     |     |     |      |

| TCC | ATC | GCT | TCG | CTG | TTG | CTT | CTG | CTT | TTT | CTC | TTC | ATT | ATC | ATC | TTT | 2502 |
| Ser | Ile | Ala | Ser | Leu | Leu | Leu | Leu | Leu | Phe | Leu | Phe | Ile | Ile | Ile | Phe |      |
|     | 650 |     |     |     |     | 655 |     |     |     | 660 |     |     |     |     |     |      |

| TCC | TTG | CTT | GGG | ATG | CAG | CTG | TTT | GGC | GGC | AAG | TTT | AAT | TTT | GAT | GAA | 2550 |
| Ser | Leu | Leu | Gly | Met | Gln | Leu | Phe | Gly | Gly | Lys | Phe | Asn | Phe | Asp | Glu |      |
| 665 |     |     |     |     | 670 |     |     |     |     | 675 |     |     |     | 680 |     |      |

| ACG | CAA | ACC | AAG | CGG | AGC | ACC | TTT | GAC | AAT | TTC | CCT | CAA | GCA | CTT | CTC | 2598 |
| Thr | Gln | Thr | Lys | Arg | Ser | Thr | Phe | Asp | Asn | Phe | Pro | Gln | Ala | Leu | Leu |      |
|     |     |     |     | 685 |     |     |     | 690 |     |     |     |     | 695 |     |     |      |

| ACA | GTG | TTC | CAG | ATC | CTG | ACA | GGC | GAA | GAC | TGG | AAT | GCT | GTG | ATG | TAC | 2646 |
| Thr | Val | Phe | Gln | Ile | Leu | Thr | Gly | Glu | Asp | Trp | Asn | Ala | Val | Met | Tyr |      |
|     |     |     |     | 700 |     |     |     |     | 705 |     |     |     |     | 710 |     |      |

| GAT | GGC | ATC | ATG | GCT | TAC | GGG | GGC | CCA | TCC | TCT | TCA | GGA | ATG | ATC | GTC | 2694 |
| Asp | Gly | Ile | Met | Ala | Tyr | Gly | Gly | Pro | Ser | Ser | Ser | Gly | Met | Ile | Val |      |
|     |     |     | 715 |     |     |     |     | 720 |     |     |     | 725 |     |     |     |      |

| TGC | ATC | TAC | TTC | ATC | ATC | CTC | TTC | ATT | TGT | GGT | AAC | TAT | ATT | CTA | CTG | 2742 |
| Cys | Ile | Tyr | Phe | Ile | Ile | Leu | Phe | Ile | Cys | Gly | Asn | Tyr | Ile | Leu | Leu |      |
|     | 730 |     |     |     |     | 735 |     |     |     | 740 |     |     |     |     |     |      |

| AAT | GTC | TTC | TTG | GCC | ATC | GCT | GTA | GAC | AAT | TTG | GCT | GAT | GCT | GAA | AGT | 2790 |
| Asn | Val | Phe | Leu | Ala | Ile | Ala | Val | Asp | Asn | Leu | Ala | Asp | Ala | Glu | Ser |      |

-continued

| | | | | |
|---|---|---|---|---|
| 745 | | 750 | 755 | 760 |
| CTG AAC ACT GCT CAG AAA GAA GAA GCG GAA GAA AAG GAG AGG AAA AAG<br>Leu Asn Thr Ala Gln Lys Glu Glu Ala Glu Glu Lys Glu Arg Lys Lys<br>765 770 775 | | | | | 2838 |
| ATT GCC AGA AAA GAG AGC CTA GAA AAT AAA AAG AAC AAC AAA CCA GAA<br>Ile Ala Arg Lys Glu Ser Leu Glu Asn Lys Lys Asn Asn Lys Pro Glu<br>780 785 790 | | | | | 2886 |
| GTC AAC CAG ATA GCC AAC AGT GAC AAC AAG GTT ACA ATT GAT GAC TAT<br>Val Asn Gln Ile Ala Asn Ser Asp Asn Lys Val Thr Ile Asp Asp Tyr<br>795 800 805 | | | | | 2934 |
| AGA GAA GAG GAT GAA GAC AAG GAC CCC TAT CCG CCT TGC GAT GTG CCA<br>Arg Glu Glu Asp Glu Asp Lys Asp Pro Tyr Pro Pro Cys Asp Val Pro<br>810 815 820 | | | | | 2982 |
| GTA GGG GAA GAG GAA GAG GAA GAG GAG GAG GAT GAA CCT GAG GTT CCT<br>Val Gly Glu Glu Glu Glu Glu Glu Glu Glu Asp Glu Pro Glu Val Pro<br>825 830 835 840 | | | | | 3030 |
| GCC GGA CCC CGT CCT CGA AGG ATC TCG GAG TTG AAC ATG AAG GAA AAA<br>Ala Gly Pro Arg Pro Arg Arg Ile Ser Glu Leu Asn Met Lys Glu Lys<br>845 850 855 | | | | | 3078 |
| ATT GCC CCC ATC CCT GAA GGG AGC GCT TTC TTC ATT CTT AGC AAG ACC<br>Ile Ala Pro Ile Pro Glu Gly Ser Ala Phe Phe Ile Leu Ser Lys Thr<br>860 865 870 | | | | | 3126 |
| AAC CCG ATC CGC GTA GGC TGC CAC AAG CTC ATC AAC CAC CAC ATC TTC<br>Asn Pro Ile Arg Val Gly Cys His Lys Leu Ile Asn His His Ile Phe<br>875 880 885 | | | | | 3174 |
| ACC AAC CTC ATC CTT GTC TTC ATC ATG CTG AGC AGT GCT GCC CTG GCC<br>Thr Asn Leu Ile Leu Val Phe Ile Met Leu Ser Ser Ala Ala Leu Ala<br>890 895 900 | | | | | 3222 |
| GCA GAG GAC CCC ATC CGC AGC CAC TCC TTC CGG AAC ACG ATA CTG GGT<br>Ala Glu Asp Pro Ile Arg Ser His Ser Phe Arg Asn Thr Ile Leu Gly<br>905 910 915 920 | | | | | 3270 |
| TAC TTT GAC TAT GCC TTC ACA GCC ATC TTT ACT GTT GAG ATC CTG TTG<br>Tyr Phe Asp Tyr Ala Phe Thr Ala Ile Phe Thr Val Glu Ile Leu Leu<br>925 930 935 | | | | | 3318 |
| AAG ATG ACA ACT TTT GGA GCT TTC CTC CAC AAA GGG GCC TTC TGC AGG<br>Lys Met Thr Thr Phe Gly Ala Phe Leu His Lys Gly Ala Phe Cys Arg<br>940 945 950 | | | | | 3366 |
| AAC TAC TTC AAT TTG CTG GAT ATG CTG GTG GTT GGG GTG TCT CTG GTG<br>Asn Tyr Phe Asn Leu Leu Asp Met Leu Val Val Gly Val Ser Leu Val<br>955 960 965 | | | | | 3414 |
| TCA TTT GGG ATT CAA TCC AGT GCC ATC TCC GTT GTG AAG ATT CTG AGG<br>Ser Phe Gly Ile Gln Ser Ser Ala Ile Ser Val Val Lys Ile Leu Arg<br>970 975 980 | | | | | 3462 |
| GTC TTA AGG GTC CTG CGT CCC CTC AGG GCC ATC AAC AGA GCA AAA GGA<br>Val Leu Arg Val Leu Arg Pro Leu Arg Ala Ile Asn Arg Ala Lys Gly<br>985 990 995 1000 | | | | | 3510 |
| CTT AAG CAC GTG GTC CAG TGC GTC TTC GTG GCC ATC CGG ACC ATC GGC<br>Leu Lys His Val Val Gln Cys Val Phe Val Ala Ile Arg Thr Ile Gly<br>1005 1010 1015 | | | | | 3558 |
| AAC ATC ATG ATC GTC ACC ACC CTC CTG CAG TTC ATG TTT GCC TGT ATC<br>Asn Ile Met Ile Val Thr Thr Leu Leu Gln Phe Met Phe Ala Cys Ile<br>1020 1025 1030 | | | | | 3606 |
| GGG GTC CAG TTG TTC AAG GGG AAG TTC TAT CGC TGT ACG GAT GAA GCC<br>Gly Val Gln Leu Phe Lys Gly Lys Phe Tyr Arg Cys Thr Asp Glu Ala<br>1035 1040 1045 | | | | | 3654 |
| AAA AGT AAC CCT GAA GAA TGC AGG GGA CTT TTC ATC CTC TAC AAG GAT<br>Lys Ser Asn Pro Glu Glu Cys Arg Gly Leu Phe Ile Leu Tyr Lys Asp<br>1050 1055 1060 | | | | | 3702 |
| GGG GAT GTT GAC AGT CCT GTG GTC CGT GAA CGG ATC TGG CAA AAC AGT<br>Gly Asp Val Asp Ser Pro Val Val Arg Glu Arg Ile Trp Gln Asn Ser | | | | | 3750 |

-continued

```
      1065                    1070                    1075                    1080

GAT  TTC  AAC  TTC  GAC  AAC  GTC  CTC  TCT  GCT  ATG  ATG  GCG  CTC  TTC  ACA         3798
Asp  Phe  Asn  Phe  Asp  Asn  Val  Leu  Ser  Ala  Met  Met  Ala  Leu  Phe  Thr
               1085                    1090                    1095

GTC  TCC  ACG  TTT  GAG  GGC  TGG  CCT  GCG  TTG  CTG  TAT  AAA  GCC  ATC  GAC         3846
Val  Ser  Thr  Phe  Glu  Gly  Trp  Pro  Ala  Leu  Leu  Tyr  Lys  Ala  Ile  Asp
               1100                    1105                    1110

TCG  AAT  GGA  GAG  AAC  ATC  GGC  CCA  ATC  TAC  AAC  CAC  CGC  GTG  GAG  ATC         3894
Ser  Asn  Gly  Glu  Asn  Ile  Gly  Pro  Ile  Tyr  Asn  His  Arg  Val  Glu  Ile
               1115                    1120                    1125

TCC  ATC  TTC  TTC  ATC  ATC  TAC  ATC  ATC  ATT  GTA  GCT  TTC  TTC  ATG  ATG         3942
Ser  Ile  Phe  Phe  Ile  Ile  Tyr  Ile  Ile  Ile  Val  Ala  Phe  Phe  Met  Met
               1130                    1135                    1140

AAC  ATC  TTT  GTG  GGC  TTT  GTC  ATC  GTT  ACA  TTT  CAG  GAA  CAA  GGA  GAA         3990
Asn  Ile  Phe  Val  Gly  Phe  Val  Ile  Val  Thr  Phe  Gln  Glu  Gln  Gly  Glu
1145                    1150                    1155                    1160

AAA  GAG  TAT  AAG  AAC  TGT  GAG  CTG  GAC  AAA  AAT  CAG  CGT  CAG  TGT  GTT         4038
Lys  Glu  Tyr  Lys  Asn  Cys  Glu  Leu  Asp  Lys  Asn  Gln  Arg  Gln  Cys  Val
               1165                    1170                    1175

GAA  TAC  GCC  TTG  AAA  GCA  CGT  CCC  TTG  CGG  AGA  TAC  ATC  CCC  AAA  AAC         4086
Glu  Tyr  Ala  Leu  Lys  Ala  Arg  Pro  Leu  Arg  Arg  Tyr  Ile  Pro  Lys  Asn
               1180                    1185                    1190

CCC  TAC  CAG  TAC  AAG  TTC  TGG  TAC  GTG  GTG  AAC  TCT  TCG  CCT  TTC  GAA         4134
Pro  Tyr  Gln  Tyr  Lys  Phe  Trp  Tyr  Val  Val  Asn  Ser  Ser  Pro  Phe  Glu
               1195                    1200                    1205

TAC  ATG  ATG  TTT  GTC  CTC  ATC  ATG  CTC  AAC  ACA  CTC  TGC  TTG  GCC  ATG         4182
Tyr  Met  Met  Phe  Val  Leu  Ile  Met  Leu  Asn  Thr  Leu  Cys  Leu  Ala  Met
               1210                    1215                    1220

CAG  CAC  TAC  GAG  CAG  TCC  AAG  ATG  TTC  AAT  GAT  GCC  ATG  GAC  ATT  CTG         4230
Gln  His  Tyr  Glu  Gln  Ser  Lys  Met  Phe  Asn  Asp  Ala  Met  Asp  Ile  Leu
1225                    1230                    1235                    1240

AAC  ATG  GTC  TTC  ACC  GGG  GTG  TTC  ACC  GTC  GAG  ATG  GTT  TTG  AAA  GTC         4278
Asn  Met  Val  Phe  Thr  Gly  Val  Phe  Thr  Val  Glu  Met  Val  Leu  Lys  Val
               1245                    1250                    1255

ATC  GCA  TTT  AAG  CCT  AAG  GGG  TAT  TTT  AGT  GAC  GCC  TGG  AAC  ACG  TTT         4326
Ile  Ala  Phe  Lys  Pro  Lys  Gly  Tyr  Phe  Ser  Asp  Ala  Trp  Asn  Thr  Phe
               1260                    1265                    1270

GAC  TCC  CTC  ATC  GTA  ATC  GGC  AGC  ATT  ATA  GAC  GTG  GCC  CTC  AGC  GAA         4374
Asp  Ser  Leu  Ile  Val  Ile  Gly  Ser  Ile  Ile  Asp  Val  Ala  Leu  Ser  Glu
               1275                    1280                    1285

GCA  GAC  CCA  ACT  GAA  AGT  GAA  AAT  GTC  CCT  GTC  CCA  ACT  GCT  ACA  CCT         4422
Ala  Asp  Pro  Thr  Glu  Ser  Glu  Asn  Val  Pro  Val  Pro  Thr  Ala  Thr  Pro
1290                    1295                    1300

GGG  AAC  TCT  GAA  GAG  AGC  AAT  AGA  ATC  TCC  ATC  ACC  TTT  TTC  CGT  CTT         4470
Gly  Asn  Ser  Glu  Glu  Ser  Asn  Arg  Ile  Ser  Ile  Thr  Phe  Phe  Arg  Leu
1305                    1310                    1315                    1320

TTC  CGA  GTG  ATG  CGA  TTG  GTG  AAG  CTT  CTC  AGC  AGG  GGG  GAA  GGC  ATC         4518
Phe  Arg  Val  Met  Arg  Leu  Val  Lys  Leu  Leu  Ser  Arg  Gly  Glu  Gly  Ile
               1325                    1330                    1335

CGG  ACA  TTG  CTG  TGG  ACT  TTT  ATT  AAG  TTC  TTT  CAG  GCG  CTC  CCG  TAT         4566
Arg  Thr  Leu  Leu  Trp  Thr  Phe  Ile  Lys  Phe  Phe  Gln  Ala  Leu  Pro  Tyr
               1340                    1345                    1350

GTG  GCC  CTC  CTC  ATA  GCC  ATG  CTG  TTC  TTC  ATC  TAT  GCG  GTC  ATT  GGC         4614
Val  Ala  Leu  Leu  Ile  Ala  Met  Leu  Phe  Phe  Ile  Tyr  Ala  Val  Ile  Gly
               1355                    1360                    1365

ATG  CAG  ATG  TTT  GGG  AAA  GTT  GCC  ATG  AGA  GAT  AAC  AAC  CAG  ATC  AAT         4662
Met  Gln  Met  Phe  Gly  Lys  Val  Ala  Met  Arg  Asp  Asn  Asn  Gln  Ile  Asn
               1370                    1375                    1380

AGG  AAC  AAT  AAC  TTC  CAG  ACG  TTT  CCC  CAG  GCG  GTG  CTG  CTG  CTC  TTC         4710
Arg  Asn  Asn  Asn  Phe  Gln  Thr  Phe  Pro  Gln  Ala  Val  Leu  Leu  Leu  Phe
```

|  |  |  |  |  |  |  |  |  |  |  |  |  |  |  |  |  |
|---|---|---|---|---|---|---|---|---|---|---|---|---|---|---|---|---|
| 1385 |  |  |  |  | 1390 |  |  |  |  | 1395 |  |  |  |  | 1400 |  |
| AGG | TGT | GCA | ACA | GGT | GAG | GCC | TGG | CAG | GAG | ATC | ATG | CTG | GCC | TGT | CTC | 4758 |
| Arg | Cys | Ala | Thr | Gly | Glu | Ala | Trp | Gln | Glu | Ile | Met | Leu | Ala | Cys | Leu |  |
|  |  |  |  | 1405 |  |  |  | 1410 |  |  |  |  | 1415 |  |  |  |
| CCA | GGG | AAG | CTC | TGT | GAC | CCT | GAG | TCA | GAT | TAC | AAC | CCC | GGG | GAG | GAG | 4806 |
| Pro | Gly | Lys | Leu | Cys | Asp | Pro | Glu | Ser | Asp | Tyr | Asn | Pro | Gly | Glu | Glu |  |
|  |  |  | 1420 |  |  |  | 1425 |  |  |  |  | 1430 |  |  |  |  |
| CAT | ACA | TGT | GGG | AGC | AAC | TTT | GCC | ATT | GTC | TAT | TTC | ATC | AGT | TTT | TAC | 4854 |
| His | Thr | Cys | Gly | Ser | Asn | Phe | Ala | Ile | Val | Tyr | Phe | Ile | Ser | Phe | Tyr |  |
|  |  | 1435 |  |  |  |  | 1440 |  |  |  | 1445 |  |  |  |  |  |
| ATG | CTC | TGT | GCA | TTT | CTG | ATC | ATC | AAT | CTG | TTT | GTG | GCT | GTC | ATC | ATG | 4902 |
| Met | Leu | Cys | Ala | Phe | Leu | Ile | Ile | Asn | Leu | Phe | Val | Ala | Val | Ile | Met |  |
|  |  | 1450 |  |  |  |  | 1455 |  |  |  | 1460 |  |  |  |  |  |
| GAT | AAT | TTC | GAC | TAT | CTG | ACC | CGG | GAC | TGG | TCT | ATT | TTG | GGG | CCT | CAC | 4950 |
| Asp | Asn | Phe | Asp | Tyr | Leu | Thr | Arg | Asp | Trp | Ser | Ile | Leu | Gly | Pro | His |  |
| 1465 |  |  |  |  | 1470 |  |  |  | 1475 |  |  |  | 1480 |  |  |  |
| CAT | TTA | GAT | GAA | TTC | AAA | AGA | ATA | TGG | TCA | GAA | TAT | GAC | CCT | GAG | GCA | 4998 |
| His | Leu | Asp | Glu | Phe | Lys | Arg | Ile | Trp | Ser | Glu | Tyr | Asp | Pro | Glu | Ala |  |
|  |  |  |  | 1485 |  |  |  | 1490 |  |  |  |  | 1495 |  |  |  |
| AAG | GGA | AGG | ATA | AAA | CAC | CTT | GAT | GTG | GTC | ACT | CTG | CTT | CGA | CGC | ATC | 5046 |
| Lys | Gly | Arg | Ile | Lys | His | Leu | Asp | Val | Val | Thr | Leu | Leu | Arg | Arg | Ile |  |
|  |  |  | 1500 |  |  |  | 1505 |  |  |  |  | 1510 |  |  |  |  |
| CAG | CCT | CCC | CTG | GGG | TTT | GGG | AAG | TTA | TGT | CCA | CAC | AGG | GTA | GCG | TGC | 5094 |
| Gln | Pro | Pro | Leu | Gly | Phe | Gly | Lys | Leu | Cys | Pro | His | Arg | Val | Ala | Cys |  |
|  |  | 1515 |  |  |  |  | 1520 |  |  |  | 1525 |  |  |  |  |  |
| AAG | AGA | TTA | GTT | GCC | ATG | AAC | ATG | CCT | CTC | AAC | AGT | GAC | GGG | ACA | GTC | 5142 |
| Lys | Arg | Leu | Val | Ala | Met | Asn | Met | Pro | Leu | Asn | Ser | Asp | Gly | Thr | Val |  |
|  | 1530 |  |  |  |  | 1535 |  |  |  |  | 1540 |  |  |  |  |  |
| ATG | TTT | AAT | GCA | ACC | CTG | TTT | GCT | TTG | GTT | CGA | ACG | GCT | CTT | AAG | ATC | 5190 |
| Met | Phe | Asn | Ala | Thr | Leu | Phe | Ala | Leu | Val | Arg | Thr | Ala | Leu | Lys | Ile |  |
| 1545 |  |  |  |  | 1550 |  |  |  | 1555 |  |  |  |  | 1560 |  |  |
| AAG | ACC | GAA | GGG | AAC | CTG | GAG | CAA | GCT | AAT | GAA | GAA | CTT | CGG | GCT | GTG | 5238 |
| Lys | Thr | Glu | Gly | Asn | Leu | Glu | Gln | Ala | Asn | Glu | Glu | Leu | Arg | Ala | Val |  |
|  |  |  |  | 1565 |  |  |  | 1570 |  |  |  |  | 1575 |  |  |  |
| ATA | AAG | AAA | ATT | TGG | AAG | AAA | ACC | AGC | ATG | AAA | TTA | CTT | GAC | CAA | GTT | 5286 |
| Ile | Lys | Lys | Ile | Trp | Lys | Lys | Thr | Ser | Met | Lys | Leu | Leu | Asp | Gln | Val |  |
|  |  |  | 1580 |  |  |  | 1585 |  |  |  |  | 1590 |  |  |  |  |
| GTC | CCT | CCA | GCT | GGT | GAT | GAT | GAG | GTA | ACC | GTG | GGG | AAG | TTC | TAT | GCC | 5334 |
| Val | Pro | Pro | Ala | Gly | Asp | Asp | Glu | Val | Thr | Val | Gly | Lys | Phe | Tyr | Ala |  |
|  |  | 1595 |  |  |  |  | 1600 |  |  |  | 1605 |  |  |  |  |  |
| ACT | TTC | CTG | ATA | CAG | GAC | TAC | TTT | AGG | AAA | TTC | AAG | AAA | CGG | AAA | GAA | 5382 |
| Thr | Phe | Leu | Ile | Gln | Asp | Tyr | Phe | Arg | Lys | Phe | Lys | Lys | Arg | Lys | Glu |  |
|  |  | 1610 |  |  |  |  | 1615 |  |  |  | 1620 |  |  |  |  |  |
| CAA | GGA | CTG | GTG | GGA | AAG | TAC | CCT | GCG | AAG | AAC | ACC | ACA | ATT | GCC | CTA | 5430 |
| Gln | Gly | Leu | Val | Gly | Lys | Tyr | Pro | Ala | Lys | Asn | Thr | Thr | Ile | Ala | Leu |  |
| 1625 |  |  |  |  | 1630 |  |  |  | 1635 |  |  |  |  | 1640 |  |  |
| CAG | GCG | GGA | TTA | AGG | ACA | CTG | CAT | GAC | ATT | GGG | CCA | GAA | ATC | CGG | CGT | 5478 |
| Gln | Ala | Gly | Leu | Arg | Thr | Leu | His | Asp | Ile | Gly | Pro | Glu | Ile | Arg | Arg |  |
|  |  |  |  | 1645 |  |  |  | 1650 |  |  |  |  | 1655 |  |  |  |
| GCT | ATA | TCG | TGT | GAT | TTG | CAA | GAT | GAC | GAG | CCT | GAG | GAA | ACA | AAA | CGA | 5526 |
| Ala | Ile | Ser | Cys | Asp | Leu | Gln | Asp | Asp | Glu | Pro | Glu | Glu | Thr | Lys | Arg |  |
|  |  |  | 1660 |  |  |  | 1665 |  |  |  |  | 1670 |  |  |  |  |
| GAA | GAA | GAA | GAT | GAT | GTG | TTC | AAA | AGA | AAT | GGT | GCC | CTG | CTT | GGA | AAC | 5574 |
| Glu | Glu | Glu | Asp | Asp | Val | Phe | Lys | Arg | Asn | Gly | Ala | Leu | Leu | Gly | Asn |  |
|  |  |  |  | 1675 |  |  |  | 1680 |  |  |  | 1685 |  |  |  |  |
| CAT | GTC | AAT | CAT | GTT | AAT | AGT | GAT | AGG | AGA | GAT | TCC | CTT | CAG | CAG | ACC | 5622 |
| His | Val | Asn | His | Val | Asn | Ser | Asp | Arg | Arg | Asp | Ser | Leu | Gln | Gln | Thr |  |
|  |  | 1690 |  |  |  |  | 1695 |  |  |  | 1700 |  |  |  |  |  |
| AAT | ACC | ACC | CAC | CGT | CCC | CTG | CAT | GTC | CAA | AGG | CCT | TCA | ATT | CCA | CCT | 5670 |
| Asn | Thr | Thr | His | Arg | Pro | Leu | His | Val | Gln | Arg | Pro | Ser | Ile | Pro | Pro |  |

```
                1705              1710              1715              1720
GCA AGT GAT ACT GAG AAA CCG CTG TTT CCT CCA GCA GGA AAT TCG GTG              5718
Ala Ser Asp Thr Glu Lys Pro Leu Phe Pro Pro Ala Gly Asn Ser Val
                    1725              1730              1735

TGT CAT AAC CAT CAT AAC CAT AAT TCC ATA GGA AAG CAA GTT CCC ACC              5766
Cys His Asn His His Asn His Asn Ser Ile Gly Lys Gln Val Pro Thr
                1740              1745              1750

TCA ACA AAT GCC AAT CTC AAT AAT GCC AAT ATG TCC AAA GCT GCC CAT              5814
Ser Thr Asn Ala Asn Leu Asn Asn Ala Asn Met Ser Lys Ala Ala His
                1755              1760              1765

GGA AAG CGG CCC AGC ATT GGG AAC CTT GAG CAT GTG TCT GAA AAT GGG              5862
Gly Lys Arg Pro Ser Ile Gly Asn Leu Glu His Val Ser Glu Asn Gly
                1770              1775              1780

CAT CAT TCT TCC CAC AAG CAT GAC CGG GAG CCT CAG AGA AGG TCC AGT              5910
His His Ser Ser His Lys His Asp Arg Glu Pro Gln Arg Arg Ser Ser
1785              1790              1795              1800

GTG AAA AGA ACC CGC TAT TAT GAA ACT TAC ATT AGG TCC GAC TCA GGA              5958
Val Lys Arg Thr Arg Tyr Tyr Glu Thr Tyr Ile Arg Ser Asp Ser Gly
                1805              1810              1815

GAT GAA CAG CTC CCA ACT ATT TGC CGG GAA GAC CCA GAG ATA CAT GGC              6006
Asp Glu Gln Leu Pro Thr Ile Cys Arg Glu Asp Pro Glu Ile His Gly
                1820              1825              1830

TAT TTC AGG GAC CCC CAC TGC TTG GGG GAG CAG GAG TAT TTC AGT AGT              6054
Tyr Phe Arg Asp Pro His Cys Leu Gly Glu Gln Glu Tyr Phe Ser Ser
                1835              1840              1845

GAG GAA TGC TAC GAG GAT GAC AGC TCG CCC ACC TGG AGC AGG CAA AAC              6102
Glu Glu Cys Tyr Glu Asp Asp Ser Ser Pro Thr Trp Ser Arg Gln Asn
1850              1855              1860

TAT GGC TAC TAC AGC AGA TAC CCA GGC AGA AAC ATC GAC TCT GAG AGG              6150
Tyr Gly Tyr Tyr Ser Arg Tyr Pro Gly Arg Asn Ile Asp Ser Glu Arg
1865              1870              1875              1880

CCC CGA GGC TAC CAT CAT CCC CAA GGA TTC TTG GAG GAC GAT GAC TCG              6198
Pro Arg Gly Tyr His His Pro Gln Gly Phe Leu Glu Asp Asp Asp Ser
                1885              1890              1895

CCC GTT TGC TAT GAT TCA CGG AGA TCT CCA AGG AGA CGC CTA CTA CCT              6246
Pro Val Cys Tyr Asp Ser Arg Arg Ser Pro Arg Arg Arg Leu Leu Pro
                1900              1905              1910

CCC ACC CCA GCA TCC CAC CGG AGA TCC TCC TTC AAC TTT GAG TGC CTG              6294
Pro Thr Pro Ala Ser His Arg Arg Ser Ser Phe Asn Phe Glu Cys Leu
                1915              1920              1925

CGC CGG CAG AGC AGC CAG GAA GAG GTC CCG TCG TCT CCC ATC TTC CCC              6342
Arg Arg Gln Ser Ser Gln Glu Glu Val Pro Ser Ser Pro Ile Phe Pro
                1930              1935              1940

CAT CGC ACG GCC CTG CCT CTG CAT CTA ATG CAG CAA CAG ATC ATG GCA              6390
His Arg Thr Ala Leu Pro Leu His Leu Met Gln Gln Gln Ile Met Ala
1945              1950              1955              1960

GTT GCC GGC CTA GAT TCA AGT AAA GCC CAG AAG TAC TCA CCG AGT CAC              6438
Val Ala Gly Leu Asp Ser Ser Lys Ala Gln Lys Tyr Ser Pro Ser His
                1965              1970              1975

TCG ACC CGG TCG TGG GCC ACC CCT CCA GCA ACC CCT CCC TAC CGG GAC              6486
Ser Thr Arg Ser Trp Ala Thr Pro Pro Ala Thr Pro Pro Tyr Arg Asp
                1980              1985              1990

TGG ACA CCG TGC TAC ACC CCC CTG ATC CAA GTG GAG CAG TCA GAG GCC              6534
Trp Thr Pro Cys Tyr Thr Pro Leu Ile Gln Val Glu Gln Ser Glu Ala
                1995              2000              2005

CTG GAC CAG GTG AAC GGC AGC CTG CCG TCC CTG CAC CGC AGC TCC TGG              6582
Leu Asp Gln Val Asn Gly Ser Leu Pro Ser Leu His Arg Ser Ser Trp
                2010              2015              2020

TAC ACA GAC GAG CCC GAC ATC TCC TAC CGG ACT TTC ACA CCA GCC AGC              6630
Tyr Thr Asp Glu Pro Asp Ile Ser Tyr Arg Thr Phe Thr Pro Ala Ser
```

```
                2025                2030                2035                2040
       CTG ACT GTC CCC AGC AGC TTC CGG AAC AAA AAC AGC GAC AAG CAG AGG          6678
       Leu Thr Val Pro Ser Ser Phe Arg Asn Lys Asn Ser Asp Lys Gln Arg
                        2045            2050                2055

AGT GCG GAC AGC TTG GTG GAG GCA GTC CTG ATA TCC GAA GGC TTG GGA          6726
       Ser Ala Asp Ser Leu Val Glu Ala Val Leu Ile Ser Glu Gly Leu Gly
                        2060            2065                2070

CGC TAT GCA AGG GAC CCA AAA TTT GTG TCA GCA ACA AAA CAC GAA ATC          6774
       Arg Tyr Ala Arg Asp Pro Lys Phe Val Ser Ala Thr Lys His Glu Ile
                        2075            2080            2085

GCT GAT GCC TGT GAC CTC ACC ATC GAC GAG ATG GAG AGT GCA GCC AGC          6822
       Ala Asp Ala Cys Asp Leu Thr Ile Asp Glu Met Glu Ser Ala Ala Ser
                        2090            2095            2100

ACC CTG CTT AAT GGG AAC GTG CGT CCC CGA GCC AAC GGG GAT GTG GGC          6870
       Thr Leu Leu Asn Gly Asn Val Arg Pro Arg Ala Asn Gly Asp Val Gly
       2105                2110            2115                2120

CCC CTC TCA CAC CGG CAG GAC TAT GAG CTA CAG GAC TTT GGT CCT GGC          6918
       Pro Leu Ser His Arg Gln Asp Tyr Glu Leu Gln Asp Phe Gly Pro Gly
                        2125            2130                2135

TAC AGC GAC GAA GAG CCA GAC CCT GGG AGG GAT GAG GAG GAC CTG GCG          6966
       Tyr Ser Asp Glu Glu Pro Asp Pro Gly Arg Asp Glu Glu Asp Leu Ala
                        2140            2145                2150

GAT GAA ATG ATA TGC ATC ACC ACC TTG TAG CCCCCAGCGA GGGGCAGACT GGCT       7020
       Asp Glu Met Ile Cys Ile Thr Thr Leu *
                        2155            2160

CTGGCCTCAG GTGGGGCGCA GGAGAGCCAG GGGAAAAGTG CCTCATAGTT AGGAAAGTTT        7080
       AGGCACTAGT TGGGAGTAAT ATTCAATTAA TTAGACTTTT GTATAAGAGA TGTCATGCCT        7140
       CAAGAAAGCC ATAAACCTGG TAGGAACAGG TCCCAAGCGG TTGAGCCTGG CAGAGTACCA        7200
       TGCGCTCGGC CCCAGCTGCA GGAAACAGCA GGCCCCGCCC TCTCACAGAG GATGGGTGAG        7260
       GAGGCCAGAC CTGCCCTGCC CCATTGTCCA GATGGGCACT GCTGTGGAGT CTGCTTCTCC        7320
       CATGTACCAG GGCACCAGGC CCACCCAACT GAAGGCATGG CGGCGGGGTG CAGGGGAAAG        7380
       TTAAAGGTGA TGACGATCAT CACACCTGTG TCGTTACCTC AGCCATCGGT CTAGCATATC        7440
       AGTCACTGGG CCCAACATAT CCATTTTTAA ACCCTTCCC CCAAATACAC TGCGTCCTGG         7500
       TTCCTGTTTA GCTGTTCTGA AATACGGTGT GTAAGTAAGT CAGAACCCAG CTACCAGTGA        7560
       TTATTGCGAG GGCAATGGGA CCTCATAAAT AAGGTTTCT GTGATGTGAC GCCAGTTTAC         7620
       ATAAGAGAAT ATCAC                                                        7635
```

( 2 ) INFORMATION FOR SEQ ID NO:24:

( i ) SEQUENCE CHARACTERISTICS:
        ( A ) LENGTH: 962 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 1..962

( i x ) FEATURE:
        ( D ) OTHER INFORMATION: /note="IMR32 1.157"

( x i ) SEQUENCE DESCRIPTION: SEQ ID NO:24:

```
       CGCTGAGGGC CTTCCGCGTG CTGCGCCCCC TGCGGCTGGT GTCCGGAGTC CCAAGTCTCC          60
       AGGTGGTCCT GAATTCCATC ATCAAGGCCA TGGTCAATGA GAATACGAGG ATGTACATTC         120
```

-continued

| | | | | | |
|---|---|---|---|---|---|
| CAGAGGAAAA | CCACCAAGGT | TCCAACTATG | GGAGCCCACG | CCCCGCCCAT | GCCAACATGA | 180
| ATGCCAATGC | GGCAGCGGGG | CTGGCCCCTG | AGCACATCCC | CACCCCGGGG | GCTGCCCTGT | 240
| CGTGGCAGGC | GGCCATCGAC | GCAGCCCGGC | AGGCTAAGCT | GATGGGCAGC | GCTGGCAATG | 300
| CGACCATCTC | CACAGTCAGC | TCCACGCAGC | GGAAGCGCCA | GCAATATGGG | AAACCCAAGA | 360
| AGCAGGGCAG | CACCACGGCC | ACACGCCCGC | CCCGAGCCCT | GCTCTGCCTG | ACCCTGAAGA | 420
| ACCCCATCCG | GAGGGCCTGC | ATCAGCATTG | TCGAATGGAA | ACCATTTGAA | ATAATTATTT | 480
| TACTGACTAT | TTTTGCCAAT | TGTGTGGCCT | TAGCGATCTA | TATTCCCTTT | CCAGAAGATG | 540
| ATTCCAACGC | CACCAATTCC | AACCTGGAAC | GAGTGGAATA | TCTCTTTCTC | ATAATTTTA | 600
| CGGTGGAAGC | GTTTTAAAA | GTAATCGCCT | ATGGACTCCT | CTTTCACCCC | AATGCCTACC | 660
| TCCGCAACGG | CTGGAACCTA | CTAGATTTTA | TAATTGTGGT | TGTGGGGCTT | TTTAGTGCAA | 720
| TTTTAGAACA | AGCAACCAAA | GCAGATGGGG | CAAACGCTCT | CGGAGGGAAA | GGGGCCGGAT | 780
| TTGATGTGAA | GGCGCTGAGG | GCCTTCCGCG | TGCTGCGCCC | CCTGCGGCTG | GTGTCCGGAG | 840
| TCCCAAGTCT | CCAGGTGGTC | CTGAATTCCA | TCATCAAGGC | CATGGTCCCC | CTGCTGCACA | 900
| TCGCCCTGCT | TGTGCTGTTT | GTCATCATCA | TCTACGCCAT | CATCGGCTTG | GAGCTCTTCA | 960
| TG | | | | | | 962

(2) INFORMATION FOR SEQ ID NO:25:

(i) SEQUENCE CHARACTERISTICS:
  (A) LENGTH: 100 base pairs
  (B) TYPE: nucleic acid
  (C) STRANDEDNESS: double
  (D) TOPOLOGY: linear (ii) MOLECULE TYPE: DNA (genomic)

(ix) FEATURE:
  (A) NAME/KEY: CDS
  (B) LOCATION: 1..100

(ix) FEATURE:
  (D) OTHER INFORMATION: /note="fragment of IMR32 1.66"

(xi) SEQUENCE DESCRIPTION: SEQ ID NO:25:

| | | | | | |
|---|---|---|---|---|---|
| GGCTGCTCCT | CCTATTAAAA | CCATTTTTGG | TCCATGGTCA | ATGAGAATAC | GAGGATGTAC | 60
| ATTCCAGAGG | AAAACCACCA | AGGTTCCAAC | TATGGGAGCC | | | 100

(2) INFORMATION FOR SEQ ID NO:26:

(i) SEQUENCE CHARACTERISTICS:
  (A) LENGTH: 100 base pairs
  (B) TYPE: nucleic acid
  (C) STRANDEDNESS: double
  (D) TOPOLOGY: linear (ii) MOLECULE TYPE: DNA (genomic)

(ix) FEATURE:
  (A) NAME/KEY: CDS
  (B) LOCATION: 1..100

(ix) FEATURE:
  (D) OTHER INFORMATION: /note="CACB-receptor"

(xi) SEQUENCE DESCRIPTION: SEQ ID NO:26:

| | | | | | |
|---|---|---|---|---|---|
| GCTGCTTCTC | CTTTTGACAC | AATTTTTTGG | TCCATGGTCA | ATGAGAATAC | GAGGATGTAC | 60
| ATTCCTGAGG | AAAACCACCA | AGGTTCCAAC | TATGGGAGCC | | | 100

(2) INFORMATION FOR SEQ ID NO:27:

( i ) SEQUENCE CHARACTERISTICS:
   ( A ) LENGTH: 44 base pairs
   ( B ) TYPE: nucleic acid
   ( C ) STRANDEDNESS: double
   ( D ) TOPOLOGY: linear ( i i ) MOLECULE TYPE: DNA (genomic)

( i x ) FEATURE:
   ( D ) OTHER INFORMATION: /note="polylinker sense"

( x i ) SEQUENCE DESCRIPTION: SEQ ID NO:27:

GGCCGCGAAT TCGTCGACCT GCAGGATATC AAGCTTAGAT CTGT      44

( 2 ) INFORMATION FOR SEQ ID NO:28:

( i ) SEQUENCE CHARACTERISTICS:
      ( A ) LENGTH: 44 base pairs
      ( B ) TYPE: nucleic acid
      ( C ) STRANDEDNESS: double
      ( D ) TOPOLOGY: linear ( i i ) MOLECULE TYPE: DNA (genomic)

( i x ) FEATURE:
      ( D ) OTHER INFORMATION: /note="polylinker antisense"

( x i ) SEQUENCE DESCRIPTION: SEQ ID NO:28:

CGCTTAAGCA GCTGGACGTC CTATAGTTCG AATCTAGACA CCGG      44

( 2 ) INFORMATION FOR SEQ ID NO:29:

( i ) SEQUENCE CHARACTERISTICS:
      ( A ) LENGTH: 1789 base pairs
      ( B ) TYPE: nucleic acid
      ( C ) STRANDEDNESS: double
      ( D ) TOPOLOGY: linear ( i i ) MOLECULE TYPE: Genomic DNA ( i i i ) HYPOTHETICAL: NO ( i v ) ANTI-SENSE: NO ( v ) FRAGMENT TYPE:

( v i ) ORIGINAL SOURCE:

( i x ) FEATURE:
      ( A ) NAME/KEY: Coding Sequence
      ( B ) LOCATION: 2...1789
      ( D ) OTHER INFORMATION: Note "CNS 1.30"

( x i ) SEQUENCE DESCRIPTION: SEQ ID NO:29:

```
G  AAT  TCG  GTG  ATG  TAT  GAT  GGG  ATC  ATG  GCT  TAT  GGG  GGC  CCC  TCT  TTT      49
   Asn  Ser  Val  Met  Tyr  Asp  Gly  Ile  Met  Ala  Tyr  Gly  Gly  Pro  Ser  Phe
   1              5                        10                       15

CCA  GGG  ATG  TTA  GTC  TGT  ATT  TAC  TTC  ATC  ATC  CTC  TTC  ATC  TCT  GGA      97
Pro  Gly  Met  Leu  Val  Cys  Ile  Tyr  Phe  Ile  Ile  Leu  Phe  Ile  Ser  Gly
              20                       25                       30

AAC  TAT  ATC  CTA  CTG  AAT  GTG  TTC  TTG  GCC  ATT  GCT  GTG  GAC  AAC  CTG     145
Asn  Tyr  Ile  Leu  Leu  Asn  Val  Phe  Leu  Ala  Ile  Ala  Val  Asp  Asn  Leu
         35                       40                       45

GCT  GAT  GCT  GAG  AGC  CTC  ACA  TCT  GCC  CTA  AAG  GAG  GAG  GAA  GAG  GAG     193
Ala  Asp  Ala  Glu  Ser  Leu  Thr  Ser  Ala  Leu  Lys  Glu  Glu  Glu  Glu  Glu
     50                       55                       60

AAG  GAG  AGA  AAG  AAG  CTG  GCC  AGG  ACT  GCC  AGC  CCA  GAG  AAG  AAA  CAA     241
Lys  Glu  Arg  Lys  Lys  Leu  Ala  Arg  Thr  Ala  Ser  Pro  Glu  Lys  Lys  Gln
65                       70                       75                       80
```

| | | | | | | | | | | | | | | | | |
|---|---|---|---|---|---|---|---|---|---|---|---|---|---|---|---|---|
| GAG | TTG | GTG | GAG | AAG | CCG | GCA | GTG | GGG | GAA | TCC | AAG | GAG | GAG | AAG | ATT | 289 |
| Glu | Leu | Val | Glu | Lys<br>85 | Pro | Ala | Val | Gly<br>90 | Glu | Ser | Lys | Glu | Glu<br>95 | Lys | Ile | |
| GAG | CTG | AAA | TCC | ATC | ACG | GCT | GAC | GGA | GAG | TCT | CCA | CCC | GCC | ACC | AAG | 337 |
| Glu | Leu | Lys | Ser<br>100 | Ile | Thr | Ala | Asp | Gly<br>105 | Glu | Ser | Pro | Pro<br>110 | Ala | Thr | Lys | |
| ATC | AAC | ATG | GAT | GAC | CTC | CAG | CCC | AAT | GAA | AAT | GAG | GAT | AAG | AGC | CCC | 385 |
| Ile | Asn | Met<br>115 | Asp | Asp | Leu | Gln | Pro<br>120 | Asn | Glu | Asn | Glu | Asp<br>125 | Lys | Ser | Pro | |
| TAC | CCC | AAC | CCA | GAA | ACT | ACA | GGA | GAA | GAG | GAT | GAG | GAG | GAG | CCA | GAG | 433 |
| Tyr | Pro<br>130 | Asn | Pro | Glu | Thr | Thr<br>135 | Gly | Glu | Glu | Asp | Glu<br>140 | Glu | Glu | Pro | Glu | |
| ATG | CCT | GTC | GGC | CCT | CGC | CCA | CGA | CCA | CTC | TCT | GAG | CTT | CAC | CTT | AAG | 481 |
| Met | Pro | Val | Gly | Pro<br>150 | Arg | Pro | Arg | Pro | Leu<br>155 | Ser | Glu | Leu | His | Leu<br>160 | Lys | |
| Met<br>145 | | | | | | | | | | | | | | | | |
| GAA | AAG | GCA | GTG | CCC | ATG | CCA | GAA | GCC | AGC | GCG | TTT | TTC | ATC | TTC | AGC | 529 |
| Glu | Lys | Ala | Val | Pro<br>165 | Met | Pro | Glu | Ala | Ser<br>170 | Ala | Phe | Phe | Ile | Phe<br>175 | Ser | |
| TCT | AAC | AAC | AGG | TTT | CGC | CTC | CAG | TGC | CAC | CGC | ATT | GTC | AAT | GAC | ACG | 577 |
| Ser | Asn | Asn | Arg<br>180 | Phe | Arg | Leu | Gln | Cys<br>185 | His | Arg | Ile | Val | Asn<br>190 | Asp | Thr | |
| ATC | TTC | ACC | AAC | CTG | ATC | CTC | TTC | TTC | ATT | CTG | CTC | AGC | AGC | ATT | TCC | 625 |
| Ile | Phe | Thr | Asn<br>195 | Leu | Ile | Leu | Phe | Phe<br>200 | Ile | Leu | Leu | Ser | Ser<br>205 | Ile | Ser | |
| CTG | GCT | GCT | GAG | GAC | CCG | GTC | CAG | CAC | ACC | TCC | TTC | AGG | AAC | CAT | ATT | 673 |
| Leu | Ala | Ala<br>210 | Glu | Asp | Pro | Val | Gln<br>215 | His | Thr | Ser | Phe | Arg<br>220 | Asn | His | Ile | |
| CTG | TTT | TAT | TTT | GAT | ATT | GTT | TTT | ACC | ACC | ATT | TTC | ACC | ATT | GAA | ATT | 721 |
| Leu | Phe | Tyr | Phe | Asp<br>230 | Ile | Val | Phe | Thr | Thr<br>235 | Ile | Phe | Thr | Ile | Glu<br>240 | Ile | |
| Leu<br>225 | | | | | | | | | | | | | | | | |
| GCT | CTG | AAG | ATG | ACT | GCT | TAT | GGG | GCT | TTC | TTG | CAC | AAG | GGT | TCT | TTC | 769 |
| Ala | Leu | Lys | Met | Thr<br>245 | Ala | Tyr | Gly | Ala | Phe<br>250 | Leu | His | Lys | Gly | Ser<br>255 | Phe | |
| TGC | CGG | AAC | TAC | TTC | AAC | ATC | CTG | GAC | CTG | CTG | GTG | GTC | AGC | GTG | TCC | 817 |
| Cys | Arg | Asn | Tyr<br>260 | Phe | Asn | Ile | Leu | Asp<br>265 | Leu | Leu | Val | Val | Ser<br>270 | Val | Ser | |
| CTC | ATC | TCC | TTT | GGC | ATC | CAG | TCC | AGT | GCA | ATC | AAT | GTC | GTG | AAG | ATC | 865 |
| Leu | Ile | Ser<br>275 | Phe | Gly | Ile | Gln | Ser<br>280 | Ser | Ala | Ile | Asn | Val<br>285 | Val | Lys | Ile | |
| TTG | CGA | GTC | CTG | CGA | GTA | CTC | AGG | CCC | CTG | AGG | GCC | ATC | AAC | AGG | GCC | 913 |
| Leu | Arg<br>290 | Val | Leu | Arg | Val | Leu<br>295 | Arg | Pro | Leu | Arg | Ala<br>300 | Ile | Asn | Arg | Ala | |
| AAG | GGG | CTA | AAG | CAT | GTG | GTT | CAG | TGT | GTG | TTT | GTC | GCC | ATC | CGG | ACC | 961 |
| Lys<br>305 | Gly | Leu | Lys | His | Val<br>310 | Val | Gln | Cys | Val | Phe<br>315 | Val | Ala | Ile | Arg | Thr<br>320 | |
| ATC | GGG | AAC | ATC | GTG | ATT | GTC | ACC | ACC | CTG | CTG | CAG | TTC | ATG | TTT | GCC | 1009 |
| Ile | Gly | Asn | Ile | Val<br>325 | Ile | Val | Thr | Thr | Leu<br>330 | Leu | Gln | Phe | Met | Phe<br>335 | Ala | |
| TGC | ATC | GGG | GTC | CAG | CTC | TTC | AAG | GGA | AAG | CTG | TAC | ACC | TGT | TCA | GAC | 1057 |
| Cys | Ile | Gly | Val | Gln<br>340 | Leu | Phe | Lys | Gly | Lys<br>345 | Leu | Tyr | Thr | Cys | Ser<br>350 | Asp | |
| AGT | TCC | AAG | CAG | ACA | GAG | GCG | GAA | TGC | AAG | GGC | AAC | TAC | ATC | ACG | TAC | 1105 |
| Ser | Ser | Lys | Gln | Thr<br>355 | Glu | Ala | Glu | Cys | Lys<br>360 | Gly | Asn | Tyr | Ile | Thr<br>365 | Tyr | |
| AAA | GAC | GGG | GAG | GTT | GAC | CAC | CCC | ATC | ATC | CAA | CCC | CGC | AGC | TGG | GAG | 1153 |
| Lys | Asp | Gly<br>370 | Glu | Val | Asp | His | Pro<br>375 | Ile | Ile | Gln | Pro | Arg<br>380 | Ser | Trp | Glu | |
| AAC | AGC | AAG | TTT | GAC | TTT | GAC | AAT | GTT | CTG | GCA | GCC | ATG | ATG | GCC | CTC | 1201 |
| Asn<br>385 | Ser | Lys | Phe | Asp | Phe<br>390 | Asp | Asn | Val | Leu | Ala<br>395 | Ala | Met | Met | Ala | Leu<br>400 | |

| | | | | | | | | | | | | | | | |
|---|---|---|---|---|---|---|---|---|---|---|---|---|---|---|---|
|TTC|ACC|GTC|TCC|ACC|TTC|GAA|GGG|TGG|CCA|GAG|CTG|CTG|TAC|CGC|TCC|
|Phe|Thr|Val|Ser|Thr|Phe|Glu|Gly|Trp|Pro|Glu|Leu|Leu|Tyr|Arg|Ser|
| | | |405| | | | |410| | | |415| | | |

1249

|ATC|GAC|TCC|CAC|ACG|GAA|GAC|AAG|GGC|CCC|ATC|TAC|AAC|TAC|CGT|GTG|
|---|---|---|---|---|---|---|---|---|---|---|---|---|---|---|---|
|Ile|Asp|Ser|His|Thr|Glu|Asp|Lys|Gly|Pro|Ile|Tyr|Asn|Tyr|Arg|Val|
| | | |420| | | |425| | | |430| | | | |

1297

|GAG|ATC|TCC|ATC|TTC|TTC|ATC|ATC|TAC|ATC|ATC|ATC|ATC|GCC|TTC|TTC|
|---|---|---|---|---|---|---|---|---|---|---|---|---|---|---|---|
|Glu|Ile|Ser|Ile|Phe|Phe|Ile|Ile|Tyr|Ile|Ile|Ile|Ile|Ala|Phe|Phe|
| | |435| | | |440| | | | |445| | | | |

1345

|ATG|ATG|AAC|ATC|TTC|GTG|GGC|TTC|GTC|ATC|GTC|ACC|TTT|CAG|GAG|CAG|
|---|---|---|---|---|---|---|---|---|---|---|---|---|---|---|---|
|Met|Met|Asn|Ile|Phe|Val|Gly|Phe|Val|Ile|Val|Thr|Phe|Gln|Glu|Gln|
| |450| | | |455| | | |460| | | | | | |

1393

|GGG|GAG|CAG|GAG|TAC|AAG|AAC|TGT|GAG|CTG|GAC|AAG|AAC|CAG|CGA|CAG|
|---|---|---|---|---|---|---|---|---|---|---|---|---|---|---|---|
|Gly|Glu|Gln|Glu|Tyr|Lys|Asn|Cys|Glu|Leu|Asp|Lys|Asn|Gln|Arg|Gln|
|465| | | | |470| | | |475| | | | | |480|

1441

|TGC|GTG|GAA|TAC|GCC|CTC|AAG|GCC|CGG|CCC|CTG|CGG|AGG|TAC|ATC|CCC|
|---|---|---|---|---|---|---|---|---|---|---|---|---|---|---|---|
|Cys|Val|Glu|Tyr|Ala|Leu|Lys|Ala|Arg|Pro|Leu|Arg|Arg|Tyr|Ile|Pro|
| | | |485| | | |490| | | |495| | | | |

1489

|AAG|AAC|CAG|CAC|CAG|TAC|AAA|GTG|TGG|TAC|GTG|GTC|AAC|TCC|ACC|TAC|
|---|---|---|---|---|---|---|---|---|---|---|---|---|---|---|---|
|Lys|Asn|Gln|His|Gln|Tyr|Lys|Val|Trp|Tyr|Val|Val|Asn|Ser|Thr|Tyr|
| | | |500| | | |505| | | |510| | | | |

1537

|TTC|GAG|TAC|CTG|ATG|TTC|GTC|CTC|ATC|CTG|CTC|AAC|ACC|ATC|TGC|CTG|
|---|---|---|---|---|---|---|---|---|---|---|---|---|---|---|---|
|Phe|Glu|Tyr|Leu|Met|Phe|Val|Leu|Ile|Leu|Leu|Asn|Thr|Ile|Cys|Leu|
| | |515| | | |520| | | |525| | | | | |

1585

|GCC|ATG|CAG|CAC|TAC|GGC|CAG|AGC|TGC|CTG|TTC|AAA|ATC|GCC|ATG|AAC|
|---|---|---|---|---|---|---|---|---|---|---|---|---|---|---|---|
|Ala|Met|Gln|His|Tyr|Gly|Gln|Ser|Cys|Leu|Phe|Lys|Ile|Ala|Met|Asn|
| |530| | | |535| | | |540| | | | | | |

1633

|ATC|CTC|AAC|ATG|CTC|TTC|ACT|GGC|CTC|TTC|ACC|GTG|GAG|ATG|ATC|CTG|
|---|---|---|---|---|---|---|---|---|---|---|---|---|---|---|---|
|Ile|Leu|Asn|Met|Leu|Phe|Thr|Gly|Leu|Phe|Thr|Val|Glu|Met|Ile|Leu|
|545| | | |550| | | |555| | | | | | |560|

1681

|AAG|CTC|ATT|GCC|TTC|AAA|CCC|AAG|CAC|TAT|TTC|TGT|GAT|GCA|TGG|AAT|
|---|---|---|---|---|---|---|---|---|---|---|---|---|---|---|---|
|Lys|Leu|Ile|Ala|Phe|Lys|Pro|Lys|His|Tyr|Phe|Cys|Asp|Ala|Trp|Asn|
| | | |565| | | |570| | | |575| | | | |

1729

|ACA|TTT|GAC|GCC|TTG|ATT|GTT|GTG|GGT|AGC|ATT|GTT|GAT|ATA|GCA|ATC|
|---|---|---|---|---|---|---|---|---|---|---|---|---|---|---|---|
|Thr|Phe|Asp|Ala|Leu|Ile|Val|Val|Gly|Ser|Ile|Val|Asp|Ile|Ala|Ile|
| | |580| | | |585| | | |590| | | | | |

1777

|ACC|GAG|GTA|AAC|
|---|---|---|---|
|Thr|Glu|Val|Asn|
| | |595| |

1789

( 2 ) INFORMATION FOR SEQ ID NO:30:

( i ) SEQUENCE CHARACTERISTICS:
        ( A ) LENGTH: 1048 base pairs
        ( B ) TYPE: nucleic acid
        ( C ) STRANDEDNESS: double
        ( D ) TOPOLOGY: linear ( i i ) MOLECULE TYPE: Genomic DNA ( i i i ) HYPOTHETICAL: NO ( i v ) ANTI-SENSE: NO ( v ) FRAGMENT TYPE:

( v i ) ORIGINAL SOURCE:

( i x ) FEATURE:

( x i ) SEQUENCE DESCRIPTION: SEQ ID NO:30:

| | | | | | |
|---|---|---|---|---|---|
|AGACCACGGC|TTCCTCGAAT|CTTGCGCGAA|GCCGCCGGCC|TCGGAGGAGG|GATTAATCCA|
|GACCCGCCGG|GGGGTGTTTT|CACATTTCTT|CCTCTTCGTG|GCTGCTCCTC|CTATTAAAAC|
|CATTTTTGGT|CCATGGTCAA|TGAGAATACG|AGGATGTACA|TTCCAGAGGA|AAACCACCAA|

60

120

180

```
GGTTCCAACT ATGGGAGCCC ACGCCCCGCC CATGCCAACA TGAATGCCAA TGCGGCAGCG    240

GGGCTGGCCC CTGAGCACAT CCCCACCCCG GGGGCTGCCC TGTCGTGGCA GGCGGCCATC    300

GACGCAGCCC GGCAGGCTAA GCTGATGGGC AGCGCTGGCA ATGCGACCAT CTCCACAGTC    360

AGCTCCACGC AGCGGAAGCG CCAGCAATAT GGGAAACCCA AGAAGCAGGG CAGCACCACG    420

GCCACACGCC CGCCCCGAGC CCTGCTCTGC CTGACCCTGA AGAACCCCAT CCGGAGGGCC    480

TGCATCAGCA TTGTCGAATG GAAACCATTT GAAATAATTA TTTTACTGAC TATTTTTGCC    540

AATTGTGTGG CCTTAGCGAT CTATATTCCC TTTCCAGAAG ATGATTCCAA CGCCACCAAT    600

TCCAACCTGG AACGAGTGGA ATATCTCTTT CTCATAATTT TTACGGTGGA AGCGTTTTTA    660

AAAGTAATCG CCTATGGACT CCTCTTTCAC CCCAATGCCT ACCTCCGCAA CGGCTGGAAC    720

CTACTAGATT TTATAATTGT GGTTGTGGGG CTTTTTAGTG CAATTTTAGA ACAAGCAACC    780

AAAGCAGATG GGGCAAACGC TCTCGGAGGG AAAGGGGCCG GATTTGATGT GAAGGCGCTG    840

AGGGCCTTCC GCGTGCTGCG CCCCCTGCGG CTGGTGTCCG GAGTCCCAAG TCTCCAGGTG    900

GTCCTGAATT CCATCATCAA GGCCATGGTC CCCCTGCTGC ACATCGCCCT GCTTGTGCTG    960

TTTGTCATCA TCATCTACGC CATCATCGGC TTGGAGCTCT TCATGGGGAA GATGCACAAG   1020

ACCTGCTACA ACCAGGAGGG CATAGCAG                                      1048
```

( 2 ) INFORMATION FOR SEQ ID NO:31:

( i ) SEQUENCE CHARACTERISTICS:
       ( A ) LENGTH: 2338 base pairs
       ( B ) TYPE: nucleic acid
       ( C ) STRANDEDNESS: single
       ( D ) TOPOLOGY: linear ( i i ) MOLECULE TYPE: DNA (genomic)

( i x ) FEATURE:
       ( D ) OTHER INFORMATION: /note="IMR32 1.38"

( x i ) SEQUENCE DESCRIPTION: SEQ ID NO:31:

```
G  GAG  AAG  CCG  GCA  GTG  GGG  GAA  TCC  AAG  GAG  GAG  AAG  ATT  GAG  CTG  AAA     49
   Glu  Lys  Pro  Ala  Val  Gly  Glu  Ser  Lys  Glu  Glu  Lys  Ile  Glu  Leu  Lys
   1              5                  10                 15

TCC  ATC  ACG  GCT  GAC  GGA  GAG  TCT  CCA  CCC  GCC  ACC  AAG  ATC  AAC  ATG        97
Ser  Ile  Thr  Ala  Asp  Gly  Glu  Ser  Pro  Pro  Ala  Thr  Lys  Ile  Asn  Met
             20                  25                      30

GAT  GAC  CTC  CAG  CCC  AAT  GAA  AAT  GAG  GAT  AAG  AGC  CCC  TAC  CCC  AAC       145
Asp  Asp  Leu  Gln  Pro  Asn  Glu  Asn  Glu  Asp  Lys  Ser  Pro  Tyr  Pro  Asn
             35                  40                      45

CCA  GAA  ACT  ACA  GGA  GAA  GAG  GAT  GAG  GAG  GAG  CCA  GAG  ATG  CCT  GTC       193
Pro  Glu  Thr  Thr  Gly  Glu  Glu  Asp  Glu  Glu  Glu  Pro  Glu  Met  Pro  Val
     50                  55                      60

GGC  CCT  CGC  CCA  CGA  CCA  CTC  TCT  GAG  CTT  CAC  CTT  AAG  GAA  AAG  GCA       241
Gly  Pro  Arg  Pro  Arg  Pro  Leu  Ser  Glu  Leu  His  Leu  Lys  Glu  Lys  Ala
65                   70                  75                      80

GTG  CCC  ATG  CCA  GAA  GCC  AGC  GCG  TTT  TTC  ATC  TTC  AGC  TCT  AAC  AAC       289
Val  Pro  Met  Pro  Glu  Ala  Ser  Ala  Phe  Phe  Ile  Phe  Ser  Ser  Asn  Asn
                 85                  90                      95

AGG  TTT  CGC  CTC  CAG  TGC  CAC  CGC  ATT  GTC  AAT  GAC  ACG  ATC  TTC  ACC       337
Arg  Phe  Arg  Leu  Gln  Cys  His  Arg  Ile  Val  Asn  Asp  Thr  Ile  Phe  Thr
             100                 105                     110

AAC  CTG  ATC  CTC  TTC  TTC  ATT  CTG  CTC  AGC  AGC  ATT  TCC  CTG  GCT  GCT       385
Asn  Leu  Ile  Leu  Phe  Phe  Ile  Leu  Leu  Ser  Ser  Ile  Ser  Leu  Ala  Ala
             115                 120                     125

GAG  GAC  CCG  GTC  CAG  CAC  ACC  TCC  TTC  AGG  AAC  CAT  ATT  CTG  TTT  TAT       433
```

```
                Glu  Asp  Pro  Val  Gln  His  Thr  Ser  Phe  Arg  Asn  His  Ile  Leu  Phe  Tyr
                     130                     135                     140

TTT  GAT  ATT  GTT  TTT  ACC  ACC  ATT  TTC  ACC  ATT  GAA  ATT  GCT  CTG  AAG                       481
Phe  Asp  Ile  Val  Phe  Thr  Thr  Ile  Phe  Thr  Ile  Glu  Ile  Ala  Leu  Lys
145                     150                     155                     160

ATG  ACT  GCT  TAT  GGG  GCT  TTC  TTG  CAC  AAG  GGT  TCT  TTC  TGC  CGG  AAC                       529
Met  Thr  Ala  Tyr  Gly  Ala  Phe  Leu  His  Lys  Gly  Ser  Phe  Cys  Arg  Asn
                     165                     170                     175

TAC  TTC  AAC  ATC  CTG  GAC  CTG  CTG  GTG  GTC  AGC  GTG  TCC  CTC  ATC  TCC                       577
Tyr  Phe  Asn  Ile  Leu  Asp  Leu  Leu  Val  Val  Ser  Val  Ser  Leu  Ile  Ser
               180                     185                     190

TTT  GGC  ATC  CAG  TCC  AGT  GCA  ATC  AAT  GTC  GTG  AAG  ATC  TTG  CGA  GTC                       625
Phe  Gly  Ile  Gln  Ser  Ser  Ala  Ile  Asn  Val  Val  Lys  Ile  Leu  Arg  Val
          195                     200                     205

CTG  CGA  GTA  CTC  AGG  CCC  CTG  AGG  GCC  ATC  AAC  AGG  GCC  AAG  GGG  CTA                       673
Leu  Arg  Val  Leu  Arg  Pro  Leu  Arg  Ala  Ile  Asn  Arg  Ala  Lys  Gly  Leu
     210                     215                     220

AAG  CAT  GTG  GTT  CAG  TGT  GTG  TTT  GTC  GCC  ATC  CGG  ACC  ATC  GGG  AAC                       721
Lys  His  Val  Val  Gln  Cys  Val  Phe  Val  Ala  Ile  Arg  Thr  Ile  Gly  Asn
225                     230                     235                     240

ATC  GTG  ATT  GTC  ACC  ACC  CTG  CTG  CAG  TTC  ATG  TTT  GCC  TGC  ATC  GGG                       769
Ile  Val  Ile  Val  Thr  Thr  Leu  Leu  Gln  Phe  Met  Phe  Ala  Cys  Ile  Gly
                     245                     250                     255

GTC  CAG  CTC  TTC  AAG  GGA  AAG  CTG  TAC  ACC  TGT  TCA  GAC  AGT  TCC  AAG                       817
Val  Gln  Leu  Phe  Lys  Gly  Lys  Leu  Tyr  Thr  Cys  Ser  Asp  Ser  Ser  Lys
               260                     265                     270

CAG  ACA  GAG  GCG  GAA  TGC  AAG  GGC  AAC  TAC  ATC  ACG  TAC  AAA  GAC  GGG                       865
Gln  Thr  Glu  Ala  Glu  Cys  Lys  Gly  Asn  Tyr  Ile  Thr  Tyr  Lys  Asp  Gly
          275                     280                     285

GAG  GTT  GAC  CAC  CCC  ATC  ATC  CAA  CCC  CGC  AGC  TGG  GAG  AAC  AGC  AAG                       913
Glu  Val  Asp  His  Pro  Ile  Ile  Gln  Pro  Arg  Ser  Trp  Glu  Asn  Ser  Lys
     290                     295                     300

TTT  GAC  TTT  GAC  AAT  GTT  CTG  GCA  GCC  ATG  ATG  GCC  CTC  TTC  ACC  GTC                       961
Phe  Asp  Phe  Asp  Asn  Val  Leu  Ala  Ala  Met  Met  Ala  Leu  Phe  Thr  Val
305                     310                     315                     320

TCC  ACC  TTC  GAA  GGG  TGG  CCA  GAG  CTG  CTG  TAC  CGC  TCC  ATC  GAC  TCC                      1009
Ser  Thr  Phe  Glu  Gly  Trp  Pro  Glu  Leu  Leu  Tyr  Arg  Ser  Ile  Asp  Ser
                     325                     330                     335

CAC  ACG  GAA  GAC  AAG  GGC  CCC  ATC  TAC  AAC  TAC  CGT  GTG  GAG  ATC  TCC                      1057
His  Thr  Glu  Asp  Lys  Gly  Pro  Ile  Tyr  Asn  Tyr  Arg  Val  Glu  Ile  Ser
               340                     345                     350

ATC  TTC  TTC  ATC  ATC  TAC  ATC  ATC  ATC  ATC  GCC  TTC  TTC  ATG  ATG  AAC                      1105
Ile  Phe  Phe  Ile  Ile  Tyr  Ile  Ile  Ile  Ile  Ala  Phe  Phe  Met  Met  Asn
          355                     360                     365

ATC  TTC  GTG  GGC  TTC  GTC  ATC  GTC  ACC  TTT  CAG  GAG  CAG  GGG  GAG  CAG                      1153
Ile  Phe  Val  Gly  Phe  Val  Ile  Val  Thr  Phe  Gln  Glu  Gln  Gly  Glu  Gln
     370                     375                     380

GAG  TAC  AAG  AAC  TGT  GAG  CTG  GAC  AAG  AAC  CAG  CGA  CAG  TGC  GTG  GAA                      1201
Glu  Tyr  Lys  Asn  Cys  Glu  Leu  Asp  Lys  Asn  Gln  Arg  Gln  Cys  Val  Glu
385                     390                     395                     400

TAC  GCC  CTC  AAG  GCC  CGG  CCC  CTG  CGG  AGG  TAC  ATC  CCC  AAG  AAC  CAG                      1249
Tyr  Ala  Leu  Lys  Ala  Arg  Pro  Leu  Arg  Arg  Tyr  Ile  Pro  Lys  Asn  Gln
                     405                     410                     415

CAC  CAG  TAC  AAA  GTG  TGG  TAC  GTG  GTC  AAC  TCC  ACC  TAC  TTC  GAG  TAC                      1297
His  Gln  Tyr  Lys  Val  Trp  Tyr  Val  Val  Asn  Ser  Thr  Tyr  Phe  Glu  Tyr
               420                     425                     430

CTG  ATG  TTC  GTC  CTC  ATC  CTG  CTC  AAC  ACC  ATC  TGC  CTG  GCC  ATG  CAG                      1345
Leu  Met  Phe  Val  Leu  Ile  Leu  Leu  Asn  Thr  Ile  Cys  Leu  Ala  Met  Gln
          435                     440                     445

CAC  TAC  GGC  CAG  AGC  TGC  CTG  TTC  AAA  ATC  GCC  ATG  AAC  ATC  CTC  AAC                      1393
```

-continued

```
His Tyr Gly Gln Ser Cys Leu Phe Lys Ile Ala Met Asn Ile Leu Asn
450                 455                 460

ATG CTC TTC ACT GGC CTC TTC ACC GTG GAG ATG ATC CTG AAG CTC ATT         1441
Met Leu Phe Thr Gly Leu Phe Thr Val Glu Met Ile Leu Lys Leu Ile
465                 470                 475                 480

GCC TTC AAA CCC AAG GGT TAC TTT AGT GAT CCC TGG AAT GTT TTT GAC         1489
Ala Phe Lys Pro Lys Gly Tyr Phe Ser Asp Pro Trp Asn Val Phe Asp
                485                 490                 495

TTC CTC ATC GTA ATT GGC AGC ATA ATT GAC GTC ATT CTC AGT GAG ACT         1537
Phe Leu Ile Val Ile Gly Ser Ile Ile Asp Val Ile Leu Ser Glu Thr
                500                 505                 510

AAT CCA GCT GAA CAT ACC CAA TGC TCT CCC TCT ATG AAC GCA GAG GAA         1585
Asn Pro Ala Glu His Thr Gln Cys Ser Pro Ser Met Asn Ala Glu Glu
                515                 520                 525

AAC TCC CGC ATC TCC ATC ACC TTC TTC CGC CTG TTC CGG GTC ATG CGT         1633
Asn Ser Arg Ile Ser Ile Thr Phe Phe Arg Leu Phe Arg Val Met Arg
530                 535                 540

CTG GTG AAG CTG CTG AGC CGT GGG GAG GGC ATC CGG ACG CTG CTG TGG         1681
Leu Val Lys Leu Leu Ser Arg Gly Glu Gly Ile Arg Thr Leu Leu Trp
545                 550                 555                 560

ACC TTC ATC AAG TCC TTC CAG GCC CTG CCC TAT GTG GCC CTC CTG ATC         1729
Thr Phe Ile Lys Ser Phe Gln Ala Leu Pro Tyr Val Ala Leu Leu Ile
                565                 570                 575

GTG ATG CTG TTC TTC ATC TAC GCG GTG ATC GGG ATG CAG GTG TTT GGG         1777
Val Met Leu Phe Phe Ile Tyr Ala Val Ile Gly Met Gln Val Phe Gly
                580                 585                 590

AAA ATT GCC CTG AAT GAT ACC ACA GAG ATC AAC CGG AAC AAC AAC TTT         1825
Lys Ile Ala Leu Asn Asp Thr Thr Glu Ile Asn Arg Asn Asn Asn Phe
                595                 600                 605

CAG ACC TTC CCC CAG GCC GTG CTC CTC CTC TTC AGG TGT GCC ACC GGG         1873
Gln Thr Phe Pro Gln Ala Val Leu Leu Leu Phe Arg Cys Ala Thr Gly
610                 615                 620

GAG GCC TGG CAG GAC ATC ATG CTG GCC TGC ATG CCA GGC AAG AAG TGT         1921
Glu Ala Trp Gln Asp Ile Met Leu Ala Cys Met Pro Gly Lys Lys Cys
625                 630                 635                 640

GCC CCA GAG TCC GAG CCC AGC AAC AGC ACG GAG GGT GAA ACA CCC TGT         1969
Ala Pro Glu Ser Glu Pro Ser Asn Ser Thr Glu Gly Glu Thr Pro Cys
                645                 650                 655

GGT AGC AGC TTT GCT GTC TTC TAC TTC ATC AGC TTC TAC ATG CGC TGT         2017
Gly Ser Ser Phe Ala Val Phe Tyr Phe Ile Ser Phe Tyr Met Arg Cys
                660                 665                 670

GCC TTC CTG ATC ATC AAC CTC TTT GTA GCT GTC ATC ATG GAC AAC TTT         2065
Ala Phe Leu Ile Ile Asn Leu Phe Val Ala Val Ile Met Asp Asn Phe
                675                 680                 685

GAC TAC CTG ACA AGG GAC TGG TCC ATC CTT GGT CCC CAC CAC CTG GAT         2113
Asp Tyr Leu Thr Arg Asp Trp Ser Ile Leu Gly Pro His His Leu Asp
690                 695                 700

GAG TTT AAA AGA ATC TGG GCA GAG TAT GAC CCT GAA GCC AAG GGT CGT         2161
Glu Phe Lys Arg Ile Trp Ala Glu Tyr Asp Pro Glu Ala Lys Gly Arg
705                 710                 715                 720

ATC AAA CAC CTG GAT GTG GTG ACC CTC CTC CGG CGG ATT CAG CCG CCA         2209
Ile Lys His Leu Asp Val Val Thr Leu Leu Arg Arg Ile Gln Pro Pro
                725                 730                 735

CTA GGT TTT GGG AAG CTG TGC CCT CAC CGC GTG GCT TGC AAA CGC CAC         2257
Leu Gly Phe Gly Lys Leu Cys Pro His Arg Val Ala Cys Lys Arg His
                740                 745                 750

TAT TTC TGT GAT GCA TGG AAT ACA TTT GAC GCC TTG ATT GTT GTG GGT         2305
Tyr Phe Cys Asp Ala Trp Asn Thr Phe Asp Ala Leu Ile Val Val Gly
                755                 760                 765

AGC ATT GTT GAT ATA GCA ATC ACC GAG GTA AAC                             2338
Ser Ile Val Asp Ile Ala Ile Thr Glu Val Asn
```

```
Ser  Ile  Val  Asp  Ile  Ala  Ile  Thr  Glu  Val  Asn
     770                      775
```

( 2 ) INFORMATION FOR SEQ ID NO:32:

( i ) SEQUENCE CHARACTERISTICS:
       ( A ) LENGTH: 3636 base pairs
       ( B ) TYPE: nucleic acid
       ( C ) STRANDEDNESS: double
       ( D ) TOPOLOGY: linear ( i i ) MOLECULE TYPE: DNA (genomic)

( i x ) FEATURE:
       ( A ) NAME/KEY: CDS
       ( B ) LOCATION: 35..3346
       ( D ) OTHER INFORMATION: /standard_name="Alpha-2a"

( i x ) FEATURE:
       ( A ) NAME/KEY: 5'UTR
       ( B ) LOCATION: 1..34

( i x ) FEATURE:
       ( A ) NAME/KEY: 3'UTR
       ( B ) LOCATION: 3347..3636

( x i ) SEQUENCE DESCRIPTION: SEQ ID NO:32:

```
GCGGGGGAGG  GGGCATTGAT  CTTCGATCGC  GAAG ATG GCT GCT GGC TGC CTG              52
                                         Met Ala Ala Gly Cys Leu
                                         1                   5

CTG  GCC  TTG  ACT  CTG  ACA  CTT  TTC  CAA  TCT  TTG  CTC  ATC  GGC  CCC  TCG    100
Leu  Ala  Leu  Thr  Leu  Thr  Leu  Phe  Gln  Ser  Leu  Leu  Ile  Gly  Pro  Ser
               10                      15                      20

TCG  GAG  GAG  CCG  TTC  CCT  TCG  GCC  GTC  ACT  ATC  AAA  TCA  TGG  GTG  GAT    148
Ser  Glu  Glu  Pro  Phe  Pro  Ser  Ala  Val  Thr  Ile  Lys  Ser  Trp  Val  Asp
          25                      30                      35

AAG  ATG  CAA  GAA  GAC  CTT  GTC  ACA  CTG  GCA  AAA  ACA  GCA  AGT  GGA  GTC    196
Lys  Met  Gln  Glu  Asp  Leu  Val  Thr  Leu  Ala  Lys  Thr  Ala  Ser  Gly  Val
     40                      45                      50

AAT  CAG  CTT  GTT  GAT  ATT  TAT  GAG  AAA  TAT  CAA  GAT  TTG  TAT  ACT  GTG    244
Asn  Gln  Leu  Val  Asp  Ile  Tyr  Glu  Lys  Tyr  Gln  Asp  Leu  Tyr  Thr  Val
55                      60                      65                      70

GAA  CCA  AAT  AAT  GCA  CGC  CAG  CTG  GTA  GAA  ATT  GCA  GCC  AGG  GAT  ATT    292
Glu  Pro  Asn  Asn  Ala  Arg  Gln  Leu  Val  Glu  Ile  Ala  Ala  Arg  Asp  Ile
                    75                      80                      85

GAG  AAA  CTT  CTG  AGC  AAC  AGA  TCT  AAA  GCC  CTG  GTG  AGC  CTG  GCA  TTG    340
Glu  Lys  Leu  Leu  Ser  Asn  Arg  Ser  Lys  Ala  Leu  Val  Ser  Leu  Ala  Leu
               90                      95                     100

GAA  GCG  GAG  AAA  GTT  CAA  GCA  GCT  CAC  CAG  TGG  AGA  GAA  GAT  TTT  GCA    388
Glu  Ala  Glu  Lys  Val  Gln  Ala  Ala  His  Gln  Trp  Arg  Glu  Asp  Phe  Ala
          105                     110                     115

AGC  AAT  GAA  GTT  GTC  TAC  TAC  AAT  GCA  AAG  GAT  GAT  CTC  GAT  CCT  GAG    436
Ser  Asn  Glu  Val  Val  Tyr  Tyr  Asn  Ala  Lys  Asp  Asp  Leu  Asp  Pro  Glu
     120                     125                     130

AAA  AAT  GAC  AGT  GAG  CCA  GGC  AGC  CAG  AGG  ATA  AAA  CCT  GTT  TTC  ATT    484
Lys  Asn  Asp  Ser  Glu  Pro  Gly  Ser  Gln  Arg  Ile  Lys  Pro  Val  Phe  Ile
135                     140                     145                     150

GAA  GAT  GCT  AAT  TTT  GGA  CGA  CAA  ATA  TCT  TAT  CAG  CAC  GCA  GCA  GTC    532
Glu  Asp  Ala  Asn  Phe  Gly  Arg  Gln  Ile  Ser  Tyr  Gln  His  Ala  Ala  Val
                    155                     160                     165

CAT  ATT  CCT  ACT  GAC  ATC  TAT  GAG  GGC  TCA  ACA  ATT  GTG  TTA  AAT  GAA    580
His  Ile  Pro  Thr  Asp  Ile  Tyr  Glu  Gly  Ser  Thr  Ile  Val  Leu  Asn  Glu
               170                     175                     180

CTC  AAC  TGG  ACA  AGT  GCC  TTA  GAT  GAA  GTT  TTC  AAA  AAG  AAT  CGC  GAG    628
Leu  Asn  Trp  Thr  Ser  Ala  Leu  Asp  Glu  Val  Phe  Lys  Lys  Asn  Arg  Glu
          185                     190                     195
```

-continued

| | | | | | | | | | | | | | | | | |
|---|---|---|---|---|---|---|---|---|---|---|---|---|---|---|---|---|
| GAA | GAC | CCT | TCA | TTA | TTG | TGG | CAG | GTT | TTT | GGC | AGT | GCC | ACT | GGC | CTA | 676 |
| Glu | Asp | Pro | Ser | Leu | Leu | Trp | Gln | Val | Phe | Gly | Ser | Ala | Thr | Gly | Leu | |
| | 200 | | | | 205 | | | | | 210 | | | | | | |
| GCT | CGA | TAT | TAT | CCA | GCT | TCA | CCA | TGG | GTT | GAT | AAT | AGT | AGA | ACT | CCA | 724 |
| Ala | Arg | Tyr | Tyr | Pro | Ala | Ser | Pro | Trp | Val | Asp | Asn | Ser | Arg | Thr | Pro | |
| 215 | | | | | 220 | | | | | 225 | | | | | 230 | |
| AAT | AAG | ATT | GAC | CTT | TAT | GAT | GTA | CGC | AGA | AGA | CCA | TGG | TAC | ATC | CAA | 772 |
| Asn | Lys | Ile | Asp | Leu | Tyr | Asp | Val | Arg | Arg | Arg | Pro | Trp | Tyr | Ile | Gln | |
| | | | | 235 | | | | | 240 | | | | | 245 | | |
| GGA | GCT | GCA | TCT | CCT | AAA | GAC | ATG | CTT | ATT | CTG | GTG | GAT | GTG | AGT | GGA | 820 |
| Gly | Ala | Ala | Ser | Pro | Lys | Asp | Met | Leu | Ile | Leu | Val | Asp | Val | Ser | Gly | |
| | | 250 | | | | | 255 | | | | | 260 | | | | |
| AGT | GTT | AGT | GGA | TTG | ACA | CTT | AAA | CTG | ATC | CGA | ACA | TCT | GTC | TCC | GAA | 868 |
| Ser | Val | Ser | Gly | Leu | Thr | Leu | Lys | Leu | Ile | Arg | Thr | Ser | Val | Ser | Glu | |
| | | 265 | | | | | 270 | | | | | 275 | | | | |
| ATG | TTA | GAA | ACC | CTC | TCA | GAT | GAT | GAT | TTC | GTG | AAT | GTA | GCT | TCA | TTT | 916 |
| Met | Leu | Glu | Thr | Leu | Ser | Asp | Asp | Asp | Phe | Val | Asn | Val | Ala | Ser | Phe | |
| | 280 | | | | | 285 | | | | | 290 | | | | | |
| AAC | AGC | AAT | GCT | CAG | GAT | GTA | AGC | TGT | TTT | CAG | CAC | CTT | GTC | CAA | GCA | 964 |
| Asn | Ser | Asn | Ala | Gln | Asp | Val | Ser | Cys | Phe | Gln | His | Leu | Val | Gln | Ala | |
| 295 | | | | | 300 | | | | | 305 | | | | | 310 | |
| AAT | GTA | AGA | AAT | AAA | AAA | GTG | TTG | AAA | GAC | GCG | GTG | AAT | AAT | ATC | ACA | 1012 |
| Asn | Val | Arg | Asn | Lys | Lys | Val | Leu | Lys | Asp | Ala | Val | Asn | Asn | Ile | Thr | |
| | | | | 315 | | | | | 320 | | | | | 325 | | |
| GCC | AAA | GGA | ATT | ACA | GAT | TAT | AAG | AAG | GGC | TTT | AGT | TTT | GCT | TTT | GAA | 1060 |
| Ala | Lys | Gly | Ile | Thr | Asp | Tyr | Lys | Lys | Gly | Phe | Ser | Phe | Ala | Phe | Glu | |
| | | | 330 | | | | | 335 | | | | | 340 | | | |
| CAG | CTG | CTT | AAT | TAT | AAT | GTT | TCC | AGA | GCA | AAC | TGC | AAT | AAG | ATT | ATT | 1108 |
| Gln | Leu | Leu | Asn | Tyr | Asn | Val | Ser | Arg | Ala | Asn | Cys | Asn | Lys | Ile | Ile | |
| | | 345 | | | | | 350 | | | | | 355 | | | | |
| ATG | CTA | TTC | ACG | GAT | GGA | GGA | GAA | GAG | AGA | GCC | CAG | GAG | ATA | TTT | AAC | 1156 |
| Met | Leu | Phe | Thr | Asp | Gly | Gly | Glu | Glu | Arg | Ala | Gln | Glu | Ile | Phe | Asn | |
| | 360 | | | | | 365 | | | | | 370 | | | | | |
| AAA | TAC | AAT | AAA | GAT | AAA | AAA | GTA | CGT | GTA | TTC | AGG | TTT | TCA | GTT | GGT | 1204 |
| Lys | Tyr | Asn | Lys | Asp | Lys | Lys | Val | Arg | Val | Phe | Arg | Phe | Ser | Val | Gly | |
| 375 | | | | | 380 | | | | | 385 | | | | | 390 | |
| CAA | CAC | AAT | TAT | GAG | AGA | GGA | CCT | ATT | CAG | TGG | ATG | GCC | TGT | GAA | AAC | 1252 |
| Gln | His | Asn | Tyr | Glu | Arg | Gly | Pro | Ile | Gln | Trp | Met | Ala | Cys | Glu | Asn | |
| | | | | 395 | | | | | 400 | | | | | 405 | | |
| AAA | GGT | TAT | TAT | TAT | GAA | ATT | CCT | TCC | ATT | GGT | GCA | ATA | AGA | ATC | AAT | 1300 |
| Lys | Gly | Tyr | Tyr | Tyr | Glu | Ile | Pro | Ser | Ile | Gly | Ala | Ile | Arg | Ile | Asn | |
| | | | 410 | | | | | 415 | | | | | 420 | | | |
| ACT | CAG | GAA | TAT | TTG | GAT | GTT | TTG | GGA | AGA | CCA | ATG | GTT | TTA | GCA | GGA | 1348 |
| Thr | Gln | Glu | Tyr | Leu | Asp | Val | Leu | Gly | Arg | Pro | Met | Val | Leu | Ala | Gly | |
| | | 425 | | | | | 430 | | | | | 435 | | | | |
| GAC | AAA | GCT | AAG | CAA | GTC | CAA | TGG | ACA | AAT | GTG | TAC | CTG | GAT | GCA | TTG | 1396 |
| Asp | Lys | Ala | Lys | Gln | Val | Gln | Trp | Thr | Asn | Val | Tyr | Leu | Asp | Ala | Leu | |
| | 440 | | | | | 445 | | | | | 450 | | | | | |
| GAA | CTG | GGA | CTT | GTC | ATT | ACT | GGA | ACT | CTT | CCG | GTC | TTC | AAC | ATA | ACC | 1444 |
| Glu | Leu | Gly | Leu | Val | Ile | Thr | Gly | Thr | Leu | Pro | Val | Phe | Asn | Ile | Thr | |
| 455 | | | | | 460 | | | | | 465 | | | | | 470 | |
| GGC | CAA | TTT | GAA | AAT | AAG | ACA | AAC | TTA | AAG | AAC | CAG | CTG | ATT | CTT | GGT | 1492 |
| Gly | Gln | Phe | Glu | Asn | Lys | Thr | Asn | Leu | Lys | Asn | Gln | Leu | Ile | Leu | Gly | |
| | | | | 475 | | | | | 480 | | | | | 485 | | |
| GTG | ATG | GGA | GTA | GAT | GTG | TCT | TTG | GAA | GAT | ATT | AAA | AGA | CTG | ACA | CCA | 1540 |
| Val | Met | Gly | Val | Asp | Val | Ser | Leu | Glu | Asp | Ile | Lys | Arg | Leu | Thr | Pro | |
| | | | 490 | | | | | 495 | | | | | 500 | | | |
| CGT | TTT | ACA | CTG | TGC | CCC | AAT | GGG | TAT | TAC | TTT | GCA | ATC | GAT | CCT | AAT | 1588 |
| Arg | Phe | Thr | Leu | Cys | Pro | Asn | Gly | Tyr | Tyr | Phe | Ala | Ile | Asp | Pro | Asn | |
| | | 505 | | | | | 510 | | | | | 515 | | | | |

| | | | | | | | | | | | | | | | | |
|---|---|---|---|---|---|---|---|---|---|---|---|---|---|---|---|---|
| GGT | TAT | GTT | TTA | TTA | CAT | CCA | AAT | CTT | CAG | CCA | AAG | CCT | ATT | GGT | GTA | 1636 |
| Gly | Tyr 520 | Val | Leu | Leu | His | Pro 525 | Asn | Leu | Gln | Pro | Lys 530 | Pro | Ile | Gly | Val | |
| GGT | ATA | CCA | ACA | ATT | AAT | TTA | AGA | AAA | AGG | AGA | CCC | AAT | ATC | CAG | AAC | 1684 |
| Gly 535 | Ile | Pro | Thr | Ile | Asn 540 | Leu | Arg | Lys | Arg | Arg 545 | Pro | Asn | Ile | Gln | Asn 550 | |
| CCC | AAA | TCT | CAG | GAG | CCA | GTA | ACA | TTG | GAT | TTC | CTT | GAT | GCA | GAG | TTA | 1732 |
| Pro | Lys | Ser | Gln | Glu 555 | Pro | Val | Thr | Leu | Asp 560 | Phe | Leu | Asp | Ala | Glu 565 | Leu | |
| GAG | AAT | GAT | ATT | AAA | GTG | GAG | ATT | CGA | AAT | AAG | ATG | ATT | GAT | GGG | GAA | 1780 |
| Glu | Asn | Asp | Ile 570 | Lys | Val | Glu | Ile | Arg 575 | Asn | Lys | Met | Ile | Asp 580 | Gly | Glu | |
| AGT | GGA | GAA | AAA | ACA | TTC | AGA | ACT | CTG | GTT | AAA | TCT | CAA | GAT | GAG | AGA | 1828 |
| Ser | Gly | Glu 585 | Lys | Thr | Phe | Arg | Thr 590 | Leu | Val | Lys | Ser | Gln 595 | Asp | Glu | Arg | |
| TAT | ATT | GAC | AAA | GGA | AAC | AGG | ACA | TAC | ACA | TGG | ACA | CCT | GTC | AAT | GGC | 1876 |
| Tyr | Ile | Asp 600 | Lys | Gly | Asn | Arg 605 | Thr | Tyr | Thr | Trp | Thr 610 | Pro | Val | Asn | Gly | |
| ACA | GAT | TAC | AGT | TTG | GCC | TTG | GTA | TTA | CCA | ACC | TAC | AGT | TTT | TAC | TAT | 1924 |
| Thr 615 | Asp | Tyr | Ser | Leu | Ala 620 | Leu | Val | Leu | Pro | Thr 625 | Tyr | Ser | Phe | Tyr | Tyr 630 | |
| ATA | AAA | GCC | AAA | CTA | GAA | GAG | ACA | ATA | ACT | CAG | GCC | AGA | TAT | TCG | GAA | 1972 |
| Ile | Lys | Ala | Lys | Leu 635 | Glu | Glu | Thr | Ile | Thr 640 | Gln | Ala | Arg | Tyr | Ser 645 | Glu | |
| ACC | CTG | AAG | CCA | GAT | AAT | TTT | GAA | GAA | TCT | GGC | TAT | ACA | TTC | ATA | GCA | 2020 |
| Thr | Leu | Lys | Pro 650 | Asp | Asn | Phe | Glu | Glu 655 | Ser | Gly | Tyr | Thr | Phe 660 | Ile | Ala | |
| CCA | AGA | GAT | TAC | TGC | AAT | GAC | CTG | AAA | ATA | TCG | GAT | AAT | AAC | ACT | GAA | 2068 |
| Pro | Arg | Asp 665 | Tyr | Cys | Asn | Asp | Leu 670 | Lys | Ile | Ser | Asp | Asn 675 | Asn | Thr | Glu | |
| TTT | CTT | TTA | AAT | TTC | AAC | GAG | TTT | ATT | GAT | AGA | AAA | ACT | CCA | AAC | AAC | 2116 |
| Phe | Leu | Leu | Asn 680 | Phe | Asn | Glu | Phe | Ile 685 | Asp | Arg | Lys | Thr | Pro 690 | Asn | Asn | |
| CCA | TCA | TGT | AAC | GCG | GAT | TTG | ATT | AAT | AGA | GTC | TTG | CTT | GAT | GCA | GGC | 2164 |
| Pro | Ser | Cys | Asn | Ala 695 | Asp | Leu | Ile | Asn | Arg 700 | Val | Leu | Leu | Asp | Ala 705 | Gly 710 | |
| TTT | ACA | AAT | GAA | CTT | GTC | CAA | AAT | TAC | TGG | AGT | AAG | CAG | AAA | AAT | ATC | 2212 |
| Phe | Thr | Asn | Glu | Leu 715 | Val | Gln | Asn | Tyr | Trp 720 | Ser | Lys | Gln | Lys | Asn 725 | Ile | |
| AAG | GGA | GTG | AAA | GCA | CGA | TTT | GTT | GTG | ACT | GAT | GGT | GGG | ATT | ACC | AGA | 2260 |
| Lys | Gly | Val | Lys 730 | Ala | Arg | Phe | Val | Val 735 | Thr | Asp | Gly | Gly | Ile 740 | Thr | Arg | |
| GTT | TAT | CCC | AAA | GAG | GCT | GGA | GAA | AAT | TGG | CAA | GAA | AAC | CCA | GAG | ACA | 2308 |
| Val | Tyr | Pro 745 | Lys | Glu | Ala | Gly | Glu 750 | Asn | Trp | Gln | Glu | Asn 755 | Pro | Glu | Thr | |
| TAT | GAG | GAC | AGC | TTC | TAT | AAA | AGG | AGC | CTA | GAT | AAT | GAT | AAC | TAT | GTT | 2356 |
| Tyr | Glu 760 | Asp | Ser | Phe | Tyr | Lys 765 | Arg | Ser | Leu | Asp | Asn 770 | Asp | Asn | Tyr | Val | |
| TTC | ACT | GCT | CCC | TAC | TTT | AAC | AAA | AGT | GGA | CCT | GGT | GCC | TAT | GAA | TCG | 2404 |
| Phe 775 | Thr | Ala | Pro | Tyr | Phe 780 | Asn | Lys | Ser | Gly | Pro 785 | Gly | Ala | Tyr | Glu | Ser 790 | |
| GGC | ATT | ATG | GTA | AGC | AAA | GCT | GTA | GAA | ATA | TAT | ATT | CAA | GGG | AAA | CTT | 2452 |
| Gly | Ile | Met | Val | Ser 795 | Lys | Ala | Val | Glu | Ile 800 | Tyr | Ile | Gln | Gly | Lys 805 | Leu | |
| CTT | AAA | CCT | GCA | GTT | GTT | GGA | ATT | AAA | ATT | GAT | GTA | AAT | TCC | TGG | ATA | 2500 |
| Leu | Lys | Pro | Ala 810 | Val | Val | Gly | Ile | Lys 815 | Ile | Asp | Val | Asn | Ser 820 | Trp | Ile | |
| GAG | AAT | TTC | ACC | AAA | ACC | TCA | ATC | AGA | GAT | CCG | TGT | GCT | GGT | CCA | GTT | 2548 |
| Glu | Asn | Phe | Thr | Lys 825 | Thr | Ser | Ile | Arg | Asp 830 | Pro | Cys | Ala | Gly | Pro 835 | Val | |

-continued

| | | | | | | | | | | | | | | | | |
|---|---|---|---|---|---|---|---|---|---|---|---|---|---|---|---|---|
| TGT | GAC | TGC | AAA | AGA | AAC | AGT | GAC | GTA | ATG | GAT | TGT | GTG | ATT | CTG | GAT | 2596 |
| Cys | Asp 840 | Cys | Lys | Arg | Asn | Ser 845 | Asp | Val | Met | Asp | Cys 850 | Val | Ile | Leu | Asp | |
| GAT | GGT | GGG | TTT | CTT | CTG | ATG | GCA | AAT | CAT | GAT | GAT | TAT | ACT | AAT | CAG | 2644 |
| Asp | Gly | Gly | Phe | Leu | Leu | Met | Ala | Asn | His | Asp | Asp | Tyr | Thr | Asn | Gln | |
| 855 | | | | | 860 | | | | | 865 | | | | | 870 | |
| ATT | GGA | AGA | TTT | TTT | GGA | GAG | ATT | GAT | CCC | AGC | TTG | ATG | AGA | CAC | CTG | 2692 |
| Ile | Gly | Arg | Phe | Phe 875 | Gly | Glu | Ile | Asp | Pro 880 | Ser | Leu | Met | Arg | His 885 | Leu | |
| GTT | AAT | ATA | TCA | GTT | TAT | GCT | TTT | AAC | AAA | TCT | TAT | GAT | TAT | CAG | TCA | 2740 |
| Val | Asn | Ile | Ser 890 | Val | Tyr | Ala | Phe | Asn 895 | Lys | Ser | Tyr | Asp | Tyr 900 | Gln | Ser | |
| GTA | TGT | GAG | CCC | GGT | GCT | GCA | CCA | AAA | CAA | GGA | GCA | GGA | CAT | CGC | TCA | 2788 |
| Val | Cys | Glu 905 | Pro | Gly | Ala | Ala | Pro 910 | Lys | Gln | Gly | Ala | Gly 915 | His | Arg | Ser | |
| GCA | TAT | GTG | CCA | TCA | GTA | GCA | GAC | ATA | TTA | CAA | ATT | GGC | TGG | TGG | GCC | 2836 |
| Ala | Tyr 920 | Val | Pro | Ser | Val | Ala 925 | Asp | Ile | Leu | Gln | Ile 930 | Gly | Trp | Trp | Ala | |
| ACT | GCT | GCT | GCC | TGG | TCT | ATT | CTA | CAG | CAG | TTT | CTC | TTG | AGT | TTG | ACC | 2884 |
| Thr 935 | Ala | Ala | Ala | Trp | Ser 940 | Ile | Leu | Gln | Gln | Phe 945 | Leu | Leu | Ser | Leu | Thr 950 | |
| TTT | CCA | CGA | CTC | CTT | GAG | GCA | GTT | GAG | ATG | GAG | GAT | GAT | GAC | TTC | ACG | 2932 |
| Phe | Pro | Arg | Leu | Leu 955 | Glu | Ala | Val | Glu | Met 960 | Glu | Asp | Asp | Asp | Phe 965 | Thr | |
| GCC | TCC | CTG | TCC | AAG | CAG | AGC | TGC | ATT | ACT | GAA | CAA | ACC | CAG | TAT | TTC | 2980 |
| Ala | Ser | Leu | Ser 970 | Lys | Gln | Ser | Cys | Ile 975 | Thr | Glu | Gln | Thr | Gln 980 | Tyr | Phe | |
| TTC | GAT | AAC | GAC | AGT | AAA | TCA | TTC | AGT | GGT | GTA | TTA | GAC | TGT | GGA | AAC | 3028 |
| Phe | Asp | Asn 985 | Asp | Ser | Lys | Ser | Phe 990 | Ser | Gly | Val | Leu | Asp 995 | Cys | Gly | Asn | |
| TGT | TCC | AGA | ATC | TTT | CAT | GGA | GAA | AAG | CTT | ATG | AAC | ACC | AAC | TTA | ATA | 3076 |
| Cys | Ser | Arg 1000 | Ile | Phe | His | Gly | Glu 1005 | Lys | Leu | Met | Asn | Thr 1010 | Asn | Leu | Ile | |
| TTC | ATA | ATG | GTT | GAG | AGC | AAA | GGG | ACA | TGT | CCA | TGT | GAC | ACA | CGA | CTG | 3124 |
| Phe 1015 | Ile | Met | Val | Glu | Ser 1020 | Lys | Gly | Thr | Cys | Pro 1025 | Cys | Asp | Thr | Arg | Leu 1030 | |
| CTC | ATA | CAA | GCG | GAG | CAG | ACT | TCT | GAC | GGT | CCA | AAT | CCT | TGT | GAC | ATG | 3172 |
| Leu | Ile | Gln | Ala | Glu 1035 | Gln | Thr | Ser | Asp | Gly 1040 | Pro | Asn | Pro | Cys | Asp 1045 | Met | |
| GTT | AAG | CAA | CCT | AGA | TAC | CGA | AAA | GGG | CCT | GAT | GTC | TGC | TTT | GAT | AAC | 3220 |
| Val | Lys | Gln | Pro 1050 | Arg | Tyr | Arg | Lys | Gly 1055 | Pro | Asp | Val | Cys | Phe 1060 | Asp | Asn | |
| AAT | GTC | TTG | GAG | GAT | TAT | ACT | GAC | TGT | GGT | GGT | GTT | TCT | GGA | TTA | AAT | 3268 |
| Asn | Val | Leu 1065 | Glu | Asp | Tyr | Thr | Asp 1070 | Cys | Gly | Gly | Val | Ser 1075 | Gly | Leu | Asn | |
| CCC | TCC | CTG | TGG | TAT | ATC | ATT | GGA | ATC | CAG | TTT | CTA | CTA | CTT | TGG | CTG | 3316 |
| Pro | Ser | Leu | Trp 1080 | Tyr | Ile | Ile | Gly | Ile 1085 | Gln | Phe | Leu | Leu | Leu 1090 | Trp | Leu | |
| GTA | TCT | GGC | AGC | ACA | CAC | CGG | CTG | TTA | TGACCTTCTA AAAACCAAAT | | | | | | | 3363 |
| Val | Ser | Gly | Ser | Thr | His 1100 | Arg | Leu | Leu | | | | | | | | |
| 1095 | | | | | | | | | | | | | | | | |

CTGCATAGTT AAACTCCAGA CCCTGCCAAA ACATGAGCCC TGCCCTCAAT TACAGTAACG 3423

TAGGGTCAGC TATAAAATCA GACAAACATT AGCTGGGCCT GTTCCATGGC ATAACACTAA 3483

GGCGCAGACT CCTAAGGCAC CCACTGGCTG CATGTCAGGG TGTCAGATCC TTAAACGTGT 3543

GTGAATGCTG CATCATCTAT GTGTAACATC AAAGCAAAAT CCTATACGTG TCCTCTATTG 3603

GAAAATTTGG GCGTTTGTTG TTGCATTGTT GGT 3636

( 2 ) INFORMATION FOR SEQ ID NO:33:

( i ) SEQUENCE CHARACTERISTICS:
        ( A ) LENGTH: 3600 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 35..3310
        ( D ) OTHER INFORMATION: /standard_name="Alpha-2b"

( i x ) FEATURE:
        ( A ) NAME/KEY: 5'UTR
        ( B ) LOCATION: 1..34

( i x ) FEATURE:
        ( A ) NAME/KEY: 3'UTR
        ( B ) LOCATION: 3308..3600

( x i ) SEQUENCE DESCRIPTION: SEQ ID NO:33:

```
GCGGGGGAGG GGGCATTGAT CTTCGATCGC GAAG ATG GCT GCT GGC TGC CTG              52
                                     Met Ala Ala Gly Cys Leu
                                      1               5

CTG GCC TTG ACT CTG ACA CTT TTC CAA TCT TTG CTC ATC GGC CCC TCG          100
Leu Ala Leu Thr Leu Thr Leu Phe Gln Ser Leu Leu Ile Gly Pro Ser
             10                  15                  20

TCG GAG GAG CCG TTC CCT TCG GCC GTC ACT ATC AAA TCA TGG GTG GAT          148
Ser Glu Glu Pro Phe Pro Ser Ala Val Thr Ile Lys Ser Trp Val Asp
         25                  30                  35

AAG ATG CAA GAA GAC CTT GTC ACA CTG GCA AAA ACA GCA AGT GGA GTC          196
Lys Met Gln Glu Asp Leu Val Thr Leu Ala Lys Thr Ala Ser Gly Val
     40                  45                  50

AAT CAG CTT GTT GAT ATT TAT GAG AAA TAT CAA GAT TTG TAT ACT GTG          244
Asn Gln Leu Val Asp Ile Tyr Glu Lys Tyr Gln Asp Leu Tyr Thr Val
 55                  60                  65                  70

GAA CCA AAT AAT GCA CGC CAG CTG GTA GAA ATT GCA GCC AGG GAT ATT          292
Glu Pro Asn Asn Ala Arg Gln Leu Val Glu Ile Ala Ala Arg Asp Ile
                 75                  80                  85

GAG AAA CTT CTG AGC AAC AGA TCT AAA GCC CTG GTG AGC CTG GCA TTG          340
Glu Lys Leu Leu Ser Asn Arg Ser Lys Ala Leu Val Ser Leu Ala Leu
             90                  95                 100

GAA GCG GAG AAA GTT CAA GCA GCT CAC CAG TGG AGA GAA GAT TTT GCA          388
Glu Ala Glu Lys Val Gln Ala Ala His Gln Trp Arg Glu Asp Phe Ala
        105                 110                 115

AGC AAT GAA GTT GTC TAC TAC AAT GCA AAG GAT GAT CTC GAT CCT GAG          436
Ser Asn Glu Val Val Tyr Tyr Asn Ala Lys Asp Asp Leu Asp Pro Glu
    120                 125                 130

AAA AAT GAC AGT GAG CCA GGC AGC CAG AGG ATA AAA CCT GTT TTC ATT          484
Lys Asn Asp Ser Glu Pro Gly Ser Gln Arg Ile Lys Pro Val Phe Ile
135                 140                 145                 150

GAA GAT GCT AAT TTT GGA CGA CAA ATA TCT TAT CAG CAC GCA GCA GTC          532
Glu Asp Ala Asn Phe Gly Arg Gln Ile Ser Tyr Gln His Ala Ala Val
                155                 160                 165

CAT ATT CCT ACT GAC ATC TAT GAG GGC TCA ACA ATT GTG TTA AAT GAA          580
His Ile Pro Thr Asp Ile Tyr Glu Gly Ser Thr Ile Val Leu Asn Glu
            170                 175                 180

CTC AAC TGG ACA AGT GCC TTA GAT GAA GTT TTC AAA AAG AAT CGC GAG          628
Leu Asn Trp Thr Ser Ala Leu Asp Glu Val Phe Lys Lys Asn Arg Glu
        185                 190                 195

GAA GAC CCT TCA TTA TTG TGG CAG GTT TTT GGC AGT GCC ACT GGC CTA          676
Glu Asp Pro Ser Leu Leu Trp Gln Val Phe Gly Ser Ala Thr Gly Leu
    200                 205                 210
```

-continued

| | | | | | | | | | | | | | | | | |
|---|---|---|---|---|---|---|---|---|---|---|---|---|---|---|---|---|
| GCT | CGA | TAT | TAT | CCA | GCT | TCA | CCA | TGG | GTT | GAT | AAT | AGT | AGA | ACT | CCA | 724 |
| Ala | Arg | Tyr | Tyr | Pro | Ala | Ser | Pro | Trp | Val | Asp | Asn | Ser | Arg | Thr | Pro | |
| 215 | | | | 220 | | | | | 225 | | | | | 230 | | |
| AAT | AAG | ATT | GAC | CTT | TAT | GAT | GTA | CGC | AGA | AGA | CCA | TGG | TAC | ATC | CAA | 772 |
| Asn | Lys | Ile | Asp | Leu | Tyr | Asp | Val | Arg | Arg | Arg | Pro | Trp | Tyr | Ile | Gln | |
| | | | | 235 | | | | | 240 | | | | | 245 | | |
| GGA | GCT | GCA | TCT | CCT | AAA | GAC | ATG | CTT | ATT | CTG | GTG | GAT | GTG | AGT | GGA | 820 |
| Gly | Ala | Ala | Ser | Pro | Lys | Asp | Met | Leu | Ile | Leu | Val | Asp | Val | Ser | Gly | |
| | | | 250 | | | | | 255 | | | | | 260 | | | |
| AGT | GTT | AGT | GGA | TTG | ACA | CTT | AAA | CTG | ATC | CGA | ACA | TCT | GTC | TCC | GAA | 868 |
| Ser | Val | Ser | Gly | Leu | Thr | Leu | Lys | Leu | Ile | Arg | Thr | Ser | Val | Ser | Glu | |
| | | 265 | | | | | 270 | | | | | 275 | | | | |
| ATG | TTA | GAA | ACC | CTC | TCA | GAT | GAT | GAT | TTC | GTG | AAT | GTA | GCT | TCA | TTT | 916 |
| Met | Leu | Glu | Thr | Leu | Ser | Asp | Asp | Asp | Phe | Val | Asn | Val | Ala | Ser | Phe | |
| | 280 | | | | | 285 | | | | | 290 | | | | | |
| AAC | AGC | AAT | GCT | CAG | GAT | GTA | AGC | TGT | TTT | CAG | CAC | CTT | GTC | CAA | GCA | 964 |
| Asn | Ser | Asn | Ala | Gln | Asp | Val | Ser | Cys | Phe | Gln | His | Leu | Val | Gln | Ala | |
| 295 | | | | 300 | | | | | 305 | | | | | 310 | | |
| AAT | GTA | AGA | AAT | AAA | AAA | GTG | TTG | AAA | GAC | GCG | GTG | AAT | AAT | ATC | ACA | 1012 |
| Asn | Val | Arg | Asn | Lys | Lys | Val | Leu | Lys | Asp | Ala | Val | Asn | Asn | Ile | Thr | |
| | | | | 315 | | | | | 320 | | | | | 325 | | |
| GCC | AAA | GGA | ATT | ACA | GAT | TAT | AAG | AAG | GGC | TTT | AGT | TTT | GCT | TTT | GAA | 1060 |
| Ala | Lys | Gly | Ile | Thr | Asp | Tyr | Lys | Lys | Gly | Phe | Ser | Phe | Ala | Phe | Glu | |
| | | | 330 | | | | | 335 | | | | | 340 | | | |
| CAG | CTG | CTT | AAT | TAT | AAT | GTT | TCC | AGA | GCA | AAC | TGC | AAT | AAG | ATT | ATT | 1108 |
| Gln | Leu | Leu | Asn | Tyr | Asn | Val | Ser | Arg | Ala | Asn | Cys | Asn | Lys | Ile | Ile | |
| | | 345 | | | | | 350 | | | | | 355 | | | | |
| ATG | CTA | TTC | ACG | GAT | GGA | GGA | GAA | GAG | AGA | GCC | CAG | GAG | ATA | TTT | AAC | 1156 |
| Met | Leu | Phe | Thr | Asp | Gly | Gly | Glu | Glu | Arg | Ala | Gln | Glu | Ile | Phe | Asn | |
| | 360 | | | | | 365 | | | | | 370 | | | | | |
| AAA | TAC | AAT | AAA | GAT | AAA | AAA | GTA | CGT | GTA | TTC | AGG | TTT | TCA | GTT | GGT | 1204 |
| Lys | Tyr | Asn | Lys | Asp | Lys | Lys | Val | Arg | Val | Phe | Arg | Phe | Ser | Val | Gly | |
| 375 | | | | 380 | | | | | 385 | | | | | 390 | | |
| CAA | CAC | AAT | TAT | GAG | AGA | GGA | CCT | ATT | CAG | TGG | ATG | GCC | TGT | GAA | AAC | 1252 |
| Gln | His | Asn | Tyr | Glu | Arg | Gly | Pro | Ile | Gln | Trp | Met | Ala | Cys | Glu | Asn | |
| | | | | 395 | | | | | 400 | | | | | 405 | | |
| AAA | GGT | TAT | TAT | TAT | GAA | ATT | CCT | TCC | ATT | GGT | GCA | ATA | AGA | ATC | AAT | 1300 |
| Lys | Gly | Tyr | Tyr | Tyr | Glu | Ile | Pro | Ser | Ile | Gly | Ala | Ile | Arg | Ile | Asn | |
| | | | 410 | | | | | 415 | | | | | 420 | | | |
| ACT | CAG | GAA | TAT | TTG | GAT | GTT | TTG | GGA | AGA | CCA | ATG | GTT | TTA | GCA | GGA | 1348 |
| Thr | Gln | Glu | Tyr | Leu | Asp | Val | Leu | Gly | Arg | Pro | Met | Val | Leu | Ala | Gly | |
| | | 425 | | | | | 430 | | | | | 435 | | | | |
| GAC | AAA | GCT | AAG | CAA | GTC | CAA | TGG | ACA | AAT | GTG | TAC | CTG | GAT | GCA | TTG | 1396 |
| Asp | Lys | Ala | Lys | Gln | Val | Gln | Trp | Thr | Asn | Val | Tyr | Leu | Asp | Ala | Leu | |
| | 440 | | | | | 445 | | | | | 450 | | | | | |
| GAA | CTG | GGA | CTT | GTC | ATT | ACT | GGA | ACT | CTT | CCG | GTC | TTC | AAC | ATA | ACC | 1444 |
| Glu | Leu | Gly | Leu | Val | Ile | Thr | Gly | Thr | Leu | Pro | Val | Phe | Asn | Ile | Thr | |
| 455 | | | | 460 | | | | | 465 | | | | | 470 | | |
| GGC | CAA | TTT | GAA | AAT | AAG | ACA | AAC | TTA | AAG | AAC | CAG | CTG | ATT | CTT | GGT | 1492 |
| Gly | Gln | Phe | Glu | Asn | Lys | Thr | Asn | Leu | Lys | Asn | Gln | Leu | Ile | Leu | Gly | |
| | | | | 475 | | | | | 480 | | | | | 485 | | |
| GTG | ATG | GGA | GTA | GAT | GTG | TCT | TTG | GAA | GAT | ATT | AAA | AGA | CTG | ACA | CCA | 1540 |
| Val | Met | Gly | Val | Asp | Val | Ser | Leu | Glu | Asp | Ile | Lys | Arg | Leu | Thr | Pro | |
| | | | 490 | | | | | 495 | | | | | 500 | | | |
| CGT | TTT | ACA | CTG | TGC | CCC | AAT | GGG | TAT | TAC | TTT | GCA | ATC | GAT | CCT | AAT | 1588 |
| Arg | Phe | Thr | Leu | Cys | Pro | Asn | Gly | Tyr | Tyr | Phe | Ala | Ile | Asp | Pro | Asn | |
| | | 505 | | | | | 510 | | | | | 515 | | | | |
| GGT | TAT | GTT | TTA | TTA | CAT | CCA | AAT | CTT | CAG | CCA | AAG | AAC | CCC | AAA | TCT | 1636 |
| Gly | Tyr | Val | Leu | Leu | His | Pro | Asn | Leu | Gln | Pro | Lys | Asn | Pro | Lys | Ser | |
| | 520 | | | | | 525 | | | | | 530 | | | | | |

| | | | | | | | | | | | | | | | | |
|---|---|---|---|---|---|---|---|---|---|---|---|---|---|---|---|---|
| CAG | GAG | CCA | GTA | ACA | TTG | GAT | TTC | CTT | GAT | GCA | GAG | TTA | GAG | AAT | GAT | 1684 |
| Gln | Glu | Pro | Val | Thr | Leu | Asp | Phe | Leu | Asp | Ala | Glu | Leu | Glu | Asn | Asp | |
| 535 | | | | 540 | | | | | 545 | | | | | | 550 | |
| ATT | AAA | GTG | GAG | ATT | CGA | AAT | AAG | ATG | ATT | GAT | GGG | GAA | AGT | GGA | GAA | 1732 |
| Ile | Lys | Val | Glu | Ile | Arg | Asn | Lys | Met | Ile | Asp | Gly | Glu | Ser | Gly | Glu | |
| | | | | 555 | | | | | 560 | | | | | 565 | | |
| AAA | ACA | TTC | AGA | ACT | CTG | GTT | AAA | TCT | CAA | GAT | GAG | AGA | TAT | ATT | GAC | 1780 |
| Lys | Thr | Phe | Arg | Thr | Leu | Val | Lys | Ser | Gln | Asp | Glu | Arg | Tyr | Ile | Asp | |
| | | | 570 | | | | | 575 | | | | | 580 | | | |
| AAA | GGA | AAC | AGG | ACA | TAC | ACA | TGG | ACA | CCT | GTC | AAT | GGC | ACA | GAT | TAC | 1828 |
| Lys | Gly | Asn | Arg | Thr | Tyr | Thr | Trp | Thr | Pro | Val | Asn | Gly | Thr | Asp | Tyr | |
| | | 585 | | | | | 590 | | | | | 595 | | | | |
| AGT | TTG | GCC | TTG | GTA | TTA | CCA | ACC | TAC | AGT | TTT | TAC | TAT | ATA | AAA | GCC | 1876 |
| Ser | Leu | Ala | Leu | Val | Leu | Pro | Thr | Tyr | Ser | Phe | Tyr | Tyr | Ile | Lys | Ala | |
| | 600 | | | | | 605 | | | | | 610 | | | | | |
| AAA | CTA | GAA | GAG | ACA | ATA | ACT | CAG | GCC | AGA | TCA | AAA | AAG | GGC | AAA | ATG | 1924 |
| Lys | Leu | Glu | Glu | Thr | Ile | Thr | Gln | Ala | Arg | Ser | Lys | Lys | Gly | Lys | Met | |
| 615 | | | | 620 | | | | | 625 | | | | | 630 | | |
| AAG | GAT | TCG | GAA | ACC | CTG | AAG | CCA | GAT | AAT | TTT | GAA | GAA | TCT | GGC | TAT | 1972 |
| Lys | Asp | Ser | Glu | Thr | Leu | Lys | Pro | Asp | Asn | Phe | Glu | Glu | Ser | Gly | Tyr | |
| | | | | 635 | | | | | 640 | | | | | 645 | | |
| ACA | TTC | ATA | GCA | CCA | AGA | GAT | TAC | TGC | AAT | GAC | CTG | AAA | ATA | TCG | GAT | 2020 |
| Thr | Phe | Ile | Ala | Pro | Arg | Asp | Tyr | Cys | Asn | Asp | Leu | Lys | Ile | Ser | Asp | |
| | | | 650 | | | | | 655 | | | | | 660 | | | |
| AAT | AAC | ACT | GAA | TTT | CTT | TTA | AAT | TTC | AAC | GAG | TTT | ATT | GAT | AGA | AAA | 2068 |
| Asn | Asn | Thr | Glu | Phe | Leu | Leu | Asn | Phe | Asn | Glu | Phe | Ile | Asp | Arg | Lys | |
| | | 665 | | | | | 670 | | | | | 675 | | | | |
| ACT | CCA | AAC | AAC | CCA | TCA | TGT | AAC | GCG | GAT | TTG | ATT | AAT | AGA | GTC | TTG | 2116 |
| Thr | Pro | Asn | Asn | Pro | Ser | Cys | Asn | Ala | Asp | Leu | Ile | Asn | Arg | Val | Leu | |
| | 680 | | | | | 685 | | | | | 690 | | | | | |
| CTT | GAT | GCA | GGC | TTT | ACA | AAT | GAA | CTT | GTC | CAA | AAT | TAC | TGG | AGT | AAG | 2164 |
| Leu | Asp | Ala | Gly | Phe | Thr | Asn | Glu | Leu | Val | Gln | Asn | Tyr | Trp | Ser | Lys | |
| 695 | | | | 700 | | | | | 705 | | | | | 710 | | |
| CAG | AAA | AAT | ATC | AAG | GGA | GTG | AAA | GCA | CGA | TTT | GTT | GTG | ACT | GAT | GGT | 2212 |
| Gln | Lys | Asn | Ile | Lys | Gly | Val | Lys | Ala | Arg | Phe | Val | Val | Thr | Asp | Gly | |
| | | | | 715 | | | | | 720 | | | | | 725 | | |
| GGG | ATT | ACC | AGA | GTT | TAT | CCC | AAA | GAG | GCT | GGA | GAA | AAT | TGG | CAA | GAA | 2260 |
| Gly | Ile | Thr | Arg | Val | Tyr | Pro | Lys | Glu | Ala | Gly | Glu | Asn | Trp | Gln | Glu | |
| | | | 730 | | | | | 735 | | | | | 740 | | | |
| AAC | CCA | GAG | ACA | TAT | GAG | GAC | AGC | TTC | TAT | AAA | AGG | AGC | CTA | GAT | AAT | 2308 |
| Asn | Pro | Glu | Thr | Tyr | Glu | Asp | Ser | Phe | Tyr | Lys | Arg | Ser | Leu | Asp | Asn | |
| | | 745 | | | | | 750 | | | | | 755 | | | | |
| GAT | AAC | TAT | GTT | TTC | ACT | GCT | CCC | TAC | TTT | AAC | AAA | AGT | GGA | CCT | GGT | 2356 |
| Asp | Asn | Tyr | Val | Phe | Thr | Ala | Pro | Tyr | Phe | Asn | Lys | Ser | Gly | Pro | Gly | |
| | 760 | | | | | 765 | | | | | 770 | | | | | |
| GCC | TAT | GAA | TCG | GGC | ATT | ATG | GTA | AGC | AAA | GCT | GTA | GAA | ATA | TAT | ATT | 2404 |
| Ala | Tyr | Glu | Ser | Gly | Ile | Met | Val | Ser | Lys | Ala | Val | Glu | Ile | Tyr | Ile | |
| 775 | | | | 780 | | | | | 785 | | | | | 790 | | |
| CAA | GGG | AAA | CTT | CTT | AAA | CCT | GCA | GTT | GTT | GGA | ATT | AAA | ATT | GAT | GTA | 2452 |
| Gln | Gly | Lys | Leu | Leu | Lys | Pro | Ala | Val | Val | Gly | Ile | Lys | Ile | Asp | Val | |
| | | | | 795 | | | | | 800 | | | | | 805 | | |
| AAT | TCC | TGG | ATA | GAG | AAT | TTC | ACC | AAA | ACC | TCA | ATC | AGA | GAT | CCG | TGT | 2500 |
| Asn | Ser | Trp | Ile | Glu | Asn | Phe | Thr | Lys | Thr | Ser | Ile | Arg | Asp | Pro | Cys | |
| | | | 810 | | | | | 815 | | | | | 820 | | | |
| GCT | GGT | CCA | GTT | TGT | GAC | TGC | AAA | AGA | AAC | AGT | GAC | GTA | ATG | GAT | TGT | 2548 |
| Ala | Gly | Pro | Val | Cys | Asp | Cys | Lys | Arg | Asn | Ser | Asp | Val | Met | Asp | Cys | |
| | | 825 | | | | | 830 | | | | | 835 | | | | |
| GTG | ATT | CTG | GAT | GAT | GGT | GGG | TTT | CTT | CTG | ATG | GCA | AAT | CAT | GAT | GAT | 2596 |
| Val | Ile | Leu | Asp | Asp | Gly | Gly | Phe | Leu | Leu | Met | Ala | Asn | His | Asp | Asp | |
| | 840 | | | | | 845 | | | | | 850 | | | | | |

```
TAT ACT AAT CAG ATT GGA AGA TTT TTT GGA GAG ATT GAT CCC AGC TTG     2644
Tyr Thr Asn Gln Ile Gly Arg Phe Phe Gly Glu Ile Asp Pro Ser Leu
855             860                 865                 870

ATG AGA CAC CTG GTT AAT ATA TCA GTT TAT GCT TTT AAC AAA TCT TAT     2692
Met Arg His Leu Val Asn Ile Ser Val Tyr Ala Phe Asn Lys Ser Tyr
                875                 880                 885

GAT TAT CAG TCA GTA TGT GAG CCC GGT GCT GCA CCA AAA CAA GGA GCA     2740
Asp Tyr Gln Ser Val Cys Glu Pro Gly Ala Ala Pro Lys Gln Gly Ala
            890                 895                 900

GGA CAT CGC TCA GCA TAT GTG CCA TCA GTA GCA GAC ATA TTA CAA ATT     2788
Gly His Arg Ser Ala Tyr Val Pro Ser Val Ala Asp Ile Leu Gln Ile
        905                 910                 915

GGC TGG TGG GCC ACT GCT GCT GCC TGG TCT ATT CTA CAG CAG TTT CTC     2836
Gly Trp Trp Ala Thr Ala Ala Ala Trp Ser Ile Leu Gln Gln Phe Leu
    920                 925                 930

TTG AGT TTG ACC TTT CCA CGA CTC CTT GAG GCA GTT GAG ATG GAG GAT     2884
Leu Ser Leu Thr Phe Pro Arg Leu Leu Glu Ala Val Glu Met Glu Asp
935                 940                 945                 950

GAT GAC TTC ACG GCC TCC CTG TCC AAG CAG AGC TGC ATT ACT GAA CAA     2932
Asp Asp Phe Thr Ala Ser Leu Ser Lys Gln Ser Cys Ile Thr Glu Gln
            955                 960                 965

ACC CAG TAT TTC TTC GAT AAC GAC AGT AAA TCA TTC AGT GGT GTA TTA     2980
Thr Gln Tyr Phe Phe Asp Asn Asp Ser Lys Ser Phe Ser Gly Val Leu
        970                 975                 980

GAC TGT GGA AAC TGT TCC AGA ATC TTT CAT GGA GAA AAG CTT ATG AAC     3028
Asp Cys Gly Asn Cys Ser Arg Ile Phe His Gly Glu Lys Leu Met Asn
    985                 990                 995

ACC AAC TTA ATA TTC ATA ATG GTT GAG AGC AAA GGG ACA TGT CCA TGT     3076
Thr Asn Leu Ile Phe Ile Met Val Glu Ser Lys Gly Thr Cys Pro Cys
1000                1005                1010

GAC ACA CGA CTG CTC ATA CAA GCG GAG CAG ACT TCT GAC GGT CCA AAT     3124
Asp Thr Arg Leu Leu Ile Gln Ala Glu Gln Thr Ser Asp Gly Pro Asn
1015                1020                1025                1030

CCT TGT GAC ATG GTT AAG CAA CCT AGA TAC CGA AAA GGG CCT GAT GTC     3172
Pro Cys Asp Met Val Lys Gln Pro Arg Tyr Arg Lys Gly Pro Asp Val
            1035                1040                1045

TGC TTT GAT AAC AAT GTC TTG GAG GAT TAT ACT GAC TGT GGT GGT GTT     3220
Cys Phe Asp Asn Asn Val Leu Glu Asp Tyr Thr Asp Cys Gly Gly Val
        1050                1055                1060

TCT GGA TTA AAT CCC TCC CTG TGG TAT ATC ATT GGA ATC CAG TTT CTA     3268
Ser Gly Leu Asn Pro Ser Leu Trp Tyr Ile Ile Gly Ile Gln Phe Leu
    1065                1070                1075

CTA CTT TGG CTG GTA TCT GGC AGC ACA CAC CGG CTG TTA TGACCTTCTA     3317
Leu Leu Trp Leu Val Ser Gly Ser Thr His Arg Leu Leu
1080                1085                1090

AAAACCAAAT CTGCATAGTT AAACTCCAGA CCCTGCCAAA ACATGAGCCC TGCCCTCAAT  3377

TACAGTAACG TAGGGTCAGC TATAAAATCA GACAAACATT AGCTGGGCCT GTTCCATGGC  3437

ATAACACTAA GGCGCAGACT CCTAAGGCAC CCACTGGCTG CATGTCAGGG TGTCAGATCC  3497

TTAAACGTGT GTGAATGCTG CATCATCTAT GTGTAACATC AAAGCAAAAT CCTATACGTG  3557

TCCTCTATTG GAAAATTTGG GCGTTTGTTG TTGCATTGTT GGT                    3600
```

( 2 ) INFORMATION FOR SEQ ID NO:34:

( i ) SEQUENCE CHARACTERISTICS:
        ( A ) LENGTH: 3585 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
    ( A ) NAME/KEY: CDS
    ( B ) LOCATION: 35..3295
    ( D ) OTHER INFORMATION: /standard_name="Alpha-2c"

( i x ) FEATURE:
    ( A ) NAME/KEY: 5'UTR
    ( B ) LOCATION: 1..34

( i x ) FEATURE:
    ( A ) NAME/KEY: 3'UTR
    ( B ) LOCATION: 3296..3585

( x i ) SEQUENCE DESCRIPTION: SEQ ID NO:34:

```
GCGGGGGAGG GGGCATTGAT CTTCGATCGC GAAG ATG GCT GCT GGC TGC CTG           52
                                     Met Ala Ala Gly Cys Leu
                                      1               5

CTG GCC TTG ACT CTG ACA CTT TTC CAA TCT TTG CTC ATC GGC CCC TCG        100
Leu Ala Leu Thr Leu Thr Leu Phe Gln Ser Leu Leu Ile Gly Pro Ser
            10                  15                  20

TCG GAG GAG CCG TTC CCT TCG GCC GTC ACT ATC AAA TCA TGG GTG GAT        148
Ser Glu Glu Pro Phe Pro Ser Ala Val Thr Ile Lys Ser Trp Val Asp
        25                  30                  35

AAG ATG CAA GAA GAC CTT GTC ACA CTG GCA AAA ACA GCA AGT GGA GTC        196
Lys Met Gln Glu Asp Leu Val Thr Leu Ala Lys Thr Ala Ser Gly Val
    40                  45                  50

AAT CAG CTT GTT GAT ATT TAT GAG AAA TAT CAA GAT TTG TAT ACT GTG        244
Asn Gln Leu Val Asp Ile Tyr Glu Lys Tyr Gln Asp Leu Tyr Thr Val
55                  60                  65                  70

GAA CCA AAT AAT GCA CGC CAG CTG GTA GAA ATT GCA GCC AGG GAT ATT        292
Glu Pro Asn Asn Ala Arg Gln Leu Val Glu Ile Ala Ala Arg Asp Ile
                75                  80                  85

GAG AAA CTT CTG AGC AAC AGA TCT AAA GCC CTG GTG AGC CTG GCA TTG        340
Glu Lys Leu Leu Ser Asn Arg Ser Lys Ala Leu Val Ser Leu Ala Leu
            90                  95                 100

GAA GCG GAG AAA GTT CAA GCA GCT CAC CAG TGG AGA GAA GAT TTT GCA        388
Glu Ala Glu Lys Val Gln Ala Ala His Gln Trp Arg Glu Asp Phe Ala
        105                 110                 115

AGC AAT GAA GTT GTC TAC TAC AAT GCA AAG GAT GAT CTC GAT CCT GAG        436
Ser Asn Glu Val Val Tyr Tyr Asn Ala Lys Asp Asp Leu Asp Pro Glu
    120                 125                 130

AAA AAT GAC AGT GAG CCA GGC AGC CAG AGG ATA AAA CCT GTT TTC ATT        484
Lys Asn Asp Ser Glu Pro Gly Ser Gln Arg Ile Lys Pro Val Phe Ile
135                 140                 145                 150

GAA GAT GCT AAT TTT GGA CGA CAA ATA TCT TAT CAG CAC GCA GCA GTC        532
Glu Asp Ala Asn Phe Gly Arg Gln Ile Ser Tyr Gln His Ala Ala Val
                155                 160                 165

CAT ATT CCT ACT GAC ATC TAT GAG GGC TCA ACA ATT GTG TTA AAT GAA        580
His Ile Pro Thr Asp Ile Tyr Glu Gly Ser Thr Ile Val Leu Asn Glu
            170                 175                 180

CTC AAC TGG ACA AGT GCC TTA GAT GAA GTT TTC AAA AAG AAT CGC GAG        628
Leu Asn Trp Thr Ser Ala Leu Asp Glu Val Phe Lys Lys Asn Arg Glu
        185                 190                 195

GAA GAC CCT TCA TTA TTG TGG CAG GTT TTT GGC AGT GCC ACT GGC CTA        676
Glu Asp Pro Ser Leu Leu Trp Gln Val Phe Gly Ser Ala Thr Gly Leu
    200                 205                 210

GCT CGA TAT TAT CCA GCT TCA CCA TGG GTT GAT AAT AGT AGA ACT CCA        724
Ala Arg Tyr Tyr Pro Ala Ser Pro Trp Val Asp Asn Ser Arg Thr Pro
215                 220                 225                 230

AAT AAG ATT GAC CTT TAT GAT GTA CGC AGA AGA CCA TGG TAC ATC CAA        772
Asn Lys Ile Asp Leu Tyr Asp Val Arg Arg Arg Pro Trp Tyr Ile Gln
                235                 240                 245
```

| | | | | | | | | | | | | | | | | |
|---|---|---|---|---|---|---|---|---|---|---|---|---|---|---|---|---|
| GGA | GCT | GCA | TCT | CCT | AAA | GAC | ATG | CTT | ATT | CTG | GTG | GAT | GTG | AGT | GGA | 820 |
| Gly | Ala | Ala | Ser 250 | Pro | Lys | Asp | Met | Leu 255 | Ile | Leu | Val | Asp | Val 260 | Ser | Gly | |
| AGT | GTT | AGT | GGA | TTG | ACA | CTT | AAA | CTG | ATC | CGA | ACA | TCT | GTC | TCC | GAA | 868 |
| Ser | Val | Ser 265 | Gly | Leu | Thr | Leu | Lys 270 | Leu | Ile | Arg | Thr | Ser 275 | Val | Ser | Glu | |
| ATG | TTA | GAA | ACC | CTC | TCA | GAT | GAT | GAT | TTC | GTG | AAT | GTA | GCT | TCA | TTT | 916 |
| Met | Leu 280 | Glu | Thr | Leu | Ser | Asp 285 | Asp | Asp | Phe | Val | Asn 290 | Val | Ala | Ser | Phe | |
| AAC | AGC | AAT | GCT | CAG | GAT | GTA | AGC | TGT | TTT | CAG | CAC | CTT | GTC | CAA | GCA | 964 |
| Asn 295 | Ser | Asn | Ala | Gln | Asp 300 | Val | Ser | Cys | Phe | Gln 305 | His | Leu | Val | Gln | Ala 310 | |
| AAT | GTA | AGA | AAT | AAA | AAA | GTG | TTG | AAA | GAC | GCG | GTG | AAT | AAT | ATC | ACA | 1012 |
| Asn | Val | Arg | Asn | Lys 315 | Lys | Val | Leu | Lys | Asp 320 | Ala | Val | Asn | Asn | Ile 325 | Thr | |
| GCC | AAA | GGA | ATT | ACA | GAT | TAT | AAG | AAG | GGC | TTT | AGT | TTT | GCT | TTT | GAA | 1060 |
| Ala | Lys | Gly | Ile 330 | Thr | Asp | Tyr | Lys | Lys 335 | Gly | Phe | Ser | Phe | Ala 340 | Phe | Glu | |
| CAG | CTG | CTT | AAT | TAT | AAT | GTT | TCC | AGA | GCA | AAC | TGC | AAT | AAG | ATT | ATT | 1108 |
| Gln | Leu | Leu | Asn 345 | Tyr | Asn | Val | Ser | Arg 350 | Ala | Asn | Cys | Asn | Lys 355 | Ile | Ile | |
| ATG | CTA | TTC | ACG | GAT | GGA | GGA | GAA | GAG | AGA | GCC | CAG | GAG | ATA | TTT | AAC | 1156 |
| Met | Leu 360 | Phe | Thr | Asp | Gly | Gly 365 | Glu | Glu | Arg | Ala | Gln 370 | Glu | Ile | Phe | Asn | |
| AAA | TAC | AAT | AAA | GAT | AAA | AAA | GTA | CGT | GTA | TTC | AGG | TTT | TCA | GTT | GGT | 1204 |
| Lys 375 | Tyr | Asn | Lys | Asp | Lys 380 | Lys | Val | Arg | Val | Phe 385 | Arg | Phe | Ser | Val | Gly 390 | |
| CAA | CAC | AAT | TAT | GAG | AGA | GGA | CCT | ATT | CAG | TGG | ATG | GCC | TGT | GAA | AAC | 1252 |
| Gln | His | Asn | Tyr | Glu 395 | Arg | Gly | Pro | Ile | Gln 400 | Trp | Met | Ala | Cys | Glu 405 | Asn | |
| AAA | GGT | TAT | TAT | TAT | GAA | ATT | CCT | TCC | ATT | GGT | GCA | ATA | AGA | ATC | AAT | 1300 |
| Lys | Gly | Tyr | Tyr 410 | Tyr | Glu | Ile | Pro | Ser 415 | Ile | Gly | Ala | Ile | Arg 420 | Ile | Asn | |
| ACT | CAG | GAA | TAT | TTG | GAT | GTT | TTG | GGA | AGA | CCA | ATG | GTT | TTA | GCA | GGA | 1348 |
| Thr | Gln | Glu | Tyr | Leu 425 | Asp | Val | Leu | Gly | Arg 430 | Pro | Met | Val | Leu | Ala 435 | Gly | |
| GAC | AAA | GCT | AAG | CAA | GTC | CAA | TGG | ACA | AAT | GTG | TAC | CTG | GAT | GCA | TTG | 1396 |
| Asp | Lys | Ala | Lys 440 | Gln | Val | Gln | Trp | Thr 445 | Asn | Val | Tyr | Leu | Asp 450 | Ala | Leu | |
| GAA | CTG | GGA | CTT | GTC | ATT | ACT | GGA | ACT | CTT | CCG | GTC | TTC | AAC | ATA | ACC | 1444 |
| Glu 455 | Leu | Gly | Leu | Val | Ile 460 | Thr | Gly | Thr | Leu | Pro 465 | Val | Phe | Asn | Ile | Thr 470 | |
| GGC | CAA | TTT | GAA | AAT | AAG | ACA | AAC | TTA | AAG | AAC | CAG | CTG | ATT | CTT | GGT | 1492 |
| Gly | Gln | Phe | Glu | Asn 475 | Lys | Thr | Asn | Leu | Lys 480 | Asn | Gln | Leu | Ile | Leu 485 | Gly | |
| GTG | ATG | GGA | GTA | GAT | GTG | TCT | TTG | GAA | GAT | ATT | AAA | AGA | CTG | ACA | CCA | 1540 |
| Val | Met | Gly | Val 490 | Asp | Val | Ser | Leu | Glu 495 | Asp | Ile | Lys | Arg | Leu 500 | Thr | Pro | |
| CGT | TTT | ACA | CTG | TGC | CCC | AAT | GGG | TAT | TAC | TTT | GCA | ATC | GAT | CCT | AAT | 1588 |
| Arg | Phe | Thr 505 | Leu | Cys | Pro | Asn | Gly 510 | Tyr | Tyr | Phe | Ala | Ile 515 | Asp | Pro | Asn | |
| GGT | TAT | GTT | TTA | TTA | CAT | CCA | AAT | CTT | CAG | CCA | AAG | GAG | CCA | GTA | ACA | 1636 |
| Gly | Tyr 520 | Val | Leu | Leu | His | Pro 525 | Asn | Leu | Gln | Pro | Lys 530 | Glu | Pro | Val | Thr | |
| TTG | GAT | TTC | CTT | GAT | GCA | GAG | TTA | GAG | AAT | GAT | ATT | AAA | GTG | GAG | ATT | 1684 |
| Leu 535 | Asp | Phe | Leu | Asp | Ala 540 | Glu | Leu | Glu | Asn | Asp 545 | Ile | Lys | Val | Glu | Ile 550 | |
| CGA | AAT | AAG | ATG | ATT | GAT | GGG | GAA | AGT | GGA | GAA | AAA | ACA | TTC | AGA | ACT | 1732 |
| Arg | Asn | Lys | Met | Ile 555 | Asp | Gly | Glu | Ser | Gly 560 | Glu | Lys | Thr | Phe | Arg 565 | Thr | |

-continued

| | | | | | | | | | | | | | | | | |
|---|---|---|---|---|---|---|---|---|---|---|---|---|---|---|---|---|
| CTG | GTT | AAA | TCT | CAA | GAT | GAG | AGA | TAT | ATT | GAC | AAA | GGA | AAC | AGG | ACA | 1780 |
| Leu | Val | Lys | Ser 570 | Gln | Asp | Glu | Arg | Tyr 575 | Ile | Asp | Lys | Gly | Asn 580 | Arg | Thr | |
| TAC | ACA | TGG | ACA | CCT | GTC | AAT | GGC | ACA | GAT | TAC | AGT | TTG | GCC | TTG | GTA | 1828 |
| Tyr | Thr | Trp 585 | Thr | Pro | Val | Asn | Gly 590 | Thr | Asp | Tyr | Ser | Leu 595 | Ala | Leu | Val | |
| TTA | CCA | ACC | TAC | AGT | TTT | TAC | TAT | ATA | AAA | GCC | AAA | CTA | GAA | GAG | ACA | 1876 |
| Leu | Pro 600 | Thr | Tyr | Ser | Phe | Tyr 605 | Tyr | Ile | Lys | Ala | Lys 610 | Leu | Glu | Glu | Thr | |
| ATA | ACT | CAG | GCC | AGA | TCA | AAA | AAG | GGC | AAA | ATG | AAG | GAT | TCG | GAA | ACC | 1924 |
| Ile 615 | Thr | Gln | Ala | Arg | Ser 620 | Lys | Lys | Gly | Lys | Met 625 | Lys | Asp | Ser | Glu | Thr 630 | |
| CTG | AAG | CCA | GAT | AAT | TTT | GAA | GAA | TCT | GGC | TAT | ACA | TTC | ATA | GCA | CCA | 1972 |
| Leu | Lys | Pro | Asp | Asn 635 | Phe | Glu | Glu | Ser | Gly 640 | Tyr | Thr | Phe | Ile | Ala 645 | Pro | |
| AGA | GAT | TAC | TGC | AAT | GAC | CTG | AAA | ATA | TCG | GAT | AAT | AAC | ACT | GAA | TTT | 2020 |
| Arg | Asp | Tyr | Cys 650 | Asn | Asp | Leu | Lys | Ile 655 | Ser | Asp | Asn | Asn | Thr 660 | Glu | Phe | |
| CTT | TTA | AAT | TTC | AAC | GAG | TTT | ATT | GAT | AGA | AAA | ACT | CCA | AAC | AAC | CCA | 2068 |
| Leu | Leu | Asn 665 | Phe | Asn | Glu | Phe | Ile 670 | Asp | Arg | Lys | Thr | Pro 675 | Asn | Asn | Pro | |
| TCA | TGT | AAC | GCG | GAT | TTG | ATT | AAT | AGA | GTC | TTG | CTT | GAT | GCA | GGC | TTT | 2116 |
| Ser | Cys 680 | Asn | Ala | Asp | Leu | Ile 685 | Asn | Arg | Val | Leu | Leu 690 | Asp | Ala | Gly | Phe | |
| ACA | AAT | GAA | CTT | GTC | CAA | AAT | TAC | TGG | AGT | AAG | CAG | AAA | AAT | ATC | AAG | 2164 |
| Thr | Asn | Glu 695 | Leu | Val | Gln | Asn | Tyr 700 | Trp | Ser | Lys | Gln | Lys 705 | Asn | Ile | Lys 710 | |
| GGA | GTG | AAA | GCA | CGA | TTT | GTT | GTG | ACT | GAT | GGT | GGG | ATT | ACC | AGA | GTT | 2212 |
| Gly | Val | Lys | Ala | Arg 715 | Phe | Val | Val | Thr | Asp 720 | Gly | Gly | Ile | Thr | Arg 725 | Val | |
| TAT | CCC | AAA | GAG | GCT | GGA | GAA | AAT | TGG | CAA | GAA | AAC | CCA | GAG | ACA | TAT | 2260 |
| Tyr | Pro | Lys | Glu | Ala 730 | Gly | Glu | Asn | Trp | Gln 735 | Glu | Asn | Pro | Glu 740 | Thr | Tyr | |
| GAG | GAC | AGC | TTC | TAT | AAA | AGG | AGC | CTA | GAT | AAT | GAT | AAC | TAT | GTT | TTC | 2308 |
| Glu | Asp | Ser 745 | Phe | Tyr | Lys | Arg | Ser 750 | Leu | Asp | Asn | Asp | Asn 755 | Tyr | Val | Phe | |
| ACT | GCT | CCC | TAC | TTT | AAC | AAA | AGT | GGA | CCT | GGT | GCC | TAT | GAA | TCG | GGC | 2356 |
| Thr | Ala | Pro | Tyr 760 | Phe | Asn | Lys | Ser | Gly 765 | Pro | Gly | Ala | Tyr | Glu 770 | Ser | Gly | |
| ATT | ATG | GTA | AGC | AAA | GCT | GTA | GAA | ATA | TAT | ATT | CAA | GGG | AAA | CTT | CTT | 2404 |
| Ile | Met | Val 775 | Ser | Lys | Ala | Val 780 | Glu | Ile | Tyr | Ile | Gln 785 | Gly | Lys | Leu | Leu 790 | |
| AAA | CCT | GCA | GTT | GTT | GGA | ATT | AAA | ATT | GAT | GTA | AAT | TCC | TGG | ATA | GAG | 2452 |
| Lys | Pro | Ala | Val | Val 795 | Gly | Ile | Lys | Ile | Asp 800 | Val | Asn | Ser | Trp | Ile 805 | Glu | |
| AAT | TTC | ACC | AAA | ACC | TCA | ATC | AGA | GAT | CCG | TGT | GCT | GGT | CCA | GTT | TGT | 2500 |
| Asn | Phe | Thr | Lys | Thr 810 | Ser | Ile | Arg | Asp | Pro 815 | Cys | Ala | Gly | Pro 820 | Val | Cys | |
| GAC | TGC | AAA | AGA | AAC | AGT | GAC | GTA | ATG | GAT | TGT | GTG | ATT | CTG | GAT | GAT | 2548 |
| Asp | Cys | Lys 825 | Arg | Asn | Ser | Asp | Val 830 | Met | Asp | Cys | Val | Ile 835 | Leu | Asp | Asp | |
| GGT | GGG | TTT | CTT | CTG | ATG | GCA | AAT | CAT | GAT | GAT | TAT | ACT | AAT | CAG | ATT | 2596 |
| Gly | Gly 840 | Phe | Leu | Leu | Met | Ala 845 | Asn | His | Asp | Asp | Tyr 850 | Thr | Asn | Gln | Ile | |
| GGA | AGA | TTT | TTT | GGA | GAG | ATT | GAT | CCC | AGC | TTG | ATG | AGA | CAC | CTG | GTT | 2644 |
| Gly | Arg 855 | Phe | Phe | Gly | Glu | Ile 860 | Asp | Pro | Ser | Leu | Met 865 | Arg | His | Leu | Val 870 | |
| AAT | ATA | TCA | GTT | TAT | GCT | TTT | AAC | AAA | TCT | TAT | GAT | TAT | CAG | TCA | GTA | 2692 |
| Asn | Ile | Ser | Val | Tyr 875 | Ala | Phe | Asn | Lys | Ser 880 | Tyr | Asp | Tyr | Gln | Ser 885 | Val | |

```
TGT GAG CCC GGT GCT GCA CCA AAA CAA GGA GCA GGA CAT CGC TCA GCA        2740
Cys Glu Pro Gly Ala Ala Pro Lys Gln Gly Ala Gly His Arg Ser Ala
            890                 895                 900

TAT GTG CCA TCA GTA GCA GAC ATA TTA CAA ATT GGC TGG TGG GCC ACT        2788
Tyr Val Pro Ser Val Ala Asp Ile Leu Gln Ile Gly Trp Trp Ala Thr
            905                 910                 915

GCT GCT GCC TGG TCT ATT CTA CAG CAG TTT CTC TTG AGT TTG ACC TTT        2836
Ala Ala Ala Trp Ser Ile Leu Gln Gln Phe Leu Leu Ser Leu Thr Phe
            920                 925                 930

CCA CGA CTC CTT GAG GCA GTT GAG ATG GAG GAT GAT GAC TTC ACG GCC        2884
Pro Arg Leu Leu Glu Ala Val Glu Met Glu Asp Asp Asp Phe Thr Ala
935                 940                 945                 950

TCC CTG TCC AAG CAG AGC TGC ATT ACT GAA CAA ACC CAG TAT TTC TTC        2932
Ser Leu Ser Lys Gln Ser Cys Ile Thr Glu Gln Thr Gln Tyr Phe Phe
                955                 960                 965

GAT AAC GAC AGT AAA TCA TTC AGT GGT GTA TTA GAC TGT GGA AAC TGT        2980
Asp Asn Asp Ser Lys Ser Phe Ser Gly Val Leu Asp Cys Gly Asn Cys
            970                 975                 980

TCC AGA ATC TTT CAT GGA GAA AAG CTT ATG AAC ACC AAC TTA ATA TTC        3028
Ser Arg Ile Phe His Gly Glu Lys Leu Met Asn Thr Asn Leu Ile Phe
            985                 990                 995

ATA ATG GTT GAG AGC AAA GGG ACA TGT CCA TGT GAC ACA CGA CTG CTC        3076
Ile Met Val Glu Ser Lys Gly Thr Cys Pro Cys Asp Thr Arg Leu Leu
1000                1005                1010

ATA CAA GCG GAG CAG ACT TCT GAC GGT CCA AAT CCT TGT GAC ATG GTT        3124
Ile Gln Ala Glu Gln Thr Ser Asp Gly Pro Asn Pro Cys Asp Met Val
1015                1020                1025                1030

AAG CAA CCT AGA TAC CGA AAA GGG CCT GAT GTC TGC TTT GAT AAC AAT        3172
Lys Gln Pro Arg Tyr Arg Lys Gly Pro Asp Val Cys Phe Asp Asn Asn
                1035                1040                1045

GTC TTG GAG GAT TAT ACT GAC TGT GGT GGT GTT TCT GGA TTA AAT CCC        3220
Val Leu Glu Asp Tyr Thr Asp Cys Gly Gly Val Ser Gly Leu Asn Pro
            1050                1055                1060

TCC CTG TGG TAT ATC ATT GGA ATC CAG TTT CTA CTA CTT TGG CTG GTA        3268
Ser Leu Trp Tyr Ile Ile Gly Ile Gln Phe Leu Leu Leu Trp Leu Val
            1065                1070                1075

TCT GGC AGC ACA CAC CGG CTG TTA TGACCTTCTA AAAACCAAAT CTGCATAGTT       3322
Ser Gly Ser Thr His Arg Leu Leu
            1080                1085

AAACTCCAGA CCCTGCCAAA ACATGAGCCC TGCCCTCAAT TACAGTAACG TAGGGTCAGC      3382

TATAAAATCA GACAAACATT AGCTGGGCCT GTTCCATGGC ATAACACTAA GGCGCAGACT      3442

CCTAAGGCAC CCACTGGCTG CATGTCAGGG TGTCAGATCC TTAAACGTGT GTGAATGCTG      3502

CATCATCTAT GTGTAACATC AAAGCAAAAT CCTATACGTG TCCTCTATTG GAAAATTTGG      3562

GCGTTTGTTG TTGCATTGTT GGT                                              3585
```

( 2 ) INFORMATION FOR SEQ ID NO:35:

( i ) SEQUENCE CHARACTERISTICS:
        ( A ) LENGTH: 3564 base pairs
        ( B ) TYPE: nucleic acid
        ( C ) STRANDEDNESS: double
        ( D ) TOPOLOGY: linear ( i i ) MOLECULE TYPE: Genomic DNA ( i i i ) HYPOTHETICAL: NO ( i v ) ANTI-SENSE: NO ( v ) FRAGMENT TYPE:

( v i ) ORIGINAL SOURCE:

( i x ) FEATURE:
- ( A ) NAME/KEY: Coding Sequence
- ( B ) LOCATION: 35...3274
- ( D ) OTHER INFORMATION: Standard name "alpha-2d"
- ( A ) NAME/KEY: 5'UTR
- ( B ) LOCATION: 1...34
- ( D ) OTHER INFORMATION:
- ( A ) NAME/KEY: 3'UTR
- ( B ) LOCATION: 3275...3564
- ( D ) OTHER INFORMATION:

( x i ) SEQUENCE DESCRIPTION: SEQ ID NO:35:

```
GCGGGGGAGG GGGCATTGAT CTTCGATCGC GAAG ATG GCT GCT GGC TGC CTG CTG        55
                                     Met Ala Ala Gly Cys Leu Leu
                                       1               5

GCC TTG ACT CTG ACA CTT TTC CAA TCT TTG CTC ATC GGC CCC TCG TCG         103
Ala Leu Thr Leu Thr Leu Phe Gln Ser Leu Leu Ile Gly Pro Ser Ser
         10              15                  20

GAG GAG CCG TTC CCT TCG GCC GTC ACT ATC AAA TCA TGG GTG GAT AAG         151
Glu Glu Pro Phe Pro Ser Ala Val Thr Ile Lys Ser Trp Val Asp Lys
     25              30                  35

ATG CAA GAA GAC CTT GTC ACA CTG GCA AAA ACA GCA AGT GGA GTC AAT         199
Met Gln Glu Asp Leu Val Thr Leu Ala Lys Thr Ala Ser Gly Val Asn
 40              45                  50                  55

CAG CTT GTT GAT ATT TAT GAG AAA TAT CAA GAT TTG TAT ACT GTG GAA         247
Gln Leu Val Asp Ile Tyr Glu Lys Tyr Gln Asp Leu Tyr Thr Val Glu
                 60                  65                  70

CCA AAT AAT GCA CGC CAG CTG GTA GAA ATT GCA GCC AGG GAT ATT GAG         295
Pro Asn Asn Ala Arg Gln Leu Val Glu Ile Ala Ala Arg Asp Ile Glu
             75                  80                  85

AAA CTT CTG AGC AAC AGA TCT AAA GCC CTG GTG AGC CTG GCA TTG GAA         343
Lys Leu Leu Ser Asn Arg Ser Lys Ala Leu Val Ser Leu Ala Leu Glu
         90                  95                 100

GCG GAG AAA GTT CAA GCA GCT CAC CAG TGG AGA GAA GAT TTT GCA AGC         391
Ala Glu Lys Val Gln Ala Ala His Gln Trp Arg Glu Asp Phe Ala Ser
     105                 110                 115

AAT GAA GTT GTC TAC TAC AAT GCA AAG GAT GAT CTC GAT CCT GAG AAA         439
Asn Glu Val Val Tyr Tyr Asn Ala Lys Asp Asp Leu Asp Pro Glu Lys
120                 125                 130                 135

AAT GAC AGT GAG CCA GGC AGC CAG AGG ATA AAA CCT GTT TTC ATT GAA         487
Asn Asp Ser Glu Pro Gly Ser Gln Arg Ile Lys Pro Val Phe Ile Glu
                 140                 145                 150

GAT GCT AAT TTT GGA CGA CAA ATA TCT TAT CAG CAC GCA GCA GTC CAT         535
Asp Ala Asn Phe Gly Arg Gln Ile Ser Tyr Gln His Ala Ala Val His
             155                 160                 165

ATT CCT ACT GAC ATC TAT GAG GGC TCA ACA ATT GTG TTA AAT GAA CTC         583
Ile Pro Thr Asp Ile Tyr Glu Gly Ser Thr Ile Val Leu Asn Glu Leu
         170                 175                 180

AAC TGG ACA AGT GCC TTA GAT GAA GTT TTC AAA AAG AAT CGC GAG GAA         631
Asn Trp Thr Ser Ala Leu Asp Glu Val Phe Lys Lys Asn Arg Glu Glu
     185                 190                 195

GAC CCT TCA TTA TTG TGG CAG GTT TTT GGC AGT GCC ACT GGC CTA GCT         679
Asp Pro Ser Leu Leu Trp Gln Val Phe Gly Ser Ala Thr Gly Leu Ala
200                 205                 210                 215

CGA TAT TAT CCA GCT TCA CCA TGG GTT GAT AAT AGT AGA ACT CCA AAT         727
Arg Tyr Tyr Pro Ala Ser Pro Trp Val Asp Asn Ser Arg Thr Pro Asn
                 220                 225                 230

AAG ATT GAC CTT TAT GAT GTA CGC AGA AGA CCA TGG TAC ATC CAA GGA         775
Lys Ile Asp Leu Tyr Asp Val Arg Arg Arg Pro Trp Tyr Ile Gln Gly
             235                 240                 245

GCT GCA TCT CCT AAA GAC ATG CTT ATT CTG GTG GAT GTG AGT GGA AGT         823
```

|  |  |  |  |  |  |  |  |  |  |  |  |  |  |  |  |
|---|---|---|---|---|---|---|---|---|---|---|---|---|---|---|---|
| Ala | Ala | Ser | Pro | Lys | Asp | Met | Leu | Ile | Leu | Val | Asp | Val | Ser | Gly | Ser |
|  |  |  | 250 |  |  |  | 255 |  |  |  |  | 260 |  |  |  |

| GTT | AGT | GGA | TTG | ACA | CTT | AAA | CTG | ATC | CGA | ACA | TCT | GTC | TCC | GAA | ATG | 871 |
|---|---|---|---|---|---|---|---|---|---|---|---|---|---|---|---|---|
| Val | Ser | Gly | Leu | Thr | Leu | Lys | Leu | Ile | Arg | Thr | Ser | Val | Ser | Glu | Met |  |
| 265 |  |  |  |  |  | 270 |  |  |  |  | 275 |  |  |  |  |  |
| TTA | GAA | ACC | CTC | TCA | GAT | GAT | GAT | TTC | GTG | AAT | GTA | GCT | TCA | TTT | AAC | 919 |
| Leu | Glu | Thr | Leu | Ser | Asp | Asp | Asp | Phe | Val | Asn | Val | Ala | Ser | Phe | Asn |  |
| 280 |  |  |  |  | 285 |  |  |  | 290 |  |  |  |  |  | 295 |  |
| AGC | AAT | GCT | CAG | GAT | GTA | AGC | TGT | TTT | CAG | CAC | CTT | GTC | CAA | GCA | AAT | 967 |
| Ser | Asn | Ala | Gln | Asp | Val | Ser | Cys | Phe | Gln | His | Leu | Val | Gln | Ala | Asn |  |
|  |  |  |  | 300 |  |  |  |  | 305 |  |  |  |  | 310 |  |  |
| GTA | AGA | AAT | AAA | AAA | GTG | TTG | AAA | GAC | GCG | GTG | AAT | AAT | ATC | ACA | GCC | 1015 |
| Val | Arg | Asn | Lys | Lys | Val | Leu | Lys | Asp | Ala | Val | Asn | Asn | Ile | Thr | Ala |  |
|  |  |  |  | 315 |  |  |  |  | 320 |  |  |  |  | 325 |  |  |
| AAA | GGA | ATT | ACA | GAT | TAT | AAG | AAG | GGC | TTT | AGT | TTT | GCT | TTT | GAA | CAG | 1063 |
| Lys | Gly | Ile | Thr | Asp | Tyr | Lys | Lys | Gly | Phe | Ser | Phe | Ala | Phe | Glu | Gln |  |
|  |  |  | 330 |  |  |  |  | 335 |  |  |  |  | 340 |  |  |  |
| CTG | CTT | AAT | TAT | AAT | GTT | TCC | AGA | GCA | AAC | TGC | AAT | AAG | ATT | ATT | ATG | 1111 |
| Leu | Leu | Asn | Tyr | Asn | Val | Ser | Arg | Ala | Asn | Cys | Asn | Lys | Ile | Ile | Met |  |
|  |  | 345 |  |  |  |  | 350 |  |  |  |  | 355 |  |  |  |  |
| CTA | TTC | ACG | GAT | GGA | GGA | GAA | GAG | AGA | GCC | CAG | GAG | ATA | TTT | AAC | AAA | 1159 |
| Leu | Phe | Thr | Asp | Gly | Gly | Glu | Glu | Arg | Ala | Gln | Glu | Ile | Phe | Asn | Lys |  |
| 360 |  |  |  |  | 365 |  |  |  |  | 370 |  |  |  |  | 375 |  |
| TAC | AAT | AAA | GAT | AAA | AAA | GTA | CGT | GTA | TTC | AGG | TTT | TCA | GTT | GGT | CAA | 1207 |
| Tyr | Asn | Lys | Asp | Lys | Lys | Val | Arg | Val | Phe | Arg | Phe | Ser | Val | Gly | Gln |  |
|  |  |  |  | 380 |  |  |  |  | 385 |  |  |  |  | 390 |  |  |
| CAC | AAT | TAT | GAG | AGA | GGA | CCT | ATT | CAG | TGG | ATG | GCC | TGT | GAA | AAC | AAA | 1255 |
| His | Asn | Tyr | Glu | Arg | Gly | Pro | Ile | Gln | Trp | Met | Ala | Cys | Glu | Asn | Lys |  |
|  |  |  |  | 395 |  |  |  |  | 400 |  |  |  |  | 405 |  |  |
| GGT | TAT | TAT | TAT | GAA | ATT | CCT | TCC | ATT | GGT | GCA | ATA | AGA | ATC | AAT | ACT | 1303 |
| Gly | Tyr | Tyr | Tyr | Glu | Ile | Pro | Ser | Ile | Gly | Ala | Ile | Arg | Ile | Asn | Thr |  |
|  |  | 410 |  |  |  |  | 415 |  |  |  |  | 420 |  |  |  |  |
| CAG | GAA | TAT | TTG | GAT | GTT | TTG | GGA | AGA | CCA | ATG | GTT | TTA | GCA | GGA | GAC | 1351 |
| Gln | Glu | Tyr | Leu | Asp | Val | Leu | Gly | Arg | Pro | Met | Val | Leu | Ala | Gly | Asp |  |
| 425 |  |  |  |  | 430 |  |  |  |  | 435 |  |  |  |  |  |  |
| AAA | GCT | AAG | CAA | GTC | CAA | TGG | ACA | AAT | GTG | TAC | CTG | GAT | GCA | TTG | GAA | 1399 |
| Lys | Ala | Lys | Gln | Val | Gln | Trp | Thr | Asn | Val | Tyr | Leu | Asp | Ala | Leu | Glu |  |
| 440 |  |  |  |  | 445 |  |  |  |  | 450 |  |  |  |  | 455 |  |
| CTG | GGA | CTT | GTC | ATT | ACT | GGA | ACT | CTT | CCG | GTC | TTC | AAC | ATA | ACC | GGC | 1447 |
| Leu | Gly | Leu | Val | Ile | Thr | Gly | Thr | Leu | Pro | Val | Phe | Asn | Ile | Thr | Gly |  |
|  |  |  |  | 460 |  |  |  |  | 465 |  |  |  |  | 470 |  |  |
| CAA | TTT | GAA | AAT | AAG | ACA | AAC | TTA | AAG | AAC | CAG | CTG | ATT | CTT | GGT | GTG | 1495 |
| Gln | Phe | Glu | Asn | Lys | Thr | Asn | Leu | Lys | Asn | Gln | Leu | Ile | Leu | Gly | Val |  |
|  |  |  |  | 475 |  |  |  |  | 480 |  |  |  |  | 485 |  |  |
| ATG | GGA | GTA | GAT | GTG | TCT | TTG | GAA | GAT | ATT | AAA | AGA | CTG | ACA | CCA | CGT | 1543 |
| Met | Gly | Val | Asp | Val | Ser | Leu | Glu | Asp | Ile | Lys | Arg | Leu | Thr | Pro | Arg |  |
|  |  |  | 490 |  |  |  |  | 495 |  |  |  |  | 500 |  |  |  |
| TTT | ACA | CTG | TGC | CCC | AAT | GGG | TAT | TAC | TTT | GCA | ATC | GAT | CCT | AAT | GGT | 1591 |
| Phe | Thr | Leu | Cys | Pro | Asn | Gly | Tyr | Tyr | Phe | Ala | Ile | Asp | Pro | Asn | Gly |  |
| 505 |  |  |  |  |  | 510 |  |  |  |  | 515 |  |  |  |  |  |
| TAT | GTT | TTA | TTA | CAT | CCA | AAT | CTT | CAG | CCA | AAG | GAG | CCA | GTA | ACA | TTG | 1639 |
| Tyr | Val | Leu | Leu | His | Pro | Asn | Leu | Gln | Pro | Lys | Glu | Pro | Val | Thr | Leu |  |
| 520 |  |  |  |  | 525 |  |  |  |  | 530 |  |  |  |  | 535 |  |
| GAT | TTC | CTT | GAT | GCA | GAG | TTA | GAG | AAT | GAT | ATT | AAA | GTG | GAG | ATT | CGA | 1687 |
| Asp | Phe | Leu | Asp | Ala | Glu | Leu | Glu | Asn | Asp | Ile | Lys | Val | Glu | Ile | Arg |  |
|  |  |  |  | 540 |  |  |  |  | 545 |  |  |  |  | 550 |  |  |
| AAT | AAG | ATG | ATT | GAT | GGG | GAA | AGT | GGA | GAA | AAA | ACA | TTC | AGA | ACT | CTG | 1735 |
| Asn | Lys | Met | Ile | Asp | Gly | Glu | Ser | Gly | Glu | Lys | Thr | Phe | Arg | Thr | Leu |  |
|  |  |  | 555 |  |  |  |  | 560 |  |  |  |  | 565 |  |  |  |
| GTT | AAA | TCT | CAA | GAT | GAG | AGA | TAT | ATT | GAC | AAA | GGA | AAC | AGG | ACA | TAC | 1783 |

| | | | | | | | | | | | | | | | | |
|---|---|---|---|---|---|---|---|---|---|---|---|---|---|---|---|---|
| Val | Lys | Ser<br>570 | Gln | Asp | Glu | Arg | Tyr<br>575 | Ile | Asp | Lys | Gly<br>580 | Asn | Arg | Thr | Tyr | |
| ACA<br>Thr | TGG<br>Trp<br>585 | ACA<br>Thr | CCT<br>Pro | GTC<br>Val | AAT<br>Asn | GGC<br>Gly<br>590 | ACA<br>Thr | GAT<br>Asp | TAC<br>Tyr | AGT<br>Ser | TTG<br>Leu<br>595 | GCC<br>Ala | TTG<br>Leu | GTA<br>Val | TTA<br>Leu | 1831 |
| CCA<br>Pro<br>600 | ACC<br>Thr | TAC<br>Tyr | AGT<br>Ser | TTT<br>Phe | TAC<br>Tyr<br>605 | TAT<br>Tyr | ATA<br>Ile | AAA<br>Lys | GCC<br>Ala | AAA<br>Lys<br>610 | CTA<br>Leu | GAA<br>Glu | GAG<br>Glu | ACA<br>Thr | ATA<br>Ile<br>615 | 1879 |
| ACT<br>Thr | CAG<br>Gln | GCC<br>Ala | AGA<br>Arg | TAT<br>Tyr<br>620 | TCG<br>Ser | GAA<br>Glu | ACC<br>Thr | CTG<br>Leu | AAG<br>Lys<br>625 | CCA<br>Pro | GAT<br>Asp | AAT<br>Asn | TTT<br>Phe | GAA<br>Glu<br>630 | GAA<br>Glu | 1927 |
| TCT<br>Ser | GGC<br>Gly | TAT<br>Tyr | ACA<br>Thr<br>635 | TTC<br>Phe | ATA<br>Ile | GCA<br>Ala | CCA<br>Pro | AGA<br>Arg<br>640 | GAT<br>Asp | TAC<br>Tyr | TGC<br>Cys | AAT<br>Asn | GAC<br>Asp<br>645 | CTG<br>Leu | AAA<br>Lys | 1975 |
| ATA<br>Ile | TCG<br>Ser | GAT<br>Asp<br>650 | AAT<br>Asn | AAC<br>Asn | ACT<br>Thr | GAA<br>Glu | TTT<br>Phe<br>655 | CTT<br>Leu | TTA<br>Leu | AAT<br>Asn | TTC<br>Phe | AAC<br>Asn<br>660 | GAG<br>Glu | TTT<br>Phe | ATT<br>Ile | 2023 |
| GAT<br>Asp | AGA<br>Arg<br>665 | AAA<br>Lys | ACT<br>Thr | CCA<br>Pro | AAC<br>Asn | AAC<br>Asn<br>670 | CCA<br>Pro | TCA<br>Ser | TGT<br>Cys | AAC<br>Asn | GCG<br>Ala<br>675 | GAT<br>Asp | TTG<br>Leu | ATT<br>Ile | AAT<br>Asn | 2071 |
| AGA<br>Arg<br>680 | GTC<br>Val | TTG<br>Leu | CTT<br>Leu | GAT<br>Asp | GCA<br>Ala<br>685 | GGC<br>Gly | TTT<br>Phe | ACA<br>Thr | AAT<br>Asn | GAA<br>Glu<br>690 | CTT<br>Leu | GTC<br>Val | CAA<br>Gln | AAT<br>Asn | TAC<br>Tyr<br>695 | 2119 |
| TGG<br>Trp | AGT<br>Ser | AAG<br>Lys | CAG<br>Gln | AAA<br>Lys<br>700 | AAT<br>Asn | ATC<br>Ile | AAG<br>Lys | GGA<br>Gly | GTG<br>Val<br>705 | AAA<br>Lys | GCA<br>Ala | CGA<br>Arg | TTT<br>Phe | GTT<br>Val<br>710 | GTG<br>Val | 2167 |
| ACT<br>Thr | GAT<br>Asp | GGT<br>Gly | GGG<br>Gly<br>715 | ATT<br>Ile | ACC<br>Thr | AGA<br>Arg | GTT<br>Val | TAT<br>Tyr<br>720 | CCC<br>Pro | AAA<br>Lys | GAG<br>Glu | GCT<br>Ala | GGA<br>Gly<br>725 | GAA<br>Glu | AAT<br>Asn | 2215 |
| TGG<br>Trp | CAA<br>Gln | GAA<br>Glu<br>730 | AAC<br>Asn | CCA<br>Pro | GAG<br>Glu | ACA<br>Thr | TAT<br>Tyr<br>735 | GAG<br>Glu | GAC<br>Asp | AGC<br>Ser | TTC<br>Phe | TAT<br>Tyr<br>740 | AAA<br>Lys | AGG<br>Arg | AGC<br>Ser | 2263 |
| CTA<br>Leu | GAT<br>Asp<br>745 | AAT<br>Asn | GAT<br>Asp | AAC<br>Asn | TAT<br>Tyr | GTT<br>Val<br>750 | TTC<br>Phe | ACT<br>Thr | GCT<br>Ala | CCC<br>Pro | TAC<br>Tyr<br>755 | TTT<br>Phe | AAC<br>Asn | AAA<br>Lys | AGT<br>Ser | 2311 |
| GGA<br>Gly<br>760 | CCT<br>Pro | GGT<br>Gly | GCC<br>Ala | TAT<br>Tyr | GAA<br>Glu<br>765 | TCG<br>Ser | GGC<br>Gly | ATT<br>Ile | ATG<br>Met | GTA<br>Val<br>770 | AGC<br>Ser | AAA<br>Lys | GCT<br>Ala | GTA<br>Val | GAA<br>Glu<br>775 | 2359 |
| ATA<br>Ile | TAT<br>Tyr | ATT<br>Ile | CAA<br>Gln | GGG<br>Gly<br>780 | AAA<br>Lys | CTT<br>Leu | CTT<br>Leu | AAA<br>Lys | CCT<br>Pro<br>785 | GCA<br>Ala | GTT<br>Val | GTT<br>Val | GGA<br>Gly | ATT<br>Ile<br>790 | AAA<br>Lys | 2407 |
| ATT<br>Ile | GAT<br>Asp | GTA<br>Val | AAT<br>Asn<br>795 | TCC<br>Ser | TGG<br>Trp | ATA<br>Ile | GAG<br>Glu | AAT<br>Asn<br>800 | TTC<br>Phe | ACC<br>Thr | AAA<br>Lys | ACC<br>Thr | TCA<br>Ser<br>805 | ATC<br>Ile | AGA<br>Arg | 2455 |
| GAT<br>Asp | CCG<br>Pro | TGT<br>Cys<br>810 | GCT<br>Ala | GGT<br>Gly | CCA<br>Pro | GTT<br>Val | TGT<br>Cys<br>815 | GAC<br>Asp | TGC<br>Cys | AAA<br>Lys | AGA<br>Arg | AAC<br>Asn<br>820 | AGT<br>Ser | GAC<br>Asp | GTA<br>Val | 2503 |
| ATG<br>Met | GAT<br>Asp<br>825 | TGT<br>Cys | GTG<br>Val | ATT<br>Ile | CTG<br>Leu | GAT<br>Asp<br>830 | GAT<br>Asp | GGT<br>Gly | GGG<br>Gly | TTT<br>Phe | CTT<br>Leu<br>835 | CTG<br>Leu | ATG<br>Met | GCA<br>Ala | AAT<br>Asn | 2551 |
| CAT<br>His<br>840 | GAT<br>Asp | GAT<br>Asp | TAT<br>Tyr | ACT<br>Thr | AAT<br>Asn<br>845 | CAG<br>Gln | ATT<br>Ile | GGA<br>Gly | AGA<br>Arg | TTT<br>Phe<br>850 | TTT<br>Phe | GGA<br>Gly | GAG<br>Glu | ATT<br>Ile | GAT<br>Asp<br>855 | 2599 |
| CCC<br>Pro | AGC<br>Ser | TTG<br>Leu | ATG<br>Met | AGA<br>Arg<br>860 | CAC<br>His | CTG<br>Leu | GTT<br>Val | AAT<br>Asn | ATA<br>Ile<br>865 | TCA<br>Ser | GTT<br>Val | TAT<br>Tyr | GCT<br>Ala | TTT<br>Phe<br>870 | AAC<br>Asn | 2647 |
| AAA<br>Lys | TCT<br>Ser | TAT<br>Tyr | GAT<br>Asp<br>875 | TAT<br>Tyr | CAG<br>Gln | TCA<br>Ser | GTA<br>Val | TGT<br>Cys<br>880 | GAG<br>Glu | CCC<br>Pro | GGT<br>Gly | GCT<br>Ala | GCA<br>Ala<br>885 | CCA<br>Pro | AAA<br>Lys | 2695 |
| CAA | GGA | GCA | GGA | CAT | CGC | TCA | GCA | TAT | GTG | CCA | TCA | GTA | GCA | GAC | ATA | 2743 |

|  |  |  |  |  |  |  |  |  |  |  |  |  |  |  |  |
|---|---|---|---|---|---|---|---|---|---|---|---|---|---|---|---|
| Gln | Gly | Ala | Gly | His | Arg | Ser | Ala | Tyr | Val | Pro | Ser | Val | Ala | Asp | Ile |
|  |  | 890 |  |  |  |  | 895 |  |  |  | 900 |  |  |  |  |
| TTA | CAA | ATT | GGC | TGG | TGG | GCC | ACT | GCT | GCT | GCC | TGG | TCT | ATT | CTA | CAG | 2791 |
| Leu | Gln | Ile | Gly | Trp | Trp | Ala | Thr | Ala | Ala | Ala | Trp | Ser | Ile | Leu | Gln |
|  | 905 |  |  |  |  | 910 |  |  |  |  | 915 |  |  |  |  |
| CAG | TTT | CTC | TTG | AGT | TTG | ACC | TTT | CCA | CGA | CTC | CTT | GAG | GCA | GTT | GAG | 2839 |
| Gln | Phe | Leu | Leu | Ser | Leu | Thr | Phe | Pro | Arg | Leu | Leu | Glu | Ala | Val | Glu |
| 920 |  |  |  |  | 925 |  |  |  |  | 930 |  |  |  |  | 935 |
| ATG | GAG | GAT | GAT | GAC | TTC | ACG | GCC | TCC | CTG | TCC | AAG | CAG | AGC | TGC | ATT | 2887 |
| Met | Glu | Asp | Asp | Asp | Phe | Thr | Ala | Ser | Leu | Ser | Lys | Gln | Ser | Cys | Ile |
|  |  |  |  | 940 |  |  |  |  | 945 |  |  |  |  | 950 |  |
| ACT | GAA | CAA | ACC | CAG | TAT | TTC | TTC | GAT | AAC | GAC | AGT | AAA | TCA | TTC | AGT | 2935 |
| Thr | Glu | Gln | Thr | Gln | Tyr | Phe | Phe | Asp | Asn | Asp | Ser | Lys | Ser | Phe | Ser |
|  |  |  | 955 |  |  |  |  | 960 |  |  |  |  | 965 |  |  |
| GGT | GTA | TTA | GAC | TGT | GGA | AAC | TGT | TCC | AGA | ATC | TTT | CAT | GGA | GAA | AAG | 2983 |
| Gly | Val | Leu | Asp | Cys | Gly | Asn | Cys | Ser | Arg | Ile | Phe | His | Gly | Glu | Lys |
|  |  | 970 |  |  |  |  |  | 975 |  |  |  |  | 980 |  |  |
| CTT | ATG | AAC | ACC | AAC | TTA | ATA | TTC | ATA | ATG | GTT | GAG | AGC | AAA | GGG | ACA | 3031 |
| Leu | Met | Asn | Thr | Asn | Leu | Ile | Phe | Ile | Met | Val | Glu | Ser | Lys | Gly | Thr |
|  | 985 |  |  |  |  |  | 990 |  |  |  | 995 |  |  |  |  |
| TGT | CCA | TGT | GAC | ACA | CGA | CTG | CTC | ATA | CAA | GCG | GAG | CAG | ACT | TCT | GAC | 3079 |
| Cys | Pro | Cys | Asp | Thr | Arg | Leu | Leu | Ile | Gln | Ala | Glu | Gln | Thr | Ser | Asp |
| 1000 |  |  |  |  | 1005 |  |  |  |  | 1010 |  |  |  |  | 1015 |
| GGT | CCA | AAT | CCT | TGT | GAC | ATG | GTT | AAG | CAA | CCT | AGA | TAC | CGA | AAA | GGG | 3127 |
| Gly | Pro | Asn | Pro | Cys | Asp | Met | Val | Lys | Gln | Pro | Arg | Tyr | Arg | Lys | Gly |
|  |  |  |  | 1020 |  |  |  |  | 1025 |  |  |  |  | 1030 |  |
| CCT | GAT | GTC | TGC | TTT | GAT | AAC | AAT | GTC | TTG | GAG | GAT | TAT | ACT | GAC | TGT | 3175 |
| Pro | Asp | Val | Cys | Phe | Asp | Asn | Asn | Val | Leu | Glu | Asp | Tyr | Thr | Asp | Cys |
|  |  |  | 1035 |  |  |  |  | 1040 |  |  |  |  | 1045 |  |  |
| GGT | GGT | GTT | TCT | GGA | TTA | AAT | CCC | TCC | CTG | TGG | TAT | ATC | ATT | GGA | ATC | 3223 |
| Gly | Gly | Val | Ser | Gly | Leu | Asn | Pro | Ser | Leu | Trp | Tyr | Ile | Ile | Gly | Ile |
|  |  | 1050 |  |  |  |  | 1055 |  |  |  |  | 1060 |  |  |  |
| CAG | TTT | CTA | CTA | CTT | TGG | CTG | GTA | TCT | GGC | AGC | ACA | CAC | CGG | CTG | TTA | 3271 |
| Gln | Phe | Leu | Leu | Leu | Trp | Leu | Val | Ser | Gly | Ser | Thr | His | Arg | Leu | Leu |
|  | 1065 |  |  |  |  | 1070 |  |  |  |  | 1075 |  |  |  |  |
| TGA | CCTTCTAAAA | ACCAAATCTG | CATAGTTAAA | CTCCAGACCC | TGCCAAAACA | TGAGCCC | 3331 |
| * |  |  |  |  |  |  |  |
| TGCCCTCAAT | TACAGTAACG | TAGGGTCAGC | TATAAAATCA | GACAAACATT | AGCTGGGCCT | 3391 |
| GTTCCATGGC | ATAACACTAA | GGCGCAGACT | CCTAAGGCAC | CCACTGGCTG | CATGTCAGGG | 3451 |
| TGTCAGATCC | TTAAACGTGT | GTGAATGCTG | CATCATCTAT | GTGTAACATC | AAAGCAAAAT | 3511 |
| CCTATACGTG | TCCTCTATTG | GAAAATTTGG | GCGTTTGTTG | TTGCATTGTT | GGT | 3564 |

( 2 ) INFORMATION FOR SEQ ID NO:36:

( i ) SEQUENCE CHARACTERISTICS:
        ( A ) LENGTH: 3579 base pairs
        ( B ) TYPE: nucleic acid
        ( C ) STRANDEDNESS: double
        ( D ) TOPOLOGY: linear ( i i ) MOLECULE TYPE: Genomic DNA ( i i i ) HYPOTHETICAL: NO ( i v ) ANTI-SENSE: NO ( v ) FRAGMENT TYPE:

( v i ) ORIGINAL SOURCE:

( i x ) FEATURE:
        ( A ) NAME/KEY: Coding Sequence
        ( B ) LOCATION: 35...3289

-continued ( D ) OTHER INFORMATION: Standard name "alpha2e"
( A ) NAME/KEY: 5'UTR
( B ) LOCATION: 1...34
( D ) OTHER INFORMATION:
( A ) NAME/KEY: 3'UTR
( B ) LOCATION: 3290...3579
( D ) OTHER INFORMATION:

( x i ) SEQUENCE DESCRIPTION: SEQ ID NO:36:

```
GCGGGGGAGG GGGCATTGAT CTTCGATCGC GAAG ATG GCT GCT GGC TGC CTG CTG       55
                                      Met Ala Ala Gly Cys Leu Leu
                                      1                   5

GCC TTG ACT CTG ACA CTT TTC CAA TCT TTG CTC ATC GGC CCC TCG TCG         103
Ala Leu Thr Leu Thr Leu Phe Gln Ser Leu Leu Ile Gly Pro Ser Ser
        10              15                  20

GAG GAG CCG TTC CCT TCG GCC GTC ACT ATC AAA TCA TGG GTG GAT AAG         151
Glu Glu Pro Phe Pro Ser Ala Val Thr Ile Lys Ser Trp Val Asp Lys
25              30                  35

ATG CAA GAA GAC CTT GTC ACA CTG GCA AAA ACA GCA AGT GGA GTC AAT         199
Met Gln Glu Asp Leu Val Thr Leu Ala Lys Thr Ala Ser Gly Val Asn
40              45                  50                  55

CAG CTT GTT GAT ATT TAT GAG AAA TAT CAA GAT TTG TAT ACT GTG GAA         247
Gln Leu Val Asp Ile Tyr Glu Lys Tyr Gln Asp Leu Tyr Thr Val Glu
                60                  65                  70

CCA AAT AAT GCA CGC CAG CTG GTA GAA ATT GCA GCC AGG GAT ATT GAG         295
Pro Asn Asn Ala Arg Gln Leu Val Glu Ile Ala Ala Arg Asp Ile Glu
            75                  80                  85

AAA CTT CTG AGC AAC AGA TCT AAA GCC CTG GTG AGC CTG GCA TTG GAA         343
Lys Leu Leu Ser Asn Arg Ser Lys Ala Leu Val Ser Leu Ala Leu Glu
        90                  95                  100

GCG GAG AAA GTT CAA GCA GCT CAC CAG TGG AGA GAA GAT TTT GCA AGC         391
Ala Glu Lys Val Gln Ala Ala His Gln Trp Arg Glu Asp Phe Ala Ser
105                 110                 115

AAT GAA GTT GTC TAC TAC AAT GCA AAG GAT GAT CTC GAT CCT GAG AAA         439
Asn Glu Val Val Tyr Tyr Asn Ala Lys Asp Asp Leu Asp Pro Glu Lys
120                 125                 130                 135

AAT GAC AGT GAG CCA GGC AGC CAG AGG ATA AAA CCT GTT TTC ATT GAA         487
Asn Asp Ser Glu Pro Gly Ser Gln Arg Ile Lys Pro Val Phe Ile Glu
            140                 145                 150

GAT GCT AAT TTT GGA CGA CAA ATA TCT TAT CAG CAC GCA GCA GTC CAT         535
Asp Ala Asn Phe Gly Arg Gln Ile Ser Tyr Gln His Ala Ala Val His
            155                 160                 165

ATT CCT ACT GAC ATC TAT GAG GGC TCA ACA ATT GTG TTA AAT GAA CTC         583
Ile Pro Thr Asp Ile Tyr Glu Gly Ser Thr Ile Val Leu Asn Glu Leu
        170                 175                 180

AAC TGG ACA AGT GCC TTA GAT GAA GTT TTC AAA AAG AAT CGC GAG GAA         631
Asn Trp Thr Ser Ala Leu Asp Glu Val Phe Lys Lys Asn Arg Glu Glu
    185                 190                 195

GAC CCT TCA TTA TTG TGG CAG GTT TTT GGC AGT GCC ACT GGC CTA GCT         679
Asp Pro Ser Leu Leu Trp Gln Val Phe Gly Ser Ala Thr Gly Leu Ala
200                 205                 210                 215

CGA TAT TAT CCA GCT TCA CCA TGG GTT GAT AAT AGT AGA ACT CCA AAT         727
Arg Tyr Tyr Pro Ala Ser Pro Trp Val Asp Asn Ser Arg Thr Pro Asn
            220                 225                 230

AAG ATT GAC CTT TAT GAT GTA CGC AGA AGA CCA TGG TAC ATC CAA GGA         775
Lys Ile Asp Leu Tyr Asp Val Arg Arg Arg Pro Trp Tyr Ile Gln Gly
        235                 240                 245

GCT GCA TCT CCT AAA GAC ATG CTT ATT CTG GTG GAT GTG AGT GGA AGT         823
Ala Ala Ser Pro Lys Asp Met Leu Ile Leu Val Asp Val Ser Gly Ser
    250                 255                 260

GTT AGT GGA TTG ACA CTT AAA CTG ATC CGA ACA TCT GTC TCC GAA ATG         871
Val Ser Gly Leu Thr Leu Lys Leu Ile Arg Thr Ser Val Ser Glu Met
```

|     |     |     |     |     |     |     |     |     |     |     |     |     |     |     |     |     |
|---|---|---|---|---|---|---|---|---|---|---|---|---|---|---|---|---|
| | | | 265 | | | | | 270 | | | | | 275 | | | |
| TTA | GAA | ACC | CTC | TCA | GAT | GAT | GAT | TTC | GTG | AAT | GTA | GCT | TCA | TTT | AAC | 919 |
| Leu | Glu | Thr | Leu | Ser | Asp | Asp | Asp | Phe | Val | Asn | Val | Ala | Ser | Phe | Asn | |
| 280 | | | | 285 | | | | | 290 | | | | | 295 | | |
| AGC | AAT | GCT | CAG | GAT | GTA | AGC | TGT | TTT | CAG | CAC | CTT | GTC | CAA | GCA | AAT | 967 |
| Ser | Asn | Ala | Gln | Asp | Val | Ser | Cys | Phe | Gln | His | Leu | Val | Gln | Ala | Asn | |
| | | | 300 | | | | | 305 | | | | | 310 | | | |
| GTA | AGA | AAT | AAA | AAA | GTG | TTG | AAA | GAC | GCG | GTG | AAT | AAT | ATC | ACA | GCC | 1015 |
| Val | Arg | Asn | Lys | Lys | Val | Leu | Lys | Asp | Ala | Val | Asn | Asn | Ile | Thr | Ala | |
| | | | 315 | | | | | 320 | | | | | 325 | | | |
| AAA | GGA | ATT | ACA | GAT | TAT | AAG | AAG | GGC | TTT | AGT | TTT | GCT | TTT | GAA | CAG | 1063 |
| Lys | Gly | Ile | Thr | Asp | Tyr | Lys | Lys | Gly | Phe | Ser | Phe | Ala | Phe | Glu | Gln | |
| | | | 330 | | | | | 335 | | | | | 340 | | | |
| CTG | CTT | AAT | TAT | AAT | GTT | TCC | AGA | GCA | AAC | TGC | AAT | AAG | ATT | ATT | ATG | 1111 |
| Leu | Leu | Asn | Tyr | Asn | Val | Ser | Arg | Ala | Asn | Cys | Asn | Lys | Ile | Ile | Met | |
| | | | 345 | | | | | 350 | | | | | 355 | | | |
| CTA | TTC | ACG | GAT | GGA | GGA | GAA | GAG | AGA | GCC | CAG | GAG | ATA | TTT | AAC | AAA | 1159 |
| Leu | Phe | Thr | Asp | Gly | Gly | Glu | Glu | Arg | Ala | Gln | Glu | Ile | Phe | Asn | Lys | |
| 360 | | | | | 365 | | | | | 370 | | | | | 375 | |
| TAC | AAT | AAA | GAT | AAA | AAA | GTA | CGT | GTA | TTC | AGG | TTT | TCA | GTT | GGT | CAA | 1207 |
| Tyr | Asn | Lys | Asp | Lys | Lys | Val | Arg | Val | Phe | Arg | Phe | Ser | Val | Gly | Gln | |
| | | | | 380 | | | | | 385 | | | | | 390 | | |
| CAC | AAT | TAT | GAG | AGA | GGA | CCT | ATT | CAG | TGG | ATG | GCC | TGT | GAA | AAC | AAA | 1255 |
| His | Asn | Tyr | Glu | Arg | Gly | Pro | Ile | Gln | Trp | Met | Ala | Cys | Glu | Asn | Lys | |
| | | | | 395 | | | | | 400 | | | | | 405 | | |
| GGT | TAT | TAT | TAT | GAA | ATT | CCT | TCC | ATT | GGT | GCA | ATA | AGA | ATC | AAT | ACT | 1303 |
| Gly | Tyr | Tyr | Tyr | Glu | Ile | Pro | Ser | Ile | Gly | Ala | Ile | Arg | Ile | Asn | Thr | |
| | | | 410 | | | | | 415 | | | | | 420 | | | |
| CAG | GAA | TAT | TTG | GAT | GTT | TTG | GGA | AGA | CCA | ATG | GTT | TTA | GCA | GGA | GAC | 1351 |
| Gln | Glu | Tyr | Leu | Asp | Val | Leu | Gly | Arg | Pro | Met | Val | Leu | Ala | Gly | Asp | |
| | | 425 | | | | | 430 | | | | | 435 | | | | |
| AAA | GCT | AAG | CAA | GTC | CAA | TGG | ACA | AAT | GTG | TAC | CTG | GAT | GCA | TTG | GAA | 1399 |
| Lys | Ala | Lys | Gln | Val | Gln | Trp | Thr | Asn | Val | Tyr | Leu | Asp | Ala | Leu | Glu | |
| 440 | | | | | 445 | | | | | 450 | | | | | 455 | |
| CTG | GGA | CTT | GTC | ATT | ACT | GGA | ACT | CTT | CCG | GTC | TTC | AAC | ATA | ACC | GGC | 1447 |
| Leu | Gly | Leu | Val | Ile | Thr | Gly | Thr | Leu | Pro | Val | Phe | Asn | Ile | Thr | Gly | |
| | | | | 460 | | | | | 465 | | | | | 470 | | |
| CAA | TTT | GAA | AAT | AAG | ACA | AAC | TTA | AAG | AAC | CAG | CTG | ATT | CTT | GGT | GTG | 1495 |
| Gln | Phe | Glu | Asn | Lys | Thr | Asn | Leu | Lys | Asn | Gln | Leu | Ile | Leu | Gly | Val | |
| | | | | 475 | | | | | 480 | | | | | 485 | | |
| ATG | GGA | GTA | GAT | GTG | TCT | TTG | GAA | GAT | ATT | AAA | AGA | CTG | ACA | CCA | CGT | 1543 |
| Met | Gly | Val | Asp | Val | Ser | Leu | Glu | Asp | Ile | Lys | Arg | Leu | Thr | Pro | Arg | |
| | | | 490 | | | | | 495 | | | | | 500 | | | |
| TTT | ACA | CTG | TGC | CCC | AAT | GGG | TAT | TAC | TTT | GCA | ATC | GAT | CCT | AAT | GGT | 1591 |
| Phe | Thr | Leu | Cys | Pro | Asn | Gly | Tyr | Tyr | Phe | Ala | Ile | Asp | Pro | Asn | Gly | |
| | 505 | | | | | 510 | | | | | 515 | | | | | |
| TAT | GTT | TTA | TTA | CAT | CCA | AAT | CTT | CAG | CCA | AAG | AAC | CCC | AAA | TCT | CAG | 1639 |
| Tyr | Val | Leu | Leu | His | Pro | Asn | Leu | Gln | Pro | Lys | Asn | Pro | Lys | Ser | Gln | |
| 520 | | | | | 525 | | | | | 530 | | | | | 535 | |
| GAG | CCA | GTA | ACA | TTG | GAT | TTC | CTT | GAT | GCA | GAG | TTA | GAG | AAT | GAT | ATT | 1687 |
| Glu | Pro | Val | Thr | Leu | Asp | Phe | Leu | Asp | Ala | Glu | Leu | Glu | Asn | Asp | Ile | |
| | | | | 540 | | | | | 545 | | | | | 550 | | |
| AAA | GTG | GAG | ATT | CGA | AAT | AAG | ATG | ATT | GAT | GGG | GAA | AGT | GGA | GAA | AAA | 1735 |
| Lys | Val | Glu | Ile | Arg | Asn | Lys | Met | Ile | Asp | Gly | Glu | Ser | Gly | Glu | Lys | |
| | | | | 555 | | | | | 560 | | | | | 565 | | |
| ACA | TTC | AGA | ACT | CTG | GTT | AAA | TCT | CAA | GAT | GAG | AGA | TAT | ATT | GAC | AAA | 1783 |
| Thr | Phe | Arg | Thr | Leu | Val | Lys | Ser | Gln | Asp | Glu | Arg | Tyr | Ile | Asp | Lys | |
| | | | 570 | | | | | 575 | | | | | 580 | | | |
| GGA | AAC | AGG | ACA | TAC | ACA | TGG | ACA | CCT | GTC | AAT | GGC | ACA | GAT | TAC | AGT | 1831 |
| Gly | Asn | Arg | Thr | Tyr | Thr | Trp | Thr | Pro | Val | Asn | Gly | Thr | Asp | Tyr | Ser | |

```
        585                    590                     595
TTG GCC TTG GTA TTA CCA ACC TAC AGT TTT TAC TAT ATA AAA GCC AAA         1879
Leu Ala Leu Val Leu Pro Thr Tyr Ser Phe Tyr Tyr Ile Lys Ala Lys
600             605             610             615

CTA GAA GAG ACA ATA ACT CAG GCC AGA TAT TCG GAA ACC TTG AAG CCA         1927
Leu Glu Glu Thr Ile Thr Gln Ala Arg Tyr Ser Glu Thr Leu Lys Pro
                620             625             630

GAT AAT TTT GAA GAA TCT GGC TAT ACA TTC ATA GCA CCA AGA GAT TAC         1975
Asp Asn Phe Glu Glu Ser Gly Tyr Thr Phe Ile Ala Pro Arg Asp Tyr
            635             640             645

TGC AAT GAC CTG AAA ATA TCG GAT AAT AAC ACT GAA TTT CTT TTA AAT         2023
Cys Asn Asp Leu Lys Ile Ser Asp Asn Asn Thr Glu Phe Leu Leu Asn
        650             655             660

TTC AAC GAG TTT ATT GAT AGA AAA ACT CCA AAC AAC CCA TCA TGT AAC         2071
Phe Asn Glu Phe Ile Asp Arg Lys Thr Pro Asn Asn Pro Ser Cys Asn
    665             670             675

GCG GAT TTG ATT AAT AGA GTC TTG CTT GAT GCA GGC TTT ACA AAT GAA         2119
Ala Asp Leu Ile Asn Arg Val Leu Leu Asp Ala Gly Phe Thr Asn Glu
680             685             690             695

CTT GTC CAA AAT TAC TGG AGT AAG CAG AAA AAT ATC AAG GGA GTG AAA         2167
Leu Val Gln Asn Tyr Trp Ser Lys Gln Lys Asn Ile Lys Gly Val Lys
                700             705             710

GCA CGA TTT GTT GTG ACT GAT GGT GGG ATT ACC AGA GTT TAT CCC AAA         2215
Ala Arg Phe Val Val Thr Asp Gly Gly Ile Thr Arg Val Tyr Pro Lys
            715             720             725

GAG GCT GGA GAA AAT TGG CAA GAA AAC CCA GAG ACA TAT GAG GAC AGC         2263
Glu Ala Gly Glu Asn Trp Gln Glu Asn Pro Glu Thr Tyr Glu Asp Ser
        730             735             740

TTC TAT AAA AGG AGC CTA GAT AAT GAT AAC TAT GTT TTC ACT GCT CCC         2311
Phe Tyr Lys Arg Ser Leu Asp Asn Asp Asn Tyr Val Phe Thr Ala Pro
    745             750             755

TAC TTT AAC AAA AGT GGA CCT GGT GCC TAT GAA TCG GGC ATT ATG GTA         2359
Tyr Phe Asn Lys Ser Gly Pro Gly Ala Tyr Glu Ser Gly Ile Met Val
760             765             770             775

AGC AAA GCT GTA GAA ATA TAT ATT CAA GGG AAA CTT CTT AAA CCT GCA         2407
Ser Lys Ala Val Glu Ile Tyr Ile Gln Gly Lys Leu Leu Lys Pro Ala
                780             785             790

GTT GTT GGA ATT AAA ATT GAT GTA AAT TCC TGG ATA GAG AAT TTC ACC         2455
Val Val Gly Ile Lys Ile Asp Val Asn Ser Trp Ile Glu Asn Phe Thr
            795             800             805

AAA ACC TCA ATC AGA GAT CCG TGT GCT GGT CCA GTT TGT GAC TGC AAA         2503
Lys Thr Ser Ile Arg Asp Pro Cys Ala Gly Pro Val Cys Asp Cys Lys
        810             815             820

AGA AAC AGT GAC GTA ATG GAT TGT GTG ATT CTG GAT GAT GGT GGG TTT         2551
Arg Asn Ser Asp Val Met Asp Cys Val Ile Leu Asp Asp Gly Gly Phe
    825             830             835

CTT CTG ATG GCA AAT CAT GAT GAT TAT ACT AAT CAG ATT GGA AGA TTT         2599
Leu Leu Met Ala Asn His Asp Asp Tyr Thr Asn Gln Ile Gly Arg Phe
840             845             850             855

TTT GGA GAG ATT GAT CCC AGC TTG ATG AGA CAC CTG GTT AAT ATA TCA         2647
Phe Gly Glu Ile Asp Pro Ser Leu Met Arg His Leu Val Asn Ile Ser
                860             865             870

GTT TAT GCT TTT AAC AAA TCT TAT GAT TAT CAG TCA GTA TGT GAG CCC         2695
Val Tyr Ala Phe Asn Lys Ser Tyr Asp Tyr Gln Ser Val Cys Glu Pro
            875             880             885

GGT GCT GCA CCA AAA CAA GGA GCA GGA CAT CGC TCA GCA TAT GTG CCA         2743
Gly Ala Ala Pro Lys Gln Gly Ala Gly His Arg Ser Ala Tyr Val Pro
        890             895             900

TCA GTA GCA GAC ATA TTA CAA ATT GGC TGG TGG GCC ACT GCT GCT GCC         2791
Ser Val Ala Asp Ile Leu Gln Ile Gly Trp Trp Ala Thr Ala Ala Ala
```

-continued

```
                905                        910                        915
TGG TCT ATT CTA CAG CAG TTT CTC TTG AGT TTG ACC TTT CCA CGA CTC        2839
Trp Ser Ile Leu Gln Gln Phe Leu Leu Ser Leu Thr Phe Pro Arg Leu
920                 925                 930                 935

CTT GAG GCA GTT GAG ATG GAG GAT GAT GAC TTC ACG GCC TCC CTG TCC        2887
Leu Glu Ala Val Glu Met Glu Asp Asp Asp Phe Thr Ala Ser Leu Ser
                    940                 945                 950

AAG CAG AGC TGC ATT ACT GAA CAA ACC CAG TAT TTC TTC GAT AAC GAC        2935
Lys Gln Ser Cys Ile Thr Glu Gln Thr Gln Tyr Phe Phe Asp Asn Asp
                955                 960                 965

AGT AAA TCA TTC AGT GGT GTA TTA GAC TGT GGA AAC TGT TCC AGA ATC        2983
Ser Lys Ser Phe Ser Gly Val Leu Asp Cys Gly Asn Cys Ser Arg Ile
        970                 975                 980

TTT CAT GGA GAA AAG CTT ATG AAC ACC AAC TTA ATA TTC ATA ATG GTT        3031
Phe His Gly Glu Lys Leu Met Asn Thr Asn Leu Ile Phe Ile Met Val
    985                 990                 995

GAG AGC AAA GGG ACA TGT CCA TGT GAC ACA CGA CTG CTC ATA CAA GCG        3079
Glu Ser Lys Gly Thr Cys Pro Cys Asp Thr Arg Leu Leu Ile Gln Ala
1000                1005                1010                1015

GAG CAG ACT TCT GAC GGT CCA AAT CCT TGT GAC ATG GTT AAG CAA CCT        3127
Glu Gln Thr Ser Asp Gly Pro Asn Pro Cys Asp Met Val Lys Gln Pro
                    1020                1025                1030

AGA TAC CGA AAA GGG CCT GAT GTC TGC TTT GAT AAC AAT GTC TTG GAG        3175
Arg Tyr Arg Lys Gly Pro Asp Val Cys Phe Asp Asn Asn Val Leu Glu
                1035                1040                1045

GAT TAT ACT GAC TGT GGT GGT GTT TCT GGA TTA AAT CCC TCC CTG TGG        3223
Asp Tyr Thr Asp Cys Gly Gly Val Ser Gly Leu Asn Pro Ser Leu Trp
            1050                1055                1060

TAT ATC ATT GGA ATC CAG TTT CTA CTA CTT TGG CTG GTA TCT GGC AGC        3271
Tyr Ile Ile Gly Ile Gln Phe Leu Leu Leu Trp Leu Val Ser Gly Ser
        1065                1070                1075

ACA CAC CGG CTG TTA TGA CCTTCTAAAA ACCAAATCTG CATAGTTAAA CTCCAGACC    3328
Thr His Arg Leu Leu
1080

CTGCCAAAAC ATGAGCCCTG CCCTCAATTA CAGTAACGTA GGGTCAGCTA TAAAATCAGA     3388

CAAACATTAG CTGGGCCTGT TCCATGGCAT AACACTAAGG CGCAGACTCC TAAGGCACCC     3448

ACTGGCTGCA TGTCAGGGTG TCAGATCCTT AAACGTGTGT GAATGCTGCA TCATCTATGT     3508

GTAACATCAA AGCAAAATCC TATACGTGTC CTCTATTGGA AAATTTGGGC GTTTGTTGTT     3568

GCATTGTTGG T                                                         3579
```

( 2 ) INFORMATION FOR SEQ ID NO:37:

( i ) SEQUENCE CHARACTERISTICS:
        ( A ) LENGTH: 1681 base pairs
        ( B ) TYPE: nucleic acid
        ( C ) STRANDEDNESS: double
        ( D ) TOPOLOGY: linear ( i i ) MOLECULE TYPE: Genomic DNA ( i i i ) HYPOTHETICAL: NO ( i v ) ANTI-SENSE: NO ( v ) FRAGMENT TYPE:

( v i ) ORIGINAL SOURCE:

( i x ) FEATURE:
        ( A ) NAME/KEY: Coding Sequence
        ( B ) LOCATION: 1...1572
        ( D ) OTHER INFORMATION: Standard name "beta1"
        ( A ) NAME/KEY: 3'UTR ( B ) LOCATION: 1573...1681
( D ) OTHER INFORMATION:

( x i ) SEQUENCE DESCRIPTION: SEQ ID NO:37:

| | | | | | | | | | | | | | | | | |
|---|---|---|---|---|---|---|---|---|---|---|---|---|---|---|---|---|
| ATG | GTC | CAG | AAG | ACC | AGC | ATG | TCC | CGG | GGC | CCT | TAC | CCA | CCC | TCC | CAG | 48 |
| Met | Val | Gln | Lys | Thr | Ser | Met | Ser | Arg | Gly | Pro | Tyr | Pro | Pro | Ser | Gln | |
| 1 | | | | 5 | | | | | 10 | | | | | 15 | | |
| GAG | ATC | CCC | ATG | GAG | GTC | TTC | GAC | CCC | AGC | CCG | CAG | GGC | AAA | TAC | AGC | 96 |
| Glu | Ile | Pro | Met | Glu | Val | Phe | Asp | Pro | Ser | Pro | Gln | Gly | Lys | Tyr | Ser | |
| | | | 20 | | | | | 25 | | | | | 30 | | | |
| AAG | AGG | AAA | GGG | CGA | TTC | AAA | CGG | TCA | GAT | GGG | AGC | ACG | TCC | TCG | GAT | 144 |
| Lys | Arg | Lys | Gly | Arg | Phe | Lys | Arg | Ser | Asp | Gly | Ser | Thr | Ser | Ser | Asp | |
| | | 35 | | | | | 40 | | | | | 45 | | | | |
| ACC | ACA | TCC | AAC | AGC | TTT | GTC | CGC | CAG | GGC | TCA | GCG | GAG | TCC | TAC | ACC | 192 |
| Thr | Thr | Ser | Asn | Ser | Phe | Val | Arg | Gln | Gly | Ser | Ala | Glu | Ser | Tyr | Thr | |
| | 50 | | | | | 55 | | | | | 60 | | | | | |
| AGC | CGT | CCA | TCA | GAC | TCT | GAT | GTA | TCT | CTG | GAG | GAG | GAC | CGG | GAA | GCC | 240 |
| Ser | Arg | Pro | Ser | Asp | Ser | Asp | Val | Ser | Leu | Glu | Glu | Asp | Arg | Glu | Ala | |
| 65 | | | | 70 | | | | | 75 | | | | | 80 | | |
| TTA | AGG | AAG | GAA | GCA | GAG | CGC | CAG | GCA | TTA | GCG | CAG | CTC | GAG | AAG | GCC | 288 |
| Leu | Arg | Lys | Glu | Ala | Glu | Arg | Gln | Ala | Leu | Ala | Gln | Leu | Glu | Lys | Ala | |
| | | | | 85 | | | | | 90 | | | | | 95 | | |
| AAG | ACC | AAG | CCA | GTG | GCA | TTT | GCT | GTG | CGG | ACA | AAT | GTT | GGC | TAC | AAT | 336 |
| Lys | Thr | Lys | Pro | Val | Ala | Phe | Ala | Val | Arg | Thr | Asn | Val | Gly | Tyr | Asn | |
| | | | 100 | | | | | 105 | | | | | 110 | | | |
| CCG | TCT | CCA | GGG | GAT | GAG | GTG | CCT | GTG | CAG | GGA | GTG | GCC | ATC | ACC | TTC | 384 |
| Pro | Ser | Pro | Gly | Asp | Glu | Val | Pro | Val | Gln | Gly | Val | Ala | Ile | Thr | Phe | |
| | | 115 | | | | | 120 | | | | | 125 | | | | |
| GAG | CCC | AAA | GAC | TTC | CTG | CAC | ATC | AAG | GAG | AAA | TAC | AAT | AAT | GAC | TGG | 432 |
| Glu | Pro | Lys | Asp | Phe | Leu | His | Ile | Lys | Glu | Lys | Tyr | Asn | Asn | Asp | Trp | |
| | 130 | | | | | 135 | | | | | 140 | | | | | |
| TGG | ATC | GGG | CGG | CTG | GTG | AAG | GAG | GGC | TGT | GAG | GTT | GGC | TTC | ATT | CCC | 480 |
| Trp | Ile | Gly | Arg | Leu | Val | Lys | Glu | Gly | Cys | Glu | Val | Gly | Phe | Ile | Pro | |
| 145 | | | | | 150 | | | | | 155 | | | | | 160 | |
| AGC | CCC | GTC | AAA | CTG | GAC | AGC | CTT | CGC | CTG | CTG | CAG | GAA | CAG | AAG | CTG | 528 |
| Ser | Pro | Val | Lys | Leu | Asp | Ser | Leu | Arg | Leu | Leu | Gln | Glu | Gln | Lys | Leu | |
| | | | 165 | | | | | 170 | | | | | 175 | | | |
| CGC | CAG | AAC | CGC | CTC | GGC | TCC | AGC | AAA | TCA | GGC | GAT | AAC | TCC | AGT | TCC | 576 |
| Arg | Gln | Asn | Arg | Leu | Gly | Ser | Ser | Lys | Ser | Gly | Asp | Asn | Ser | Ser | Ser | |
| | | 180 | | | | | 185 | | | | | 190 | | | | |
| AGT | CTG | GGA | GAT | GTG | GTG | ACT | GGC | ACC | CGC | CGC | CCC | ACA | CCC | CCT | GCC | 624 |
| Ser | Leu | Gly | Asp | Val | Val | Thr | Gly | Thr | Arg | Arg | Pro | Thr | Pro | Pro | Ala | |
| | 195 | | | | | 200 | | | | | 205 | | | | | |
| AGT | GGT | AAT | GAA | ATG | ACT | AAC | TTA | GCC | TTT | GAA | CTA | GAC | CCC | CTA | GAG | 672 |
| Ser | Gly | Asn | Glu | Met | Thr | Asn | Leu | Ala | Phe | Glu | Leu | Asp | Pro | Leu | Glu | |
| 210 | | | | | 215 | | | | | 220 | | | | | | |
| TTA | GAG | GAG | GAA | GAG | GCT | GAG | CTT | GGT | GAG | CAG | AGT | GGC | TCT | GCC | AAG | 720 |
| Leu | Glu | Glu | Glu | Glu | Ala | Glu | Leu | Gly | Glu | Gln | Ser | Gly | Ser | Ala | Lys | |
| 225 | | | | | 230 | | | | | 235 | | | | | 240 | |
| ACT | AGT | GTT | AGC | AGT | GTC | ACC | ACC | CCG | CCA | CCC | CAT | GGC | AAA | CGC | ATC | 768 |
| Thr | Ser | Val | Ser | Ser | Val | Thr | Thr | Pro | Pro | Pro | His | Gly | Lys | Arg | Ile | |
| | | | | 245 | | | | | 250 | | | | | 255 | | |
| CCC | TTC | TTT | AAG | AAG | ACA | GAG | CAT | GTG | CCC | CCC | TAT | GAC | GTG | GTG | CCT | 816 |
| Pro | Phe | Phe | Lys | Lys | Thr | Glu | His | Val | Pro | Pro | Tyr | Asp | Val | Val | Pro | |
| | | | 260 | | | | | 265 | | | | | 270 | | | |
| TCC | ATG | AGG | CCC | ATC | ATC | CTG | GTG | GGA | CCG | TCG | CTC | AAG | GGC | TAC | GAG | 864 |
| Ser | Met | Arg | Pro | Ile | Ile | Leu | Val | Gly | Pro | Ser | Leu | Lys | Gly | Tyr | Glu | |
| | | 275 | | | | | 280 | | | | | 285 | | | | |
| GTT | ACA | GAC | ATG | ATG | CAG | AAA | GCT | TTA | TTT | GAC | TTC | TTG | AAG | CAT | CGG | 912 |
| Val | Thr | Asp | Met | Met | Gln | Lys | Ala | Leu | Phe | Asp | Phe | Leu | Lys | His | Arg | |
| | 290 | | | | | 295 | | | | | 300 | | | | | |

| | | | | | | | | | | | | | | | | |
|---|---|---|---|---|---|---|---|---|---|---|---|---|---|---|---|---|
| TTT | GAT | GGC | AGG | ATC | TCC | ATC | ACT | CGT | GTG | ACG | GCA | GAT | ATT | TCC | CTG | 960 |
| Phe | Asp | Gly | Arg | Ile | Ser | Ile | Thr | Arg | Val | Thr | Ala | Asp | Ile | Ser | Leu | |
| 305 | | | | 310 | | | | | 315 | | | | | | 320 | |
| GCT | AAG | CGC | TCA | GTT | CTC | AAC | AAC | CCC | AGC | AAA | CAC | ATC | ATC | ATT | GAG | 1008 |
| Ala | Lys | Arg | Ser | Val | Leu | Asn | Asn | Pro | Ser | Lys | His | Ile | Ile | Ile | Glu | |
| | | | 325 | | | | | 330 | | | | | 335 | | | |
| CGC | TCC | AAC | ACA | CGC | TCC | AGC | CTG | GCT | GAG | GTG | CAG | AGT | GAA | ATC | GAG | 1056 |
| Arg | Ser | Asn | Thr | Arg | Ser | Ser | Leu | Ala | Glu | Val | Gln | Ser | Glu | Ile | Glu | |
| | | | 340 | | | | | 345 | | | | | 350 | | | |
| CGA | ATC | TTC | GAG | CTG | GCC | CGG | ACC | CTT | CAG | TTG | GTC | GCT | CTG | GAT | GCT | 1104 |
| Arg | Ile | Phe | Glu | Leu | Ala | Arg | Thr | Leu | Gln | Leu | Val | Ala | Leu | Asp | Ala | |
| | | 355 | | | | | 360 | | | | | 365 | | | | |
| GAC | ACC | ATC | AAT | CAC | CCA | GCC | CAG | CTG | TCC | AAG | ACC | TCG | CTG | GCC | CCC | 1152 |
| Asp | Thr | Ile | Asn | His | Pro | Ala | Gln | Leu | Ser | Lys | Thr | Ser | Leu | Ala | Pro | |
| | 370 | | | | | 375 | | | | | 380 | | | | | |
| ATC | ATT | GTT | TAC | ATC | AAG | ATC | ACC | TCT | CCC | AAG | GTA | CTT | CAA | AGG | CTC | 1200 |
| Ile | Ile | Val | Tyr | Ile | Lys | Ile | Thr | Ser | Pro | Lys | Val | Leu | Gln | Arg | Leu | |
| 385 | | | | | 390 | | | | | 395 | | | | | 400 | |
| ATC | AAG | TCC | CGA | GGA | AAG | TCT | CAG | TCC | AAA | CAC | CTC | AAT | GTC | CAA | ATA | 1248 |
| Ile | Lys | Ser | Arg | Gly | Lys | Ser | Gln | Ser | Lys | His | Leu | Asn | Val | Gln | Ile | |
| | | | | 405 | | | | | 410 | | | | | 415 | | |
| GCG | GCC | TCG | GAA | AAG | CTG | GCA | CAG | TGC | CCC | CCT | GAA | ATG | TTT | GAC | ATC | 1296 |
| Ala | Ala | Ser | Glu | Lys | Leu | Ala | Gln | Cys | Pro | Pro | Glu | Met | Phe | Asp | Ile | |
| | | | 420 | | | | | 425 | | | | | 430 | | | |
| ATC | CTG | GAT | GAG | AAC | CAA | TTG | GAG | GAT | GCC | TGC | GAG | CAT | CTG | GCG | GAG | 1344 |
| Ile | Leu | Asp | Glu | Asn | Gln | Leu | Glu | Asp | Ala | Cys | Glu | His | Leu | Ala | Glu | |
| | | | 435 | | | | | 440 | | | | | 445 | | | |
| TAC | TTG | GAA | GCC | TAT | TGG | AAG | GCC | ACA | CAC | CCG | CCC | AGC | AGC | ACG | CCA | 1392 |
| Tyr | Leu | Glu | Ala | Tyr | Trp | Lys | Ala | Thr | His | Pro | Pro | Ser | Ser | Thr | Pro | |
| | | 450 | | | | | 455 | | | | | 460 | | | | |
| CCC | AAT | CCG | CTG | CTG | AAC | CGC | ACC | ATG | GCT | ACC | GCA | GCC | CTG | GCT | GCC | 1440 |
| Pro | Asn | Pro | Leu | Leu | Asn | Arg | Thr | Met | Ala | Thr | Ala | Ala | Leu | Ala | Ala | |
| 465 | | | | | 470 | | | | | 475 | | | | | 480 | |
| AGC | CCT | GCC | CCT | GTC | TCC | AAC | CTC | CAG | GTA | CAG | GTG | CTC | ACC | TCG | CTC | 1488 |
| Ser | Pro | Ala | Pro | Val | Ser | Asn | Leu | Gln | Val | Gln | Val | Leu | Thr | Ser | Leu | |
| | | | | 485 | | | | | 490 | | | | | 495 | | |
| AGG | AGA | AAC | CTC | GGC | TTC | TGG | GGC | GGG | CTG | GAG | TCC | TCA | CAG | CGG | GGC | 1536 |
| Arg | Arg | Asn | Leu | Gly | Phe | Trp | Gly | Gly | Leu | Glu | Ser | Ser | Gln | Arg | Gly | |
| | | | 500 | | | | 505 | | | | | 510 | | | | |
| AGT | GTG | GTG | CCC | CAG | GAG | CAG | GAA | CAT | GCC | ATG | TAG | TGGGCGCCCT | | GCCCGTC | | 1589 |
| Ser | Val | Val | Pro | Gln | Glu | Gln | Glu | His | Ala | Met | * | | | | | |
| | | 515 | | | | | 520 | | | | | | | | | |

TTCCCTCCTG CTCTGGGGTC GGAACTGGAG TGCAGGGAAC ATGGAGGAGG AAGGGAAGAG  1649

CTTTATTTTG TAAAAAAATA AGATGAGCGG CA  1681

( 2 ) INFORMATION FOR SEQ ID NO:38:

( i ) SEQUENCE CHARACTERISTICS:
        ( A ) LENGTH: 1526 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 1..651
        ( D ) OTHER INFORMATION: /standard_name="Beta4"

( x i ) SEQUENCE DESCRIPTION: SEQ ID NO:38:

ATG GTC CAG AAG ACC AGC ATG TCC CGG GGC CCT TAC CCA CCC TCC CAG     48

|     |     |     |     |     |     |     |     |     |     |     |     |     |     |     |     |
| --- | --- | --- | --- | --- | --- | --- | --- | --- | --- | --- | --- | --- | --- | --- | --- |
| Met | Val | Gln | Lys | Thr | Ser | Met | Ser | Arg | Gly | Pro | Tyr | Pro | Pro | Ser | Gln |
| 1   |     |     |     | 5   |     |     |     |     | 10  |     |     |     |     | 15  |     |

| GAG | ATC | CCC | ATG | GAG | GTC | TTC | GAC | CCC | AGC | CCG | CAG | GGC | AAA | TAC | AGC | 96 |
| --- | --- | --- | --- | --- | --- | --- | --- | --- | --- | --- | --- | --- | --- | --- | --- | --- |
| Glu | Ile | Pro | Met | Glu | Val | Phe | Asp | Pro | Ser | Pro | Gln | Gly | Lys | Tyr | Ser |    |
|     |     |     | 20  |     |     |     |     | 25  |     |     |     |     | 30  |     |     |    |

| AAG | AGG | AAA | GGG | CGA | TTC | AAA | CGG | TCA | GAT | GGG | AGC | ACG | TCC | TCG | GAT | 144 |
| --- | --- | --- | --- | --- | --- | --- | --- | --- | --- | --- | --- | --- | --- | --- | --- | --- |
| Lys | Arg | Lys | Gly | Arg | Phe | Lys | Arg | Ser | Asp | Gly | Ser | Thr | Ser | Ser | Asp |     |
|     |     | 35  |     |     |     |     | 40  |     |     |     |     | 45  |     |     |     |     |

| ACC | ACA | TCC | AAC | AGC | TTT | GTC | CGC | CAG | GGC | TCA | GCG | GAG | TCC | TAC | ACC | 192 |
| --- | --- | --- | --- | --- | --- | --- | --- | --- | --- | --- | --- | --- | --- | --- | --- | --- |
| Thr | Thr | Ser | Asn | Ser | Phe | Val | Arg | Gln | Gly | Ser | Ala | Glu | Ser | Tyr | Thr |     |
|     | 50  |     |     |     |     | 55  |     |     |     |     | 60  |     |     |     |     |     |

| AGC | CGT | CCA | TCA | GAC | TCT | GAT | GTA | TCT | CTG | GAG | GAG | GAC | CGG | GAA | GCC | 240 |
| --- | --- | --- | --- | --- | --- | --- | --- | --- | --- | --- | --- | --- | --- | --- | --- | --- |
| Ser | Arg | Pro | Ser | Asp | Ser | Asp | Val | Ser | Leu | Glu | Glu | Asp | Arg | Glu | Ala |     |
| 65  |     |     |     |     | 70  |     |     |     |     | 75  |     |     |     |     | 80  |     |

| TTA | AGG | AAG | GAA | GCA | GAG | CGC | CAG | GCA | TTA | GCG | CAG | CTC | GAG | AAG | GCC | 288 |
| --- | --- | --- | --- | --- | --- | --- | --- | --- | --- | --- | --- | --- | --- | --- | --- | --- |
| Leu | Arg | Lys | Glu | Ala | Glu | Arg | Gln | Ala | Leu | Ala | Gln | Leu | Glu | Lys | Ala |     |
|     |     |     |     | 85  |     |     |     |     | 90  |     |     |     |     | 95  |     |     |

| AAG | ACC | AAG | CCA | GTG | GCA | TTT | GCT | GTG | CGG | ACA | AAT | GTT | GGC | TAC | AAT | 336 |
| --- | --- | --- | --- | --- | --- | --- | --- | --- | --- | --- | --- | --- | --- | --- | --- | --- |
| Lys | Thr | Lys | Pro | Val | Ala | Phe | Ala | Val | Arg | Thr | Asn | Val | Gly | Tyr | Asn |     |
|     |     |     | 100 |     |     |     |     | 105 |     |     |     |     | 110 |     |     |     |

| CCG | TCT | CCA | GGG | GAT | GAG | GTG | CCT | GTG | CAG | GGA | GTG | GCC | ATC | ACC | TTC | 384 |
| --- | --- | --- | --- | --- | --- | --- | --- | --- | --- | --- | --- | --- | --- | --- | --- | --- |
| Pro | Ser | Pro | Gly | Asp | Glu | Val | Pro | Val | Gln | Gly | Val | Ala | Ile | Thr | Phe |     |
|     |     | 115 |     |     |     |     | 120 |     |     |     |     | 125 |     |     |     |     |

| GAG | CCC | AAA | GAC | TTC | CTG | CAC | ATC | AAG | GAG | AAA | TAC | AAT | AAT | GAC | TGG | 432 |
| --- | --- | --- | --- | --- | --- | --- | --- | --- | --- | --- | --- | --- | --- | --- | --- | --- |
| Glu | Pro | Lys | Asp | Phe | Leu | His | Ile | Lys | Glu | Lys | Tyr | Asn | Asn | Asp | Trp |     |
| 130 |     |     |     |     | 135 |     |     |     |     | 140 |     |     |     |     |     |     |

| TGG | ATC | GGG | CGG | CTG | GTG | AAG | GAG | GGC | TGT | GAG | GTT | GGC | TTC | ATT | CCC | 480 |
| --- | --- | --- | --- | --- | --- | --- | --- | --- | --- | --- | --- | --- | --- | --- | --- | --- |
| Trp | Ile | Gly | Arg | Leu | Val | Lys | Glu | Gly | Cys | Glu | Val | Gly | Phe | Ile | Pro |     |
| 145 |     |     |     |     | 150 |     |     |     |     | 155 |     |     |     |     | 160 |     |

| AGC | CCC | GTC | AAA | CTG | GAC | AGC | CTT | CGC | CTG | CTG | CAG | GAA | CAG | AAG | CTG | 528 |
| --- | --- | --- | --- | --- | --- | --- | --- | --- | --- | --- | --- | --- | --- | --- | --- | --- |
| Ser | Pro | Val | Lys | Leu | Asp | Ser | Leu | Arg | Leu | Leu | Gln | Glu | Gln | Lys | Leu |     |
|     |     |     |     | 165 |     |     |     |     | 170 |     |     |     |     | 175 |     |     |

| CGC | CAG | AAC | CGC | CTC | GGC | TCC | AGC | AAA | TCA | GGC | GAT | AAC | TCC | AGT | TCC | 576 |
| --- | --- | --- | --- | --- | --- | --- | --- | --- | --- | --- | --- | --- | --- | --- | --- | --- |
| Arg | Gln | Asn | Arg | Leu | Gly | Ser | Ser | Lys | Ser | Gly | Asp | Asn | Ser | Ser | Ser |     |
|     |     |     | 180 |     |     |     |     | 185 |     |     |     |     | 190 |     |     |     |

| AGT | CTG | GGA | GAT | GTG | GTG | ACT | GGC | ACC | CGC | CGC | CCC | ACA | CCC | CCT | GCC | 624 |
| --- | --- | --- | --- | --- | --- | --- | --- | --- | --- | --- | --- | --- | --- | --- | --- | --- |
| Ser | Leu | Gly | Asp | Val | Val | Thr | Gly | Thr | Arg | Arg | Pro | Thr | Pro | Pro | Ala |     |
|     |     | 195 |     |     |     |     | 200 |     |     |     |     | 205 |     |     |     |     |

| AGT | GAC | AGA | GCA | TGT | GCC | CCC | CTA | TGACGTGGTG | CCTTCCATGA | GGCCCATCAT | 678 |
| --- | --- | --- | --- | --- | --- | --- | --- | --- | --- | --- | --- |
| Ser | Asp | Arg | Ala | Cys | Ala | Pro | Leu |   |   |   |   |
| 210 |     |     |     |     | 215 |     |     |   |   |   |   |

| CCTGGTGGGA | CCGTCGCTCA | AGGGCTACGA | GGTTACAGAC | ATGATGCAGA | AAGCTTTATT | 738  |
| ---------- | ---------- | ---------- | ---------- | ---------- | ---------- | ---- |
| TGACTTCTTG | AAGCATCGGT | TGATGGCAG  | GATCTCCATC | ACTCGTGTGA | CGGCAGATAT | 798  |
| TTCCCTGGCT | AAGCGCTCAG | TTCTCAACAA | CCCCAGCAAA | CACATCATCA | TTGAGCGCTC | 858  |
| CAACACACGC | TCCAGCCTGG | CTGAGGTGCA | GAGTGAAATC | GAGCGAATCT | TCGAGCTGGC | 918  |
| CCGGACCCTT | CAGTTGGTCG | CTCTGGATGC | TGACACCATC | AATCACCCAG | CCCAGCTGTC | 978  |
| CAAGACCTCG | CTGGCCCCCA | TCATTGTTTA | CATCAAGATC | ACCTCTCCCA | AGGTACTTCA | 1038 |
| AAGGCTCATC | AAGTCCCGAG | GAAAGTCTCA | GTCCAAACAC | CTCAATGTCC | AAATAGCGGC | 1098 |
| CTCGGAAAAG | CTGGCACAGT | GCCCCCCTGA | AATGTTTGAC | ATCATCCTGG | ATGAGAACCA | 1158 |
| ATTGGAGGAT | GCCTGCGAGC | ATCTGGCGGA | GTACTTGGAA | GCCTATTGGA | AGGCCACACA | 1218 |
| CCCGCCCAGC | AGCACGCCAC | CCAATCCGCT | GCTGAACCGC | ACCATGGCTA | CCGCAGCCCT | 1278 |
| GGCTGCCAGC | CCTGCCCCTG | TCTCCAACCT | CCAGGTACAG | GTGCTCACCT | CGCTCAGGAG | 1338 |
| AAACCTCGGC | TTCTGGGGCG | GGCTGGAGTC | CTCACAGCGG | GGCAGTGTGG | TGCCCCAGGA | 1398 |
| GCAGGAACAT | GCCATGTAGT | GGGCGCCCTG | CCCGTCTTCC | CTCCTGCTCT | GGGGTCGGAA | 1458 |

```
CTGGAGTGCA GGGAACATGG AGGAGGAAGG GAAGAGCTTT ATTTGTAAA AAAATAAGAT      1518

GAGCGGCA                                                              1526
```

(2) INFORMATION FOR SEQ ID NO:39:

(i) SEQUENCE CHARACTERISTICS:
        (A) LENGTH: 1393 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..660
        (D) OTHER INFORMATION: /standard_name="Beta5"

(xi) SEQUENCE DESCRIPTION: SEQ ID NO:39:

```
ATG GTC CAG AAG ACC AGC ATG TCC CGG GGC CCT TAC CCA CCC TCC CAG        48
Met Val Gln Lys Thr Ser Met Ser Arg Gly Pro Tyr Pro Pro Ser Gln
 1           5                  10                  15

GAG ATC CCC ATG GAG GTC TTC GAC CCC AGC CCG CAG GGC AAA TAC AGC        96
Glu Ile Pro Met Glu Val Phe Asp Pro Ser Pro Gln Gly Lys Tyr Ser
             20                  25                  30

AAG AGG AAA GGG CGA TTC AAA CGG TCA GAT GGG AGC ACG TCC TCG GAT       144
Lys Arg Lys Gly Arg Phe Lys Arg Ser Asp Gly Ser Thr Ser Ser Asp
         35                  40                  45

ACC ACA TCC AAC AGC TTT GTC CGC CAG GGC TCA GCG GAG TCC TAC ACC       192
Thr Thr Ser Asn Ser Phe Val Arg Gln Gly Ser Ala Glu Ser Tyr Thr
 50                  55                  60

AGC CGT CCA TCA GAC TCT GAT GTA TCT CTG GAG GAG GAC CGG GAA GCC       240
Ser Arg Pro Ser Asp Ser Asp Val Ser Leu Glu Glu Asp Arg Glu Ala
 65                  70                  75                  80

TTA AGG AAG GAA GCA GAG CGC CAG GCA TTA GCG CAG CTC GAG AAG GCC       288
Leu Arg Lys Glu Ala Glu Arg Gln Ala Leu Ala Gln Leu Glu Lys Ala
             85                  90                  95

AAG ACC AAG CCA GTG GCA TTT GCT GTG CGG ACA AAT GTT GGC TAC AAT       336
Lys Thr Lys Pro Val Ala Phe Ala Val Arg Thr Asn Val Gly Tyr Asn
            100                 105                 110

CCG TCT CCA GGG GAT GAG GTG CCT GTG CAG GGA GTG GCC ATC ACC TTC       384
Pro Ser Pro Gly Asp Glu Val Pro Val Gln Gly Val Ala Ile Thr Phe
        115                 120                 125

GAG CCC AAA GAC TTC CTG CAC ATC AAG GAG AAA TAC AAT AAT GAC TGG       432
Glu Pro Lys Asp Phe Leu His Ile Lys Glu Lys Tyr Asn Asn Asp Trp
    130                 135                 140

TGG ATC GGG CGG CTG GTG AAG GAG GGC TGT GAG GTT GGC TTC ATT CCC       480
Trp Ile Gly Arg Leu Val Lys Glu Gly Cys Glu Val Gly Phe Ile Pro
145                 150                 155                 160

AGC CCC GTC AAA CTG GAC AGC CTT CGC CTG CTG CAG GAA CAG AAG CTG       528
Ser Pro Val Lys Leu Asp Ser Leu Arg Leu Leu Gln Glu Gln Lys Leu
                165                 170                 175

CGC CAG AAC CGC CTC GGC TCC AGC AAA TCA GGC GAT AAC TCC AGT TCC       576
Arg Gln Asn Arg Leu Gly Ser Ser Lys Ser Gly Asp Asn Ser Ser Ser
            180                 185                 190

AGT CTG GGA GAT GTG GTG ACT GGC ACC CGC CGC CCC ACA CCC CCT GCC       624
Ser Leu Gly Asp Val Val Thr Gly Thr Arg Arg Pro Thr Pro Pro Ala
        195                 200                 205

AGT GGT TAC AGA CAT GAT GCA GAA AGC TTT ATT TGACTTCTTG AAGCATCGGT     677
Ser Gly Tyr Arg His Asp Ala Glu Ser Phe Ile
    210                 215                 220

TTGATGGCAG GATCTCCATC ACTCGTGTGA CGGCAGATAT TTCCCTGGCT AAGCGCTCAG     737
```

| | | | | | |
|---|---|---|---|---|---|
| TTCTCAACAA | CCCCAGCAAA | CACATCATCA | TTGAGCGCTC | CAACACACGC | TCCAGCCTGG | 797 |
| CTGAGGTGCA | GAGTGAAATC | GAGCGAATCT | TCGAGCTGGC | CCGGACCCTT | CAGTTGGTCG | 857 |
| CTCTGGATGC | TGACACCATC | AATCACCCAG | CCCAGCTGTC | CAAGACCTCG | CTGGCCCCCA | 917 |
| TCATTGTTTA | CATCAAGATC | ACCTCTCCCA | AGGTACTTCA | AAGGCTCATC | AAGTCCCGAG | 977 |
| GAAAGTCTCA | GTCCAAACAC | CTCAATGTCC | AAATAGCGGC | CTCGGAAAAG | CTGGCACAGT | 1037 |
| GCCCCCCTGA | AATGTTTGAC | ATCATCCTGG | ATGAGAACCA | ATTGGAGGAT | GCCTGCGAGC | 1097 |
| ATCTGGCGGA | GTACTTGGAA | GCCTATTGGA | AGGCCACACA | CCCGCCCAGC | AGCACGCCAC | 1157 |
| CCAATCCGCT | GCTGAACCGC | ACCATGGCTA | CCGCAGCCCT | GGCTGCCAGC | CCTGCCCCTG | 1217 |
| TCTCCAACCT | CCAGGTACAG | GTGCTCACCT | CGCTCAGGAG | AAACCTCGGC | TTCTGGGGCG | 1277 |
| GGCTGGAGTC | CTCACAGCGG | GGCAGTGTGG | TGCCCCAGGA | GCAGGAACAT | GCCATGTAGT | 1337 |
| GGGCGCCCTG | CCCGTCTTCC | CTCCTGCTCT | GGGGTCGGAA | CTGGAGTGCA | GGGAAC | 1393 |

( 2 ) INFORMATION FOR SEQ ID NO:40:

( i ) SEQUENCE CHARACTERISTICS:
        ( A ) LENGTH: 478 amino acids
        ( B ) TYPE: amino acid
        ( C ) STRANDEDNESS: single
        ( D ) TOPOLOGY: linear ( i i ) MOLECULE TYPE: protein ( v ) FRAGMENT TYPE: internal ( x i ) SEQUENCE DESCRIPTION: SEQ ID NO:40:

| Met | Val | Gln | Lys | Thr | Ser | Met | Ser | Arg | Gly | Pro | Tyr | Pro | Pro | Ser | Gln |
|---|---|---|---|---|---|---|---|---|---|---|---|---|---|---|---|
| 1 | | | | 5 | | | | | 10 | | | | | 15 | |
| Glu | Ile | Pro | Met | Glu | Val | Phe | Asp | Pro | Ser | Pro | Gln | Gly | Lys | Tyr | Ser |
| | | | 20 | | | | | 25 | | | | | 30 | | |
| Lys | Arg | Lys | Gly | Arg | Phe | Lys | Arg | Ser | Asp | Gly | Ser | Thr | Ser | Ser | Asp |
| | | 35 | | | | | 40 | | | | | 45 | | | |
| Thr | Thr | Ser | Asn | Ser | Phe | Val | Arg | Gln | Gly | Ser | Ala | Glu | Ser | Tyr | Thr |
| | 50 | | | | | 55 | | | | | 60 | | | | |
| Ser | Arg | Pro | Ser | Asp | Ser | Asp | Val | Ser | Leu | Glu | Glu | Asp | Arg | Glu | Ala |
| 65 | | | | | 70 | | | | | 75 | | | | | 80 |
| Leu | Arg | Lys | Glu | Ala | Glu | Arg | Gln | Ala | Leu | Ala | Gln | Leu | Glu | Lys | Ala |
| | | | | 85 | | | | | 90 | | | | | 95 | |
| Lys | Thr | Lys | Pro | Val | Ala | Phe | Ala | Val | Arg | Thr | Asn | Val | Gly | Tyr | Asn |
| | | | 100 | | | | | 105 | | | | | 110 | | |
| Pro | Ser | Pro | Gly | Asp | Glu | Val | Pro | Val | Gln | Gly | Val | Ala | Ile | Thr | Phe |
| | | 115 | | | | | 120 | | | | | 125 | | | |
| Glu | Pro | Lys | Asp | Phe | Leu | His | Ile | Lys | Glu | Lys | Tyr | Asn | Asn | Asp | Trp |
| | 130 | | | | | 135 | | | | | 140 | | | | |
| Trp | Ile | Gly | Arg | Leu | Val | Lys | Glu | Gly | Cys | Glu | Val | Gly | Phe | Ile | Pro |
| 145 | | | | | 150 | | | | | 155 | | | | | 160 |
| Ser | Pro | Val | Lys | Leu | Asp | Ser | Leu | Arg | Leu | Leu | Gln | Glu | Gln | Lys | Leu |
| | | | | 165 | | | | | 170 | | | | | 175 | |
| Arg | Gln | Asn | Arg | Leu | Gly | Ser | Ser | Lys | Ser | Gly | Asp | Asn | Ser | Ser | Ser |
| | | | 180 | | | | | 185 | | | | | 190 | | |
| Ser | Leu | Gly | Asp | Val | Val | Thr | Gly | Thr | Arg | Arg | Pro | Thr | Pro | Pro | Ala |
| | | 195 | | | | | 200 | | | | | 205 | | | |
| Ser | Ala | Lys | Gln | Lys | Gln | Lys | Ser | Thr | Glu | His | Val | Pro | Pro | Tyr | Asp |
| | 210 | | | | | 215 | | | | | 220 | | | | |

| Val<br>225 | Val | Pro | Ser | Met | Arg<br>230 | Pro | Ile | Ile | Leu | Val<br>235 | Gly | Pro | Ser | Leu | Lys<br>240 |
|---|---|---|---|---|---|---|---|---|---|---|---|---|---|---|---|
| Gly | Tyr | Glu | Val | Thr<br>245 | Asp | Met | Met | Gln | Lys<br>250 | Ala | Leu | Phe | Asp | Phe<br>255 | Leu |
| Lys | His | Arg | Phe<br>260 | Asp | Gly | Arg | Ile | Ser<br>265 | Ile | Thr | Arg | Val | Thr<br>270 | Ala | Asp |
| Ile | Ser | Leu<br>275 | Ala | Lys | Arg | Ser | Val<br>280 | Leu | Asn | Asn | Pro | Ser<br>285 | Lys | His | Ile |
| Ile | Ile<br>290 | Glu | Arg | Ser | Asn | Thr<br>295 | Arg | Ser | Ser | Leu | Ala<br>300 | Glu | Val | Gln | Ser |
| Glu<br>305 | Ile | Glu | Arg | Ile | Phe<br>310 | Glu | Leu | Ala | Arg | Thr<br>315 | Leu | Gln | Leu | Val | Ala<br>320 |
| Leu | Asp | Ala | Asp | Thr<br>325 | Ile | Asn | His | Pro | Ala<br>330 | Gln | Leu | Ser | Lys | Thr<br>335 | Ser |
| Leu | Ala | Pro | Ile<br>340 | Ile | Val | Tyr | Ile | Lys<br>345 | Ile | Thr | Ser | Pro | Lys<br>350 | Val | Leu |
| Gln | Arg | Leu<br>355 | Ile | Lys | Ser | Arg | Gly<br>360 | Lys | Ser | Gln | Ser | Lys<br>365 | His | Leu | Asn |
| Val | Gln<br>370 | Ile | Ala | Ala | Ser | Glu<br>375 | Lys | Leu | Ala | Gln | Cys<br>380 | Pro | Pro | Glu | Met |
| Phe<br>385 | Asp | Ile | Ile | Leu | Asp<br>390 | Glu | Asn | Gln | Leu | Glu<br>395 | Asp | Ala | Cys | Glu | His<br>400 |
| Leu | Ala | Glu | Tyr | Leu<br>405 | Glu | Ala | Tyr | Trp | Lys<br>410 | Ala | Thr | His | Pro | Pro<br>415 | Ser |
| Ser | Thr | Pro | Pro<br>420 | Asn | Pro | Leu | Leu | Asn<br>425 | Arg | Thr | Met | Ala | Thr<br>430 | Ala | Ala |
| Leu | Ala | Ala<br>435 | Ser | Pro | Ala | Pro | Val<br>440 | Ser | Asn | Leu | Gln | Val<br>445 | Gln | Val | Leu |
| Thr | Ser<br>450 | Leu | Arg | Arg | Asn | Leu<br>455 | Gly | Phe | Trp | Gly | Gly<br>460 | Leu | Glu | Ser | Ser |
| Gln<br>465 | Arg | Gly | Ser | Val | Val<br>470 | Pro | Gln | Glu | Gln | Glu<br>475 | His | Ala | Met | | |

( 2 ) INFORMATION FOR SEQ ID NO:41:

( i ) SEQUENCE CHARACTERISTICS:
        ( A ) LENGTH: 598 amino acids
        ( B ) TYPE: amino acid
        ( C ) STRANDEDNESS: single
        ( D ) TOPOLOGY: linear ( i i ) MOLECULE TYPE: protein ( v ) FRAGMENT TYPE: internal ( x i ) SEQUENCE DESCRIPTION: SEQ ID NO:41:

| Met<br>1 | Val | Gln | Lys | Thr<br>5 | Ser | Met | Ser | Arg | Glu<br>10 | Pro | Tyr | Pro | Pro | Ser<br>15 | Gln |
|---|---|---|---|---|---|---|---|---|---|---|---|---|---|---|---|
| Glu | Ile | Pro | Met<br>20 | Glu | Val | Phe | Asp | Pro<br>25 | Ser | Pro | Gln | Gly | Lys<br>30 | Tyr | Ser |
| Lys | Arg | Lys<br>35 | Gly | Arg | Phe | Lys | Arg<br>40 | Ser | Asp | Gly | Ser | Thr<br>45 | Ser | Ser | Asp |
| Thr | Thr<br>50 | Ser | Asn | Ser | Phe | Val<br>55 | Arg | Gln | Gly | Ser | Ala<br>60 | Glu | Ser | Tyr | Thr |
| Ser<br>65 | Arg | Pro | Ser | Asp | Ser<br>70 | Asp | Val | Ser | Leu | Glu<br>75 | Glu | Asp | Arg | Glu | Ala<br>80 |
| Leu | Arg | Lys | Glu | Ala<br>85 | Glu | Arg | Gln | Ala | Leu<br>90 | Ala | Gln | Leu | Glu | Lys<br>95 | Ala |

```
Lys Thr Lys Pro Val Ala Phe Ala Val Arg Thr Asn Val Gly Tyr Asn
            100             105             110

Pro Ser Pro Gly Asp Glu Val Pro Val Gln Gly Val Ala Ile Thr Phe
        115             120             125

Glu Pro Lys Asp Phe Leu His Ile Lys Glu Lys Tyr Asn Asn Asp Trp
    130             135             140

Trp Ile Gly Arg Leu Val Lys Glu Gly Cys Glu Val Gly Phe Ile Pro
145             150             155             160

Ser Pro Val Lys Leu Asp Ser Leu Arg Leu Leu Gln Glu Gln Lys Leu
            165             170             175

Arg Gln Asn Arg Leu Gly Ser Ser Lys Ser Gly Asp Asn Ser Ser Ser
            180             185             190

Ser Leu Gly Asp Val Val Thr Gly Thr Arg Arg Pro Thr Pro Pro Ala
            195             200             205

Ser Ala Lys Gln Lys Gln Lys Ser Thr Glu His Val Pro Pro Tyr Asp
        210             215             220

Val Val Pro Ser Met Arg Pro Ile Ile Leu Val Gly Pro Ser Leu Lys
225             230             235             240

Gly Tyr Glu Val Thr Asp Met Met Gln Lys Ala Leu Phe Asp Phe Leu
            245             250             255

Lys His Arg Phe Asp Gly Arg Ile Ser Ile Thr Arg Val Thr Ala Asp
            260             265             270

Ile Ser Leu Ala Lys Arg Ser Val Leu Asn Asn Pro Ser Lys His Ile
        275             280             285

Ile Ile Glu Arg Ser Asn Thr Arg Ser Ser Leu Ala Glu Val Gln Ser
    290             295             300

Glu Ile Glu Arg Ile Phe Glu Leu Ala Arg Thr Leu Gln Leu Val Ala
305             310             315             320

Leu Asp Ala Asp Thr Ile Asn His Pro Ala Gln Leu Ser Lys Thr Ser
            325             330             335

Leu Ala Pro Ile Ile Val Tyr Ile Lys Ile Thr Ser Pro Lys Val Leu
            340             345             350

Gln Arg Leu Ile Lys Ser Arg Gly Lys Ser Gln Ser Lys His Leu Asn
            355             360             365

Val Gln Ile Ala Ala Ser Glu Lys Leu Ala Gln Cys Pro Pro Glu Met
    370             375             380

Phe Asp Ile Ile Leu Asp Glu Asn Gln Leu Glu Asp Ala Cys Glu His
385             390             395             400

Leu Ala Glu Tyr Leu Glu Ala Tyr Trp Lys Ala Thr His Pro Pro Ser
            405             410             415

Ser Thr Pro Pro Asn Pro Leu Leu Asn Arg Thr Met Ala Thr Ala Ala
            420             425             430

Leu Ala Ala Ser Pro Ala Pro Val Ser Asn Leu Gln Gly Pro Tyr Leu
        435             440             445

Ala Ser Gly Asp Gln Pro Leu Glu Arg Ala Thr Gly Glu His Ala Ser
        450             455             460

Met His Glu Tyr Pro Gly Glu Leu Gly Gln Pro Pro Gly Leu Tyr Pro
465             470             475             480

Ser Ser His Pro Pro Gly Arg Ala Gly Thr Leu Arg Ala Leu Ser Arg
            485             490             495

Gln Asp Thr Phe Asp Ala Asp Thr Pro Gly Ser Arg Asn Ser Ala Tyr
            500             505             510

Thr Glu Leu Gly Asp Ser Cys Val Asp Met Glu Thr Asp Pro Ser Glu
```

|  | 515 |  |  |  |  | 520 |  |  |  |  | 525 |  |  |
|---|---|---|---|---|---|---|---|---|---|---|---|---|---|
| Gly | Pro | Gly | Leu | Gly | Asp | Pro | Ala | Gly | Gly | Gly | Thr | Pro | Pro | Ala | Arg |
|  | 530 |  |  |  |  | 535 |  |  |  |  | 540 |  |  |
| Gln | Gly | Ser | Trp | Glu | Asp | Glu | Glu | Glu | Asp | Tyr | Glu | Glu | Glu | Leu | Thr |
| 545 |  |  |  |  | 550 |  |  |  |  | 555 |  |  |  |  | 560 |
| Asp | Asn | Arg | Asn | Arg | Gly | Arg | Asn | Lys | Ala | Arg | Tyr | Cys | Ala | Glu | Gly |
|  |  |  |  | 565 |  |  |  |  | 570 |  |  |  |  | 575 |  |
| Gly | Gly | Pro | Val | Leu | Gly | Arg | Asn | Lys | Asn | Glu | Leu | Glu | Gly | Trp | Gly |
|  |  |  | 580 |  |  |  |  | 585 |  |  |  |  | 590 |  |  |
| Arg | Gly | Val | Tyr | Ile | Arg |
|  |  | 595 |  |  |  |

( 2 ) INFORMATION FOR SEQ ID NO:42:

( i ) SEQUENCE CHARACTERISTICS:
        ( A ) LENGTH: 523 amino acids
        ( B ) TYPE: amino acid
        ( C ) STRANDEDNESS: single
        ( D ) TOPOLOGY: linear ( i i ) MOLECULE TYPE: protein ( v ) FRAGMENT TYPE: internal ( x i ) SEQUENCE DESCRIPTION: SEQ ID NO:42:

| Met | Val | Gln | Lys | Thr | Ser | Met | Ser | Arg | Gly | Pro | Tyr | Pro | Pro | Ser | Gln |
|---|---|---|---|---|---|---|---|---|---|---|---|---|---|---|---|
| 1 |  |  |  | 5 |  |  |  |  | 10 |  |  |  |  | 15 |  |
| Glu | Ile | Pro | Met | Glu | Val | Phe | Asp | Pro | Ser | Pro | Gln | Gly | Lys | Tyr | Ser |
|  |  |  | 20 |  |  |  |  | 25 |  |  |  |  | 30 |  |  |
| Lys | Arg | Lys | Gly | Arg | Phe | Lys | Arg | Ser | Asp | Gly | Ser | Thr | Ser | Ser | Asp |
|  |  | 35 |  |  |  |  | 40 |  |  |  |  | 45 |  |  |  |
| Thr | Thr | Ser | Asn | Ser | Phe | Val | Arg | Gln | Gly | Ser | Ala | Glu | Ser | Tyr | Thr |
|  | 50 |  |  |  |  | 55 |  |  |  |  | 60 |  |  |  |  |
| Ser | Arg | Pro | Ser | Asp | Ser | Asp | Val | Ser | Leu | Glu | Glu | Asp | Arg | Glu | Ala |
| 65 |  |  |  |  | 70 |  |  |  |  | 75 |  |  |  |  | 80 |
| Leu | Arg | Lys | Glu | Ala | Glu | Arg | Gln | Ala | Leu | Ala | Gln | Leu | Glu | Lys | Ala |
|  |  |  |  | 85 |  |  |  |  | 90 |  |  |  |  | 95 |  |
| Lys | Thr | Lys | Pro | Val | Ala | Phe | Ala | Val | Arg | Thr | Asn | Val | Gly | Tyr | Asn |
|  |  |  | 100 |  |  |  |  | 105 |  |  |  |  | 110 |  |  |
| Pro | Ser | Pro | Gly | Asp | Glu | Val | Pro | Val | Gln | Gly | Val | Ala | Ile | Thr | Phe |
|  |  | 115 |  |  |  |  | 120 |  |  |  |  | 125 |  |  |  |
| Glu | Pro | Lys | Asp | Phe | Leu | His | Ile | Lys | Glu | Lys | Tyr | Asn | Asn | Asp | Trp |
|  | 130 |  |  |  |  | 135 |  |  |  |  | 140 |  |  |  |  |
| Trp | Ile | Gly | Arg | Leu | Val | Lys | Glu | Gly | Cys | Glu | Val | Gly | Phe | Ile | Pro |
| 145 |  |  |  |  | 150 |  |  |  |  | 155 |  |  |  |  | 160 |
| Ser | Pro | Val | Lys | Leu | Asp | Ser | Leu | Arg | Leu | Leu | Gln | Glu | Gln | Lys | Leu |
|  |  |  |  | 165 |  |  |  |  | 170 |  |  |  |  | 175 |  |
| Arg | Gln | Asn | Arg | Leu | Gly | Ser | Ser | Lys | Ser | Gly | Asp | Asn | Ser | Ser | Ser |
|  |  |  | 180 |  |  |  |  | 185 |  |  |  |  | 190 |  |  |
| Ser | Leu | Gly | Asp | Val | Val | Thr | Gly | Thr | Arg | Arg | Pro | Thr | Pro | Pro | Ala |
|  |  | 195 |  |  |  |  | 200 |  |  |  |  | 205 |  |  |  |
| Ser | Gly | Asn | Glu | Met | Thr | Asn | Leu | Ala | Phe | Glu | Leu | Asp | Pro | Leu | Glu |
|  | 210 |  |  |  |  | 215 |  |  |  |  | 220 |  |  |  |  |
| Leu | Glu | Glu | Glu | Glu | Ala | Glu | Leu | Gly | Glu | Gln | Ser | Gly | Ser | Ala | Lys |
| 225 |  |  |  |  | 230 |  |  |  |  | 235 |  |  |  |  | 240 |
| Thr | Ser | Val | Ser | Ser | Val | Thr | Thr | Pro | Pro | Pro | His | Gly | Lys | Arg | Ile |
|  |  |  |  | 245 |  |  |  |  | 250 |  |  |  |  | 255 |  |

| Pro | Phe | Phe | Lys | Thr | Glu | His | Val | Pro | Pro | Tyr | Asp | Val | Pro |
|---|---|---|---|---|---|---|---|---|---|---|---|---|---|
| | | | 260 | | | 265 | | | | 270 | | | |

| Ser | Met | Arg | Pro | Ile | Ile | Leu | Val | Gly | Pro | Ser | Leu | Lys | Gly | Tyr | Glu |
|---|---|---|---|---|---|---|---|---|---|---|---|---|---|---|---|
| | | 275 | | | | 280 | | | | 285 | | | | | |

| Val | Thr | Asp | Met | Met | Gln | Lys | Ala | Leu | Phe | Asp | Phe | Leu | Lys | His | Arg |
|---|---|---|---|---|---|---|---|---|---|---|---|---|---|---|---|
| | 290 | | | | 295 | | | | | 300 | | | | | |

| Phe | Asp | Gly | Arg | Ile | Ser | Ile | Thr | Arg | Val | Thr | Ala | Asp | Ile | Ser | Leu |
|---|---|---|---|---|---|---|---|---|---|---|---|---|---|---|---|
| 305 | | | | | 310 | | | | | 315 | | | | | 320 |

| Ala | Lys | Arg | Ser | Val | Leu | Asn | Asn | Pro | Ser | Lys | His | Ile | Ile | Ile | Glu |
|---|---|---|---|---|---|---|---|---|---|---|---|---|---|---|---|
| | | | | 325 | | | | | 330 | | | | | 335 | |

| Arg | Ser | Asn | Thr | Arg | Ser | Ser | Leu | Ala | Glu | Val | Gln | Ser | Glu | Ile | Glu |
|---|---|---|---|---|---|---|---|---|---|---|---|---|---|---|---|
| | | | 340 | | | | | 345 | | | | | 350 | | |

| Arg | Ile | Phe | Glu | Leu | Ala | Arg | Thr | Leu | Gln | Leu | Val | Ala | Leu | Asp | Ala |
|---|---|---|---|---|---|---|---|---|---|---|---|---|---|---|---|
| | | 355 | | | | | 360 | | | | | 365 | | | |

| Asp | Thr | Ile | Asn | His | Pro | Ala | Gln | Leu | Ser | Lys | Thr | Ser | Leu | Ala | Pro |
|---|---|---|---|---|---|---|---|---|---|---|---|---|---|---|---|
| | 370 | | | | | 375 | | | | | 380 | | | | |

| Ile | Ile | Val | Tyr | Ile | Lys | Ile | Thr | Ser | Pro | Lys | Val | Leu | Gln | Arg | Leu |
|---|---|---|---|---|---|---|---|---|---|---|---|---|---|---|---|
| 385 | | | | | 390 | | | | | 395 | | | | | 400 |

| Ile | Lys | Ser | Arg | Gly | Lys | Ser | Gln | Ser | Lys | His | Leu | Asn | Val | Gln | Ile |
|---|---|---|---|---|---|---|---|---|---|---|---|---|---|---|---|
| | | | | 405 | | | | | 410 | | | | | 415 | |

| Ala | Ala | Ser | Glu | Lys | Leu | Ala | Gln | Cys | Pro | Pro | Glu | Met | Phe | Asp | Ile |
|---|---|---|---|---|---|---|---|---|---|---|---|---|---|---|---|
| | | | 420 | | | | | 425 | | | | | 430 | | |

| Ile | Leu | Asp | Glu | Asn | Gln | Leu | Glu | Asp | Ala | Cys | Glu | His | Leu | Ala | Glu |
|---|---|---|---|---|---|---|---|---|---|---|---|---|---|---|---|
| | | 435 | | | | | 440 | | | | | 445 | | | |

| Tyr | Leu | Glu | Ala | Tyr | Trp | Lys | Ala | Thr | His | Pro | Pro | Ser | Ser | Thr | Pro |
|---|---|---|---|---|---|---|---|---|---|---|---|---|---|---|---|
| | 450 | | | | | 455 | | | | | 460 | | | | |

| Pro | Asn | Pro | Leu | Leu | Asn | Arg | Thr | Met | Ala | Thr | Ala | Ala | Leu | Ala | Ala |
|---|---|---|---|---|---|---|---|---|---|---|---|---|---|---|---|
| 465 | | | | | 470 | | | | | 475 | | | | | 480 |

| Ser | Pro | Ala | Pro | Val | Ser | Asn | Leu | Gln | Val | Gln | Val | Leu | Thr | Ser | Leu |
|---|---|---|---|---|---|---|---|---|---|---|---|---|---|---|---|
| | | | | 485 | | | | | 490 | | | | | 495 | |

| Arg | Arg | Asn | Leu | Gly | Phe | Trp | Gly | Gly | Leu | Glu | Ser | Ser | Gln | Arg | Gly |
|---|---|---|---|---|---|---|---|---|---|---|---|---|---|---|---|
| | | | 500 | | | | | 505 | | | | | 510 | | |

| Ser | Val | Val | Pro | Gln | Glu | Gln | Glu | His | Ala | Met |
|---|---|---|---|---|---|---|---|---|---|---|
| | | 515 | | | | | 520 | | | |

(2) INFORMATION FOR SEQ ID NO:43:

(i) SEQUENCE CHARACTERISTICS:
        (A) LENGTH: 216 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:43:

| Met | Val | Gln | Lys | Thr | Ser | Met | Ser | Arg | Gly | Pro | Tyr | Pro | Pro | Ser | Gln |
|---|---|---|---|---|---|---|---|---|---|---|---|---|---|---|---|
| 1 | | | | 5 | | | | | 10 | | | | | 15 | |

| Glu | Ile | Pro | Met | Glu | Val | Phe | Asp | Pro | Ser | Pro | Gln | Gly | Lys | Tyr | Ser |
|---|---|---|---|---|---|---|---|---|---|---|---|---|---|---|---|
| | | | 20 | | | | | 25 | | | | | 30 | | |

| Lys | Arg | Lys | Gly | Arg | Phe | Lys | Arg | Ser | Asp | Gly | Ser | Thr | Ser | Ser | Asp |
|---|---|---|---|---|---|---|---|---|---|---|---|---|---|---|---|
| | | 35 | | | | | 40 | | | | | 45 | | | |

| Thr | Thr | Ser | Asn | Ser | Phe | Val | Arg | Gln | Gly | Ser | Ala | Glu | Ser | Tyr | Thr |
|---|---|---|---|---|---|---|---|---|---|---|---|---|---|---|---|
| | 50 | | | | | 55 | | | | | 60 | | | | |

| Ser | Arg | Pro | Ser | Asp | Ser | Asp | Val | Ser | Leu | Glu | Glu | Asp | Arg | Glu | Ala |
|---|---|---|---|---|---|---|---|---|---|---|---|---|---|---|---|
| 65 | | | | | 70 | | | | | 75 | | | | | 80 |

```
Leu Arg Lys Glu Ala Glu Arg Gln Ala Leu Ala Gln Leu Glu Lys Ala
                 85              90                      95
Lys Thr Lys Pro Val Ala Phe Ala Val Arg Thr Asn Val Gly Tyr Asn
            100             105                 110
Pro Ser Pro Gly Asp Glu Val Pro Val Gln Gly Val Ala Ile Thr Phe
        115             120                 125
Glu Pro Lys Asp Phe Leu His Ile Lys Glu Lys Tyr Asn Asn Asp Trp
    130             135                 140
Trp Ile Gly Arg Leu Val Lys Glu Gly Cys Glu Val Gly Phe Ile Pro
145             150             155                         160
Ser Pro Val Lys Leu Asp Ser Leu Arg Leu Leu Gln Glu Gln Lys Leu
            165             170                     175
Arg Gln Asn Arg Leu Gly Ser Ser Lys Ser Gly Asp Asn Ser Ser Ser
            180             185                 190
Ser Leu Gly Asp Val Val Thr Gly Thr Arg Arg Pro Thr Pro Pro Ala
            195             200             205
Ser Asp Arg Ala Cys Ala Pro Leu
210                 215
```

( 2 ) INFORMATION FOR SEQ ID NO:44:

( i ) SEQUENCE CHARACTERISTICS:
        ( A ) LENGTH: 219 amino acids
        ( B ) TYPE: amino acid
        ( C ) STRANDEDNESS: single
        ( D ) TOPOLOGY: linear ( i i ) MOLECULE TYPE: protein ( v ) FRAGMENT TYPE: internal ( x i ) SEQUENCE DESCRIPTION: SEQ ID NO:44:

```
Met Val Gln Lys Thr Ser Met Ser Arg Gly Pro Tyr Pro Pro Ser Gln
1               5                   10                  15
Glu Ile Pro Met Glu Val Phe Asp Pro Ser Pro Gln Gly Lys Tyr Ser
            20              25                  30
Lys Arg Lys Gly Arg Phe Lys Arg Ser Asp Gly Ser Thr Ser Ser Asp
        35              40                  45
Thr Thr Ser Asn Ser Phe Val Arg Gln Gly Ser Ala Glu Ser Tyr Thr
    50              55                  60
Ser Arg Pro Ser Asp Ser Asp Val Ser Leu Glu Glu Asp Arg Glu Ala
65              70              75                          80
Leu Arg Lys Glu Ala Glu Arg Gln Ala Leu Ala Gln Leu Glu Lys Ala
                85              90                      95
Lys Thr Lys Pro Val Ala Phe Ala Val Arg Thr Asn Val Gly Tyr Asn
            100             105                 110
Pro Ser Pro Gly Asp Glu Val Pro Val Gln Gly Val Ala Ile Thr Phe
        115             120                 125
Glu Pro Lys Asp Phe Leu His Ile Lys Glu Lys Tyr Asn Asn Asp Trp
    130             135                 140
Trp Ile Gly Arg Leu Val Lys Glu Gly Cys Glu Val Gly Phe Ile Pro
145             150             155                         160
Ser Pro Val Lys Leu Asp Ser Leu Arg Leu Leu Gln Glu Gln Lys Leu
            165             170                     175
Arg Gln Asn Arg Leu Gly Ser Ser Lys Ser Gly Asp Asn Ser Ser Ser
            180             185                 190
Ser Leu Gly Asp Val Val Thr Gly Thr Arg Arg Pro Thr Pro Pro Ala
```

Ser Gly Tyr Arg His Asp Ala Glu Ser Phe Ile
210                     215

( 2 ) INFORMATION FOR SEQ ID NO:45:

( i ) SEQUENCE CHARACTERISTICS:
      ( A ) LENGTH: 1968 amino acids
      ( B ) TYPE: amino acid
      ( C ) STRANDEDNESS: single
      ( D ) TOPOLOGY: linear ( i i ) MOLECULE TYPE: protein ( v ) FRAGMENT TYPE: internal ( x i ) SEQUENCE DESCRIPTION: SEQ ID NO:45:

Met Val Asn Glu Asn Thr Arg Met Tyr Ile Pro Glu Glu Asn His Gln
1               5                   10                  15

Gly Ser Asn Tyr Gly Ser Pro Arg Pro Ala His Ala Asn Met Asn Ala
            20                  25                  30

Asn Ala Ala Ala Gly Leu Ala Pro Glu His Ile Pro Thr Pro Gly Ala
        35                  40                  45

Ala Leu Ser Trp Gln Ala Ala Ile Asp Ala Ala Arg Gln Ala Lys Leu
50                  55                  60

Met Gly Ser Ala Gly Asn Ala Thr Ile Ser Thr Val Ser Ser Thr Gln
65                  70                  75                  80

Arg Lys Arg Gln Gln Tyr Gly Lys Pro Lys Lys Gln Gly Ser Thr Thr
                85                  90                  95

Ala Thr Arg Pro Pro Arg Ala Leu Leu Cys Leu Thr Leu Lys Asn Pro
            100                 105                 110

Ile Arg Arg Ala Cys Ile Ser Ile Val Glu Trp Lys Pro Phe Glu Ile
        115                 120                 125

Ile Ile Leu Leu Thr Ile Phe Ala Asn Cys Val Ala Leu Ala Ile Tyr
130                 135                 140

Ile Pro Phe Pro Glu Asp Asp Ser Asn Ala Thr Asn Ser Asn Leu Glu
145                 150                 155                 160

Arg Val Glu Tyr Leu Phe Leu Ile Ile Phe Thr Val Glu Ala Phe Leu
                165                 170                 175

Lys Val Ile Ala Tyr Gly Leu Leu Phe His Pro Asn Ala Tyr Leu Arg
            180                 185                 190

Asn Gly Trp Asn Leu Leu Asp Phe Ile Ile Val Val Val Gly Leu Phe
        195                 200                 205

Ser Ala Ile Leu Glu Gln Ala Thr Lys Ala Asp Gly Ala Asn Ala Leu
210                 215                 220

Gly Gly Lys Gly Ala Gly Phe Asp Val Lys Ala Leu Arg Ala Phe Arg
225                 230                 235                 240

Val Leu Arg Pro Leu Arg Leu Val Ser Gly Val Pro Ser Leu Gln Val
                245                 250                 255

Val Leu Asn Ser Ile Ile Lys Ala Met Val Pro Leu Leu His Ile Ala
            260                 265                 270

Leu Leu Val Leu Phe Val Ile Ile Ile Tyr Ala Ile Ile Gly Leu Glu
        275                 280                 285

Leu Phe Met Gly Lys Met His Lys Thr Cys Tyr Asn Gln Glu Gly Ile
290                 295                 300

Ala Asp Val Pro Ala Glu Asp Asp Pro Ser Pro Cys Ala Leu Glu Thr
305                 310                 315                 320

Gly His Gly Arg Gln Cys Gln Asn Gly Thr Val Cys Lys Pro Gly Trp
                    325                 330                 335

Asp Gly Pro Lys His Gly Ile Thr Asn Phe Asp Asn Phe Ala Phe Ala
            340                 345                 350

Met Leu Thr Val Phe Gln Cys Ile Thr Met Glu Gly Trp Thr Asp Val
                355                 360                 365

Leu Tyr Trp Val Asn Asp Ala Val Gly Arg Asp Trp Pro Trp Ile Tyr
        370                 375                 380

Phe Val Thr Leu Ile Ile Ile Gly Ser Phe Phe Val Leu Asn Leu Val
385                 390                 395                 400

Leu Gly Val Leu Ser Gly Glu Phe Ser Lys Glu Arg Glu Lys Ala Lys
                405                 410                 415

Ala Arg Gly Asp Phe Gln Lys Leu Arg Glu Lys Gln Gln Leu Glu Glu
            420                 425                 430

Asp Leu Lys Gly Tyr Leu Asp Trp Ile Thr Gln Ala Glu Asp Ile Xaa
            435                 440                 445

Pro Glu Asn Glu Asp Glu Gly Met Asp Glu Glu Lys Pro Arg Asn Arg
        450                 455                 460

Gly Thr Pro Ala Gly Met Leu Asp Gln Lys Lys Gly Lys Phe Ala Trp
465                 470                 475                 480

Phe Ser His Ser Thr Glu Thr His Val Ser Met Pro Thr Ser Glu Thr
                485                 490                 495

Glu Ser Val Asn Thr Glu Asn Val Ala Gly Gly Asp Ile Glu Gly Glu
                500                 505                 510

Asn Cys Gly Ala Arg Leu Ala His Arg Ile Ser Lys Ser Lys Phe Ser
            515                 520                 525

Arg Tyr Trp Arg Arg Trp Asn Arg Phe Cys Arg Arg Lys Cys Arg Ala
        530                 535                 540

Ala Val Lys Ser Asn Val Phe Tyr Trp Leu Val Ile Phe Leu Val Phe
545                 550                 555                 560

Leu Asn Thr Leu Thr Ile Ala Ser Glu His Tyr Asn Gln Pro Asn Trp
                565                 570                 575

Leu Thr Glu Val Gln Asp Thr Ala Asn Lys Ala Leu Leu Ala Leu Phe
            580                 585                 590

Thr Ala Glu Met Leu Leu Lys Met Tyr Ser Leu Gly Leu Gln Ala Tyr
            595                 600                 605

Phe Val Ser Leu Phe Asn Arg Phe Asp Cys Phe Val Val Cys Gly Gly
610                 615                 620

Ile Leu Glu Thr Ile Leu Val Glu Thr Lys Ile Met Ser Pro Leu Gly
625                 630                 635                 640

Ile Ser Val Leu Arg Cys Val Arg Leu Leu Arg Ile Phe Lys Ile Thr
            645                 650                 655

Arg Tyr Trp Asn Ser Leu Ser Asn Leu Val Ala Ser Leu Leu Asn Ser
        660                 665                 670

Val Arg Ser Ile Ala Ser Leu Leu Leu Leu Phe Leu Phe Ile Ile
            675                 680                 685

Ile Phe Ser Leu Leu Gly Met Gln Leu Phe Gly Gly Lys Phe Asn Phe
    690                 695                 700

Asp Glu Met Gln Thr Arg Arg Ser Thr Phe Asp Asn Phe Pro Gln Ser
705                 710                 715                 720

Leu Leu Thr Val Phe Gln Ile Leu Thr Gly Glu Asp Trp Asn Ser Val
                725                 730                 735

Met Tyr Asp Gly Ile Met Ala Tyr Gly Gly Pro Ser Phe Pro Gly Met
            740                 745                 750

| | | | | | | | | | | | | | | |
|---|---|---|---|---|---|---|---|---|---|---|---|---|---|---|
| Leu | Val | Cys | Ile | Tyr | Phe | Ile | Ile | Leu | Phe | Ile | Ser | Gly | Asn | Tyr | Ile |
| | | 755 | | | | | 760 | | | | | 765 | | | |
| Leu | Leu | Asn | Val | Phe | Leu | Ala | Ile | Ala | Val | Asp | Asn | Leu | Ala | Asp | Ala |
| | 770 | | | | | 775 | | | | | 780 | | | | |
| Glu | Ser | Leu | Thr | Ser | Ala | Leu | Lys | Glu | Glu | Glu | Glu | Glu | Lys | Glu | Arg |
| 785 | | | | | 790 | | | | 795 | | | | | | 800 |
| Lys | Lys | Leu | Ala | Arg | Thr | Ala | Ser | Pro | Glu | Lys | Lys | Gln | Glu | Leu | Val |
| | | | | 805 | | | | | 810 | | | | | 815 | |
| Glu | Lys | Pro | Ala | Val | Gly | Glu | Ser | Lys | Glu | Glu | Lys | Ile | Glu | Leu | Lys |
| | | | 820 | | | | | 825 | | | | | 830 | | |
| Ser | Ile | Thr | Ala | Asp | Gly | Glu | Ser | Pro | Pro | Ala | Thr | Lys | Ile | Asn | Met |
| | | 835 | | | | | 840 | | | | | 845 | | | |
| Asp | Asp | Leu | Gln | Pro | Asn | Glu | Asn | Glu | Asp | Lys | Ser | Pro | Tyr | Pro | Asn |
| | 850 | | | | | 855 | | | | | 860 | | | | |
| Pro | Glu | Thr | Thr | Gly | Glu | Glu | Asp | Glu | Glu | Glu | Pro | Glu | Met | Pro | Val |
| 865 | | | | | 870 | | | | 875 | | | | | | 880 |
| Gly | Pro | Arg | Pro | Arg | Pro | Leu | Ser | Glu | Leu | His | Leu | Lys | Glu | Lys | Ala |
| | | | | 885 | | | | | 890 | | | | | 895 | |
| Val | Pro | Met | Pro | Glu | Ala | Ser | Ala | Phe | Phe | Ile | Phe | Ser | Ser | Asn | Asn |
| | | | 900 | | | | | 905 | | | | | 910 | | |
| Arg | Phe | Arg | Leu | Gln | Cys | His | Arg | Ile | Val | Asn | Asp | Thr | Ile | Phe | Thr |
| | | 915 | | | | | 920 | | | | | 925 | | | |
| Asn | Leu | Ile | Leu | Phe | Phe | Ile | Leu | Leu | Ser | Ser | Ile | Ser | Leu | Ala | Ala |
| | 930 | | | | | 935 | | | | | 940 | | | | |
| Glu | Asp | Pro | Val | Gln | His | Thr | Ser | Phe | Arg | Asn | His | Ile | Leu | Phe | Tyr |
| 945 | | | | | 950 | | | | 955 | | | | | | 960 |
| Phe | Asp | Ile | Val | Phe | Thr | Thr | Ile | Phe | Thr | Ile | Glu | Ile | Ala | Leu | Lys |
| | | | | 965 | | | | | 970 | | | | | 975 | |
| Met | Thr | Ala | Tyr | Gly | Ala | Phe | Leu | His | Lys | Gly | Ser | Phe | Cys | Arg | Asn |
| | | | 980 | | | | | 985 | | | | | 990 | | |
| Tyr | Phe | Asn | Ile | Leu | Asp | Leu | Leu | Val | Val | Ser | Val | Ser | Leu | Ile | Ser |
| | | 995 | | | | | 1000 | | | | | 1005 | | | |
| Phe | Gly | Ile | Gln | Ser | Ser | Ala | Ile | Asn | Val | Val | Lys | Ile | Leu | Arg | Val |
| | 1010 | | | | | 1015 | | | | | 1020 | | | | |
| Leu | Arg | Val | Leu | Arg | Pro | Leu | Arg | Ala | Ile | Asn | Arg | Ala | Lys | Gly | Leu |
| 1025 | | | | | 1030 | | | | 1035 | | | | | | 1040 |
| Lys | His | Val | Val | Gln | Cys | Val | Phe | Val | Ala | Ile | Arg | Thr | Ile | Gly | Asn |
| | | | | 1045 | | | | | 1050 | | | | | 1055 | |
| Ile | Val | Ile | Val | Thr | Thr | Leu | Leu | Gln | Phe | Met | Phe | Ala | Cys | Ile | Gly |
| | | | 1060 | | | | | 1065 | | | | | 1070 | | |
| Val | Gln | Leu | Phe | Lys | Gly | Lys | Leu | Tyr | Thr | Cys | Ser | Asp | Ser | Ser | Lys |
| | | | 1075 | | | | | 1080 | | | | | 1085 | | |
| Gln | Thr | Glu | Ala | Glu | Cys | Lys | Gly | Asn | Tyr | Ile | Thr | Tyr | Lys | Asp | Gly |
| | 1090 | | | | | 1095 | | | | | 1100 | | | | |
| Glu | Val | Asp | His | Pro | Ile | Ile | Gln | Pro | Arg | Ser | Trp | Glu | Asn | Ser | Lys |
| 1105 | | | | | 1110 | | | | 1115 | | | | | | 1120 |
| Phe | Asp | Phe | Asp | Asn | Val | Leu | Ala | Ala | Met | Met | Ala | Leu | Phe | Thr | Val |
| | | | | 1125 | | | | | 1130 | | | | | 1135 | |
| Ser | Thr | Phe | Glu | Gly | Trp | Pro | Glu | Leu | Leu | Tyr | Arg | Ser | Ile | Asp | Ser |
| | | | 1140 | | | | | 1145 | | | | | 1150 | | |
| His | Thr | Glu | Asp | Lys | Gly | Pro | Ile | Tyr | Asn | Tyr | Arg | Val | Glu | Ile | Ser |
| | | | 1155 | | | | | 1160 | | | | | 1165 | | |
| Ile | Phe | Phe | Ile | Ile | Tyr | Ile | Ile | Ile | Ile | Ala | Phe | Phe | Met | Met | Asn |

-continued

```
               1170                    1175                    1180
Ile Phe Val Gly Phe Val Ile Val Thr Phe Gln Glu Gln Gly Glu Gln
1185                    1190                    1195                    1200
Glu Tyr Lys Asn Cys Glu Leu Asp Lys Asn Gln Arg Gln Cys Val Glu
                        1205                    1210                    1215
Tyr Ala Leu Lys Ala Arg Pro Leu Arg Arg Tyr Ile Pro Lys Asn Gln
                  1220                    1225                    1230
His Gln Tyr Lys Val Trp Tyr Val Val Asn Ser Thr Tyr Phe Glu Tyr
            1235                    1240                    1245
Leu Met Phe Val Leu Ile Leu Leu Asn Thr Ile Cys Leu Ala Met Gln
            1250                    1255                    1260
His Tyr Gly Gln Ser Cys Leu Phe Lys Ile Ala Met Asn Ile Leu Asn
1265                    1270                    1275                    1280
Met Leu Phe Thr Gly Leu Phe Thr Val Glu Met Ile Leu Lys Leu Ile
                        1285                    1290                    1295
Ala Phe Lys Pro Lys Gly Tyr Phe Ser Asp Pro Trp Asn Val Phe Asp
                  1300                    1305                    1310
Phe Leu Ile Val Ile Gly Ser Ile Ile Asp Val Ile Leu Ser Glu Thr
            1315                    1320                    1325
Asn Pro Ala Glu His Thr Gln Cys Ser Pro Ser Met Asn Ala Glu Glu
            1330                    1335                    1340
Asn Ser Arg Ile Ser Ile Thr Phe Phe Arg Leu Phe Arg Val Met Arg
1345                    1350                    1355                    1360
Leu Val Lys Leu Leu Ser Arg Gly Glu Gly Ile Arg Thr Leu Leu Trp
                  1365                    1370                    1375
Thr Phe Ile Lys Ser Phe Gln Ala Leu Pro Tyr Val Ala Leu Leu Ile
            1380                    1385                    1390
Val Met Leu Phe Phe Ile Tyr Ala Val Ile Gly Met Gln Val Phe Gly
            1395                    1400                    1405
Lys Ile Ala Leu Asn Asp Thr Thr Glu Ile Asn Arg Asn Asn Asn Phe
            1410                    1415                    1420
Gln Thr Phe Pro Gln Ala Val Leu Leu Leu Phe Arg Cys Ala Thr Gly
1425                    1430                    1435                    1440
Glu Ala Trp Gln Asp Ile Met Leu Ala Cys Met Pro Gly Lys Lys Cys
                        1445                    1450                    1455
Ala Pro Glu Ser Glu Pro Ser Asn Ser Thr Glu Gly Glu Thr Pro Cys
                  1460                    1465                    1470
Gly Ser Ser Phe Ala Val Phe Tyr Phe Ile Ser Phe Tyr Met Arg Cys
            1475                    1480                    1485
Ala Phe Leu Ile Ile Asn Leu Phe Val Ala Val Ile Met Asp Asn Phe
      1490                    1495                    1500
Asp Tyr Leu Thr Arg Asp Trp Ser Ile Leu Gly Pro His His Leu Asp
1505                    1510                    1515                    1520
Glu Phe Lys Arg Ile Trp Ala Glu Tyr Asp Pro Glu Ala Lys Gly Arg
                        1525                    1530                    1535
Ile Lys His Leu Asp Val Val Thr Leu Leu Arg Arg Ile Gln Pro Pro
                  1540                    1545                    1550
Leu Gly Phe Gly Lys Leu Cys Pro His Arg Val Ala Cys Lys Arg Leu
            1555                    1560                    1565
Val Ser Met Asn Met Pro Leu Asn Ser Asp Gly Thr Val Met Phe Asn
      1570                    1575                    1580
Ala Thr Leu Phe Ala Leu Val Arg Thr Ala Leu Arg Ile Lys Thr Glu
1585                    1590                    1595                    1600
```

Gly Asn Leu Glu Gln Ala Asn Glu Glu Leu Arg Ala Ile Ile Lys Lys
                1605                1610                1615

Ile Trp Lys Arg Thr Ser Met Lys Leu Leu Asp Gln Val Val Pro Pro
            1620                1625                1630

Ala Gly Asp Asp Glu Val Thr Val Gly Lys Phe Tyr Ala Thr Phe Leu
            1635                1640                1645

Ile Gln Glu Tyr Phe Arg Lys Phe Lys Lys Arg Lys Glu Gln Gly Leu
1650                1655                1660

Val Gly Lys Pro Ser Gln Arg Asn Ala Leu Ser Leu Gln Ala Gly Leu
1665                1670                1675                1680

Arg Thr Leu His Asp Ile Gly Pro Glu Ile Arg Arg Ala Ile Ser Gly
                1685                1690                1695

Asp Leu Thr Ala Glu Glu Glu Leu Asp Lys Ala Met Lys Glu Ala Val
            1700                1705                1710

Ser Ala Ala Ser Glu Asp Asp Ile Phe Arg Arg Ala Gly Gly Leu Phe
            1715                1720                1725

Gly Asn His Val Ser Tyr Tyr Gln Ser Asp Gly Arg Ser Ala Phe Pro
            1730                1735                1740

Gln Thr Phe Thr Thr Gln Arg Pro Leu His Ile Asn Lys Ala Gly Ser
1745                1750                1755                1760

Ser Gln Gly Asp Thr Glu Ser Pro Ser His Glu Lys Leu Val Asp Ser
                1765                1770                1775

Thr Phe Thr Pro Ser Ser Tyr Ser Ser Thr Gly Ser Asn Ala Asn Ile
            1780                1785                1790

Asn Asn Ala Asn Asn Thr Ala Leu Gly Arg Leu Pro Arg Pro Ala Gly
            1795                1800                1805

Tyr Pro Ser Thr Val Ser Thr Val Glu Gly His Gly Pro Pro Leu Ser
            1810                1815                1820

Pro Ala Ile Arg Val Gln Glu Val Ala Trp Lys Leu Ser Ser Asn Arg
1825                1830                1835                1840

Cys His Ser Arg Glu Ser Gln Ala Ala Met Ala Arg Gln Glu Glu Thr
                1845                1850                1855

Ser Gln Asp Glu Thr Tyr Glu Val Lys Met Asn His Asp Thr Glu Ala
            1860                1865                1870

Cys Ser Glu Pro Ser Leu Leu Ser Thr Glu Met Leu Ser Tyr Gln Asp
            1875                1880                1885

Asp Glu Asn Arg Gln Leu Thr Leu Pro Glu Glu Asp Lys Arg Asp Ile
            1890                1895                1900

Arg Gln Ser Pro Lys Arg Gly Phe Leu Arg Ser Ser Ser Leu Gly Arg
1905                1910                1915                1920

Arg Ala Ser Phe His Leu Glu Cys Leu Lys Arg Gln Lys Asp Arg Gly
            1925                1930                1935

Gly Asp Ile Ser Gln Lys Thr Val Leu Pro Leu His Leu Val His His
            1940                1945                1950

Gln Ala Leu Ala Val Ala Gly Leu Ser Pro Leu Leu Gln Arg Ser His
            1955                1960                1965

( 2 ) INFORMATION FOR SEQ ID NO:46:

( i ) SEQUENCE CHARACTERISTICS:
      ( A ) LENGTH: 28 amino acids
      ( B ) TYPE: amino acid
      ( C ) STRANDEDNESS: single
      ( D ) TOPOLOGY: linear ( i i ) MOLECULE TYPE: protein ( v ) FRAGMENT TYPE: internal ( x i ) SEQUENCE DESCRIPTION: SEQ ID NO:46:

| His | Tyr | Phe | Cys | Asp | Ala | Trp | Asn | Thr | Phe | Asp | Ala | Leu | Ile | Val | Val |
|---|---|---|---|---|---|---|---|---|---|---|---|---|---|---|---|
| 1 | | | | 5 | | | | | 10 | | | | | 15 | |

| Gly | Ser | Ile | Val | Asp | Ile | Ala | Ile | Thr | Glu | Val | Asn |
|---|---|---|---|---|---|---|---|---|---|---|---|
| | | | 20 | | | | | 25 | | | |

( 2 ) INFORMATION FOR SEQ ID NO:47:

( i ) SEQUENCE CHARACTERISTICS:
  ( A ) LENGTH: 2339 amino acids
  ( B ) TYPE: amino acid
  ( C ) STRANDEDNESS: single
  ( D ) TOPOLOGY: linear ( i i ) MOLECULE TYPE: protein ( v ) FRAGMENT TYPE: internal ( x i ) SEQUENCE DESCRIPTION: SEQ ID NO:47:

| Met | Val | Arg | Phe | Gly | Asp | Glu | Leu | Gly | Gly | Arg | Tyr | Gly | Gly | Pro | Gly |
|---|---|---|---|---|---|---|---|---|---|---|---|---|---|---|---|
| 1 | | | | 5 | | | | | 10 | | | | | 15 | |

| Gly | Gly | Glu | Arg | Ala | Arg | Gly | Gly | Gly | Ala | Gly | Gly | Ala | Gly | Gly | Pro |
|---|---|---|---|---|---|---|---|---|---|---|---|---|---|---|---|
| | | | 20 | | | | | 25 | | | | | 30 | | |

| Gly | Pro | Gly | Gly | Leu | Gln | Pro | Gly | Gln | Arg | Val | Leu | Tyr | Lys | Gln | Ser |
|---|---|---|---|---|---|---|---|---|---|---|---|---|---|---|---|
| | | 35 | | | | | 40 | | | | | 45 | | | |

| Ile | Ala | Gln | Arg | Ala | Arg | Thr | Met | Ala | Leu | Tyr | Asn | Pro | Ile | Pro | Val |
|---|---|---|---|---|---|---|---|---|---|---|---|---|---|---|---|
| | 50 | | | | | 55 | | | | | 60 | | | | |

| Lys | Gln | Asn | Cys | Phe | Thr | Val | Asn | Arg | Ser | Leu | Phe | Val | Phe | Ser | Glu |
|---|---|---|---|---|---|---|---|---|---|---|---|---|---|---|---|
| 65 | | | | | 70 | | | | | 75 | | | | | 80 |

| Asp | Asn | Val | Val | Arg | Lys | Tyr | Ala | Lys | Arg | Ile | Thr | Glu | Trp | Pro | Pro |
|---|---|---|---|---|---|---|---|---|---|---|---|---|---|---|---|
| | | | | 85 | | | | | 90 | | | | | 95 | |

| Phe | Glu | Asn | Met | Ile | Leu | Ala | Thr | Ile | Ile | Ala | Asn | Cys | Ile | Val | Leu |
|---|---|---|---|---|---|---|---|---|---|---|---|---|---|---|---|
| | | | | 100 | | | | | 105 | | | | | 110 | |

| Ala | Leu | Glu | Gln | His | Leu | Pro | Asp | Gly | Asp | Lys | Thr | Pro | Met | Ser | Glu |
|---|---|---|---|---|---|---|---|---|---|---|---|---|---|---|---|
| | | | 115 | | | | | 120 | | | | | 125 | | |

| Arg | Leu | Asp | Asp | Thr | Glu | Pro | Tyr | Phe | Ile | Gly | Ile | Phe | Cys | Phe | Glu |
|---|---|---|---|---|---|---|---|---|---|---|---|---|---|---|---|
| | | 130 | | | | | 135 | | | | | 140 | | | |

| Ala | Gly | Ile | Lys | Ile | Ile | Ala | Leu | Gly | Phe | Val | Phe | His | Lys | Gly | Ser |
|---|---|---|---|---|---|---|---|---|---|---|---|---|---|---|---|
| 145 | | | | | 150 | | | | | 155 | | | | | 160 |

| Tyr | Leu | Arg | Asn | Gly | Trp | Asn | Val | Met | Asp | Phe | Val | Val | Val | Leu | Thr |
|---|---|---|---|---|---|---|---|---|---|---|---|---|---|---|---|
| | | | | 165 | | | | | 170 | | | | | 175 | |

| Gly | Ile | Leu | Ala | Thr | Ala | Gly | Thr | Asp | Phe | Asp | Leu | Arg | Thr | Leu | Arg |
|---|---|---|---|---|---|---|---|---|---|---|---|---|---|---|---|
| | | | 180 | | | | | 185 | | | | | 190 | | |

| Ala | Val | Arg | Val | Leu | Arg | Pro | Leu | Lys | Leu | Val | Ser | Gly | Ile | Pro | Ser |
|---|---|---|---|---|---|---|---|---|---|---|---|---|---|---|---|
| | | 195 | | | | | 200 | | | | | 205 | | | |

| Leu | Gln | Val | Val | Leu | Lys | Ser | Ile | Met | Lys | Ala | Met | Val | Pro | Leu | Leu |
|---|---|---|---|---|---|---|---|---|---|---|---|---|---|---|---|
| | 210 | | | | | 215 | | | | | 220 | | | | |

| Gln | Ile | Gly | Leu | Leu | Leu | Phe | Phe | Ala | Ile | Leu | Met | Phe | Ala | Ile | Ile |
|---|---|---|---|---|---|---|---|---|---|---|---|---|---|---|---|
| 225 | | | | | 230 | | | | | 235 | | | | | 240 |

| Gly | Leu | Glu | Phe | Tyr | Met | Gly | Lys | Phe | His | Lys | Ala | Cys | Phe | Pro | Asn |
|---|---|---|---|---|---|---|---|---|---|---|---|---|---|---|---|
| | | | | 245 | | | | | 250 | | | | | 255 | |

| Ser | Thr | Asp | Ala | Glu | Pro | Val | Gly | Asp | Phe | Pro | Cys | Gly | Lys | Glu | Ala |
|---|---|---|---|---|---|---|---|---|---|---|---|---|---|---|---|
| | | | 260 | | | | | 265 | | | | | 270 | | |

| Pro | Ala | Arg | Leu | Cys | Glu | Gly | Asp | Thr | Glu | Cys | Arg | Glu | Tyr | Trp | Pro |
|---|---|---|---|---|---|---|---|---|---|---|---|---|---|---|---|
| | | 275 | | | | | 280 | | | | | 285 | | | |

| Gly | Pro | Asn | Phe | Gly | Ile | Thr | Asn | Phe | Asp | Asn | Ile | Leu | Phe | Ala | Ile |
|---|---|---|---|---|---|---|---|---|---|---|---|---|---|---|---|

-continued

|   | 290 |   |   |   |   | 295 |   |   |   |   | 300 |   |   |   |   |
|---|---|---|---|---|---|---|---|---|---|---|---|---|---|---|---|
| Leu<br>305 | Thr | Val | Phe | Gln | Cys<br>310 | Ile | Thr | Met | Glu | Gly<br>315 | Trp | Thr | Asp | Ile | Leu<br>320 |
| Tyr | Asn | Thr | Asn | Asp<br>325 | Ala | Ala | Gly | Asn | Thr<br>330 | Trp | Asn | Trp | Leu | Tyr<br>335 | Phe |
| Ile | Pro | Leu | Ile<br>340 | Ile | Ile | Gly | Ser | Phe<br>345 | Phe | Met | Leu | Asn | Leu<br>350 | Val | Leu |
| Gly | Val | Leu<br>355 | Ser | Gly | Glu | Phe | Ala<br>360 | Lys | Glu | Arg | Glu | Arg<br>365 | Val | Glu | Asn |
| Arg<br>370 | Arg | Ala | Phe | Leu | Lys<br>375 | Leu | Arg | Gln | Gln | Gln<br>380 | Ile | Glu | Arg | Glu |
| Leu<br>385 | Asn | Gly | Tyr | Leu | Glu<br>390 | Trp | Ile | Phe | Lys | Ala<br>395 | Glu | Glu | Val | Met | Leu<br>400 |
| Ala | Glu | Glu | Asp | Arg<br>405 | Asn | Ala | Glu | Glu | Lys<br>410 | Ser | Pro | Leu | Asp | Val<br>415 | Leu |
| Lys | Arg | Ala | Ala<br>420 | Thr | Lys | Lys | Ser | Arg<br>425 | Asn | Asp | Leu | Ile | His<br>430 | Ala | Glu |
| Glu | Gly | Glu<br>435 | Asp | Arg | Phe | Ala | Asp<br>440 | Leu | Cys | Ala | Val | Gly<br>445 | Ser | Pro | Phe |
| Ala | Arg<br>450 | Ala | Ser | Leu | Lys | Ser<br>455 | Gly | Lys | Thr | Glu | Ser<br>460 | Ser | Ser | Tyr | Phe |
| Arg<br>465 | Arg | Lys | Glu | Lys | Met<br>470 | Phe | Arg | Phe | Phe | Ile<br>475 | Arg | Arg | Met | Val | Lys<br>480 |
| Ala | Gln | Ser | Phe | Tyr<br>485 | Trp | Val | Val | Leu | Cys<br>490 | Val | Val | Ala | Leu | Asn<br>495 | Thr |
| Leu | Cys | Val | Ala<br>500 | Met | Val | His | Tyr | Asn<br>505 | Gln | Pro | Arg | Arg | Leu<br>510 | Thr | Thr |
| Thr | Leu | Tyr<br>515 | Phe | Ala | Glu | Phe | Val<br>520 | Phe | Leu | Gly | Leu | Phe<br>525 | Leu | Thr | Glu |
| Met | Ser<br>530 | Leu | Lys | Met | Tyr<br>535 | Gly | Leu | Gly | Pro | Arg<br>540 | Ser | Tyr | Phe | Arg | Ser |
| Ser<br>545 | Phe | Asn | Cys | Phe | Asp<br>550 | Phe | Gly | Val | Ile | Val<br>555 | Gly | Ser | Val | Phe | Glu<br>560 |
| Val | Val | Trp | Ala | Ala<br>565 | Ile | Lys | Pro | Gly | Ser<br>570 | Ser | Phe | Gly | Ile | Ser<br>575 | Val |
| Leu | Arg | Ala | Leu<br>580 | Arg | Leu | Leu | Arg | Ile<br>585 | Phe | Lys | Val | Thr | Lys<br>590 | Tyr | Trp |
| Ser | Ser | Leu<br>595 | Arg | Asn | Leu | Val | Val<br>600 | Ser | Leu | Leu | Asn | Ser<br>605 | Met | Lys | Ser |
| Ile | Ile | Ser<br>610 | Leu | Leu | Phe | Leu | Leu<br>615 | Phe | Leu | Phe | Ile<br>620 | Val | Val | Phe | Ala |
| Leu<br>625 | Leu | Gly | Met | Gln | Leu<br>630 | Phe | Gly | Gly | Gln | Phe<br>635 | Asn | Phe | Gln | Asp | Glu<br>640 |
| Thr | Pro | Thr | Thr | Asn<br>645 | Phe | Asp | Thr | Phe | Pro<br>650 | Ala | Ala | Ile | Leu | Thr<br>655 | Val |
| Phe | Gln | Ile | Leu<br>660 | Thr | Gly | Glu | Asp | Trp<br>665 | Asn | Ala | Val | Met | Tyr<br>670 | His | Gly |
| Ile | Glu | Ser<br>675 | Gln | Gly | Gly | Val | Ser<br>680 | Lys | Gly | Met | Phe | Ser<br>685 | Ser | Phe | Tyr |
| Phe | Ile<br>690 | Val | Leu | Thr | Leu | Phe<br>695 | Gly | Asn | Tyr | Thr | Leu<br>700 | Leu | Asn | Val | Phe |
| Leu<br>705 | Ala | Ile | Ala | Val | Asp<br>710 | Asn | Leu | Ala | Asn | Ala<br>715 | Gln | Glu | Leu | Thr | Lys<br>720 |

Asp Glu Glu Glu Met Glu Glu Ala Ala Asn Gln Lys Leu Ala Leu Gln
              725                 730                 735

Lys Ala Lys Glu Val Ala Glu Val Ser Pro Met Ser Ala Ala Asn Ile
              740                 745                 750

Ser Ile Ala Ala Arg Gln Gln Asn Ser Ala Lys Ala Arg Ser Val Trp
              755                 760                 765

Glu Gln Arg Ala Ser Gln Leu Arg Leu Gln Asn Leu Arg Ala Ser Cys
              770                 775                 780

Glu Ala Leu Tyr Ser Glu Met Asp Pro Glu Glu Arg Leu Arg Phe Ala
785                 790                 795                 800

Thr Thr Arg His Leu Arg Pro Asp Met Lys Thr His Leu Asp Arg Pro
              805                 810                 815

Leu Val Val Glu Leu Gly Arg Asp Gly Ala Arg Gly Pro Val Gly Gly
              820                 825                 830

Lys Ala Arg Pro Glu Ala Ala Ala Pro Glu Gly Val Asp Pro Pro
              835                 840                 845

Arg Arg His His Arg His Arg Asp Lys Asp Lys Thr Pro Ala Ala Gly
850                 855                 860

Asp Gln Asp Arg Ala Glu Ala Pro Lys Ala Glu Ser Gly Glu Pro Gly
865                 870                 875                 880

Ala Arg Glu Glu Arg Pro Arg Pro His Arg Ser His Ser Lys Glu Ala
              885                 890                 895

Ala Gly Pro Pro Glu Ala Arg Ser Glu Arg Gly Arg Gly Pro Gly Pro
              900                 905                 910

Glu Gly Gly Arg Arg His His Arg Arg Gly Ser Pro Glu Glu Ala Ala
              915                 920                 925

Glu Arg Glu Pro Arg Arg His Arg Ala His Arg His Gln Asp Pro Ser
930                 935                 940

Lys Glu Cys Ala Gly Ala Lys Gly Glu Arg Arg Ala Arg His Arg Gly
945                 950                 955                 960

Gly Pro Arg Ala Gly Pro Arg Glu Ala Glu Ser Gly Glu Glu Pro Ala
              965                 970                 975

Arg Arg His Arg Ala Arg His Lys Ala Gln Pro Ala His Glu Ala Val
              980                 985                 990

Glu Lys Glu Thr Thr Glu Lys Glu Ala Thr Glu Lys Glu Ala Glu Ile
              995                1000                1005

Val Glu Ala Asp Lys Glu Lys Glu Leu Arg Asn His Gln Pro Arg Glu
             1010                1015                1020

Pro His Cys Asp Leu Glu Thr Ser Gly Thr Val Thr Val Gly Pro Met
1025                1030                1035                1040

His Thr Leu Pro Ser Thr Cys Leu Gln Lys Val Glu Glu Gln Pro Glu
             1045                1050                1055

Asp Ala Asp Asn Gln Arg Asn Val Thr Arg Met Gly Ser Gln Pro Pro
             1060                1065                1070

Asp Pro Asn Thr Ile Val His Ile Pro Val Met Leu Thr Gly Pro Leu
             1075                1080                1085

Gly Glu Ala Thr Val Val Pro Ser Gly Asn Val Asp Leu Glu Ser Gln
             1090                1095                1100

Ala Glu Gly Lys Lys Glu Val Glu Ala Asp Asp Val Met Arg Ser Gly
1105                1110                1115                1120

Pro Arg Pro Ile Val Pro Tyr Ser Ser Met Phe Cys Leu Ser Pro Thr
             1125                1130                1135

Asn Leu Leu Arg Arg Phe Cys His Tyr Ile Val Thr Met Arg Tyr Phe
             1140                1145                1150

-continued

```
Glu Val Val Ile Leu Val Val Ile Ala Leu Ser Ser Ile Ala Leu Ala
    1155            1160            1165
Ala Glu Asp Pro Val Arg Thr Asp Ser Pro Arg Asn Asn Ala Leu Lys
    1170            1175            1180
Tyr Leu Asp Tyr Ile Phe Thr Gly Val Phe Thr Phe Glu Met Val Ile
1185            1190            1195            1200
Lys Met Ile Asp Leu Gly Leu Leu His Pro Gly Ala Tyr Phe Arg
            1205            1210            1215
Asp Leu Trp Asn Ile Leu Asp Phe Ile Val Ser Gly Ala Leu Val
        1220            1225            1230
Ala Phe Ala Phe Ser Gly Ser Lys Gly Lys Asp Ile Asn Thr Ile Lys
    1235            1240            1245
Ser Leu Arg Val Leu Arg Val Leu Arg Pro Leu Lys Thr Ile Lys Arg
1250            1255            1260
Leu Pro Lys Leu Lys Ala Val Phe Asp Cys Val Val Asn Ser Leu Lys
1265            1270            1275            1280
Asn Val Leu Asn Ile Leu Ile Val Tyr Met Leu Phe Met Phe Ile Phe
            1285            1290            1295
Ala Val Ile Ala Val Gln Leu Phe Lys Gly Lys Phe Phe Tyr Cys Thr
        1300            1305            1310
Asp Glu Ser Lys Glu Leu Glu Arg Asp Cys Arg Gly Gln Tyr Leu Asp
        1315            1320            1325
Tyr Glu Lys Glu Glu Val Glu Ala Gln Pro Arg Gln Trp Lys Lys Tyr
    1330            1335            1340
Asp Phe His Tyr Asp Asn Val Leu Trp Ala Leu Leu Thr Leu Phe Thr
1345            1350            1355            1360
Val Ser Thr Gly Glu Gly Trp Pro Met Val Leu Lys His Ser Val Asp
            1365            1370            1375
Ala Thr Tyr Glu Glu Gln Gly Pro Ser Pro Gly Tyr Arg Met Glu Leu
        1380            1385            1390
Ser Ile Phe Tyr Val Val Tyr Phe Val Val Phe Pro Phe Phe Phe Val
    1395            1400            1405
Asn Ile Phe Val Ala Leu Ile Ile Ile Thr Phe Gln Glu Gln Gly Asp
    1410            1415            1420
Lys Val Met Ser Glu Cys Ser Leu Glu Lys Asn Glu Arg Ala Cys Ile
1425            1430            1435            1440
Asp Phe Ala Ile Ser Ala Lys Pro Leu Thr Arg Tyr Met Pro Gln Asn
            1445            1450            1455
Arg Gln Ser Phe Gln Tyr Lys Thr Trp Thr Phe Val Val Ser Pro Pro
        1460            1465            1470
Phe Glu Tyr Phe Ile Met Ala Met Ile Ala Leu Asn Thr Val Val Leu
    1475            1480            1485
Met Met Lys Phe Tyr Asp Ala Pro Tyr Glu Tyr Glu Leu Met Leu Lys
    1490            1495            1500
Cys Leu Asn Ile Val Phe Thr Ser Met Phe Ser Met Glu Cys Val Leu
1505            1510            1515            1520
Lys Ile Ile Ala Phe Gly Val Leu Asn Tyr Phe Arg Asp Ala Trp Asn
            1525            1530            1535
Val Phe Asp Phe Val Thr Val Leu Gly Ser Ile Thr Asp Ile Leu Val
        1540            1545            1550
Thr Glu Ile Ala Glu Thr Asn Asn Phe Ile Asn Leu Ser Phe Leu Arg
    1555            1560            1565
Leu Phe Arg Ala Ala Arg Leu Ile Lys Leu Leu Arg Gln Gly Tyr Thr
```

```
       1570                        1575                    1580
Ile  Arg  Ile  Leu  Leu  Trp  Thr  Phe  Val  Gln  Ser  Phe  Lys  Ala  Leu  Pro
1585                        1590                    1595                    1600
Tyr  Val  Cys  Leu  Leu  Ile  Ala  Met  Leu  Phe  Phe  Ile  Tyr  Ala  Ile  Ile
                    1605                    1610                    1615
Gly  Met  Gln  Val  Phe  Gly  Asn  Ile  Ala  Leu  Asp  Asp  Asp  Thr  Ser  Ile
                    1620                    1625                    1630
Asn  Arg  His  Asn  Asn  Phe  Arg  Thr  Phe  Leu  Gln  Ala  Leu  Met  Leu  Leu
                    1635                    1640                    1645
Phe  Arg  Ser  Ala  Thr  Gly  Glu  Ala  Trp  His  Glu  Ile  Met  Leu  Ser  Cys
          1650                    1655                    1660
Leu  Ser  Asn  Gln  Ala  Cys  Asp  Glu  Gln  Ala  Asn  Ala  Thr  Glu  Cys  Gly
1665                    1670                    1675                    1680
Ser  Asp  Phe  Ala  Tyr  Phe  Tyr  Phe  Val  Ser  Phe  Ile  Phe  Leu  Cys  Ser
                    1685                    1690                    1695
Phe  Leu  Met  Leu  Asn  Leu  Phe  Val  Ala  Val  Ile  Met  Asp  Asn  Phe  Glu
                    1700                    1705                    1710
Tyr  Leu  Thr  Arg  Asp  Ser  Ser  Ile  Leu  Gly  Pro  His  His  Leu  Asp  Glu
          1715                    1720                    1725
Phe  Ile  Arg  Val  Trp  Ala  Glu  Tyr  Asp  Pro  Ala  Ala  Cys  Gly  Arg  Ile
          1730                    1735                    1740
Ser  Tyr  Asn  Asp  Met  Phe  Glu  Met  Leu  Lys  His  Met  Ser  Pro  Pro  Leu
1745                    1750                    1755                    1760
Gly  Leu  Gly  Lys  Lys  Cys  Pro  Ala  Arg  Val  Ala  Tyr  Lys  Arg  Leu  Val
                    1765                    1770                    1775
Arg  Met  Asn  Met  Pro  Ile  Ser  Asn  Glu  Asp  Met  Thr  Val  His  Phe  Thr
                    1780                    1785                    1790
Ser  Thr  Leu  Met  Ala  Leu  Ile  Arg  Thr  Ala  Leu  Glu  Ile  Lys  Leu  Ala
          1795                    1800                    1805
Pro  Ala  Gly  Thr  Lys  Gln  His  Gln  Cys  Asp  Ala  Glu  Leu  Arg  Lys  Glu
1810                    1815                    1820
Ile  Ser  Val  Val  Trp  Ala  Asn  Leu  Pro  Gln  Lys  Thr  Leu  Asp  Leu  Leu
1825                    1830                    1835                    1840
Val  Pro  Pro  His  Lys  Pro  Asp  Glu  Met  Thr  Val  Gly  Lys  Val  Tyr  Ala
                    1845                    1850                    1855
Ala  Leu  Met  Ile  Phe  Asp  Phe  Tyr  Lys  Gln  Asn  Lys  Thr  Thr  Arg  Asp
          1860                    1865                    1870
Gln  Met  Gln  Gln  Ala  Pro  Gly  Gly  Leu  Ser  Gln  Met  Gly  Pro  Val  Ser
          1875                    1880                    1885
Leu  Phe  His  Pro  Leu  Lys  Ala  Thr  Leu  Glu  Gln  Thr  Gln  Pro  Ala  Val
          1890                    1895                    1900
Leu  Arg  Gly  Ala  Arg  Val  Phe  Leu  Arg  Gln  Lys  Ser  Ser  Thr  Ser  Leu
1905                    1910                    1915                    1920
Ser  Asn  Gly  Gly  Ala  Ile  Gln  Asn  Gln  Glu  Ser  Gly  Ile  Lys  Glu  Ser
                    1925                    1930                    1935
Val  Ser  Trp  Gly  Thr  Gln  Arg  Thr  Gln  Asp  Ala  Pro  His  Glu  Ala  Arg
                    1940                    1945                    1950
Pro  Pro  Leu  Glu  Arg  Gly  His  Ser  Thr  Glu  Ile  Pro  Val  Gly  Arg  Ser
          1955                    1960                    1965
Gly  Ala  Leu  Ala  Val  Asp  Val  Gln  Met  Gln  Ser  Ile  Thr  Arg  Arg  Gly
          1970                    1975                    1980
Pro  Asp  Gly  Glu  Pro  Gln  Pro  Gly  Leu  Glu  Ser  Gln  Gly  Arg  Ala  Ala
1985                    1990                    1995                    2000
```

```
Ser Met Pro Arg Leu Ala Ala Glu Thr Gln Pro Val Thr Asp Ala Ser
            2005                2010                2015
Pro Met Lys Arg Ser Ile Ser Thr Leu Ala Gln Arg Pro Arg Gly Thr
        2020                2025                2030
His Leu Cys Ser Thr Thr Pro Asp Arg Pro Pro Ser Gln Ala Ser
        2035                2040                2045
Ser His His His His Arg Cys His Arg Arg Asp Arg Lys Gln
    2050                2055                2060
Arg Ser Leu Glu Lys Gly Pro Ser Leu Ser Ala Asp Met Asp Gly Ala
2065                2070                2075                2080
Pro Ser Ser Ala Val Gly Pro Gly Leu Pro Pro Gly Glu Gly Pro Thr
                2085                2090                2095
Gly Cys Arg Arg Glu Arg Glu Arg Arg Gln Glu Arg Gly Arg Ser Gln
            2100                2105                2110
Glu Arg Arg Gln Pro Ser Ser Ser Ser Glu Lys Gln Arg Phe Tyr
        2115                2120                2125
Ser Cys Asp Arg Phe Gly Gly Arg Glu Pro Pro Lys Pro Lys Pro. Ser
    2130                2135                2140
Leu Ser Ser His Pro Thr Ser Pro Thr Ala Gly Gln Glu Pro Gly Pro
2145                2150                2155                2160
His Pro Gln Gly Ser Gly Ser Val Asn Gly Ser Pro Leu Leu Ser Thr
                2165                2170                2175
Ser Gly Ala Ser Thr Pro Gly Arg Gly Gly Arg Arg Gln Leu Pro Gln
            2180                2185                2190
Thr Pro Leu Thr Pro Arg Pro Ser Ile Thr Tyr Lys Thr Ala Asn Ser
        2195                2200                2205
Ser Pro Ile His Phe Ala Gly Ala Gln Thr Ser Leu Pro Ala Phe Ser
    2210                2215                2220
Pro Gly Arg Leu Ser Arg Gly Leu Ser Glu His Asn Ala Leu Leu Gln
2225                2230                2235                2240
Arg Asp Pro Leu Ser Gln Pro Leu Ala Pro Gly Ser Arg Ile Gly Ser
            2245                2250                2255
Asp Pro Tyr Leu Gly Gln Arg Leu Asp Ser Glu Ala Ser Val His Ala
        2260                2265                2270
Leu Pro Glu Asp Thr Leu Thr Phe Glu Glu Ala Val Ala Thr Asn Ser
    2275                2280                2285
Gly Arg Ser Ser Arg Thr Ser Tyr Val Ser Ser Leu Thr Ser Gln Ser
2290                2295                2300
His Pro Leu Arg Arg Val Pro Asn Gly Tyr His Cys Thr Leu Gly Leu
2305                2310                2315                2320
Ser Ser Gly Gly Arg Ala Arg His Ser Tyr His His Pro Asp Gln Asp
            2325                2330                2335
His Trp Cys
```

(2) INFORMATION FOR SEQ ID NO:48:

(i) SEQUENCE CHARACTERISTICS:
        (A) LENGTH: 2237 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:48:

| | | | | | | | | | | | | | | |
|---|---|---|---|---|---|---|---|---|---|---|---|---|---|---|
| Met 1 | Val | Arg | Phe | Gly 5 | Asp | Glu | Leu | Gly | Arg 10 | Tyr | Gly | Gly | Pro 15 | Gly |
| Gly | Gly | Glu | Arg 20 | Ala | Arg | Gly | Gly 25 | Gly | Ala | Gly | Ala 30 | Gly | Gly | Pro |
| Gly | Pro | Gly 35 | Gly | Leu | Gln | Pro | Gly 40 | Gln | Arg | Val | Leu | Tyr 45 | Lys | Gln | Ser |
| Ile | Ala 50 | Gln | Arg | Ala | Arg | Thr 55 | Met | Ala | Leu | Tyr | Asn 60 | Pro | Ile | Pro | Val |
| Lys 65 | Gln | Asn | Cys | Phe | Thr 70 | Val | Asn | Arg | Ser | Leu 75 | Phe | Val | Phe | Ser | Glu 80 |
| Asp | Asn | Val | Val | Arg 85 | Lys | Tyr | Ala | Lys | Arg 90 | Ile | Thr | Glu | Trp | Pro 95 | Pro |
| Phe | Glu | Asn | Met 100 | Ile | Leu | Ala | Thr | Ile 105 | Ile | Ala | Asn | Cys | Ile 110 | Val | Leu |
| Ala | Leu | Glu 115 | Gln | His | Leu | Pro | Asp 120 | Gly | Asp | Lys | Thr | Pro 125 | Met | Ser | Glu |
| Arg | Leu 130 | Asp | Asp | Thr | Glu | Pro 135 | Tyr | Phe | Ile | Gly | Ile 140 | Phe | Cys | Phe | Glu |
| Ala 145 | Gly | Ile | Lys | Ile | Ile 150 | Ala | Leu | Gly | Phe | Val 155 | Phe | His | Lys | Gly | Ser 160 |
| Tyr | Leu | Arg | Asn | Gly 165 | Trp | Asn | Val | Met | Asp 170 | Phe | Val | Val | Leu 175 | Thr |
| Gly | Ile | Leu | Ala 180 | Thr | Ala | Gly | Thr | Asp 185 | Phe | Asp | Leu | Arg | Thr 190 | Leu | Arg |
| Ala | Val | Arg 195 | Val | Leu | Arg | Pro | Leu 200 | Lys | Leu | Val | Ser | Gly 205 | Ile | Pro | Ser |
| Leu | Gln 210 | Val | Val | Leu | Lys | Ser 215 | Ile | Met | Lys | Ala | Met 220 | Val | Pro | Leu | Leu |
| Gln 225 | Ile | Gly | Leu | Leu | Leu 230 | Phe | Phe | Ala | Ile | Leu 235 | Met | Phe | Ala | Ile | Ile 240 |
| Gly | Leu | Glu | Phe | Tyr 245 | Met | Gly | Lys | Phe | His 250 | Lys | Ala | Cys | Phe | Pro 255 | Asn |
| Ser | Thr | Asp | Ala 260 | Glu | Pro | Val | Gly | Asp 265 | Phe | Pro | Cys | Gly | Lys 270 | Glu | Ala |
| Pro | Ala | Arg 275 | Leu | Cys | Glu | Gly | Asp 280 | Thr | Glu | Cys | Arg | Glu 285 | Tyr | Trp | Pro |
| Gly | Pro 290 | Asn | Phe | Gly | Ile | Thr 295 | Asn | Phe | Asp | Asn | Ile 300 | Leu | Phe | Ala | Ile |
| Leu 305 | Thr | Val | Phe | Gln | Cys 310 | Ile | Thr | Met | Glu | Gly 315 | Trp | Thr | Asp | Ile | Leu 320 |
| Tyr | Asn | Thr | Asn | Asp 325 | Ala | Ala | Gly | Asn | Thr 330 | Trp | Asn | Trp | Leu | Tyr 335 | Phe |
| Ile | Pro | Leu | Ile 340 | Ile | Ile | Gly | Ser | Phe 345 | Phe | Met | Leu | Asn | Leu 350 | Val | Leu |
| Gly | Val | Leu 355 | Ser | Gly | Glu | Phe | Ala 360 | Lys | Glu | Arg | Glu | Arg 365 | Val | Glu | Asn |
| Arg | Arg 370 | Ala | Phe | Leu | Lys | Leu 375 | Arg | Arg | Gln | Gln | Gln 380 | Ile | Glu | Arg | Glu |
| Leu 385 | Asn | Gly | Tyr | Leu | Glu 390 | Trp | Ile | Phe | Lys | Ala 395 | Glu | Glu | Val | Met 400 | Leu |
| Ala | Glu | Glu | Asp | Arg 405 | Asn | Ala | Glu | Glu | Lys 410 | Ser | Pro | Leu | Asp | Val 415 | Leu |
| Lys | Arg | Ala | Ala 420 | Thr | Lys | Lys | Ser | Arg 425 | Asn | Asp | Leu | Ile | His 430 | Ala | Glu |

-continued

| | | | | | | | | | | | | | | |
|---|---|---|---|---|---|---|---|---|---|---|---|---|---|---|
| Glu | Gly | Glu 435 | Asp | Arg | Phe | Ala 440 | Asp | Leu | Cys | Ala | Val 445 | Gly | Ser | Pro | Phe |
| Ala | Arg 450 | Ala | Ser | Leu | Lys | Ser 455 | Gly | Lys | Thr | Glu 460 | Ser | Ser | Ser | Tyr | Phe |
| Arg 465 | Arg | Lys | Glu | Lys | Met 470 | Phe | Arg | Phe | Phe | Ile 475 | Arg | Arg | Met | Val | Lys 480 |
| Ala | Gln | Ser | Phe | Tyr 485 | Trp | Val | Val | Leu | Cys 490 | Val | Val | Ala | Leu | Asn 495 | Thr |
| Leu | Cys | Val | Ala 500 | Met | Val | His | Tyr | Asn 505 | Gln | Pro | Arg | Arg | Leu 510 | Thr | Thr |
| Thr | Leu | Tyr 515 | Phe | Ala | Glu | Phe 520 | Val | Phe | Leu | Gly | Leu 525 | Phe | Leu | Thr | Glu |
| Met | Ser 530 | Leu | Lys | Met | Tyr | Gly 535 | Leu | Gly | Pro | Arg 540 | Ser | Tyr | Phe | Arg | Ser |
| Ser 545 | Phe | Asn | Cys | Phe | Asp 550 | Phe | Gly | Val | Ile | Val 555 | Gly | Ser | Val | Phe | Glu 560 |
| Val | Val | Trp | Ala | Ala 565 | Ile | Lys | Pro | Gly | Ser 570 | Ser | Phe | Gly | Ile | Ser 575 | Val |
| Leu | Arg | Ala | Leu 580 | Arg | Leu | Leu | Arg | Ile 585 | Phe | Lys | Val | Thr | Lys 590 | Tyr | Trp |
| Ser | Ser | Leu 595 | Arg | Asn | Leu | Val | Val 600 | Ser | Leu | Leu | Asn | Ser 605 | Met | Lys | Ser |
| Ile | Ile 610 | Ser | Leu | Leu | Phe | Leu 615 | Leu | Phe | Leu | Phe | Ile 620 | Val | Val | Phe | Ala |
| Leu 625 | Leu | Gly | Met | Gln | Leu 630 | Phe | Gly | Gly | Gln | Phe 635 | Asn | Phe | Gln | Asp | Glu 640 |
| Thr | Pro | Thr | Thr | Asn 645 | Phe | Asp | Thr | Phe | Pro 650 | Ala | Ala | Ile | Leu | Thr 655 | Val |
| Phe | Gln | Ile | Leu 660 | Thr | Gly | Glu | Asp | Trp 665 | Asn | Ala | Val | Met | Tyr 670 | His | Gly |
| Ile | Glu | Ser 675 | Gln | Gly | Gly | Val | Ser 680 | Lys | Gly | Met | Phe | Ser 685 | Ser | Phe | Tyr |
| Phe | Ile 690 | Val | Leu | Thr | Leu | Phe 695 | Gly | Asn | Tyr | Thr | Leu 700 | Leu | Asn | Val | Phe |
| Leu 705 | Ala | Ile | Ala | Val | Asp 710 | Asn | Leu | Ala | Asn | Ala 715 | Gln | Glu | Leu | Thr | Lys 720 |
| Asp | Glu | Glu | Glu | Met 725 | Glu | Glu | Ala | Ala | Asn 730 | Gln | Lys | Leu | Ala | Leu 735 | Gln |
| Lys | Ala | Lys | Glu 740 | Val | Ala | Glu | Val | Ser 745 | Pro | Met | Ser | Ala | Ala 750 | Asn | Ile |
| Ser | Ile | Ala 755 | Ala | Arg | Gln | Gln | Asn 760 | Ser | Ala | Lys | Ala | Arg 765 | Ser | Val | Trp |
| Glu | Gln 770 | Arg | Ala | Ser | Gln | Leu 775 | Arg | Leu | Gln | Asn | Leu 780 | Arg | Ala | Ser | Cys |
| Glu 785 | Ala | Leu | Tyr | Ser | Glu 790 | Met | Asp | Pro | Glu | Glu 795 | Arg | Leu | Arg | Phe | Ala 800 |
| Thr | Thr | Arg | His | Leu 805 | Arg | Pro | Asp | Met | Lys 810 | Thr | His | Leu | Asp | Arg 815 | Pro |
| Leu | Val | Val | Glu 820 | Leu | Gly | Arg | Asp | Gly 825 | Ala | Arg | Gly | Pro | Val 830 | Gly | Gly |
| Lys | Ala | Arg 835 | Pro | Glu | Ala | Ala | Glu 840 | Ala | Pro | Glu | Gly | Val 845 | Asp | Pro | Pro |
| Arg | Arg | His | His | Arg | His | Arg | Asp | Lys | Asp | Lys | Thr | Pro | Ala | Ala | Gly |

-continued

```
            850                       855                       860
Asp  Gln  Asp  Arg  Ala  Glu  Ala  Pro  Lys  Ala  Glu  Ser  Gly  Glu  Pro  Gly
865                      870                      875                      880
Ala  Arg  Glu  Glu  Arg  Pro  Arg  Pro  His  Arg  Ser  His  Ser  Lys  Glu  Ala
                         885                      890                      895
Ala  Gly  Pro  Pro  Glu  Ala  Arg  Ser  Glu  Arg  Gly  Arg  Gly  Pro  Gly  Pro
               900                      905                      910
Glu  Gly  Gly  Arg  Arg  His  His  Arg  Arg  Gly  Ser  Pro  Glu  Glu  Ala  Ala
               915                      920                      925
Glu  Arg  Glu  Pro  Arg  Arg  His  Arg  Ala  His  Arg  His  Gln  Asp  Pro  Ser
          930                      935                      940
Lys  Glu  Cys  Ala  Gly  Ala  Lys  Gly  Glu  Arg  Arg  Ala  Arg  His  Arg  Gly
945                      950                      955                      960
Gly  Pro  Arg  Ala  Gly  Pro  Arg  Glu  Ala  Glu  Ser  Gly  Glu  Glu  Pro  Ala
               965                      970                      975
Arg  Arg  His  Arg  Ala  Arg  His  Lys  Ala  Gln  Pro  Ala  His  Glu  Ala  Val
               980                      985                      990
Glu  Lys  Glu  Thr  Thr  Glu  Lys  Glu  Ala  Thr  Glu  Lys  Glu  Ala  Glu  Ile
          995                      1000                     1005
Val  Glu  Ala  Asp  Lys  Glu  Lys  Glu  Leu  Arg  Asn  His  Gln  Pro  Arg  Glu
1010                     1015                     1020
Pro  His  Cys  Asp  Leu  Glu  Thr  Ser  Gly  Thr  Val  Thr  Val  Gly  Pro  Met
1025                     1030                     1035                     1040
His  Thr  Leu  Pro  Ser  Thr  Cys  Leu  Gln  Lys  Val  Glu  Glu  Gln  Pro  Glu
               1045                     1050                     1055
Asp  Ala  Asp  Asn  Gln  Arg  Asn  Val  Thr  Arg  Met  Gly  Ser  Gln  Pro  Pro
               1060                     1065                     1070
Asp  Pro  Asn  Thr  Ile  Val  His  Ile  Pro  Val  Met  Leu  Thr  Gly  Pro  Leu
               1075                     1080                     1085
Gly  Glu  Ala  Thr  Val  Val  Pro  Ser  Gly  Asn  Val  Asp  Leu  Glu  Ser  Gln
               1090                     1095                     1100
Ala  Glu  Gly  Lys  Lys  Glu  Val  Glu  Ala  Asp  Asp  Val  Met  Arg  Ser  Gly
1105                     1110                     1115                     1120
Pro  Arg  Pro  Ile  Val  Pro  Tyr  Ser  Ser  Met  Phe  Cys  Leu  Ser  Pro  Thr
                    1125                     1130                     1135
Asn  Leu  Leu  Arg  Arg  Phe  Cys  His  Tyr  Ile  Val  Thr  Met  Arg  Tyr  Phe
                    1140                     1145                     1150
Glu  Val  Val  Ile  Leu  Val  Val  Ile  Ala  Leu  Ser  Ser  Ile  Ala  Leu  Ala
                    1155                     1160                     1165
Ala  Glu  Asp  Pro  Val  Arg  Thr  Asp  Ser  Pro  Arg  Asn  Asn  Ala  Leu  Lys
     1170                     1175                     1180
Tyr  Leu  Asp  Tyr  Ile  Phe  Thr  Gly  Val  Phe  Thr  Phe  Glu  Met  Val  Ile
1185                     1190                     1195                     1200
Lys  Met  Ile  Asp  Leu  Gly  Leu  Leu  Leu  His  Pro  Gly  Ala  Tyr  Phe  Arg
                    1205                     1210                     1215
Asp  Leu  Trp  Asn  Ile  Leu  Asp  Phe  Ile  Val  Val  Ser  Gly  Ala  Leu  Val
                    1220                     1225                     1230
Ala  Phe  Ala  Phe  Ser  Gly  Ser  Lys  Gly  Lys  Asp  Ile  Asn  Thr  Ile  Lys
                    1235                     1240                     1245
Ser  Leu  Arg  Val  Leu  Arg  Val  Leu  Arg  Pro  Leu  Lys  Thr  Ile  Lys  Arg
     1250                     1255                     1260
Leu  Pro  Lys  Leu  Lys  Ala  Val  Phe  Asp  Cys  Val  Val  Asn  Ser  Leu  Lys
1265                     1270                     1275                     1280
```

```
Asn Val Leu Asn Ile Leu Ile Val Tyr Met Leu Phe Met Phe Ile Phe
            1285            1290                1295

Ala Val Ile Ala Val Gln Leu Phe Lys Gly Lys Phe Phe Tyr Cys Thr
            1300            1305                1310

Asp Glu Ser Lys Glu Leu Glu Arg Asp Cys Arg Gly Gln Tyr Leu Asp
            1315            1320                1325

Tyr Glu Lys Glu Glu Val Glu Ala Gln Pro Arg Gln Trp Lys Lys Tyr
            1330            1335                1340

Asp Phe His Tyr Asp Asn Val Leu Trp Ala Leu Leu Thr Leu Phe Thr
1345            1350            1355                        1360

Val Ser Thr Gly Glu Gly Trp Pro Met Val Leu Lys His Ser Val Asp
            1365            1370                1375

Ala Thr Tyr Glu Glu Gln Gly Pro Ser Pro Gly Tyr Arg Met Glu Leu
            1380            1385                1390

Ser Ile Phe Tyr Val Val Tyr Phe Val Val Phe Pro Phe Phe Phe Val
            1395            1400                1405

Asn Ile Phe Val Ala Leu Ile Ile Ile Thr Phe Gln Glu Gln Gly Asp
            1410            1415                1420

Lys Val Met Ser Glu Cys Ser Leu Glu Lys Asn Glu Arg Ala Cys Ile
1425            1430            1435                        1440

Asp Phe Ala Ile Ser Ala Lys Pro Leu Thr Arg Tyr Met Pro Gln Asn
            1445            1450                1455

Arg Gln Ser Phe Gln Tyr Lys Thr Trp Thr Phe Val Val Ser Pro Pro
            1460            1465                1470

Phe Glu Tyr Phe Ile Met Ala Met Ile Ala Leu Asn Thr Val Val Leu
            1475            1480                1485

Met Met Lys Phe Tyr Asp Ala Pro Tyr Glu Tyr Glu Leu Met Leu Lys
            1490            1495            1500

Cys Leu Asn Ile Val Phe Thr Ser Met Phe Ser Met Glu Cys Val Leu
1505            1510            1515                        1520

Lys Ile Ile Ala Phe Gly Val Leu Asn Tyr Phe Arg Asp Ala Trp Asn
            1525            1530                1535

Val Phe Asp Phe Val Thr Val Leu Gly Ser Ile Thr Asp Ile Leu Val
            1540            1545                1550

Thr Glu Ile Ala Glu Thr Asn Asn Phe Ile Asn Leu Ser Phe Leu Arg
            1555            1560                1565

Leu Phe Arg Ala Ala Arg Leu Ile Lys Leu Leu Arg Gln Gly Tyr Thr
            1570            1575                1580

Ile Arg Ile Leu Leu Trp Thr Phe Val Gln Ser Phe Lys Ala Leu Pro
1585            1590            1595                        1600

Tyr Val Cys Leu Leu Ile Ala Met Leu Phe Phe Ile Tyr Ala Ile Ile
            1605            1610                1615

Gly Met Gln Val Phe Gly Asn Ile Ala Leu Asp Asp Asp Thr Ser Ile
            1620            1625                1630

Asn Arg His Asn Asn Phe Arg Thr Phe Leu Gln Ala Leu Met Leu Leu
            1635            1640                1645

Phe Arg Ser Ala Thr Gly Glu Ala Trp His Glu Ile Met Leu Ser Cys
            1650            1655                1660

Leu Ser Asn Gln Ala Cys Asp Glu Gln Ala Asn Ala Thr Glu Cys Gly
            1665            1670                1675            1680

Ser Asp Phe Ala Tyr Phe Tyr Phe Val Ser Phe Ile Phe Leu Cys Ser
            1685            1690                1695

Phe Leu Met Leu Asn Leu Phe Val Ala Val Ile Met Asp Asn Phe Glu
            1700            1705                1710
```

Tyr Leu Thr Arg Asp Ser Ser Ile Leu Gly Pro His His Leu Asp Glu
           1715              1720              1725

Phe Ile Arg Val Trp Ala Glu Tyr Asp Pro Ala Ala Cys Gly Arg Ile
        1730              1735              1740

Ser Tyr Asn Asp Met Phe Glu Met Leu Lys His Met Ser Pro Pro Leu
1745              1750              1755                  1760

Gly Leu Gly Lys Lys Cys Pro Ala Arg Val Ala Tyr Lys Arg Leu Val
            1765              1770              1775

Arg Met Asn Met Pro Ile Ser Asn Glu Asp Met Thr Val His Phe Thr
        1780              1785              1790

Ser Thr Leu Met Ala Leu Ile Arg Thr Ala Leu Glu Ile Lys Leu Ala
        1795              1800              1805

Pro Ala Gly Thr Lys Gln His Gln Cys Asp Ala Glu Leu Arg Lys Glu
        1810              1815              1820

Ile Ser Val Val Trp Ala Asn Leu Pro Gln Lys Thr Leu Asp Leu Leu
1825              1830              1835              1840

Val Pro Pro His Lys Pro Asp Glu Met Thr Val Gly Lys Val Tyr Ala
            1845              1850              1855

Ala Leu Met Ile Phe Asp Phe Tyr Lys Gln Asn Lys Thr Thr Arg Asp
            1860              1865              1870

Gln Met Gln Gln Ala Pro Gly Gly Leu Ser Gln Met Gly Pro Val Ser
        1875              1880              1885

Leu Phe His Pro Leu Lys Ala Thr Leu Glu Gln Thr Gln Pro Ala Val
        1890              1895              1900

Leu Arg Gly Ala Arg Val Phe Leu Arg Gln Lys Ser Ser Thr Ser Leu
1905              1910              1915              1920

Ser Asn Gly Gly Ala Ile Gln Asn Gln Glu Ser Gly Ile Lys Glu Ser
            1925              1930              1935

Val Ser Trp Gly Thr Gln Arg Thr Gln Asp Ala Pro His Glu Ala Arg
            1940              1945              1950

Pro Pro Leu Glu Arg Gly His Ser Thr Glu Ile Pro Val Gly Arg Ser
        1955              1960              1965

Gly Ala Leu Ala Val Asp Val Gln Met Gln Ser Ile Thr Arg Arg Gly
1970              1975              1980

Pro Asp Gly Glu Pro Gln Pro Gly Leu Glu Ser Gln Gly Arg Ala Ala
1985              1990              1995              2000

Ser Met Pro Arg Leu Ala Ala Glu Thr Gln Pro Val Thr Asp Ala Ser
            2005              2010              2015

Pro Met Lys Arg Ser Ile Ser Thr Leu Ala Gln Arg Pro Arg Gly Thr
            2020              2025              2030

His Leu Cys Ser Thr Thr Pro Asp Arg Pro Pro Ser Gln Ala Ser
        2035              2040              2045

Ser His His His His His Arg Cys His Arg Arg Asp Arg Lys Gln
2050              2055              2060

Arg Ser Leu Glu Lys Gly Pro Ser Leu Ser Ala Asp Met Asp Gly Ala
2065              2070              2075              2080

Pro Ser Ser Ala Val Gly Pro Gly Leu Pro Pro Gly Glu Gly Pro Thr
            2085              2090              2095

Gly Cys Arg Arg Glu Arg Glu Arg Arg Gln Glu Arg Gly Arg Ser Gln
            2100              2105              2110

Glu Arg Arg Gln Pro Ser Ser Ser Ser Glu Lys Gln Arg Phe Tyr
        2115              2120              2125

Ser Cys Asp Arg Phe Gly Gly Arg Glu Pro Pro Lys Pro Lys Pro Ser

-continued

```
                    2130                         2135                          2140
Leu  Ser  Ser  His  Pro  Thr  Ser  Pro  Thr  Ala  Gly  Gln  Glu  Pro  Gly  Pro
2145                     2150                         2155                     2160

His  Pro  Gln  Ala  Gly  Ser  Ala  Val  Gly  Phe  Pro  Asn  Thr  Thr  Pro  Cys
                    2165                         2170                     2175

Cys  Arg  Glu  Thr  Pro  Ser  Ala  Ser  Pro  Trp  Pro  Leu  Ala  Leu  Glu  Leu
                2180                         2185                    2190

Ala  Leu  Thr  Leu  Thr  Trp  Gly  Ser  Val  Trp  Thr  Val  Arg  Pro  Leu  Ser
              2195                    2200                    2205

Thr  Pro  Cys  Leu  Arg  Thr  Arg  Ser  Leu  Ser  Arg  Arg  Leu  Trp  Pro  Pro
         2210                    2215                    2220

Thr  Arg  Ala  Ala  Pro  Pro  Gly  Leu  Pro  Thr  Cys  Pro  Pro
2225                     2230                        2235
```

( 2 ) INFORMATION FOR SEQ ID NO:49:

( i ) SEQUENCE CHARACTERISTICS:
        ( A ) LENGTH: 2161 amino acids
        ( B ) TYPE: amino acid
        ( C ) STRANDEDNESS: single
        ( D ) TOPOLOGY: linear ( i i ) MOLECULE TYPE: protein ( v ) FRAGMENT TYPE: internal ( x i ) SEQUENCE DESCRIPTION: SEQ ID NO:49:

```
Met  Met  Met  Met  Met  Met  Met  Lys  Lys  Met  Gln  His  Gln  Arg  Gln  Gln
1                   5                   10                      15

Gln  Ala  Asp  His  Ala  Asn  Glu  Ala  Asn  Tyr  Ala  Arg  Gly  Thr  Arg  Leu
                20                      25                      30

Pro  Leu  Ser  Gly  Glu  Gly  Pro  Thr  Ser  Gln  Pro  Asn  Ser  Ser  Lys  Gln
            35                      40                      45

Thr  Val  Leu  Ser  Trp  Gln  Ala  Ala  Ile  Asp  Ala  Ala  Arg  Gln  Ala  Lys
         50                      55                      60

Ala  Ala  Gln  Thr  Met  Ser  Thr  Ser  Ala  Pro  Pro  Pro  Val  Gly  Ser  Leu
65                      70                      75                           80

Ser  Gln  Arg  Lys  Arg  Gln  Gln  Tyr  Ala  Lys  Ser  Lys  Lys  Gln  Gly  Asn
                    85                      90                           95

Ser  Ser  Asn  Ser  Arg  Pro  Ala  Arg  Ala  Leu  Phe  Cys  Leu  Ser  Leu  Asn
                100                     105                     110

Asn  Pro  Ile  Arg  Arg  Ala  Cys  Ile  Ser  Ile  Val  Glu  Trp  Lys  Pro  Phe
            115                     120                     125

Asp  Ile  Phe  Ile  Leu  Leu  Ala  Ile  Phe  Ala  Asn  Cys  Val  Ala  Leu  Ala
         130                     135                     140

Ile  Tyr  Ile  Pro  Phe  Pro  Glu  Asp  Asp  Ser  Asn  Ser  Thr  Asn  His  Asn
145                     150                     155                          160

Leu  Glu  Lys  Val  Glu  Tyr  Ala  Phe  Leu  Ile  Ile  Phe  Thr  Val  Glu  Thr
                    165                     170                     175

Phe  Leu  Lys  Ile  Ile  Ala  Tyr  Gly  Leu  Leu  Leu  His  Pro  Asn  Ala  Tyr
                180                     185                     190

Val  Arg  Asn  Gly  Trp  Asn  Leu  Leu  Asp  Phe  Val  Ile  Val  Ile  Val  Gly
            195                     200                     205

Leu  Phe  Ser  Val  Ile  Leu  Glu  Gln  Leu  Thr  Lys  Glu  Thr  Glu  Gly  Gly
         210                     215                     220

Asn  His  Ser  Ser  Gly  Lys  Ser  Gly  Gly  Phe  Asp  Val  Lys  Ala  Leu  Arg
225                     230                     235                          240
```

```
Ala Phe Arg Val Leu Arg Pro Leu Arg Leu Val Ser Gly Val Pro Ser
                245             250             255
Leu Gln Val Val Leu Asn Ser Ile Ile Lys Ala Met Val Pro Leu Leu
                260             265             270
His Ile Ala Leu Leu Val Leu Phe Val Ile Ile Ile Tyr Ala Ile Ile
            275             280             285
Gly Leu Glu Leu Phe Ile Gly Lys Met His Lys Thr Cys Phe Phe Ala
        290             295             300
Asp Ser Asp Ile Val Ala Glu Asp Pro Ala Pro Cys Ala Phe Ser
305             310             315                 320
Gly Asn Gly Arg Gln Cys Thr Ala Asn Gly Thr Glu Cys Arg Ser Gly
                325             330             335
Trp Val Gly Pro Asn Gly Gly Ile Thr Asn Phe Asp Asn Phe Ala Phe
            340             345             350
Ala Met Leu Thr Val Phe Gln Cys Ile Thr Met Glu Gly Trp Thr Asp
        355             360             365
Val Leu Tyr Trp Met Asn Asp Ala Met Gly Phe Glu Leu Pro Trp Val
    370             375             380
Tyr Phe Val Ser Leu Val Ile Phe Gly Ser Phe Phe Val Leu Asn Leu
385             390             395                 400
Val Leu Gly Val Leu Ser Gly Glu Phe Ser Lys Glu Arg Glu Lys Ala
                405             410             415
Lys Ala Arg Gly Asp Phe Gln Lys Leu Arg Glu Lys Gln Gln Leu Glu
            420             425             430
Glu Asp Leu Lys Gly Tyr Leu Asp Trp Ile Thr Gln Ala Glu Asp Ile
        435             440             445
Asp Pro Glu Asn Glu Glu Gly Gly Glu Glu Gly Lys Arg Asn Thr
450             455             460
Ser Met Pro Thr Ser Glu Thr Glu Ser Val Asn Thr Glu Asn Val Ser
465             470             475                 480
Gly Glu Gly Glu Asn Arg Gly Cys Cys Gly Ser Leu Cys Gln Ala Ile
                485             490             495
Ser Lys Ser Lys Leu Ser Arg Arg Trp Arg Arg Trp Asn Arg Phe Asn
            500             505             510
Arg Arg Arg Cys Arg Ala Ala Val Lys Ser Val Thr Phe Tyr Trp Leu
        515             520             525
Val Ile Val Leu Val Phe Leu Asn Thr Leu Thr Ile Ser Ser Glu His
    530             535             540
Tyr Asn Gln Pro Asp Trp Leu Thr Gln Ile Gln Asp Ile Ala Asn Lys
545             550             555                 560
Val Leu Leu Ala Leu Phe Thr Cys Glu Met Leu Val Lys Met Tyr Ser
                565             570             575
Leu Gly Leu Gln Ala Tyr Phe Val Ser Leu Phe Asn Arg Phe Asp Cys
            580             585             590
Phe Val Val Cys Gly Gly Ile Thr Glu Thr Ile Leu Val Glu Leu Glu
        595             600             605
Ile Met Ser Pro Leu Gly Ile Ser Val Phe Arg Cys Val Arg Leu Leu
    610             615             620
Arg Ile Phe Lys Val Thr Arg His Trp Thr Ser Leu Ser Asn Leu Val
625             630             635                 640
Ala Ser Leu Leu Asn Ser Met Lys Ser Ile Ala Ser Leu Leu Leu Leu
                645             650             655
Leu Phe Leu Phe Ile Ile Ile Phe Ser Leu Leu Gly Met Gln Leu Phe
            660             665             670
```

```
Gly Gly Lys Phe Asn Phe Asp Glu Thr Gln Thr Lys Arg Ser Thr Phe
        675                 680                 685
Asp Asn Phe Pro Gln Ala Leu Leu Thr Val Phe Gln Ile Leu Thr Gly
        690                 695                 700
Glu Asp Trp Asn Ala Val Met Tyr Asp Gly Ile Met Ala Tyr Gly Gly
705                 710                 715                 720
Pro Ser Ser Ser Gly Met Ile Val Cys Ile Tyr Phe Ile Ile Leu Phe
            725                 730                 735
Ile Cys Gly Asn Tyr Ile Leu Leu Asn Val Phe Leu Ala Ile Ala Val
            740                 745                 750
Asp Asn Leu Ala Asp Ala Glu Ser Leu Asn Thr Ala Gln Lys Glu Glu
        755                 760                 765
Ala Glu Glu Lys Glu Arg Lys Lys Ile Ala Arg Lys Glu Ser Leu Glu
        770                 775                 780
Asn Lys Lys Asn Asn Lys Pro Glu Val Asn Gln Ile Ala Asn Ser Asp
785                 790                 795                 800
Asn Lys Val Thr Ile Asp Asp Tyr Arg Glu Glu Asp Glu Asp Lys Asp
            805                 810                 815
Pro Tyr Pro Pro Cys Asp Val Pro Val Gly Glu Glu Glu Glu Glu Glu
        820                 825                 830
Glu Glu Asp Glu Pro Glu Val Pro Ala Gly Pro Arg Pro Arg Arg Ile
        835                 840                 845
Ser Glu Leu Asn Met Lys Glu Lys Ile Ala Pro Ile Pro Glu Gly Ser
    850                 855                 860
Ala Phe Phe Ile Leu Ser Lys Thr Asn Pro Ile Arg Val Gly Cys His
865                 870                 875                 880
Lys Leu Ile Asn His His Ile Phe Thr Asn Leu Ile Leu Val Phe Ile
                885                 890                 895
Met Leu Ser Ser Ala Ala Leu Ala Ala Glu Asp Pro Ile Arg Ser His
            900                 905                 910
Ser Phe Arg Asn Thr Ile Leu Gly Tyr Phe Asp Tyr Ala Phe Thr Ala
        915                 920                 925
Ile Phe Thr Val Glu Ile Leu Leu Lys Met Thr Thr Phe Gly Ala Phe
    930                 935                 940
Leu His Lys Gly Ala Phe Cys Arg Asn Tyr Phe Asn Leu Leu Asp Met
945                 950                 955                 960
Leu Val Val Gly Val Ser Leu Val Ser Phe Gly Ile Gln Ser Ser Ala
            965                 970                 975
Ile Ser Val Val Lys Ile Leu Arg Val Leu Arg Val Leu Arg Pro Leu
            980                 985                 990
Arg Ala Ile Asn Arg Ala Lys Gly Leu Lys His Val Val Gln Cys Val
        995                 1000                1005
Phe Val Ala Ile Arg Thr Ile Gly Asn Ile Met Ile Val Thr Thr Leu
    1010                1015                1020
Leu Gln Phe Met Phe Ala Cys Ile Gly Val Gln Leu Phe Lys Gly Lys
1025                1030                1035                1040
Phe Tyr Arg Cys Thr Asp Glu Ala Lys Ser Asn Pro Glu Glu Cys Arg
            1045                1050                1055
Gly Leu Phe Ile Leu Tyr Lys Asp Gly Asp Val Asp Ser Pro Val Val
            1060                1065                1070
Arg Glu Arg Ile Trp Gln Asn Ser Asp Phe Asn Phe Asp Asn Val Leu
        1075                1080                1085
Ser Ala Met Met Ala Leu Phe Thr Val Ser Thr Phe Glu Gly Trp Pro
```

-continued

| | 1090 | | | | 1095 | | | | 1100 | | |
|---|---|---|---|---|---|---|---|---|---|---|---|
| Ala | Leu | Leu | Tyr | Lys | Ala | Ile | Asp | Ser | Asn | Gly | Glu | Asn | Ile | Gly | Pro |
| 1105 | | | | | 1110 | | | | 1115 | | | | | | 1120 |
| Ile | Tyr | Asn | His | Arg | Val | Glu | Ile | Ser | Ile | Phe | Phe | Ile | Ile | Tyr | Ile |
| | | | | 1125 | | | | | 1130 | | | | | 1135 | |
| Ile | Ile | Val | Ala | Phe | Phe | Met | Met | Asn | Ile | Phe | Val | Gly | Phe | Val | Ile |
| | | | | 1140 | | | | | 1145 | | | | | 1150 | |
| Val | Thr | Phe | Gln | Glu | Gln | Gly | Glu | Lys | Glu | Tyr | Lys | Asn | Cys | Glu | Leu |
| | | | | 1155 | | | | | 1160 | | | | | 1165 | |
| Asp | Lys | Asn | Gln | Arg | Gln | Cys | Val | Glu | Tyr | Ala | Leu | Lys | Ala | Arg | Pro |
| | | | | 1170 | | | | | 1175 | | | | | 1180 | |
| Leu | Arg | Arg | Tyr | Ile | Pro | Lys | Asn | Pro | Tyr | Gln | Tyr | Lys | Phe | Trp | Tyr |
| 1185 | | | | | 1190 | | | | | 1195 | | | | | 1200 |
| Val | Val | Asn | Ser | Ser | Pro | Phe | Glu | Tyr | Met | Met | Phe | Val | Leu | Ile | Met |
| | | | | 1205 | | | | | 1210 | | | | | 1215 | |
| Leu | Asn | Thr | Leu | Cys | Leu | Ala | Met | Gln | His | Tyr | Glu | Gln | Ser | Lys | Met |
| | | | | 1220 | | | | | 1225 | | | | | 1230 | |
| Phe | Asn | Asp | Ala | Met | Asp | Ile | Leu | Asn | Met | Val | Phe | Thr | Gly | Val | Phe |
| | | | | 1235 | | | | | 1240 | | | | | 1245 | |
| Thr | Val | Glu | Met | Val | Leu | Lys | Val | Ile | Ala | Phe | Lys | Pro | Lys | Gly | Tyr |
| | | | | 1250 | | | | | 1255 | | | | | 1260 | |
| Phe | Ser | Asp | Ala | Trp | Asn | Thr | Phe | Asp | Ser | Leu | Ile | Val | Ile | Gly | Ser |
| 1265 | | | | | 1270 | | | | | 1275 | | | | | 1280 |
| Ile | Ile | Asp | Val | Ala | Leu | Ser | Glu | Ala | Asp | Pro | Thr | Glu | Ser | Glu | Asn |
| | | | | 1285 | | | | | 1290 | | | | | 1295 | |
| Val | Pro | Val | Pro | Thr | Ala | Thr | Pro | Gly | Asn | Ser | Glu | Glu | Ser | Asn | Arg |
| | | | | 1300 | | | | | 1305 | | | | | 1310 | |
| Ile | Ser | Ile | Thr | Phe | Phe | Arg | Leu | Phe | Arg | Val | Met | Arg | Leu | Val | Lys |
| | | | | 1315 | | | | | 1320 | | | | | 1325 | |
| Leu | Leu | Ser | Arg | Gly | Glu | Gly | Ile | Arg | Thr | Leu | Leu | Trp | Thr | Phe | Ile |
| | | | | 1330 | | | | | 1335 | | | | | 1340 | |
| Lys | Phe | Phe | Gln | Ala | Leu | Pro | Tyr | Val | Ala | Leu | Leu | Ile | Ala | Met | Leu |
| 1345 | | | | | 1350 | | | | | 1355 | | | | | 1360 |
| Phe | Phe | Ile | Tyr | Ala | Val | Ile | Gly | Met | Gln | Met | Phe | Gly | Lys | Val | Ala |
| | | | | 1365 | | | | | 1370 | | | | | 1375 | |
| Met | Arg | Asp | Asn | Asn | Gln | Ile | Asn | Arg | Asn | Asn | Phe | Gln | Thr | Phe |
| | | | | 1380 | | | | | 1385 | | | | | 1390 | |
| Pro | Gln | Ala | Val | Leu | Leu | Leu | Phe | Arg | Cys | Ala | Thr | Gly | Glu | Ala | Trp |
| | | | | 1395 | | | | | 1400 | | | | | 1405 | |
| Gln | Glu | Ile | Met | Leu | Ala | Cys | Leu | Pro | Gly | Lys | Leu | Cys | Asp | Pro | Glu |
| | | | | 1410 | | | | | 1415 | | | | | 1420 | |
| Ser | Asp | Tyr | Asn | Pro | Gly | Glu | Glu | His | Thr | Cys | Gly | Ser | Asn | Phe | Ala |
| 1425 | | | | | 1430 | | | | | 1435 | | | | | 1440 |
| Ile | Val | Tyr | Phe | Ile | Ser | Phe | Tyr | Met | Leu | Cys | Ala | Phe | Leu | Ile | Ile |
| | | | | 1445 | | | | | 1450 | | | | | 1455 | |
| Asn | Leu | Phe | Val | Ala | Val | Ile | Met | Asp | Asn | Phe | Asp | Tyr | Leu | Thr | Arg |
| | | | | 1460 | | | | | 1465 | | | | | 1470 | |
| Asp | Trp | Ser | Ile | Leu | Gly | Pro | His | His | Leu | Asp | Glu | Phe | Lys | Arg | Ile |
| | | | | 1475 | | | | | 1480 | | | | | 1485 | |
| Trp | Ser | Glu | Tyr | Asp | Pro | Glu | Ala | Lys | Gly | Arg | Ile | Lys | His | Leu | Asp |
| | | | | 1490 | | | | | 1495 | | | | | 1500 | |
| Val | Val | Thr | Leu | Leu | Arg | Arg | Ile | Gln | Pro | Pro | Leu | Gly | Phe | Gly | Lys |
| 1505 | | | | | 1510 | | | | | 1515 | | | | | 1520 |

Leu Cys Pro His Arg Val Ala Cys Lys Arg Leu Val Ala Met Asn Met
1525                    1530                    1535

Pro Leu Asn Ser Asp Gly Thr Val Met Phe Asn Ala Thr Leu Phe Ala
            1540                    1545                    1550

Leu Val Arg Thr Ala Leu Lys Ile Lys Thr Glu Gly Asn Leu Glu Gln
        1555                    1560                    1565

Ala Asn Glu Glu Leu Arg Ala Val Ile Lys Lys Ile Trp Lys Lys Thr
    1570                    1575                    1580

Ser Met Lys Leu Leu Asp Gln Val Val Pro Pro Ala Gly Asp Asp Glu
1585                    1590                    1595                    1600

Val Thr Val Gly Lys Phe Tyr Ala Thr Phe Leu Ile Gln Asp Tyr Phe
                1605                    1610                    1615

Arg Lys Phe Lys Lys Arg Lys Glu Gln Gly Leu Val Gly Lys Tyr Pro
            1620                    1625                    1630

Ala Lys Asn Thr Thr Ile Ala Leu Gln Ala Gly Leu Arg Thr Leu His
                1635                    1640                    1645

Asp Ile Gly Pro Glu Ile Arg Arg Ala Ile Ser Cys Asp Leu Gln Asp
        1650                    1655                    1660

Asp Glu Pro Glu Glu Thr Lys Arg Glu Glu Glu Asp Asp Val Phe Lys
1665                    1670                    1675                    1680

Arg Asn Gly Ala Leu Leu Gly Asn His Val Asn His Val Asn Ser Asp
                    1685                    1690                    1695

Arg Arg Asp Ser Leu Gln Gln Thr Asn Thr Thr His Arg Pro Leu His
            1700                    1705                    1710

Val Gln Arg Pro Ser Ile Pro Pro Ala Ser Asp Thr Glu Lys Pro Leu
        1715                    1720                    1725

Phe Pro Pro Ala Gly Asn Ser Val Cys His Asn His Asn His Asn
    1730                    1735                    1740

Ser Ile Gly Lys Gln Val Pro Thr Ser Thr Asn Ala Asn Leu Asn Asn
1745                    1750                    1755                    1760

Ala Asn Met Ser Lys Ala Ala His Gly Lys Arg Pro Ser Ile Gly Asn
                1765                    1770                    1775

Leu Glu His Val Ser Glu Asn Gly His His Ser Ser His Lys His Asp
            1780                    1785                    1790

Arg Glu Pro Gln Arg Arg Ser Ser Val Lys Arg Thr Arg Tyr Tyr Glu
        1795                    1800                    1805

Thr Tyr Ile Arg Ser Asp Ser Gly Asp Glu Gln Leu Pro Thr Ile Cys
    1810                    1815                    1820

Arg Glu Asp Pro Glu Ile His Gly Tyr Phe Arg Asp Pro His Cys Leu
1825                    1830                    1835                    1840

Gly Glu Gln Glu Tyr Phe Ser Ser Glu Glu Cys Tyr Glu Asp Asp Ser
                    1845                    1850                    1855

Ser Pro Thr Trp Ser Arg Gln Asn Tyr Gly Tyr Tyr Ser Arg Tyr Pro
            1860                    1865                    1870

Gly Arg Asn Ile Asp Ser Glu Arg Pro Arg Gly Tyr His His Pro Gln
        1875                    1880                    1885

Gly Phe Leu Glu Asp Asp Asp Ser Pro Val Cys Tyr Asp Ser Arg Arg
    1890                    1895                    1900

Ser Pro Arg Arg Arg Leu Leu Pro Pro Thr Pro Ala Ser His Arg Arg
1905                    1910                    1915                    1920

Ser Ser Phe Asn Phe Glu Cys Leu Arg Arg Gln Ser Ser Gln Glu Glu
                1925                    1930                    1935

Val Pro Ser Ser Pro Ile Phe Pro His Arg Thr Ala Leu Pro Leu His
            1940                    1945                    1950

| Leu | Met | Gln | Gln | Gln | Ile | Met | Ala | Val | Ala | Gly | Leu | Asp | Ser | Ser | Lys |
|---|---|---|---|---|---|---|---|---|---|---|---|---|---|---|---|
| | | 1955 | | | | 1960 | | | | 1965 | | | | | |

| Ala | Gln | Lys | Tyr | Ser | Pro | Ser | His | Ser | Thr | Arg | Ser | Trp | Ala | Thr | Pro |
|---|---|---|---|---|---|---|---|---|---|---|---|---|---|---|---|
| 1970 | | | | | 1975 | | | | | 1980 | | | | | |

| Pro | Ala | Thr | Pro | Pro | Tyr | Arg | Asp | Trp | Thr | Pro | Cys | Tyr | Thr | Pro | Leu |
|---|---|---|---|---|---|---|---|---|---|---|---|---|---|---|---|
| 1985 | | | | | 1990 | | | | | 1995 | | | | | 2000 |

| Ile | Gln | Val | Glu | Gln | Ser | Glu | Ala | Leu | Asp | Gln | Val | Asn | Gly | Ser | Leu |
|---|---|---|---|---|---|---|---|---|---|---|---|---|---|---|---|
| | | | | 2005 | | | | | 2010 | | | | | 2015 | |

| Pro | Ser | Leu | His | Arg | Ser | Ser | Trp | Tyr | Thr | Asp | Glu | Pro | Asp | Ile | Ser |
|---|---|---|---|---|---|---|---|---|---|---|---|---|---|---|---|
| | | | | 2020 | | | | | 2025 | | | | | 2030 | |

| Tyr | Arg | Thr | Phe | Thr | Pro | Ala | Ser | Leu | Thr | Val | Pro | Ser | Ser | Phe | Arg |
|---|---|---|---|---|---|---|---|---|---|---|---|---|---|---|---|
| | | 2035 | | | | | 2040 | | | | | 2045 | | | |

| Asn | Lys | Asn | Ser | Asp | Lys | Gln | Arg | Ser | Ala | Asp | Ser | Leu | Val | Glu | Ala |
|---|---|---|---|---|---|---|---|---|---|---|---|---|---|---|---|
| 2050 | | | | | 2055 | | | | | 2060 | | | | | |

| Val | Leu | Ile | Ser | Glu | Gly | Leu | Gly | Arg | Tyr | Ala | Arg | Asp | Pro | Lys | Phe |
|---|---|---|---|---|---|---|---|---|---|---|---|---|---|---|---|
| 2065 | | | | | 2070 | | | | | 2075 | | | | | 2080 |

| Val | Ser | Ala | Thr | Lys | His | Glu | Ile | Ala | Asp | Ala | Cys | Asp | Leu | Thr | Ile |
|---|---|---|---|---|---|---|---|---|---|---|---|---|---|---|---|
| | | | | 2085 | | | | | 2090 | | | | | 2095 | |

| Asp | Glu | Met | Glu | Ser | Ala | Ala | Ser | Thr | Leu | Leu | Asn | Gly | Asn | Val | Arg |
|---|---|---|---|---|---|---|---|---|---|---|---|---|---|---|---|
| | | | 2100 | | | | | 2105 | | | | | 2110 | | |

| Pro | Arg | Ala | Asn | Gly | Asp | Val | Gly | Pro | Leu | Ser | His | Arg | Gln | Asp | Tyr |
|---|---|---|---|---|---|---|---|---|---|---|---|---|---|---|---|
| | | 2115 | | | | | 2120 | | | | | 2125 | | | |

| Glu | Leu | Gln | Asp | Phe | Gly | Pro | Gly | Tyr | Ser | Asp | Glu | Glu | Pro | Asp | Pro |
|---|---|---|---|---|---|---|---|---|---|---|---|---|---|---|---|
| 2130 | | | | | 2135 | | | | | 2140 | | | | | |

| Gly | Arg | Asp | Glu | Glu | Asp | Leu | Ala | Asp | Glu | Met | Ile | Cys | Ile | Thr | Thr |
|---|---|---|---|---|---|---|---|---|---|---|---|---|---|---|---|
| 2145 | | | | | 2150 | | | | | 2155 | | | | | 2160 |

Leu ( 2 ) INFORMATION FOR SEQ ID NO:50:

( i ) SEQUENCE CHARACTERISTICS:
        ( A ) LENGTH: 34 amino acids
        ( B ) TYPE: amino acid
        ( C ) STRANDEDNESS: single
        ( D ) TOPOLOGY: linear ( i i ) MOLECULE TYPE: protein ( v ) FRAGMENT TYPE: internal ( x i ) SEQUENCE DESCRIPTION: SEQ ID NO:50:

| Val | Asn | Asp | Ala | Ile | Gly | Trp | Glu | Trp | Pro | Trp | Val | Tyr | Phe | Val | Ser |
|---|---|---|---|---|---|---|---|---|---|---|---|---|---|---|---|
| 1 | | | | 5 | | | | | 10 | | | | | 15 | |

| Leu | Ile | Ile | Leu | Gly | Ser | Phe | Phe | Val | Leu | Asn | Leu | Val | Leu | Gly | Val |
|---|---|---|---|---|---|---|---|---|---|---|---|---|---|---|---|
| | | | 20 | | | | | 25 | | | | | 30 | | |

Leu Ser ( 2 ) INFORMATION FOR SEQ ID NO:51:

( i ) SEQUENCE CHARACTERISTICS:
        ( A ) LENGTH: 2161 amino acids
        ( B ) TYPE: amino acid
        ( C ) STRANDEDNESS: single
        ( D ) TOPOLOGY: linear ( i i ) MOLECULE TYPE: protein ( v ) FRAGMENT TYPE: internal ( x i ) SEQUENCE DESCRIPTION: SEQ ID NO:51:

| | | | | | | | | | | | | | | |
|---|---|---|---|---|---|---|---|---|---|---|---|---|---|---|
| Met 1 | Met | Met | Met | Met 5 | Met | Met | Lys | Lys | Met 10 | Gln | His | Gln | Arg | Gln 15 |
| Gln | Ala | Asp | His 20 | Ala | Asn | Glu | Ala | Asn 25 | Tyr | Ala | Arg | Gly | Thr 30 | Arg | Leu |
| Pro | Leu | Ser 35 | Gly | Glu | Gly | Pro | Thr 40 | Ser | Gln | Pro | Asn | Ser 45 | Ser | Lys | Gln |
| Thr | Val 50 | Leu | Ser | Trp | Gln | Ala 55 | Ala | Ile | Asp | Ala | Ala 60 | Arg | Gln | Ala | Lys |
| Ala 65 | Ala | Gln | Thr | Met | Ser 70 | Thr | Ser | Ala | Pro | Pro 75 | Pro | Val | Gly | Ser | Leu 80 |
| Ser | Gln | Arg | Lys | Arg 85 | Gln | Gln | Tyr | Ala | Lys 90 | Ser | Lys | Lys | Gln | Gly 95 | Asn |
| Ser | Ser | Asn | Ser 100 | Arg | Pro | Ala | Arg | Ala 105 | Leu | Phe | Cys | Leu | Ser 110 | Leu | Asn |
| Asn | Pro | Ile 115 | Arg | Arg | Ala | Cys | Ile 120 | Ser | Ile | Val | Glu | Trp 125 | Lys | Pro | Phe |
| Asp | Ile 130 | Phe | Ile | Leu | Leu | Ala 135 | Ile | Phe | Ala | Asn | Cys 140 | Val | Ala | Leu | Ala |
| Ile 145 | Tyr | Ile | Pro | Phe | Pro 150 | Glu | Asp | Asp | Ser | Asn 155 | Ser | Thr | Asn | His | Asn 160 |
| Leu | Glu | Lys | Val | Glu 165 | Tyr | Ala | Phe | Leu | Ile 170 | Ile | Phe | Thr | Val | Glu 175 | Thr |
| Phe | Leu | Lys | Ile 180 | Ile | Ala | Tyr | Gly | Leu 185 | Leu | Leu | His | Pro | Asn 190 | Ala | Tyr |
| Val | Arg | Asn 195 | Gly | Trp | Asn | Leu | Leu 200 | Asp | Phe | Val | Ile | Val 205 | Ile | Val | Gly |
| Leu | Phe 210 | Ser | Val | Ile | Leu | Glu 215 | Gln | Leu | Thr | Lys | Glu 220 | Thr | Glu | Gly | Gly |
| Asn 225 | His | Ser | Ser | Gly | Lys 230 | Ser | Gly | Gly | Phe | Asp 235 | Val | Lys | Ala | Leu | Arg 240 |
| Ala | Phe | Arg | Val | Leu 245 | Arg | Pro | Leu | Arg | Leu 250 | Val | Ser | Gly | Val | Pro 255 | Ser |
| Leu | Gln | Val | Val 260 | Leu | Asn | Ser | Ile | Ile 265 | Lys | Ala | Met | Val | Pro 270 | Leu | Leu |
| His | Ile | Ala 275 | Leu | Leu | Val | Leu | Phe 280 | Val | Ile | Ile | Ile | Tyr 285 | Ala | Ile | Ile |
| Gly | Leu 290 | Glu | Leu | Phe | Ile | Gly 295 | Lys | Met | His | Lys | Thr 300 | Cys | Phe | Phe | Ala |
| Asp 305 | Ser | Asp | Ile | Val | Ala 310 | Glu | Glu | Asp | Pro | Ala 315 | Pro | Cys | Ala | Phe | Ser 320 |
| Gly | Asn | Gly | Arg | Gln 325 | Cys | Thr | Ala | Asn | Gly 330 | Thr | Glu | Cys | Arg | Ser 335 | Gly |
| Trp | Val | Gly | Pro 340 | Asn | Gly | Gly | Ile | Thr 345 | Asn | Phe | Asp | Asn | Phe 350 | Ala | Phe |
| Ala | Met | Leu 355 | Thr | Val | Phe | Gln | Cys 360 | Ile | Thr | Met | Glu | Gly 365 | Trp | Thr | Asp |
| Val | Leu | Tyr 370 | Trp | Val | Asn | Asp | Ala 375 | Ile | Gly | Trp | Glu | Trp 380 | Pro | Trp | Val |
| Tyr 385 | Phe | Val | Ser | Leu | Ile 390 | Ile | Leu | Gly | Ser | Phe 395 | Phe | Val | Leu | Asn | Leu 400 |
| Val | Leu | Gly | Val | Leu 405 | Ser | Gly | Glu | Phe | Ser 410 | Lys | Glu | Arg | Glu | Lys 415 | Ala |
| Lys | Ala | Arg | Gly 420 | Asp | Phe | Gln | Lys | Leu 425 | Arg | Glu | Lys | Gln | Gln 430 | Leu | Glu |

-continued

| | | | | | | | | | | | | | |
|---|---|---|---|---|---|---|---|---|---|---|---|---|---|
| Glu | Asp | Leu 435 | Lys | Gly | Tyr | Leu | Asp 440 | Trp | Ile | Thr | Gln | Ala 445 | Glu | Asp | Ile |
| Asp | Pro 450 | Glu | Asn | Glu | Glu | Glu 455 | Gly | Gly | Glu | Gly 460 | Lys | Arg | Asn | Thr |
| Ser 465 | Met | Pro | Thr | Ser | Glu 470 | Thr | Glu | Ser | Val | Asn 475 | Thr | Glu | Asn | Val | Ser 480 |
| Gly | Glu | Gly | Glu | Asn 485 | Arg | Gly | Cys | Cys 490 | Gly | Ser | Leu | Cys | Gln | Ala 495 | Ile |
| Ser | Lys | Ser | Lys 500 | Leu | Ser | Arg | Arg | Trp 505 | Arg | Arg | Trp | Asn | Arg 510 | Phe | Asn |
| Arg | Arg | Arg 515 | Cys | Arg | Ala | Ala | Val 520 | Lys | Ser | Val | Thr | Phe 525 | Tyr | Trp | Leu |
| Val | Ile 530 | Val | Leu | Val | Phe | Leu 535 | Asn | Thr | Leu | Thr | Ile 540 | Ser | Ser | Glu | His |
| Tyr 545 | Asn | Gln | Pro | Asp | Trp 550 | Leu | Thr | Gln | Ile | Gln 555 | Asp | Ile | Ala | Asn | Lys 560 |
| Val | Leu | Leu | Ala | Leu 565 | Phe | Thr | Cys | Glu | Met 570 | Leu | Val | Lys | Met | Tyr 575 | Ser |
| Leu | Gly | Leu | Gln 580 | Ala | Tyr | Phe | Val | Ser 585 | Leu | Phe | Asn | Arg | Phe 590 | Asp | Cys |
| Phe | Val | Val 595 | Cys | Gly | Gly | Ile | Thr 600 | Glu | Thr | Ile | Leu | Val 605 | Glu | Leu | Glu |
| Ile | Met 610 | Ser | Pro | Leu | Gly | Ile 615 | Ser | Val | Phe | Arg | Cys 620 | Val | Arg | Leu | Leu |
| Arg 625 | Ile | Phe | Lys | Val | Thr 630 | Arg | His | Trp | Thr | Ser 635 | Leu | Ser | Asn | Leu | Val 640 |
| Ala | Ser | Leu | Leu | Asn 645 | Ser | Met | Lys | Ser | Ile 650 | Ala | Ser | Leu | Leu | Leu 655 | Leu |
| Leu | Phe | Leu | Phe 660 | Ile | Ile | Ile | Phe | Ser 665 | Leu | Leu | Gly | Met | Gln 670 | Leu | Phe |
| Gly | Gly | Lys 675 | Phe | Asn | Phe | Asp | Glu 680 | Thr | Gln | Thr | Lys | Arg 685 | Ser | Thr | Phe |
| Asp | Asn 690 | Phe | Pro | Gln | Ala | Leu 695 | Leu | Thr | Val | Phe | Gln 700 | Ile | Leu | Thr | Gly |
| Glu 705 | Asp | Trp | Asn | Ala | Val 710 | Met | Tyr | Asp | Gly | Ile 715 | Met | Ala | Tyr | Gly | Gly 720 |
| Pro | Ser | Ser | Ser | Gly 725 | Met | Ile | Val | Cys | Ile 730 | Tyr | Phe | Ile | Ile | Leu 735 | Phe |
| Ile | Cys | Gly | Asn 740 | Tyr | Ile | Leu | Leu | Asn 745 | Val | Phe | Leu | Ala | Ile 750 | Ala | Val |
| Asp | Asn | Leu 755 | Ala | Asp | Ala | Glu | Ser 760 | Leu | Asn | Thr | Ala | Gln 765 | Lys | Glu | Glu |
| Ala | Glu 770 | Glu | Lys | Glu | Arg | Lys 775 | Lys | Ile | Ala | Arg | Lys 780 | Glu | Ser | Leu | Glu |
| Asn 785 | Lys | Lys | Asn | Asn 790 | Lys | Pro | Glu | Val | Asn 795 | Gln | Ile | Ala | Asn | Ser 800 | Asp |
| Asn | Lys | Val | Thr 805 | Ile | Asp | Asp | Tyr | Arg 810 | Glu | Glu | Asp | Glu | Asp 815 | Lys | Asp |
| Pro | Tyr | Pro | Pro 820 | Cys | Asp | Val | Pro | Val 825 | Gly | Glu | Glu | Glu | Glu 830 | Glu | Glu |
| Glu | Glu | Asp 835 | Glu | Pro | Glu | Val | Pro 840 | Ala | Gly | Pro | Arg | Pro 845 | Arg | Arg | Ile |
| Ser | Glu | Leu | Asn | Met | Lys | Glu | Lys | Ile | Ala | Pro | Ile | Pro | Glu | Gly | Ser |

-continued

```
             850                      855                      860
Ala   Phe   Phe   Ile   Leu   Ser   Lys   Thr   Asn   Pro   Ile   Arg   Val   Gly   Cys   His
865                     870                     875                                       880
Lys   Leu   Ile   Asn   His   Ile   Phe   Thr   Asn   Leu   Ile   Leu   Val   Phe   Ile
                        885                     890                             895
Met   Leu   Ser   Ser   Ala   Ala   Leu   Ala   Ala   Glu   Asp   Pro   Ile   Arg   Ser   His
                  900                     905                           910
Ser   Phe   Arg   Asn   Thr   Ile   Leu   Gly   Tyr   Phe   Asp   Tyr   Ala   Phe   Thr   Ala
            915                     920                           925
Ile   Phe   Thr   Val   Glu   Ile   Leu   Leu   Lys   Met   Thr   Thr   Phe   Gly   Ala   Phe
      930                     935                           940
Leu   His   Lys   Gly   Ala   Phe   Cys   Arg   Asn   Tyr   Phe   Asn   Leu   Leu   Asp   Met
945                     950                           955                                 960
Leu   Val   Val   Gly   Val   Ser   Leu   Val   Ser   Phe   Gly   Ile   Gln   Ser   Ser   Ala
                  965                           970                           975
Ile   Ser   Val   Val   Lys   Ile   Leu   Arg   Val   Leu   Arg   Val   Leu   Arg   Pro   Leu
                  980                           985                     990
Arg   Ala   Ile   Asn   Arg   Ala   Lys   Gly   Leu   Lys   His   Val   Val   Gln   Cys   Val
            995                     1000                          1005
Phe   Val   Ala   Ile   Arg   Thr   Ile   Gly   Asn   Ile   Met   Ile   Val   Thr   Thr   Leu
      1010                    1015                          1020
Leu   Gln   Phe   Met   Phe   Ala   Cys   Ile   Gly   Val   Gln   Leu   Phe   Lys   Gly   Lys
1025                    1030                          1035                                1040
Phe   Tyr   Arg   Cys   Thr   Asp   Glu   Ala   Lys   Ser   Asn   Pro   Glu   Glu   Cys   Arg
                  1045                          1050                          1055
Gly   Leu   Phe   Ile   Leu   Tyr   Lys   Asp   Gly   Asp   Val   Asp   Ser   Pro   Val   Val
                  1060                          1065                    1070
Arg   Glu   Arg   Ile   Trp   Gln   Asn   Ser   Asp   Phe   Asn   Phe   Asp   Asn   Val   Leu
            1075                    1080                          1085
Ser   Ala   Met   Met   Ala   Leu   Phe   Thr   Val   Ser   Thr   Phe   Glu   Gly   Trp   Pro
            1090                    1095                          1100
Ala   Leu   Leu   Tyr   Lys   Ala   Ile   Asp   Ser   Asn   Gly   Glu   Asn   Ile   Gly   Pro
1105                          1110                    1115                          1120
Ile   Tyr   Asn   His   Arg   Val   Glu   Ile   Ser   Ile   Phe   Phe   Ile   Ile   Tyr   Ile
                  1125                          1130                          1135
Ile   Ile   Val   Ala   Phe   Phe   Met   Met   Asn   Ile   Phe   Val   Gly   Phe   Val   Ile
            1140                          1145                    1150
Val   Thr   Phe   Gln   Glu   Gln   Gly   Glu   Lys   Glu   Tyr   Lys   Asn   Cys   Glu   Leu
      1155                          1160                    1165
Asp   Lys   Asn   Gln   Arg   Gln   Cys   Val   Glu   Tyr   Ala   Leu   Lys   Ala   Arg   Pro
1170                          1175                    1180
Leu   Arg   Arg   Tyr   Ile   Pro   Lys   Asn   Pro   Tyr   Gln   Tyr   Lys   Phe   Trp   Tyr
1185                          1190                    1195                                1200
Val   Val   Asn   Ser   Ser   Pro   Phe   Glu   Tyr   Met   Met   Phe   Val   Leu   Ile   Met
                  1205                          1210                          1215
Leu   Asn   Thr   Leu   Cys   Leu   Ala   Met   Gln   His   Tyr   Glu   Gln   Ser   Lys   Met
                  1220                          1225                    1230
Phe   Asn   Asp   Ala   Met   Asp   Ile   Leu   Asn   Met   Val   Phe   Thr   Gly   Val   Phe
            1235                          1240                    1245
Thr   Val   Glu   Met   Val   Leu   Lys   Val   Ile   Ala   Phe   Lys   Pro   Lys   Gly   Tyr
      1250                          1255                    1260
Phe   Ser   Asp   Ala   Trp   Asn   Thr   Phe   Asp   Ser   Leu   Ile   Val   Ile   Gly   Ser
1265                          1270                    1275                                1280
```

| | | | | | | | | | | | | | |
|---|---|---|---|---|---|---|---|---|---|---|---|---|---|
| Ile | Ile | Asp | Val | Ala | Leu | Ser | Glu | Ala | Asp | Pro | Thr | Glu | Ser | Glu | Asn |
| | | | | 1285 | | | | 1290 | | | | 1295 | |
| Val | Pro | Val | Pro | Thr | Ala | Thr | Pro | Gly | Asn | Ser | Glu | Glu | Ser | Asn | Arg |
| | | | 1300 | | | | 1305 | | | | 1310 | | |
| Ile | Ser | Ile | Thr | Phe | Phe | Arg | Leu | Phe | Arg | Val | Met | Arg | Leu | Val | Lys |
| | | 1315 | | | | 1320 | | | | 1325 | | | |
| Leu | Leu | Ser | Arg | Gly | Glu | Gly | Ile | Arg | Thr | Leu | Leu | Trp | Thr | Phe | Ile |
| 1330 | | | | | 1335 | | | | 1340 | | | | |
| Lys | Phe | Phe | Gln | Ala | Leu | Pro | Tyr | Val | Ala | Leu | Leu | Ile | Ala | Met | Leu |
| 1345 | | | | | 1350 | | | | 1355 | | | | 1360 |
| Phe | Phe | Ile | Tyr | Ala | Val | Ile | Gly | Met | Gln | Met | Phe | Gly | Lys | Val | Ala |
| | | | 1365 | | | | 1370 | | | | 1375 | | |
| Met | Arg | Asp | Asn | Asn | Gln | Ile | Asn | Arg | Asn | Asn | Asn | Phe | Gln | Thr | Phe |
| | | | 1380 | | | | 1385 | | | | 1390 | | |
| Pro | Gln | Ala | Val | Leu | Leu | Leu | Phe | Arg | Cys | Ala | Thr | Gly | Glu | Ala | Trp |
| | | 1395 | | | | 1400 | | | | 1405 | | | |
| Gln | Glu | Ile | Met | Leu | Ala | Cys | Leu | Pro | Gly | Lys | Leu | Cys | Asp | Pro | Glu |
| | | 1410 | | | | 1415 | | | | 1420 | | | |
| Ser | Asp | Tyr | Asn | Pro | Gly | Glu | Glu | His | Thr | Cys | Gly | Ser | Asn | Phe | Ala |
| 1425 | | | | | 1430 | | | | 1435 | | | | 1440 |
| Ile | Val | Tyr | Phe | Ile | Ser | Phe | Tyr | Met | Leu | Cys | Ala | Phe | Leu | Ile | Ile |
| | | | 1445 | | | | 1450 | | | | 1455 | | |
| Asn | Leu | Phe | Val | Ala | Val | Ile | Met | Asp | Asn | Phe | Asp | Tyr | Leu | Thr | Arg |
| | | | 1460 | | | | 1465 | | | | 1470 | | |
| Asp | Trp | Ser | Ile | Leu | Gly | Pro | His | His | Leu | Asp | Glu | Phe | Lys | Arg | Ile |
| | | | 1475 | | | | 1480 | | | | 1485 | | |
| Trp | Ser | Glu | Tyr | Asp | Pro | Glu | Ala | Lys | Gly | Arg | Ile | Lys | His | Leu | Asp |
| | | | 1490 | | | | 1495 | | | | 1500 | | |
| Val | Val | Thr | Leu | Leu | Arg | Arg | Ile | Gln | Pro | Pro | Leu | Gly | Phe | Gly | Lys |
| 1505 | | | | | 1510 | | | | 1515 | | | | 1520 |
| Leu | Cys | Pro | His | Arg | Val | Ala | Cys | Lys | Arg | Leu | Val | Ala | Met | Asn | Met |
| | | | 1525 | | | | 1530 | | | | 1535 | | |
| Pro | Leu | Asn | Ser | Asp | Gly | Thr | Val | Met | Phe | Asn | Ala | Thr | Leu | Phe | Ala |
| | | | 1540 | | | | 1545 | | | | 1550 | | |
| Leu | Val | Arg | Thr | Ala | Leu | Lys | Ile | Lys | Thr | Glu | Gly | Asn | Leu | Glu | Gln |
| | | | 1555 | | | | 1560 | | | | 1565 | | |
| Ala | Asn | Glu | Glu | Leu | Arg | Ala | Val | Ile | Lys | Lys | Ile | Trp | Lys | Lys | Thr |
| | 1570 | | | | 1575 | | | | 1580 | | | | |
| Ser | Met | Lys | Leu | Leu | Asp | Gln | Val | Val | Pro | Pro | Ala | Gly | Asp | Asp | Glu |
| 1585 | | | | | 1590 | | | | 1595 | | | | 1600 |
| Val | Thr | Val | Gly | Lys | Phe | Tyr | Ala | Thr | Phe | Leu | Ile | Gln | Asp | Tyr | Phe |
| | | | 1605 | | | | 1610 | | | | 1615 | | |
| Arg | Lys | Phe | Lys | Lys | Arg | Lys | Glu | Gln | Gly | Leu | Val | Gly | Lys | Tyr | Pro |
| | | | 1620 | | | | 1625 | | | | 1630 | | |
| Ala | Lys | Asn | Thr | Thr | Ile | Ala | Leu | Gln | Ala | Gly | Leu | Arg | Thr | Leu | His |
| | | | 1635 | | | | 1640 | | | | 1645 | | |
| Asp | Ile | Gly | Pro | Glu | Ile | Arg | Arg | Ala | Ile | Ser | Cys | Asp | Leu | Gln | Asp |
| 1650 | | | | | 1655 | | | | 1660 | | | | |
| Asp | Glu | Pro | Glu | Glu | Thr | Lys | Arg | Glu | Glu | Glu | Asp | Asp | Val | Phe | Lys |
| 1665 | | | | | 1670 | | | | 1675 | | | | 1680 |
| Arg | Asn | Gly | Ala | Leu | Leu | Gly | Asn | His | Val | Asn | His | Val | Asn | Ser | Asp |
| | | | | 1685 | | | | 1690 | | | | 1695 | |
| Arg | Arg | Asp | Ser | Leu | Gln | Gln | Thr | Asn | Thr | Thr | His | Arg | Pro | Leu | His |
| | | | 1700 | | | | 1705 | | | | 1710 | | |

| | | | | | | | | | | | | | |
|---|---|---|---|---|---|---|---|---|---|---|---|---|---|
| Val | Gln | Arg | Pro | Ser | Ile | Pro | Pro | Ala | Ser | Asp | Thr | Glu | Lys | Pro | Leu |
| | 1715 | | | | | 1720 | | | | | 1725 | | | |
| Phe | Pro | Pro | Ala | Gly | Asn | Ser | Val | Cys | His | Asn | His | His | Asn | His | Asn |
| | 1730 | | | | | 1735 | | | | | 1740 | | | |
| Ser | Ile | Gly | Lys | Gln | Val | Pro | Thr | Ser | Thr | Asn | Ala | Asn | Leu | Asn | Asn |
| 1745 | | | | | 1750 | | | | | 1755 | | | | | 1760 |
| Ala | Asn | Met | Ser | Lys | Ala | Ala | His | Gly | Lys | Arg | Pro | Ser | Ile | Gly | Asn |
| | | 1765 | | | | | 1770 | | | | | 1775 | | |
| Leu | Glu | His | Val | Ser | Glu | Asn | Gly | His | His | Ser | Ser | His | Lys | His | Asp |
| | | | 1780 | | | | | 1785 | | | | | 1790 | | |
| Arg | Glu | Pro | Gln | Arg | Arg | Ser | Ser | Val | Lys | Arg | Thr | Arg | Tyr | Tyr | Glu |
| | | 1795 | | | | | 1800 | | | | | 1805 | | |
| Thr | Tyr | Ile | Arg | Ser | Asp | Ser | Gly | Asp | Glu | Gln | Leu | Pro | Thr | Ile | Cys |
| | | 1810 | | | | | 1815 | | | | | 1820 | | |
| Arg | Glu | Asp | Pro | Glu | Ile | His | Gly | Tyr | Phe | Arg | Asp | Pro | His | Cys | Leu |
| 1825 | | | | | 1830 | | | | | 1835 | | | | | 1840 |
| Gly | Glu | Gln | Glu | Tyr | Phe | Ser | Ser | Glu | Glu | Cys | Tyr | Glu | Asp | Asp | Ser |
| | | | 1845 | | | | | 1850 | | | | | 1855 | | |
| Ser | Pro | Thr | Trp | Ser | Arg | Gln | Asn | Tyr | Gly | Tyr | Tyr | Ser | Arg | Tyr | Pro |
| | | | 1860 | | | | | 1865 | | | | | 1870 | | |
| Gly | Arg | Asn | Ile | Asp | Ser | Glu | Arg | Pro | Arg | Gly | Tyr | His | His | Pro | Gln |
| | | 1875 | | | | | 1880 | | | | | 1885 | | |
| Gly | Phe | Leu | Glu | Asp | Asp | Asp | Ser | Pro | Val | Cys | Tyr | Asp | Ser | Arg | Arg |
| | 1890 | | | | | 1895 | | | | | 1900 | | | | |
| Ser | Pro | Arg | Arg | Arg | Leu | Leu | Pro | Pro | Thr | Pro | Ala | Ser | His | Arg | Arg |
| 1905 | | | | | 1910 | | | | | 1915 | | | | | 1920 |
| Ser | Ser | Phe | Asn | Phe | Glu | Cys | Leu | Arg | Arg | Gln | Ser | Ser | Gln | Glu | Glu |
| | | | 1925 | | | | | 1930 | | | | | 1935 | | |
| Val | Pro | Ser | Ser | Pro | Ile | Phe | Pro | His | Arg | Thr | Ala | Leu | Pro | Leu | His |
| | | | 1940 | | | | | 1945 | | | | | 1950 | | |
| Leu | Met | Gln | Gln | Gln | Ile | Met | Ala | Val | Ala | Gly | Leu | Asp | Ser | Ser | Lys |
| | | 1955 | | | | | 1960 | | | | | 1965 | | |
| Ala | Gln | Lys | Tyr | Ser | Pro | Ser | His | Ser | Thr | Arg | Ser | Trp | Ala | Thr | Pro |
| | 1970 | | | | | 1975 | | | | | 1980 | | | | |
| Pro | Ala | Thr | Pro | Pro | Tyr | Arg | Asp | Trp | Thr | Pro | Cys | Tyr | Thr | Pro | Leu |
| 1985 | | | | | 1990 | | | | | 1995 | | | | | 2000 |
| Ile | Gln | Val | Glu | Gln | Ser | Glu | Ala | Leu | Asp | Gln | Val | Asn | Gly | Ser | Leu |
| | | | 2005 | | | | | 2010 | | | | | 2015 | | |
| Pro | Ser | Leu | His | Arg | Ser | Ser | Trp | Tyr | Thr | Asp | Glu | Pro | Asp | Ile | Ser |
| | | | 2020 | | | | | 2025 | | | | | 2030 | | |
| Tyr | Arg | Thr | Phe | Thr | Pro | Ala | Ser | Leu | Thr | Val | Pro | Ser | Ser | Phe | Arg |
| | | 2035 | | | | | 2040 | | | | | 2045 | | |
| Asn | Lys | Asn | Ser | Asp | Lys | Gln | Arg | Ser | Ala | Asp | Ser | Leu | Val | Glu | Ala |
| | 2050 | | | | | 2055 | | | | | 2060 | | | | |
| Val | Leu | Ile | Ser | Glu | Gly | Leu | Gly | Arg | Tyr | Ala | Arg | Asp | Pro | Lys | Phe |
| 2065 | | | | | 2070 | | | | | 2075 | | | | | 2080 |
| Val | Ser | Ala | Thr | Lys | His | Glu | Ile | Ala | Asp | Ala | Cys | Asp | Leu | Thr | Ile |
| | | | 2085 | | | | | 2090 | | | | | 2095 | | |
| Asp | Glu | Met | Glu | Ser | Ala | Ala | Ser | Thr | Leu | Leu | Asn | Gly | Asn | Val | Arg |
| | | | 2100 | | | | | 2105 | | | | | 2110 | | |
| Pro | Arg | Ala | Asn | Gly | Asp | Val | Gly | Pro | Leu | Ser | His | Arg | Gln | Asp | Tyr |
| | | 2115 | | | | | 2120 | | | | | 2125 | | |
| Glu | Leu | Gln | Asp | Phe | Gly | Pro | Gly | Tyr | Ser | Asp | Glu | Glu | Pro | Asp | Pro |

|  |  |  |  | 2130 |  |  |  |  | 2135 |  |  |  |  | 2140 |
|---|---|---|---|---|---|---|---|---|---|---|---|---|---|---|
| Gly | Arg | Asp | Glu | Glu | Asp | Leu | Ala | Asp | Glu | Met | Ile | Cys | Ile | Thr | Thr |
| 2145 |  |  |  |  | 2150 |  |  |  |  | 2155 |  |  |  |  | 2160 |
| Leu |

( 2 ) INFORMATION FOR SEQ ID NO:52:

( i ) SEQUENCE CHARACTERISTICS:
        ( A ) LENGTH: 1091 amino acids
        ( B ) TYPE: amino acid
        ( C ) STRANDEDNESS: single
        ( D ) TOPOLOGY: linear ( i i ) MOLECULE TYPE: protein ( v ) FRAGMENT TYPE: internal ( x i ) SEQUENCE DESCRIPTION: SEQ ID NO:52:

| Met | Ala | Ala | Gly | Cys | Leu | Leu | Ala | Leu | Thr | Leu | Thr | Leu | Phe | Gln | Ser |
|---|---|---|---|---|---|---|---|---|---|---|---|---|---|---|---|
| 1 |  |  |  | 5 |  |  |  |  | 10 |  |  |  |  | 15 |  |
| Leu | Leu | Ile | Gly | Pro | Ser | Ser | Glu | Glu | Pro | Phe | Pro | Ser | Ala | Val | Thr |
|  |  |  | 20 |  |  |  |  | 25 |  |  |  |  | 30 |  |  |
| Ile | Lys | Ser | Trp | Val | Asp | Lys | Met | Gln | Glu | Asp | Leu | Val | Thr | Leu | Ala |
|  |  | 35 |  |  |  |  | 40 |  |  |  |  | 45 |  |  |  |
| Lys | Thr | Ala | Ser | Gly | Val | Asn | Gln | Leu | Val | Asp | Ile | Tyr | Glu | Lys | Tyr |
|  | 50 |  |  |  |  | 55 |  |  |  |  | 60 |  |  |  |  |
| Gln | Asp | Leu | Tyr | Thr | Val | Glu | Pro | Asn | Asn | Ala | Arg | Gln | Leu | Val | Glu |
| 65 |  |  |  |  | 70 |  |  |  |  | 75 |  |  |  |  | 80 |
| Ile | Ala | Ala | Arg | Asp | Ile | Glu | Lys | Leu | Leu | Ser | Asn | Arg | Ser | Lys | Ala |
|  |  |  |  | 85 |  |  |  |  | 90 |  |  |  |  | 95 |  |
| Leu | Val | Ser | Leu | Ala | Leu | Glu | Ala | Glu | Lys | Val | Gln | Ala | Ala | His | Gln |
|  |  |  | 100 |  |  |  |  | 105 |  |  |  |  | 110 |  |  |
| Trp | Arg | Glu | Asp | Phe | Ala | Ser | Asn | Glu | Val | Val | Tyr | Tyr | Asn | Ala | Lys |
|  |  | 115 |  |  |  |  | 120 |  |  |  |  | 125 |  |  |  |
| Asp | Asp | Leu | Asp | Pro | Glu | Lys | Asn | Asp | Ser | Glu | Pro | Gly | Ser | Gln | Arg |
| 130 |  |  |  |  | 135 |  |  |  |  | 140 |  |  |  |  |  |
| Ile | Lys | Pro | Val | Phe | Ile | Glu | Asp | Ala | Asn | Phe | Gly | Arg | Gln | Ile | Ser |
| 145 |  |  |  |  | 150 |  |  |  |  | 155 |  |  |  |  | 160 |
| Tyr | Gln | His | Ala | Ala | Val | His | Ile | Pro | Thr | Asp | Ile | Tyr | Glu | Gly | Ser |
|  |  |  |  | 165 |  |  |  |  | 170 |  |  |  |  | 175 |  |
| Thr | Ile | Val | Leu | Asn | Glu | Leu | Asn | Trp | Thr | Ser | Ala | Leu | Asp | Glu | Val |
|  |  |  | 180 |  |  |  |  | 185 |  |  |  |  | 190 |  |  |
| Phe | Lys | Lys | Asn | Arg | Glu | Glu | Asp | Pro | Ser | Leu | Leu | Trp | Gln | Val | Phe |
|  |  | 195 |  |  |  |  | 200 |  |  |  |  | 205 |  |  |  |
| Gly | Ser | Ala | Thr | Gly | Leu | Ala | Arg | Tyr | Tyr | Pro | Ala | Ser | Pro | Trp | Val |
|  | 210 |  |  |  |  | 215 |  |  |  |  | 220 |  |  |  |  |
| Asp | Asn | Ser | Arg | Thr | Pro | Asn | Lys | Ile | Asp | Leu | Tyr | Asp | Val | Arg | Arg |
| 225 |  |  |  |  | 230 |  |  |  |  | 235 |  |  |  |  | 240 |
| Arg | Pro | Trp | Tyr | Ile | Gln | Gly | Ala | Ala | Ser | Pro | Lys | Asp | Met | Leu | Ile |
|  |  |  |  | 245 |  |  |  |  | 250 |  |  |  |  | 255 |  |
| Leu | Val | Asp | Val | Ser | Gly | Ser | Val | Ser | Gly | Leu | Thr | Leu | Lys | Leu | Ile |
|  |  |  | 260 |  |  |  |  | 265 |  |  |  |  | 270 |  |  |
| Arg | Thr | Ser | Val | Ser | Glu | Met | Leu | Glu | Thr | Leu | Ser | Asp | Asp | Asp | Phe |
|  |  | 275 |  |  |  |  | 280 |  |  |  |  | 285 |  |  |  |
| Val | Asn | Val | Ala | Ser | Phe | Asn | Ser | Asn | Ala | Gln | Asp | Val | Ser | Cys | Phe |
|  | 290 |  |  |  |  | 295 |  |  |  |  | 300 |  |  |  |  |
| Gln | His | Leu | Val | Gln | Ala | Asn | Val | Arg | Asn | Lys | Lys | Val | Leu | Lys | Asp |

-continued

```
                        305                                  310                                  315                                  320
Ala  Val  Asn  Asn  Ile  Thr  Ala  Lys  Gly  Ile  Thr  Asp  Tyr  Lys  Lys  Gly
                    325                          330                          335

Phe  Ser  Phe  Ala  Phe  Glu  Gln  Leu  Leu  Asn  Tyr  Asn  Val  Ser  Arg  Ala
               340                          345                          350

Asn  Cys  Asn  Lys  Ile  Ile  Met  Leu  Phe  Thr  Asp  Gly  Gly  Glu  Glu  Arg
               355                          360                     365

Ala  Gln  Glu  Ile  Phe  Asn  Lys  Tyr  Asn  Lys  Asp  Lys  Lys  Val  Arg  Val
          370                          375                     380

Phe  Arg  Phe  Ser  Val  Gly  Gln  His  Asn  Tyr  Glu  Arg  Gly  Pro  Ile  Gln
385                          390                          395                     400

Trp  Met  Ala  Cys  Glu  Asn  Lys  Gly  Tyr  Tyr  Tyr  Glu  Ile  Pro  Ser  Ile
                    405                          410                          415

Gly  Ala  Ile  Arg  Ile  Asn  Thr  Gln  Glu  Tyr  Leu  Asp  Val  Leu  Gly  Arg
                    420                          425                     430

Pro  Met  Val  Leu  Ala  Gly  Asp  Lys  Ala  Lys  Gln  Val  Gln  Trp  Thr  Asn
               435                          440                          445

Val  Tyr  Leu  Asp  Ala  Leu  Glu  Leu  Gly  Leu  Val  Ile  Thr  Gly  Thr  Leu
          450                          455                          460

Pro  Val  Phe  Asn  Ile  Thr  Gly  Gln  Phe  Glu  Asn  Lys  Thr  Asn  Leu  Lys
465                          470                          475                     480

Asn  Gln  Leu  Ile  Leu  Gly  Val  Met  Gly  Val  Asp  Val  Ser  Leu  Glu  Asp
                    485                          490                          495

Ile  Lys  Arg  Leu  Thr  Pro  Arg  Phe  Thr  Leu  Cys  Pro  Asn  Gly  Tyr  Tyr
                    500                          505                          510

Phe  Ala  Ile  Asp  Pro  Asn  Gly  Tyr  Val  Leu  Leu  His  Pro  Asn  Leu  Gln
               515                          520                          525

Pro  Lys  Asn  Pro  Lys  Ser  Gln  Glu  Pro  Val  Thr  Leu  Asp  Phe  Leu  Asp
     530                          535                          540

Ala  Glu  Leu  Glu  Asn  Asp  Ile  Lys  Val  Glu  Ile  Arg  Asn  Lys  Met  Ile
545                          550                          555                     560

Asp  Gly  Glu  Ser  Gly  Glu  Lys  Thr  Phe  Arg  Thr  Leu  Val  Lys  Ser  Gln
                    565                          570                          575

Asp  Glu  Arg  Tyr  Ile  Asp  Lys  Gly  Asn  Arg  Thr  Tyr  Thr  Trp  Thr  Pro
               580                          585                          590

Val  Asn  Gly  Thr  Asp  Tyr  Ser  Leu  Ala  Leu  Val  Leu  Pro  Thr  Tyr  Ser
               595                          600                          605

Phe  Tyr  Tyr  Ile  Lys  Ala  Lys  Leu  Glu  Glu  Thr  Ile  Thr  Gln  Ala  Arg
     610                          615                          620

Ser  Lys  Lys  Gly  Lys  Met  Lys  Asp  Ser  Glu  Thr  Leu  Lys  Pro  Asp  Asn
625                          630                          635                     640

Phe  Glu  Glu  Ser  Gly  Tyr  Thr  Phe  Ile  Ala  Pro  Arg  Asp  Tyr  Cys  Asn
                    645                          650                          655

Asp  Leu  Lys  Ile  Ser  Asp  Asn  Asn  Thr  Glu  Phe  Leu  Leu  Asn  Phe  Asn
               660                          665                          670

Glu  Phe  Ile  Asp  Arg  Lys  Thr  Pro  Asn  Asn  Pro  Ser  Cys  Asn  Ala  Asp
          675                          680                          685

Leu  Ile  Asn  Arg  Val  Leu  Leu  Asp  Ala  Gly  Phe  Thr  Asn  Glu  Leu  Val
          690                          695                          700

Gln  Asn  Tyr  Trp  Ser  Lys  Gln  Lys  Asn  Ile  Lys  Gly  Val  Lys  Ala  Arg
705                          710                          715                     720

Phe  Val  Val  Thr  Asp  Gly  Gly  Ile  Thr  Arg  Val  Tyr  Pro  Lys  Glu  Ala
                    725                          730                          735
```

```
Gly Glu Asn Trp Gln Glu Asn Pro Glu Thr Tyr Glu Asp Ser Phe Tyr
            740             745             750

Lys Arg Ser Leu Asp Asn Asp Asn Tyr Val Phe Thr Ala Pro Tyr Phe
        755             760             765

Asn Lys Ser Gly Pro Gly Ala Tyr Glu Ser Gly Ile Met Val Ser Lys
    770             775             780

Ala Val Glu Ile Tyr Ile Gln Gly Lys Leu Leu Lys Pro Ala Val Val
785             790             795             800

Gly Ile Lys Ile Asp Val Asn Ser Trp Ile Glu Asn Phe Thr Lys Thr
            805             810             815

Ser Ile Arg Asp Pro Cys Ala Gly Pro Val Cys Asp Cys Lys Arg Asn
            820             825             830

Ser Asp Val Met Asp Cys Val Ile Leu Asp Asp Gly Gly Phe Leu Leu
            835             840             845

Met Ala Asn His Asp Asp Tyr Thr Asn Gln Ile Gly Arg Phe Phe Gly
    850             855             860

Glu Ile Asp Pro Ser Leu Met Arg His Leu Val Asn Ile Ser Val Tyr
865             870             875             880

Ala Phe Asn Lys Ser Tyr Asp Tyr Gln Ser Val Cys Glu Pro Gly Ala
                885             890             895

Ala Pro Lys Gln Gly Ala Gly His Arg Ser Ala Tyr Val Pro Ser Val
            900             905             910

Ala Asp Ile Leu Gln Ile Gly Trp Trp Ala Thr Ala Ala Ala Trp Ser
            915             920             925

Ile Leu Gln Gln Phe Leu Leu Ser Leu Thr Phe Pro Arg Leu Leu Glu
            930             935             940

Ala Val Glu Met Glu Asp Asp Asp Phe Thr Ala Ser Leu Ser Lys Gln
945             950             955             960

Ser Cys Ile Thr Glu Gln Thr Gln Tyr Phe Phe Asp Asn Asp Ser Lys
                965             970             975

Ser Phe Ser Gly Val Leu Asp Cys Gly Asn Cys Ser Arg Ile Phe His
            980             985             990

Gly Glu Lys Leu Met Asn Thr Asn Leu Ile Phe Ile Met Val Glu Ser
        995             1000            1005

Lys Gly Thr Cys Pro Cys Asp Thr Arg Leu Leu Ile Gln Ala Glu Gln
    1010            1015            1020

Thr Ser Asp Gly Pro Asn Pro Cys Asp Met Val Lys Gln Pro Arg Tyr
1025            1030            1035            1040

Arg Lys Gly Pro Asp Val Cys Phe Asp Asn Asn Val Leu Glu Asp Tyr
            1045            1050            1055

Thr Asp Cys Gly Gly Val Ser Gly Leu Asn Pro Ser Leu Trp Tyr Ile
            1060            1065            1070

Ile Gly Ile Gln Phe Leu Leu Leu Trp Leu Val Ser Gly Ser Thr His
            1075            1080            1085

Arg Leu Leu
    1090
```

(2) INFORMATION FOR SEQ ID NO:53:

(i) SEQUENCE CHARACTERISTICS:
        (A) LENGTH: 1103 amino acids
        (B) TYPE: amino acid
        (C) STRANDEDNESS: single
        (D) TOPOLOGY: linear (ii) MOLECULE TYPE: protein ( v ) FRAGMENT TYPE: internal ( x i ) SEQUENCE DESCRIPTION: SEQ ID NO:53:

| Met | Ala | Ala | Gly | Cys | Leu | Leu | Ala | Leu | Thr | Leu | Thr | Leu | Phe | Gln | Ser |
| 1 | | | | 5 | | | | | 10 | | | | | 15 | |
| Leu | Leu | Ile | Gly | Pro | Ser | Ser | Glu | Glu | Pro | Phe | Pro | Ser | Ala | Val | Thr |
| | | | 20 | | | | 25 | | | | | 30 | | | |
| Ile | Lys | Ser | Trp | Val | Asp | Lys | Met | Gln | Glu | Asp | Leu | Val | Thr | Leu | Ala |
| | | 35 | | | | | 40 | | | | | 45 | | | |
| Lys | Thr | Ala | Ser | Gly | Val | Asn | Gln | Leu | Val | Asp | Ile | Tyr | Glu | Lys | Tyr |
| | 50 | | | | | 55 | | | | | 60 | | | | |
| Gln | Asp | Leu | Tyr | Thr | Val | Glu | Pro | Asn | Asn | Ala | Arg | Gln | Leu | Val | Glu |
| 65 | | | | | 70 | | | | | 75 | | | | | 80 |
| Ile | Ala | Ala | Arg | Asp | Ile | Glu | Lys | Leu | Leu | Ser | Asn | Arg | Ser | Lys | Ala |
| | | | | 85 | | | | | 90 | | | | | 95 | |
| Leu | Val | Ser | Leu | Ala | Leu | Glu | Ala | Glu | Lys | Val | Gln | Ala | Ala | His | Gln |
| | | | 100 | | | | | 105 | | | | | 110 | | |
| Trp | Arg | Glu | Asp | Phe | Ala | Ser | Asn | Glu | Val | Val | Tyr | Tyr | Asn | Ala | Lys |
| | | 115 | | | | | 120 | | | | | 125 | | | |
| Asp | Asp | Leu | Asp | Pro | Glu | Lys | Asn | Asp | Ser | Glu | Pro | Gly | Ser | Gln | Arg |
| | 130 | | | | | 135 | | | | | 140 | | | | |
| Ile | Lys | Pro | Val | Phe | Ile | Glu | Asp | Ala | Asn | Phe | Gly | Arg | Gln | Ile | Ser |
| 145 | | | | | 150 | | | | | 155 | | | | | 160 |
| Tyr | Gln | His | Ala | Ala | Val | His | Ile | Pro | Thr | Asp | Ile | Tyr | Glu | Gly | Ser |
| | | | | 165 | | | | | 170 | | | | | 175 | |
| Thr | Ile | Val | Leu | Asn | Glu | Leu | Asn | Trp | Thr | Ser | Ala | Leu | Asp | Glu | Val |
| | | | 180 | | | | | 185 | | | | | 190 | | |
| Phe | Lys | Lys | Asn | Arg | Glu | Glu | Asp | Pro | Ser | Leu | Leu | Trp | Gln | Val | Phe |
| | | 195 | | | | | 200 | | | | | 205 | | | |
| Gly | Ser | Ala | Thr | Gly | Leu | Ala | Arg | Tyr | Tyr | Pro | Ala | Ser | Pro | Trp | Val |
| | 210 | | | | | 215 | | | | | 220 | | | | |
| Asp | Asn | Ser | Arg | Thr | Pro | Asn | Lys | Ile | Asp | Leu | Tyr | Asp | Val | Arg | Arg |
| 225 | | | | | 230 | | | | | 235 | | | | | 240 |
| Arg | Pro | Trp | Tyr | Ile | Gln | Gly | Ala | Ala | Ser | Pro | Lys | Asp | Met | Leu | Ile |
| | | | | 245 | | | | | 250 | | | | | 255 | |
| Leu | Val | Asp | Val | Ser | Gly | Ser | Val | Ser | Gly | Leu | Thr | Leu | Lys | Leu | Ile |
| | | | 260 | | | | | 265 | | | | | 270 | | |
| Arg | Thr | Ser | Val | Ser | Glu | Met | Leu | Glu | Thr | Leu | Ser | Asp | Asp | Asp | Phe |
| | | 275 | | | | | 280 | | | | | 285 | | | |
| Val | Asn | Val | Ala | Ser | Phe | Asn | Ser | Asn | Ala | Gln | Asp | Val | Ser | Cys | Phe |
| | 290 | | | | | 295 | | | | | 300 | | | | |
| Gln | His | Leu | Val | Gln | Ala | Asn | Val | Arg | Asn | Lys | Lys | Val | Leu | Lys | Asp |
| 305 | | | | | 310 | | | | | 315 | | | | | 320 |
| Ala | Val | Asn | Asn | Ile | Thr | Ala | Lys | Gly | Ile | Thr | Asp | Tyr | Lys | Lys | Gly |
| | | | | 325 | | | | | 330 | | | | | 335 | |
| Phe | Ser | Phe | Ala | Phe | Glu | Gln | Leu | Leu | Asn | Tyr | Asn | Val | Ser | Arg | Ala |
| | | | 340 | | | | | 345 | | | | | 350 | | |
| Asn | Cys | Asn | Lys | Ile | Ile | Met | Leu | Phe | Thr | Asp | Gly | Gly | Glu | Glu | Arg |
| | | 355 | | | | | 360 | | | | | 365 | | | |
| Ala | Gln | Glu | Ile | Phe | Asn | Lys | Tyr | Asn | Lys | Asp | Lys | Lys | Val | Arg | Val |
| | 370 | | | | | 375 | | | | | 380 | | | | |
| Phe | Arg | Phe | Ser | Val | Gly | Gln | His | Asn | Tyr | Glu | Arg | Gly | Pro | Ile | Gln |
| 385 | | | | | 390 | | | | | 395 | | | | | 400 |
| Trp | Met | Ala | Cys | Glu | Asn | Lys | Gly | Tyr | Tyr | Tyr | Glu | Ile | Pro | Ser | Ile |

```
                                    405                           410                           415
Gly  Ala  Ile  Arg  Ile  Asn  Thr  Gln  Glu  Tyr  Leu  Asp  Val  Leu  Gly  Arg
                    420                      425                      430

Pro  Met  Val  Leu  Ala  Gly  Asp  Lys  Ala  Lys  Gln  Val  Gln  Trp  Thr  Asn
               435                      440                      445

Val  Tyr  Leu  Asp  Ala  Leu  Glu  Leu  Gly  Leu  Val  Ile  Thr  Gly  Thr  Leu
          450                      455                      460

Pro  Val  Phe  Asn  Ile  Thr  Gly  Gln  Phe  Glu  Asn  Lys  Thr  Asn  Leu  Lys
465                      470                      475                      480

Asn  Gln  Leu  Ile  Leu  Gly  Val  Met  Gly  Val  Asp  Val  Ser  Leu  Glu  Asp
                    485                      490                      495

Ile  Lys  Arg  Leu  Thr  Pro  Arg  Phe  Thr  Leu  Cys  Pro  Asn  Gly  Tyr  Tyr
               500                      505                      510

Phe  Ala  Ile  Asp  Pro  Asn  Gly  Tyr  Val  Leu  Leu  His  Pro  Asn  Leu  Gln
               515                      520                      525

Pro  Lys  Pro  Ile  Gly  Val  Gly  Ile  Pro  Thr  Ile  Asn  Leu  Arg  Lys  Arg
     530                      535                      540

Arg  Pro  Asn  Ile  Gln  Asn  Pro  Lys  Ser  Gln  Glu  Pro  Val  Thr  Leu  Asp
545                      550                      555                      560

Phe  Leu  Asp  Ala  Glu  Leu  Glu  Asn  Asp  Ile  Lys  Val  Glu  Ile  Arg  Asn
                    565                      570                      575

Lys  Met  Ile  Asp  Gly  Glu  Ser  Gly  Glu  Lys  Thr  Phe  Arg  Thr  Leu  Val
               580                      585                      590

Lys  Ser  Gln  Asp  Glu  Arg  Tyr  Ile  Asp  Lys  Gly  Asn  Arg  Thr  Tyr  Thr
          595                      600                      605

Trp  Thr  Pro  Val  Asn  Gly  Thr  Asp  Tyr  Ser  Leu  Ala  Leu  Val  Leu  Pro
     610                      615                      620

Thr  Tyr  Ser  Phe  Tyr  Tyr  Ile  Lys  Ala  Lys  Leu  Glu  Glu  Thr  Ile  Thr
625                      630                      635                      640

Gln  Ala  Arg  Tyr  Ser  Glu  Thr  Leu  Lys  Pro  Asp  Asn  Phe  Glu  Glu  Ser
                    645                      650                      655

Gly  Tyr  Thr  Phe  Ile  Ala  Pro  Arg  Asp  Tyr  Cys  Asn  Asp  Leu  Lys  Ile
               660                      665                      670

Ser  Asp  Asn  Asn  Thr  Glu  Phe  Leu  Leu  Asn  Phe  Asn  Glu  Phe  Ile  Asp
          675                      680                      685

Arg  Lys  Thr  Pro  Asn  Asn  Pro  Ser  Cys  Asn  Ala  Asp  Leu  Ile  Asn  Arg
     690                      695                      700

Val  Leu  Leu  Asp  Ala  Gly  Phe  Thr  Asn  Glu  Leu  Val  Gln  Asn  Tyr  Trp
705                      710                      715                      720

Ser  Lys  Gln  Lys  Asn  Ile  Lys  Gly  Val  Lys  Ala  Arg  Phe  Val  Val  Thr
                    725                      730                      735

Asp  Gly  Gly  Ile  Thr  Arg  Val  Tyr  Pro  Lys  Glu  Ala  Gly  Glu  Asn  Trp
               740                      745                      750

Gln  Glu  Asn  Pro  Glu  Thr  Tyr  Glu  Asp  Ser  Phe  Tyr  Lys  Arg  Ser  Leu
          755                      760                      765

Asp  Asn  Asp  Asn  Tyr  Val  Phe  Thr  Ala  Pro  Tyr  Phe  Asn  Lys  Ser  Gly
     770                      775                      780

Pro  Gly  Ala  Tyr  Glu  Ser  Gly  Ile  Met  Val  Ser  Lys  Ala  Val  Glu  Ile
785                      790                      795                      800

Tyr  Ile  Gln  Gly  Lys  Leu  Leu  Lys  Pro  Ala  Val  Val  Gly  Ile  Lys  Ile
                    805                      810                      815

Asp  Val  Asn  Ser  Trp  Ile  Glu  Asn  Phe  Thr  Lys  Thr  Ser  Ile  Arg  Asp
               820                      825                      830
```

-continued

```
Pro  Cys  Ala  Gly  Pro  Val  Cys  Asp  Cys  Lys  Arg  Asn  Ser  Asp  Val  Met
          835                 840                     845

Asp  Cys  Val  Ile  Leu  Asp  Asp  Gly  Gly  Phe  Leu  Leu  Met  Ala  Asn  His
          850                 855                     860

Asp  Asp  Tyr  Thr  Asn  Gln  Ile  Gly  Arg  Phe  Phe  Gly  Glu  Ile  Asp  Pro
865                      870                     875                      880

Ser  Leu  Met  Arg  His  Leu  Val  Asn  Ile  Ser  Val  Tyr  Ala  Phe  Asn  Lys
                    885                      890                     895

Ser  Tyr  Asp  Tyr  Gln  Ser  Val  Cys  Glu  Pro  Gly  Ala  Ala  Pro  Lys  Gln
               900                      905                     910

Gly  Ala  Gly  His  Arg  Ser  Ala  Tyr  Val  Pro  Ser  Val  Ala  Asp  Ile  Leu
          915                 920                     925

Gln  Ile  Gly  Trp  Trp  Ala  Thr  Ala  Ala  Ala  Trp  Ser  Ile  Leu  Gln  Gln
     930                      935                          940

Phe  Leu  Leu  Ser  Leu  Thr  Phe  Pro  Arg  Leu  Leu  Glu  Ala  Val  Glu  Met
945                      950                     955                      960

Glu  Asp  Asp  Asp  Phe  Thr  Ala  Ser  Leu  Ser  Lys  Gln  Ser  Cys  Ile  Thr
               965                      970                     975

Glu  Gln  Thr  Gln  Tyr  Phe  Phe  Asp  Asn  Asp  Ser  Lys  Ser  Phe  Ser  Gly
               980                      985                     990

Val  Leu  Asp  Cys  Gly  Asn  Cys  Ser  Arg  Ile  Phe  His  Gly  Glu  Lys  Leu
          995                 1000                    1005

Met  Asn  Thr  Asn  Leu  Ile  Phe  Ile  Met  Val  Glu  Ser  Lys  Gly  Thr  Cys
     1010                    1015                         1020

Pro  Cys  Asp  Thr  Arg  Leu  Leu  Ile  Gln  Ala  Glu  Gln  Thr  Ser  Asp  Gly
1025                     1030                    1035                     1040

Pro  Asn  Pro  Cys  Asp  Met  Val  Lys  Gln  Pro  Arg  Tyr  Arg  Lys  Gly  Pro
               1045                     1050                    1055

Asp  Val  Cys  Phe  Asp  Asn  Asn  Val  Leu  Glu  Asp  Tyr  Thr  Asp  Cys  Gly
               1060                     1065                    1070

Gly  Val  Ser  Gly  Leu  Asn  Pro  Ser  Leu  Trp  Tyr  Ile  Ile  Gly  Ile  Gln
          1075                     1080                    1085

Phe  Leu  Leu  Leu  Trp  Leu  Val  Ser  Gly  Ser  Thr  His  Arg  Leu  Leu
     1090                     1095                    1100
```

(2) INFORMATION FOR SEQ ID NO:54:

(i) SEQUENCE CHARACTERISTICS:
        (A) LENGTH: 1086 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:54:

```
Met  Ala  Ala  Gly  Cys  Leu  Leu  Ala  Leu  Thr  Leu  Thr  Leu  Phe  Gln  Ser
1                   5                   10                      15

Leu  Leu  Ile  Gly  Pro  Ser  Ser  Glu  Glu  Pro  Phe  Pro  Ser  Ala  Val  Thr
               20                  25                      30

Ile  Lys  Ser  Trp  Val  Asp  Lys  Met  Gln  Glu  Asp  Leu  Val  Thr  Leu  Ala
          35                  40                      45

Lys  Thr  Ala  Ser  Gly  Val  Asn  Gln  Leu  Val  Asp  Ile  Tyr  Glu  Lys  Tyr
     50                  55                      60

Gln  Asp  Leu  Tyr  Thr  Val  Glu  Pro  Asn  Asn  Ala  Arg  Gln  Leu  Val  Glu
65                  70                      75                      80
```

```
Ile Ala Ala Arg Asp Ile Glu Lys Leu Leu Ser Asn Arg Ser Lys Ala
                85              90                  95
Leu Val Ser Leu Ala Leu Glu Ala Glu Lys Val Gln Ala Ala His Gln
            100             105                 110
Trp Arg Glu Asp Phe Ala Ser Asn Glu Val Val Tyr Tyr Asn Ala Lys
        115             120              125
Asp Asp Leu Asp Pro Glu Lys Asn Asp Ser Glu Pro Gly Ser Gln Arg
    130              135             140
Ile Lys Pro Val Phe Ile Glu Asp Ala Asn Phe Gly Arg Gln Ile Ser
145             150              155                     160
Tyr Gln His Ala Ala Val His Ile Pro Thr Asp Ile Tyr Glu Gly Ser
                165             170              175
Thr Ile Val Leu Asn Glu Leu Asn Trp Thr Ser Ala Leu Asp Glu Val
            180              185              190
Phe Lys Lys Asn Arg Glu Glu Asp Pro Ser Leu Leu Trp Gln Val Phe
        195             200              205
Gly Ser Ala Thr Gly Leu Ala Arg Tyr Tyr Pro Ala Ser Pro Trp Val
    210             215              220
Asp Asn Ser Arg Thr Pro Asn Lys Ile Asp Leu Tyr Asp Val Arg Arg
225             230              235              240
Arg Pro Trp Tyr Ile Gln Gly Ala Ala Ser Pro Lys Asp Met Leu Ile
                245             250              255
Leu Val Asp Val Ser Gly Ser Val Ser Gly Leu Thr Leu Lys Leu Ile
            260             265              270
Arg Thr Ser Val Ser Glu Met Leu Glu Thr Leu Ser Asp Asp Asp Phe
        275             280              285
Val Asn Val Ala Ser Phe Asn Ser Asn Ala Gln Asp Val Ser Cys Phe
    290             295              300
Gln His Leu Val Gln Ala Asn Val Arg Asn Lys Lys Val Leu Lys Asp
305             310              315             320
Ala Val Asn Asn Ile Thr Ala Lys Gly Ile Thr Asp Tyr Lys Lys Gly
                325             330              335
Phe Ser Phe Ala Phe Glu Gln Leu Leu Asn Tyr Asn Val Ser Arg Ala
            340             345              350
Asn Cys Asn Lys Ile Ile Met Leu Phe Thr Asp Gly Gly Glu Glu Arg
        355             360              365
Ala Gln Glu Ile Phe Asn Lys Tyr Asn Lys Asp Lys Lys Val Arg Val
    370             375              380
Phe Arg Phe Ser Val Gly Gln His Asn Tyr Glu Arg Gly Pro Ile Gln
385             390              395              400
Trp Met Ala Cys Glu Asn Lys Gly Tyr Tyr Tyr Glu Ile Pro Ser Ile
                405             410              415
Gly Ala Ile Arg Ile Asn Thr Gln Glu Tyr Leu Asp Val Leu Gly Arg
            420             425              430
Pro Met Val Leu Ala Gly Asp Lys Ala Lys Gln Val Gln Trp Thr Asn
        435             440              445
Val Tyr Leu Asp Ala Leu Glu Leu Gly Leu Val Ile Thr Gly Thr Leu
    450             455              460
Pro Val Phe Asn Ile Thr Gly Gln Phe Glu Asn Lys Thr Asn Leu Lys
465             470              475              480
Asn Gln Leu Ile Leu Gly Val Met Gly Val Asp Val Ser Leu Glu Asp
                485             490              495
Ile Lys Arg Leu Thr Pro Arg Phe Thr Leu Cys Pro Asn Gly Tyr Tyr
```

```
                     500                      505                        510
Phe  Ala  Ile  Asp  Pro  Asn  Gly  Tyr  Val  Leu  Leu  His  Pro  Asn  Leu  Gln
          515                      520                      525
Pro  Lys  Glu  Pro  Val  Thr  Leu  Asp  Phe  Leu  Asp  Ala  Glu  Leu  Glu  Asn
     530                      535                      540
Asp  Ile  Lys  Val  Glu  Ile  Arg  Asn  Lys  Met  Ile  Asp  Gly  Glu  Ser  Gly
545                      550                      555                           560
Glu  Lys  Thr  Phe  Arg  Thr  Leu  Val  Lys  Ser  Gln  Asp  Glu  Arg  Tyr  Ile
                    565                      570                      575
Asp  Lys  Gly  Asn  Arg  Thr  Tyr  Thr  Trp  Thr  Pro  Val  Asn  Gly  Thr  Asp
               580                      585                      590
Tyr  Ser  Leu  Ala  Leu  Val  Leu  Pro  Thr  Tyr  Ser  Phe  Tyr  Tyr  Ile  Lys
               595                      600                      605
Ala  Lys  Leu  Glu  Glu  Thr  Ile  Thr  Gln  Ala  Arg  Ser  Lys  Lys  Gly  Lys
          610                      615                      620
Met  Lys  Asp  Ser  Glu  Thr  Leu  Lys  Pro  Asp  Asn  Phe  Glu  Glu  Ser  Gly
625                      630                      635                           640
Tyr  Thr  Phe  Ile  Ala  Pro  Arg  Asp  Tyr  Cys  Asn  Asp  Leu  Lys  Ile  Ser
                    645                      650                      655
Asp  Asn  Asn  Thr  Glu  Phe  Leu  Leu  Asn  Phe  Asn  Glu  Phe  Ile  Asp  Arg
               660                      665                      670
Lys  Thr  Pro  Asn  Asn  Pro  Ser  Cys  Asn  Ala  Asp  Leu  Ile  Asn  Arg  Val
          675                      680                      685
Leu  Leu  Asp  Ala  Gly  Phe  Thr  Asn  Glu  Leu  Val  Gln  Asn  Tyr  Trp  Ser
          690                      695                      700
Lys  Gln  Lys  Asn  Ile  Lys  Gly  Val  Lys  Ala  Arg  Phe  Val  Val  Thr  Asp
705                      710                      715                           720
Gly  Gly  Ile  Thr  Arg  Val  Tyr  Pro  Lys  Glu  Ala  Gly  Glu  Asn  Trp  Gln
                    725                      730                      735
Glu  Asn  Pro  Glu  Thr  Tyr  Glu  Asp  Ser  Phe  Tyr  Lys  Arg  Ser  Leu  Asp
               740                      745                      750
Asn  Asp  Asn  Tyr  Val  Phe  Thr  Ala  Pro  Tyr  Phe  Asn  Lys  Ser  Gly  Pro
          755                      760                      765
Gly  Ala  Tyr  Glu  Ser  Gly  Ile  Met  Val  Ser  Lys  Ala  Val  Glu  Ile  Tyr
          770                      775                      780
Ile  Gln  Gly  Lys  Leu  Leu  Lys  Pro  Ala  Val  Val  Gly  Ile  Lys  Ile  Asp
785                      790                      795                           800
Val  Asn  Ser  Trp  Ile  Glu  Asn  Phe  Thr  Lys  Thr  Ser  Ile  Arg  Asp  Pro
                    805                      810                      815
Cys  Ala  Gly  Pro  Val  Cys  Asp  Cys  Lys  Arg  Asn  Ser  Asp  Val  Met  Asp
               820                      825                      830
Cys  Val  Ile  Leu  Asp  Asp  Gly  Gly  Phe  Leu  Leu  Met  Ala  Asn  His  Asp
          835                      840                      845
Asp  Tyr  Thr  Asn  Gln  Ile  Gly  Arg  Phe  Phe  Gly  Glu  Ile  Asp  Pro  Ser
          850                      855                      860
Leu  Met  Arg  His  Leu  Val  Asn  Ile  Ser  Val  Tyr  Ala  Phe  Asn  Lys  Ser
865                      870                      875                           880
Tyr  Asp  Tyr  Gln  Ser  Val  Cys  Glu  Pro  Gly  Ala  Ala  Pro  Lys  Gln  Gly
                    885                      890                      895
Ala  Gly  His  Arg  Ser  Ala  Tyr  Val  Pro  Ser  Val  Ala  Asp  Ile  Leu  Gln
               900                      905                      910
Ile  Gly  Trp  Trp  Ala  Thr  Ala  Ala  Ala  Trp  Ser  Ile  Leu  Gln  Gln  Phe
          915                      920                      925
```

| | | | | | | | | | | | | | | |
|---|---|---|---|---|---|---|---|---|---|---|---|---|---|---|
| Leu | Leu | Ser | Leu | Thr | Phe | Pro | Arg | Leu | Leu | Glu | Ala | Val | Glu | Met | Glu |
| | | 930 | | | | 935 | | | | 940 | | | | | |
| Asp | Asp | Asp | Phe | Thr | Ala | Ser | Leu | Ser | Lys | Gln | Ser | Cys | Ile | Thr | Glu |
| 945 | | | | | 950 | | | | | 955 | | | | | 960 |
| Gln | Thr | Gln | Tyr | Phe | Phe | Asp | Asn | Asp | Ser | Lys | Ser | Phe | Ser | Gly | Val |
| | | | | 965 | | | | | 970 | | | | | 975 | |
| Leu | Asp | Cys | Gly | Asn | Cys | Ser | Arg | Ile | Phe | His | Gly | Glu | Lys | Leu | Met |
| | | | | 980 | | | | | 985 | | | | | 990 | |
| Asn | Thr | Asn | Leu | Ile | Phe | Ile | Met | Val | Glu | Ser | Lys | Gly | Thr | Cys | Pro |
| | | 995 | | | | | 1000 | | | | | 1005 | | | |
| Cys | Asp | Thr | Arg | Leu | Leu | Ile | Gln | Ala | Glu | Gln | Thr | Ser | Asp | Gly | Pro |
| | | 1010 | | | | | 1015 | | | | | 1020 | | | |
| Asn | Pro | Cys | Asp | Met | Val | Lys | Gln | Pro | Arg | Tyr | Arg | Lys | Gly | Pro | Asp |
| 1025 | | | | | 1030 | | | | | 1035 | | | | | 1040 |
| Val | Cys | Phe | Asp | Asn | Asn | Val | Leu | Glu | Asp | Tyr | Thr | Asp | Cys | Gly | Gly |
| | | | | 1045 | | | | | 1050 | | | | | 1055 | |
| Val | Ser | Gly | Leu | Asn | Pro | Ser | Leu | Trp | Tyr | Ile | Ile | Gly | Ile | Gln | Phe |
| | | | 1060 | | | | | 1065 | | | | | 1070 | | |
| Leu | Leu | Leu | Trp | Leu | Val | Ser | Gly | Ser | Thr | His | Arg | Leu | Leu | | |
| | | 1075 | | | | | 1080 | | | | | 1085 | | | |

( 2 ) INFORMATION FOR SEQ ID NO:55:

( i ) SEQUENCE CHARACTERISTICS:
        ( A ) LENGTH: 1079 amino acids
        ( B ) TYPE: amino acid
        ( C ) STRANDEDNESS: single
        ( D ) TOPOLOGY: linear ( i i ) MOLECULE TYPE: protein ( v ) FRAGMENT TYPE: internal ( x i ) SEQUENCE DESCRIPTION: SEQ ID NO:55:

| | | | | | | | | | | | | | | | |
|---|---|---|---|---|---|---|---|---|---|---|---|---|---|---|---|
| Met | Ala | Ala | Gly | Cys | Leu | Leu | Ala | Leu | Thr | Leu | Thr | Leu | Phe | Gln | Ser |
| 1 | | | | 5 | | | | | 10 | | | | | 15 | |
| Leu | Leu | Ile | Gly | Pro | Ser | Ser | Glu | Glu | Pro | Phe | Pro | Ser | Ala | Val | Thr |
| | | | 20 | | | | | 25 | | | | | 30 | | |
| Ile | Lys | Ser | Trp | Val | Asp | Lys | Met | Gln | Glu | Asp | Leu | Val | Thr | Leu | Ala |
| | | 35 | | | | | 40 | | | | | 45 | | | |
| Lys | Thr | Ala | Ser | Gly | Val | Asn | Gln | Leu | Val | Asp | Ile | Tyr | Glu | Lys | Tyr |
| | 50 | | | | | 55 | | | | | 60 | | | | |
| Gln | Asp | Leu | Tyr | Thr | Val | Glu | Pro | Asn | Asn | Ala | Arg | Gln | Leu | Val | Glu |
| 65 | | | | | 70 | | | | | 75 | | | | | 80 |
| Ile | Ala | Ala | Arg | Asp | Ile | Glu | Lys | Leu | Leu | Ser | Asn | Arg | Ser | Lys | Ala |
| | | | | 85 | | | | | 90 | | | | | 95 | |
| Leu | Val | Ser | Leu | Ala | Leu | Glu | Ala | Glu | Lys | Val | Gln | Ala | Ala | His | Gln |
| | | | 100 | | | | | 105 | | | | | 110 | | |
| Trp | Arg | Glu | Asp | Phe | Ala | Ser | Asn | Glu | Val | Val | Tyr | Tyr | Asn | Ala | Lys |
| | | 115 | | | | | 120 | | | | | 125 | | | |
| Asp | Asp | Leu | Asp | Pro | Glu | Lys | Asn | Asp | Ser | Glu | Pro | Gly | Ser | Gln | Arg |
| | 130 | | | | | 135 | | | | | 140 | | | | |
| Ile | Lys | Pro | Val | Phe | Ile | Glu | Asp | Ala | Asn | Phe | Gly | Arg | Gln | Ile | Ser |
| 145 | | | | | 150 | | | | | 155 | | | | | 160 |
| Tyr | Gln | His | Ala | Ala | Val | His | Ile | Pro | Thr | Asp | Ile | Tyr | Glu | Gly | Ser |
| | | | | 165 | | | | | 170 | | | | | 175 | |
| Thr | Ile | Val | Leu | Asn | Glu | Leu | Asn | Trp | Thr | Ser | Ala | Leu | Asp | Glu | Val |
| | | | 180 | | | | | 185 | | | | | 190 | | |

-continued

| | | | | | | | | | | | | | |
|---|---|---|---|---|---|---|---|---|---|---|---|---|---|
| Phe | Lys | Lys | Asn | Arg | Glu | Glu | Asp | Pro | Ser | Leu | Leu | Trp | Gln | Val | Phe |
| | | 195 | | | | 200 | | | | | 205 | | | |
| Gly | Ser | Ala | Thr | Gly | Leu | Ala | Arg | Tyr | Tyr | Pro | Ala | Ser | Pro | Trp | Val |
| | 210 | | | | | 215 | | | | | 220 | | | | |
| Asp | Asn | Ser | Arg | Thr | Pro | Asn | Lys | Ile | Asp | Leu | Tyr | Asp | Val | Arg | Arg |
| 225 | | | | | 230 | | | | | 235 | | | | | 240 |
| Arg | Pro | Trp | Tyr | Ile | Gln | Gly | Ala | Ala | Ser | Pro | Lys | Asp | Met | Leu | Ile |
| | | | | 245 | | | | | 250 | | | | | | 255 |
| Leu | Val | Asp | Val | Ser | Gly | Ser | Val | Ser | Gly | Leu | Thr | Leu | Lys | Leu | Ile |
| | | | 260 | | | | | 265 | | | | 270 | | | |
| Arg | Thr | Ser | Val | Ser | Glu | Met | Leu | Glu | Thr | Leu | Ser | Asp | Asp | Asp | Phe |
| | | 275 | | | | | 280 | | | | | 285 | | | |
| Val | Asn | Val | Ala | Ser | Phe | Asn | Ser | Asn | Ala | Gln | Asp | Val | Ser | Cys | Phe |
| | 290 | | | | | 295 | | | | | 300 | | | | |
| Gln | His | Leu | Val | Gln | Ala | Asn | Val | Arg | Asn | Lys | Lys | Val | Leu | Lys | Asp |
| 305 | | | | | 310 | | | | | 315 | | | | | 320 |
| Ala | Val | Asn | Asn | Ile | Thr | Ala | Lys | Gly | Ile | Thr | Asp | Tyr | Lys | Lys | Gly |
| | | | | 325 | | | | | 330 | | | | | | 335 |
| Phe | Ser | Phe | Ala | Phe | Glu | Gln | Leu | Leu | Asn | Tyr | Asn | Val | Ser | Arg | Ala |
| | | | 340 | | | | | 345 | | | | | 350 | | |
| Asn | Cys | Asn | Lys | Ile | Ile | Met | Leu | Phe | Thr | Asp | Gly | Gly | Glu | Glu | Arg |
| | | | 355 | | | | | 360 | | | | | 365 | | |
| Ala | Gln | Glu | Ile | Phe | Asn | Lys | Tyr | Asn | Lys | Asp | Lys | Lys | Val | Arg | Val |
| | 370 | | | | | 375 | | | | | 380 | | | | |
| Phe | Arg | Phe | Ser | Val | Gly | Gln | His | Asn | Tyr | Glu | Arg | Gly | Pro | Ile | Gln |
| 385 | | | | | 390 | | | | | 395 | | | | | 400 |
| Trp | Met | Ala | Cys | Glu | Asn | Lys | Gly | Tyr | Tyr | Tyr | Glu | Ile | Pro | Ser | Ile |
| | | | | 405 | | | | | 410 | | | | | 415 | |
| Gly | Ala | Ile | Arg | Ile | Asn | Thr | Gln | Glu | Tyr | Leu | Asp | Val | Leu | Gly | Arg |
| | | | 420 | | | | | 425 | | | | | 430 | | |
| Pro | Met | Val | Leu | Ala | Gly | Asp | Lys | Ala | Lys | Gln | Val | Gln | Trp | Thr | Asn |
| | | 435 | | | | | 440 | | | | | 445 | | | |
| Val | Tyr | Leu | Asp | Ala | Leu | Glu | Leu | Gly | Leu | Val | Ile | Thr | Gly | Thr | Leu |
| | 450 | | | | | 455 | | | | | 460 | | | | |
| Pro | Val | Phe | Asn | Ile | Thr | Gly | Gln | Phe | Glu | Asn | Lys | Thr | Asn | Leu | Lys |
| 465 | | | | | 470 | | | | | 475 | | | | | 480 |
| Asn | Gln | Leu | Ile | Leu | Gly | Val | Met | Gly | Val | Asp | Val | Ser | Leu | Glu | Asp |
| | | | | 485 | | | | | 490 | | | | | 495 | |
| Ile | Lys | Arg | Leu | Thr | Pro | Arg | Phe | Thr | Leu | Cys | Pro | Asn | Gly | Tyr | Tyr |
| | | | 500 | | | | | 505 | | | | | 510 | | |
| Phe | Ala | Ile | Asp | Pro | Asn | Gly | Tyr | Val | Leu | Leu | His | Pro | Asn | Leu | Gln |
| | | 515 | | | | | 520 | | | | | 525 | | | |
| Pro | Lys | Glu | Pro | Val | Thr | Leu | Asp | Phe | Leu | Asp | Ala | Glu | Leu | Glu | Asn |
| | 530 | | | | | 535 | | | | | 540 | | | | |
| Asp | Ile | Lys | Val | Glu | Ile | Arg | Asn | Lys | Met | Ile | Asp | Gly | Glu | Ser | Gly |
| 545 | | | | | 550 | | | | | 555 | | | | | 560 |
| Glu | Lys | Thr | Phe | Arg | Thr | Leu | Val | Lys | Ser | Gln | Asp | Glu | Arg | Tyr | Ile |
| | | | | 565 | | | | | 570 | | | | | 575 | |
| Asp | Lys | Gly | Asn | Arg | Thr | Tyr | Thr | Trp | Thr | Pro | Val | Asn | Gly | Thr | Asp |
| | | | 580 | | | | | 585 | | | | | 590 | | |
| Tyr | Ser | Leu | Ala | Leu | Val | Leu | Pro | Thr | Tyr | Ser | Phe | Tyr | Tyr | Ile | Lys |
| | | 595 | | | | | 600 | | | | | 605 | | | |
| Ala | Lys | Leu | Glu | Glu | Thr | Ile | Thr | Gln | Ala | Arg | Tyr | Ser | Glu | Thr | Leu |

-continued

|     |     |     | 610 |     |     | 615 |     |     |     | 620 |     |     |     |     |
|---|---|---|---|---|---|---|---|---|---|---|---|---|---|---|
| Lys 625 | Pro | Asp | Asn | Phe | Glu 630 | Glu | Ser | Gly | Tyr | Thr 635 | Phe | Ile | Ala | Pro | Arg 640 |
| Asp | Tyr | Cys | Asn | Asp 645 | Leu | Lys | Ile | Ser | Asp 650 | Asn | Asn | Thr | Glu | Phe 655 | Leu |
| Leu | Asn | Phe | Asn 660 | Glu | Phe | Ile | Asp | Arg 665 | Lys | Thr | Pro | Asn | Asn 670 | Pro | Ser |
| Cys | Asn | Ala 675 | Asp | Leu | Ile | Asn | Arg 680 | Val | Leu | Leu | Asp | Ala 685 | Gly | Phe | Thr |
| Asn | Glu 690 | Leu | Val | Gln | Asn | Tyr 695 | Trp | Ser | Lys | Gln | Lys 700 | Asn | Ile | Lys | Gly |
| Val 705 | Lys | Ala | Arg | Phe | Val 710 | Val | Thr | Asp | Gly | Gly 715 | Ile | Thr | Arg | Val | Tyr 720 |
| Pro | Lys | Glu | Ala | Gly 725 | Glu | Asn | Trp | Gln | Glu 730 | Asn | Pro | Glu | Thr | Tyr 735 | Glu |
| Asp | Ser | Phe | Tyr 740 | Lys | Arg | Ser | Leu | Asp 745 | Asn | Asp | Asn | Tyr | Val 750 | Phe | Thr |
| Ala | Pro | Tyr 755 | Phe | Asn | Lys | Ser | Gly 760 | Pro | Gly | Ala | Tyr | Glu 765 | Ser | Gly | Ile |
| Met | Val 770 | Ser | Lys | Ala | Val | Glu 775 | Ile | Tyr | Ile | Gln | Gly 780 | Lys | Leu | Leu | Lys |
| Pro 785 | Ala | Val | Val | Gly | Ile 790 | Lys | Ile | Asp | Val | Asn 795 | Ser | Trp | Ile | Glu | Asn 800 |
| Phe | Thr | Lys | Thr | Ser 805 | Ile | Arg | Asp | Pro | Cys 810 | Ala | Gly | Pro | Val | Cys 815 | Asp |
| Cys | Lys | Arg | Asn 820 | Ser | Asp | Val | Met | Asp 825 | Cys | Val | Ile | Leu | Asp 830 | Asp | Gly |
| Gly | Phe | Leu 835 | Leu | Met | Ala | Asn | His 840 | Asp | Asp | Tyr | Thr | Asn 845 | Gln | Ile | Gly |
| Arg | Phe 850 | Phe | Gly | Glu | Ile | Asp 855 | Pro | Ser | Leu | Met | Arg 860 | His | Leu | Val | Asn |
| Ile 865 | Ser | Val | Tyr | Ala | Phe 870 | Asn | Lys | Ser | Tyr | Asp 875 | Tyr | Gln | Ser | Val | Cys 880 |
| Glu | Pro | Gly | Ala | Ala 885 | Pro | Lys | Gln | Gly | Ala 890 | Gly | His | Arg | Ser | Ala 895 | Tyr |
| Val | Pro | Ser | Val 900 | Ala | Asp | Ile | Leu | Gln 905 | Ile | Gly | Trp | Trp | Ala 910 | Thr | Ala |
| Ala | Ala | Trp 915 | Ser | Ile | Leu | Gln | Gln 920 | Phe | Leu | Leu | Ser | Leu 925 | Thr | Phe | Pro |
| Arg | Leu 930 | Leu | Glu | Ala | Val | Glu 935 | Met | Glu | Asp | Asp | Asp 940 | Phe | Thr | Ala | Ser |
| Leu 945 | Ser | Lys | Gln | Ser | Cys 950 | Ile | Thr | Glu | Gln | Thr 955 | Gln | Tyr | Phe | Phe | Asp 960 |
| Asn | Asp | Ser | Lys | Ser 965 | Phe | Ser | Gly | Val | Leu 970 | Asp | Cys | Gly | Asn | Cys 975 | Ser |
| Arg | Ile | Phe | His 980 | Gly | Glu | Lys | Leu | Met 985 | Asn | Thr | Asn | Leu | Ile 990 | Phe | Ile |
| Met | Val | Glu 995 | Ser | Lys | Gly | Thr | Cys 1000 | Pro | Cys | Asp | Thr | Arg 1005 | Leu | Leu | Ile |
| Gln | Ala 1010 | Glu | Gln | Thr | Ser | Asp 1015 | Gly | Pro | Asn | Pro | Cys 1020 | Asp | Met | Val | Lys |
| Gln 1025 | Pro | Arg | Tyr | Arg | Lys 1030 | Gly | Pro | Asp | Val | Cys 1035 | Phe | Asp | Asn | Asn | Val 1040 |

-continued

```
Leu  Glu  Asp  Tyr  Thr  Asp  Cys  Gly  Gly  Val  Ser  Gly  Leu  Asn  Pro  Ser
               1045                    1050                    1055

Leu  Trp  Tyr  Ile  Ile  Gly  Ile  Gln  Phe  Leu  Leu  Leu  Trp  Leu  Val  Ser
               1060                    1065                    1070

Gly  Ser  Thr  His  Arg  Leu  Leu
               1075
```

( 2 ) INFORMATION FOR SEQ ID NO:56:

( i ) SEQUENCE CHARACTERISTICS:
      ( A ) LENGTH: 1084 amino acids
      ( B ) TYPE: amino acid
      ( C ) STRANDEDNESS: single
      ( D ) TOPOLOGY: linear ( i i ) MOLECULE TYPE: protein ( v ) FRAGMENT TYPE: internal ( x i ) SEQUENCE DESCRIPTION: SEQ ID NO:56:

```
Met  Ala  Ala  Gly  Cys  Leu  Leu  Ala  Leu  Thr  Leu  Thr  Leu  Phe  Gln  Ser
 1                 5                      10                      15

Leu  Leu  Ile  Gly  Pro  Ser  Ser  Glu  Glu  Pro  Phe  Pro  Ser  Ala  Val  Thr
               20                      25                      30

Ile  Lys  Ser  Trp  Val  Asp  Lys  Met  Gln  Glu  Asp  Leu  Val  Thr  Leu  Ala
          35                      40                      45

Lys  Thr  Ala  Ser  Gly  Val  Asn  Gln  Leu  Val  Asp  Ile  Tyr  Glu  Lys  Tyr
     50                      55                      60

Gln  Asp  Leu  Tyr  Thr  Val  Glu  Pro  Asn  Asn  Ala  Arg  Gln  Leu  Val  Glu
65                       70                      75                       80

Ile  Ala  Ala  Arg  Asp  Ile  Glu  Lys  Leu  Leu  Ser  Asn  Arg  Ser  Lys  Ala
               85                      90                      95

Leu  Val  Ser  Leu  Ala  Leu  Glu  Ala  Glu  Lys  Val  Gln  Ala  Ala  His  Gln
               100                     105                     110

Trp  Arg  Glu  Asp  Phe  Ala  Ser  Asn  Glu  Val  Val  Tyr  Tyr  Asn  Ala  Lys
          115                     120                     125

Asp  Asp  Leu  Asp  Pro  Glu  Lys  Asn  Asp  Ser  Glu  Pro  Gly  Ser  Gln  Arg
     130                     135                     140

Ile  Lys  Pro  Val  Phe  Ile  Glu  Asp  Ala  Asn  Phe  Gly  Arg  Gln  Ile  Ser
145                      150                     155                      160

Tyr  Gln  His  Ala  Ala  Val  His  Ile  Pro  Thr  Asp  Ile  Tyr  Glu  Gly  Ser
               165                     170                     175

Thr  Ile  Val  Leu  Asn  Glu  Leu  Asn  Trp  Thr  Ser  Ala  Leu  Asp  Glu  Val
               180                     185                     190

Phe  Lys  Lys  Asn  Arg  Glu  Glu  Asp  Pro  Ser  Leu  Leu  Trp  Gln  Val  Phe
          195                     200                     205

Gly  Ser  Ala  Thr  Gly  Leu  Ala  Arg  Tyr  Tyr  Pro  Ala  Ser  Pro  Trp  Val
     210                     215                     220

Asp  Asn  Ser  Arg  Thr  Pro  Asn  Lys  Ile  Asp  Leu  Tyr  Asp  Val  Arg  Arg
225                      230                     235                      240

Arg  Pro  Trp  Tyr  Ile  Gln  Gly  Ala  Ala  Ser  Pro  Lys  Asp  Met  Leu  Ile
               245                     250                     255

Leu  Val  Asp  Val  Ser  Gly  Ser  Val  Ser  Gly  Leu  Thr  Leu  Lys  Leu  Ile
               260                     265                     270

Arg  Thr  Ser  Val  Ser  Glu  Met  Leu  Glu  Thr  Leu  Ser  Asp  Asp  Asp  Phe
          275                     280                     285

Val  Asn  Val  Ala  Ser  Phe  Asn  Ser  Asn  Ala  Gln  Asp  Val  Ser  Cys  Phe
     290                     295                     300
```

| | | | | | | | | | | | | | | | |
|---|---|---|---|---|---|---|---|---|---|---|---|---|---|---|---|
| Gln | His | Leu | Val | Gln | Ala | Asn | Val | Arg | Asn | Lys | Lys | Val | Leu | Lys | Asp |
| 305 | | | | 310 | | | | | 315 | | | | | | 320 |
| Ala | Val | Asn | Asn | Ile | Thr | Ala | Lys | Gly | Ile | Thr | Asp | Tyr | Lys | Lys | Gly |
| | | | | 325 | | | | | 330 | | | | | 335 | |
| Phe | Ser | Phe | Ala | Phe | Glu | Gln | Leu | Leu | Asn | Tyr | Asn | Val | Ser | Arg | Ala |
| | | | 340 | | | | | 345 | | | | | 350 | | |
| Asn | Cys | Asn | Lys | Ile | Ile | Met | Leu | Phe | Thr | Asp | Gly | Gly | Glu | Glu | Arg |
| | | 355 | | | | | 360 | | | | | 365 | | | |
| Ala | Gln | Glu | Ile | Phe | Asn | Lys | Tyr | Asn | Lys | Asp | Lys | Lys | Val | Arg | Val |
| | 370 | | | | | 375 | | | | | 380 | | | | |
| Phe | Arg | Phe | Ser | Val | Gly | Gln | His | Asn | Tyr | Glu | Arg | Gly | Pro | Ile | Gln |
| 385 | | | | | 390 | | | | | 395 | | | | | 400 |
| Trp | Met | Ala | Cys | Glu | Asn | Lys | Gly | Tyr | Tyr | Glu | Ile | Pro | Ser | Ile | |
| | | | | 405 | | | | | 410 | | | | | 415 | |
| Gly | Ala | Ile | Arg | Ile | Asn | Thr | Gln | Glu | Tyr | Leu | Asp | Val | Leu | Gly | Arg |
| | | | 420 | | | | | | 425 | | | | | 430 | |
| Pro | Met | Val | Leu | Ala | Gly | Asp | Lys | Ala | Lys | Gln | Val | Gln | Trp | Thr | Asn |
| | | 435 | | | | | 440 | | | | | 445 | | | |
| Val | Tyr | Leu | Asp | Ala | Leu | Glu | Leu | Gly | Leu | Val | Ile | Thr | Gly | Thr | Leu |
| | 450 | | | | | 455 | | | | | 460 | | | | |
| Pro | Val | Phe | Asn | Ile | Thr | Gly | Gln | Phe | Glu | Asn | Lys | Thr | Asn | Leu | Lys |
| 465 | | | | | 470 | | | | | 475 | | | | | 480 |
| Asn | Gln | Leu | Ile | Leu | Gly | Val | Met | Gly | Val | Asp | Val | Ser | Leu | Glu | Asp |
| | | | | 485 | | | | | 490 | | | | | 495 | |
| Ile | Lys | Arg | Leu | Thr | Pro | Arg | Phe | Thr | Leu | Cys | Pro | Asn | Gly | Tyr | Tyr |
| | | | 500 | | | | | 505 | | | | | 510 | | |
| Phe | Ala | Ile | Asp | Pro | Asn | Gly | Tyr | Val | Leu | Leu | His | Pro | Asn | Leu | Gln |
| | | | 515 | | | | | 520 | | | | | 525 | | |
| Pro | Lys | Asn | Pro | Lys | Ser | Gln | Glu | Pro | Val | Thr | Leu | Asp | Phe | Leu | Asp |
| | 530 | | | | | 535 | | | | | 540 | | | | |
| Ala | Glu | Leu | Glu | Asn | Asp | Ile | Lys | Val | Glu | Ile | Arg | Asn | Lys | Met | Ile |
| 545 | | | | | 550 | | | | | 555 | | | | | 560 |
| Asp | Gly | Glu | Ser | Gly | Glu | Lys | Thr | Phe | Arg | Thr | Leu | Val | Lys | Ser | Gln |
| | | | | 565 | | | | | 570 | | | | | 575 | |
| Asp | Glu | Arg | Tyr | Ile | Asp | Lys | Gly | Asn | Arg | Thr | Tyr | Thr | Trp | Thr | Pro |
| | | | 580 | | | | | 585 | | | | | 590 | | |
| Val | Asn | Gly | Thr | Asp | Tyr | Ser | Leu | Ala | Leu | Val | Leu | Pro | Thr | Tyr | Ser |
| | | 595 | | | | | 600 | | | | | 605 | | | |
| Phe | Tyr | Tyr | Ile | Lys | Ala | Lys | Leu | Glu | Glu | Thr | Ile | Thr | Gln | Ala | Arg |
| | 610 | | | | | 615 | | | | | 620 | | | | |
| Tyr | Ser | Glu | Thr | Leu | Lys | Pro | Asp | Asn | Phe | Glu | Glu | Ser | Gly | Tyr | Thr |
| 625 | | | | | 630 | | | | | 635 | | | | | 640 |
| Phe | Ile | Ala | Pro | Arg | Asp | Tyr | Cys | Asn | Asp | Leu | Lys | Ile | Ser | Asp | Asn |
| | | | | 645 | | | | | 650 | | | | | 655 | |
| Asn | Thr | Glu | Phe | Leu | Leu | Asn | Phe | Asn | Glu | Phe | Ile | Asp | Arg | Lys | Thr |
| | | | 660 | | | | | 665 | | | | | 670 | | |
| Pro | Asn | Asn | Pro | Ser | Cys | Asn | Ala | Asp | Leu | Ile | Asn | Arg | Val | Leu | Leu |
| | | 675 | | | | | 680 | | | | | 685 | | | |
| Asp | Ala | Gly | Phe | Thr | Asn | Glu | Leu | Val | Gln | Asn | Tyr | Trp | Ser | Lys | Gln |
| | 690 | | | | | 695 | | | | | 700 | | | | |
| Lys | Asn | Ile | Lys | Gly | Val | Lys | Ala | Arg | Phe | Val | Val | Thr | Asp | Gly | Gly |
| 705 | | | | | 710 | | | | | 715 | | | | | 720 |
| Ile | Thr | Arg | Val | Tyr | Pro | Lys | Glu | Ala | Gly | Glu | Asn | Trp | Gln | Glu | Asn |

|   |   |   |   |   | 725 |   |   |   |   | 730 |   |   |   |   | 735 |   |
|---|---|---|---|---|-----|---|---|---|---|-----|---|---|---|---|-----|---|
| Pro | Glu | Thr | Tyr | Glu | Asp | Ser | Phe | Tyr | Lys | Arg | Ser | Leu | Asp | Asn | Asp |
|   |   |   | 740 |   |   |   |   | 745 |   |   |   | 750 |   |   |   |
| Asn | Tyr | Val | Phe | Thr | Ala | Pro | Tyr | Phe | Asn | Lys | Ser | Gly | Pro | Gly | Ala |
|   |   | 755 |   |   |   | 760 |   |   |   |   | 765 |   |   |   |   |
| Tyr | Glu | Ser | Gly | Ile | Met | Val | Ser | Lys | Ala | Val | Glu | Ile | Tyr | Ile | Gln |
|   | 770 |   |   |   |   | 775 |   |   |   |   | 780 |   |   |   |   |
| Gly | Lys | Leu | Leu | Lys | Pro | Ala | Val | Val | Gly | Ile | Lys | Ile | Asp | Val | Asn |
| 785 |   |   |   |   | 790 |   |   |   |   | 795 |   |   |   |   | 800 |
| Ser | Trp | Ile | Glu | Asn | Phe | Thr | Lys | Thr | Ser | Ile | Arg | Asp | Pro | Cys | Ala |
|   |   |   |   | 805 |   |   |   |   | 810 |   |   |   |   | 815 |   |
| Gly | Pro | Val | Cys | Asp | Cys | Lys | Arg | Asn | Ser | Asp | Val | Met | Asp | Cys | Val |
|   |   |   | 820 |   |   |   |   | 825 |   |   |   | 830 |   |   |   |
| Ile | Leu | Asp | Asp | Gly | Gly | Phe | Leu | Leu | Met | Ala | Asn | His | Asp | Asp | Tyr |
|   |   | 835 |   |   |   |   | 840 |   |   |   |   | 845 |   |   |   |
| Thr | Asn | Gln | Ile | Gly | Arg | Phe | Phe | Gly | Glu | Ile | Asp | Pro | Ser | Leu | Met |
|   | 850 |   |   |   |   | 855 |   |   |   |   | 860 |   |   |   |   |
| Arg | His | Leu | Val | Asn | Ile | Ser | Val | Tyr | Ala | Phe | Asn | Lys | Ser | Tyr | Asp |
| 865 |   |   |   |   | 870 |   |   |   |   | 875 |   |   |   |   | 880 |
| Tyr | Gln | Ser | Val | Cys | Glu | Pro | Gly | Ala | Ala | Pro | Lys | Gln | Gly | Ala | Gly |
|   |   |   |   | 885 |   |   |   |   | 890 |   |   |   |   | 895 |   |
| His | Arg | Ser | Ala | Tyr | Val | Pro | Ser | Val | Ala | Asp | Ile | Leu | Gln | Ile | Gly |
|   |   |   | 900 |   |   |   |   | 905 |   |   |   |   | 910 |   |   |
| Trp | Trp | Ala | Thr | Ala | Ala | Ala | Trp | Ser | Ile | Leu | Gln | Gln | Phe | Leu | Leu |
|   |   | 915 |   |   |   |   | 920 |   |   |   |   | 925 |   |   |   |
| Ser | Leu | Thr | Phe | Pro | Arg | Leu | Leu | Glu | Ala | Val | Glu | Met | Glu | Asp | Asp |
|   |   | 930 |   |   |   |   | 935 |   |   |   |   | 940 |   |   |   |
| Asp | Phe | Thr | Ala | Ser | Leu | Ser | Lys | Gln | Ser | Cys | Ile | Thr | Glu | Gln | Thr |
| 945 |   |   |   |   | 950 |   |   |   |   | 955 |   |   |   |   | 960 |
| Gln | Tyr | Phe | Phe | Asp | Asn | Asp | Ser | Lys | Ser | Phe | Ser | Gly | Val | Leu | Asp |
|   |   |   |   | 965 |   |   |   |   | 970 |   |   |   |   | 975 |   |
| Cys | Gly | Asn | Cys | Ser | Arg | Ile | Phe | His | Gly | Glu | Lys | Leu | Met | Asn | Thr |
|   |   |   | 980 |   |   |   |   | 985 |   |   |   |   | 990 |   |   |
| Asn | Leu | Ile | Phe | Ile | Met | Val | Glu | Ser | Lys | Gly | Thr | Cys | Pro | Cys | Asp |
|   |   | 995 |   |   |   |   | 1000 |   |   |   |   | 1005 |   |   |   |
| Thr | Arg | Leu | Leu | Ile | Gln | Ala | Glu | Gln | Thr | Ser | Asp | Gly | Pro | Asn | Pro |
|   | 1010 |   |   |   |   | 1015 |   |   |   |   | 1020 |   |   |   |   |
| Cys | Asp | Met | Val | Lys | Gln | Pro | Arg | Tyr | Arg | Lys | Gly | Pro | Asp | Val | Cys |
| 1025 |   |   |   |   | 1030 |   |   |   |   | 1035 |   |   |   |   | 1040 |
| Phe | Asp | Asn | Asn | Val | Leu | Glu | Asp | Tyr | Thr | Asp | Cys | Gly | Gly | Val | Ser |
|   |   |   |   | 1045 |   |   |   |   | 1050 |   |   |   |   | 1055 |   |
| Gly | Leu | Asn | Pro | Ser | Leu | Trp | Tyr | Ile | Ile | Gly | Ile | Gln | Phe | Leu | Leu |
|   |   |   | 1060 |   |   |   |   | 1065 |   |   |   |   | 1070 |   |   |
| Leu | Trp | Leu | Val | Ser | Gly | Ser | Thr | His | Arg | Leu | Leu |   |   |   |   |
|   |   | 1075 |   |   |   |   | 1080 |   |   |   |   |   |   |   |   |

( 2 ) INFORMATION FOR SEQ ID NO:57:

( i ) SEQUENCE CHARACTERISTICS:
        ( A ) LENGTH: 43 amino acids
        ( B ) TYPE: amino acid
        ( C ) STRANDEDNESS: single
        ( D ) TOPOLOGY: linear ( i i ) MOLECULE TYPE: protein ( v ) FRAGMENT TYPE: internal ( x i ) SEQUENCE DESCRIPTION: SEQ ID NO:57:

```
Trp Ser Phe Ala Cys Ala Cys Ala Ala Phe Ile Leu Leu Phe Leu Gly
 1               5                   10                  15

Gly Leu Ala Leu Leu Leu Phe Ser Leu Pro Arg Met Pro Arg Asn Pro
            20                  25                  30

Trp Glu Ser Cys Met Asp Ala Glu Pro Glu His
            35                  40
```